US012774275B2

(12) United States Patent
Bao et al.

(10) Patent No.: US 12,774,275 B2
(45) Date of Patent: Oct. 27, 2026

(54) COMPOUNDS AND COMPOSITIONS FOR THE TREATMENT OF CORONAVIRAL RELATED DISEASES

(71) Applicant: NOVARTIS AG, Basel (CH)

(72) Inventors: Denghui Bao, Changshu (CN); Fengfeng Guo, Nantong (CN); Matthew James Hesse, Pittsburgh, PA (US); Viktor Hornak, Arlington, MA (US); Sajan Joseph, Sudbury, MA (US); Thomas Martin Kirrane, Jr., San Ramon, CA (US); Haiyao Lin, Minhang (CN); Bo Liu, Pudong New Area (CN); Yanan Miao, Changshu (CN); Heinz Ernst Moser, San Mateo, CA (US); Julien Papillon, Somerville, MA (US); Yang Qu, Changshu (CN); Lei Shi, Changshu (CN); Jun Yuan, Boston, MA (US); Teng Zhang, Pudong New Area (CN)

(73) Assignee: NOVARTIS AG, Basel (CH)

( * ) Notice: Subject to any disclaimer, the term of this patent is extended or adjusted under 35 U.S.C. 154(b) by 333 days.

(21) Appl. No.: 18/580,986

(22) PCT Filed: Jul. 20, 2022

(86) PCT No.: PCT/IB2022/056712
§ 371 (c)(1),
(2) Date: Jan. 19, 2024

(87) PCT Pub. No.: WO2023/002409
PCT Pub. Date: Jan. 26, 2023

(65) Prior Publication Data

US 2025/0092016 A1 Mar. 20, 2025

Related U.S. Application Data

(60) Provisional application No. 63/289,009, filed on Dec. 13, 2021, provisional application No. 63/224,793, filed on Jul. 22, 2021.

(51) Int. Cl.

| | |
|---|---|
| ***C07D 401/14*** | (2006.01) |
| ***A61K 31/4725*** | (2006.01) |
| ***A61K 31/501*** | (2006.01) |
| ***A61K 31/506*** | (2006.01) |
| ***A61P 31/14*** | (2006.01) |
| ***C07D 401/04*** | (2006.01) |

(52) U.S. Cl.
CPC ........ *C07D 401/14* (2013.01); *A61K 31/4725* (2013.01); *A61K 31/501* (2013.01); *A61K 31/506* (2013.01); *A61P 31/14* (2018.01); *C07D 401/04* (2013.01)

(58) Field of Classification Search
CPC ........................... C07D 401/04; C07D 401/14; A61K 31/4725; A61K 31/501
See application file for complete search history.

(56) References Cited

U.S. PATENT DOCUMENTS

2010/0331326 A1* 12/2010 Bock .................... C07D 401/14 514/249

FOREIGN PATENT DOCUMENTS

| | | | |
|---|---|---|---|
| DE | 1200825 | B | 9/1965 |
| RU | 2744429 | C1 | 3/2021 |
| WO | 2009013171 | A2 | 1/2009 |
| WO | 2010149755 | A1 | 12/2010 |
| WO | 2023002409 | A1 | 1/2023 |

OTHER PUBLICATIONS

Hoffman, et al., Discovery of Ketone-Based Covalent Inhibitors of Coronavirus 3CL Proteases for the Potential Therapeutic Treatment of Covid-19, Journal of Medicinal Chemistry, 63(21), 12725-12747, Nov. 12, 2020.
Chande, et al., Synthesis of new 1-benzothiazol-2'''-yl-triazole derivatives as potential anti-cancer anti-caner agents, Indian Journal of Chemistry, 34B, 654-657, Jul. 1995.
El-Ansary , et al., Synthesis of Trioxo-perhydro-imidazolyl-benzopyrones with Hypnotic activity, Egzpt.J. Pharm. Sci., 36 (1-6), 219-233, 1995.
Bastin, et al., Salt Selection and Optimisation Procedures for Pharmaceutical New Chemical Entities, Organic Process Research & Development, 4(5), 427-435, 2000.
Belikov, Relationship between the chemical structure, properties of compounds and their action on the body, Pharmaceutical Chemistry, chapters 1.1, 1.2, 2.5, 2.6, 2.7, 11, 27-29, 2007.
Mohd, et al., SARS-CoV-2: A critical review of its history, pathogenesis, transmission, diagnosis and treatment, Biosafety and Health, 2, 217-225, 2020.

* cited by examiner

*Primary Examiner* — Kamal A Saeed
(74) *Attorney, Agent, or Firm* — Daniel E. Raymond

(57) ABSTRACT

Provided herein are compounds and compositions for treating, managing or preventing coronaviral related diseases. In particular, provided herein are compounds which are inhibitors of SARS-CoV-2 main protease (Mpro), pharmaceutical compositions comprising such compounds, method for synthesizing such compounds and methods of using such compounds and compositions for the treatment, management or prevention of coronaviral related diseases.

41 Claims, 3 Drawing Sheets

Specification includes a Sequence Listing.

SEQUENCE LISTING

```
Sequence total quantity: 3
SEQ ID NO: 1            moltype = AA  length = 549
FEATURE                 Location/Qualifiers
source                  1..549
                        mol_type = protein
                        organism = synthetic construct
SEQUENCE: 1
MSPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LEVLFQGPLG SAVLQSGFRK  240
MAFPSGKVEG CMVQVTCGTT TLNGLWLDDV VYCPRHVICT SEDMLNPNYE DLLIRKSNHN  300
FLVQAGNVQL RVIGHSMQNC VLKLKVDTAN PKTPKYKFVR IQPGQTFSVL ACYNGSPSGV  360
YQCAMRPNFT IKGSFLNGSC GSVGFNIDYD CVSFCYMHHM ELPTGVHAGT DLEGNFYGPF  420
VDRQTAQAAG TDTTITVNVL AWLYAAVING DRWFLNRFTT TLNDFNLVAM KYNYEPLTQD  480
HVDILGPLSA QTGIAVLDMC ASLKELLQNG MNGRTILGSA LLEDEFTPFD VVRQCSGVTF  540
QGPHHHHHH                                                         549

SEQ ID NO: 2            moltype = AA  length = 9
FEATURE                 Location/Qualifiers
source                  1..9
                        mol_type = protein
                        organism = synthetic construct
SEQUENCE: 2
AVLSGFRKK                                                         9

SEQ ID NO: 3            moltype = AA  length = 10
FEATURE                 Location/Qualifiers
source                  1..10
                        mol_type = protein
                        organism = synthetic construct
SEQUENCE: 3
AVLQSGFRKK                                                        10
```

COMPOUNDS AND COMPOSITIONS FOR THE TREATMENT OF CORONAVIRAL RELATED DISEASES

RELATED APPLICATIONS

This application claims priority to, and the benefit of U.S. Provisional Application No. 63/224,793 filed 22 Jul. 2021 and U.S. Provisional Application No. 63/289,009 filed 13 Dec. 2021, the contents of each of which are hereby incorporated by reference in their entireties.

SEQUENCE LISTING

The instant application contains Sequence Listings which have been submitted electronically in XML format and are hereby incorporated by reference in their entirety. Said XML copy, created on, Jun. 30, 2022, is named PAT059164-WO-PCT Sequence listing.xml and is 3930 bytes in size.

FIELD OF THE INVENTION

The present invention relates to compounds and compositions for the treatment, management and/or prevention of coronaviral related diseases. In particular, the present invention relates to compounds which are inhibitors of SARS-CoV-2 main protease ($M^{pro}$), to pharmaceutical compositions comprising such compounds, to methods for synthesizing such 20 compounds and to methods of using such compounds and compositions for the treatment, management or prevention of coronaviral related diseases.

BACKGROUND OF THE INVENTION

SARS-CoV-2 is a single positive-stranded RNA virus belonging to the genus Coronavirus β. The SARS-CoV-2 genome is about 30 kb in length, has untranslated regions (UTR) at both ends, and at least 6 complete open reading frame genes (ORF). Of these ORF's, ORF 1a/b directly encodes two polyproteins: polyprotein 1a (pp1a) and polyprotein 1ab (pp1 ab). These polypeptides are cleaved by the main protease ($M^{pro}$), also known as 3C-like protease (3CLpro), and the papain-like protease (PLpro) into 16 non-structural proteins (nsps). These nsps play key roles in the production of subgenomic RNA, which encodes four major structural proteins, namely surface spike glycoprotein (S), envelope protein (E), membrane protein (M) and Nucleocapsid protein (N). Thus $M^{pro}$ plays a vital role in the replication cycle of SARS-CoV-2. Therefore, inhibiting the activity of $M^{pro}$ would block viral replication and may provide an effective therapeutic approach for the treatment of COVID-19, the disease caused by SARS-CoV-2, or for diseases caused by other beta-coronaviruses.

The identification of $M^{pro}$ inhibitors has been the subject of several reports. Most of these inhibitors are peptidomimetics, and typically come from previously studied protease inhibitors Dai, W. et al. (2020) Structure-based design of antiviral drug candidates targeting the SARS-CoV-2 main protease. Science, 368(6497), 1331-1335; Zhang, L., et al. (2020) Crystal structure of SARS-CoV-2 main protease provides a basis for design of improved a-ketoamide inhibitors. Science, 368(6489), 409-412; Ma, C. et al. (2020) Boceprevir, GC-376, and calpain inhibitors II, XII inhibit SARS-CoV-2 viral replication by targeting the viral main protease. Cell Research, 30(8), 678-692; Jin, Z. et al. (2020) Structure of $M^{pro}$ from SARS-CoV-2 and discovery of its inhibitors. Nature, 582(7811), 289-293).

A peptidomimetic originally developed for SARS-CoV virus is currently in the clinic as an intravenous treatment for Covid-19 (Hoffman, R. L. et al. (2020). Discovery of Ketone-Based Covalent Inhibitors of Coronavirus 3CL Proteases for the Potential Therapeutic Treatment of COVID-19. Journal of Medicinal Chemistry, 63(21), 12725-12747).

A smaller number of publications describes non-peptidic small molecule inhibitors (Riva, L. et al. (2020). Discovery of SARS-CoV-2 antiviral drugs through large-scale compound repurposing. Nature, 586(7827), 113-119; Ghahremanpour, M. M. et al. (2020). Identification of 14 Known Drugs as Inhibitors of the Main Protease of SARS-CoV-2. ACS Med Chem Lett, 11, 2526; Guenther, S. et al. (2021) X-ray screening identifies active site and allosteric inhibitors of SARS-CoV-2 main protease. Science. https://doi.org/10.1126/science.abf7945; Douangamath, A. et al. (2020). Crystallographic and electrophilic fragment screening of the SARS-CoV-2 main protease. Nature Communications, 11(1):5047, however there continues to be a need for effective treatments of diseases caused by beta-coronaviruses, especially COVID-19.

SUMMARY OF THE INVENTION

In one aspect the invention therefore provides a compound of the Formula (I), a stereoisomer thereof, or a pharmaceutically acceptable salt thereof,

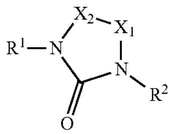

(I)

wherein $X_1$, $X_2$, $R^1$ and $R^2$ are as defined herein.

Another aspect of the present invention is a pharmaceutical composition comprising a therapeutically effective amount of a compound of the invention, a stereoisomer thereof, or a pharmaceutically acceptable salt thereof, and one or more pharmaceutically acceptable carriers.

Another aspect of the present invention is a pharmaceutical composition comprising a compound of the invention, a stereoisomer thereof, or a pharmaceutically acceptable salt thereof, and one or more pharmaceutically acceptable carriers.

In another aspect, the invention provides a methods for treating, preventing and/or managing a coronaviral-related disease or disorder, wherein the method comprises administering to a subject in need of such treatment, prevention or management a therapeutically or prophylactically effective amount of a compound of the invention, a stereoisomer thereof, or a pharmaceutically acceptable salt thereof. In certain embodiments the coronaviral-related disease are COVID-19, other acute respiratory syndromes, non-respiratory coronavirus syndromes and post-infectious coronavirus syndromes.

In another aspect, the invention provides a methods for treating, preventing and/or managing a coronaviral-related disease or disorder, wherein the method comprises administering to a subject in need of such treatment, prevention or management a compound of the invention, a stereoisomer thereof, or a pharmaceutically acceptable salt thereof. In certain embodiments the coronaviral-related disease is COVID-19.

In another aspect, the invention provides use of a compound of the invention, a stereoisomer thereof, or a pharmaceutically acceptable salt thereof, in the manufacture of a medicament for the treatment, prevention and/or management of a coronalviral-related disease or disorder.

In another aspect, the invention provides use of a compound of the invention, a stereoisomer thereof, or a pharmaceutically acceptable salt thereof, in the manufacture of a medicament for the treatment, prevention and/or management of COVID-19.

In another aspect, the invention provides the use of a compound of the invention, a stereoisomer thereof, or a pharmaceutically acceptable salt thereof, in the treatment, prevention and/or management of a coronalviral-related disease or disorder.

In another aspect, the invention provides the use of a compound of the invention, a stereoisomer thereof, or a pharmaceutically acceptable salt thereof, in the treatment, prevention and/or management of COVID-19.

In another aspect, the invention provides a compound of the invention, a stereoisomer thereof, or a pharmaceutically acceptable salt thereof, for use in the treatment, prevention and/or management of a coronalviral-related disease or disorder.

In another aspect, the invention provides a compound of the invention, a stereoisomer thereof, or a pharmaceutically acceptable salt thereof, for use in the treatment, prevention and/or management of COVID-19.

In another aspect, the invention provides kits comprising a compound of the invention, a stereoisomer thereof, or a pharmaceutically acceptable salt thereof, for treating, preventing and/or managing a coronaviral-related disease.

In another aspect, the invention provides kits comprising a compound of the invention, a stereoisomer thereof, or a pharmaceutically acceptable salt thereof, for treating, preventing and/or managing COVID-19.

In another aspect, the invention provides combinations for the treatment, prevention and/or management of a coronaviral related disease, wherein a compound of the invention, a stereoisomer thereof, or a pharmaceutically acceptable salt thereof, is used in combination with one or more other active agents. In certain embodiments the active agent(s) is selected from a neutralizing antibody and an antiviral agent. In certain embodiments the active agent(s) is selected from neutralizing antibody, an antiviral agent and other agents selected from alvelestat, Lenzilumab, Octagam, Remestemcel-L, RPH-104+olokizumab, Bucillamine, CD24FC (MK-7110), Tradipitant, Ifenprodil, Tocilizumab, Leronlimab, Fenretinide, ATYR-1923, CYTO-205, APN-01, and Ampion. In certain embodiments, the neutralizing antibody is selected 5 from Bamlanivimab, bamlanivimab+etesevimab, bamlanivimab+VIR-7831, REGN-COV2, VIR-7831, AZD7442, Regdanvimab/CT-P59, ABP 300, COVI-AM/STI-2020, VIR-7832, SAB-185, JS016/etesevimab, C-135LS/C-144LS, BRII-196, BRII-198, SCTA-01, MW-33, DXP593, HFB-30132A, ADG20, COVI-GUARD (STI-1499) and convalescent plasma, and the antiviral agents is selected from remdesivir, Avigan/favipiravir, EIDD-2801/molnupiravir, AT-527, PF-00835231, PF-07321332, Ensovibep/DARPins, galidesivir, lopinavir-ritonavir, Virazole (ribavirin), levovir, elsulfavirine, thimerosal, UNI91103, silmitasertib/CX-4945, RBT-9, AT-301, Traneurocin/Neurosivir, Opaganib, ABX-464, SNG001, alisporivir, nafamostat mesylate, Vidofludimus/IMU-838, Emvododstat/PTC299, Brequinar, ATR-002, maraviroc.

In another aspect, the invention provides combinations for the treatment, prevention and/or management of a coronaviral related disease, wherein a compound of the invention is used in combination with remdesivir (also known as 2-ethylbutyl((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate).

DETAILED DESCRIPTION

Definitions

Figure 1:
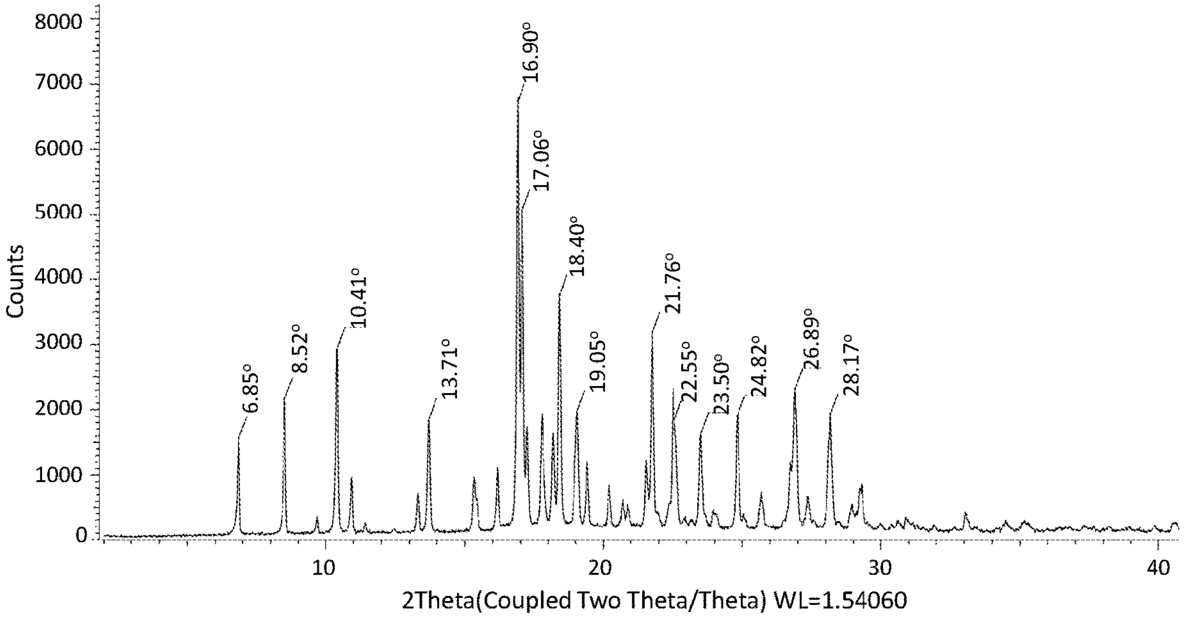
FIG. 1: illustrates a representative powder X-ray diffractogram (PXRD) curve of (R)-3-(isoquinolin-4-yl)-2-oxo-1-(6-(trifluoromethyl)pyridin-3-yl)imidazolidine-4-carbonitrile Modification A. The x-axis shows the scattering angle in ° 2-Theta, the y-axis shows the intensity of the scattered X-ray beam in counts of detected photons.

The term "alkyl," as used herein, refers to a fully saturated branched or straight hydrocarbon chain. In certain embodiments an alkyl group is a "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_8$alkyl" or "$C_1$-$C_{10}$alkyl", wherein the terms "$C_1$-$C_2$alkyl", "$C_1$-$C_3$alkyl", "$C_1$-$C_4$alkyl", "$C_1$-$C_8$alkyl", "$C_1$-$C_6$alkyl", "$C_1$-$C_7$alkyl", "$C_1$-$C_8$alkyl", "$C_1$-$C_9$alkyl" and "$C_1$-$C_{10}$alkyl", as used herein, refer to an alkyl group containing at least 1, and at most 2, 3, 4, 5, 6, 7, 8, 9 or 10 carbon atoms, respectively. Non-limiting examples of alkyl groups include methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkenyl," as used herein, refers to a partially saturated branched or straight hydrocarbon chain having one more double bonds. In certain embodiments an alkenyl group is a "$C_2$-$C_3$alkenyl", "$C_2$-$C_4$alkenyl", "$C_2$-

$C_5$alkenyl", "$C_2$-$C_6$alkenyl", "$C_2$-$C_7$alkenyl", "$C_2$-$C_8$alkenyl", "$C_2$-$C_5$alkenyl" or "$C_2$-$C_{10}$alkenyl", wherein the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", "$C_2$-$C_8$alkenyl", "$C_2$-$C_5$alkenyl" and "$C_2$-$C_{10}$alkenyl", as used herein, refer to an alkenyl group containing at least 2, and at most 3, 4, 5, 6, 7, 8, 9 or 10 carbon atoms, respectively. Non-limiting examples of alkenyl groups include ethenyl, n-propenyl, isopropenyl, n-butenyl, isobutenyl, sec-butenyl, tert-butenyl, n-pentenyl, isopentenyl, n-hexenyl, n-heptenyl, n-octenyl, n-nonenyl and n-decenyl.

The term "alkoxy", as used herein, refers to —O-alkyl or -alkyl-O—, wherein "alkyl" is as defined herein. In certain embodiments an alkoxy group is a "$C_1$-$C_2$alkoxy", "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_4$alkoxy", "$C_1$-$C_5$alkoxy" or "$C_1$-$C_{10}$alkoxy", wherein the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" and "$C_1$-$C_{10}$alkoxy", as used herein refer to —O—$C_1$-$C_2$alkyl, —O—$C_1$-$C_3$alkyl, —O—$C_1$-$C_4$alkyl, —O—$C_1$-$C_8$alkyl, —O—$C_1$-$C_7$alkyl, —O—$C_1$-$C_7$alkyl, —O—$C_1$-$C_8$alkyl, —O—$C_1$-$C_8$alkyl or —O—$C_1$-$C_{10}$alkyl, respectively. Non-limiting examples of "alkoxy" groups include methoxy, ethoxy, n-propoxy, isopropoxy, n-butoxy, isobutoxy, sec-butoxy, tert-butoxy, n-pentoxy, isopentoxy, hexoxy, heptoxy, octoxy, nonoxy and decoxy.

The term "$C_3$-$C_8$cycloalkyl", as used herein, refers to a fully saturated, monocyclic hydrocarbon ring system having 3 to 8 carbon atoms as ring members. Non-limiting examples of such "$C_3$-$C_8$cycloalkyl" groups include cyclopropyl, cyclobutyl, cyclopentyl, cyclohexyl, cycloheptyl and cyclooctyl.

The term "bicyclic $C_3$-$C_8$cycloalkyl", as used herein, refers to a fully saturated, fused bicyclic hydrocarbon ring system having 3 to 8 carbon atoms as ring members, or the term "bicyclic $C_3$-$C_8$cycloalkyl", as used herein, refers a fully saturated, bridged bicyclic hydrocarbon ring system having 3 to 8 carbon atoms as ring members, or the term "bicyclic $C_3$-$C_8$cycloalkyl", as used herein, refers a fully saturated, spiro bicyclic hydrocarbon ring system having 3 to 8 carbon atoms as ring members. Non-limiting examples of such "bicyclic $C_3$-$C_8$cycloalkyl" groups include bicyclo [1.1.1]pentanyl, spiro[3.3]heptanyl, spiro[2.3]hexanyl, and the like.

The term "$C_5$-$C_6$cycloalkenyl" as used herein, refers to a partially saturated (but not aromatic), monocyclic hydrocarbon ring system having 5 to 6 carbon atoms as ring members. Non-limiting examples of "$C_5$-$C_6$cycloalkenyl", as used herein, include cyclopent-1-enyl, cyclopenta-1,3-dienyl, cyclohex-1-enyl and cyclohexa-1,3-dienyl.

The term "$C_1$-$C_6$alkyl-phenyl" as used herein, refer to a $C_1$-$C_6$alkyl as defined above which is substituted with a phenyl group. Non-limiting example of a $C_1$-$C_6$alkyl-phenyl is benzyl.

The term "haloalkyl" as used herein, refers to an alkyl group as defined herein, wherein at least one of the hydrogen atoms of the alkyl is replaced by a halo group (as defined herein). The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically, the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. Preferred haloalkyl groups, unless specified otherwise, include monofluoro-, difluoro- and trifluoro-substituted methyl and ethyl groups, e.g. $CF_3$, $CHF_2$, $CH_2F$, $CH_2CHF_2$ and $CH_2CF_3$.

The term "$C_1$-$C_6$haloalkyl" as used herein, refers to the respective "$C_1$-$C_6$alkyl", as defined herein, wherein at least one of the hydrogen atoms of the "$C_1$-$C_6$alkyl" is replaced by a halo group (as defined herein). The $C_1$-$C_6$haloalkyl groups can be mono$C_1$-$C_6$haloalkyl, wherein such $C_1$-$C_6$haloalkyl groups have one iodo, one bromo, one chloro or one fluoro. Additionally, the $C_1$-$C_6$haloalkyl groups can be di$C_1$-$C_6$haloalkyl wherein such $C_1$-$C_6$haloalkyl groups can have two halo atoms independently selected from iodo, bromo, chloro or fluoro. Furthermore, the $C_1$-$C_6$haloalkyl groups can be poly$C_1$-$C_6$haloalkyl wherein such $C_1$-$C_6$haloalkyl groups can have two or more of the same halo atoms or a combination of two or more different halo atoms. Such poly$C_1$-$C_6$haloalkyl can be perhalo$C_1$-$C_6$haloalkyl where all the hydrogen atoms of the respective $C_1$-$C_6$alkyl have been replaced with halo atoms and the halo atoms can be the same or a combination of different halo atoms. Non-limiting examples of "$C_1$-$C_6$haloalkyl" groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, fluoroethyl, difluoroethyl, trifluoroethyl, difluoropropyl, dichloroethyl and dichloropropyl.

The term "haloalkoxy" as used herein, refers to the group —O-haloalkyl wherein the term "haloalkyl" is as defined herein. Non-limiting examples of haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhalo-alkoxy refers to an alkoxy having all hydrogen atoms replaced with halo atoms, e.g., trifluoromethoxy.

Preferred haloalkoxy groups, unless specified otherwise, include monofluoro-, difluoro- and trifluoro-substituted methoxy and ethoxygroups, e.g. —$OCF_3$, —$OCHF_2$, —$OCH_2F$, —$OCH_2CHF_2$ and —$OCH_2CF_3$.

The term "$C_1$-$C_6$haloalkoxy" as used herein, refers to the group —O—$C_1$-$C_6$haloalkyl, wherein the term $C_1$-$C_6$haloalkyl is as defined herein. Non-limiting examples of "$C_1$-$C_6$haloalkoxy" groups include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, fluoroethoxy, difluoroethoxy, trifluoroethoxy, difluoropropoxy, dichloroethoxy and dichloropropoxy.

The terms "halogen" or "halo" as used herein, refer to fluoro (F), chloro($C_1$), bromo (Br) and iodo (I).

The term "heteroatoms", as used herein, refers to nitrogen (N), oxygen (O) or sulfur (S) atoms.

The term "heteroaryl," as used herein, refers to an aromatic ring system containing one or more heteroatoms which may be the same or different. The term "heteroaryl," as used herein, also refers to an aromatic ring system having one or more ring members which are each independently selected from N, $NR^6$, O and S, where $R^6$ is as defined herein. Heteroaryl groups may be monocyclic ring systems or fused bicyclic ring systems. Monocyclic heteroaryl rings have from 5 to 6 ring atoms. Bicyclic heteroaryl rings have from 7 to 12 ring member atoms. Bicyclic heteroaryl rings include those ring systems wherein a heteroaryl ring is fused to a phenyl ring. Non-limiting examples of heteroaryl groups, as used herein, include benzofuranyl, benzo[c]thiophenyl, benzothiophenyl, benzoxazolyl, benzothiazolyl, benzimidazolyl, cinnolinyl, furazanyl, furyl, imidazolyl, indolyl, indolizinyl, indazolyl, isoindolyl, isoquinolinyl, isoxazolyl, isothiazolyl, oxazolyl, oxaindolyl, oxadiazolyl (including 1,3,4-oxadiazolyl and 1,2,4-oxadiazolyl), purinyl, pyrazolyl, pyrrolyl, phthalazinyl, pyridyl (including 2-, 3-, and 4-pyridyl), pyridazinyl, pyrazinyl, pyrimidinyl, quinoxalinyl, quinolinyl, quinazolinyl, tetrazinyl, tetrazolyl, tetrazolo[1,5-a]pyridinyl, thiazolyl, thiadiazolyl (including 1,3,4-thiadiazolyl), thienyl, triazinyl, and triazolyl.

The term "5 or 6 membered heteroaryl", as used herein, refers to an aromatic, 5 or 6 membered monocyclic ring system wherein 1, 2, 3 or 4 ring members are each independently selected from N, $NR^6$, O and S, where $R^6$ is as defined herein. Non-limiting examples of such 5 or 6 membered heteroaryl groups, as used herein, include furyl, imidazolyl, isoxazolyl, isothiazolyl, oxazolyl, pyrrolyl, pyrazolyl, thiadiazolyl, thiazolyl, thienyl, triazolyl, tetrazolyl, pyridyl (including 2-, 3-, and 4-pyridyl), pyridazinyl, pyrazinyl and pyrimidinyl. In certain embodiments, the term "5 or 6 membered heteroaryl", as used herein, also refers to an aromatic, 5 or 6 membered monocyclic ring system wherein 1, 2, or 3 ring members are each independently selected from N, $NR^6$, O and S, where $R^6$ is as defined herein. Non-limiting examples of such 5 or 6 membered heteroaryl groups, as used herein, include furyl, imidazolyl, isoxazolyl, isothiazolyl, oxazolyl, pyrrolyl, pyrazolyl, thiadiazolyl, thiazolyl, thienyl, triazolyl, pyridyl (including 2-, 3-, and 4-pyridyl), pyridazinyl, pyrazinyl and pyrimidinyl.

The term "6 membered heteroaryl", as used herein, refers to an aromatic, 6 membered monocyclic ring system wherein 1, 2 or 3 ring members are each independently selected from N, O and S. Non-limiting examples of such 6 membered heteroaryl groups, as used herein, include pyridyl (including 2-, 3-, and 4-pyridyl), pyridazinyl, pyrazinyl and pyrimidinyl.

The term "5 membered heteroaryl", as used herein, refers to an aromatic, 5 membered monocyclic ring system wherein 1, 2, 3 or 4 ring members are each independently selected from N, $NR^6$, O and S, where $R^6$ is as defined herein. Non-limiting examples of such 5 membered heteroaryl groups, as used herein, include furyl, imidazolyl, isoxazolyl, isothiazolyl, oxazolyl, pyrrolyl, pyrazolyl, thiadiazolyl, thiazolyl, thienyl, triazolyl and tetrazolyl. In certain embodiments, the term "5 membered heteroaryl", as used herein, also refers to an aromatic, 5 membered monocyclic ring system wherein 1, 2, or 3 ring members are each independently selected from N, $NR^6$, O and S, where $R^6$ is as defined herein. Non-limiting examples of such 5 membered heteroaryl groups, as used herein, include furyl, imidazolyl, isoxazolyl, isothiazolyl, oxazolyl, pyrrolyl, pyrazolyl, thiadiazolyl, thiazolyl, thienyl and triazolyl.

The term "9 or 10 membered bicyclic heteroaryl", as used herein, refers to a 9 or 10 membered fused, bicyclic aromatic ring system wherein 1, 2, 3, 4 or 5 ring members are each independently selected from N, $NR^6$, O and S, where $R^6$ is as defined herein. Non-limiting examples of such bicyclic heteroaryl groups, as used herein, include indolyl, quinolinyl, isoquinolinyl, indazolyl, purinyl, phthalazinyl, naphthyridinyl, quinazolinyl, cinnolinyl, thieno[2,3-b]furanyl, 1H-pyrazolo[4,3-d]-oxazolyl, imidazo[2,1-b]thiazolyl, imidazo[1,2-c]pyrimidinyl, imidazo[1,2-a]pyrazinyl, imidazo[1,2-a]pyridinyl, pyrazolo[1,5-a]pyrazinyl, pyrazino[2,3-d]pyridazinyl, imidazo[1,2-b][1,2,4]triazinyl, benzoxazolyl, benzimidazolyl, imidazopyridinyl, benzo[c]isoxazolyl and benzothiazolyl.

The term "4 to 7 membered heterocycloalkyl" as used herein, refers to a 4 to 7 membered, saturated hydrocarbon ring wherein 1, 2, 3 or 4 ring members are each independently selected from N, $NR^6$, O or S, where $R^6$ is as defined herein. The heterocycloalkyl group can be attached to another group at a nitrogen or a carbon atom. Non-limiting examples of 4 to 6 membered heterocycloalkyl groups, as used herein, include azetadinyl (which includes azetadin-1-yl, azetadin-2-yl and azetadin-3-yl), oxetanyl (which includes oxetan-2-yl, oxetan-3-yl and oxetan-4-yl), thietanyl (which includes thietan-2-yl, thietan-3-yl and thietan-4-yl), pyrrolidinyl (which includes pyrrolidin-1-yl, pyrrolidin-2-yl, pyrrolidin-3-yl, pyrrolidin-4-yl and pyrrolidin-5-yl), tetrahydrofuranyl (which includes tetrahydrofuran-2-yl, tetrahydrofuran-3-yl, tetrahydrofuran-4-yl and tetrahydrofuran-5-yl), tetrahydrothienyl (which includes tetrahydrothien-2-yl, tetrahydrothien-3-yl, tetrahydrothien-4-yl and tetrahydrothien-5-yl), piperidinyl (which includes piperidin-1-yl, piperidin-2-yl, piperidin-3-yl, piperidin-4-yl, piperidin-5-yl and piperidin-6-yl), tetrahydropyranyl (which includes tetrahydropyran-2-yl, tetrahydropyran-3-yl, tetrahydropyran-4-yl, tetrahydropyran-5-yl and tetrahydropyran-6-yl), tetrahydrothiopyranyl (which includes tetrahydrothiopyran-2-yl, tetrahydrothiopyran-3-yl, tetrahydrothiopyran-4-yl, tetrahydrothiopyran-5-yl and tetrahydrothiopyran-6-yl), piperazinyl (which includes piperazin-1-yl, piperazin-2-yl, piperazin-3-yl, piperazin-4-yl, piperazin-5-yl and piperazin-6-yl), morpholinyl (which includes morpholin-2-yl, morpholin-3-yl, morpholin-4-yl, morpholin-5-yl and morpholin-6-yl), thiomorpholinyl (which includes thiomorpholin-2-yl, thiomorpholin-3-yl, thiomorpholin-4-yl, thiomorpholin-5-yl and thiomorpholin-6-yl), oxathianyl (which includes oxathian-2-yl, oxathian-3-yl, oxathian-5-yl and oxathian-6-yl), dithianyl (which includes dithian-2-yl, dithian-3-yl, dithian-5-yl and dithian-6-yl), dioxolanyl (which includes dioxolan-2-yl, dioxolan-4-yl and dioxolan-5-yl), thioxanyl (which includes thioxan-2-yl, thioxan-3-yl, thioxan-4-yl and thioxan-5-yl), dithiolanyl (which includes dithiolan-2-yl, dithiolan-4-yl and dithiolan-5-yl), and pyrazolidinyl (which includes pyrazolidin-1-yl, pyrazolidin-2-yl, pyrazolidin-3-yl, pyrazolidin-4-yl and pyrazolidin-5-yl), azepanyl, diazepanyl, triazepanyl, ozazepanyl, oxadiazepanyl, oxepanyl, thiepanyl, thiazepanyl and thiadiazepanyl.

The term "3 to 6 membered heterocycloalkyl" as used herein, refers to a 3 to 6 membered, saturated hydrocarbon ring wherein 1, 2 or 3 ring members are each independently selected from N, $NR^6$, O or S, where $R^6$ is as defined herein. The heterocycloalkyl group can be attached to another group at a nitrogen or a carbon atom. Non-limiting examples of 3 to 6 membered heterocycloalkyl groups, as used herein, include oxiranyl, aziridinyl, thiiranyl, azetadinyl (which includes azetadin-1-yl, azetadin-2-yl and azetadin-3-yl), oxetanyl (which includes oxetan-2-yl, oxetan-3-yl and oxetan-4-yl), thietanyl (which includes thietan-2-yl, thietan-3-yl and thietan-4-yl), pyrrolidinyl (which includes pyrrolidin-1-yl, pyrrolidin-2-yl, pyrrolidin-3-yl, pyrrolidin-4-yl and pyrrolidin-5-yl), tetrahydrofuranyl (which includes tetrahydrofuran-2-yl, tetrahydrofuran-3-yl, tetrahydrofuran-4-yl and tetrahydrofuran-5-yl), tetrahydrothienyl (which includes tetrahydrothien-2-yl, tetrahydrothien-3-yl, tetrahydrothien-4-yl and tetrahydrothien-5-yl), piperidinyl (which includes piperidin-1-yl, piperidin-2-yl, piperidin-3-yl, piperidin-4-yl, piperidin-5-yl and piperidin-6-yl), tetrahydropyranyl (which includes tetrahydropyran-2-yl, tetrahydropyran-3-yl, tetrahydropyran-4-yl, tetrahydropyran-5-yl and tetrahydropyran-6-yl), tetrahydrothiopyranyl (which includes tetrahydrothiopyran-2-yl, tetrahydrothiopyran-3-yl, tetrahydrothiopyran-4-yl, tetrahydrothiopyran-5-yl and tetrahydrothiopyran-6-yl), piperazinyl (which includes piperazin-1-yl, piperazin-2-yl, piperazin-3-yl, piperazin-4-yl, piperazin-5-yl and piperazin-6-yl), morpholinyl (which includes morpholin-2-yl, morpholin-3-yl, morpholin-4-yl, morpholin-5-yl and morpholin-6-yl), thiomorpholinyl (which includes thiomorpholin-2-yl, thiomorpholin-3-yl, thiomorpholin-4-yl, thiomorpholin-5-yl and thiomorpholin-6-yl), oxathianyl (which includes oxathian-2-yl, oxathian-3-yl, oxathian-5-yl and oxathian-6-yl), dithianyl (which includes dithian-2-yl, dithian-3-yl, dithian-5-yl and dithian-6-yl), dioxolanyl (which includes dioxolan-2-yl, dioxolan-4-yl and dioxolan-5-yl), thioxanyl (which includes thioxan-2-yl, thioxan-3-yl, thioxan-4-yl and thioxan-5-yl), dithiolanyl (which includes dithiolan-2-yl, dithiolan-4-yl and dithiolan-5-yl), pyrazolidinyl (which includes pyrazolidin-1-yl, pyrazolidin-2-yl, pyrazolidin-3-yl, pyrazolidin-4-yl and pyrazolidin-5-yl), hexahydropyridazinyl and hexahydropyrimidinyl.

The term “4 to 6 membered heterocycloalkyl” as used herein, refers to a 4 to 6 membered, saturated hydrocarbon ring wherein 1, 2, 3 or 4 ring members are each independently selected from N, $NR^6$, O or S, where $R^6$ is as defined herein. The heterocycloalkyl group can be attached to another group at a nitrogen or a carbon atom. Non-limiting examples of 4 to 6 membered heterocycloalkyl groups, as used herein, include azetadinyl (which includes azetadin-1-yl, azetadin-2-yl and azetadin-3-yl), oxetanyl (which includes oxetan-2-yl, oxetan-3-yl and oxetan-4-yl), thietanyl (which includes thietan-2-yl, thietan-3-yl and thietan-4-yl), pyrrolidinyl (which includes pyrrolidin-1-yl, pyrrolidin-2-yl, pyrrolidin-3-yl, pyrrolidin-4-yl and pyrrolidin-5-yl), tetrahydrofuranyl (which includes tetrahydrofuran-2-yl, tetrahydrofuran-3-yl, tetrahydrofuran-4-yl and tetrahydrofuran-5-yl), tetrahydrothienyl (which includes tetrahydrothien-2-yl, tetrahydrothien-3-yl, tetrahydrothien-4-yl and tetrahydrothien-5-yl), piperidinyl (which includes piperidin-1-yl, piperidin-2-yl, piperidin-3-yl, piperidin-4-yl, piperidin-5-yl and piperidin-6-yl), tetrahydropyranyl (which includes tetrahydropyran-2-yl, tetrahydropyran-3-yl, tetrahydropyran-4-yl, tetrahydropyran-5-yl and tetrahydropyran-6-yl), tetrahydrothiopyranyl (which includes tetrahydrothiopyran-2-yl, tetrahydrothiopyran-3-yl, tetrahydrothiopyran-4-yl, tetrahydrothiopyran-5-yl and tetrahydrothiopyran-6-yl), piperazinyl (which includes piperazin-1-yl, piperazin-2-yl, piperazin-3-yl, piperazin-4-yl, piperazin-5-yl and piperazin-6-yl), morpholinyl (which includes morpholin-2-yl, morpholin-3-yl, morpholin-4-yl, morpholin-5-yl and morpholin-6-yl), thiomorpholinyl (which includes thiomorpholin-2-yl, thiomorpholin-3-yl, thiomorpholin-4-yl, thiomorpholin-5-yl and thiomorpholin-6-yl), oxathianyl (which includes oxathian-2-yl, oxathian-3-yl, oxathian-5-yl and oxathian-6-yl), dithianyl (which includes dithian-2-yl, dithian-3-yl, dithian-5-yl and dithian-6-yl), dioxolanyl (which includes dioxolan-2-yl, dioxolan-4-yl and dioxolan-5-yl), thioxanyl (which includes thioxan-2-yl, thioxan-3-yl, thioxan-4-yl and thioxan-5-yl), dithiolanyl (which includes dithiolan-2-yl, dithiolan-4-yl and dithiolan-5-yl), pyrazolidinyl (which includes pyrazolidin-1-yl, pyrazolidin-2-yl, pyrazolidin-3-yl, pyrazolidin-4-yl and pyrazolidin-5-yl), hexahydropyridazinyl and hexahydropyrimidinyl.

The term “5 or 6 membered heterocycloalkyl” as used herein, refers to a 5 or 6 membered, saturated hydrocarbon ring wherein 1, 2, 3 or 4 ring members are each independently selected from N, $NR^6$, O or S, where $R^6$ is as defined herein. The heterocycloalkyl group can be attached to another group at a nitrogen or a carbon atom. Non-limiting examples of 5 or 6 membered heterocycloalkyl groups, as used herein, include pyrrolidinyl (which includes pyrrolidin-1-yl, pyrrolidin-2-yl, pyrrolidin-3-yl, pyrrolidin-4-yl and pyrrolidin-5-yl), tetrahydrofuranyl (which includes tetrahydrofuran-2-yl, tetrahydrofuran-3-yl, tetrahydrofuran-4-yl and tetrahydrofuran-5-yl), tetrahydrothienyl (which includes tetrahydrothien-2-yl, tetrahydrothien-3-yl, tetrahydrothien-4-yl and tetrahydrothien-5-yl), piperidinyl (which includes piperidin-1-yl, piperidin-2-yl, piperidin-3-yl, piperidin-4-yl, piperidin-5-yl and piperidin-6-yl), tetrahydropyranyl (which includes tetrahydropyran-2-yl, tetrahydropyran-3-yl, tetrahydropyran-4-yl, tetrahydropyran-5-yl and tetrahydropyran-6-yl), tetrahydrothiopyranyl (which includes tetrahydrothiopyran-2-yl, tetrahydrothiopyran-3-yl, tetrahydrothiopyran-4-yl, tetrahydrothiopyran-5-yl and tetrahydrothiopyran-6-yl), piperazinyl (which includes piperazin-1-yl, piperazin-2-yl, piperazin-3-yl, piperazin-4-yl, piperazin-5-yl and piperazin-6-yl), morpholinyl (which includes morpholin-2-yl, morpholin-3-yl, morpholin-4-yl, morpholin-5-yl and morpholin-6-yl), thiomorpholinyl (which includes thiomorpholin-2-yl, thiomorpholin-3-yl, thiomorpholin-4-yl, thiomorpholin-5-yl and thiomorpholin-6-yl), oxathianyl (which includes oxathian-2-yl, oxathian-3-yl, oxathian-5-yl and oxathian-6-yl), dithianyl (which includes dithian-2-yl, dithian-3-yl, dithian-5-yl and dithian-6-yl), dioxolanyl (which includes dioxolan-2-yl, dioxolan-4-yl and dioxolan-5-yl), thioxanyl (which includes thioxan-2-yl, thioxan-3-yl, thioxan-4-yl and thioxan-5-yl), dithiolanyl (which includes dithiolan-2-yl, dithiolan-4-yl and dithiolan-5-yl), pyrazolidinyl (which includes pyrazolidin-1-yl, pyrazolidin-2-yl, pyrazolidin-3-yl, pyrazolidin-4-yl and pyrazolidin-5-yl), hexahydropyridazinyl and hexahydropyrimidinyl.

The term “6 membered heterocycloalkyl” as used herein, refers to a 6 membered, saturated hydrocarbon ring wherein 1, 2, 3 or 4 ring members are each independently selected from N, $NR^6$, O or S, where $R^6$ is as defined herein. The heterocycloalkyl group can be attached to another group at a nitrogen or a carbon atom. Non-limiting examples of 6 membered heterocycloalkyl groups, as used herein, include piperidinyl (which includes piperidin-1-yl, piperidin-2-yl, piperidin-3-yl, piperidin-4-yl, piperidin-5-yl and piperidin-6-yl), tetrahydropyranyl (which includes tetrahydropyran-2-yl, tetrahydropyran-3-yl, tetrahydropyran-4-yl, tetrahydropyran-5-yl and tetrahydropyran-6-yl), tetrahydrothiopyranyl (which includes tetrahydrothiopyran-2-yl, tetrahydrothiopyran-3-yl, tetrahydrothiopyran-4-yl, tetrahydrothiopyran-5-yl and tetrahydrothiopyran-6-yl), piperazinyl (which includes piperazin-1-yl, piperazin-2-yl, piperazin-3-yl, piperazin-4-yl, piperazin-5-yl and piperazin-6-yl), morpholinyl (which includes morpholin-2-yl, morpholin-3-yl, morpholin-4-yl, morpholin-5-yl and morpholin-6-yl), thiomorpholinyl (which includes thiomorpholin-2-yl, thiomorpholin-3-yl, thiomorpholin-4-yl, thiomorpholin-5-yl and thiomorpholin-6-yl), oxathianyl (which includes oxathian-2-yl, oxathian-3-yl, oxathian-5-yl and oxathian-6-yl), dithianyl (which includes dithian-2-yl, dithian-3-yl, dithian-5-yl and dithian-6-yl), thioxanyl (which includes thioxan-2-yl, thioxan-3-yl, thioxan-4-yl and thioxan-5-yl), hexahydropyridazinyl and hexahydropyrimidinyl.

The term “3 membered heterocycloalkyl” as used herein, refers to a 3 membered, saturated hydrocarbon ring wherein 1 or 2 ring members are each independently selected from N, $NR^6$, O or S, where $R^6$ is as defined herein. The heterocycloalkyl group can be attached to another group at a nitrogen or a carbon atom. Non-limiting examples of 3 membered heterocycloalkyl groups, as used herein, include oxiranyl, aziridinyl and thiiranyl.

The term "5 or 6 membered heterocyclyl" as used herein, refers to a partially saturated (but not aromatic) 5 or 6 membered monocyclic ring system wherein 1, 2 or 3 ring members are each independently selected from N, $NR^6$, O or S, where $R^6$ is as defined herein. In certain embodiments the term "5 or 6 membered heterocyclyl" as used herein, also refers to a partially saturated 5 or 6 membered monocyclic ring system wherein 1, 2 or 3 ring members are each independently selected from W, Y and Z, wherein W is $NR^6$, O, S, S═O or $S(═O)_2$, Y is $NR^6$, O, S, S═O or $S(═O)_2$ and Z is $NR^6$, O or S, and wherein the 5 or 6 membered heterocyclyl is optionally substituted with oxo. The 5 or 6 membered heterocyclyl group can be attached to another group at a nitrogen or a carbon atom. Non-limiting examples of 5 or 6 membered heterocyclyl groups, as used herein, include 1,2-dihydropyridinyl and 2,3-dihydro-1H-pyrrolyl.

The term "6 membered heterocyclyl" as used herein, refers to a partially saturated (but not aromatic) 6 membered monocyclic ring system wherein 1, 2 or 3 ring members are each independently selected from N, $NR^6$, O or S, where $R^6$ is as defined herein. In certain embodiments the term "6 membered heterocyclyl" as used herein, also refers to a partially saturated 6 membered monocyclic ring system wherein 1, 2 or 3 ring members are each independently selected from W, Y and Z, wherein W is $NR^6$, O, S, S═O or $S(═O)_2$, Y is $NR^6$, O, S, S═O or $S(═O)_2$ and Z is $NR^6$, O or S, and wherein the 6 membered heterocyclyl is optionally substituted with oxo. The 6 membered heterocyclyl group can be attached to another group at a nitrogen or a carbon atom. Non-limiting examples of membered heterocyclyl groups, as used herein, include 1,2-dihydropyridinyl.

The term "5 membered heterocyclyl" as used herein, refers to a partially saturated (but not aromatic) 5 membered monocyclic ring system wherein 1, 2 or 3 ring members are each independently selected from N, $NR^6$, O or S, where $R^6$ is as defined herein. In certain embodiments the term "5 membered heterocyclyl" as used herein, also refers to a partially saturated 5 membered monocyclic ring system wherein 1, 2 or 3 ring members are each independently selected from W, Y and Z, wherein W is $NR^6$, O, S, S═O or $S(═O)_2$, Y is $NR^6$, O, S, S═O or $S(═O)_2$ and Z is $NR^6$, O or S, and wherein the 5 membered heterocyclyl is optionally substituted with oxo. The 5 membered heterocyclyl group can be attached to another group at a nitrogen or a carbon atom. Non-limiting examples of 5 membered heterocyclyl groups, as used herein, include 2,3-dihydro-1H-pyrrolyl.

The term "9 or 10 membered bicyclic heterocyclyl" as used herein, refers to a partially saturated (but not aromatic) 9 or 10 membered bicyclic ring system wherein 1, 2, 3, 4 or 5 ring members are each independently selected from N, $NR^6$, O or S, where $R^6$ is as defined herein.

The $C_5$-$C_6$heterocycloalkenyl group can be attached to another group at a nitrogen or a carbon atom. Non-limiting examples of 9 or 10 membered bicyclic heterocyclyl groups, as used herein, include isochromanyl, 1,2-dihydroquinolinyl, 3a, 7a-dihydro-1H-pyrrolo[2,3-c]pyridinyl and 3a, 7a-dihydro-1H-indazolyl.

The term "oxo", as used herein, refers to the group ═O.

The term "spiro attached", as used herein, refers to the attachment of one ring system to another ring system via one carbon atom common to both rings.

The term "located at a beta (β) position relative to the attachment point", as used herein, refers to the location of a heteroatom or substituent relative to the point of attachment of $R^2$ to the rest of the molecule. By way of example, in the structures below the N hetero atom is located at the beta (β) position relative to the attachment point indicated by the asterix (*)

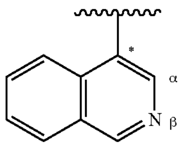

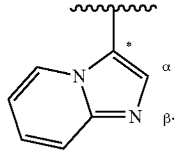

Similarly, in the structure below the carbon atom which is a ring member substituted with oxo is located at the beta (β) position relative to the attachment point indicated by the asterix (*)

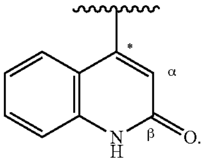 [SMILES: *c1cc(=O)[nH]c2ccccc12]

The term "isomers", as used herein, refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "optionally substituted", as used herein, means unsubstituted or substituted with the substituent(s) subsequently listed.

The term "coronaviral related disease" means a disease caused by a member of the Coronavirus family (i.e., may belong to the Coronaviridae family). Coronaviruses (CoV) are positive-stranded RNA viruses with a crown-like appearance under an electron microscope due to the presence of spike glycoproteins on the envelope. Any member of the coronavirus family (e.g., those belonging to the alphacoronavirus, betacoronavirus, deltacoronavirus, or gammacoronavirus genuses) that have a respiratory component are contemplated in the methods and uses described herein. As a non-limiting set of examples, the respiratory virus could be a betacoronavirus such as severe acute respiratory syndrome-related coronavirus (SARS-CoV), severe acute respiratory syndrome coronavirus 2 (SARS-CoV-2), Middle East respiratory syndrome related coronavirus (MERS-CoV), OC43 and HKU1, or an alphacoronavirus such as 229E and NL63. The respiratory virus could also be a coronavirus other than SARS-CoV, SARS-CoV-2, MERS-CoV, OC43, HKU1, 229E or NL63. Patients infected with SARS-CoV-2 present with a wide range of clinical severity varying from asymptomatic to a severe form of interstitial pneumonia, which may progress towards acute respiratory distress syndrome (ARDS), a severe form of acute lung injury (ALI), a form of diffuse alveolar injury, and is a serious lung condition that causes low blood oxygenation and respiratory failure and/or multi organ failure (MOF), associated symptoms and death. The clinical symptoms of COVID-19 patients include fever, cough, fatigue, loss of smell, and shortness of breath within 2-14 days after exposure. SARS-CoV-2 uses the same receptor as SARS-CoV, angiotensin-converting enzyme 2 (ACE2), and mainly spreads through the respiratory tract. Cytokine profiling of patients with severe COVID-19 demonstrates elevated levels of interleukin (IL)-2, IL-7, IL-6, IL-1, granulocyte-colony stimulating factor, interferon-y inducible protein 10, monocyte chemoattractant protein 1, macrophage inflammatory protein 1-a and tumor necrosis factor-a.

The terms "inhibit", "inhibition" or "inhibiting", as used herein, refers to the reduction or suppression of a given condition, symptom, or disorder, or disease, or a significant decrease in the baseline activity of a biological activity or process.

The term "subject" as used herein may refer to an animal. The animal may be a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human. Except when noted, the terms "patient" or "subject" are used herein interchangeably.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both.

As used herein, the term "prevent", "preventing" or "prevention" of any disease or disorder refers to the prophylactic treatment of the disease or disorder; or delaying the onset or progression of the disease or disorder.

As used herein, and unless otherwise indicated, the terms "manage," "managing," and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, manage a condition, alleviate conditions, slow or delay disease progression, or prevent a disease. In one non-limiting embodiment, the term "a therapeutically effective amount" refers to the amount of the compound of the present invention that, when administered to a subject, is effective to (1) at least partially alleviating, inhibiting, preventing managing and/or ameliorating a condition, or a disorder or a disease (i) mediated by SARS-CoV-2 main protease ($M^{pro}$), or (ii) associated with or mediated by SARS-CoV-2 main protease ($M^{pro}$) activity, or (iii) characterized by activity (normal or abnormal) of SARS-CoV-2 main protease ($M^{pro}$); or (2) reducing or inhibiting the activity of SARS-CoV-2 main protease ($M^{pro}$). In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SARS-CoV-2 main protease ($M^{pro}$).

The term "co-administer" refers to the presence of two active agents in the blood of an individual. Active agents that are co-administered can be concurrently or sequentially delivered.

As used herein, the term "a," "an," "the" and similar terms used in the context of the present invention (especially in the context of the claims) are to be construed to cover both the singular and plural unless otherwise indicated herein or clearly contradicted by the context.

Unless specified otherwise, the terms "compound of the invention", "compounds of the invention", "compound of the present invention" or "compounds of the present invention" refers to a compound or compounds of Formula (I), or subformulae thereof such as Formula (I-a), Formula (I-b), Formula (I-c), Formula (I-d), Formula (I-e), Formula (I-f, Formula (I-g), Formula (I-h) and Formula (I-i), and exemplified compounds, and salts thereof, as well as all stereoisomers (including diastereoisomers and enantiomers) thereof.

Various enumerated embodiments of the present invention are described herein. It will be recognized that features specified in each embodiment may be combined with other specified features to provide further embodiments of the present invention.

Compounds of the Invention

The invention provides a compounds of Formula (I), a stereoisomer thereof, or a pharmaceutically acceptable salt thereof,

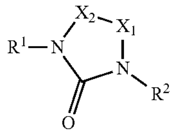

(I)

wherein:

$X_1$ is $CR^{3a}R^{3b}$, C═O or $NR^{3c}$;

$X_2$ is $CR^{4a}R^{4b}$ or C═O;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups and wherein the 5 or 6 membered heterocycloalkyl is optionally substituted with oxo;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is unsubstituted or substituted with 1, 2, 3 or 4 $R^{12}$ groups and is optionally substituted with oxo;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

viii) spiro attached $C_3$-$C_8$cycloalkyl which is unsubstituted or is substituted with 1 to 4 $R^5$groups;

ix) bicyclic $C_3$-$C_8$cycloalkyl which is unsubstituted or is substituted with 1 to 4 $R^5$ groups;

x) $C_5$-$C_6$cycloalkenyl; and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) —$(CH_2)_{0-6}CHR^{13}R^{14}$;

ii) benzyl which is unsubstituted or is substituted with 1, 2, 3 or 4 $R^{12}$ groups;

iii) a 6 membered heteroaryl wherein 1, 2 or 3 ring members are each independently selected from N, O and S, and wherein the 6 membered heteroaryl is unsubstituted or is substituted with 1, 2, 3 or 4 $R^{12}$ groups;

iv) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

v) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

vi) a 9 membered bicyclic heteroaryl with an attachment point at a carbon atom ring member and with a N heteroatom as a ring member which is located at a beta (β) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

vii) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

viii) a 5 or 6 membered heterocycloalkyl with an attachment point at a carbon atom ring member and with a $NR^6$ as a ring member which is located at a beta (1) position relative to the attachment point, wherein the 5 or 6 membered heterocycloalkyl further has 0, 1, or 2 ring members each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

ix) a 5 or 6 membered heterocyclyl with an attachment point at a carbon atom ring member and with a $NR^6$ as a ring member which is located at a beta (1) position relative to the attachment point, wherein the 5 or 6 membered heterocyclyl further has 0, 1, or 2 ring members each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

x) a 9 or 10 membered bicyclic heterocyclyl with an attachment point at a carbon atom ring member and with a $NR^6$ as a ring member which is located at a beta (3) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xi) a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, the 9 or 10 membered heterocyclyl or is unsubstituted or substituted with 1, 2, 3 or 4 $R^{12}$ groups and optionally substituted with 1 or 2 oxo;

xii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

xiii) a 5 or 6 membered heterocycloalkyl wherein 1, 2 or 3 ring members are each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

xiv) a 5 or 6 membered heterocyclyl wherein 1, 2 or 3 ring members are each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

xv) a 6 membered heterocyclyl with an attachment point at a carbon atom ring member and with a carbon atom as a ring member which is substituted with oxo and located at a beta (β) position relative to the attachment point, wherein the 6 membered heterocyclyl further has 1 or 2 ring members each independently selected from N, $NR^6$, O and S, and wherein the 6 membered heterocyclyl is unsubstituted or substituted with 1, 2, 3 or 4 $R^{12}$ groups and optionally substituted with an oxo;

xvi) a 9 or 10 membered bicyclic heterocyclyl wherein 1, 2, 3, 4 or 5 ring members are each independently selected from N, $NR^6$, O and S, and wherein the 9 or membered bicyclic heterocyclyl is substituted with 1 or 2 oxo, or the 9 or 10 membered bicyclic heterocyclyl is unsubstituted or substituted with 1, 2, 3 or $4R^{12}$ groups and optionally substituted with 1 or 2 oxo;

xvii) a 6 membered heterocyclyl wherein 1 ring member is selected from $NR^6$, and wherein the 6 membered heterocyclyl substituted with an oxo;

xviii) a 6 membered heteroaryl with an attachment point at a carbon atom ring member and with a N heteroatom as a ring member which is located at a beta (β) position relative to the attachment point, wherein the 6 membered heteroaryl has 0, 1 or 2 additional N heteroatoms as ring members, and wherein the 6 membered heteroaryl is unsubstituted or is substituted with 1, 2, 3 or 4 $R^{12}$groups;

and xix) a 10 membered bicyclic heterocyclyl with an attachment point at a carbon atom ring member and with a carbon atom as a ring member which is substituted with oxo and located at a beta (β) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo;

$R^{3a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or is substituted with —C(═O)OH, —OH, CN or $NH_2$;

$R^{3b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or is substituted with —C(═O)OH, —OH, CN or $NH_2$;

$R^{4a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or is substituted with —C(═O)OH, —OH, CN or $NH_2$;

$R^{4b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or is substituted with —C(═O)OH, —OH, CN or $NH_2$;

$R^{3c}$ is H, —C(═O)$C_2$-$C_6$alkenyl or $C_1$-$C_6$alkyl substituted with one or more $R^{15}$ groups;

each $R^5$ is independently selected from the group consisting of —CN, —OH, —$NR^7R^8$, $NR^6C(=O)C_2$-$C_6$alkenyl, —$SF_5$, $S(=O)_2C_1$-$C_6$alkyl, —C(=O)N($R^7$)$_2$, $C_1$-$C_6$haloalkyl, halo, $C_1$-$C_6$haloalkoxy, $C_1$-$C_6$alkoxy, $C_3$-$C_8$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and a $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, $C_1$-$C_6$haloalkyl, $C_1$-$C_6$haloalkoxy, —$S(=O)_2N(R^7)_2$, $S(=O)_2C_1$-$C_6$alkyl, $S(=O)_2C_1$-$C_6$haloalkyl, —$S(=O)_2C_3$-$C_6$cycloalkyl, —C(=O)$R^7$, —C(=O)N($R^7$)$_2$, $C_3$-$C_6$cycloalkyl, and $C_1$-$C_6$alkyl that is unsubstituted or is substituted with —OH, CN or —C(=O)OH;

each $R^7$ is independently selected from the group consisting of H and $C_1$-$C_6$alkyl that is unsubstituted or is substituted with OH or $C_1$-$C_6$alkoxy; $R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^{10}R^{11}$, —C(=O)N($R^7$)$_2$ and $C_1$-$C_6$alkyl substituted with —OH or —N($R^7$)$_2$; $R^{10}$ is H or $C_1$-$C_6$alkyl that is unsubstituted; $R^{11}$ is H, $C_1$-$C_6$alkyl that is unsubstituted, or —$S(=O)_2C_1$-$C_6$alkyl;

each $R^{12}$ is independently selected from the group consisting of —C(=O)N($R^7$)$_2$, —C(=O)OH, —N($R^7$)$_2$, —CN, —OH, —$S(=O)_2R^6$, —$S(=O)_2R^7$, —$S(=O)_2N(R^7)_2$

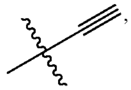 [SMILES: *C#C]

, halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is unsubstituted or is substituted with $NH_2$, CN or OH, and wherein the phenyl, heterocycloalkyl and heteroaryl are unsubstituted or are substituted with 1 or 2 substituents independently selected from the group consisting of OH;

$R^{13}$ is H, —C(=O)N($R^7$)$_2$, or a 5 or 6 membered heteroaryl wherein 1, 2 3 or 4 ring members are each independently selected from N, $NR^6$, O and S;

$R^{14}$ is selected from the group consisting of i) a 5 or 6 membered heterocyclyl wherein 1, 2, 3 or 4 ring members are each independently selected from N, $NR^6$, O and S, and wherein the 5 or 6 membered heterocyclyl is unsubstituted, or is substituted with 1, 2, 3 or 4 $R^{12}$ groups and optionally substituted with 1 or 2 oxo;

and ii) a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1, 2, 3 or 4 $R^{12}$ groups;

and each $R^{15}$ is independently selected from the group consisting of CN, $NH_2$, —OH, —C(=O)OH, —C(=O)N($R^7$)$_2$, —C(=O)C(=O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(=O)OH, $NH_2$, OH and $C_1$-$C_6$alkyl that is unsubstituted;

provided that at least one of $R^{3a}$, $R^{3b}$, $R^{4a}$ or $R^{4b}$ is not H.

Various embodiments of the compounds of the invention are described herein. It will be recognized that features specified in each embodiment may be combined with other specified features to provide further embodiments. The following enumerated embodiments are representative of the compounds of Formula (I) of the invention.

Embodiment 1. A compound of Formula (I), a stereoisomer thereof, or a pharmaceutically acceptable salt thereof,

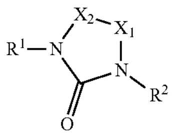

(I)

wherein:

$X_1$ is $CR^{3a}R^{3b}$, C=O or $NR^{3c}$;

$X_2$ is $CR^{4a}R^{4b}$ or C=O;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups and wherein the 5 or 6 membered heterocycloalkyl is optionally substituted with oxo;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S=O or $S(=O)_2$, Y is $NR^6$, O, S, S=O or $S(=O)_2$ and Z is $NR^6$, O or S, and wherein the 5 or 6 membered heterocyclyl is unsubstituted or substituted with 1, 2, 3 or 4 $R^{12}$ groups and is optionally substituted with oxo;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

viii) spiro attached $C_3$-$C_8$cycloalkyl which is unsubstituted or is substituted with 1 to 4 $R^5$ groups;

ix) bicyclic $C_3$-$C_8$cycloalkyl which is unsubstituted or is substituted with 1 to 4 $R^5$ groups;

x) $C_5$-$C_6$cycloalkenyl;

and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) —$(CH_2)_{0-6}CHR^{13}R^{14}$;

ii) benzyl which is unsubstituted or is substituted with 1, 2, 3 or 4 $R^{12}$ groups;

iii) a 6 membered heteroaryl wherein 1, 2 or 3 ring members are each independently selected from N, O and S, and wherein the 6 membered heteroaryl is unsubstituted or is substituted with 1, 2, 3 or 4 $R^{12}$ groups;

iv) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

v) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

vi) a 9 membered bicyclic heteroaryl with an attachment point at a carbon atom ring member and with a N heteroatom as a ring member which is located at a beta (β) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

vii) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

viii) a 5 or 6 membered heterocycloalkyl with an attachment point at a carbon atom ring member and with a $NR^6$ as a ring member which is located at a beta (3) position relative to the attachment point, wherein the 5 or 6 membered heterocycloalkyl further has 0, 1, or 2 ring members each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

ix) a 5 or 6 membered heterocyclyl with an attachment point at a carbon atom ring member and with a $NR^6$ as a ring member which is located at a beta (β) position relative to the attachment point, wherein the 5 or 6 membered heterocyclyl further has 0, 1, or 2 ring members each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

x) a 9 or 10 membered bicyclic heterocyclyl with an attachment point at a carbon atom ring member and with a $NR^6$ as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xi) a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

xiii) a 5 or 6 membered heterocycloalkyl wherein 1, 2 or 3 ring members are each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

xiv) a 5 or 6 membered heterocyclyl wherein 1, 2 or 3 ring members are each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

xv) a 6 membered heterocyclyl with an attachment point at a carbon atom ring member and with a carbon atom as a ring member which is substituted with oxo and located at a beta (β) position relative to the attachment point, wherein the 6 membered heterocyclyl further has 1 or 2 ring members each independently selected from N, $NR^6$, O and S, and wherein the 6 membered heterocyclyl is unsubstituted or substituted with 1, 2, 3 or 4 $R^{12}$ groups and optionally substituted with an oxo;

xvi) a 9 or 10 membered bicyclic heterocyclyl wherein 1, 2, 3, 4 or 5 ring members are each independently selected from N, $NR^6$, O and S, and wherein the 9 or membered bicyclic heterocyclyl is substituted with 1 or 2 oxo, or the 9 or 10 membered bicyclic heterocyclyl is unsubstituted or substituted with 1, 2, 3 or $4R^{12}$ groups and optionally substituted with 1 or 2 oxo;

xvii) a 6 membered heterocyclyl wherein 1 ring member is selected from $NR^6$, and wherein the 6 membered heterocyclyl substituted with an oxo;

xviii) a 6 membered heteroaryl with an attachment point at a carbon atom ring member and with a N heteroatom as a ring member which is located at a beta (β) position relative to the attachment point, wherein the 6 membered heteroaryl has 0, 1 or 2 additional N heteroatoms as ring members, and wherein the 6 membered heteroaryl is unsubstituted or is substituted with 1, 2, 3 or 4 $R^{12}$ groups;

and xix) a 10 membered bicyclic heterocyclyl with an attachment point at a carbon atom ring member and with a carbon atom as a ring member which is substituted with oxo and located at a beta (β) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo;

$R^{3a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{3b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{4a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{4b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{3c}$ is H, —C(═O)$C_2$-$C_6$alkenyl or $C_1$-$C_6$alkyl substituted with one or more $R^{15}$ groups;

each $R^5$ is independently selected from the group consisting of —CN, —OH, —$NR^7R^8$, $NR^6$C(═O)$C_2$-$C_6$alkenyl, —$SF_5$, S(═O)$_2C_1$-$C_6$alkyl, —C(═O)N$(R^7)_2$, $C_1$-$C_6$haloalkyl, halo, $C_1$-$C_6$haloalkoxy, $C_1$-$C_6$alkoxy, $C_3$-$C_8$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and a $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, $C_1$-$C_6$haloalkyl, $C_1$-$C_6$haloalkoxy, —S(═O)$_2$N$(R^7)_2$, S(═O)$_2C_1$-$C_6$alkyl, S(═O)$_2C_1$-$C_6$haloalkyl, —S(═O)$_2C_3$-$C_8$cycloalkyl, —C(═O)$R^7$, —C(═O)N$(R^7)_2$, $C_3$-$C_6$cycloalkyl, and $C_1$-$C_6$alkyl that is unsubstituted or is substituted with —OH, CN or —C(═O)OH;

each $R^7$ is independently selected from the group consisting of H and $C_1$-$C_6$alkyl that is unsubstituted or is substituted with OH or $C_1$-$C_6$alkoxy; $R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^{10}R^{11}$, —C(═O)N$(R^7)_2$ and $C_1$-$C_6$alkyl substituted with —OH or —N$(R^7)_2$;

$R^{10}$ is H or $C_1$-$C_6$alkyl that is unsubstituted;

$R^{11}$ is H, $C_1$-$C_6$alkyl that is unsubstituted, or —S(═O)$_2$ $C_1$-$C_6$alkyl;

each $R^{12}$ is independently selected from the group consisting of —C(═O)N$(R^7)_2$, —C(═O)OH, —N$(R^7)_2$, —CN, —OH, —S(═O)$_2R^7$, —S(═O)$_2$N$(R^7)_2$,

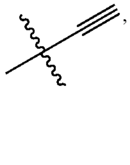 [SMILES: *C#C], halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is unsubstituted or is substituted with $NH_2$, CN or OH, and wherein the phenyl, heterocycloalkyl and heteroaryl are unsubstituted or are substituted with 1 or 2 substituents independently selected from the group consisting of OH;

$R^{13}$ is H, —C(═O)N($R^7$)$_2$, or a 5 or 6 membered heteroaryl wherein 1, 2 3 or 4 ring members are each independently selected from N, $NR^6$, O and S;

$R^{14}$ is selected from the group consisting of i) a 5 or 6 membered heterocyclyl wherein 1, 2, 3 or 4 ring members are each independently selected from N, $NR^6$, O and S, and wherein the 5 or 6 membered heterocyclyl is unsubstituted, or is substituted with 1, 2, 3 or 4 $R^{12}$ groups and optionally substituted with 1 or 2 oxo;

and ii) a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1, 2, 3 or 4 $R^{12}$ groups; and each $R^{15}$ is independently selected from the group consisting of CN, $NH_2$, —OH, —C(═O)OH, —C(═O)N($R^7$)$_2$, —C(═O)C(═O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(═O)OH, $NH_2$, OH and $C_1$-$C_6$alkyl that is unsubstituted;

provided that at least one of $R^{3a}$, $R^{3b}$, $R^{4a}$ or $R^{4b}$ is not H.

Embodiment 2. The compound of Embodiment 1, a stereoisomer thereof, or a pharmaceutically acceptable salt thereof,

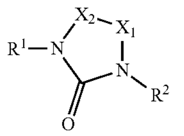

(I)

wherein:

$X_1$ is $CR^{3a}R^{3b}$, C═O or $NR^{3c}$;

$X_2$ is $CR^{4a}R^{4b}$ or C═O;

$R^1$ is selected from the group consisting of:

i) phenyl which is unsubstituted or is substituted with 1 to 4 $R^5$ groups;

ii) spiro attached $C_3$-$C_8$cycloalkyl which is unsubstituted or is substituted with 1 to 4 $R^5$ groups;

iii) bicyclic $C_3$-$C_8$cycloalkyl which is unsubstituted or is substituted with 1 to 4 $R^5$ groups;

iv) $C_3$-$C_8$cycloalkyl which is unsubstituted or is substituted with 1 to 4 $R^5$ groups;

v) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

vi) $C_1$-$C_6$alkyl that is unsubstituted;

vii) $C_5$-$C_6$cycloalkenyl;

viii) 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is optionally substituted with oxo;

ix) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

x) a 5 or 6 membered heterocycloalkyl wherein 1, 2, 3 or 4 ring members are each independently selected from N, $NR^6$, O and S, wherein the 5 or 6 membered heterocycloalkyl is unsubstituted or is substituted with 1 to 4 $R^5$ groups and wherein the 5 or 6 membered heterocycloalkyl is optionally substituted with oxo;

and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) —($CH_2$)$_{0-6}$$CHR^{13}R^{14}$;

ii) benzyl which is unsubstituted or is substituted with 1, 2, 3 or 4 $R^{12}$ groups;

iii) a 6 membered heteroaryl wherein 1, 2 or 3 ring members are each independently selected from N, O and S, and wherein the 6 membered heteroaryl is unsubstituted or is substituted with 1, 2, 3 or 4 $R^{12}$ groups;

iv) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

v) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

vi) a 9 membered bicyclic heteroaryl with an attachment point at a carbon atom ring member and with a N heteroatom as a ring member which is located at a beta (3) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

vii) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

viii) a 5 or 6 membered heterocycloalkyl with an attachment point at a carbon atom ring member and with a $NR^6$ as a ring member which is located at a beta (R) position relative to the attachment point, wherein the 5 or 6 membered heterocycloalkyl further has 0, 1, or 2 ring members each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

ix) a 5 or 6 membered heterocyclyl with an attachment point at a carbon atom ring member and with a $NR^6$ as a ring member which is located at a beta (R) position relative to the attachment point, wherein the 5 or 6 membered heterocyclyl further has 0, 1, or 2 ring members each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

x) a 9 or 10 membered bicyclic heterocyclyl with an attachment point at a carbon atom ring member and with a $NR^6$ as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xi) a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

xiii) a 5 or 6 membered heterocycloalkyl wherein 1, 2 or 3 ring members are each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

xiv) a 5 or 6 membered heterocyclyl wherein 1, 2 or 3 ring members are each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

xv) a 6 membered heterocyclyl with an attachment point at a carbon atom ring member and with a carbon atom as a ring member which is substituted with oxo and located at a beta (β) position relative to the attachment point, wherein the 6 membered heterocyclyl further has 1 or 2 ring members each independently selected from N, $NR^6$, O and S, and wherein the 6 membered heterocyclyl is unsubstituted or substituted with 1, 2, 3 or 4 $R^{12}$ groups and optionally substituted with an oxo;

xvi) a 9 or 10 membered bicyclic heterocyclyl wherein 1, 2, 3, 4 or 5 ring members are each independently selected from N, $NR^6$, O and S, and wherein the 9 or membered bicyclic heterocyclyl is substituted with 1 or 2 oxo, or the 9 or 10 membered bicyclic heterocyclyl is unsubstituted or substituted with 1, 2, 3 or $4R^{12}$ groups and optionally substituted with 1 or 2 oxo;

xvii) a 6 membered heterocyclyl wherein 1 ring member is selected from $NR^6$, and wherein the 6 membered heterocyclyl substituted with an oxo;

xviii) a 6 membered heteroaryl with an attachment point at a carbon atom ring member and with a N heteroatom as a ring member which is located at a beta (β) position relative to the attachment point, wherein the 6 membered heteroaryl has 0, 1 or 2 additional N heteroatoms as ring members, and wherein the 6 membered heteroaryl is unsubstituted or is substituted with 1, 2, 3 or 4 $R^{12}$ groups;

and xix) a 10 membered bicyclic heterocyclyl with an attachment point at a carbon atom ring member and with a carbon atom as a ring member which is substituted with oxo and located at a beta (3) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo;

$R^{3a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{3b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{4a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{4b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{3c}$ is H, —C(=O)$C_2$-$C_6$alkenyl or $C_1$-$C_6$alkyl substituted with one or more $R^{15}$ groups;

each $R^5$ is independently selected from the group consisting of —OH, —$NR^7R^8$, $NR^6C$(=O)$C_2$-$C_6$alkenyl, —$SF_5$, —C(=O)N($R^7$)$_2$, $C_1$-$C_6$haloalkyl, halo, $C_1$-$C_6$haloalkoxy, $C_1$-$C_6$alkoxy, $C_3$-$C_8$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, —S(=O)$_2$N($R^7$)$_2$, —C(=O)N($R^7$)$_2$ and $C_1$-$C_6$alkyl that is unsubstituted or is substituted with —OH, CN or —C(=O)OH;

each $R^7$ is independently selected from the group consisting of H and $C_1$-$C_6$alkyl that is unsubstituted;

$R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^1R$, —C(=O)N($R^7$)$_2$ and $C_1$-$C_6$alkyl substituted with —OH or —N($R^7$)$_2$;

$R^{10}$ is H or $C_1$-$C_6$alkyl that is unsubstituted;

$R^{11}$ is H, $C_1$-$C_6$alkyl that is unsubstituted, or —S(=O)$_2$ $C_1$-$C_6$alkyl;

each $R^{12}$ is independently selected from the group consisting of —C(=O)N($R^7$)$_2$, —C(=O)OH, —N($R^7$)$_2$, —CN, —OH, —S(=O)$_2R^6$, —S(=O)$_2$N($R^7$)$_2$,

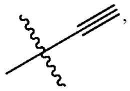 [SMILES: *C#C], halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is unsubstituted or is substituted with $NH_2$, CN or OH, and wherein the phenyl, heterocycloalkyl and heteroaryl are unsubstituted or are substituted with 1 or 2 substituents independently selected from the group consisting of OH;

$R^{13}$ is H, —C(=O)N($R^7$)$_2$, or a 5 or 6 membered heteroaryl wherein 1, 2 3 or 4 ring members are each independently selected from N, $NR^6$, O and S;

$R^{14}$ is selected from the group consisting of i) a 5 or 6 membered heterocyclyl wherein 1, 2, 3 or 4 ring members are each independently selected from N, $NR^6$, O and S, and wherein the 5 or 6 membered heterocyclyl is unsubstituted, or is substituted with 1, 2, 3 or 4 $R^{12}$ groups and optionally substituted with 1 or 2 oxo;

and ii) a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1, 2, 3 or 4 $R^{12}$ groups; and each $R^{15}$ is independently selected from the group consisting of CN, $NH_2$, —OH, —C(=O)OH, —C(=O)N($R^7$)$_2$, —C(=O)C(=O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(=O)OH, $NH_2$, OH and $C_1$-$C_6$alkyl that is unsubstituted;

provided that at least one of $R^{3a}$, $R^{3b}$, $R^{4a}$ or $R^{4b}$ is not H.

Embodiment 3. The compound of Embodiment 1, a stereoisomer thereof, or a pharmaceutically acceptable salt thereof, wherein:

$X_1$ is $CR^{3a}R^{3b}$, C=O or $NR^{3c}$;

$X_2$ is $CR^{4a}R^{4b}$ or C=O;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups and wherein the 5 or 6 membered heterocycloalkyl is optionally substituted with oxo;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is unsubstituted or substituted with 1, 2, 3 or 4 $R^{12}$ groups and is optionally substituted with oxo;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

viii) spiro attached $C_3$-$C_8$cycloalkyl which is unsubstituted or is substituted with 1 to 4 $R^5$ groups;

ix) bicyclic $C_3$-$C_8$cycloalkyl which is unsubstituted or is substituted with 1 to 4 $R^5$ groups;

x) $C_5$-$C_6$cycloalkenyl;

and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) —$(CH_2)_{0-6}CHR^{13}R^{14}$;

ii) benzyl which is unsubstituted or is substituted with 1, 2, 3 or 4 $R^{12}$ groups;

iii) a 6 membered heteroaryl wherein 1, 2 or 3 ring members are each independently selected from N, O and S, and wherein the 6 membered heteroaryl is unsubstituted or is substituted with 1, 2, 3 or 4 $R^{12}$ groups;

iv) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

v) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

vi) a 9 membered bicyclic heteroaryl with an attachment point at a carbon atom ring member and with a N heteroatom as a ring member which is located at a beta (3) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

vii) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

viii) a 5 or 6 membered heterocycloalkyl with an attachment point at a carbon atom ring member and with a $NR^6$ as a ring member which is located at a beta (R) position relative to the attachment point, wherein the 5 or 6 membered heterocycloalkyl further has 0, 1, or 2 ring members each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

ix) a 5 or 6 membered heterocyclyl with an attachment point at a carbon atom ring member and with a $NR^6$ as a ring member which is located at a beta (1) position relative to the attachment point, wherein the 5 or 6 membered heterocyclyl further has 0, 1, or 2 ring members each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

x) a 9 or 10 membered bicyclic heterocyclyl with an attachment point at a carbon atom ring member and with a $NR^6$ as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xi) a 9 or 10 membered bicyclic heterocyclyl with an attachment point at a carbon atom ring member and with a O heteroatom as a ring member which is located at a beta (3) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

xii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

xiii) a 5 or 6 membered heterocycloalkyl wherein 1, 2 or 3 ring members are each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo;

xiv) a 5 or 6 membered heterocyclyl wherein 1, 2 or 3 ring members are each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo;

xv) a 6 membered heterocyclyl with an attachment point at a carbon atom ring member and with a carbon atom as a ring member which is substituted with oxo and located at a beta (β) position relative to the attachment point, wherein the 6 membered heterocyclyl further has 1 or 2 ring members each independently selected from N, $NR^6$, O and S, and wherein the 6 membered heterocyclyl is unsubstituted or substituted with 1, 2, 3 or 4 $R^{12}$ groups and optionally substituted with an oxo;

xvi) a 9 or 10 membered bicyclic heterocyclyl wherein 1, 2, 3, 4 or 5 ring members are each independently selected from N, $NR^6$, O and S, and wherein the 9 or membered bicyclic heterocyclyl is substituted with 1 or 2 oxo, or the 9 or 10 membered bicyclic heterocyclyl is unsubstituted or substituted with 1, 2, 3 or $4R^{12}$ groups and optionally substituted with 1 or 2 oxo;

xvii) a 6 membered heterocyclyl wherein 1 ring member is selected from $NR^6$, and wherein the 6 membered heterocyclyl substituted with an oxo;

xviii) a 6 membered heteroaryl with an attachment point at a carbon atom ring member and with a N heteroatom as a ring member which is located at a beta (β) position relative to the attachment point, wherein the 6 membered heteroaryl has 0, 1 or 2 additional N heteroatoms as ring members, and wherein the 6 membered heteroaryl is unsubstituted or is substituted with 1, 2, 3 or 4 $R^{12}$groups;

and xix) a 10 membered bicyclic heterocyclyl with an attachment point at a carbon atom ring member and with a carbon atom as a ring member which is substituted with oxo and located at a beta (β) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo;

$R^{3a}$ is —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{3b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{4a}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{4b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$;

$R^{3c}$ is H, —C(═O)$C_2$-$C_6$alkenyl or $C_1$-$C_6$alkyl substituted with one or more $R^{15}$ groups;

each $R^5$ is independently selected from the group consisting of —CN, —OH, —$NR^7R^8$, $NR^6C$(═O)$C_2$-$C_6$alkenyl, —$SF_5$, S(═O)$_2C_1$-$C_6$alkyl, —C(═O)N$(R^7)_2$, $C_1$-$C_6$haloalkyl, halo, $C_1$-$C_6$haloalkoxy, $C_1$-$C_6$alkoxy, $C_3$-$C_8$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and a $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, $C_1$-$C_6$haloalkyl, $C_1$-$C_6$haloalkoxy, —S(═O)$_2$N$(R^7)_2$, S(═O)$_2C_1$-$C_6$alkyl, S(═O)$_2C_1$-$C_6$haloalkyl, —S(═O)$_2C_3$-$C_6$cycloalkyl, —C(═O)$R^7$, —C(═O)N$(R^7)_2$, $C_3$-$C_6$cycloalkyl, and $C_1$-$C_6$alkyl that is unsubstituted or is substituted with —OH, CN or —C(═O)OH;

each $R^7$ is independently selected from the group consisting of H, and $C_1$-$C_6$alkyl that is unsubstituted or is substituted with OH or $C_1$-$C_6$alkoxy;

$R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^1R$, —C(═O)N$(R^7)_2$ and $C_1$-$C_6$alkyl substituted with —OH or —N$(R^7)_2$;

$R^{10}$ is H or $C_1$-$C_6$alkyl that is unsubstituted;

$R^{11}$ is H, $C_1$-$C_6$alkyl or —S(═O)$_2C_1$-$C_6$alkyl;

each $R^{12}$ is independently selected from the group consisting of —C(═O)N($R^7$)$_2$, —C(═O)OH, —N($R^7$)$_2$, —CN, —OH, —S(═O)$_2R^7$, —S(═O)$_2$N($R^7$)$_2$,

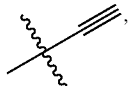 [SMILES: *C#C]

halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is unsubstituted or is substituted with $NH_2$, CN or OH, and wherein the phenyl, heterocycloalkyl and heteroaryl are unsubstituted or are substituted with 1 or 2 substituents independently selected from the group consisting of OH;

$R^{13}$ is H, —C(═O)N($R^7$)$_2$, or a 5 or 6 membered heteroaryl wherein 1, 2 3 or 4 ring members are each independently selected from N, $NR^6$, O and S; $R^{14}$ is selected from the group consisting of i) a 5 or 6 membered heterocyclyl wherein 1, 2, 3 or 4 ring members are each independently selected from N, $NR^6$, O and S, and wherein the 5 or 6 membered heterocyclyl is unsubstituted, or is substituted with 1, 2, 3 or 4 $R^{12}$ groups and optionally substituted with 1 or 2 oxo;

and ii) a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1, 2, 3 or 4 $R^{12}$ groups; and each $R^{15}$ is independently selected from the group consisting of CN, $NH_2$, —OH, —C(═O)OH, —C(═O)N($R^7$)$_2$, —C(═O)C(═O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(═O)OH, $NH_2$, OH and $C_1$-$C_6$alkyl that is unsubstituted.

Embodiment 4. The compound of Embodiment 1, or a pharmaceutically acceptable salt or stereoisomer thereof, wherein:

$X_1$ is $CR^{3a}R^{3b}$, C═O or $NR^{3c}$;

$X_2$ is $CR^{4a}R^{4b}$ or C═O;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups and wherein the 5 or 6 membered heterocycloalkyl is optionally substituted with oxo;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is unsubstituted or substituted with 1, 2, 3 or 4 $R^{12}$ groups and is optionally substituted with oxo;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

viii) spiro attached $C_3$-$C_8$cycloalkyl which is unsubstituted or is substituted with 1 to 4 $R^5$ groups;

ix) bicyclic $C_3$-$C_8$cycloalkyl which is unsubstituted or is substituted with 1 to 4 $R^5$ groups;

x) $C_5$-$C_6$cycloalkenyl;

and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

ii) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

iii) a 9 membered bicyclic heteroaryl with an attachment point at a carbon atom ring member and with a N heteroatom as a ring member which is located at a beta (3) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

iv) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

v) a 9 or 10 membered bicyclic heterocyclyl with an attachment point at a carbon atom ring member and with a $NR^6$ as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

vi) a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

vii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

viii) a 9 or 10 membered bicyclic heterocyclyl wherein 1, 2, 3, 4 or 5 ring members are each independently selected from N, $NR^6$, O and S, and wherein the 9 or membered bicyclic heterocyclyl is substituted with 1 or 2 oxo, or the 9 or 10 membered bicyclic heterocyclyl is unsubstituted or substituted with 1, 2, 3 or $4R^{12}$ groups and optionally substituted with 1 or 2 oxo;

and ix) a 10 membered bicyclic heterocyclyl with an attachment point at a carbon atom ring member and with a carbon atom as a ring member which is substituted with oxo and located at a beta (3) position relative to the attachment point, wherein the 10 membered heterocyclyl further has 1, 2, 3, or 4 ring members each independently selected from N, $NR^6$, O and S, and wherein the 10 membered heterocyclyl is unsubstituted or is substituted with 1, 2, 3 or 4 $R^{12}$ groups and optionally substituted with an additional oxo;

$R^{3a}$ is —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{3b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{4a}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{4b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$;

$R^{3c}$ is H, —C(=O)$C_2$-$C_6$alkenyl or $C_1$-$C_6$alkyl substituted with one or more $R^{15}$ groups;

each $R^5$ is independently selected from the group consisting of —CN, —OH, —$NR^7R^8$, $NR^6$C(=O)$C_2$-$C_6$alkenyl, —$SF_5$, S(=O)$_2C_1$-$C_6$alkyl, —C(=O)N$(R^7)_2$, $C_1$-$C_6$haloalkyl, halo, $C_1$-$C_6$haloalkoxy, $C_1$-$C_6$alkoxy, $C_3$-$C_6$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and a $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, $C_1$-$C_6$haloalkyl, $C_1$-$C_6$haloalkoxy, —S(=O)$_2$N$(R^7)_2$, S(=O)$_2C_1$-$C_6$alkyl, S(=O)$_2C_1$-$C_6$haloalkyl, —S(=O)$_2C_3$-$C_6$cycloalkyl, —C(=O)$R^7$, —C(=O)N$(R^7)_2$, $C_3$-$C_6$cycloalkyl, and $C_1$-$C_6$alkyl that is unsubstituted or is substituted with —OH, CN or —C(=O)OH;

each $R^7$ is independently selected from the group consisting of H, and $C_1$-$C_6$alkyl that is unsubstituted or is substituted with OH or $C_1$-$C_6$alkoxy;

$R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^1R$, —C(=O)N$(R^7)_2$ and $C_1$-$C_6$alkyl substituted with —OH or —N$(R^7)_2$;

$R^{10}$ is H or $C_1$-$C_6$alkyl that is unsubstituted;

$R^{11}$ is H, $C_1$-$C_6$alkyl that is unsubstituted or —S(═O)$_2$ $C_1$-$C_6$alkyl;

each $R^{12}$ is independently selected from the group consisting of —C(═O)N($R^7$)$_2$, —C(═O)OH, —N($R^7$)$_2$, —CN, —OH, —S(═O)$_2R^7$, —S(═O)$_2$N($R^7$)$_2$,

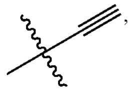 [SMILES: *C#C], halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is unsubstituted or is substituted with $NH_2$, CN or OH, and wherein the phenyl, heterocycloalkyl and heteroaryl are unsubstituted or are substituted with 1 or 2 substituents independently selected from the group consisting of OH; and each $R^{15}$ is independently selected from the group consisting of CN, $NH_2$, —OH, —C(═O)OH, —C(═O)N($R^7$)$_2$, —C(═O)C(═O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(═O)OH, $NH_2$, OH and $C_1$-$C_6$alkyl that is unsubstituted.

Embodiment 5. The compound of Embodiment 4, a stereoisomer thereof, or a pharmaceutically acceptable salt thereof, wherein:

$X_1$ is $CR^{3a}R^{3b}$;

$X_2$ is $CR^{4a}R^{4b}$;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 5 or 6 membered heterocycloalkyl is unsubstituted or is substituted with 1 to 4 $R^5$ groups;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is unsubstituted or substituted with 1 or 2 $R^{12}$ groups and is optionally substituted with oxo;

vii) a 9 or 10 membered bicyclic heterocyclyl wherein 1 or 2 ring members is each independently selected from N and $NR^6$, wherein the 9 or 10 membered bicyclic heterocyclyl is unsubstituted or is substituted with 1 to 2 $R^5$ groups;

and viii) bicyclic $C_3$-$C_8$cycloalkyl which is unsubstituted or is substituted with 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

and ii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or is substituted with 1, 2, 3 or 4 $R^{12}$ groups;

$R^{3a}$ is —CN;

$R^{3b}$ is H or $C_1$-$C_6$alkyl that is unsubstituted;

$R^{4a}$ is H or $C_1$-$C_6$alkyl that is unsubstituted;

$R^{4b}$ is H or $C_1$-$C_6$alkyl that is unsubstituted;

each $R^5$ is independently selected from the group consisting of CN, —OH, S(═O)$_2$$C_1$-$C_6$alkyl, $C_1$-$C_6$haloalkyl, halo, $C_1$-$C_6$haloalkoxy, $C_1$-$C_6$alkoxy, $C_3$-$C_8$cycloalkyl that is unsubstituted, and $C_1$-$C_6$alkyl that is unsubstituted or is substituted with OH;

each $R^6$ is independently selected from the group consisting of H, $C_1$-$C_6$haloalkyl, $C_1$-$C_6$haloalkoxy, S(═O)$_2$ $C_1$-$C_6$alkyl, S(═O)$_2$$C_1$-$C_6$haloalkyl, —S(═O)$_2$$C_3$-$C_6$cycloalkyl, —C(═O)$R^7$, $C_3$-$C_6$cycloalkyl, and $C_1$-$C_6$alkyl that is unsubstituted or is substituted with —OH;

each $R^7$ is independently selected from the group consisting of H, and $C_1$-$C_6$alkyl that is unsubstituted or is substituted with OH or $C_1$-$C_6$alkoxy; and each $R^{12}$ is independently selected from the group consisting of —C(═O)N($R^7$)$_2$, —C(═O)OH, —CN, —S(═O)$_2R^7$ and $C_1$-$C_6$alkyl substituted with OH.

Embodiment 6. The compound of any one of Embodiments 1 to 5, a stereoisomer thereof, or a pharmaceutically acceptable salt thereof, wherein $X_1$ is $CR^{3a}R^{3b}$, C═O or $NR^{3c}$.

Embodiment 7. The compound of any one of Embodiments 1 to 5, a stereoisomer thereof, or a pharmaceutically acceptable salt thereof, wherein $X_1$ is $CR^{3a}R^{3b}$.

Embodiment 8. The compound of any one of Embodiments 1 to 5, a stereoisomer thereof, or a pharmaceutically acceptable salt thereof, wherein $X_1$ is C═O.

Embodiment 9. The compound of any one of Embodiments 1 to 5, a stereoisomer thereof, or a pharmaceutically acceptable salt thereof, wherein $X_1$ is $NR^{3c}$.

Embodiment 10. The compound of any one of Embodiment 1 to 9, a stereoisomer thereof, or a pharmaceutically acceptable salt thereof, wherein $X_2$ is $CR^{4a}R^{4b}$ or C═O.

Embodiment 11. The compound of any one of Embodiment 1 to 10, a stereoisomer thereof, or a pharmaceutically acceptable salt thereof, wherein $X_2$ is $CR^{4a}R^{4b}$.

Embodiment 12. The compound of any one of Embodiment 1 to 10, a stereoisomer thereof, or a pharmaceutically acceptable salt thereof, wherein $X_2$ is C═O.

Embodiment 13. The compound of Formula (I) of any one of Embodiments 1 to 5, a stereoisomer thereof, or a pharmaceutically acceptable salt thereof, selected from a compound having the structure of the following sub-formulae (Formula (I-a), Formula (I-b), Formula (I-c), Formula (I-d), Formula (I-e), Formula (I-f) and Formula (I-g):

(I-a)

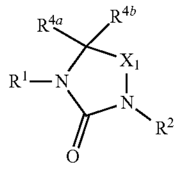

(I-b)

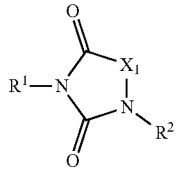

(I-c)

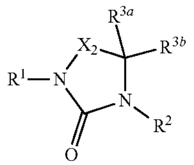

(I-d)

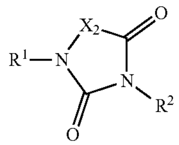

(I-e)

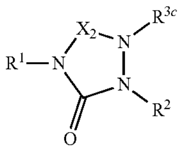

(I-f)

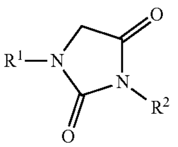

and (I-g)

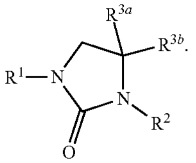

Embodiment 14. The compound of any one of Embodiments 1 to 5, a stereoisomer thereof, or a pharmaceutically acceptable salt thereof, selected from a compound having the structure of Formula (I-g), (I-g)

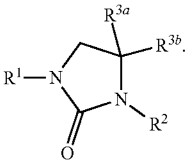

Embodiment 15. The compound of any one of Embodiments 1 to 5, a stereoisomer thereof, or a pharmaceutically acceptable salt thereof, selected from a compound having the structure of Formula (I-h) or Formula (I-i), or a pharmaceutically acceptable salt or stereoisomer thereof, (I-h)

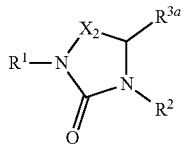

(I-i)

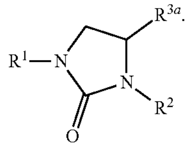

Embodiment 16. The compound of any one of Embodiments 1 to 5, a stereoisomer thereof, or a pharmaceutically acceptable salt thereof, selected from a compound having the structure of Formula (I-i), or a pharmaceutically acceptable salt or stereoisomer thereof, (I-i)

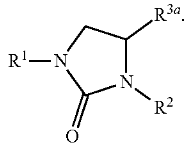

Embodiment 17. The compound of any one of Embodiments 1 to 16, a stereoisomer thereof, or a pharmaceutically acceptable salt thereof, wherein $R^2$ is $—(CH_2)_{0-6}CHR^{13}R^{14}$.

Embodiment 18. The compound of any one of Embodiments 1 to 16, a stereoisomer thereof, or a pharmaceutically acceptable salt thereof, wherein $R^2$ is $—CHR^{13}R^{14}$.

Embodiment 19. The compound of any one of Embodiments 1 to 16, a stereoisomer thereof, or a pharmaceutically acceptable salt thereof, wherein $R^2$ is benzyl which is unsubstituted or is substituted with 1, 2, 3 or 4 $R^{12}$ groups.

Embodiment 20. The compound of any one of Embodiments 1 to 16, a stereoisomer thereof, or a pharmaceutically acceptable salt thereof, wherein $R^2$ is benzyl which is unsubstituted or is substituted with 1 $R^{12}$ groups.

Embodiment 21. The compound of any one of Embodiments 1 to 16, a stereoisomer thereof, or a pharmaceutically acceptable salt thereof, wherein $R^2$ is a 6 membered heteroaryl wherein 1, 2 or 3 ring members are each independently selected from N, O and S, and wherein the 6 membered heteroaryl is unsubstituted or is substituted with 1, 2, 3 or 4 $R^{12}$ groups.

Embodiment 22. The compound of any one of Embodiments 1 to 16, a stereoisomer thereof, or a pharmaceutically acceptable salt thereof, wherein $R^2$ is a 6 membered heteroaryl wherein 1, ring member is selected from N, and wherein the 6 membered heteroaryl is unsubstituted or is substituted with 1 or 2 $R^{12}$ groups.

Embodiment 23. The compound of any one of Embodiments 1 to 16, a stereoisomer thereof, or a pharmaceutically acceptable salt thereof, wherein $R^2$ is pyridyl which is unsubstituted or is substituted with 1, 2, 3 or 4 $R^{12}$ groups.

Embodiment 24. The compound of any one of Embodiments 1 to 16, a stereoisomer thereof, or a pharmaceutically acceptable salt thereof, wherein $R^2$ is pyrid-3-yl which is unsubstituted or is substituted with 1 or 2 $R^{12}$ groups.

Embodiment 25. The compound of any one of Embodiments 1 to 16, a stereoisomer thereof, or a pharmaceutically acceptable salt thereof, wherein $R^2$ is a 9 or 10 membered bicyclic heteroaryl wherein 1, 2, 3, 4 or 5 ring members are each independently selected from N, $NR^6$, O and S, and wherein the 9 or 10 membered bicyclic heteroaryl is unsubstituted or is substituted with 1, 2, 3 or 4 $R^{12}$ groups.

Embodiment 26. The compound of any one of Embodiments 1 to 16, a stereoisomer thereof, or a pharmaceutically acceptable salt thereof, wherein $R^2$ is a 9 or 10 membered bicyclic heteroaryl wherein 1, 2 or 3 ring members are each independently selected from N, $NR^6$ and O and S, and wherein the 9 or 10 membered bicyclic heteroaryl is unsubstituted or is substituted with 1 or 2 $R^{12}$ groups.

Embodiment 27. The compound of any one of Embodiments 1 to 16, a stereoisomer thereof, or a pharmaceutically acceptable salt thereof, wherein $R^2$ is isoquinolinyl, phthalazinyl, cinnolinyl, imidazo[1,2-c]pyrimidinyl, pyrazolo[1,5-a]pyrazinyl, benzo[c]isoxazolyl, imidazo[1,2-a]pyrazinyl, imidazo[1,2-a]pyridinyl or naphthyridinyl, each of which is unsubstituted or substituted with 1, 2, 3 or 4 $R^{12}$ groups.

Embodiment 28. The compound of any one of Embodiments 1 to 16, a stereoisomer thereof, or a pharmaceutically acceptable salt thereof, wherein $R^2$ is isoquinolin-4-yl, phthalazin-4-yl, cinnolin-4-yl, imidazo[1,2-c]pyrimidin-8-yl, pyrazolo[1,5-a]pyrazin-7-yl, benzo[c]isoxazol-3-yl, imidazo[1,2-a]pyrazine-5-yl, imidazo[1,2-a]pyridine-3-yl or naphthyridin-4-yl, each of which is unsubstituted or substituted with 1, 2, 3 or 4 $R^{12}$ groups.

Embodiment 29. The compound of any one of Embodiments 1 to 16, a stereoisomer thereof, or a pharmaceutically acceptable salt thereof, wherein $R^2$ is

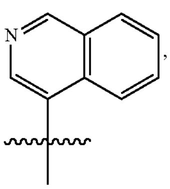
,
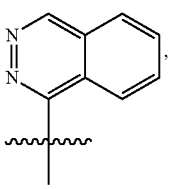
,
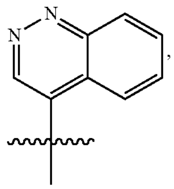
,

-continued

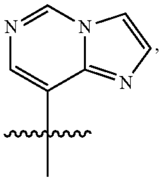
,
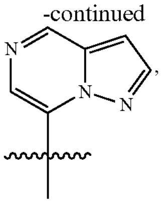
,
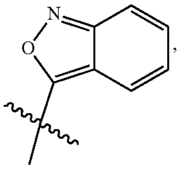
,
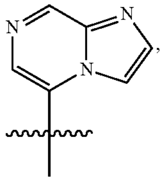
,
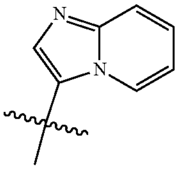
or
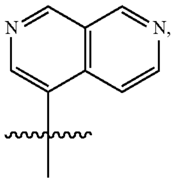

each of which is unsubstituted or substituted with 1 or 2 $R^{12}$ groups.

Embodiment 30. The compound of any one of Embodiments 1 to 16, a stereoisomer thereof, or a pharmaceutically acceptable salt thereof, wherein $R^2$ is isoquinolinyl which is unsubstituted or substituted with 1 or 2 $R^{12}$ groups.

Embodiment 31. The compound of any one of Embodiments 1 to 16, a stereoisomer thereof, or a pharmaceutically acceptable salt thereof, wherein $R^2$ is isoquinolin-4-yl which is unsubstituted or substituted with 1 or 2 $R^{12}$ groups.

Embodiment 32. The compound of any one of Embodiments 1 to 16, a stereoisomer thereof, or a pharmaceutically acceptable salt thereof, wherein $R^2$ is 3-(isoquinolin-4-yl) which is unsubstituted or substituted with 1 or 2 $R^{12}$ groups.

Embodiment 33. The compound of any one of Embodiments 1 to 16, a stereoisomer thereof, or a pharmaceutically acceptable salt thereof, wherein $R^2$ is isoquinolin-4-yl which is unsubstituted.

Embodiment 34. The compound of any one of Embodiments 1 to 16, a stereoisomer thereof, or a pharmaceutically acceptable salt thereof, wherein $R^2$ is 3-(isoquinolin-4-yl) which is unsubstituted.

Embodiment 35. The compound of any one of Embodiments 1 to 16, a stereoisomer thereof, or a pharmaceutically acceptable salt thereof, wherein $R^2$ is phthalazinyl which is unsubstituted or substituted with 1 or 2 $R^{12}$ groups.

Embodiment 36. The compound of any one of Embodiments 1 to 16, a stereoisomer thereof, or a pharmaceutically acceptable salt thereof, wherein $R^2$ is phthalaziny-4-yl which is unsubstituted or substituted with 1 or 2 $R^{12}$ groups.

Embodiment 37. The compound of any one of Embodiments 1 to 16, a stereoisomer thereof, or a pharmaceutically acceptable salt thereof, wherein $R^2$ is phthalaziny-4-yl which is unsubstituted.

Embodiment 38. The compound of any one of Embodiments 1 to 16, a stereoisomer thereof, or a pharmaceutically acceptable salt thereof, wherein $R^2$ is a 5 or 6 membered heterocycloalkyl wherein 1, 2 or 3 ring members are each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo.

Embodiment 39. The compound of any one of Embodiments 1 to 16, a stereoisomer thereof, or a pharmaceutically acceptable salt thereof, wherein $R^2$ is a 5 or 6 membered heterocyclyl wherein 1, 2 or 3 ring members are each independently selected from N, $NR^6$, O and S, and wherein the 5 or 6 membered heterocyclyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo.

Embodiment 40. The compound of any one of Embodiments 1 to 16, a stereoisomer thereof, or a pharmaceutically acceptable salt thereof, wherein $R^2$ is a 6 membered heterocyclyl wherein 1 ring member is selected from $NR^6$, and wherein the 6 membered heterocyclyl substituted with an oxo.

Embodiment 41. The compound of any one of Embodiments 1 to 16, a stereoisomer thereof, or a pharmaceutically acceptable salt thereof, wherein $R^2$ is pyridinyl-2(1H)-one which is unsubstituted or substituted with 1, 2, 3 or 4 $R^{12}$ groups.

Embodiment 42. The compound of any one of Embodiments 1 to 16, a stereoisomer thereof, or a pharmaceutically acceptable salt thereof, wherein $R^2$ is pyridine-3-yl-2(1H)-one or pyridine-4-yl-2(1H)-one, each of which is unsubstituted or substituted with 1, 2, 3 or 4 $R^{12}$ groups.

Embodiment 43. The compound of any one of Embodiments 1 to 16, a stereoisomer thereof, or a pharmaceutically acceptable salt thereof, wherein $R^2$ is

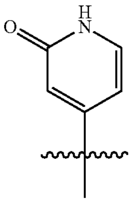
or
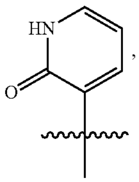
, each of which is unsubstituted or substituted with 1 or 2 $R^{12}$ groups.

Embodiment 44. The compound of any one of Embodiments 1 to 16, a stereoisomer thereof, or a pharmaceutically acceptable salt thereof, wherein $R^2$ is a 9 or 10 membered bicyclic heterocyclyl wherein 1, 2, 3, 4 or 5 ring members are each independently selected from N, $NR^6$, O and S, and wherein the 9 or 10 membered bicyclic heterocyclyl is substituted with 1 or 2 oxo, or the 9 or 10 membered bicyclic heterocyclyl is unsubstituted or substituted with 1, 2, 3 or 4 $R^{12}$ groups and optionally substituted with 1 or 2 oxo.

Embodiment 45. The compound of any one of Embodiments 1 to 16, a stereoisomer thereof, or a pharmaceutically acceptable salt thereof, wherein $R^2$ is a 9 or 10 membered bicyclic heterocyclyl wherein 1 ring member is selected from N, $NR^6$ and O, and wherein the 9 or 10 membered bicyclic heterocyclyl is unsubstituted, or substituted with an oxo.

Embodiment 46. The compound of any one of Embodiments 1 to 16, a stereoisomer thereof, or a pharmaceutically acceptable salt thereof, wherein $R^2$ is isochromanyl, quinolinyl-2(1H)-one, 3a, 7a-dihydro-1H-pyrrolo[2,3-c]pyridinyl or 3a, 7a-dihydro-1H-indazolyl, each of which is unsubstituted, or is substituted with 1, 2, 3 or 4 $R^{12}$ groups.

Embodiment 47. The compound of any one of Embodiments 1 to 16, a stereoisomer thereof, or a pharmaceutically acceptable salt thereof, wherein $R^2$ is isochroman-4-yl, quinolin-4-yl-2(1H)-one, 3a, 7a-dihydro-1H-pyrrolo[2,3-c]pyridine-4-yl or 3a, 7a-dihydro-1H-indazol-4-yl, each of which is unsubstituted, or is substituted with 1, 2, 3 or 4 $R^{12}$ groups.

Embodiment 48. The compound of any one of Embodiments 1 to 16, a stereoisomer thereof, or a pharmaceutically acceptable salt thereof, wherein $R^2$ is

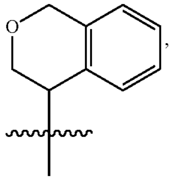
,
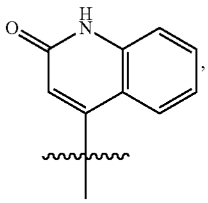
,
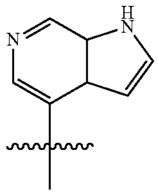
or
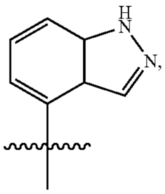
, each of which is unsubstituted or substituted with 1 or 2 $R^{12}$ groups.

Embodiment 49. The compound of any one of Embodiments 1 to 16, a stereoisomer thereof, or a pharmaceutically acceptable salt thereof, wherein $R^2$ is isoquinolinyl, isochromanyl, pyridyl, phthalazinyl, cinnolinyl, imidazo[1,2-c]pyrimidinyl, pyrazolo[1,5-a]pyrazinyl, 3a, 7a-dihydro-1H-pyrrolo[2,3-c]pyridinyl, benzo[c]isoxazolyl, imidazo[1,2-a]pyrazinyl, pyridinyl-2(1H)-one, quinolinyl-2(1H)-one, imidazo[1,2-a]pyridinyl, naphthyridinyl or 3a, 7a-dihydro-1H-indazolyl, each of which is unsubstituted or substituted with 1 or 2 $R^{12}$ groups.

Embodiment 50. The compound of any one of Embodiments 1 to 16, a stereoisomer thereof, or a pharmaceutically acceptable salt thereof, wherein $R^2$ is

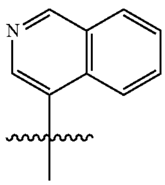
,
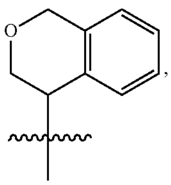
,
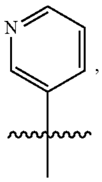
,
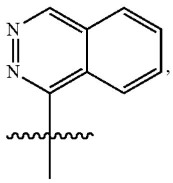
,
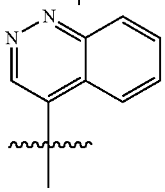
,
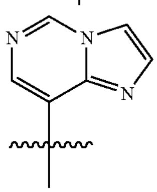
,

-continued

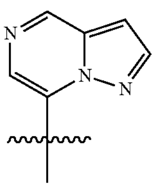, 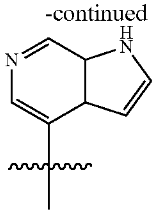, 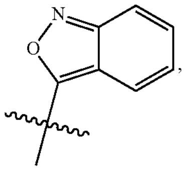,

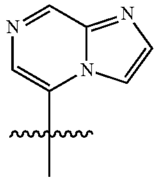, 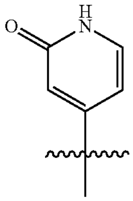, 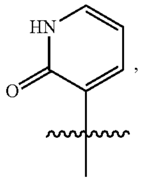,

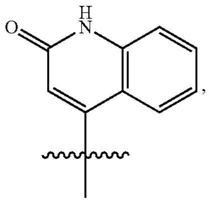, 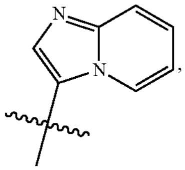, 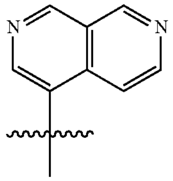

or 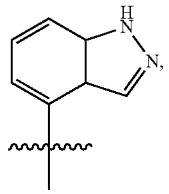, each of which is unsubstituted or substituted with 1 or 2 $R^{12}$ groups.

Embodiment 51. The compound of any one of Embodiments 1 to 16, a stereoisomer thereof, or a pharmaceutically acceptable salt thereof, wherein $R^2$ is a 6 membered heteroaryl with an attachment point at a carbon atom ring member and with a N heteroatom as a ring member which is located at a beta (β) position relative to the attachment point, wherein the 6 membered heteroaryl has 0, 1 or 2 additional N heteroatoms as ring members, and wherein the 6 membered heteroaryl is unsubstituted or is substituted with 1, 2, 3 or 4 $R^{12}$ groups.

Embodiment 52. The compound of any one of Embodiments 1 to 16, a stereoisomer thereof, or a pharmaceutically acceptable salt thereof, wherein $R^2$ is a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups.

Embodiment 53. The compound of any one of Embodiments 1 to 16, a stereoisomer thereof, or a pharmaceutically acceptable salt thereof, wherein $R^2$ is a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups.

Embodiment 54. The compound of any one of Embodiments 1 to 16, a stereoisomer thereof, or a pharmaceutically acceptable salt thereof, wherein $R^2$ is a 9 membered bicyclic heteroaryl with an attachment point at a carbon atom ring member and with a N heteroatom as a ring member which is located at a beta (3) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups.

Embodiment 55. The compound of any one of Embodiments 1 to 16, a stereoisomer thereof, or a pharmaceutically acceptable salt thereof, wherein $R^2$ is a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups.

Embodiment 56. The compound of any one of Embodiments 1 to 16, a stereoisomer thereof, or a pharmaceutically acceptable salt thereof, wherein $R^2$ is a 5 or 6 membered heterocycloalkyl with an attachment point at a carbon atom ring member and with a $NR^6$ as a ring member which is located at a beta (β) position relative to the attachment point, wherein the 5 or 6 membered heterocycloalkyl further has 0, 1, or 2 ring members each independently selected from N, $NR^6$, O and S, and wherein the 5 or 6 membered heterocycloalkyl is substituted with 1 or 2 oxo, or the 5 or 6 membered heterocycloalkyl is unsubstituted or substituted with 1, 2, 3 or 4 $R^{12}$ groups and optionally substituted with 1 or 2 oxo.

Embodiment 57. The compound of any one of Embodiments 1 to 16, a stereoisomer thereof, or a pharmaceutically acceptable salt thereof, wherein $R^2$ is a 5 or 6 membered heterocyclyl with an attachment point at a carbon atom ring member and with a $NR^6$ as a ring member which is located at a beta (β) position relative to the attachment point, wherein the 5 or 6 membered heterocyclyl further has 0, 1, or 2 ring members each independently selected from N, $NR^6$, O and S, and wherein the 5 or 6 membered heterocyclyl is substituted with 1 or 2 oxo, or the 5 or 6 membered heterocyclyl is unsubstituted or substituted with 1, 2, 3 or 4 $R^{12}$ groups and optionally substituted with 1 or 2 oxo.

Embodiment 58. The compound of any one of Embodiments 1 to 16, a stereoisomer thereof, or a pharmaceutically acceptable salt thereof, wherein $R^2$ is a 9 or 10 membered bicyclic heterocyclyl with an attachment point at a carbon atom ring member and with a $NR^6$ as a ring member which is located at a beta (3) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo.

Embodiment 59. The compound of any one of Embodiments 1 to 16, a stereoisomer thereof, or a pharmaceutically acceptable salt thereof, wherein $R^2$ is a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo.

Embodiment 60. The compound of any one of Embodiments 1 to 16, a stereoisomer thereof, or a pharmaceutically acceptable salt thereof, wherein $R^2$ is a 6 membered heterocyclyl with an attachment point at a carbon atom ring member and with a carbon atom as a ring member which is substituted with oxo and located at a beta (β) position relative to the attachment point, wherein the 6 membered heterocyclyl further has 1 or 2 ring members each independently selected from N, $NR^6$, O and S, and wherein the 6 membered heterocyclyl is unsubstituted or is substituted with 1, 2, 3 or 4 $R^{12}$ groups and optionally substituted with an oxo.

Embodiment 61. The compound of any one of Embodiments 1 to 16, a stereoisomer thereof, or a pharmaceutically acceptable salt thereof, wherein $R^2$ is a 10 membered bicyclic heterocyclyl with an attachment point at a carbon atom ring member and with a carbon atom as a ring member which is substituted with oxo and located at a beta (1) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo.

Embodiment 62. The compound of any one of Embodiments 1 to 61, a stereoisomer thereof, or a pharmaceutically acceptable salt thereof, wherein each $R^{12}$ is independently selected from the group consisting of $—C(=O)N(R^7)_2$, $—C(=O)OH$, $—N(R^7)_2$, —CN, —OH,

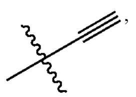 [SMILES: *C#C]

halo, and 4 to 6 membered heterocycloalkyl wherein 1, 2, 3 or 4 ring members are each independently selected from N, $NR^6$, O and $C_1$-$C_6$alkyl that is unsubstituted or is substituted with $NH_2$, CN or OH, wherein the heterocycloalkyl is unsubstituted or are substituted with 1 or 2 substituents independently selected from the group consisting of OH.

Embodiment 63. The compound of any one of Embodiments 1 to 61, a stereoisomer thereof, or a pharmaceutically acceptable salt thereof, wherein each $R^{12}$ is independently selected from the group consisting of $—C(=O)N(R^7)_2$, $—C(=O)OH$, $—N(R^7)_2$, —CN, —OH,

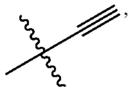 [SMILES: *C#C]

$C_1$-$C_6$alkyl that is unsubstituted and halo.

Embodiment 64. The compound of any one of Embodiments 1 to 61, a stereoisomer thereof, or a pharmaceutically acceptable salt thereof, wherein each $R^{12}$ is independently selected from the group consisting of $—C(=O)N(R^7)_2$, $—C(=O)OH$, —CN, $—S(=O)_2R^7$ and $C_1$-$C_6$alkyl substituted with OH.

Embodiment 65. The compound of any one of Embodiments 1 to 61, a stereoisomer thereof, or a pharmaceutically acceptable salt thereof, wherein each $R^{12}$ is independently selected from the group consisting of $—C(=O)NH_2$, $—C(=O)NH(CH_2)_2OCH_3$, —C(=O)OH, —CN, $—S(=O)_2CH_3$ and $—C(CH_3)_2OH$.

Embodiment 66. The compound of any one of Embodiments 1 to 61, a stereoisomer thereof, or a pharmaceutically acceptable salt thereof, wherein each $R^{12}$ is independently selected from $—S(=O)_2R^6$, $—S(=O)_2N(R^7)_2$, phenyl, $C_3$-$C_8$cycloalkyl, 4 to 6 membered heterocycloalkyl wherein 1, 2, 3 or 4 ring members are each independently selected from N, $NR^6$, O and S, and 5 or 6 membered heteroaryl wherein 1, 2 or 3 ring members are each independently selected from N, O and S, wherein the phenyl, heterocycloalkyl and heteroaryl are unsubstituted or are substituted with 1 or 2 substituents independently selected from the group consisting of OH.

Embodiment 67. The compound of any one of Embodiments 1 to 66, a stereoisomer thereof, or a pharmaceutically acceptable salt thereof, wherein $R^1$ is phenyl or pyridyl, each of which is unsubstituted or is substituted with 1 to 4 $R^5$ groups.

Embodiment 68. The compound of any one of Embodiments 1 to 66, a stereoisomer thereof, or a pharmaceutically acceptable salt thereof, wherein $R^1$ is phenyl or a 5 or 6 membered heteroaryl wherein 1 or 2 ring members are each independently selected from N, $NR^6$, O and S, wherein the phenyl or heteroaryl is unsubstituted or is substituted with 1 to 2 $R^5$ groups.

Embodiment 69. The compound of any one of Embodiments 1 to 66, a stereoisomer thereof, or a pharmaceutically acceptable salt thereof, wherein $R^1$ is phenyl, pyridyl, pyridazinyl, pyrimidinyl or pyrazinyl, each of which is unsubstituted or is substituted with 1 to 2 $R^5$ group independently selected from $C_1$, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

Embodiment 70. The compound of any one of Embodiments 1 to 66, a stereoisomer thereof, or a pharmaceutically acceptable salt thereof, wherein $R^1$ is phenyl or pyridyl, each of which is unsubstituted or is substituted with 1 to 2 $R^5$ group independently selected from Cl, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

Embodiment 71. The compound of any one of Embodiments 1 to 66, a stereoisomer thereof, or a pharmaceutically acceptable salt thereof, wherein $R^1$ is pyridyl, which is unsubstituted or is substituted with 1 to 2 $R^5$ group independently selected from $C_1$, F, $CF_3$, —$CHF_2$, —$CH_3$, —$CH(CH_3)_2$, —$OCH_3$, —$OCHF_2$, —$OCF_3$, CN, —$SO_2CH_3$ and —$C(CH_3)_2OH$.

Embodiment 72. The compound of any one of Embodiments 1 to 66, a stereoisomer thereof, or a pharmaceutically acceptable salt thereof, wherein $R^1$ is pyridyl, which is unsubstituted or is substituted with $CF_3$.

Embodiment 73. The compound of any one of Embodiments 1 to 66, a stereoisomer thereof, or a pharmaceutically acceptable salt thereof, wherein $R^1$ is pyridyl, which is substituted with $CF_3$.

Embodiment 74. The compound of any one of Embodiments 1 to 66, a stereoisomer thereof, or a pharmaceutically acceptable salt thereof, wherein $R^1$ is pyrazolyl or imidazolyl, each of which is unsubstituted or is substituted with 1 to 2 $R^5$ group independently selected from C, F, $CF_3$, —$CHF_2$, —$CH_3$, —$CH(CH_3)_2$, —$OCH_3$, —$OCHF_2$, —$OCF_3$, CN, —$SO_2CH_3$ and —$C(CH_3)_2OH$.

Embodiment 75. The compound of any one of Embodiments 1 to 66, a stereoisomer thereof, or a pharmaceutically acceptable salt thereof, wherein $R^1$ is pyrazolyl or imidazolyl, each of which is unsubstituted or is substituted with 1 to 2 $R^5$ groups independently selected from C, —$CH_3$, and —$CH(CH_3)_2$.

Embodiment 76. The compound of any one of Embodiments 1 to 66, a stereoisomer thereof, or a pharmaceutically acceptable salt thereof, wherein $R^1$ is phenyl which is unsubstituted or is substituted with 1 to 4 $R^5$ groups.

Embodiment 77. The compound of any one of Embodiments 1 to 66, a stereoisomer thereof, or a pharmaceutically acceptable salt thereof, wherein $R^1$ is phenyl which is unsubstituted or is substituted with 1 to 2 $R^5$ groups.

Embodiment 78. The compound of any one of Embodiments 1 to 66, a stereoisomer thereof, or a pharmaceutically acceptable salt thereof, wherein $R^1$ is phenyl which is unsubstituted or is substituted with 1 to 2 $R^5$ groups independently selected from —CN, —OH, —$S(=O)_2C_1$-$C_6$alkyl, $C_1$-$C_6$alkyl, $C_1$-$C_6$haloalkyl, halo, $C_1$-$C_6$haloalkoxy, $C_1$-$C_6$alkoxy, $C_3$-$C_8$cycloalkyl, and a $C_1$-$C_6$alkyl substituted with OH.

Embodiment 79. The compound of any one of Embodiments 1 to 66, a stereoisomer thereof, or a pharmaceutically acceptable salt thereof, wherein $R^1$ is phenyl which is unsubstituted or is substituted with 1 to 2 $R^5$ groups independently selected from C, F, —$CF_3$, —$OCF_3$, —$CH_3$, —$OCH_3$, —CN, —$CHF_2$, —$OCHF_2$, —$SO_2CH_3$, —$CH(CH_3)_2$ and —$C(CH_3)_2OH$.

Embodiment 80. The compound of any one of Embodiments 1 to 66, a stereoisomer thereof, or a pharmaceutically acceptable salt thereof, wherein $R^1$ is phenyl which is unsubstituted or is substituted with 1 to 2 $R^5$ groups independently selected from C, F, —$CF_3$, —$OCF_3$, —$CH_3$, —$OCH_3$, —CN, —$CHF_2$, —$OCHF_2$, —$SO_2CH_3$, and —$C(CH_3)_2OH$.

Embodiment 81. The compound of any one of Embodiments 1 to 66, a stereoisomer thereof, or a pharmaceutically acceptable salt thereof, wherein $R^1$ is

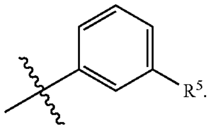

Embodiment 82. The compound of any one of Embodiments 1 to 66, a stereoisomer thereof, or a pharmaceutically acceptable salt thereof, wherein $R^1$ is spiro attached $C_3$-$C_8$cycloalkyl which is unsubstituted or is substituted with 1 to 4 $R^5$ groups.

Embodiment 83. The compound of any one of Embodiments 1 to 66, a stereoisomer thereof, or a pharmaceutically acceptable salt thereof, wherein $R^1$ is bicyclic $C_3$-$C_8$cycloalkyl which is unsubstituted or is substituted with 1 to 4 $R^5$ groups.

Embodiment 84. The compound of any one of Embodiments 1 to 66, a stereoisomer thereof, or a pharmaceutically acceptable salt thereof, wherein $R^1$ is bicyclic $C_3$-$C_8$cycloalkyl which is unsubstituted or is substituted with 1 to 2 $R^5$ groups.

Embodiment 85. The compound of any one of Embodiments 1 to 66, a stereoisomer thereof, or a pharmaceutically acceptable salt thereof, wherein $R^1$ is bicyclic $C_3$-$C_8$cycloalkyl which is unsubstituted or is substituted with 1 to 2 $R^5$ groups, where each $R^5$ is independently selected from the group consisting of halo, $C_1$-$C_6$haloalkyl and $C_1$-$C_6$alkyl that is unsubstituted.

Embodiment 86. The compound of any one of Embodiments 1 to 66, a stereoisomer thereof, or a pharmaceutically acceptable salt thereof, wherein $R^1$ is bicyclo[1.1.1]pentan-1-yl), (spiro[3.3]heptan-2-yl) or (spiro[2.3]hexan-5-yl), each of which is unsubstituted or is substituted with 1 to 2 $R^5$ groups, where each $R^5$ is independently selected from the group consisting of F, —$CF_3$, and —$CH_3$.

Embodiment 87. The compound of any one of Embodiments 1 to 66, a stereoisomer thereof, or a pharmaceutically acceptable salt thereof, wherein $R^1$ is $C_3$-$C_8$cycloalkyl which is unsubstituted or is substituted with 1 to 4 $R^5$ groups.

Embodiment 88. The compound of any one of Embodiments 1 to 66, a stereoisomer thereof, or a pharmaceutically acceptable salt thereof, wherein $R^1$ is $C_3$-$C_8$cycloalkyl which is unsubstituted or is substituted with 1 to 2 $R^5$ groups.

Embodiment 89. The compound of any one of Embodiments 1 to 66, a stereoisomer thereof, or a pharmaceutically acceptable salt thereof, wherein $R^1$ is $C_3$-$C_8$cycloalkyl which is unsubstituted or is substituted with 1 to 2 $R^5$ groups, where each $R^5$ is independently selected from the group consisting of halo, OH, $C_1$-$C_6$haloalkyl, $C_1$-$C_6$alkyl that is unsubstituted and $C_3$-$C_8$cycloalkyl that is unsubstituted.

Embodiment 90. The compound of any one of Embodiments 1 to 66, a stereoisomer thereof, or a pharmaceutically acceptable salt thereof, wherein $R^1$ is cyclobutyl, cyclopentyl or cyclohexyl, each of which is unsubstituted or is substituted with 1 to 2 $R^5$ groups, where each $R^5$ is independently selected from the group consisting of F, —$CF_3$, —$CH_3$, —$CH(CH_3)_2$ and cyclopropyl.

Embodiment 91. The compound of any one of Embodiments 1 to 66, a stereoisomer thereof, or a pharmaceutically acceptable salt thereof, wherein $R^1$ is $C_3$-$C_8$cycloalkyl or bicyclic $C_3$-$C_8$cycloalkyl, each of which is unsubstituted or is substituted with 1 to 2 $R^5$ groups.

Embodiment 92. The compound of any one of Embodiments 1 to 66, a stereoisomer thereof, or a pharmaceutically acceptable salt thereof, wherein $R^1$ is $C_3$-$C_8$cycloalkyl or bicyclic $C_3$-$C_8$cycloalkyl, each of which is unsubstituted or is substituted with 1 to 2 $R^5$ groups, where each $R^5$ is independently selected from the group consisting of halo, OH, $C_1$-$C_6$haloalkyl, $C_1$-$C_6$alkyl that is unsubstituted and $C_3$-$C_8$cycloalkyl that is unsubstituted.

Embodiment 93. The compound of any one of Embodiments 1 to 66, a stereoisomer thereof, or a pharmaceutically acceptable salt thereof, wherein $R^1$ is cyclobutyl, cyclopentyl, cyclohexyl, bicyclo[1.1.1]pentan-1-yl), (spiro[3.3]heptan-2-yl) or (spiro[2.3]hexan-5-yl), each of which is unsubstituted or is substituted with 1 to 2 $R^5$ groups, where each $R^5$ is independently selected from the group consisting of F, —$CF_3$, —$CH_3$, —$CH(CH_3)_2$ and cyclopropyl.

Embodiment 94. The compound of any one of Embodiments 1 to 66, a stereoisomer thereof, or a pharmaceutically acceptable salt thereof, wherein $R^1$ is a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups.

Embodiment 95. The compound of any one of Embodiments 1 to 66, a stereoisomer thereof, or a pharmaceutically acceptable salt thereof, wherein $R^1$ is a 5 or 6 membered heteroaryl wherein 1 or 2 ring members are each independently selected from N, $NR^6$, O and S, wherein the 5 or 6 membered heteroaryl is unsubstituted or is substituted with 1 to $4R^5$ groups.

Embodiment 96. The compound of any one of Embodiments 1 to 66, a stereoisomer thereof, or a pharmaceutically acceptable salt thereof, wherein $R^1$ is a 5 or 6 membered heteroaryl wherein 1 or 2 ring members are each independently selected from N, $NR^6$, O and S, wherein the 5 or 6 membered heteroaryl is unsubstituted or is substituted with 1 to $2R^5$ groups.

Embodiment 97. The compound of any one of Embodiments 1 to 66, a stereoisomer thereof, or a pharmaceutically acceptable salt thereof, wherein $R^1$ is a 5 or 6 membered heteroaryl wherein 1 ring member is selected from N, $NR^6$, O and S, wherein the 5 or 6 membered heteroaryl is unsubstituted or is substituted with 1 to 4 $R^5$ groups.

Embodiment 98. The compound of any one of Embodiments 1 to 66, a stereoisomer thereof, or a pharmaceutically acceptable salt thereof, wherein $R^1$ is pyridyl, pyrazinyl, pyrimidinyl, pyridazinyl, pyrazolyl, pyrrolyl, imidazolyl, thienyl, furyl, thiazolyl, oxazolyl, isoxazolyl or triazolyl, each of which is unsubstituted or is substituted with 1 to 4 $R^5$ groups.

Embodiment 99. The compound of any one of Embodiments 1 to 66, a stereoisomer thereof, or a pharmaceutically acceptable salt thereof, wherein $R^1$ is

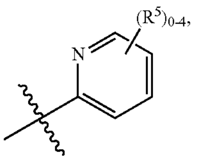
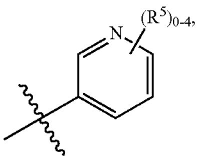

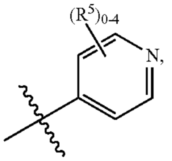
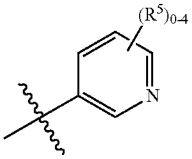
,

-continued

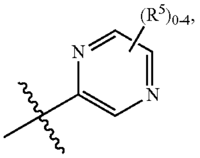
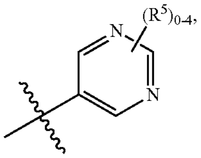

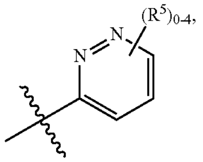
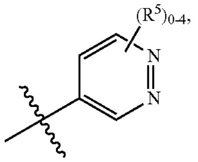

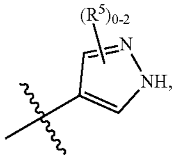
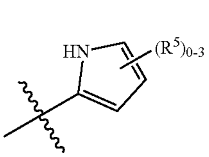
,

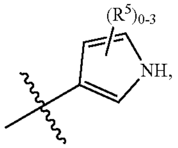
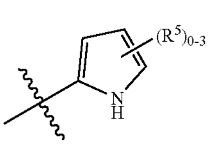
,

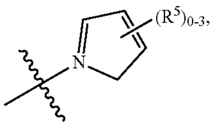
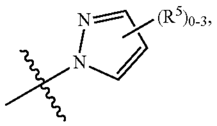

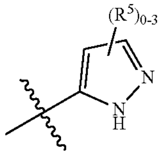
,
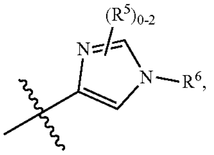

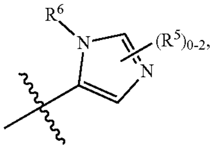
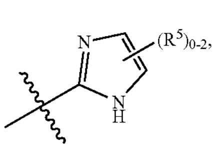

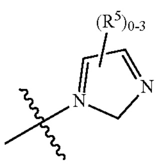
,
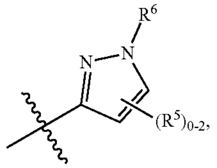

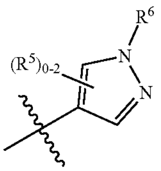
,
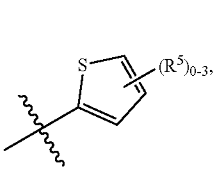

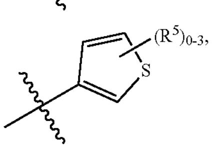
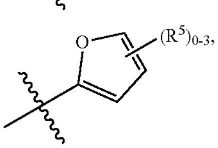

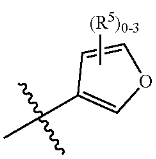
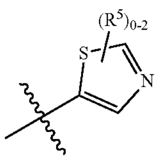

-continued

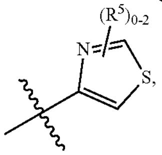 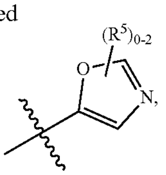

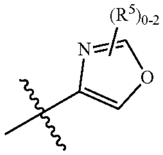 , 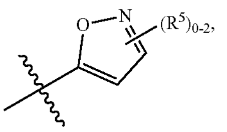

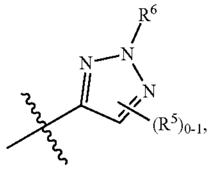 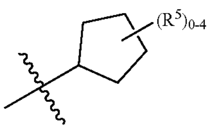 ,

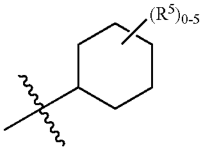 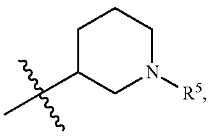

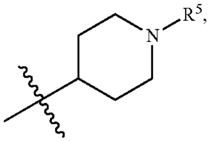 or 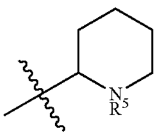 .

Embodiment 100. The compound of any one of Embodiments 1 to 66, a stereoisomer thereof, or a pharmaceutically acceptable salt thereof, wherein $R^1$ is pyridyl or pyrazolyl, each of which is unsubstituted or is substituted with 1 to 4 $R^5$ groups.

Embodiment 101. The compound of any one of Embodiments 1 to 66, a stereoisomer thereof, or a pharmaceutically acceptable salt thereof, wherein $R^1$ is

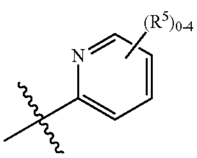 or 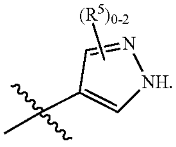

Embodiment 102. The compound of any one of Embodiments 1 to 66, a stereoisomer thereof, or a pharmaceutically acceptable salt thereof, wherein $R^1$ is $C_1$-$C_6$alkyl.

Embodiment 103. The compound of any one of Embodiments 1 to 66, a stereoisomer thereof, or a pharmaceutically acceptable salt thereof, wherein $R^1$ is neopentyl.

Embodiment 104. The compound of any one of Embodiments 1 to 66, a stereoisomer thereof, or a pharmaceutically acceptable salt thereof, wherein $R^1$ is $C_5$-$C_6$cycloalkenyl.

Embodiment 105. The compound of any one of Embodiments 1 to 66, a stereoisomer thereof, or a pharmaceutically acceptable salt thereof, wherein $R^1$ is $C_8$cycloalkenyl;

Embodiment 106. The compound of any one of Embodiments 1 to 66, a stereoisomer thereof, or a pharmaceutically acceptable salt thereof, wherein $R^1$ is cyclopent-1-enyl or cyclopenta-1,3-dienyl.

Embodiment 107. The compound of any one of Embodiments 1 to 66, a stereoisomer thereof, or a pharmaceutically acceptable salt thereof, wherein $R^1$ is $C_6$cycloalkenyl.

Embodiment 108. The compound of any one of Embodiments 1 to 66, a stereoisomer thereof, or a pharmaceutically acceptable salt thereof, wherein $R^1$ is cyclohex-1-enyl or cyclohexa-1,3-dienyl.

Embodiment 109. The compound of any one of Embodiments 1 to 66, a stereoisomer thereof, or a pharmaceutically acceptable salt thereof, wherein $R^1$ is 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is unsubstituted or substituted with 1, 2, 3 or 4 $R^{12}$ groups and is optionally substituted with oxo.

Embodiment 110. The compound of any one of Embodiments 1 to 66, a stereoisomer thereof, or a pharmaceutically acceptable salt thereof, wherein $R^1$ is 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is substituted with oxo and substituted with an $R^5$ group.

Embodiment 111. The compound of any one of Embodiments 1 to 66, a stereoisomer thereof, or a pharmaceutically acceptable salt thereof, wherein $R^1$ is 5 or 6 membered heterocyclyl wherein 1, 2 or 3 ring members are each independently selected from W, Y and Z, wherein W is $NR^6$, O, S, S═O or S(═O)$_2$, Y is $NR^6$, O, S, S═O or S(═O)$_2$ and Z is $NR^6$, O or S, and wherein the 5 or 6 membered heterocyclyl is substituted with oxo, wherein $R^6$ is H or —$CH_3$, and wherein $R^5$ is —$CF_3$.

Embodiment 112. The compound of any one of Embodiments 1 to 66, a stereoisomer thereof, or a pharmaceutically acceptable salt thereof, wherein $R^1$ is 1,2-dihydropyridinyl substituted with oxo, —$CH_3$ and —$CF_3$.

Embodiment 113. The compound of any one of Embodiments 1 to 66, a stereoisomer thereof, or a pharmaceutically acceptable salt thereof, wherein $R^1$ is 1,2-dihydropyridinyl, pyridinyl-2(1H)-one, 2,3-dihydro-1H-pyrrolyl or 1,3-dihydro-2H-pyrrolyl-2-one.

Embodiment 114. The compound of any one of Embodiments 1 to 66, a stereoisomer thereof, or a pharmaceutically acceptable salt thereof, wherein $R^1$ is a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups.

Embodiment 115. The compound of any one of Embodiments 1 to 66, a stereoisomer thereof, or a pharmaceutically acceptable salt thereof, wherein $R^1$ is a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

Embodiment 116. The compound of any one of Embodiments 1 to 66, a stereoisomer thereof, or a pharmaceutically acceptable salt thereof, wherein $R^1$ is a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 2 $R^5$ groups.

Embodiment 117. The compound of any one of Embodiments 1 to 66, a stereoisomer thereof, or a pharmaceutically acceptable salt thereof, wherein $R^1$ is a 9 or 10 membered bicyclic heterocyclyl wherein 1 or 2 ring members is each independently selected from N and $NR^6$, wherein the 9 or 10 membered bicyclic heterocyclyl is unsubstituted or is substituted with 1 to 2 $R^5$ groups.

Embodiment 118. The compound of any one of Embodiments 1 to 66, a stereoisomer thereof, or a pharmaceutically acceptable salt thereof, wherein $R^1$ is 1H-indazolyl) or indazolyl.

Embodiment 119. The compound of any one of Embodiments 1 to 66, a stereoisomer thereof, or a pharmaceutically acceptable salt thereof, wherein $R^1$ is a 9 or 10 membered bicyclic heterocyclyl wherein 1 ring member is selected from N, $NR^6$, O and S, wherein the 9 or 10 membered bicyclic heterocyclyl is unsubstituted or is substituted with 1 to 2 $R^5$ groups.

Embodiment 120. The compound of any one of Embodiments 1 to 66, a stereoisomer thereof, or a pharmaceutically acceptable salt thereof, wherein $R^1$ is a 9 or 10 membered bicyclic heterocyclyl wherein 1 ring member is selected from $NR^6$, wherein the 9 or 10 membered bicyclic heterocyclyl is unsubstituted or is substituted with 1 to 2 $R^5$ groups Embodiment 121. The compound of any one of Embodiments 1 to 66, a stereoisomer thereof, or a pharmaceutically acceptable salt thereof, wherein $R^1$ is a 5 or 6 membered heterocycloalkyl wherein 1, 2, 3 or 4 ring members are each independently selected from N, $NR^6$, O and S, and wherein the 5 or 6 membered heterocycloalkyl is optionally substituted with oxo.

Embodiment 122. The compound of any one of Embodiments 1 to 66, a stereoisomer thereof, or a pharmaceutically acceptable salt thereof, wherein $R^1$ is a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups.

Embodiment 123. The compound of any one of Embodiments 1 to 66, a stereoisomer thereof, or a pharmaceutically acceptable salt thereof, wherein $R^1$ is a 4, 5 or 6 membered heterocycloalkyl wherein 1 or 2 ring members are each independently selected from N, $NR^6$, O and S, and wherein the 4, 5 or 6 membered heterocycloalkyl is unsubstituted.

Embodiment 124. The compound of any one of Embodiments 1 to 66, a stereoisomer thereof, or a pharmaceutically acceptable salt thereof, wherein $R^1$ is a 4 or 5 membered heterocycloalkyl wherein 1 ring member is selected from N, $NR^6$, O and S, and wherein $R^6$ is $—C(═O)CH_2OH$, $—(CH_2)_2OH$, $—(CH_2)_2CF_3$, $—CH_2CF_3$, $—C(═O)CH_3$, $—SO_2CH_3$, $—SO_2CF_3$, $—SO_2—$ cyclopropyl or cyclopropyl.

Embodiment 125. The compound of any one of Embodiments 1 to 66, a stereoisomer thereof, or a pharmaceutically acceptable salt thereof, wherein $R^1$ is azetidinyl or pyrrolidinyl, each of which is substituted with a group selected from $—C(═O)CH_2OH$, $—(CH_2)_2OH$, $—(CH_2)_2CF_3$, $—CH_2CF_3$, $—C(═O)CH_3$, $—SO_2CH_3$, $—SO_2CF_3$, $—SO_2$-cyclopropyl and cyclopropyl.

Embodiment 126. The compound of any one of Embodiments 1 to 66, a stereoisomer thereof, or a pharmaceutically acceptable salt thereof, wherein $R^1$ is pyrrolidinyl-2-one.

Embodiment 127. The compound of any one of Embodiments 1 to 66, a stereoisomer thereof, or a pharmaceutically acceptable salt thereof, wherein $R^1$ is a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups.

Embodiment 128. The compound of any one of Embodiments 1 to 127, a stereoisomer thereof, or a pharmaceutically acceptable salt thereof, wherein each $R^5$ is independently selected from the group consisting of $NR^6C(═O)C_2$-$C_6$alkenyl, $—SF_5$, $C_1$-$C_6$alkyl that is unsubstituted, $C_1$-$C_6$haloalkyl, halo, $C_1$-$C_6$haloalkoxy, $C_1$-$C_6$alkoxy, $C_3$-$C_8$cycloalkyl, wherein the cycloalkyl is unsubstituted or are substituted with 1, 2, 3 or 4 $R^9$.

Embodiment 129. The compound of any one of Embodiments 1 to 127, a stereoisomer thereof, or a pharmaceutically acceptable salt thereof, wherein each $R^5$ is independently selected from the group consisting of $NR^6C(═O)C_2$-$C_6$alkenyl, $—SF_5$, $C_1$-$C_6$alkyl that is unsubstituted, $C_1$-$C_6$haloalkyl, halo, $C_1$-$C_6$haloalkoxy, $C_1$-$C_6$alkoxy, $C_3$-$C_8$cycloalkyl, wherein the cycloalkyl is unsubstituted or are substituted with 1 $R^9$.

Embodiment 130. The compound of any one of Embodiments 1 to 127, a stereoisomer thereof, or a pharmaceutically acceptable salt thereof, wherein each $R^5$ is independently selected from the group consisting of $NR^6C(═O)C_2$-$C_6$alkenyl, $—SF_5$, $C_1$-$C_6$alkyl that is unsubstituted, $C_1$-$C_6$haloalkyl, halo, $C_1$-$C_6$haloalkoxy, $C_1$-$C_6$alkoxy, $C_3$-$C_8$cycloalkyl, wherein the cycloalkyl is unsubstituted or are substituted with 1 or 2 $R^9$.

Embodiment 131. The compound of any one of Embodiments 1 to 127, a stereoisomer thereof, or a pharmaceutically acceptable salt thereof, wherein each $R^5$ is independently selected from the group consisting of $—OH$, $—NR^7R^8$, $—C(═O)N(R^7)_2$, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and $C_1$-$C_6$alkyl substituted with CN, $NH_2$ or OH, and wherein the heterocycloalkyl is unsubstituted or are substituted with 1, 2, 3 or 4 $R^9$.

Embodiment 132. The compound of any one of Embodiments 1 to 127, a stereoisomer thereof, or a pharmaceutically acceptable salt thereof, wherein each $R^5$ is independently selected from the group consisting of $—OH$, $—NR^7R^8$, $—C(═O)N(R^7)_2$, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and $C_1$-$C_6$alkyl substituted with CN, $NH_2$ or OH, and wherein the heterocycloalkyl is unsubstituted or are substituted with 1 or 2 $R^9$.

Embodiment 133. The compound of any one of Embodiments 1 to 127, a stereoisomer thereof, or a pharmaceutically acceptable salt thereof, wherein each $R^5$ is independently selected from the group consisting of CN, $—OH$, $S(═O)_2C_1$-$C_6$alkyl, $C_1$-$C_6$haloalkyl, halo, $C_1$-$C_6$haloalkoxy, $C_1$-$C_6$alkoxy, $C_3$-$C_8$cycloalkyl, and $C_1$-$C_6$alkyl that is unsubstituted or is substituted with OH.

Embodiment 134. The compound of any one of Embodiments 1 to 127, a stereoisomer thereof, or a pharmaceutically acceptable salt thereof, wherein each $R^5$ group independently selected from $C_1$, F, $CF_3$, —$CHF_2$, —$CH_3$, —$CH(CH_3)_2$, —$OCH_3$, —$OCHF_2$, —$OCF_3$, CN, —$SO_2CH_3$ and —$C(CH_3)_2OH$.

Embodiment 135. The compound of any one of Embodiments 1 to 127, a stereoisomer thereof, or a pharmaceutically acceptable salt thereof, wherein $R^5$ is $C_1$-$C_6$haloalkyl, halo or $C_1$-$C_6$haloalkoxy.

Embodiment 136. The compound of any one of Embodiments 1 to 127, a stereoisomer thereof, or a pharmaceutically acceptable salt thereof, wherein $R^5$ is —$CF_3$, F, $C_1$, —$OCHF_2$ or —$OCF_3$.

Embodiment 137. The compound of any one of Embodiments 1 to 127, a stereoisomer thereof, or a pharmaceutically acceptable salt thereof, wherein each $R^5$ is independently selected from the group consisting of halo, OH, $C_1$-$C_6$haloalkyl, $C_1$-$C_6$alkyl that is unsubstituted and $C_3$-$C_8$cycloalkyl that is unsubstituted.

Embodiment 138. The compound of any one of Embodiments 1 to 127, a stereoisomer thereof, or a pharmaceutically acceptable salt thereof, wherein each $R^5$ is independently selected from the group consisting of F, —$CF_3$, —$CH_3$, —$CH(CH_3)_2$ and cyclopropyl.

Embodiment 139. The compound of any one of Embodiments 1 to 138, a stereoisomer thereof, or a pharmaceutically acceptable salt thereof, wherein each $R^6$ is independently selected from the group consisting of H and $C_1$-$C_6$alkyl that is unsubstituted.

Embodiment 140. The compound of any one of Embodiments 1 to 138, a stereoisomer thereof, or a pharmaceutically acceptable salt thereof, wherein each $R^6$ is independently selected from the group consisting of H, $C_1$-$C_6$haloalkyl, $C_1$-$C_6$haloalkoxy, $S(=O)_2C_1$-$C_6$alkyl, $S(=O)_2C_1$-$C_6$haloalkyl, —$S(=O)_2C_3$-$C_6$cycloalkyl, —$C(=O)R^7$, $C_3$-$C_6$cycloalkyl, and $C_1$-$C_6$alkyl that is unsubstituted or is substituted with —OH or $C_1$-$C_6$haloalkyl.

Embodiment 141. The compound of any one of Embodiments 1 to 138, a stereoisomer thereof, or a pharmaceutically acceptable salt thereof, wherein each $R^6$ is independently selected from the group consisting of H, —$CH_3$, —$C(=O)CH_2OH$, —$(CH_2)_2OH$, —$(CH_2)_2CF_3$, —$CH_2CF_3$, —$C(=O)CH_3$, —$SO_2CH_3$, —$SO_2CF_3$, —$SO_2$-cyclopropyl or cyclopropyl Embodiment 142. The compound of any one of Embodiments 1 to 141, a stereoisomer thereof, or a pharmaceutically acceptable salt thereof, wherein $R^{3a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$.

Embodiment 143. The compound of any one of Embodiments 1 to 141, a stereoisomer thereof, or a pharmaceutically acceptable salt thereof, wherein $R^{3a}$ is H, —CN, a 4 to 7 membered heterocycloalkyl wherein 1, 2 or 3 ring members are each independently selected from N, $NR^6$, O and S, or a $C_1$-$C_6$alkyl substituted with one or more $R^{15}$ groups.

Embodiment 144. The compound of any one of Embodiments 1 to 141, a stereoisomer thereof, or a pharmaceutically acceptable salt thereof, wherein $R^{3a}$ is —CN or a $C_1$-$C_6$alkyl substituted with one or more $R^{15}$ groups.

Embodiment 145. The compound of any one of Embodiments 1 to 141, a stereoisomer thereof, or a pharmaceutically acceptable salt thereof, wherein $R^{3a}$ is —CN or —$CH_3$.

Embodiment 146. The compound of any one of Embodiments 1 to 141, a stereoisomer thereof, or a pharmaceutically acceptable salt thereof, wherein $R^{3a}$ is —CN.

Embodiment 147. The compound of any one of Embodiments 1 to 146, a stereoisomer thereof, or a pharmaceutically acceptable salt thereof, wherein $R^{3b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)OH, $NH_2$, OH, $C_1$-$C_6$haloalkyl, $C_1$-$C_6$alkyl or $C_1$-$C_6$alkyl substituted with —C(=O)OH, —OH, CN or $NH_2$.

Embodiment 148. The compound of any one of Embodiments 1 to 146, a stereoisomer thereof, or a pharmaceutically acceptable salt thereof, wherein $R^{3b}$ is H, —CN, a 4 to 7 membered heterocycloalkyl wherein 1, 2 or 3 ring members are each independently selected from N, $NR^6$, O and S, or a $C_1$-$C_6$alkyl that is unsubstituted or is substituted with one or more $R^{15}$ groups.

Embodiment 149. The compound of any one of Embodiments 1 to 146, a stereoisomer thereof, or a pharmaceutically acceptable salt thereof, wherein $R^{3b}$ is H, —CN, or a $C_1$-$C_6$alkyl that is unsubstituted or is substituted with one or more $R^{15}$ groups.

Embodiment 150. The compound of any one of Embodiments 1 to 146, a stereoisomer thereof, or a pharmaceutically acceptable salt thereof, wherein $R^{3b}$ is H or $C_1$-$C_6$alkyl that is unsubstituted.

Embodiment 151. The compound of any one of Embodiments 1 to 146, or a pharmaceutically acceptable salt or stereoisomer thereof, wherein $R^{3b}$ is H or —$CH_3$.

Embodiment 152. The compound of any one of Embodiments 1 to 151, a stereoisomer thereof, or a pharmaceutically acceptable salt thereof, wherein $R^{4a}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(=O)

OH, $NH_2$, OH, $C_1$-$C_6$haloalkyl, $C_1$-$C_6$alkyl or $C_1$-$C_6$alkyl substituted with —C(═O)OH, —OH, CN or $NH_2$.

Embodiment 153. The compound of any one of Embodiments 1 to 151, a stereoisomer thereof, or a pharmaceutically acceptable salt thereof, wherein $R^{4a}$ is H, —CN, a 4 to 7 membered heterocycloalkyl wherein 1, 2 or 3 ring members are each independently selected from N, $NR^6$, O and S, or a $C_1$-$C_6$alkyl that is unsubstituted or is substituted with one or more $R^{15}$ groups.

Embodiment 154. The compound of any one of Embodiments 1 to 151, a stereoisomer thereof, or a pharmaceutically acceptable salt thereof, wherein $R^{4a}$ is H, —CN, or a $C_1$-$C_6$alkyl that is unsubstituted or is substituted with one or more $R^{15}$ groups.

Embodiment 155. The compound of any one of Embodiments 1 to 151, a stereoisomer thereof, or a pharmaceutically acceptable salt thereof, wherein $R^{4a}$ is H or $C_1$-$C_6$alkyl that is unsubstituted.

Embodiment 156. The compound of any one of Embodiments 1 to 151, a stereoisomer thereof, or a pharmaceutically acceptable salt thereof, wherein $R^{4a}$ is H or —$CH_3$ Embodiment 157. The compound of any one of Embodiments 1 to 156, a stereoisomer thereof, or a pharmaceutically acceptable salt thereof, wherein $R^{4b}$ is H, —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, $C_1$-$C_6$alkyl or $C_1$-$C_6$alkyl substituted with —C(═O)OH, —OH, CN or $NH_2$.

Embodiment 158. The compound of any one of Embodiments 1 to 156, a stereoisomer thereof, or a pharmaceutically acceptable salt thereof, wherein $R^{4b}$ is H, —CN, a 4 to 7 membered heterocycloalkyl wherein 1, 2 or 3 ring members are each independently selected from N, $NR^6$, O and S, or a $C_1$-$C_6$alkyl that is unsubstituted or is substituted with one or more $R^{15}$ groups.

Embodiment 159. The compound of any one of Embodiments 1 to 156, a stereoisomer thereof, or a pharmaceutically acceptable salt thereof, wherein $R^{4b}$ is H, —CN, or a $C_1$-$C_6$alkyl that is unsubstituted or is substituted with one or more $R^{15}$ groups.

Embodiment 160. The compound of any one of Embodiments 1 to 156, a stereoisomer thereof, or a pharmaceutically acceptable salt thereof, wherein $R^{4b}$ is H or $C_1$-$C_6$alkyl that is unsubstituted.

Embodiment 161. The compound of any one of Embodiments 1 to 156, a stereoisomer thereof, or a pharmaceutically acceptable salt thereof, wherein $R^{4b}$ is H or —$CH_3$ Embodiment 162. The compound of any one of Embodiments 1 to 161, a stereoisomer thereof, or a pharmaceutically acceptable salt thereof, wherein $R^{3c}$ is H, —C(═O)$C_2$-$C_6$alkenyl or $C_1$-$C_6$alkyl substituted with one or more $R^{15}$ groups.

Embodiment 163. The compound of any one of Embodiments 1 to 161, a stereoisomer thereof, or a pharmaceutically acceptable salt thereof, wherein $R^{3c}$ is —C(═O)$C_2$-$C_6$alkenyl or $C_1$-$C_6$alkyl substituted with one or more $R^{15}$ groups.

Embodiment 164. The compound of any one of Embodiments 1 to 161, a stereoisomer thereof, or a pharmaceutically acceptable salt thereof, wherein $R^{3c}$ is —C(═O)$C_2$-$C_6$alkenyl.

Embodiment 165. The compound of any one of Embodiments 1 to 161, a stereoisomer thereof, or a pharmaceutically acceptable salt thereof, wherein $R^{3c}$ is $C_1$-$C_6$alkyl substituted with one or more $R^{15}$ groups.

Embodiment 166. The compound of any one of Embodiments 1 to 165, a stereoisomer thereof, or a pharmaceutically acceptable salt thereof, wherein each $R^6$ is independently selected from the group consisting of H, $C_1$-$C_6$alkyl, —S(═O)$_2$N($R^7$)$_2$, —C(═O)N($R^7$)$_2$ and $C_1$-$C_6$alkyl substituted with —OH, CN or —C(═O)OH.

Embodiment 167. The compound of any one of Embodiments 1 to 165, a stereoisomer thereof, or a pharmaceutically acceptable salt thereof, wherein each $R^6$ is independently selected from the group consisting of H and $C_1$-$C_6$alkyl that is unsubstituted.

Embodiment 168. The compound of any one of Embodiments 1 to 165, a stereoisomer thereof, or a pharmaceutically acceptable salt thereof, wherein each $R^6$ is independently selected from the group consisting of —S(═O)$_2$N($R^7$)$_2$, —C(═O)N($R^7$)$_2$ and $C_1$-$C_6$alkyl substituted with —OH, CN or —C(═O)OH.

Embodiment 169. The compound of any one of Embodiments 1 to 168, a stereoisomer thereof, or a pharmaceutically acceptable salt thereof, wherein each $R^7$ is H.

Embodiment 170. The compound of any one of Embodiments 1 to 168, a stereoisomer thereof, or a pharmaceutically acceptable salt thereof, wherein each $R^7$ is $C_1$-$C_6$alkyl that is unsubstituted.

Embodiment 171. The compound of any one of Embodiments 1 to 168, a stereoisomer thereof, or a pharmaceutically acceptable salt thereof, wherein each $R^7$ is independently selected from the group consisting of H, and $C_1$-$C_6$alkyl that is unsubstituted or is substituted with OH or $C_1$-$C_6$alkoxy.

Embodiment 172. The compound of any one of Embodiments 1 to 168, a stereoisomer thereof, or a pharmaceutically acceptable salt thereof, wherein each $R^7$ is independently selected from the group consisting of H, —$CH_3$, and —($CH_2$)$_2$O$CH_3$.

Embodiment 173. The compound of any one of Embodiments 1 to 172, a stereoisomer thereof, or a pharmaceutically acceptable salt thereof, wherein $R^8$ is H.

Embodiment 174. The compound of any one of Embodiments 1 to 172, a stereoisomer thereof, or a pharmaceutically acceptable salt thereof, wherein $R^8$ is $C_1$-$C_6$alkyl that is unsubstituted.

Embodiment 175. The compound of any one of Embodiments 1 to 172, a stereoisomer thereof, or a pharmaceutically acceptable salt thereof, wherein $R^8$ is $C_3$-$C_8$cycloalkyl, wherein the cycloalkyl is unsubstituted or is substituted with 1, 2, 3 or 4 $R^9$.

Embodiment 176. The compound of any one of Embodiments 1 to 172, a stereoisomer thereof, or a pharmaceutically acceptable salt thereof, wherein $R^8$ is $C_3$-$C_8$cycloalkyl, wherein the cycloalkyl is unsubstituted or is substituted with 1 or 2 $R^9$.

Embodiment 177. The compound of any one of Embodiments 1 to 172, a stereoisomer thereof, or a pharmaceutically acceptable salt thereof, wherein $R^8$ is a 4 to 6 membered heterocycloalkyl wherein 1, 2, 3 or 4 ring members are each independently selected from N, $NR^6$, O and S, and wherein the heterocycloalkyl is unsubstituted or is substituted with 1, 2,3 or 4 $R^9$.

Embodiment 178. The compound of any one of Embodiments 1 to 172, a stereoisomer thereof, or a pharmaceutically acceptable salt thereof, wherein $R^8$ is a 4 to 6 membered heterocycloalkyl wherein 1, 2, 3 or 4 ring members are each independently selected from N, $NR^6$, O and S, and wherein the heterocycloalkyl is unsubstituted or is substituted with 1, or 2 $R^9$.

Embodiment 179. The compound of any one of Embodiments 1 to 178, a stereoisomer thereof, or a pharmaceutically acceptable salt thereof, wherein $R^9$ is $NR^{10}R^{11}$.

Embodiment 180. The compound of any one of Embodiments 1 to 178, a stereoisomer thereof, or a pharmaceutically acceptable salt thereof, wherein $R^9$ is C(═O)N($R^7$)$_2$.

Embodiment 181. The compound of any one of Embodiments 1 to 178, a stereoisomer thereof, or a pharmaceutically acceptable salt thereof, wherein $R^9$ is $C_1$-$C_6$alkyl substituted with —OH or —N($R^7$)$_2$.

Embodiment 182. The compound of any one of Embodiments 1 to 181, a stereoisomer thereof, or a pharmaceutically acceptable salt thereof, wherein $R^{10}$ is H.

Embodiment 183. The compound of any one of Embodiments 1 to 181, a stereoisomer thereof, or a pharmaceutically acceptable salt thereof, wherein $R^{10}$ is $C_1$-$C_6$alkyl that is unsubstituted.

Embodiment 184. The compound of any one of Embodiments 1 to 183, a stereoisomer thereof, or a pharmaceutically acceptable salt thereof, wherein $R^{11}$ is H.

Embodiment 185. The compound of any one of Embodiments 1 to 183, a stereoisomer thereof, or a pharmaceutically acceptable salt thereof, wherein $R^{11}$ is $C_1$-$C_6$alkyl that is unsubstituted.

Embodiment 186. The compound of any one of Embodiments 1 to 183, a stereoisomer thereof, or a pharmaceutically acceptable salt thereof, wherein $R^{11}$ is —S(═O)$_2$$C_1$-$C_6$alkyl.

Embodiment 187. The compound of any one of Embodiments 1 to 186, a stereoisomer thereof, or a pharmaceutically acceptable salt thereof, wherein $R^{13}$ is H.

Embodiment 188. The compound of any one of Embodiments 1 to 186, a stereoisomer thereof, or a pharmaceutically acceptable salt thereof, wherein $R^{13}$ is —C(═O)N($R^7$)$_2$.

Embodiment 189. The compound of any one of Embodiments 1 to 186, a stereoisomer thereof, or a pharmaceutically acceptable salt thereof, wherein $R^{13}$ is a 5 or 6 membered heteroaryl wherein 1, 2 3 or 4 ring members are each independently selected from N, $NR^6$, 0 and S.

Embodiment 190. The compound of any one of Embodiments 1 to 189, a stereoisomer thereof, or a pharmaceutically acceptable salt thereof, wherein $R^{14}$ is a 5 or 6 membered heterocyclyl wherein 1, 2, 3 or 4 ring members are each independently selected from N, $NR^6$, O and S, and wherein the 5 or 6 membered heterocyclyl is unsubstituted, or is substituted with 1, 2, 3 or 4 $R^4$ and optionally substituted with 1 or 2 oxo.

Embodiment 191. The compound of any one of Embodiments 1 to 189, a stereoisomer thereof, or a pharmaceutically acceptable salt thereof, wherein $R^{14}$ is 6 membered heterocyclyl wherein 1, 2, 3 or 4 ring members are each independently selected from N, $NR^6$, O and S, and wherein the 6 membered heterocyclyl is unsubstituted, or is substituted with 1, 2, 3 or 4 $R^4$ and optionally substituted with 1 or 2 oxo.

Embodiment 192. The compound of any one of Embodiments 1 to 189, a stereoisomer thereof, or a pharmaceutically acceptable salt thereof, wherein $R^{14}$ is 6 membered heterocyclyl wherein 1 ring member is selected from N, $NR^6$, O and S, and wherein the 6 membered heterocyclyl is substituted with an oxo.

Embodiment 193. The compound of any one of Embodiments 1 to 189, a stereoisomer thereof, or a pharmaceutically acceptable salt thereof, wherein $R^{14}$ is 6 membered heterocyclyl wherein 1 ring member is selected from $NR^6$, and wherein the 6 membered heterocyclyl is substituted with an oxo.

Embodiment 194. The compound of any one of Embodiments 1 to 189, a stereoisomer thereof, or a pharmaceutically acceptable salt thereof, wherein $R^{14}$ is a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1, 2, 3 or 4 $R^4$.

Embodiment 195. The compound of any one of Embodiments 1 to 189, a stereoisomer thereof, or a pharmaceutically acceptable salt thereof, wherein $R^{14}$ is a 5 or a 6 membered heteroaryl wherein 1, 2, 3 or 4 ring members are each independently selected from N, $NR^6$, O and S, and wherein the 5 or a 6 membered heteroaryl is unsubstituted, or is substituted with 1 or 2 $R^4$.

Embodiment 196. The compound of any one of Embodiments 1 to 195, a stereoisomer thereof, or a pharmaceutically acceptable salt thereof, wherein each $R^{15}$ is independently selected from the group consisting of CN, $NH_2$, —OH, —C(═O)OH, —C(═O)N($R^7$)$_2$, —C(═O)C(═O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(═O)OH, $NH_2$, OH and $C_1$-$C_6$alkyl that is unsubstituted.

Embodiment 197. The compound of any one of Embodiments 1 to 195, a stereoisomer thereof, or a pharmaceutically acceptable salt thereof, wherein each $R^{15}$ is independently selected from the group consisting of CN, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S.

Embodiment 198. The compound of any one of Embodiments 1 to 195, a stereoisomer thereof, or a pharmaceutically acceptable salt thereof, wherein each $R^{15}$ is independently selected from the group consisting of CN and a 3 to 6 membered heterocycloalkyl wherein 1, 2 or 3 ring members are each independently selected from N, $NR^6$, O and S.

Embodiment 199. The compound of any one of Embodiments 1 to 195, a stereoisomer thereof, or a pharmaceutically acceptable salt thereof, wherein each $R^{15}$ is independently selected from the group consisting of CN and a 3 to 6 membered heterocycloalkyl wherein 1, 2 or 3 ring members are each independently selected from N, $NR^6$, O and S.

Embodiment 200. The compound of any one of Embodiments 1 to 195, a stereoisomer thereof, or a pharmaceutically acceptable salt thereof, wherein each $R^{15}$ is independently selected from the group consisting of CN and oxiranyl.

Embodiment 201. The compound of Embodiment 1, a stereoisomer thereof, or a pharmaceutically acceptable salt thereof, wherein:

$X_1$ is $CR^{3a}R^{3b}$, C═O or $NR^{3c}$;

$X_2$ is $CR^{4a}R^{4b}$ or C═O;

$R^1$ is selected from the group consisting of:

i) phenyl which is unsubstituted or is substituted 1 to 4 $R^5$ groups;

ii) spiro attached $C_3$-$C_8$cycloalkyl which is unsubstituted or is substituted 1 to 4 $R^5$ groups;

iii) bicyclic $C_3$-$C_8$cycloalkyl which is unsubstituted or is substituted 1 to 4 $R^5$ groups;

iv) $C_3$-$C_8$cycloalkyl which is unsubstituted or is substituted 1 to 4 $R^5$ groups;

v) a 5 or 6 membered heteroaryl wherein 1, 2, 3 or 4 ring members are each independently selected from N, $NR^6$, O and S, wherein the 5 or 6 membered heteroaryl is unsubstituted or is substituted 1 to 4 $R^5$ groups;

vi) $C_1$-$C_6$alkyl that is unsubstituted;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted 1 to 4 $R^5$ groups; and viii) a 5 or 6 membered heterocycloalkyl wherein 1, 2, 3 or 4 ring members are each independently selected from N, $NR^6$, O and S, wherein the 5 or 6 membered heterocycloalkyl is unsubstituted or is substituted 1 to 4 $R^5$ groups and wherein the 5 or 6 membered heterocycloalkyl is optionally substituted with oxo;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or substituted with 1 or 2 $R^{12}$ groups;

ii) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or substituted with 1 or 2 $R^{12}$ groups; and iii) a 9 or 10 membered bicyclic heteroaryl wherein 1, 2, 3, 4 or 5 ring members are each independently selected from N, $NR^6$, O and S, and wherein the 9 or membered bicyclic heteroaryl is unsubstituted or substituted with 1 or 2 $R^{12}$ groups;

$R^{3a}$ is —CN, or $C_1$-$C_6$alkyl substituted with one or more $R^{15}$ groups;

$R^{3b}$ is H or $C_1$-$C_6$alkyl that is unsubstituted;

$R^{4a}$ is H or $C_1$-$C_6$alkyl that is unsubstituted;

$R^{4b}$ is H;

$R^{3c}$ is H, —C(═O)$C_2$-$C_6$alkenyl or $C_1$-$C_6$alkyl substituted with one or more $R^{15}$ groups; each $R^5$ is independently selected from the group consisting of $C_1$-$C_6$alkyl that is unsubstituted, $C_1$-$C_6$haloalkyl and halo; and each $R^6$ is independently selected from the group consisting of H and $C_1$-$C_6$alkyl that is unsubstituted.

Embodiment 202. The compound of Embodiment 1, a stereoisomer thereof, or a pharmaceutically acceptable salt thereof, wherein $X_1$ is $CR^{3a}R^{3b}$, C═O or $NR^{3c}$;

$X_2$ is $CR^{4a}R^{4b}$ or C═O;

$R^1$ is phenyl or pyridyl, each of which is unsubstituted or is substituted 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1 $R^{12}$ groups; and ii) a 9 or 10 membered bicyclic heteroaryl wherein 1, 2, 3, 4 or 5 ring members are each independently selected from N, and wherein the 9 or 10 membered bicyclic heteroaryl is unsubstituted or is substituted with 1 $R^{12}$ groups;

$R^{3a}$ is —CN;

$R^{3b}$ is H;

$R^{4a}$ is H; and $R^{4b}$ is H.

Embodiment 203. The compound of Embodiment 16, a stereoisomer thereof, or a pharmaceutically acceptable salt thereof, wherein:

$R^1$ is phenyl or pyridyl, each of which is unsubstituted or is substituted 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1 $R^{12}$ groups; and ii) a 9 or 10 membered bicyclic heteroaryl wherein 1, 2, 3, 4 or 5 ring members are each independently selected from N, and wherein the 9 or 10 membered bicyclic heteroaryl is unsubstituted or is substituted with 1 $R^{12}$ groups;

$R^{3a}$ is —CN;

$R^{3b}$ is H;

$R^{4a}$ is H; and $R^{4b}$ is H.

Embodiment 204. The compound of Embodiment 16, a stereoisomer thereof, or a pharmaceutically acceptable salt thereof, wherein $R^1$ is phenyl or pyridyl, each of which is unsubstituted or is substituted 1 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1 $R^{12}$ groups;

and ii) a 9 or 10 membered bicyclic heteroaryl wherein 1, 2, 3, 4 or 5 ring members are each independently selected from N, and wherein the 9 or 10 membered bicyclic heteroaryl is unsubstituted or is substituted with 1 $R^{12}$ groups;

$R^{3a}$ is —CN;

$R^{3b}$ is H;

$R^{4a}$ is H;

$R^{4b}$ is H, and $R^5$ is $C_1$-$C_6$haloalkyl, halo or $C_1$-$C_6$haloalkoxy.

Embodiment 205. The compound of Embodiment 16, a stereoisomer thereof, or a pharmaceutically acceptable salt thereof, wherein $R^1$ is pyridin-3-yl substituted with —$CF_3$;

$R^2$ is 3-(isoquinolin-4-yl) which is unsubstituted;

$R^{3a}$ is —CN.

Embodiment 206. The compound of Embodiment 1, a stereoisomer thereof, or a pharmaceutically acceptable salt thereof, wherein the compound is selected from: 3-(isoquinolin-4-yl)-2-oxo-1-phenylimidazolidine-4-carbonitrile; 1-(3-chlorophenyl)-3-(isoquinolin-4-yl)-2-oxoimidazolidine-4-carbonitrile; 3-(isoquinolin-4-yl)-2-oxo-1-(5-(trifluoromethyl)pyridin-2-yl) imidazolidine-4-carbonitrile; 3-(isoquinolin-4-yl)-2-oxo-1-(4-(trifluoromethyl)phenyl)imidazolidine-4-carbonitrile; 1-(4-chlorophenyl)-3-(isoquinolin-4-yl)-2-oxoimidazolidine-4-carbonitrile; 1-(4-fluorophenyl)-3-(isoquinolin-4-yl)-2-oxoimidazolidine-4-carbonitrile; 1-(3-fluorophenyl)-3-(isoquinolin-4-yl)-2-oxoimidazolidine-4-carbonitrile; 1-(5-fluoropyridin-2-yl)-3-(isoquinolin-4-yl)-2-oxoimidazolidine-4-carbonitrile; 3-(isoquinolin-4-yl)-2-oxo-1-(6-(trifluoromethyl)pyridin-3-yl)imidazolidine-4-carbonitrile; and 1-(5-chloropyridin-2-yl)-3-(isoquinolin-4-yl)-2-oxoimidazolidine-4-carbonitrile.

Embodiment 207. The compound of Embodiment 1, a stereoisomer thereof, or a pharmaceutically acceptable salt thereof, wherein the compound is selected from:

3-(isoquinolin-4-yl)-2-oxo-1-phenylimidazolidine-4-carbonitrile;

(R)-3-(isoquinolin-4-yl)-2-oxo-1-phenylimidazolidine-4-carbonitrile;

(S)-3-(isoquinolin-4-yl)-2-oxo-1-phenylimidazolidine-4-carbonitrile;

1-(3-chlorophenyl)-3-(isoquinolin-4-yl)-2-oxoimidazolidine-4-carbonitrile;

(R)-1-(3-chlorophenyl)-3-(isoquinolin-4-yl)-2-oxoimidazolidine-4-carbonitrile;

(S)-1-(3-chlorophenyl)-3-(isoquinolin-4-yl)-2-oxoimidazolidine-4-carbonitrile;

3-(isoquinolin-4-yl)-2-oxo-1-(5-(trifluoromethyl)pyridin-2-yl)imidazolidine-4-carbonitrile;

(R)-3-(isoquinolin-4-yl)-2-oxo-1-(5-(trifluoromethyl)pyridin-2-yl)imidazolidine-4-carbonitrile;

(S)-3-(isoquinolin-4-yl)-2-oxo-1-(5-(trifluoromethyl)pyridin-2-yl)imidazolidine-4-carbonitrile;

3-(isoquinolin-4-yl)-2-oxo-1-(4-(trifluoromethyl)phenyl) imidazolidine-4-carbonitrile;

(R)-3-(isoquinolin-4-yl)-2-oxo-1-(4-(trifluoromethyl)phenyl)imidazolidine-4-carbonitrile;

(S)-3-(isoquinolin-4-yl)-2-oxo-1-(4-(trifluoromethyl)phenyl)imidazolidine-4-carbonitrile;

1-(4-chlorophenyl)-3-(isoquinolin-4-yl)-2-oxoimidazolidine-4-carbonitrile;

(R)-1-(4-chlorophenyl)-3-(isoquinolin-4-yl)-2-oxoimidazolidine-4-carbonitrile;

(S)-1-(4-chlorophenyl)-3-(isoquinolin-4-yl)-2-oxoimidazolidine-4-carbonitrile;

1-(4-fluorophenyl)-3-(isoquinolin-4-yl)-2-oxoimidazolidine-4-carbonitrile;

(R)-1-(4-fluorophenyl)-3-(isoquinolin-4-yl)-2-oxoimidazolidine-4-carbonitrile;

(S)-1-(4-fluorophenyl)-3-(isoquinolin-4-yl)-2-oxoimidazolidine-4-carbonitrile;

1-(3-fluorophenyl)-3-(isoquinolin-4-yl)-2-oxoimidazolidine-4-carbonitrile;

(R)-1-(3-fluorophenyl)-3-(isoquinolin-4-yl)-2-oxoimidazolidine-4-carbonitrile;

(S)-1-(3-fluorophenyl)-3-(isoquinolin-4-yl)-2-oxoimidazolidine-4-carbonitrile;

1-(5-fluoropyridin-2-yl)-3-(isoquinolin-4-yl)-2-oxoimidazolidine-4-carbonitrile;

(R)-1-(5-fluoropyridin-2-yl)-3-(isoquinolin-4-yl)-2-oxoimidazolidine-4-carbonitrile;

(S)-1-(5-fluoropyridin-2-yl)-3-(isoquinolin-4-yl)-2-oxoimidazolidine-4-carbonitrile;

3-(isoquinolin-4-yl)-2-oxo-1-(6-(trifluoromethyl)pyridin-3-yl)imidazolidine-4-carbonitrile;

(R)-3-(isoquinolin-4-yl)-2-oxo-1-(6-(trifluoromethyl)pyridin-3-yl)imidazolidine-4-carbonitrile;

(S)-3-(isoquinolin-4-yl)-2-oxo-1-(6-(trifluoromethyl)pyridin-3-yl)imidazolidine-4-carbonitrile;

1-(5-chloropyridin-2-yl)-3-(isoquinolin-4-yl)-2-oxoimidazolidine-4-carbonitrile;

(R)-1-(5-chloropyridin-2-yl)-3-(isoquinolin-4-yl)-2-oxoimidazolidine-4-carbonitrile, and (S)-1-(5-chloropyridin-2-yl)-3-(isoquinolin-4-yl)-2-oxoimidazolidine-4-carbonitrile.

Embodiment 208. The compound of Embodiment 1, a stereoisomer thereof, or a pharmaceutically acceptable salt thereof, wherein the compound is selected from:

3-(isoquinolin-4-yl)-2-oxo-1-phenylimidazolidine-4-carbonitrile;

(R)-3-(isoquinolin-4-yl)-2-oxo-1-phenylimidazolidine-4-carbonitrile;

(S)-3-(isoquinolin-4-yl)-2-oxo-1-phenylimidazolidine-4-carbonitrile;

1-(3-chlorophenyl)-3-(isoquinolin-4-yl)-2-oxoimidazolidine-4-carbonitrile;

(R)-1-(3-chlorophenyl)-3-(isoquinolin-4-yl)-2-oxoimidazolidine-4-carbonitrile;

(S)-1-(3-chlorophenyl)-3-(isoquinolin-4-yl)-2-oxoimidazolidine-4-carbonitrile;

3-(isoquinolin-4-yl)-2-oxo-1-(5-(trifluoromethyl)pyridin-2-yl)imidazolidine-4-carbonitrile;

3-(isoquinolin-4-yl)-2-oxo-1-(4-(trifluoromethyl)phenyl) imidazolidine-4-carbonitrile;

1-(4-chlorophenyl)-3-(isoquinolin-4-yl)-2-oxoimidazolidine-4-carbonitrile;

1-(4-fluorophenyl)-3-(isoquinolin-4-yl)-2-oxoimidazolidine-4-carbonitrile;

1-(3-fluorophenyl)-3-(isoquinolin-4-yl)-2-oxoimidazolidine-4-carbonitrile;

1-(5-fluoropyridin-2-yl)-3-(isoquinolin-4-yl)-2-oxoimidazolidine-4-carbonitrile;

3-(isoquinolin-4-yl)-2-oxo-1-(6-(trifluoromethyl)pyridin-3-yl)imidazolidine-4-carbonitrile;

1-(5-chloropyridin-2-yl)-3-(isoquinolin-4-yl)-2-oxoimidazolidine-4-carbonitrile;

(R)-3-(isoquinolin-4-yl)-2-oxo-1-(6-(trifluoromethyl)pyridin-3-yl)imidazolidine-4-carbonitrile;

(S)-3-(isoquinolin-4-yl)-2-oxo-1-(6-(trifluoromethyl)pyridin-3-yl)imidazolidine-4-carbonitrile;

3-(isoquinolin-4-yl)-1-(2-methoxy-4-(trifluoromethyl)phenyl)-2-oxoimidazolidine-4-carbonitrile;

(R)-3-(isoquinolin-4-yl)-1-(2-methoxy-4-(trifluoromethyl)phenyl)-2-oxoimidazolidine-4-carbonitrile;

(S)-3-(isoquinolin-4-yl)-1-(2-methoxy-4-(trifluoromethyl)phenyl)-2-oxoimidazolidine-4-carbonitrile;

3-(isoquinolin-4-yl)-2-oxo-1-(6-(trifluoromethyl)pyridazin-4-yl)imidazolidine-4-carbonitrile;

(R)-3-(isoquinolin-4-yl)-2-oxo-1-(6-(trifluoromethyl)pyridazin-4-yl)imidazolidine-4-carbonitrile;

(S)-3-(isoquinolin-4-yl)-2-oxo-1-(6-(trifluoromethyl)pyridazin-4-yl)imidazolidine-4-carbonitrile;

3-(isoquinolin-4-yl)-1-(5-methoxy-2-(trifluoromethyl)pyridin-4-yl)-2-oxoimidazolidine-4-carbonitrile;

(R)-3-(isoquinolin-4-yl)-1-(5-methoxy-2-(trifluoromethyl)pyridin-4-yl)-2-oxoimidazolidine-4-carbonitrile;

(S)-3-(isoquinolin-4-yl)-1-(5-methoxy-2-(trifluoromethyl)pyridin-4-yl)-2-oxoimidazolidine-4-carbonitrile;

1-(5-cyano-2-methoxyphenyl)-3-(isoquinolin-4-yl)-2-oxoimidazolidine-4-carbonitrile;

(R)-1-(5-cyano-2-methoxyphenyl)-3-(isoquinolin-4-yl)-2-oxoimidazolidine-4-carbonitrile;

(S)-1-(5-cyano-2-methoxyphenyl)-3-(isoquinolin-4-yl)-2-oxoimidazolidine-4-carbonitrile;

1-(5-chloropyrimidin-2-yl)-3-(isoquinolin-4-yl)-2-oxoimidazolidine-4-carbonitrile;

(R)-1-(5-chloropyrimidin-2-yl)-3-(isoquinolin-4-yl)-2-oxoimidazolidine-4-carbonitrile;

(S)-1-(5-chloropyrimidin-2-yl)-3-(isoquinolin-4-yl)-2-oxoimidazolidine-4-carbonitrile;

3-(isoquinolin-4-yl)-1-(2-methoxy-5-(trifluoromethyl)phenyl)-2-oxoimidazolidine-4-carbonitrile;

(R)-3-(isoquinolin-4-yl)-1-(2-methoxy-5-(trifluoromethyl)phenyl)-2-oxoimidazolidine-4-carbonitrile:

(S)-3-(isoquinolin-4-yl)-1-(2-methoxy-5-(trifluoromethyl)phenyl)-2-oxoimidazolidine-4-carbonitrile;

5-(4-cyano-3-(isoquinolin-4-yl)-2-oxoimidazolidin-1-yl)-2-(trifluoromethyl)isonicotinonitrile;

(R)-5-(4-cyano-3-(isoquinolin-4-yl)-2-oxoimidazolidin-1-yl)-2-(trifluoromethyl)isonicotinonitrile;

(S)-5-(4-cyano-3-(isoquinolin-4-yl)-2-oxoimidazolidin-1-yl)-2-(trifluoromethyl)isonicotinonitrile;

1-(4-cyano-2-methoxyphenyl)-3-(isoquinolin-4-yl)-2-oxoimidazolidine-4-carbonitrile;

(R)-1-(4-cyano-2-methoxyphenyl)-3-(isoquinolin-4-yl)-2-oxoimidazolidine-4-carbonitrile;

(S)-1-(4-cyano-2-methoxyphenyl)-3-(isoquinolin-4-yl)-2-oxoimidazolidine-4-carbonitrile;

1-(5-chloro-2-cyanophenyl)-3-(isoquinolin-4-yl)-2-oxoimidazolidine-4-carbonitrile;

(R)-1-(5-chloro-2-cyanophenyl)-3-(isoquinolin-4-yl)-2-oxoimidazolidine-4-carbonitrile;

(S)-1-(5-chloro-2-cyanophenyl)-3-(isoquinolin-4-yl)-2-oxoimidazolidine-4-carbonitrile;

1-(5-fluoro-2-methylphenyl)-3-(isoquinolin-4-yl)-2-oxoimidazolidine-4-carbonitrile;

(R)-1-(5-fluoro-2-methylphenyl)-3-(isoquinolin-4-yl)-2-oxoimidazolidine-4-carbonitrile;

(S)-1-(5-fluoro-2-methylphenyl)-3-(isoquinolin-4-yl)-2-oxoimidazolidine-4-carbonitrile;

1-(3-(difluoromethyl)phenyl)-3-(isoquinolin-4-yl)-2-oxoimidazolidine-4-carbonitrile;

(R)-1-(3-(difluoromethyl)phenyl)-3-(isoquinolin-4-yl)-2-oxoimidazolidine-4-carbonitrile;

(S)-1-(3-(difluoromethyl)phenyl)-3-(isoquinolin-4-yl)-2-oxoimidazolidine-4-carbonitrile;

3-(isoquinolin-4-yl)-1-(2-methoxypyridin-4-yl)-2-oxoimidazolidine-4-carbonitrile;

(R)-3-(isoquinolin-4-yl)-1-(2-methoxypyridin-4-yl)-2-oxoimidazolidine-4-carbonitrile;

(S)-3-(isoquinolin-4-yl)-1-(2-methoxypyridin-4-yl)-2-oxoimidazolidine-4-carbonitrile;

3-(isoquinolin-4-yl)-1-(2-methyl-5-(trifluoromethyl)phenyl)-2-oxoimidazolidine-4-carbonitrile;

(R)-3-(isoquinolin-4-yl)-1-(2-methyl-5-(trifluoromethyl)phenyl)-2-oxoimidazolidine-4-carbonitrile;

(S)-3-(isoquinolin-4-yl)-1-(2-methyl-5-(trifluoromethyl)phenyl)-2-oxoimidazolidine-4-carbonitrile;

1-((R)-1-(2-hydroxyacetyl)pyrrolidin-3-yl)-3-(isoquinolin-4-yl)-2-oxoimidazolidine-4-carbonitrile;

(R)-1-((R)-1-(2-hydroxyacetyl)pyrrolidin-3-yl)-3-(isoquinolin-4-yl)-2-oxoimidazolidine-4-carbonitrile;

(S)-1-((R)-1-(2-hydroxyacetyl)pyrrolidin-3-yl)-3-(isoquinolin-4-yl)-2-oxoimidazolidine-4-carbonitrile;

3-(isoquinolin-4-yl)-2-oxo-1-((R)-1-(3,3,3-trifluoropropyl)pyrrolidin-3-yl)imidazolidine-4-carbonitrile;

(R)-3-(isoquinolin-4-yl)-2-oxo-1-((R)-1-(3,3,3-trifluoropropyl)pyrrolidin-3-yl)imidazolidine-4-carbonitrile:

(S)-3-(isoquinolin-4-yl)-2-oxo-1-((R)-1-(3,3,3-trifluoropropyl)pyrrolidin-3-yl)imidazolidine-4-carbonitrile;

1-(3,3-difluorocyclobutyl)-3-(isoquinolin-4-yl)-2-oxoimidazolidine-4-carbonitrile;

1-(3-hydroxy-3-(trifluoromethyl)cyclobutyl)-3-(isoquinolin-4-yl)-2-oxoimidazolidine-4-carbonitrile;

1-(3,3-difluorocyclohexyl)-3-(isoquinolin-4-yl)-2-oxoimidazolidine-4-carbonitrile;

3-(isoquinolin-4-yl)-2-oxo-1-(5-(trifluoromethyl)pyridazin-3-yl)imidazolidine-4-carbonitrile;

(R)-3-(isoquinolin-4-yl)-2-oxo-1-(5-(trifluoromethyl)pyridazin-3-yl)imidazolidine-4-carbonitrile;

(S)-3-(isoquinolin-4-yl)-2-oxo-1-(5-(trifluoromethyl)pyridazin-3-yl)imidazolidine-4-carbonitrile;

3-(isoquinolin-4-yl)-1-(5-methoxy-2-(trifluoromethyl)pyrimidin-4-yl)-2-oxoimidazolidine-4-carbonitrile;

(R)-3-(isoquinolin-4-yl)-1-(5-methoxy-2-(trifluoromethyl)pyrimidin-4-yl)-2-oxoimidazolidine-4-carbonitrile;

(S)-3-(isoquinolin-4-yl)-1-(5-methoxy-2-(trifluoromethyl)pyrimidin-4-yl)-2-oxoimidazolidine-4-carbonitrile;

3-(isoquinolin-4-yl)-2-oxo-1-(5-(trifluoromethyl)pyrazin-2-yl)imidazolidine-4-carbonitrile;

(R)-3-(isoquinolin-4-yl)-2-oxo-1-(5-(trifluoromethyl)pyrazin-2-yl)imidazolidine-4-carbonitrile;

(S)-3-(isoquinolin-4-yl)-2-oxo-1-(5-(trifluoromethyl)pyrazin-2-yl)imidazolidine-4-carbonitrile;

4-(3-(3-chlorophenyl)-5-cyano-2-oxoimidazolidin-1-yl)isoquinoline-6-carboxylic acid;

(R)-4-(3-(3-chlorophenyl)-5-cyano-2-oxoimidazolidin-1-yl)isoquinoline-6-carboxylic acid;

(S)-4-(3-(3-chlorophenyl)-5-cyano-2-oxoimidazolidin-1-yl)isoquinoline-6-carboxylic acid;

1-(3-chlorophenyl)-3-(6-(2-hydroxypropan-2-yl)isoquinolin-4-yl)-2-oxoimidazolidine-4-carbonitrile;

4-(3-(3-chlorophenyl)-5-cyano-2-oxoimidazolidin-1-yl)isoquinoline-6-carboxamide;

4-(3-(3-chlorophenyl)-5-cyano-2-oxoimidazolidin-1-yl)-N-(2-methoxyethyl)isoquinoline-6-carboxamide;

1-(3-chlorophenyl)-3-(6-(methylsulfonyl)isoquinolin-4-yl)-2-oxoimidazolidine-4-carbonitrile;
(R)-1-(3-chlorophenyl)-3-(6-(methylsulfonyl)isoquinolin-4-yl)-2-oxoimidazolidine-4-carbonitrile;
(S)-1-(3-chlorophenyl)-3-(6-(methylsulfonyl)isoquinolin-4-yl)-2-oxoimidazolidine-4-carbonitrile;
1-(2-methoxy-5-(trifluoromethyl)phenyl)-3-(6-(methylsulfonyl)isoquinolin-4-yl)-2-oxoimidazolidine-4-carbonitrile;
(R)-1-(2-methoxy-5-(trifluoromethyl)phenyl)-3-(6-(methylsulfonyl)isoquinolin-4-yl)-2-oxoimidazolidine-4-carbonitrile;
(S)-1-(2-methoxy-5-(trifluoromethyl)phenyl)-3-(6-(methylsulfonyl)isoquinolin-4-yl)-2-oxoimidazolidine-4-carbonitrile;
4-(3-(3-chlorophenyl)-5-cyano-2-oxoimidazolidin-1-yl)isoquinoline-6-carbonitrile;
(R)-4-(3-(3-chlorophenyl)-5-cyano-2-oxoimidazolidin-1-yl) isoquinoline-6-carbonitrile;
(S)-4-(3-(3-chlorophenyl)-5-cyano-2-oxoimidazolidin-1-yl) isoquinoline-6-carbonitrile;
1-(3-chlorophenyl)-3-(isoquinolin-4-yl)-4-methyl-2-oxoimidazolidine-4-carbonitrile;
(R)-1-(3-chlorophenyl)-3-(isoquinolin-4-yl)-4-methyl-2-oxoimidazolidine-4-carbonitrile;
(S)-1-(3-chlorophenyl)-3-(isoquinolin-4-yl)-4-methyl-2-oxoimidazolidine-4-carbonitrile;
(R)-1-(5-chloropyridin-2-yl)-3-(isoquinolin-4-yl)-2-oxoimidazolidine-4-carbonitrile;
(S)-1-(5-chloropyridin-2-yl)-3-(isoquinolin-4-yl)-2-oxoimidazolidine-4-carbonitrile;
3-(isoquinolin-4-yl)-2-oxo-1-(5-(trifluoromethyl)pyrimidin-2-yl)imidazolidine-4-carbonitrile;
(R)-3-(isoquinolin-4-yl)-2-oxo-1-(5-(trifluoromethyl)pyrimidin-2-yl)imidazolidine-4-carbonitrile;
(S)-3-(isoquinolin-4-yl)-2-oxo-1-(5-(trifluoromethyl)pyrimidin-2-yl)imidazolidine-4-carbonitrile;
(5S)-1-(3-chlorophenyl)-3-(isoquinolin-4-yl)-5-methyl-2-oxoimidazolidine-4-carbonitrile;
(4R,5S)-1-(3-chlorophenyl)-3-(isoquinolin-4-yl)-5-methyl-2-oxoimidazolidine-4-carbonitrile;
(4S,5S)-1-(3-chlorophenyl)-3-(isoquinolin-4-yl)-5-methyl-2-oxoimidazolidine-4-carbonitrile;
3-(isoquinolin-4-yl)-1-(2-methylpyridin-4-yl)-2-oxoimidazolidine-4-carbonitrile;
(R)-3-(isoquinolin-4-yl)-1-(2-methylpyridin-4-yl)-2-oxoimidazolidine-4-carbonitrile;
(S)-3-(isoquinolin-4-yl)-1-(2-methylpyridin-4-yl)-2-oxoimidazolidine-4-carbonitrile;
(R)-3-(isoquinolin-4-yl)-2-oxo-1-(3-(trifluoromethyl)cyclobutyl)imidazolidine-4-carbonitrile;
(R)-3-(isoquinolin-4-yl)-2-oxo-1-((1 r,3R)-3-(trifluoromethyl)cyclobutyl)imidazolidine-4-carbonitrile;
(R)-3-(isoquinolin-4-yl)-2-oxo-1-((1s,3S)-3-(trifluoromethyl)cyclobutyl)imidazolidine-4-carbonitrile;
1-((R)-1-(2-hydroxyethyl)pyrrolidin-3-yl)-3-(isoquinolin-4-yl)-2-oxoimidazolidine-4-carbonitrile;
(R)-1-((R)-1-(2-hydroxyethyl)pyrrolidin-3-yl)-3-(isoquinolin-4-yl)-2-oxoimidazolidine-4-carbonitrile;
(S)-1-((R)-1-(2-hydroxyethyl)pyrrolidin-3-yl)-3-(isoquinolin-4-yl)-2-oxoimidazolidine-4-carbonitrile;
3-(isoquinolin-4-yl)-1-(3-methoxy-6-(trifluoromethyl)pyridin-2-yl)-2-oxoimidazolidine-4-carbonitrile;
(R)-3-(isoquinolin-4-yl)-1-(3-methoxy-6-(trifluoromethyl) pyridin-2-yl)-2-oxoimidazolidine-4-carbonitrile;
(S)-3-(isoquinolin-4-yl)-1-(3-methoxy-6-(trifluoromethyl) pyridin-2-yl)-2-oxoimidazolidine-4-carbonitrile:
3-(isoquinolin-4-yl)-1-(3-(methylsulfonyl)phenyl)-2-oxoimidazolidine-4-carbonitrile;
(R)-3-(isoquinolin-4-yl)-1-(3-(methylsulfonyl)phenyl)-2-oxoimidazolidine-4-carbonitrile;
(S)-3-(isoquinolin-4-yl)-1-(3-(methylsulfonyl)phenyl)-2-oxoimidazolidine-4-carbonitrile;
3-(isoquinolin-4-yl)-2-oxo-1-(4-(trifluoromethyl)pyrimidin-2-yl)imidazolidine-4-carbonitrile;
(R)-3-(isoquinolin-4-yl)-2-oxo-1-(4-(trifluoromethyl)pyrimidin-2-yl)imidazolidine-4-carbonitrile;
(S)-3-(isoquinolin-4-yl)-2-oxo-1-(4-(trifluoromethyl)pyrimidin-2-yl)imidazolidine-4-carbonitrile;
1-(4-cyanophenyl)-3-(isoquinolin-4-yl)-2-oxoimidazolidine-4-carbonitrile;
(R)-1-(4-cyanophenyl)-3-(isoquinolin-4-yl)-2-oxoimidazolidine-4-carbonitrile;
(S)-1-(4-cyanophenyl)-3-(isoquinolin-4-yl)-2-oxoimidazolidine-4-carbonitrile;
3-(isoquinolin-4-yl)-2-oxo-1-(6-(trifluoromethyl)pyridin-2-yl)imidazolidine-4-carbonitrile;
(R)-3-(isoquinolin-4-yl)-2-oxo-1-(6-(trifluoromethyl)pyridin-2-yl)imidazolidine-4-carbonitrile;
(S)-3-(isoquinolin-4-yl)-2-oxo-1-(6-(trifluoromethyl)pyridin-2-yl)imidazolidine-4-carbonitrile;
1-(3-cyanophenyl)-3-(isoquinolin-4-yl)-2-oxoimidazolidine-4-carbonitrile;
(R)-1-(3-cyanophenyl)-3-(isoquinolin-4-yl)-2-oxoimidazolidine-4-carbonitrile;
(S)-1-(3-cyanophenyl)-3-(isoquinolin-4-yl)-2-oxoimidazolidine-4-carbonitrile;
3-(isoquinolin-4-yl)-1-(4-methylpyrimidin-2-yl)-2-oxoimidazolidine-4-carbonitrile;
(R)-3-(isoquinolin-4-yl)-1-(4-methylpyrimidin-2-yl)-2-oxoimidazolidine-4-carbonitrile;
(S)-3-(isoquinolin-4-yl)-1-(4-methylpyrimidin-2-yl)-2-oxoimidazolidine-4-carbonitrile;
1-(5-chloropyridazin-3-yl)-3-(isoquinolin-4-yl)-2-oxoimidazolidine-4-carbonitrile;
(R)-1-(5-chloropyridazin-3-yl)-3-(isoquinolin-4-yl)-2-oxoimidazolidine-4-carbonitrile;
(S)-1-(5-chloropyridazin-3-yl)-3-(isoquinolin-4-yl)-2-oxoimidazolidine-4-carbonitrile;
1-(6-fluoropyridin-3-yl)-3-(isoquinolin-4-yl)-2-oxoimidazolidine-4-carbonitrile;
(R)-1-(6-fluoropyridin-3-yl)-3-(isoquinolin-4-yl)-2-oxoimidazolidine-4-carbonitrile;
(S)-1-(6-fluoropyridin-3-yl)-3-(isoquinolin-4-yl)-2-oxoimidazolidine-4-carbonitrile;
1-(2-fluorophenyl)-3-(isoquinolin-4-yl)-2-oxoimidazolidine-4-carbonitrile;
(R)-1-(2-fluorophenyl)-3-(isoquinolin-4-yl)-2-oxoimidazolidine-4-carbonitrile;
(S)-1-(2-fluorophenyl)-3-(isoquinolin-4-yl)-2-oxoimidazolidine-4-carbonitrile;
3-(isoquinolin-4-yl)-2-oxo-1-(2-(trifluoromethyl)pyridin-4-yl)imidazolidine-4-carbonitrile;
(R)-3-(isoquinolin-4-yl)-2-oxo-1-(2-(trifluoromethyl)pyridin-4-yl)imidazolidine-4-carbonitrile;
(S)-3-(isoquinolin-4-yl)-2-oxo-1-(2-(trifluoromethyl)pyridin-4-yl)imidazolidine-4-carbonitrile;
1-(5-chloro-3-methoxypyridin-2-yl)-3-(isoquinolin-4-yl)-2-oxoimidazolidine-4-carbonitrile;
(R)-1-(5-chloro-3-methoxypyridin-2-yl)-3-(isoquinolin-4-yl)-2-oxoimidazolidine-4-carbonitrile;
(S)-1-(5-chloro-3-methoxypyridin-2-yl)-3-(isoquinolin-4-yl)-2-oxoimidazolidine-4-carbonitrile;

1-(5-(difluoromethoxy)-2-fluorophenyl)-3-(isoquinolin-4-yl)-2-oxoimidazolidine-4-carbonitrile;

(R)-1-(5-(difluoromethoxy)-2-fluorophenyl)-3-(isoquinolin-4-yl)-2-oxoimidazolidine-4-carbonitrile:

(S)-1-(5-(difluoromethoxy)-2-fluorophenyl)-3-(isoquinolin-4-yl)-2-oxoimidazolidine-4-carbonitrile;

1-(4-chloro-2-cyanophenyl)-3-(isoquinolin-4-yl)-2-oxoimidazolidine-4-carbonitrile;

(R)-1-(4-chloro-2-cyanophenyl)-3-(isoquinolin-4-yl)-2-oxoimidazolidine-4-carbonitrile;

(S)-1-(4-chloro-2-cyanophenyl)-3-(isoquinolin-4-yl)-2-oxoimidazolidine-4-carbonitrile;

1-(6-fluoropyridin-2-yl)-3-(isoquinolin-4-yl)-2-oxoimidazolidine-4-carbonitrile;

(R)-1-(6-fluoropyridin-2-yl)-3-(isoquinolin-4-yl)-2-oxoimidazolidine-4-carbonitrile;

(S)-1-(6-fluoropyridin-2-yl)-3-(isoquinolin-4-yl)-2-oxoimidazolidine-4-carbonitrile;

3-(isoquinolin-4-yl)-1-(5-methyl-2-(trifluoromethyl)pyrimidin-4-yl)-2-oxoimidazolidine-4-carbonitrile;

(R)-3-(isoquinolin-4-yl)-1-(5-methyl-2-(trifluoromethyl)pyrimidin-4-yl)-2-oxoimidazolidine-4-carbonitrile;

(S)-3-(isoquinolin-4-yl)-1-(5-methyl-2-(trifluoromethyl)pyrimidin-4-yl)-2-oxoimidazolidine-4-carbonitrile;

1-(1H-indazol-7-yl)-3-(isoquinolin-4-yl)-2-oxoimidazolidine-4-carbonitrile;

(R)-1-(1H-indazol-7-yl)-3-(isoquinolin-4-yl)-2-oxoimidazolidine-4-carbonitrile;

(S)-1-(1H-indazol-7-yl)-3-(isoquinolin-4-yl)-2-oxoimidazolidine-4-carbonitrile;

1-(1-isopropyl-1H-pyrazol-4-yl)-3-(isoquinolin-4-yl)-2-oxoimidazolidine-4-carbonitrile;

(R)-1-(1-isopropyl-1H-pyrazol-4-yl)-3-(isoquinolin-4-yl)-2-oxoimidazolidine-4-carbonitrile;

(S)-1-(1-isopropyl-1H-pyrazol-4-yl)-3-(isoquinolin-4-yl)-2-oxoimidazolidine-4-carbonitrile;

3-(isoquinolin-4-yl)-1-(1-methyl-1H-pyrazol-4-yl)-2-oxoimidazolidine-4-carbonitrile;

(R)-3-(isoquinolin-4-yl)-1-(1-methyl-1H-pyrazol-4-yl)-2-oxoimidazolidine-4-carbonitrile;

(S)-3-(isoquinolin-4-yl)-1-(1-methyl-1H-pyrazol-4-yl)-2-oxoimidazolidine-4-carbonitrile;

1-(2,4-difluorophenyl)-3-(isoquinolin-4-yl)-2-oxoimidazolidine-4-carbonitrile;

(R)-1-(2,4-difluorophenyl)-3-(isoquinolin-4-yl)-2-oxoimidazolidine-4-carbonitrile;

(S)-1-(2,4-difluorophenyl)-3-(isoquinolin-4-yl)-2-oxoimidazolidine-4-carbonitrile;

3-(isoquinolin-4-yl)-1-(1-methyl-2-oxo-1,2-dihydropyridin-4-yl)-2-oxoimidazolidine-4-carbonitrile;

(R)-3-(isoquinolin-4-yl)-1-(1-methyl-2-oxo-1,2-dihydropyridin-4-yl)-2-oxoimidazolidine-4-carbonitrile;

(S)-3-(isoquinolin-4-yl)-1-(1-methyl-2-oxo-1,2-dihydropyridin-4-yl)-2-oxoimidazolidine-4-carbonitrile;

3-(isoquinolin-4-yl)-2-oxo-1-(5-(trifluoromethyl)-1H-imidazol-2-yl)imidazolidine-4-carbonitrile;

(R)-3-(isoquinolin-4-yl)-2-oxo-1-(5-(trifluoromethyl)-1H-imidazol-2-yl)imidazolidine-4-carbonitrile;

(S)-3-(isoquinolin-4-yl)-2-oxo-1-(5-(trifluoromethyl)-1H-imidazol-2-yl)imidazolidine-4-carbonitrile:

1-(3-(2-hydroxypropan-2-yl)phenyl)-3-(isoquinolin-4-yl)-2-oxoimidazolidine-4-carbonitrile;

(R)-1-(3-(2-hydroxypropan-2-yl)phenyl)-3-(isoquinolin-4-yl)-2-oxoimidazolidine-4-carbonitrile;

(S)-1-(3-(2-hydroxypropan-2-yl)phenyl)-3-(isoquinolin-4-yl)-2-oxoimidazolidine-4-carbonitrile;

1-(5-chloro-2-(trifluoromethyl)pyridin-4-yl)-3-(isoquinolin-4-yl)-2-oxoimidazolidine-4-carbonitrile;

3-(isoquinolin-4-yl)-1-(5-methyl-2-(trifluoromethyl)pyridin-4-yl)-2-oxoimidazolidine-4-carbonitrile;

(R)-3-(isoquinolin-4-yl)-1-(5-methyl-2-(trifluoromethyl)pyridin-4-yl)-2-oxoimidazolidine-4-carbonitrile;

(S)-3-(isoquinolin-4-yl)-1-(5-methyl-2-(trifluoromethyl)pyridin-4-yl)-2-oxoimidazolidine-4-carbonitrile;

1-(4-(difluoromethoxy)phenyl)-3-(isoquinolin-4-yl)-2-oxoimidazolidine-4-carbonitrile;

(R)-1-(4-(difluoromethoxy)phenyl)-3-(isoquinolin-4-yl)-2-oxoimidazolidine-4-carbonitrile;

(S)-1-(4-(difluoromethoxy)phenyl)-3-(isoquinolin-4-yl)-2-oxoimidazolidine-4-carbonitrile;

1-(3,4-difluorophenyl)-3-(isoquinolin-4-yl)-2-oxoimidazolidine-4-carbonitrile;

(R)-1-(3,4-difluorophenyl)-3-(isoquinolin-4-yl)-2-oxoimidazolidine-4-carbonitrile;

(S)-1-(3,4-difluorophenyl)-3-(isoquinolin-4-yl)-2-oxoimidazolidine-4-carbonitrile;

1-(4-cyano-3-fluorophenyl)-3-(isoquinolin-4-yl)-2-oxoimidazolidine-4-carbonitrile;

(R)-1-(4-cyano-3-fluorophenyl)-3-(isoquinolin-4-yl)-2-oxoimidazolidine-4-carbonitrile;

(S)-1-(4-cyano-3-fluorophenyl)-3-(isoquinolin-4-yl)-2-oxoimidazolidine-4-carbonitrile;

3-(isoquinolin-4-yl)-1-(2-methylpyridin-3-yl)-2-oxoimidazolidine-4-carbonitrile;

(R)-3-(isoquinolin-4-yl)-1-(2-methylpyridin-3-yl)-2-oxoimidazolidine-4-carbonitrile;

(S)-3-(isoquinolin-4-yl)-1-(2-methylpyridin-3-yl)-2-oxoimidazolidine-4-carbonitrile;

1-(6-(difluoromethyl)pyridin-3-yl)-3-(isoquinolin-4-yl)-2-oxoimidazolidine-4-carbonitrile;

(R)-1-(6-(difluoromethyl)pyridin-3-yl)-3-(isoquinolin-4-yl)-2-oxoimidazolidine-4-carbonitrile;

(S)-1-(6-(difluoromethyl)pyridin-3-yl)-3-(isoquinolin-4-yl)-2-oxoimidazolidine-4-carbonitrile;

(R)-1-(3-fluorophenyl)-3-(isoquinolin-4-yl)-2-oxoimidazolidine-4-carbonitrile;

(S)-1-(3-fluorophenyl)-3-(isoquinolin-4-yl)-2-oxoimidazolidine-4-carbonitrile;

1-(5-fluoro-6-(trifluoromethyl)pyridin-3-yl)-3-(isoquinolin-4-yl)-2-oxoimidazolidine-4-carbonitrile;

(R)-1-(5-fluoro-6-(trifluoromethyl)pyridin-3-yl)-3-(isoquinolin-4-yl)-2-oxoimidazolidine-4-carbonitrile;

(S)-1-(5-fluoro-6-(trifluoromethyl)pyridin-3-yl)-3-(isoquinolin-4-yl)-2-oxoimidazolidine-4-carbonitrile;

1-(5-(difluoromethyl)pyridin-2-yl)-3-(isoquinolin-4-yl)-2-oxoimidazolidine-4-carbonitrile;

(R)-1-(5-(difluoromethyl)pyridin-2-yl)-3-(isoquinolin-4-yl)-2-oxoimidazolidine-4-carbonitrile;

(S)-1-(5-(difluoromethyl)pyridin-2-yl)-3-(isoquinolin-4-yl)-2-oxoimidazolidine-4-carbonitrile;

3-(isoquinolin-4-yl)-1-(2-methylpyrimidin-5-yl)-2-oxoimidazolidine-4-carbonitrile;

(R)-3-(isoquinolin-4-yl)-1-(2-methylpyrimidin-5-yl)-2-oxoimidazolidine-4-carbonitrile;

(S)-3-(isoquinolin-4-yl)-1-(2-methylpyrimidin-5-yl)-2-oxoimidazolidine-4-carbonitrile;

1-(5-chloro-3-methylpyridin-2-yl)-3-(isoquinolin-4-yl)-2-oxoimidazolidine-4-carbonitrile;

(R)-1-(5-chloro-3-methylpyridin-2-yl)-3-(isoquinolin-4-yl)-2-oxoimidazolidine-4-carbonitrile;

(S)-1-(5-chloro-3-methylpyridin-2-yl)-3-(isoquinolin-4-yl)-2-oxoimidazolidine-4-carbonitrile;

3-(isoquinolin-4-yl)-2-oxo-1-(6-(trifluoromethyl)pyridazin-3-yl)imidazolidine-4-carbonitrile;

(R)-3-(isoquinolin-4-yl)-2-oxo-1-(6-(trifluoromethyl)pyridazin-3-yl)imidazolidine-4-carbonitrile;

(S)-3-(isoquinolin-4-yl)-2-oxo-1-(6-(trifluoromethyl)pyridazin-3-yl)imidazolidine-4-carbonitrile;

3-(isoquinolin-4-yl)-1-(3-methyl-6-(trifluoromethyl)pyridin-2-yl)-2-oxoimidazolidine-4-carbonitrile;

(R)-3-(isoquinolin-4-yl)-1-(3-methyl-6-(trifluoromethyl)pyridin-2-yl)-2-oxoimidazolidine-4-carbonitrile;

(S)-3-(isoquinolin-4-yl)-1-(3-methyl-6-(trifluoromethyl)pyridin-2-yl)-2-oxoimidazolidine-4-carbonitrile;

1-(4-(difluoromethoxy)-2-fluorophenyl)-3-(isoquinolin-4-yl)-2-oxoimidazolidine-4-carbonitrile;

(R)-1-(4-(difluoromethoxy)-2-fluorophenyl)-3-(isoquinolin-4-yl)-2-oxoimidazolidine-4-carbonitrile;

(S)-1-(4-(difluoromethoxy)-2-fluorophenyl)-3-(isoquinolin-4-yl)-2-oxoimidazolidine-4-carbonitrile;

1-(4-(2-hydroxypropan-2-yl)phenyl)-3-(isoquinolin-4-yl)-2-oxoimidazolidine-4-carbonitrile;

(R)-1-(4-(2-hydroxypropan-2-yl)phenyl)-3-(isoquinolin-4-yl)-2-oxoimidazolidine-4-carbonitrile;

(S)-1-(4-(2-hydroxypropan-2-yl)phenyl)-3-(isoquinolin-4-yl)-2-oxoimidazolidine-4-carbonitrile;

1-(3,4-difluorophenyl)-3-(6-(methylsulfonyl)isoquinolin-4-yl)-2-oxoimidazolidine-4-carbonitrile;

(R)-1-(3,4-difluorophenyl)-3-(6-(methylsulfonyl)isoquinolin-4-yl)-2-oxoimidazolidine-4-carbonitrile;

(S)-1-(3,4-difluorophenyl)-3-(6-(methylsulfonyl)isoquinolin-4-yl)-2-oxoimidazolidine-4-carbonitrile;

1-(3,5-difluorophenyl)-3-(6-(methylsulfonyl)isoquinolin-4-yl)-2-oxoimidazolidine-4-carbonitrile;

(R)-1-(3,5-difluorophenyl)-3-(6-(methylsulfonyl)isoquinolin-4-yl)-2-oxoimidazolidine-4-carbonitrile:

(S)-1-(3,5-difluorophenyl)-3-(6-(methylsulfonyl)isoquinolin-4-yl)-2-oxoimidazolidine-4-carbonitrile;

1-(3-chloro-4-fluorophenyl)-3-(isoquinolin-4-yl)-2-oxoimidazolidine-4-carbonitrile;

(R)-1-(3-chloro-4-fluorophenyl)-3-(isoquinolin-4-yl)-2-oxoimidazolidine-4-carbonitrile;

(S)-1-(3-chloro-4-fluorophenyl)-3-(isoquinolin-4-yl)-2-oxoimidazolidine-4-carbonitrile;

3-(isoquinolin-4-yl)-1-(2-methyl-5-(trifluoromethyl)pyridin-3-yl)-2-oxoimidazolidine-4-carbonitrile;

(R)-3-(isoquinolin-4-yl)-1-(2-methyl-5-(trifluoromethyl)pyridin-3-yl)-2-oxoimidazolidine-4-carbonitrile;

(S)-3-(isoquinolin-4-yl)-1-(2-methyl-5-(trifluoromethyl)pyridin-3-yl)-2-oxoimidazolidine-4-carbonitrile;

1-(3-(difluoromethoxy)phenyl)-3-(isoquinolin-4-yl)-2-oxoimidazolidine-4-carbonitrile;

(R)-1-(3-(difluoromethoxy)phenyl)-3-(isoquinolin-4-yl)-2-oxoimidazolidine-4-carbonitrile;

(S)-1-(3-(difluoromethoxy)phenyl)-3-(isoquinolin-4-yl)-2-oxoimidazolidine-4-carbonitrile;

1-(2-cyano-5-(trifluoromethyl)phenyl)-3-(isoquinolin-4-yl)-2-oxoimidazolidine-4-carbonitrile;

(R)-1-(2-cyano-5-(trifluoromethyl)phenyl)-3-(isoquinolin-4-yl)-2-oxoimidazolidine-4-carbonitrile;

(S)-1-(2-cyano-5-(trifluoromethyl)phenyl)-3-(isoquinolin-4-yl)-2-oxoimidazolidine-4-carbonitrile;

3-(isoquinolin-4-yl)-2-oxo-1-(4-(trifluoromethoxy)phenyl)imidazolidine-4-carbonitrile;

(R)-3-(isoquinolin-4-yl)-2-oxo-1-(4-(trifluoromethoxy)phenyl)imidazolidine-4-carbonitrile;

(S)-3-(isoquinolin-4-yl)-2-oxo-1-(4-(trifluoromethoxy)phenyl)imidazolidine-4-carbonitrile;

3-(isoquinolin-4-yl)-2-oxo-1-(3-(trifluoromethoxy)phenyl)imidazolidine-4-carbonitrile;

(R)-3-(isoquinolin-4-yl)-2-oxo-1-(3-(trifluoromethoxy)phenyl)imidazolidine-4-carbonitrile;

(S)-3-(isoquinolin-4-yl)-2-oxo-1-(3-(trifluoromethoxy)phenyl)imidazolidine-4-carbonitrile;

3-(isoquinolin-4-yl)-2-oxo-1-(2-(trifluoromethyl)pyrimidin-5-yl)imidazolidine-4-carbonitrile;

(R)-3-(isoquinolin-4-yl)-2-oxo-1-(2-(trifluoromethyl)pyrimidin-5-yl)imidazolidine-4-carbonitrile;

(S)-3-(isoquinolin-4-yl)-2-oxo-1-(2-(trifluoromethyl)pyrimidin-5-yl)imidazolidine-4-carbonitrile;

1-(6-isopropylpyridin-3-yl)-3-(isoquinolin-4-yl)-2-oxoimidazolidine-4-carbonitrile;

(R)-1-(6-isopropylpyridin-3-yl)-3-(isoquinolin-4-yl)-2-oxoimidazolidine-4-carbonitrile;

(S)-1-(6-isopropylpyridin-3-yl)-3-(isoquinolin-4-yl)-2-oxoimidazolidine-4-carbonitrile;

3-(isoquinolin-4-yl)-1-(2-methoxy-6-(trifluoromethyl)pyridin-3-yl)-2-oxoimidazolidine-4-carbonitrile;

(R)-3-(isoquinolin-4-yl)-1-(2-methoxy-6-(trifluoromethyl)pyridin-3-yl)-2-oxoimidazolidine-4-carbonitrile:

(S)-3-(isoquinolin-4-yl)-1-(2-methoxy-6-(trifluoromethyl)pyridin-3-yl)-2-oxoimidazolidine-4-carbonitrile;

3-(isoquinolin-4-yl)-1-(1-methyl-2-oxo-6-(trifluoromethyl)-1,2-dihydropyridin-3-yl)-2-oxoimidazolidine-4-carbonitrile;

(R)-3-(isoquinolin-4-yl)-1-(1-methyl-2-oxo-6-(trifluoromethyl)-1,2-dihydropyridin-3-yl)-2-oxoimidazolidine-4-carbonitrile;

(S)-3-(isoquinolin-4-yl)-1-(1-methyl-2-oxo-6-(trifluoromethyl)-1,2-dihydropyridin-3-yl)-2-oxoimidazolidine-4-carbonitrile;

(R)-3-(isoquinolin-4-yl)-2-oxo-1-(5-(trifluoromethyl)pyridin-2-yl)imidazolidine-4-carbonitrile;

(S)-3-(isoquinolin-4-yl)-2-oxo-1-(5-(trifluoromethyl)pyridin-2-yl)imidazolidine-4-carbonitrile;

1-(5,6-dimethylpyridin-3-yl)-3-(isoquinolin-4-yl)-2-oxoimidazolidine-4-carbonitrile;

(R)-1-(5,6-dimethylpyridin-3-yl)-3-(isoquinolin-4-yl)-2-oxoimidazolidine-4-carbonitrile;

(S)-1-(5,6-dimethylpyridin-3-yl)-3-(isoquinolin-4-yl)-2-oxoimidazolidine-4-carbonitrile;

(R)-3-(isoquinolin-4-yl)-2-oxo-1-(4-(trifluoromethyl)phenyl)imidazolidine-4-carbonitrile;

(S)-3-(isoquinolin-4-yl)-2-oxo-1-(4-(trifluoromethyl)phenyl)imidazolidine-4-carbonitrile;

3-(isoquinolin-4-yl)-1-(2-methoxy-5-(trifluoromethyl)pyridin-3-yl)-2-oxoimidazolidine-4-carbonitrile;

(R)-3-(isoquinolin-4-yl)-1-(2-methoxy-5-(trifluoromethyl)pyridin-3-yl)-2-oxoimidazolidine-4-carbonitrile;

(S)-3-(isoquinolin-4-yl)-1-(2-methoxy-5-(trifluoromethyl)pyridin-3-yl)-2-oxoimidazolidine-4-carbonitrile;

1-(5-(difluoromethoxy)-2-methylphenyl)-3-(isoquinolin-4-yl)-2-oxoimidazolidine-4-carbonitrile;

(R)-1-(5-(difluoromethoxy)-2-methylphenyl)-3-(isoquinolin-4-yl)-2-oxoimidazolidine-4-carbonitrile;

(S)-1-(5-(difluoromethoxy)-2-methylphenyl)-3-(isoquinolin-4-yl)-2-oxoimidazolidine-4-carbonitrile;

1-(2,6-dimethylpyridin-4-yl)-3-(isoquinolin-4-yl)-2-oxoimidazolidine-4-carbonitrile;

(R)-1-(2,6-dimethylpyridin-4-yl)-3-(isoquinolin-4-yl)-2-oxoimidazolidine-4-carbonitrile;

(S)-1-(2,6-dimethylpyridin-4-yl)-3-(isoquinolin-4-yl)-2-oxoimidazolidine-4-carbonitrile;

1-(4-chloro-2-methoxyphenyl)-3-(isoquinolin-4-yl)-2-oxoimidazolidine-4-carbonitrile;

(R)-1-(4-chloro-2-methoxyphenyl)-3-(isoquinolin-4-yl)-2-oxoimidazolidine-4-carbonitrile;

(S)-1-(4-chloro-2-methoxyphenyl)-3-(isoquinolin-4-yl)-2-oxoimidazolidine-4-carbonitrile;

3-(isoquinolin-4-yl)-2-oxo-1-(5-(trifluoromethyl)pyridin-3-yl)imidazolidine-4-carbonitrile;

(R)-3-(isoquinolin-4-yl)-2-oxo-1-(5-(trifluoromethyl)pyridin-3-yl)imidazolidine-4-carbonitrile;

(S)-3-(isoquinolin-4-yl)-2-oxo-1-(5-(trifluoromethyl)pyridin-3-yl)imidazolidine-4-carbonitrile;

1-(5-fluoro-2-methoxyphenyl)-3-(isoquinolin-4-yl)-2-oxoimidazolidine-4-carbonitrile;

(R)-1-(5-fluoro-2-methoxyphenyl)-3-(isoquinolin-4-yl)-2-oxoimidazolidine-4-carbonitrile:

(S)-1-(5-fluoro-2-methoxyphenyl)-3-(isoquinolin-4-yl)-2-oxoimidazolidine-4-carbonitrile;

3-(isoquinolin-4-yl)-2-oxo-1-(3-(trifluoromethyl)phenyl)imidazolidine-4-carbonitrile;

(R)-3-(isoquinolin-4-yl)-2-oxo-1-(3-(trifluoromethyl)phenyl)imidazolidine-4-carbonitrile;

(S)-3-(isoquinolin-4-yl)-2-oxo-1-(3-(trifluoromethyl)phenyl)imidazolidine-4-carbonitrile;

3-(isoquinolin-4-yl)-1-(4-methoxy-6-(trifluoromethyl)pyridin-3-yl)-2-oxoimidazolidine-4-carbonitrile;

(R)-3-(isoquinolin-4-yl)-1-(4-methoxy-6-(trifluoromethyl)pyridin-3-yl)-2-oxoimidazolidine-4-carbonitrile;

(S)-3-(isoquinolin-4-yl)-1-(4-methoxy-6-(trifluoromethyl)pyridin-3-yl)-2-oxoimidazolidine-4-carbonitrile;

1-(4-(difluoromethyl)phenyl)-3-(isoquinolin-4-yl)-2-oxoimidazolidine-4-carbonitrile;

(R)-1-(4-(difluoromethyl)phenyl)-3-(isoquinolin-4-yl)-2-oxoimidazolidine-4-carbonitrile;

(S)-1-(4-(difluoromethyl)phenyl)-3-(isoquinolin-4-yl)-2-oxoimidazolidine-4-carbonitrile;

1-(2,5-difluorophenyl)-3-(isoquinolin-4-yl)-2-oxoimidazolidine-4-carbonitrile;

(R)-1-(2,5-difluorophenyl)-3-(isoquinolin-4-yl)-2-oxoimidazolidine-4-carbonitrile;

(S)-1-(2,5-difluorophenyl)-3-(isoquinolin-4-yl)-2-oxoimidazolidine-4-carbonitrile;

1-(3,5-difluorophenyl)-3-(isoquinolin-4-yl)-2-oxoimidazolidine-4-carbonitrile;

(R)-1-(3,5-difluorophenyl)-3-(isoquinolin-4-yl)-2-oxoimidazolidine-4-carbonitrile;

(S)-1-(3,5-difluorophenyl)-3-(isoquinolin-4-yl)-2-oxoimidazolidine-4-carbonitrile;

1-(6-chloropyridin-2-yl)-3-(isoquinolin-4-yl)-2-oxoimidazolidine-4-carbonitrile;

(R)-1-(6-chloropyridin-2-yl)-3-(isoquinolin-4-yl)-2-oxoimidazolidine-4-carbonitrile;

(S)-1-(6-chloropyridin-2-yl)-3-(isoquinolin-4-yl)-2-oxoimidazolidine-4-carbonitrile;

3-(isoquinolin-4-yl)-1-(6-methoxypyridin-3-yl)-2-oxoimidazolidine-4-carbonitrile;

(R)-3-(isoquinolin-4-yl)-1-(6-methoxypyridin-3-yl)-2-oxoimidazolidine-4-carbonitrile;

(S)-3-(isoquinolin-4-yl)-1-(6-methoxypyridin-3-yl)-2-oxoimidazolidine-4-carbonitrile;

3-(isoquinolin-4-yl)-2-oxo-1-(6-oxo-1,6-dihydropyridin-3-yl)imidazolidine-4-carbonitrile;

1-(5-chloro-2-methylphenyl)-3-(isoquinolin-4-yl)-2-oxoimidazolidine-4-carbonitrile;

(R)-1-(5-chloro-2-methylphenyl)-3-(isoquinolin-4-yl)-2-oxoimidazolidine-4-carbonitrile;

(S)-1-(5-chloro-2-methylphenyl)-3-(isoquinolin-4-yl)-2-oxoimidazolidine-4-carbonitrile;

1-(5-chloro-2-methoxyphenyl)-3-(isoquinolin-4-yl)-2-oxoimidazolidine-4-carbonitrile;

(R)-1-(5-chloro-2-methoxyphenyl)-3-(isoquinolin-4-yl)-2-oxoimidazolidine-4-carbonitrile;

(S)-1-(5-chloro-2-methoxyphenyl)-3-(isoquinolin-4-yl)-2-oxoimidazolidine-4-carbonitrile;

1-(2-cyano-5-methylphenyl)-3-(isoquinolin-4-yl)-2-oxoimidazolidine-4-carbonitrile;

(R)-1-(2-cyano-5-methylphenyl)-3-(isoquinolin-4-yl)-2-oxoimidazolidine-4-carbonitrile;

(S)-1-(2-cyano-5-methylphenyl)-3-(isoquinolin-4-yl)-2-oxoimidazolidine-4-carbonitrile;

4-(4-cyano-3-(isoquinolin-4-yl)-2-oxoimidazolidin-1-yl)-6-(trifluoromethyl)nicotinonitrile;

(R)-4-(4-cyano-3-(isoquinolin-4-yl)-2-oxoimidazolidin-1-yl)-6-(trifluoromethyl)nicotinonitrile;

(S)-4-(4-cyano-3-(isoquinolin-4-yl)-2-oxoimidazolidin-1-yl)-6-(trifluoromethyl)nicotinonitrile;

3-(isoquinolin-4-yl)-1-(4-methyl-1H-imidazol-2-yl)-2-oxoimidazolidine-4-carbonitrile;

(R)-3-(isoquinolin-4-yl)-1-(4-methyl-1H-imidazol-2-yl)-2-oxoimidazolidine-4-carbonitrile;

(S)-3-(isoquinolin-4-yl)-1-(4-methyl-1H-imidazol-2-yl)-2-oxoimidazolidine-4-carbonitrile;

1-(4-chloro-1H-imidazol-2-yl)-3-(isoquinolin-4-yl)-2-oxoimidazolidine-4-carbonitrile;

(R)-1-(4-chloro-1H-imidazol-2-yl)-3-(isoquinolin-4-yl)-2-oxoimidazolidine-4-carbonitrile;

(S)-1-(4-chloro-1H-imidazol-2-yl)-3-(isoquinolin-4-yl)-2-oxoimidazolidine-4-carbonitrile;

3-(isoquinolin-4-yl)-1-(3-methylcyclobutyl)-2-oxoimidazolidine-4-carbonitrile;

(R)-3-(isoquinolin-4-yl)-1-((1s,3S)-3-methylcyclobutyl)-2-oxoimidazolidine-4-carbonitrile;

(R)-3-(isoquinolin-4-yl)-1-((1 r,3R)-3-methylcyclobutyl)-2-oxoimidazolidine-4-carbonitrile;

(S)-3-(isoquinolin-4-yl)-1-((1s,3R)-3-methylcyclobutyl)-2-oxoimidazolidine-4-carbonitrile;

(S)-3-(isoquinolin-4-yl)-1-((1 r,3S)-3-methylcyclobutyl)-2-oxoimidazolidine-4-carbonitrile;

1-(4-fluorocyclohexyl)-3-(isoquinolin-4-yl)-2-oxoimidazolidine-4-carbonitrile;

(R)-1-((1 r,4R)-4-fluorocyclohexyl)-3-(isoquinolin-4-yl)-2-oxoimidazolidine-4-carbonitrile;

(R)-1-((1s,4S)-4-fluorocyclohexyl)-3-(isoquinolin-4-yl)-2-oxoimidazolidine-4-carbonitrile;

(S)-1-((1 r,4S)-4-fluorocyclohexyl)-3-(isoquinolin-4-yl)-2-oxoimidazolidine-4-carbonitrile;

(S)-1-((1s,4R)-4-fluorocyclohexyl)-3-(isoquinolin-4-yl)-2-oxoimidazolidine-4-carbonitrile;

3-(isoquinolin-4-yl)-2-oxo-1-(spiro[3.3]heptan-2-yl)imidazolidine-4-carbonitrile;

(R)-3-(isoquinolin-4-yl)-2-oxo-1-(spiro[3.3]heptan-2-yl)imidazolidine-4-carbonitrile;

(S)-3-(isoquinolin-4-yl)-2-oxo-1-(spiro[3.3]heptan-2-yl)imidazolidine-4-carbonitrile;

1-(3-isopropylcyclobutyl)-3-(isoquinolin-4-yl)-2-oxoimidazolidine-4-carbonitrile;

(R)-1-((1s,3S)-3-isopropylcyclobutyl)-3-(isoquinolin-4-yl)-2-oxoimidazolidine-4-carbonitrile;

(R)-1-((1r,3R)-3-isopropylcyclobutyl)-3-(isoquinolin-4-yl)-2-oxoimidazolidine-4-carbonitrile;

(S)-1-((1s,3R)-3-isopropylcyclobutyl)-3-(isoquinolin-4-yl)-2-oxoimidazolidine-4-carbonitrile;

(S)-1-((1r,3S)-3-isopropylcyclobutyl)-3-(isoquinolin-4-yl)-2-oxoimidazolidine-4-carbonitrile;

1-(3-cyclopropylcyclobutyl)-3-(isoquinolin-4-yl)-2-oxoimidazolidine-4-carbonitrile;

(R)-1-((1s,3S)-3-cyclopropylcyclobutyl)-3-(isoquinolin-4-yl)-2-oxoimidazolidine-4-carbonitrile;

(R)-1-((1 r,3R)-3-cyclopropylcyclobutyl)-3-(isoquinolin-4-yl)-2-oxoimidazolidine-4-carbonitrile;

(S)-1-((1 r,3S)-3-cyclopropylcyclobutyl)-3-(isoquinolin-4-yl)-2-oxoimidazolidine-4-carbonitrile;

(S)-1-((1s,3R)-3-cyclopropylcyclobutyl)-3-(isoquinolin-4-yl)-2-oxoimidazolidine-4-carbonitrile;

3-(isoquinolin-4-yl)-2-oxo-1-(spiro[2.3]hexan-5-yl)imidazolidine-4-carbonitrile;

(R)-3-(isoquinolin-4-yl)-2-oxo-1-(spiro[2.3]hexan-5-yl)imidazolidine-4-carbonitrile;

(S)-3-(isoquinolin-4-yl)-2-oxo-1-(spiro[2.3]hexan-5-yl)imidazolidine-4-carbonitrile;

1-(3,3-dimethylcyclobutyl)-3-(isoquinolin-4-yl)-2-oxoimidazolidine-4-carbonitrile;

(R)-1-(3,3-dimethylcyclobutyl)-3-(isoquinolin-4-yl)-2-oxoimidazolidine-4-carbonitrile;

(S)-1-(3,3-dimethylcyclobutyl)-3-(isoquinolin-4-yl)-2-oxoimidazolidine-4-carbonitrile;

1-(6,6-difluorospiro[3.3]heptan-2-yl)-3-(isoquinolin-4-yl)-2-oxoimidazolidine-4-carbonitrile;

(R)-1-(6,6-difluorospiro[3.3]heptan-2-yl)-3-(isoquinolin-4-yl)-2-oxoimidazolidine-4-carbonitrile;

(S)-1-(6,6-difluorospiro[3.3]heptan-2-yl)-3-(isoquinolin-4-yl)-2-oxoimidazolidine-4-carbonitrile;

3-(isoquinolin-4-yl)-2-oxo-1-((1 r,4r)-4-(trifluoromethyl)cyclohexyl)imidazolidine-4-carbonitrile;

(R)-3-(isoquinolin-4-yl)-2-oxo-1-((1 r,4R)-4-(trifluoromethyl)cyclohexyl)imidazolidine-4-carbonitrile;

(S)-3-(isoquinolin-4-yl)-2-oxo-1-((1 r,4S)-4-(trifluoromethyl)cyclohexyl)imidazolidine-4-carbonitrile;

3-(isoquinolin-4-yl)-2-oxo-1-(1-((trifluoromethyl)sulfonyl)azetidin-3-yl)imidazolidine-4-carbonitrile;

(R)-3-(isoquinolin-4-yl)-2-oxo-1-(1-((trifluoromethyl)sulfonyl)azetidin-3-yl)imidazolidine-4-carbonitrile;

(S)-3-(isoquinolin-4-yl)-2-oxo-1-(1-((trifluoromethyl)sulfonyl)azetidin-3-yl)imidazolidine-4-carbonitrile;

3-(isoquinolin-4-yl)-1-(1-(methylsulfonyl)azetidin-3-yl)-2-oxoimidazolidine-4-carbonitrile;

(R)-3-(isoquinolin-4-yl)-1-(1-(methylsulfonyl)azetidin-3-yl)-2-oxoimidazolidine-4-carbonitrile;

(S)-3-(isoquinolin-4-yl)-1-(1-(methylsulfonyl)azetidin-3-yl)-2-oxoimidazolidine-4-carbonitrile;

1-(1-(cyclopropylsulfonyl)azetidin-3-yl)-3-(isoquinolin-4-yl)-2-oxoimidazolidine-4-carbonitrile;

(R)-1-(1-(cyclopropylsulfonyl)azetidin-3-yl)-3-(isoquinolin-4-yl)-2-oxoimidazolidine-4-carbonitrile;

(S)-1-(1-(cyclopropylsulfonyl)azetidin-3-yl)-3-(isoquinolin-4-yl)-2-oxoimidazolidine-4-carbonitrile;

3-(isoquinolin-4-yl)-1-(1-methylazetidin-3-yl)-2-oxoimidazolidine-4-carbonitrile;

3-(isoquinolin-4-yl)-2-oxo-1-(1-(2,2,2-trifluoroethyl)azetidin-3-yl)imidazolidine-4-carbonitrile;

(R)-3-(isoquinolin-4-yl)-2-oxo-1-(1-(2,2,2-trifluoroethyl)azetidin-3-yl)imidazolidine-4-carbonitrile;

(S)-3-(isoquinolin-4-yl)-2-oxo-1-(1-(2,2,2-trifluoroethyl)azetidin-3-yl)imidazolidine-4-carbonitrile;

1-(1-acetylazetidin-3-yl)-3-(isoquinolin-4-yl)-2-oxoimidazolidine-4-carbonitrile;

(R)-1-(1-acetylazetidin-3-yl)-3-(isoquinolin-4-yl)-2-oxoimidazolidine-4-carbonitrile;

(S)-1-(1-acetylazetidin-3-yl)-3-(isoquinolin-4-yl)-2-oxoimidazolidine-4-carbonitrile;

1-(1-cyclopropylazetidin-3-yl)-3-(isoquinolin-4-yl)-2-oxoimidazolidine-4-carbonitrile;

(R)-1-(1-cyclopropylazetidin-3-yl)-3-(isoquinolin-4-yl)-2-oxoimidazolidine-4-carbonitrile;

(S)-1-(1-cyclopropylazetidin-3-yl)-3-(isoquinolin-4-yl)-2-oxoimidazolidine-4-carbonitrile;

3-(isoquinolin-4-yl)-2-oxo-1-(3-(trifluoromethyl)bicyclo[1.1.1]pentan-1-yl)imidazolidine-4-carbonitrile;

(R)-3-(isoquinolin-4-yl)-2-oxo-1-(3-(trifluoromethyl)bicyclo[1.1.1]pentan-1-yl)imidazolidine-4-carbonitrile;

(S)-3-(isoquinolin-4-yl)-2-oxo-1-(3-(trifluoromethyl)bicyclo[1.1.1]pentan-1-yl)imidazolidine-4-carbonitrile;

1-(4,4-difluorocyclohexyl)-3-(isoquinolin-4-yl)-2-oxoimidazolidine-4-carbonitrile;

(R)-1-(4,4-difluorocyclohexyl)-3-(isoquinolin-4-yl)-2-oxoimidazolidine-4-carbonitrile;

(S)-1-(4,4-difluorocyclohexyl)-3-(isoquinolin-4-yl)-2-oxoimidazolidine-4-carbonitrile;

1-(3-fluorobicyclo[1.1.1]pentan-1-yl)-3-(isoquinolin-4-yl)-2-oxoimidazolidine-4-carbonitrile;

(R)-1-(3-fluorobicyclo[1.1.1]pentan-1-yl)-3-(isoquinolin-4-yl)-2-oxoimidazolidine-4-carbonitrile;

(S)-1-(3-fluorobicyclo[1.1.1]pentan-1-yl)-3-(isoquinolin-4-yl)-2-oxoimidazolidine-4-carbonitrile;

3-(isoquinolin-4-yl)-1-neopentyl-2-oxoimidazolidine-4-carbonitrile;

(R)-3-(isoquinolin-4-yl)-1-neopentyl-2-oxoimidazolidine-4-carbonitrile;

(S)-3-(isoquinolin-4-yl)-1-neopentyl-2-oxoimidazolidine-4-carbonitrile;

1-(3,3-difluorocyclopentyl)-3-(isoquinolin-4-yl)-2-oxoimidazolidine-4-carbonitrile;

(R)-1-((R or S)-3,3-difluorocyclopentyl)-3-(isoquinolin-4-yl)-2-oxoimidazolidine-4-carbonitrile;

(S)-1-((R or S)-3,3-difluorocyclopentyl)-3-(isoquinolin-4-yl)-2-oxoimidazolidine-4-carbonitrile;

(S)-1-((R or S)-3,3-difluorocyclopentyl)-3-(isoquinolin-4-yl)-2-oxoimidazolidine-4-carbonitrile, and (R)-1-((R or S)-3,3-difluorocyclopentyl)-3-(isoquinolin-4-yl)-2-oxoimidazolidine-4-carbonitrile.

Embodiment 209. The compound of Embodiment 1, a stereoisomer thereof, or a pharmaceutically acceptable salt thereof, wherein the compound is selected from:

3-(isoquinolin-4-yl)-2-oxo-1-phenylimidazolidine-4-carbonitrile;

(R)-3-(isoquinolin-4-yl)-2-oxo-1-phenylimidazolidine-4-carbonitrile;

1-(3-chlorophenyl)-3-(isoquinolin-4-yl)-2-oxoimidazolidine-4-carbonitrile;

(R)-1-(3-chlorophenyl)-3-(isoquinolin-4-yl)-2-oxoimidazolidine-4-carbonitrile;

3-(isoquinolin-4-yl)-2-oxo-1-(5-(trifluoromethyl)pyridin-2-yl)imidazolidine-4-carbonitrile;

3-(isoquinolin-4-yl)-2-oxo-1-(4-(trifluoromethyl)phenyl)imidazolidine-4-carbonitrile;

1-(4-chlorophenyl)-3-(isoquinolin-4-yl)-2-oxoimidazolidine-4-carbonitrile;

1-(4-fluorophenyl)-3-(isoquinolin-4-yl)-2-oxoimidazolidine-4-carbonitrile;

1-(3-fluorophenyl)-3-(isoquinolin-4-yl)-2-oxoimidazolidine-4-carbonitrile;

1-(5-fluoropyridin-2-yl)-3-(isoquinolin-4-yl)-2-oxoimidazolidine-4-carbonitrile;

3-(isoquinolin-4-yl)-2-oxo-1-(6-(trifluoromethyl)pyridin-3-yl)imidazolidine-4-carbonitrile;

1-(5-chloropyridin-2-yl)-3-(isoquinolin-4-yl)-2-oxoimidazolidine-4-carbonitrile;

(R)-3-(isoquinolin-4-yl)-2-oxo-1-(6-(trifluoromethyl)pyridin-3-yl)imidazolidine-4-carbonitrile;

3-(isoquinolin-4-yl)-1-(2-methoxy-4-(trifluoromethyl)phenyl)-2-oxoimidazolidine-4-carbonitrile;

(R)-3-(isoquinolin-4-yl)-1-(2-methoxy-4-(trifluoromethyl)phenyl)-2-oxoimidazolidine-4-carbonitrile;

3-(isoquinolin-4-yl)-2-oxo-1-(6-(trifluoromethyl)pyridazin-4-yl)imidazolidine-4-carbonitrile;

(R)-3-(isoquinolin-4-yl)-2-oxo-1-(6-(trifluoromethyl)pyridazin-4-yl)imidazolidine-4-carbonitrile;

3-(isoquinolin-4-yl)-1-(5-methoxy-2-(trifluoromethyl)pyridin-4-yl)-2-oxoimidazolidine-4-carbonitrile;

(R)-3-(isoquinolin-4-yl)-1-(5-methoxy-2-(trifluoromethyl)pyridin-4-yl)-2-oxoimidazolidine-4-carbonitrile;

1-(5-cyano-2-methoxyphenyl)-3-(isoquinolin-4-yl)-2-oxoimidazolidine-4-carbonitrile;

(R)-1-(5-cyano-2-methoxyphenyl)-3-(isoquinolin-4-yl)-2-oxoimidazolidine-4-carbonitrile;

1-(5-chloropyrimidin-2-yl)-3-(isoquinolin-4-yl)-2-oxoimidazolidine-4-carbonitrile;

(R)-1-(5-chloropyrimidin-2-yl)-3-(isoquinolin-4-yl)-2-oxoimidazolidine-4-carbonitrile;

3-(isoquinolin-4-yl)-1-(2-methoxy-5-(trifluoromethyl)phenyl)-2-oxoimidazolidine-4-carbonitrile;

(R)-3-(isoquinolin-4-yl)-1-(2-methoxy-5-(trifluoromethyl)phenyl)-2-oxoimidazolidine-4-carbonitrile;

5-(4-cyano-3-(isoquinolin-4-yl)-2-oxoimidazolidin-1-yl)-2-(trifluoromethyl)isonicotinonitrile;

(R)-5-(4-cyano-3-(isoquinolin-4-yl)-2-oxoimidazolidin-1-yl)-2-(trifluoromethyl)isonicotinonitrile;

1-(4-cyano-2-methoxyphenyl)-3-(isoquinolin-4-yl)-2-oxoimidazolidine-4-carbonitrile;

(R)-1-(4-cyano-2-methoxyphenyl)-3-(isoquinolin-4-yl)-2-oxoimidazolidine-4-carbonitrile;

1-(5-chloro-2-cyanophenyl)-3-(isoquinolin-4-yl)-2-oxoimidazolidine-4-carbonitrile;

(R)-1-(5-chloro-2-cyanophenyl)-3-(isoquinolin-4-yl)-2-oxoimidazolidine-4-carbonitrile;

1-(5-fluoro-2-methylphenyl)-3-(isoquinolin-4-yl)-2-oxoimidazolidine-4-carbonitrile;

(R)-1-(5-fluoro-2-methylphenyl)-3-(isoquinolin-4-yl)-2-oxoimidazolidine-4-carbonitrile;

1-(3-(difluoromethyl)phenyl)-3-(isoquinolin-4-yl)-2-oxoimidazolidine-4-carbonitrile;

(R)-1-(3-(difluoromethyl)phenyl)-3-(isoquinolin-4-yl)-2-oxoimidazolidine-4-carbonitrile;

3-(isoquinolin-4-yl)-1-(2-methoxypyridin-4-yl)-2-oxoimidazolidine-4-carbonitrile;

(R)-3-(isoquinolin-4-yl)-1-(2-methoxypyridin-4-yl)-2-oxoimidazolidine-4-carbonitrile;

3-(isoquinolin-4-yl)-1-(2-methyl-5-(trifluoromethyl)phenyl)-2-oxoimidazolidine-4-carbonitrile;

(R)-3-(isoquinolin-4-yl)-1-(2-methyl-5-(trifluoromethyl)phenyl)-2-oxoimidazolidine-4-carbonitrile;

1-((R)-1-(2-hydroxyacetyl)pyrrolidin-3-yl)-3-(isoquinolin-4-yl)-2-oxoimidazolidine-4-carbonitrile;

(R)-1-((R)-1-(2-hydroxyacetyl)pyrrolidin-3-yl)-3-(isoquinolin-4-yl)-2-oxoimidazolidine-4-carbonitrile;

3-(isoquinolin-4-yl)-2-oxo-1-((R)-1-(3,3,3-trifluoropropyl)pyrrolidin-3-yl)imidazolidine-4-carbonitrile;

(R)-3-(isoquinolin-4-yl)-2-oxo-1-((R)-1-(3,3,3-trifluoropropyl)pyrrolidin-3-yl)imidazolidine-4-carbonitrile;

1-(3,3-difluorocyclobutyl)-3-(isoquinolin-4-yl)-2-oxoimidazolidine-4-carbonitrile;

1-(3-hydroxy-3-(trifluoromethyl)cyclobutyl)-3-(isoquinolin-4-yl)-2-oxoimidazolidine-4-carbonitrile;

1-(3,3-difluorocyclohexyl)-3-(isoquinolin-4-yl)-2-oxoimidazolidine-4-carbonitrile;

3-(isoquinolin-4-yl)-2-oxo-1-(5-(trifluoromethyl)pyridazin-3-yl)imidazolidine-4-carbonitrile;

(R)-3-(isoquinolin-4-yl)-2-oxo-1-(5-(trifluoromethyl)pyridazin-3-yl)imidazolidine-4-carbonitrile;

3-(isoquinolin-4-yl)-1-(5-methoxy-2-(trifluoromethyl)pyrimidin-4-yl)-2-oxoimidazolidine-4-carbonitrile;

(R)-3-(isoquinolin-4-yl)-1-(5-methoxy-2-(trifluoromethyl)pyrimidin-4-yl)-2-oxoimidazolidine-4-carbonitrile;

3-(isoquinolin-4-yl)-2-oxo-1-(5-(trifluoromethyl)pyrazin-2-yl)imidazolidine-4-carbonitrile;

(R)-3-(isoquinolin-4-yl)-2-oxo-1-(5-(trifluoromethyl)pyrazin-2-yl)imidazolidine-4-carbonitrile;

4-(3-(3-chlorophenyl)-5-cyano-2-oxoimidazolidin-1-yl)isoquinoline-6-carboxylic acid;

(R)-4-(3-(3-chlorophenyl)-5-cyano-2-oxoimidazolidin-1-yl)isoquinoline-6-carboxylic acid;

1-(3-chlorophenyl)-3-(6-(2-hydroxypropan-2-yl)isoquinolin-4-yl)-2-oxoimidazolidine-4-carbonitrile;

4-(3-(3-chlorophenyl)-5-cyano-2-oxoimidazolidin-1-yl)isoquinoline-6-carboxamide;

4-(3-(3-chlorophenyl)-5-cyano-2-oxoimidazolidin-1-yl)-N-(2-methoxyethyl)isoquinoline-6-carboxamide;

1-(3-chlorophenyl)-3-(6-(methylsulfonyl)isoquinolin-4-yl)-2-oxoimidazolidine-4-carbonitrile;

(R)-1-(3-chlorophenyl)-3-(6-(methylsulfonyl)isoquinolin-4-yl)-2-oxoimidazolidine-4-carbonitrile;

1-(2-methoxy-5-(trifluoromethyl)phenyl)-3-(6-(methylsulfonyl)isoquinolin-4-yl)-2-oxoimidazolidine-4-carbonitrile;

(R)-1-(2-methoxy-5-(trifluoromethyl)phenyl)-3-(6-(methylsulfonyl)isoquinolin-4-yl)-2-oxoimidazolidine-4-carbonitrile;

4-(3-(3-chlorophenyl)-5-cyano-2-oxoimidazolidin-1-yl)isoquinoline-6-carbonitrile;

(R)-4-(3-(3-chlorophenyl)-5-cyano-2-oxoimidazolidin-1-yl)isoquinoline-6-carbonitrile;

1-(3-chlorophenyl)-3-(isoquinolin-4-yl)-4-methyl-2-oxoimidazolidine-4-carbonitrile;

(R)-1-(3-chlorophenyl)-3-(isoquinolin-4-yl)-4-methyl-2-oxoimidazolidine-4-carbonitrile;

(R)-1-(5-chloropyridin-2-yl)-3-(isoquinolin-4-yl)-2-oxoimidazolidine-4-carbonitrile;

3-(isoquinolin-4-yl)-2-oxo-1-(5-(trifluoromethyl)pyrimidin-2-yl)imidazolidine-4-carbonitrile;

(R)-3-(isoquinolin-4-yl)-2-oxo-1-(5-(trifluoromethyl)pyrimidin-2-yl)imidazolidine-4-carbonitrile;

(5S)-1-(3-chlorophenyl)-3-(isoquinolin-4-yl)-5-methyl-2-oxoimidazolidine-4-carbonitrile;

(4R,5S)-1-(3-chlorophenyl)-3-(isoquinolin-4-yl)-5-methyl-2-oxoimidazolidine-4-carbonitrile;

3-(isoquinolin-4-yl)-1-(2-methylpyridin-4-yl)-2-oxoimidazolidine-4-carbonitrile;

(R)-3-(isoquinolin-4-yl)-1-(2-methylpyridin-4-yl)-2-oxoimidazolidine-4-carbonitrile;

(R)-3-(isoquinolin-4-yl)-2-oxo-1-((1 r,3R)-3-(trifluoromethyl)cyclobutyl)imidazolidine-4-carbonitrile;

(R)-3-(isoquinolin-4-yl)-2-oxo-1-((1s,3S)-3-(trifluoromethyl)cyclobutyl)imidazolidine-4-carbonitrile;

1-((R)-1-(2-hydroxyethyl)pyrrolidin-3-yl)-3-(isoquinolin-4-yl)-2-oxoimidazolidine-4-carbonitrile;

(R)-1-((R)-1-(2-hydroxyethyl)pyrrolidin-3-yl)-3-(isoquinolin-4-yl)-2-oxoimidazolidine-4-carbonitrile;

3-(isoquinolin-4-yl)-1-(3-methoxy-6-(trifluoromethyl)pyridin-2-yl)-2-oxoimidazolidine-4-carbonitrile;

(R)-3-(isoquinolin-4-yl)-1-(3-methoxy-6-(trifluoromethyl)pyridin-2-yl)-2-oxoimidazolidine-4-carbonitrile;

3-(isoquinolin-4-yl)-1-(3-(methylsulfonyl)phenyl)-2-oxoimidazolidine-4-carbonitrile;

(R)-3-(isoquinolin-4-yl)-1-(3-(methylsulfonyl)phenyl)-2-oxoimidazolidine-4-carbonitrile;

3-(isoquinolin-4-yl)-2-oxo-1-(4-(trifluoromethyl)pyrimidin-2-yl)imidazolidine-4-carbonitrile;

(R)-3-(isoquinolin-4-yl)-2-oxo-1-(4-(trifluoromethyl)pyrimidin-2-yl)imidazolidine-4-carbonitrile;

1-(4-cyanophenyl)-3-(isoquinolin-4-yl)-2-oxoimidazolidine-4-carbonitrile;

(R)-1-(4-cyanophenyl)-3-(isoquinolin-4-yl)-2-oxoimidazolidine-4-carbonitrile;

3-(isoquinolin-4-yl)-2-oxo-1-(6-(trifluoromethyl)pyridin-2-yl)imidazolidine-4-carbonitrile;

(R)-3-(isoquinolin-4-yl)-2-oxo-1-(6-(trifluoromethyl)pyridin-2-yl)imidazolidine-4-carbonitrile;

1-(3-cyanophenyl)-3-(isoquinolin-4-yl)-2-oxoimidazolidine-4-carbonitrile;

(R)-1-(3-cyanophenyl)-3-(isoquinolin-4-yl)-2-oxoimidazolidine-4-carbonitrile;

3-(isoquinolin-4-yl)-1-(4-methylpyrimidin-2-yl)-2-oxoimidazolidine-4-carbonitrile;

(R)-3-(isoquinolin-4-yl)-1-(4-methylpyrimidin-2-yl)-2-oxoimidazolidine-4-carbonitrile;

1-(5-chloropyridazin-3-yl)-3-(isoquinolin-4-yl)-2-oxoimidazolidine-4-carbonitrile;

(R)-1-(5-chloropyridazin-3-yl)-3-(isoquinolin-4-yl)-2-oxoimidazolidine-4-carbonitrile;

1-(6-fluoropyridin-3-yl)-3-(isoquinolin-4-yl)-2-oxoimidazolidine-4-carbonitrile;

(R)-1-(6-fluoropyridin-3-yl)-3-(isoquinolin-4-yl)-2-oxoimidazolidine-4-carbonitrile;

1-(2-fluorophenyl)-3-(isoquinolin-4-yl)-2-oxoimidazolidine-4-carbonitrile;

(R)-1-(2-fluorophenyl)-3-(isoquinolin-4-yl)-2-oxoimidazolidine-4-carbonitrile;

3-(isoquinolin-4-yl)-2-oxo-1-(2-(trifluoromethyl)pyridin-4-yl)imidazolidine-4-carbonitrile;

(R)-3-(isoquinolin-4-yl)-2-oxo-1-(2-(trifluoromethyl)pyridin-4-yl)imidazolidine-4-carbonitrile;

1-(5-chloro-3-methoxypyridin-2-yl)-3-(isoquinolin-4-yl)-2-oxoimidazolidine-4-carbonitrile;

(R)-1-(5-chloro-3-methoxypyridin-2-yl)-3-(isoquinolin-4-yl)-2-oxoimidazolidine-4-carbonitrile;

1-(5-(difluoromethoxy)-2-fluorophenyl)-3-(isoquinolin-4-yl)-2-oxoimidazolidine-4-carbonitrile;

(R)-1-(5-(difluoromethoxy)-2-fluorophenyl)-3-(isoquinolin-4-yl)-2-oxoimidazolidine-4-carbonitrile;

1-(4-chloro-2-cyanophenyl)-3-(isoquinolin-4-yl)-2-oxoimidazolidine-4-carbonitrile;

(R)-1-(4-chloro-2-cyanophenyl)-3-(isoquinolin-4-yl)-2-oxoimidazolidine-4-carbonitrile;

1-(6-fluoropyridin-2-yl)-3-(isoquinolin-4-yl)-2-oxoimidazolidine-4-carbonitrile;

(R)-1-(6-fluoropyridin-2-yl)-3-(isoquinolin-4-yl)-2-oxoimidazolidine-4-carbonitrile;

3-(isoquinolin-4-yl)-1-(5-methyl-2-(trifluoromethyl)pyrimidin-4-yl)-2-oxoimidazolidine-4-carbonitrile;

(R)-3-(isoquinolin-4-yl)-1-(5-methyl-2-(trifluoromethyl)pyrimidin-4-yl)-2-oxoimidazolidine-4-carbonitrile;

1-(1H-indazol-7-yl)-3-(isoquinolin-4-yl)-2-oxoimidazolidine-4-carbonitrile;

(R)-1-(1H-indazol-7-yl)-3-(isoquinolin-4-yl)-2-oxoimidazolidine-4-carbonitrile;

1-(1-isopropyl-1H-pyrazol-4-yl)-3-(isoquinolin-4-yl)-2-oxoimidazolidine-4-carbonitrile;

(R)-1-(1-isopropyl-1H-pyrazol-4-yl)-3-(isoquinolin-4-yl)-2-oxoimidazolidine-4-carbonitrile;

3-(isoquinolin-4-yl)-1-(1-methyl-1H-pyrazol-4-yl)-2-oxoimidazolidine-4-carbonitrile;

(R)-3-(isoquinolin-4-yl)-1-(1-methyl-1H-pyrazol-4-yl)-2-oxoimidazolidine-4-carbonitrile;

1-(2,4-difluorophenyl)-3-(isoquinolin-4-yl)-2-oxoimidazolidine-4-carbonitrile;

(R)-1-(2,4-difluorophenyl)-3-(isoquinolin-4-yl)-2-oxoimidazolidine-4-carbonitrile;

3-(isoquinolin-4-yl)-1-(1-methyl-2-oxo-1,2-dihydropyridin-4-yl)-2-oxoimidazolidine-4-carbonitrile;

(R)-3-(isoquinolin-4-yl)-1-(1-methyl-2-oxo-1,2-dihydropyridin-4-yl)-2-oxoimidazolidine-4-carbonitrile;

3-(isoquinolin-4-yl)-2-oxo-1-(5-(trifluoromethyl)-1H-imidazol-2-yl)imidazolidine-4-carbonitrile;

(R)-3-(isoquinolin-4-yl)-2-oxo-1-(5-(trifluoromethyl)-1H-imidazol-2-yl)imidazolidine-4-carbonitrile;

1-(3-(2-hydroxypropan-2-yl)phenyl)-3-(isoquinolin-4-yl)-2-oxoimidazolidine-4-carbonitrile;

(R)-1-(3-(2-hydroxypropan-2-yl)phenyl)-3-(isoquinolin-4-yl)-2-oxoimidazolidine-4-carbonitrile;

1-(5-chloro-2-(trifluoromethyl)pyridin-4-yl)-3-(isoquinolin-4-yl)-2-oxoimidazolidine-4-carbonitrile;

3-(isoquinolin-4-yl)-1-(5-methyl-2-(trifluoromethyl)pyridin-4-yl)-2-oxoimidazolidine-4-carbonitrile;

(R)-3-(isoquinolin-4-yl)-1-(5-methyl-2-(trifluoromethyl)pyridin-4-yl)-2-oxoimidazolidine-4-carbonitrile;

1-(4-(difluoromethoxy)phenyl)-3-(isoquinolin-4-yl)-2-oxoimidazolidine-4-carbonitrile;

(R)-1-(4-(difluoromethoxy)phenyl)-3-(isoquinolin-4-yl)-2-oxoimidazolidine-4-carbonitrile;

1-(3,4-difluorophenyl)-3-(isoquinolin-4-yl)-2-oxoimidazolidine-4-carbonitrile;

(R)-1-(3,4-difluorophenyl)-3-(isoquinolin-4-yl)-2-oxoimidazolidine-4-carbonitrile;

1-(4-cyano-3-fluorophenyl)-3-(isoquinolin-4-yl)-2-oxoimidazolidine-4-carbonitrile;

(R)-1-(4-cyano-3-fluorophenyl)-3-(isoquinolin-4-yl)-2-oxoimidazolidine-4-carbonitrile;

3-(isoquinolin-4-yl)-1-(2-methylpyridin-3-yl)-2-oxoimidazolidine-4-carbonitrile;

(R)-3-(isoquinolin-4-yl)-1-(2-methylpyridin-3-yl)-2-oxoimidazolidine-4-carbonitrile;

1-(6-(difluoromethyl)pyridin-3-yl)-3-(isoquinolin-4-yl)-2-oxoimidazolidine-4-carbonitrile;

(R)-1-(6-(difluoromethyl)pyridin-3-yl)-3-(isoquinolin-4-yl)-2-oxoimidazolidine-4-carbonitrile;

(R)-1-(3-fluorophenyl)-3-(isoquinolin-4-yl)-2-oxoimidazolidine-4-carbonitrile;

1-(5-fluoro-6-(trifluoromethyl)pyridin-3-yl)-3-(isoquinolin-4-yl)-2-oxoimidazolidine-4-carbonitrile;

(R)-1-(5-fluoro-6-(trifluoromethyl)pyridin-3-yl)-3-(isoquinolin-4-yl)-2-oxoimidazolidine-4-carbonitrile;

1-(5-(difluoromethyl)pyridin-2-yl)-3-(isoquinolin-4-yl)-2-oxoimidazolidine-4-carbonitrile;

(R)-1-(5-(difluoromethyl)pyridin-2-yl)-3-(isoquinolin-4-yl)-2-oxoimidazolidine-4-carbonitrile;

3-(isoquinolin-4-yl)-1-(2-methylpyrimidin-5-yl)-2-oxoimidazolidine-4-carbonitrile;

(R)-3-(isoquinolin-4-yl)-1-(2-methylpyrimidin-5-yl)-2-oxoimidazolidine-4-carbonitrile;

1-(5-chloro-3-methylpyridin-2-yl)-3-(isoquinolin-4-yl)-2-oxoimidazolidine-4-carbonitrile;

(R)-1-(5-chloro-3-methylpyridin-2-yl)-3-(isoquinolin-4-yl)-2-oxoimidazolidine-4-carbonitrile;
3-(isoquinolin-4-yl)-2-oxo-1-(6-(trifluoromethyl)pyridazin-3-yl)imidazolidine-4-carbonitrile;
(R)-3-(isoquinolin-4-yl)-2-oxo-1-(6-(trifluoromethyl)pyridazin-3-yl)imidazolidine-4-carbonitrile;
3-(isoquinolin-4-yl)-1-(3-methyl-6-(trifluoromethyl)pyridin-2-yl)-2-oxoimidazolidine-4-carbonitrile;
(R)-3-(isoquinolin-4-yl)-1-(3-methyl-6-(trifluoromethyl)pyridin-2-yl)-2-oxoimidazolidine-4-carbonitrile;
1-(4-(difluoromethoxy)-2-fluorophenyl)-3-(isoquinolin-4-yl)-2-oxoimidazolidine-4-carbonitrile;
(R)-1-(4-(difluoromethoxy)-2-fluorophenyl)-3-(isoquinolin-4-yl)-2-oxoimidazolidine-4-carbonitrile;
1-(4-(2-hydroxypropan-2-yl)phenyl)-3-(isoquinolin-4-yl)-2-oxoimidazolidine-4-carbonitrile;
(R)-1-(4-(2-hydroxypropan-2-yl)phenyl)-3-(isoquinolin-4-yl)-2-oxoimidazolidine-4-carbonitrile;
1-(3,4-difluorophenyl)-3-(6-(methylsulfonyl)isoquinolin-4-yl)-2-oxoimidazolidine-4-carbonitrile;
(R)-1-(3,4-difluorophenyl)-3-(6-(methylsulfonyl)isoquinolin-4-yl)-2-oxoimidazolidine-4-carbonitrile;
1-(3,5-difluorophenyl)-3-(6-(methylsulfonyl)isoquinolin-4-yl)-2-oxoimidazolidine-4-carbonitrile;
(R)-1-(3,5-difluorophenyl)-3-(6-(methylsulfonyl)isoquinolin-4-yl)-2-oxoimidazolidine-4-carbonitrile;
1-(3-chloro-4-fluorophenyl)-3-(isoquinolin-4-yl)-2-oxoimidazolidine-4-carbonitrile;
(R)-1-(3-chloro-4-fluorophenyl)-3-(isoquinolin-4-yl)-2-oxoimidazolidine-4-carbonitrile;
3-(isoquinolin-4-yl)-1-(2-methyl-5-(trifluoromethyl)pyridin-3-yl)-2-oxoimidazolidine-4-carbonitrile;
(R)-3-(isoquinolin-4-yl)-1-(2-methyl-5-(trifluoromethyl)pyridin-3-yl)-2-oxoimidazolidine-4-carbonitrile;
1-(3-(difluoromethoxy)phenyl)-3-(isoquinolin-4-yl)-2-oxoimidazolidine-4-carbonitrile;
(R)-1-(3-(difluoromethoxy)phenyl)-3-(isoquinolin-4-yl)-2-oxoimidazolidine-4-carbonitrile;
1-(2-cyano-5-(trifluoromethyl)phenyl)-3-(isoquinolin-4-yl)-2-oxoimidazolidine-4-carbonitrile;
(R)-1-(2-cyano-5-(trifluoromethyl)phenyl)-3-(isoquinolin-4-yl)-2-oxoimidazolidine-4-carbonitrile;
3-(isoquinolin-4-yl)-2-oxo-1-(4-(trifluoromethoxy)phenyl)imidazolidine-4-carbonitrile;
(R)-3-(isoquinolin-4-yl)-2-oxo-1-(4-(trifluoromethoxy)phenyl)imidazolidine-4-carbonitrile;
3-(isoquinolin-4-yl)-2-oxo-1-(3-(trifluoromethoxy)phenyl)imidazolidine-4-carbonitrile;
(R)-3-(isoquinolin-4-yl)-2-oxo-1-(3-(trifluoromethoxy)phenyl)imidazolidine-4-carbonitrile;
3-(isoquinolin-4-yl)-2-oxo-1-(2-(trifluoromethyl)pyrimidin-5-yl)imidazolidine-4-carbonitrile;
(R)-3-(isoquinolin-4-yl)-2-oxo-1-(2-(trifluoromethyl)pyrimidin-5-yl)imidazolidine-4-carbonitrile;
1-(6-isopropylpyridin-3-yl)-3-(isoquinolin-4-yl)-2-oxoimidazolidine-4-carbonitrile;
(R)-1-(6-isopropylpyridin-3-yl)-3-(isoquinolin-4-yl)-2-oxoimidazolidine-4-carbonitrile;
3-(isoquinolin-4-yl)-1-(2-methoxy-6-(trifluoromethyl)pyridin-3-yl)-2-oxoimidazolidine-4-carbonitrile;
(R)-3-(isoquinolin-4-yl)-1-(2-methoxy-6-(trifluoromethyl)pyridin-3-yl)-2-oxoimidazolidine-4-carbonitrile;
3-(isoquinolin-4-yl)-1-(1-methyl-2-oxo-6-(trifluoromethyl)-1,2-dihydropyridin-3-yl)-2-oxoimidazolidine-4-carbonitrile;
(R)-3-(isoquinolin-4-yl)-1-(1-methyl-2-oxo-6-(trifluoromethyl)-1,2-dihydropyridin-3-yl)-2-oxoimidazolidine-4-carbonitrile;
(R)-3-(isoquinolin-4-yl)-2-oxo-1-(5-(trifluoromethyl)pyridin-2-yl)imidazolidine-4-carbonitrile;
1-(5,6-dimethylpyridin-3-yl)-3-(isoquinolin-4-yl)-2-oxoimidazolidine-4-carbonitrile;
(R)-1-(5,6-dimethylpyridin-3-yl)-3-(isoquinolin-4-yl)-2-oxoimidazolidine-4-carbonitrile;
(R)-3-(isoquinolin-4-yl)-2-oxo-1-(4-(trifluoromethyl)phenyl)imidazolidine-4-carbonitrile;
3-(isoquinolin-4-yl)-1-(2-methoxy-5-(trifluoromethyl)pyridin-3-yl)-2-oxoimidazolidine-4-carbonitrile;
(R)-3-(isoquinolin-4-yl)-1-(2-methoxy-5-(trifluoromethyl)pyridin-3-yl)-2-oxoimidazolidine-4-carbonitrile;
1-(5-(difluoromethoxy)-2-methylphenyl)-3-(isoquinolin-4-yl)-2-oxoimidazolidine-4-carbonitrile;
(R)-1-(5-(difluoromethoxy)-2-methylphenyl)-3-(isoquinolin-4-yl)-2-oxoimidazolidine-4-carbonitrile;
1-(2,6-dimethylpyridin-4-yl)-3-(isoquinolin-4-yl)-2-oxoimidazolidine-4-carbonitrile;
(R)-1-(2,6-dimethylpyridin-4-yl)-3-(isoquinolin-4-yl)-2-oxoimidazolidine-4-carbonitrile;
1-(4-chloro-2-methoxyphenyl)-3-(isoquinolin-4-yl)-2-oxoimidazolidine-4-carbonitrile;
(R)-1-(4-chloro-2-methoxyphenyl)-3-(isoquinolin-4-yl)-2-oxoimidazolidine-4-carbonitrile;
3-(isoquinolin-4-yl)-2-oxo-1-(5-(trifluoromethyl)pyridin-3-yl)imidazolidine-4-carbonitrile;
(R)-3-(isoquinolin-4-yl)-2-oxo-1-(5-(trifluoromethyl)pyridin-3-yl)imidazolidine-4-carbonitrile;
1-(5-fluoro-2-methoxyphenyl)-3-(isoquinolin-4-yl)-2-oxoimidazolidine-4-carbonitrile;
(R)-1-(5-fluoro-2-methoxyphenyl)-3-(isoquinolin-4-yl)-2-oxoimidazolidine-4-carbonitrile;
3-(isoquinolin-4-yl)-2-oxo-1-(3-(trifluoromethyl)phenyl)imidazolidine-4-carbonitrile;
(R)-3-(isoquinolin-4-yl)-2-oxo-1-(3-(trifluoromethyl)phenyl)imidazolidine-4-carbonitrile;
3-(isoquinolin-4-yl)-1-(4-methoxy-6-(trifluoromethyl)pyridin-3-yl)-2-oxoimidazolidine-4-carbonitrile;
(R)-3-(isoquinolin-4-yl)-1-(4-methoxy-6-(trifluoromethyl)pyridin-3-yl)-2-oxoimidazolidine-4-carbonitrile;
1-(4-(difluoromethyl)phenyl)-3-(isoquinolin-4-yl)-2-oxoimidazolidine-4-carbonitrile;
(R)-1-(4-(difluoromethyl)phenyl)-3-(isoquinolin-4-yl)-2-oxoimidazolidine-4-carbonitrile;
1-(2,5-difluorophenyl)-3-(isoquinolin-4-yl)-2-oxoimidazolidine-4-carbonitrile;
(R)-1-(2,5-difluorophenyl)-3-(isoquinolin-4-yl)-2-oxoimidazolidine-4-carbonitrile;
1-(3,5-difluorophenyl)-3-(isoquinolin-4-yl)-2-oxoimidazolidine-4-carbonitrile;
(R)-1-(3,5-difluorophenyl)-3-(isoquinolin-4-yl)-2-oxoimidazolidine-4-carbonitrile;
1-(6-chloropyridin-2-yl)-3-(isoquinolin-4-yl)-2-oxoimidazolidine-4-carbonitrile;
(R)-1-(6-chloropyridin-2-yl)-3-(isoquinolin-4-yl)-2-oxoimidazolidine-4-carbonitrile;
3-(isoquinolin-4-yl)-1-(6-methoxypyridin-3-yl)-2-oxoimidazolidine-4-carbonitrile;
(R)-3-(isoquinolin-4-yl)-1-(6-methoxypyridin-3-yl)-2-oxoimidazolidine-4-carbonitrile;
3-(isoquinolin-4-yl)-2-oxo-1-(6-oxo-1,6-dihydropyridin-3-yl)imidazolidine-4-carbonitrile;
1-(5-chloro-2-methylphenyl)-3-(isoquinolin-4-yl)-2-oxoimidazolidine-4-carbonitrile;

(R)-1-(5-chloro-2-methylphenyl)-3-(isoquinolin-4-yl)-2-oxoimidazolidine-4-carbonitrile;

1-(5-chloro-2-methoxyphenyl)-3-(isoquinolin-4-yl)-2-oxoimidazolidine-4-carbonitrile;

(R)-1-(5-chloro-2-methoxyphenyl)-3-(isoquinolin-4-yl)-2-oxoimidazolidine-4-carbonitrile;

1-(2-cyano-5-methylphenyl)-3-(isoquinolin-4-yl)-2-oxoimidazolidine-4-carbonitrile;

(R)-1-(2-cyano-5-methylphenyl)-3-(isoquinolin-4-yl)-2-oxoimidazolidine-4-carbonitrile;

4-(4-cyano-3-(isoquinolin-4-yl)-2-oxoimidazolidin-1-yl)-6-(trifluoromethyl)nicotinonitrile;

(R)-4-(4-cyano-3-(isoquinolin-4-yl)-2-oxoimidazolidin-1-yl)-6-(trifluoromethyl)nicotinonitrile;

3-(isoquinolin-4-yl)-1-(4-methyl-1H-imidazol-2-yl)-2-oxoimidazolidine-4-carbonitrile;

(R)-3-(isoquinolin-4-yl)-1-(4-methyl-1H-imidazol-2-yl)-2-oxoimidazolidine-4-carbonitrile;

1-(4-chloro-1H-imidazol-2-yl)-3-(isoquinolin-4-yl)-2-oxoimidazolidine-4-carbonitrile;

(R)-1-(4-chloro-1H-imidazol-2-yl)-3-(isoquinolin-4-yl)-2-oxoimidazolidine-4-carbonitrile;

3-(isoquinolin-4-yl)-1-(3-methylcyclobutyl)-2-oxoimidazolidine-4-carbonitrile;

(R)-3-(isoquinolin-4-yl)-1-((1s,3S)-3-methylcyclobutyl)-2-oxoimidazolidine-4-carbonitrile;

(R)-3-(isoquinolin-4-yl)-1-((1 r,3R)-3-methylcyclobutyl)-2-oxoimidazolidine-4-carbonitrile;

1-(4-fluorocyclohexyl)-3-(isoquinolin-4-yl)-2-oxoimidazolidine-4-carbonitrile;

(R)-1-((1 r,4R)-4-fluorocyclohexyl)-3-(isoquinolin-4-yl)-2-oxoimidazolidine-4-carbonitrile;

(R)-1-((1s,4S)-4-fluorocyclohexyl)-3-(isoquinolin-4-yl)-2-oxoimidazolidine-4-carbonitrile;

3-(isoquinolin-4-yl)-2-oxo-1-(spiro[3.3]heptan-2-yl)imidazolidine-4-carbonitrile;

(R)-3-(isoquinolin-4-yl)-2-oxo-1-(spiro[3.3]heptan-2-yl)imidazolidine-4-carbonitrile;

1-(3-isopropylcyclobutyl)-3-(isoquinolin-4-yl)-2-oxoimidazolidine-4-carbonitrile;

(R)-1-((1s,3S)-3-isopropylcyclobutyl)-3-(isoquinolin-4-yl)-2-oxoimidazolidine-4-carbonitrile;

(R)-1-((1r,3R)-3-isopropylcyclobutyl)-3-(isoquinolin-4-yl)-2-oxoimidazolidine-4-carbonitrile;

1-(3-cyclopropylcyclobutyl)-3-(isoquinolin-4-yl)-2-oxoimidazolidine-4-carbonitrile;

(R)-1-((1s,3S)-3-cyclopropylcyclobutyl)-3-(isoquinolin-4-yl)-2-oxoimidazolidine-4-carbonitrile;

(R)-1-((1 r,3R)-3-cyclopropylcyclobutyl)-3-(isoquinolin-4-yl)-2-oxoimidazolidine-4-carbonitrile;

3-(isoquinolin-4-yl)-2-oxo-1-(spiro[2.3]hexan-5-yl)imidazolidine-4-carbonitrile;

(R)-3-(isoquinolin-4-yl)-2-oxo-1-(spiro[2.3]hexan-5-yl)imidazolidine-4-carbonitrile;

1-(3,3-dimethylcyclobutyl)-3-(isoquinolin-4-yl)-2-oxoimidazolidine-4-carbonitrile;

(R)-1-(3,3-dimethylcyclobutyl)-3-(isoquinolin-4-yl)-2-oxoimidazolidine-4-carbonitrile;

1-(6,6-difluorospiro[3.3]heptan-2-yl)-3-(isoquinolin-4-yl)-2-oxoimidazolidine-4-carbonitrile;

(R)-1-(6,6-difluorospiro[3.3]heptan-2-yl)-3-(isoquinolin-4-yl)-2-oxoimidazolidine-4-carbonitrile;

3-(isoquinolin-4-yl)-2-oxo-1-((1 r,4r)-4-(trifluoromethyl)cyclohexyl)imidazolidine-4-carbonitrile;

(R)-3-(isoquinolin-4-yl)-2-oxo-1-((1 r,4R)-4-(trifluoromethyl)cyclohexyl)imidazolidine-4-carbonitrile;

3-(isoquinolin-4-yl)-2-oxo-1-(1-((trifluoromethyl)sulfonyl)azetidin-3-yl)imidazolidine-4-carbonitrile;

(R)-3-(isoquinolin-4-yl)-2-oxo-1-(1-((trifluoromethyl)sulfonyl)azetidin-3-yl)imidazolidine-4-carbonitrile;

3-(isoquinolin-4-yl)-1-(1-(methylsulfonyl)azetidin-3-yl)-2-oxoimidazolidine-4-carbonitrile;

(R)-3-(isoquinolin-4-yl)-1-(1-(methylsulfonyl)azetidin-3-yl)-2-oxoimidazolidine-4-carbonitrile;

1-(1-(cyclopropylsulfonyl)azetidin-3-yl)-3-(isoquinolin-4-yl)-2-oxoimidazolidine-4-carbonitrile;

(R)-1-(1-(cyclopropylsulfonyl)azetidin-3-yl)-3-(isoquinolin-4-yl)-2-oxoimidazolidine-4-carbonitrile;

3-(isoquinolin-4-yl)-1-(1-methylazetidin-3-yl)-2-oxoimidazolidine-4-carbonitrile;

3-(isoquinolin-4-yl)-2-oxo-1-(1-(2,2,2-trifluoroethyl)azetidin-3-yl)imidazolidine-4-carbonitrile;

(R)-3-(isoquinolin-4-yl)-2-oxo-1-(1-(2,2,2-trifluoroethyl)azetidin-3-yl)imidazolidine-4-carbonitrile;

1-(1-acetylazetidin-3-yl)-3-(isoquinolin-4-yl)-2-oxoimidazolidine-4-carbonitrile;

(R)-1-(1-acetylazetidin-3-yl)-3-(isoquinolin-4-yl)-2-oxoimidazolidine-4-carbonitrile;

1-(1-cyclopropylazetidin-3-yl)-3-(isoquinolin-4-yl)-2-oxoimidazolidine-4-carbonitrile;

(R)-1-(1-cyclopropylazetidin-3-yl)-3-(isoquinolin-4-yl)-2-oxoimidazolidine-4-carbonitrile;

3-(isoquinolin-4-yl)-2-oxo-1-(3-(trifluoromethyl)bicyclo[1.1.1]pentan-1-yl)imidazolidine-4-carbonitrile;

(R)-3-(isoquinolin-4-yl)-2-oxo-1-(3-(trifluoromethyl)bicyclo[1.1.1]pentan-1-yl)imidazolidine-4-carbonitrile;

1-(4,4-difluorocyclohexyl)-3-(isoquinolin-4-yl)-2-oxoimidazolidine-4-carbonitrile;

(R)-1-(4,4-difluorocyclohexyl)-3-(isoquinolin-4-yl)-2-oxoimidazolidine-4-carbonitrile;

1-(3-fluorobicyclo[1.1.1]pentan-1-yl)-3-(isoquinolin-4-yl)-2-oxoimidazolidine-4-carbonitrile;

(R)-1-(3-fluorobicyclo[1.1.1]pentan-1-yl)-3-(isoquinolin-4-yl)-2-oxoimidazolidine-4-carbonitrile;

3-(isoquinolin-4-yl)-1-neopentyl-2-oxoimidazolidine-4-carbonitrile;

(R)-3-(isoquinolin-4-yl)-1-neopentyl-2-oxoimidazolidine-4-carbonitrile;

1-(3,3-difluorocyclopentyl)-3-(isoquinolin-4-yl)-2-oxoimidazolidine-4-carbonitrile;

(R)-1-((R or S)-3,3-difluorocyclopentyl)-3-(isoquinolin-4-yl)-2-oxoimidazolidine-4-carbonitrile, and (R)-1-((R or S)-3,3-difluorocyclopentyl)-3-(isoquinolin-4-yl)-2-oxoimidazolidine-4-carbonitrile.

Embodiment 210. The compound of Embodiment 1, a stereoisomer thereof, or a pharmaceutically acceptable salt thereof, wherein the compound is selected from:

3-(isoquinolin-4-yl)-2-oxo-1-phenylimidazolidine-4-carbonitrile;

(R)-3-(isoquinolin-4-yl)-2-oxo-1-phenylimidazolidine-4-carbonitrile;

1-(3-chlorophenyl)-3-(isoquinolin-4-yl)-2-oxoimidazolidine-4-carbonitrile;

(R)-1-(3-chlorophenyl)-3-(isoquinolin-4-yl)-2-oxoimidazolidine-4-carbonitrile;

3-(isoquinolin-4-yl)-2-oxo-1-(5-(trifluoromethyl)pyridin-2-yl)imidazolidine-4-carbonitrile;

3-(isoquinolin-4-yl)-2-oxo-1-(4-(trifluoromethyl)phenyl)imidazolidine-4-carbonitrile;

1-(4-chlorophenyl)-3-(isoquinolin-4-yl)-2-oxoimidazolidine-4-carbonitrile;

1-(4-fluorophenyl)-3-(isoquinolin-4-yl)-2-oxoimidazolidine-4-carbonitrile;

1-(3-fluorophenyl)-3-(isoquinolin-4-yl)-2-oxoimidazolidine-4-carbonitrile;

1-(5-fluoropyridin-2-yl)-3-(isoquinolin-4-yl)-2-oxoimidazolidine-4-carbonitrile;

3-(isoquinolin-4-yl)-2-oxo-1-(6-(trifluoromethyl)pyridin-3-yl)imidazolidine-4-carbonitrile;

1-(5-chloropyridin-2-yl)-3-(isoquinolin-4-yl)-2-oxoimidazolidine-4-carbonitrile;

(R)-3-(isoquinolin-4-yl)-2-oxo-1-(6-(trifluoromethyl)pyridin-3-yl)imidazolidine-4-carbonitrile;

3-(isoquinolin-4-yl)-1-(2-methoxy-4-(trifluoromethyl)phenyl)-2-oxoimidazolidine-4-carbonitrile;

(R)-3-(isoquinolin-4-yl)-1-(2-methoxy-4-(trifluoromethyl)phenyl)-2-oxoimidazolidine-4-carbonitrile;

(R)-3-(isoquinolin-4-yl)-2-oxo-1-(6-(trifluoromethyl)pyridazin-4-yl)imidazolidine-4-carbonitrile;

(R)-3-(isoquinolin-4-yl)-1-(5-methoxy-2-(trifluoromethyl)pyridin-4-yl)-2-oxoimidazolidine-4-carbonitrile;

1-(5-cyano-2-methoxyphenyl)-3-(isoquinolin-4-yl)-2-oxoimidazolidine-4-carbonitrile;

(R)-1-(5-cyano-2-methoxyphenyl)-3-(isoquinolin-4-yl)-2-oxoimidazolidine-4-carbonitrile;

(R)-1-(5-chloropyrimidin-2-yl)-3-(isoquinolin-4-yl)-2-oxoimidazolidine-4-carbonitrile;

(R)-3-(isoquinolin-4-yl)-1-(2-methoxy-5-(trifluoromethyl)phenyl)-2-oxoimidazolidine-4-carbonitrile;

(R)-5-(4-cyano-3-(isoquinolin-4-yl)-2-oxoimidazolidin-1-yl)-2-(trifluoromethyl)isonicotinonitrile;

1-(4-cyano-2-methoxyphenyl)-3-(isoquinolin-4-yl)-2-oxoimidazolidine-4-carbonitrile;

(R)-1-(4-cyano-2-methoxyphenyl)-3-(isoquinolin-4-yl)-2-oxoimidazolidine-4-carbonitrile;

1-(5-chloro-2-cyanophenyl)-3-(isoquinolin-4-yl)-2-oxoimidazolidine-4-carbonitrile;

(R)-1-(5-chloro-2-cyanophenyl)-3-(isoquinolin-4-yl)-2-oxoimidazolidine-4-carbonitrile;

(R)-1-(5-fluoro-2-methylphenyl)-3-(isoquinolin-4-yl)-2-oxoimidazolidine-4-carbonitrile;

(R)-1-(3-(difluoromethyl)phenyl)-3-(isoquinolin-4-yl)-2-oxoimidazolidine-4-carbonitrile;

(R)-3-(isoquinolin-4-yl)-1-(2-methoxypyridin-4-yl)-2-oxoimidazolidine-4-carbonitrile;

(R)-3-(isoquinolin-4-yl)-1-(2-methyl-5-(trifluoromethyl)phenyl)-2-oxoimidazolidine-4-carbonitrile;

(R)-1-((R)-1-(2-hydroxyacetyl)pyrrolidin-3-yl)-3-(isoquinolin-4-yl)-2-oxoimidazolidine-4-carbonitrile;

(R)-3-(isoquinolin-4-yl)-2-oxo-1-((R)-1-(3,3,3-trifluoropropyl)pyrrolidin-3-yl)imidazolidine-4-carbonitrile;

1-(3,3-difluorocyclobutyl)-3-(isoquinolin-4-yl)-2-oxoimidazolidine-4-carbonitrile;

1-(3-hydroxy-3-(trifluoromethyl)cyclobutyl)-3-(isoquinolin-4-yl)-2-oxoimidazolidine-4-carbonitrile;

1-(3,3-difluorocyclohexyl)-3-(isoquinolin-4-yl)-2-oxoimidazolidine-4-carbonitrile;

(R)-3-(isoquinolin-4-yl)-2-oxo-1-(5-(trifluoromethyl)pyridazin-3-yl)imidazolidine-4-carbonitrile;

(R)-3-(isoquinolin-4-yl)-1-(5-methoxy-2-(trifluoromethyl)pyrimidin-4-yl)-2-oxoimidazolidine-4-carbonitrile;

(R)-3-(isoquinolin-4-yl)-2-oxo-1-(5-(trifluoromethyl)pyrazin-2-yl)imidazolidine-4-carbonitrile;

4-(3-(3-chlorophenyl)-5-cyano-2-oxoimidazolidin-1-yl)isoquinoline-6-carboxylic acid;

(R)-4-(3-(3-chlorophenyl)-5-cyano-2-oxoimidazolidin-1-yl)isoquinoline-6-carboxylic acid;

1-(3-chlorophenyl)-3-(6-(2-hydroxypropan-2-yl)isoquinolin-4-yl)-2-oxoimidazolidine-4-carbonitrile;

4-(3-(3-chlorophenyl)-5-cyano-2-oxoimidazolidin-1-yl)isoquinoline-6-carboxamide;

4-(3-(3-chlorophenyl)-5-cyano-2-oxoimidazolidin-1-yl)-N-(2-methoxyethyl)isoquinoline-6-carboxamide;

1-(3-chlorophenyl)-3-(6-(methylsulfonyl)isoquinolin-4-yl)-2-oxoimidazolidine-4-carbonitrile;

(R)-1-(3-chlorophenyl)-3-(6-(methylsulfonyl)isoquinolin-4-yl)-2-oxoimidazolidine-4-carbonitrile;

(R)-1-(2-methoxy-5-(trifluoromethyl)phenyl)-3-(6-(methylsulfonyl)isoquinolin-4-yl)-2-oxoimidazolidine-4-carbonitrile;

(R)-4-(3-(3-chlorophenyl)-5-cyano-2-oxoimidazolidin-1-yl)isoquinoline-6-carbonitrile;

(R)-1-(3-chlorophenyl)-3-(isoquinolin-4-yl)-4-methyl-2-oxoimidazolidine-4-carbonitrile;

(R)-1-(5-chloropyridin-2-yl)-3-(isoquinolin-4-yl)-2-oxoimidazolidine-4-carbonitrile;

(R)-3-(isoquinolin-4-yl)-2-oxo-1-(5-(trifluoromethyl)pyrimidin-2-yl)imidazolidine-4-carbonitrile;

(4R,5S)-1-(3-chlorophenyl)-3-(isoquinolin-4-yl)-5-methyl-2-oxoimidazolidine-4-carbonitrile;

(R)-3-(isoquinolin-4-yl)-1-(2-methylpyridin-4-yl)-2-oxoimidazolidine-4-carbonitrile;

(R)-3-(isoquinolin-4-yl)-2-oxo-1-((1 r,3R)-3-(trifluoromethyl)cyclobutyl)imidazolidine-4-carbonitrile;

(R)-3-(isoquinolin-4-yl)-2-oxo-1-((1s,3S)-3-(trifluoromethyl)cyclobutyl)imidazolidine-4-carbonitrile;

(R)-1-((R)-1-(2-hydroxyethyl)pyrrolidin-3-yl)-3-(isoquinolin-4-yl)-2-oxoimidazolidine-4-carbonitrile;

(R)-3-(isoquinolin-4-yl)-1-(3-methoxy-6-(trifluoromethyl)pyridin-2-yl)-2-oxoimidazolidine-4-carbonitrile;

(R)-3-(isoquinolin-4-yl)-1-(3-(methylsulfonyl)phenyl)-2-oxoimidazolidine-4-carbonitrile;

(R)-3-(isoquinolin-4-yl)-2-oxo-1-(4-(trifluoromethyl)pyrimidin-2-yl)imidazolidine-4-carbonitrile;

(R)-1-(4-cyanophenyl)-3-(isoquinolin-4-yl)-2-oxoimidazolidine-4-carbonitrile;

(R)-3-(isoquinolin-4-yl)-2-oxo-1-(6-(trifluoromethyl)pyridin-2-yl)imidazolidine-4-carbonitrile;

(R)-1-(3-cyanophenyl)-3-(isoquinolin-4-yl)-2-oxoimidazolidine-4-carbonitrile;

(R)-3-(isoquinolin-4-yl)-1-(4-methylpyrimidin-2-yl)-2-oxoimidazolidine-4-carbonitrile;

(R)-1-(5-chloropyridazin-3-yl)-3-(isoquinolin-4-yl)-2-oxoimidazolidine-4-carbonitrile;

(R)-1-(6-fluoropyridin-3-yl)-3-(isoquinolin-4-yl)-2-oxoimidazolidine-4-carbonitrile;

(R)-1-(2-fluorophenyl)-3-(isoquinolin-4-yl)-2-oxoimidazolidine-4-carbonitrile;

3-(isoquinolin-4-yl)-2-oxo-1-(2-(trifluoromethyl)pyridin-4-yl)imidazolidine-4-carbonitrile;

(R)-3-(isoquinolin-4-yl)-2-oxo-1-(2-(trifluoromethyl)pyridin-4-yl)imidazolidine-4-carbonitrile;

1-(5-chloro-3-methoxypyridin-2-yl)-3-(isoquinolin-4-yl)-2-oxoimidazolidine-4-carbonitrile;

(R)-1-(5-chloro-3-methoxypyridin-2-yl)-3-(isoquinolin-4-yl)-2-oxoimidazolidine-4-carbonitrile;

(R)-1-(5-(difluoromethoxy)-2-fluorophenyl)-3-(isoquinolin-4-yl)-2-oxoimidazolidine-4-carbonitrile;

1-(4-chloro-2-cyanophenyl)-3-(isoquinolin-4-yl)-2-oxoimidazolidine-4-carbonitrile;

(R)-1-(4-chloro-2-cyanophenyl)-3-(isoquinolin-4-yl)-2-oxoimidazolidine-4-carbonitrile;

(R)-1-(6-fluoropyridin-2-yl)-3-(isoquinolin-4-yl)-2-oxoimidazolidine-4-carbonitrile;

(R)-3-(isoquinolin-4-yl)-1-(5-methyl-2-(trifluoromethyl)pyrimidin-4-yl)-2-oxoimidazolidine-4-carbonitrile;

(R)-1-(1H-indazol-7-yl)-3-(isoquinolin-4-yl)-2-oxoimidazolidine-4-carbonitrile;

1-(1-isopropyl-1H-pyrazol-4-yl)-3-(isoquinolin-4-yl)-2-oxoimidazolidine-4-carbonitrile;

(R)-1-(1-isopropyl-1H-pyrazol-4-yl)-3-(isoquinolin-4-yl)-2-oxoimidazolidine-4-carbonitrile;

3-(isoquinolin-4-yl)-1-(1-methyl-1H-pyrazol-4-yl)-2-oxoimidazolidine-4-carbonitrile;

(R)-3-(isoquinolin-4-yl)-1-(1-methyl-1H-pyrazol-4-yl)-2-oxoimidazolidine-4-carbonitrile;

1-(2,4-difluorophenyl)-3-(isoquinolin-4-yl)-2-oxoimidazolidine-4-carbonitrile;

(R)-1-(2,4-difluorophenyl)-3-(isoquinolin-4-yl)-2-oxoimidazolidine-4-carbonitrile;

(R)-3-(isoquinolin-4-yl)-1-(1-methyl-2-oxo-1,2-dihydropyridin-4-yl)-2-oxoimidazolidine-4-carbonitrile;

(R)-3-(isoquinolin-4-yl)-2-oxo-1-(5-(trifluoromethyl)-1H-imidazol-2-yl)imidazolidine-4-carbonitrile;

(R)-1-(3-(2-hydroxypropan-2-yl)phenyl)-3-(isoquinolin-4-yl)-2-oxoimidazolidine-4-carbonitrile;

1-(5-chloro-2-(trifluoromethyl)pyridin-4-yl)-3-(isoquinolin-4-yl)-2-oxoimidazolidine-4-carbonitrile;

(R)-3-(isoquinolin-4-yl)-1-(5-methyl-2-(trifluoromethyl)pyridin-4-yl)-2-oxoimidazolidine-4-carbonitrile;

(R)-1-(4-(difluoromethoxy)phenyl)-3-(isoquinolin-4-yl)-2-oxoimidazolidine-4-carbonitrile;

1-(3,4-difluorophenyl)-3-(isoquinolin-4-yl)-2-oxoimidazolidine-4-carbonitrile;

(R)-1-(3,4-difluorophenyl)-3-(isoquinolin-4-yl)-2-oxoimidazolidine-4-carbonitrile;

(R)-1-(4-cyano-3-fluorophenyl)-3-(isoquinolin-4-yl)-2-oxoimidazolidine-4-carbonitrile;

3-(isoquinolin-4-yl)-1-(2-methylpyridin-3-yl)-2-oxoimidazolidine-4-carbonitrile;

(R)-3-(isoquinolin-4-yl)-1-(2-methylpyridin-3-yl)-2-oxoimidazolidine-4-carbonitrile;

(R)-1-(6-(difluoromethyl)pyridin-3-yl)-3-(isoquinolin-4-yl)-2-oxoimidazolidine-4-carbonitrile;

(R)-1-(3-fluorophenyl)-3-(isoquinolin-4-yl)-2-oxoimidazolidine-4-carbonitrile;

(R)-1-(5-fluoro-6-(trifluoromethyl)pyridin-3-yl)-3-(isoquinolin-4-yl)-2-oxoimidazolidine-4-carbonitrile;

(R)-1-(5-(difluoromethyl)pyridin-2-yl)-3-(isoquinolin-4-yl)-2-oxoimidazolidine-4-carbonitrile;

(R)-3-(isoquinolin-4-yl)-1-(2-methylpyrimidin-5-yl)-2-oxoimidazolidine-4-carbonitrile;

1-(5-chloro-3-methylpyridin-2-yl)-3-(isoquinolin-4-yl)-2-oxoimidazolidine-4-carbonitrile;

(R)-1-(5-chloro-3-methylpyridin-2-yl)-3-(isoquinolin-4-yl)-2-oxoimidazolidine-4-carbonitrile;

(R)-3-(isoquinolin-4-yl)-2-oxo-1-(6-(trifluoromethyl)pyridazin-3-yl)imidazolidine-4-carbonitrile;

(R)-3-(isoquinolin-4-yl)-1-(3-methyl-6-(trifluoromethyl)pyridin-2-yl)-2-oxoimidazolidine-4-carbonitrile;

(R)-1-(4-(difluoromethoxy)-2-fluorophenyl)-3-(isoquinolin-4-yl)-2-oxoimidazolidine-4-carbonitrile;

(R)-1-(4-(2-hydroxypropan-2-yl)phenyl)-3-(isoquinolin-4-yl)-2-oxoimidazolidine-4-carbonitrile;

(R)-1-(3,4-difluorophenyl)-3-(6-(methylsulfonyl)isoquinolin-4-yl)-2-oxoimidazolidine-4-carbonitrile;

(R)-1-(3,5-difluorophenyl)-3-(6-(methylsulfonyl)isoquinolin-4-yl)-2-oxoimidazolidine-4-carbonitrile;

1-(3-chloro-4-fluorophenyl)-3-(isoquinolin-4-yl)-2-oxoimidazolidine-4-carbonitrile;

(R)-1-(3-chloro-4-fluorophenyl)-3-(isoquinolin-4-yl)-2-oxoimidazolidine-4-carbonitrile;

(R)-3-(isoquinolin-4-yl)-1-(2-methyl-5-(trifluoromethyl)pyridin-3-yl)-2-oxoimidazolidine-4-carbonitrile;

1-(3-(difluoromethoxy)phenyl)-3-(isoquinolin-4-yl)-2-oxoimidazolidine-4-carbonitrile;

(R)-1-(3-(difluoromethoxy)phenyl)-3-(isoquinolin-4-yl)-2-oxoimidazolidine-4-carbonitrile;

1-(2-cyano-5-(trifluoromethyl)phenyl)-3-(isoquinolin-4-yl)-2-oxoimidazolidine-4-carbonitrile;

(R)-1-(2-cyano-5-(trifluoromethyl)phenyl)-3-(isoquinolin-4-yl)-2-oxoimidazolidine-4-carbonitrile;

(R)-3-(isoquinolin-4-yl)-2-oxo-1-(4-(trifluoromethoxy)phenyl)imidazolidine-4-carbonitrile;

3-(isoquinolin-4-yl)-2-oxo-1-(3-(trifluoromethoxy)phenyl)imidazolidine-4-carbonitrile;

(R)-3-(isoquinolin-4-yl)-2-oxo-1-(3-(trifluoromethoxy)phenyl)imidazolidine-4-carbonitrile;

(R)-3-(isoquinolin-4-yl)-2-oxo-1-(2-(trifluoromethyl)pyrimidin-5-yl)imidazolidine-4-carbonitrile;

(R)-1-(6-isopropylpyridin-3-yl)-3-(isoquinolin-4-yl)-2-oxoimidazolidine-4-carbonitrile;

(R)-3-(isoquinolin-4-yl)-1-(2-methoxy-6-(trifluoromethyl)pyridin-3-yl)-2-oxoimidazolidine-4-carbonitrile;

(R)-3-(isoquinolin-4-yl)-1-(1-methyl-2-oxo-6-(trifluoromethyl)-1,2-dihydropyridin-3-yl)-2-oxoimidazolidine-4-carbonitrile;

(R)-3-(isoquinolin-4-yl)-2-oxo-1-(5-(trifluoromethyl)pyridin-2-yl)imidazolidine-4-carbonitrile;

(R)-1-(5,6-dimethylpyridin-3-yl)-3-(isoquinolin-4-yl)-2-oxoimidazolidine-4-carbonitrile;

(R)-3-(isoquinolin-4-yl)-2-oxo-1-(4-(trifluoromethyl)phenyl)imidazolidine-4-carbonitrile;

(R)-3-(isoquinolin-4-yl)-1-(2-methoxy-5-(trifluoromethyl)pyridin-3-yl)-2-oxoimidazolidine-4-carbonitrile;

(R)-1-(5-(difluoromethoxy)-2-methylphenyl)-3-(isoquinolin-4-yl)-2-oxoimidazolidine-4-carbonitrile;

(R)-1-(2,6-dimethylpyridin-4-yl)-3-(isoquinolin-4-yl)-2-oxoimidazolidine-4-carbonitrile;

1-(4-chloro-2-methoxyphenyl)-3-(isoquinolin-4-yl)-2-oxoimidazolidine-4-carbonitrile;

(R)-1-(4-chloro-2-methoxyphenyl)-3-(isoquinolin-4-yl)-2-oxoimidazolidine-4-carbonitrile;

(R)-3-(isoquinolin-4-yl)-2-oxo-1-(5-(trifluoromethyl)pyridin-3-yl)imidazolidine-4-carbonitrile;

(R)-1-(5-fluoro-2-methoxyphenyl)-3-(isoquinolin-4-yl)-2-oxoimidazolidine-4-carbonitrile;

(R)-3-(isoquinolin-4-yl)-2-oxo-1-(3-(trifluoromethyl)phenyl)imidazolidine-4-carbonitrile;

(R)-3-(isoquinolin-4-yl)-1-(4-methoxy-6-(trifluoromethyl)pyridin-3-yl)-2-oxoimidazolidine-4-carbonitrile;

(R)-1-(4-(difluoromethyl)phenyl)-3-(isoquinolin-4-yl)-2-oxoimidazolidine-4-carbonitrile;

(R)-1-(2,5-difluorophenyl)-3-(isoquinolin-4-yl)-2-oxoimidazolidine-4-carbonitrile;

1-(3,5-difluorophenyl)-3-(isoquinolin-4-yl)-2-oxoimidazolidine-4-carbonitrile;

(R)-1-(3,5-difluorophenyl)-3-(isoquinolin-4-yl)-2-oxoimidazolidine-4-carbonitrile;

(R)-1-(6-chloropyridin-2-yl)-3-(isoquinolin-4-yl)-2-oxoimidazolidine-4-carbonitrile;

(R)-3-(isoquinolin-4-yl)-1-(6-methoxypyridin-3-yl)-2-oxoimidazolidine-4-carbonitrile;

(R)-1-(5-chloro-2-methylphenyl)-3-(isoquinolin-4-yl)-2-oxoimidazolidine-4-carbonitrile;

(R)-1-(5-chloro-2-methoxyphenyl)-3-(isoquinolin-4-yl)-2-oxoimidazolidine-4-carbonitrile:

1-(2-cyano-5-methylphenyl)-3-(isoquinolin-4-yl)-2-oxoimidazolidine-4-carbonitrile;

(R)-1-(2-cyano-5-methylphenyl)-3-(isoquinolin-4-yl)-2-oxoimidazolidine-4-carbonitrile;

(R)-4-(4-cyano-3-(isoquinolin-4-yl)-2-oxoimidazolidin-1-yl)-6-(trifluoromethyl)nicotinonitrile;

3-(isoquinolin-4-yl)-1-(4-methyl-1H-imidazol-2-yl)-2-oxoimidazolidine-4-carbonitrile;

(R)-3-(isoquinolin-4-yl)-1-(4-methyl-1H-imidazol-2-yl)-2-oxoimidazolidine-4-carbonitrile;

1-(4-chloro-1H-imidazol-2-yl)-3-(isoquinolin-4-yl)-2-oxoimidazolidine-4-carbonitrile;

(R)-1-(4-chloro-1H-imidazol-2-yl)-3-(isoquinolin-4-yl)-2-oxoimidazolidine-4-carbonitrile;

(R)-3-(isoquinolin-4-yl)-1-((1s,3S)-3-methylcyclobutyl)-2-oxoimidazolidine-4-carbonitrile;

(R)-3-(isoquinolin-4-yl)-1-((1 r,3R)-3-methylcyclobutyl)-2-oxoimidazolidine-4-carbonitrile;

(R)-1-((1r,4R)-4-fluorocyclohexyl)-3-(isoquinolin-4-yl)-2-oxoimidazolidine-4-carbonitrile;

(R)-1-((1s,4S)-4-fluorocyclohexyl)-3-(isoquinolin-4-yl)-2-oxoimidazolidine-4-carbonitrile;

(R)-3-(isoquinolin-4-yl)-2-oxo-1-(spiro[3.3]heptan-2-yl)imidazolidine-4-carbonitrile;

(R)-1-((1s,3S)-3-isopropylcyclobutyl)-3-(isoquinolin-4-yl)-2-oxoimidazolidine-4-carbonitrile;

(R)-1-((1r,3R)-3-isopropylcyclobutyl)-3-(isoquinolin-4-yl)-2-oxoimidazolidine-4-carbonitrile;

(R)-1-((1s,3S)-3-cyclopropylcyclobutyl)-3-(isoquinolin-4-yl)-2-oxoimidazolidine-4-carbonitrile;

(R)-1-((1 r,3R)-3-cyclopropylcyclobutyl)-3-(isoquinolin-4-yl)-2-oxoimidazolidine-4-carbonitrile;

(R)-3-(isoquinolin-4-yl)-2-oxo-1-(spiro[2.3]hexan-5-yl)imidazolidine-4-carbonitrile;

(R)-1-(3,3-dimethylcyclobutyl)-3-(isoquinolin-4-yl)-2-oxoimidazolidine-4-carbonitrile;

1-(6,6-difluorospiro[3.3]heptan-2-yl)-3-(isoquinolin-4-yl)-2-oxoimidazolidine-4-carbonitrile;

(R)-1-(6,6-difluorospiro[3.3]heptan-2-yl)-3-(isoquinolin-4-yl)-2-oxoimidazolidine-4-carbonitrile;

3-(isoquinolin-4-yl)-2-oxo-1-((1 r,4r)-4-(trifluoromethyl)cyclohexyl)imidazolidine-4-carbonitrile;

(R)-3-(isoquinolin-4-yl)-2-oxo-1-((1 r,4R)-4-(trifluoromethyl)cyclohexyl)imidazolidine-4-carbonitrile;

(R)-3-(isoquinolin-4-yl)-2-oxo-1-(1-((trifluoromethyl)sulfonyl)azetidin-3-yl)imidazolidine-4-carbonitrile;

(R)-3-(isoquinolin-4-yl)-1-(1-(methylsulfonyl)azetidin-3-yl)-2-oxoimidazolidine-4-carbonitrile;

(R)-1-(1-(cyclopropylsulfonyl)azetidin-3-yl)-3-(isoquinolin-4-yl)-2-oxoimidazolidine-4-carbonitrile;

3-(isoquinolin-4-yl)-2-oxo-1-(1-(2,2,2-trifluoroethyl)azetidin-3-yl)imidazolidine-4-carbonitrile;

(R)-3-(isoquinolin-4-yl)-2-oxo-1-(1-(2,2,2-trifluoroethyl)azetidin-3-yl)imidazolidine-4-carbonitrile;

(R)-1-(1-acetylazetidin-3-yl)-3-(isoquinolin-4-yl)-2-oxoimidazolidine-4-carbonitrile;

1-(1-cyclopropylazetidin-3-yl)-3-(isoquinolin-4-yl)-2-oxoimidazolidine-4-carbonitrile;

(R)-1-(1-cyclopropylazetidin-3-yl)-3-(isoquinolin-4-yl)-2-oxoimidazolidine-4-carbonitrile;

(R)-3-(isoquinolin-4-yl)-2-oxo-1-(3-(trifluoromethyl)bicyclo[1.1.1]pentan-1-yl)imidazolidine-4-carbonitrile;

(R)-1-(4,4-difluorocyclohexyl)-3-(isoquinolin-4-yl)-2-oxoimidazolidine-4-carbonitrile;

1-(3-fluorobicyclo[1.1.1]pentan-1-yl)-3-(isoquinolin-4-yl)-2-oxoimidazolidine-4-carbonitrile;

(R)-1-(3-fluorobicyclo[1.1.1]pentan-1-yl)-3-(isoquinolin-4-yl)-2-oxoimidazolidine-4-carbonitrile;

(R)-3-(isoquinolin-4-yl)-1-neopentyl-2-oxoimidazolidine-4-carbonitrile;

(R)-1-((R or S)-3,3-difluorocyclopentyl)-3-(isoquinolin-4-yl)-2-oxoimidazolidine-4-carbonitrile, and (R)-1-((R or S)-3,3-difluorocyclopentyl)-3-(isoquinolin-4-yl)-2-oxoimidazolidine-4-carbonitrile.

Embodiment 211. The compound of Embodiment 1, a stereoisomer thereof, or a pharmaceutically acceptable salt thereof, wherein the compound is selected from:

(R)-3-(isoquinolin-4-yl)-2-oxo-1-phenylimidazolidine-4-carbonitrile;

(R)-1-(3-chlorophenyl)-3-(isoquinolin-4-yl)-2-oxoimidazolidine-4-carbonitrile;

(R)-3-(isoquinolin-4-yl)-2-oxo-1-(6-(trifluoromethyl)pyridin-3-yl)imidazolidine-4-carbonitrile;

(R)-3-(isoquinolin-4-yl)-1-(2-methoxy-4-(trifluoromethyl)phenyl)-2-oxoimidazolidine-4-carbonitrile;

(R)-3-(isoquinolin-4-yl)-2-oxo-1-(6-(trifluoromethyl)pyridazin-4-yl)imidazolidine-4-carbonitrile;

(R)-3-(isoquinolin-4-yl)-1-(5-methoxy-2-(trifluoromethyl)pyridin-4-yl)-2-oxoimidazolidine-4-carbonitrile;

(R)-1-(5-cyano-2-methoxyphenyl)-3-(isoquinolin-4-yl)-2-oxoimidazolidine-4-carbonitrile;

(R)-1-(5-chloropyrimidin-2-yl)-3-(isoquinolin-4-yl)-2-oxoimidazolidine-4-carbonitrile;

(R)-3-(isoquinolin-4-yl)-1-(2-methoxy-5-(trifluoromethyl)phenyl)-2-oxoimidazolidine-4-carbonitrile;

(R)-5-(4-cyano-3-(isoquinolin-4-yl)-2-oxoimidazolidin-1-yl)-2-(trifluoromethyl)isonicotinonitrile;

(R)-1-(4-cyano-2-methoxyphenyl)-3-(isoquinolin-4-yl)-2-oxoimidazolidine-4-carbonitrile;

(R)-1-(5-chloro-2-cyanophenyl)-3-(isoquinolin-4-yl)-2-oxoimidazolidine-4-carbonitrile;

(R)-1-(5-fluoro-2-methylphenyl)-3-(isoquinolin-4-yl)-2-oxoimidazolidine-4-carbonitrile;

(R)-1-(3-(difluoromethyl)phenyl)-3-(isoquinolin-4-yl)-2-oxoimidazolidine-4-carbonitrile;

(R)-3-(isoquinolin-4-yl)-1-(2-methoxypyridin-4-yl)-2-oxoimidazolidine-4-carbonitrile;

(R)-3-(isoquinolin-4-yl)-1-(2-methyl-5-(trifluoromethyl)phenyl)-2-oxoimidazolidine-4-carbonitrile;

(R)-1-((R)-1-(2-hydroxyacetyl)pyrrolidin-3-yl)-3-(isoquinolin-4-yl)-2-oxoimidazolidine-4-carbonitrile;

(R)-3-(isoquinolin-4-yl)-2-oxo-1-((R)-1-(3,3,3-trifluoropropyl)pyrrolidin-3-yl)imidazolidine-4-carbonitrile;

(R)-3-(isoquinolin-4-yl)-2-oxo-1-(5-(trifluoromethyl)pyridazin-3-yl)imidazolidine-4-carbonitrile;

(R)-3-(isoquinolin-4-yl)-1-(5-methoxy-2-(trifluoromethyl)pyrimidin-4-yl)-2-oxoimidazolidine-4-carbonitrile;

(R)-3-(isoquinolin-4-yl)-2-oxo-1-(5-(trifluoromethyl)pyrazin-2-yl)imidazolidine-4-carbonitrile;

(R)-4-(3-(3-chlorophenyl)-5-cyano-2-oxoimidazolidin-1-yl)isoquinoline-6-carboxylic acid;

(R)-1-(3-chlorophenyl)-3-(6-(methylsulfonyl)isoquinolin-4-yl)-2-oxoimidazolidine-4-carbonitrile;

(R)-1-(2-methoxy-5-(trifluoromethyl)phenyl)-3-(6-(methylsulfonyl)isoquinolin-4-yl)-2-oxoimidazolidine-4-carbonitrile;

(R)-4-(3-(3-chlorophenyl)-5-cyano-2-oxoimidazolidin-1-yl)isoquinoline-6-carbonitrile;

(R)-1-(3-chlorophenyl)-3-(isoquinolin-4-yl)-4-methyl-2-oxoimidazolidine-4-carbonitrile;

(R)-1-(5-chloropyridin-2-yl)-3-(isoquinolin-4-yl)-2-oxoimidazolidine-4-carbonitrile;

(R)-3-(isoquinolin-4-yl)-2-oxo-1-(5-(trifluoromethyl)pyrimidin-2-yl)imidazolidine-4-carbonitrile;

(4R,5S)-1-(3-chlorophenyl)-3-(isoquinolin-4-yl)-5-methyl-2-oxoimidazolidine-4-carbonitrile;
(R)-3-(isoquinolin-4-yl)-1-(2-methylpyridin-4-yl)-2-oxoimidazolidine-4-carbonitrile;
(R)-3-(isoquinolin-4-yl)-2-oxo-1-((1 r,3R)-3-(trifluoromethyl)cyclobutyl)imidazolidine-4-carbonitrile;
(R)-3-(isoquinolin-4-yl)-2-oxo-1-((1s,3S)-3-(trifluoromethyl)cyclobutyl)imidazolidine-4-carbonitrile;
(R)-1-((R)-1-(2-hydroxyethyl)pyrrolidin-3-yl)-3-(isoquinolin-4-yl)-2-oxoimidazolidine-4-carbonitrile;
(R)-3-(isoquinolin-4-yl)-1-(3-methoxy-6-(trifluoromethyl)pyridin-2-yl)-2-oxoimidazolidine-4-carbonitrile;
(R)-3-(isoquinolin-4-yl)-1-(3-(methylsulfonyl)phenyl)-2-oxoimidazolidine-4-carbonitrile;
(R)-3-(isoquinolin-4-yl)-2-oxo-1-(4-(trifluoromethyl)pyrimidin-2-yl)imidazolidine-4-carbonitrile;
(R)-1-(4-cyanophenyl)-3-(isoquinolin-4-yl)-2-oxoimidazolidine-4-carbonitrile;
(R)-3-(isoquinolin-4-yl)-2-oxo-1-(6-(trifluoromethyl)pyridin-2-yl)imidazolidine-4-carbonitrile;
(R)-1-(3-cyanophenyl)-3-(isoquinolin-4-yl)-2-oxoimidazolidine-4-carbonitrile;
(R)-3-(isoquinolin-4-yl)-1-(4-methylpyrimidin-2-yl)-2-oxoimidazolidine-4-carbonitrile;
(R)-1-(5-chloropyridazin-3-yl)-3-(isoquinolin-4-yl)-2-oxoimidazolidine-4-carbonitrile;
(R)-1-(6-fluoropyridin-3-yl)-3-(isoquinolin-4-yl)-2-oxoimidazolidine-4-carbonitrile;
(R)-1-(2-fluorophenyl)-3-(isoquinolin-4-yl)-2-oxoimidazolidine-4-carbonitrile;
(R)-3-(isoquinolin-4-yl)-2-oxo-1-(2-(trifluoromethyl)pyridin-4-yl)imidazolidine-4-carbonitrile;
(R)-1-(5-chloro-3-methoxypyridin-2-yl)-3-(isoquinolin-4-yl)-2-oxoimidazolidine-4-carbonitrile;
(R)-1-(5-(difluoromethoxy)-2-fluorophenyl)-3-(isoquinolin-4-yl)-2-oxoimidazolidine-4-carbonitrile;
(R)-1-(4-chloro-2-cyanophenyl)-3-(isoquinolin-4-yl)-2-oxoimidazolidine-4-carbonitrile;
(R)-1-(6-fluoropyridin-2-yl)-3-(isoquinolin-4-yl)-2-oxoimidazolidine-4-carbonitrile;
(R)-3-(isoquinolin-4-yl)-1-(5-methyl-2-(trifluoromethyl)pyrimidin-4-yl)-2-oxoimidazolidine-4-carbonitrile;
(R)-1-(1H-indazol-7-yl)-3-(isoquinolin-4-yl)-2-oxoimidazolidine-4-carbonitrile;
(R)-1-(1-isopropyl-1H-pyrazol-4-yl)-3-(isoquinolin-4-yl)-2-oxoimidazolidine-4-carbonitrile;
(R)-3-(isoquinolin-4-yl)-1-(1-methyl-1H-pyrazol-4-yl)-2-oxoimidazolidine-4-carbonitrile;
(R)-1-(2,4-difluorophenyl)-3-(isoquinolin-4-yl)-2-oxoimidazolidine-4-carbonitrile;
(R)-3-(isoquinolin-4-yl)-1-(1-methyl-2-oxo-1,2-dihydropyridin-4-yl)-2-oxoimidazolidine-4-carbonitrile;
(R)-3-(isoquinolin-4-yl)-2-oxo-1-(5-(trifluoromethyl)-1H-imidazol-2-yl)imidazolidine-4-carbonitrile;
(R)-1-(3-(2-hydroxypropan-2-yl)phenyl)-3-(isoquinolin-4-yl)-2-oxoimidazolidine-4-carbonitrile;
(R)-3-(isoquinolin-4-yl)-1-(5-methyl-2-(trifluoromethyl)pyridin-4-yl)-2-oxoimidazolidine-4-carbonitrile;
(R)-1-(4-(difluoromethoxy)phenyl)-3-(isoquinolin-4-yl)-2-oxoimidazolidine-4-carbonitrile;
(R)-1-(3,4-difluorophenyl)-3-(isoquinolin-4-yl)-2-oxoimidazolidine-4-carbonitrile;
(R)-1-(4-cyano-3-fluorophenyl)-3-(isoquinolin-4-yl)-2-oxoimidazolidine-4-carbonitrile;
(R)-3-(isoquinolin-4-yl)-1-(2-methylpyridin-3-yl)-2-oxoimidazolidine-4-carbonitrile;
(R)-1-(6-(difluoromethyl)pyridin-3-yl)-3-(isoquinolin-4-yl)-2-oxoimidazolidine-4-carbonitrile;
(R)-1-(3-fluorophenyl)-3-(isoquinolin-4-yl)-2-oxoimidazolidine-4-carbonitrile;
(R)-1-(5-fluoro-6-(trifluoromethyl)pyridin-3-yl)-3-(isoquinolin-4-yl)-2-oxoimidazolidine-4-carbonitrile;
(R)-1-(5-(difluoromethyl)pyridin-2-yl)-3-(isoquinolin-4-yl)-2-oxoimidazolidine-4-carbonitrile;
(R)-3-(isoquinolin-4-yl)-1-(2-methylpyrimidin-5-yl)-2-oxoimidazolidine-4-carbonitrile;
(R)-1-(5-chloro-3-methylpyridin-2-yl)-3-(isoquinolin-4-yl)-2-oxoimidazolidine-4-carbonitrile;
(R)-3-(isoquinolin-4-yl)-2-oxo-1-(6-(trifluoromethyl)pyridazin-3-yl)imidazolidine-4-carbonitrile;
(R)-3-(isoquinolin-4-yl)-1-(3-methyl-6-(trifluoromethyl)pyridin-2-yl)-2-oxoimidazolidine-4-carbonitrile;
(R)-1-(4-(difluoromethoxy)-2-fluorophenyl)-3-(isoquinolin-4-yl)-2-oxoimidazolidine-4-carbonitrile;
(R)-1-(4-(2-hydroxypropan-2-yl)phenyl)-3-(isoquinolin-4-yl)-2-oxoimidazolidine-4-carbonitrile;
(R)-1-(3,4-difluorophenyl)-3-(6-(methylsulfonyl)isoquinolin-4-yl)-2-oxoimidazolidine-4-carbonitrile;
(R)-1-(3,5-difluorophenyl)-3-(6-(methylsulfonyl)isoquinolin-4-yl)-2-oxoimidazolidine-4-carbonitrile;
(R)-1-(3-chloro-4-fluorophenyl)-3-(isoquinolin-4-yl)-2-oxoimidazolidine-4-carbonitrile;
(R)-3-(isoquinolin-4-yl)-1-(2-methyl-5-(trifluoromethyl)pyridin-3-yl)-2-oxoimidazolidine-4-carbonitrile;
(R)-1-(3-(difluoromethoxy)phenyl)-3-(isoquinolin-4-yl)-2-oxoimidazolidine-4-carbonitrile;
(R)-1-(2-cyano-5-(trifluoromethyl)phenyl)-3-(isoquinolin-4-yl)-2-oxoimidazolidine-4-carbonitrile;
(R)-3-(isoquinolin-4-yl)-2-oxo-1-(4-(trifluoromethoxy)phenyl)imidazolidine-4-carbonitrile;
(R)-3-(isoquinolin-4-yl)-2-oxo-1-(3-(trifluoromethoxy)phenyl)imidazolidine-4-carbonitrile;
(R)-3-(isoquinolin-4-yl)-2-oxo-1-(2-(trifluoromethyl)pyrimidin-5-yl)imidazolidine-4-carbonitrile;
(R)-1-(6-isopropylpyridin-3-yl)-3-(isoquinolin-4-yl)-2-oxoimidazolidine-4-carbonitrile;
(R)-3-(isoquinolin-4-yl)-1-(2-methoxy-6-(trifluoromethyl)pyridin-3-yl)-2-oxoimidazolidine-4-carbonitrile;
(R)-3-(isoquinolin-4-yl)-1-(1-methyl-2-oxo-6-(trifluoromethyl)-1,2-dihydropyridin-3-yl)-2-oxoimidazolidine-4-carbonitrile;
(R)-3-(isoquinolin-4-yl)-2-oxo-1-(5-(trifluoromethyl)pyridin-2-yl)imidazolidine-4-carbonitrile;
(R)-1-(5,6-dimethylpyridin-3-yl)-3-(isoquinolin-4-yl)-2-oxoimidazolidine-4-carbonitrile;
(R)-3-(isoquinolin-4-yl)-2-oxo-1-(4-(trifluoromethyl)phenyl)imidazolidine-4-carbonitrile;
(R)-3-(isoquinolin-4-yl)-1-(2-methoxy-5-(trifluoromethyl)pyridin-3-yl)-2-oxoimidazolidine-4-carbonitrile;
(R)-1-(5-(difluoromethoxy)-2-methylphenyl)-3-(isoquinolin-4-yl)-2-oxoimidazolidine-4-carbonitrile;
(R)-1-(2,6-dimethylpyridin-4-yl)-3-(isoquinolin-4-yl)-2-oxoimidazolidine-4-carbonitrile;
(R)-1-(4-chloro-2-methoxyphenyl)-3-(isoquinolin-4-yl)-2-oxoimidazolidine-4-carbonitrile;
(R)-3-(isoquinolin-4-yl)-2-oxo-1-(5-(trifluoromethyl)pyridin-3-yl)imidazolidine-4-carbonitrile;
(R)-1-(5-fluoro-2-methoxyphenyl)-3-(isoquinolin-4-yl)-2-oxoimidazolidine-4-carbonitrile;
(R)-3-(isoquinolin-4-yl)-2-oxo-1-(3-(trifluoromethyl)phenyl)imidazolidine-4-carbonitrile;
(R)-3-(isoquinolin-4-yl)-1-(4-methoxy-6-(trifluoromethyl)pyridin-3-yl)-2-oxoimidazolidine-4-carbonitrile;

(R)-1-(4-(difluoromethyl)phenyl)-3-(isoquinolin-4-yl)-2-oxoimidazolidine-4-carbonitrile;

(R)-1-(2,5-difluorophenyl)-3-(isoquinolin-4-yl)-2-oxoimidazolidine-4-carbonitrile;

(R)-1-(3,5-difluorophenyl)-3-(isoquinolin-4-yl)-2-oxoimidazolidine-4-carbonitrile;

(R)-1-(6-chloropyridin-2-yl)-3-(isoquinolin-4-yl)-2-oxoimidazolidine-4-carbonitrile;

(R)-3-(isoquinolin-4-yl)-1-(6-methoxypyridin-3-yl)-2-oxoimidazolidine-4-carbonitrile;

(R)-1-(5-chloro-2-methylphenyl)-3-(isoquinolin-4-yl)-2-oxoimidazolidine-4-carbonitrile;

(R)-1-(5-chloro-2-methoxyphenyl)-3-(isoquinolin-4-yl)-2-oxoimidazolidine-4-carbonitrile;

(R)-1-(2-cyano-5-methylphenyl)-3-(isoquinolin-4-yl)-2-oxoimidazolidine-4-carbonitrile;

(R)-4-(4-cyano-3-(isoquinolin-4-yl)-2-oxoimidazolidin-1-yl)-6-(trifluoromethyl)nicotinonitrile;

(R)-3-(isoquinolin-4-yl)-1-(4-methyl-1H-imidazol-2-yl)-2-oxoimidazolidine-4-carbonitrile;

(R)-1-(4-chloro-1H-imidazol-2-yl)-3-(isoquinolin-4-yl)-2-oxoimidazolidine-4-carbonitrile;

(R)-3-(isoquinolin-4-yl)-1-((1s,3S)-3-methylcyclobutyl)-2-oxoimidazolidine-4-carbonitrile;

(R)-3-(isoquinolin-4-yl)-1-((1 r,3R)-3-methylcyclobutyl)-2-oxoimidazolidine-4-carbonitrile;

(R)-1-((1 r,4R)-4-fluorocyclohexyl)-3-(isoquinolin-4-yl)-2-oxoimidazolidine-4-carbonitrile;

(R)-1-((1s,4S)-4-fluorocyclohexyl)-3-(isoquinolin-4-yl)-2-oxoimidazolidine-4-carbonitrile;

(R)-3-(isoquinolin-4-yl)-2-oxo-1-(spiro[3.3]heptan-2-yl) imidazolidine-4-carbonitrile;

(R)-1-((1s,3S)-3-isopropylcyclobutyl)-3-(isoquinolin-4-yl)-2-oxoimidazolidine-4-carbonitrile;

(R)-1-((1r,3R)-3-isopropylcyclobutyl)-3-(isoquinolin-4-yl)-2-oxoimidazolidine-4-carbonitrile;

(R)-1-((1s,3S)-3-cyclopropylcyclobutyl)-3-(isoquinolin-4-yl)-2-oxoimidazolidine-4-carbonitrile;

(R)-1-((1 r,3R)-3-cyclopropylcyclobutyl)-3-(isoquinolin-4-yl)-2-oxoimidazolidine-4-carbonitrile;

(R)-3-(isoquinolin-4-yl)-2-oxo-1-(spiro[2.3]hexan-5-yl) imidazolidine-4-carbonitrile;

(R)-1-(3,3-dimethylcyclobutyl)-3-(isoquinolin-4-yl)-2-oxoimidazolidine-4-carbonitrile;

(R)-1-(6,6-difluorospiro[3.3]heptan-2-yl)-3-(isoquinolin-4-yl)-2-oxoimidazolidine-4-carbonitrile;

(R)-3-(isoquinolin-4-yl)-2-oxo-1-((1 r,4R)-4-(trifluoromethyl)cyclohexyl)imidazolidine-4-carbonitrile;

(R)-3-(isoquinolin-4-yl)-2-oxo-1-(1-((trifluoromethyl) sulfonyl)azetidin-3-yl)imidazolidine-4-carbonitrile;

(R)-3-(isoquinolin-4-yl)-1-(1-(methylsulfonyl)azetidin-3-yl)-2-oxoimidazolidine-4-carbonitrile;

(R)-1-(1-(cyclopropylsulfonyl)azetidin-3-yl)-3-(isoquinolin-4-yl)-2-oxoimidazolidine-4-carbonitrile;

(R)-3-(isoquinolin-4-yl)-2-oxo-1-(1-(2,2,2-trifluoroethyl) azetidin-3-yl)imidazolidine-4-carbonitrile;

(R)-1-(1-acetylazetidin-3-yl)-3-(isoquinolin-4-yl)-2-oxoimidazolidine-4-carbonitrile;

(R)-1-(1-cyclopropylazetidin-3-yl)-3-(isoquinolin-4-yl)-2-oxoimidazolidine-4-carbonitrile:

(R)-3-(isoquinolin-4-yl)-2-oxo-1-(3-(trifluoromethyl)bicyclo[1.1.1]pentan-1-yl)imidazolidine-4-carbonitrile;

(R)-1-(4,4-difluorocyclohexyl)-3-(isoquinolin-4-yl)-2-oxoimidazolidine-4-carbonitrile;

(R)-1-(3-fluorobicyclo[1.1.1]pentan-1-yl)-3-(isoquinolin-4-yl)-2-oxoimidazolidine-4-carbonitrile;

(R)-3-(isoquinolin-4-yl)-1-neopentyl-2-oxoimidazolidine-4-carbonitrile;

(R)-1-((R or S)-3,3-difluorocyclopentyl)-3-(isoquinolin-4-yl)-2-oxoimidazolidine-4-carbonitrile, and (R)-1-((R or S)-3,3-difluorocyclopentyl)-3-(isoquinolin-4-yl)-2-oxoimidazolidine-4-carbonitrile.

Embodiment 212. The compound of Formula (I) of any one of Embodiments 1 to 5 or 16, wherein the compound is (R)-3-(isoquinolin-4-yl)-2-oxo-1-(6-(trifluoromethyl)pyridin-3-yl)imidazolidine-4-carbonitrile and has the structure

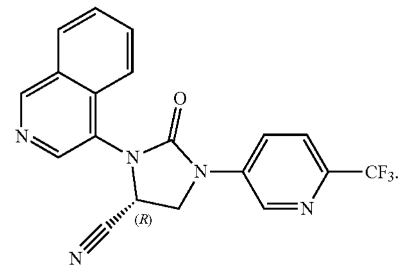

Embodiment 213. The compound of Embodiment 212, which is crystalline (R)-3-(isoquinolin-4-yl)-2-oxo-1-(6-(trifluoromethyl)pyridin-3-yl)imidazolidine-4-carbonitrile.

Embodiment 214. The compound of Embodiment 213 which is characterized by having a powder X-ray diffractogram comprising at least four reflections at 2-Theta angles selected from the group consisting of (6.85±0.2°), (8.52±0.2°), (10.41±0.2°), (13.71±0.2°), (16.90±0.2°), (17.06±0.2°), (18.40±0.2°), (19.05±0.2°), (21.76±0.2°), (22.55±0.2°), (23.50±0.2°), (24.82±0.2°), (26.89±0.2°), and (28.17±0.2°), when measured at a temperature in the range of from 20 to 40° C. with Cu-Kalpha radiation having a wavelength of 0.15418 nm.

Embodiment 215. The compound of Embodiment 213, which characterized by having a powder X-ray diffractogram comprising reflections at 2-Theta angles of (10.41±0.2°), (16.90±0.2°), (17.06±0.2°) and (21.76±0.2°), when measured at a temperature in the range of from 20 to 40° C. with Cu-Kalpha radiation having a wavelength of 0.15418 nm.

Embodiment 216. The compound of any one of Embodiments 213 to 215, which is characterized by having a differential scanning calorimetry curve comprising an endothermic peak having a peak temperature of (235.2° C.±0.5) ° C., when measured at a heating rate of 10 K/min.

Embodiment 217. The compound of any one of Embodiments 213 to 216, which is characterized by having a thermogravimetric analysis curve showing a mass loss of not more than 0.51 weight %, based on the weight of the crystalline form, when heated from 30° C. to 210° C. at a rate of 10 K/min.

Embodiment 218. The compound of Embodiment 213, which is (R)-3-(isoquinolin-4-yl)-2-oxo-1-(6-(trifluoromethyl)pyridin-3-yl)imidazolidine-4-carbonitrile Modification A.

Embodiment 219. The compound of Embodiment 213, which is characterized by having a powder X-ray diffractogram comprising at least four reflections at 2-Theta angles selected from the group consisting of (6.99±0.2°), (9.11±0.2°), (13.99±0.2°), (15.96±0.2°), (18.26±0.2°), (19.82±0.2°), (20.63±0.2°), (22.03±0.2°), (23.80±0.2°), (25.29±0.2°), (27.30±0.2°), (30.57±0.2°), and (33.47±0.2°), when measured at a temperature in the range of from 20 to 40° C. with Cu-Kalpha radiation having a wavelength of 0.15418 nm.

Embodiment 220. The compound of Embodiment 219, which is characterized by having a powder X-ray diffractogram comprising reflections at 2-Theta angles of (15.96±0.2°), (18.26±0.2°), (19.82±0.2°), and (23.80±0.2°), when measured at a temperature in the range of from 20 to 40° C. with Cu-Kalpha radiation having a wavelength of 0.15418 nm.

Embodiment 221. The compound of any one of Embodiments 219 to 220, which is characterized by having a differential scanning calorimetry curve comprising an endothermic peak having a peak temperature of (161.3° C.±0.5) ° C., when measured at a heating rate of 10 K/min.

Embodiment 222. The compound of any one of Embodiments 219 to 221, which is characterized by having a thermogravimetric analysis curve showing a mass loss of not more than 0.21 weight %, based on the weight of the crystalline form, when heated from 30° C. to 150° C. at a rate of 10 K/min.

Embodiment 223. The compound of Embodiment 213, which is (R)-3-(isoquinolin-4-yl)-2-oxo-1-(6-(trifluoromethyl)pyridin-3-yl)imidazolidine-4-carbonitrile Modification B.

Embodiment 224. The compound of Embodiment 212 which is amorphous (R)-3-(isoquinolin-4-yl)-2-oxo-1-(6-(trifluoromethyl)pyridin-3-yl)imidazolidine-4-carbonitrile.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms “salt” or “salts” refers to an acid addition or base addition salt of a compound of the invention. “Salts” include in particular “pharmaceutical acceptable salts”. The terms “pharmaceutically acceptable salt” or “pharmaceutically acceptable salts”, as used herein, refers to a salt or salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. The organic acid or inorganic acids used to form pharmaceutically acceptable acid addition salts of compounds of the present invention include, but are not limited to, acetic acid, adipic acid, ascorbic acid, aspartic acid, benzoic acid, benzenesulfonic acid, carbonic acid, camphor sulfonic acid, capric acid, chlorotheophyllinate, citric acid, ethanedisulfonic acid, fumaric acid, D-glycero-D-gulo-Heptonicacid, galactaric aid, galactaric acid/mucic acid, gluceptic acid, glucoheptonoic acid, gluconic acid, glucuronic acid, glutamatic acid, glutaric acid, glycolic acid, hippuric acid, hydrobromic acid, hydrochloric acid, hydroiodic acid, isethionic acid, lactic acid, lactobionic acid, lauryl sulfuric acid, malic acid, maleic acid, malonic acid, mandelic acid, mesylic acid, methanesulfonic acid, mucic acid, naphthoic acid, 1-hydroxy-2-naphthoic acid, naphthalenesulfonic acid, 2-naphthalenesulfonic acid, nicotinic acid, nitric acid, octadecanoic acid, oleaic acid, oxalic acid, palmitic acid, pamoic acid, phosphoric acid, polygalacturonic acid, propionic acid, sebacic acid, stearic acid, succinic acid, sulfosalicylic acid, sulfuric acid, tartaric acid, p-toluenesulfonic acid, trifluoroacetic acid and triphenylacetic acid.

Salt forms of the compounds of the present invention can be converted into the free compounds by treatment with a suitable basic agent.

Pharmaceutically acceptable acid addition salts of compounds of the present invention include, but are not limited to, a acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlorotheophyllinate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete and xinafoate salt forms.

Pharmaceutically acceptable base addition salts can be formed with inorganic and organic bases. Organic bases used to form pharmaceutically acceptable base addition salts of compounds of the present invention include, but are not limited to, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine. Inorganic bases used to form pharmaceutically acceptable base addition salts of compounds of the present invention include, but are not limited to, sodium hydroxide, potassium hydroxide, ammonium hydroxide, ammonium salts and metals from columns I to XII of the periodic table. Pharmaceutically acceptable base addition salts of compounds of the present invention include, but are not limited to, sodium, potassium, ammonium, calcium, magnesium, iron, silver, zinc, and copper salts; particularly suitable salts include ammonium, potassium, sodium, calcium and magnesium salts.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the present invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the present invention include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly, it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent& in place of the non-labeled reagent previously employed).

By way of example, compounds of the present invention can exist in a deuterated form as shown below:

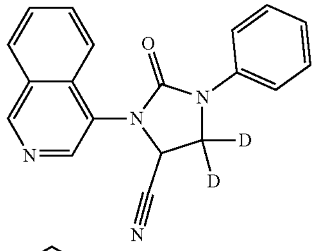

;

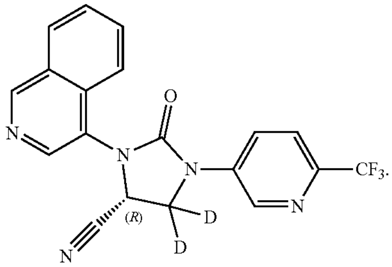

.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Processes for Making Compounds of Invention

General procedures for preparing compounds of the present invention are described herein.

In the reactions described, reactive functional groups, for example hydroxy, amino, imino or carboxy groups, where these are desired in the final product, may be protected to avoid their unwanted participation in the reactions. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Methods of synthesizing compounds of the invention

Compounds of the present invention were made by processes described herein and as illustrated in the Examples. The combination of various building blocks and intermediates described herein can be applied to yield compounds of the invention. Non-limiting examples of synthetic schemes used to make compounds of the present invention are illustrated below in Schemes 1 to 8. Further guidance can be found in the examples section.

Scheme 1

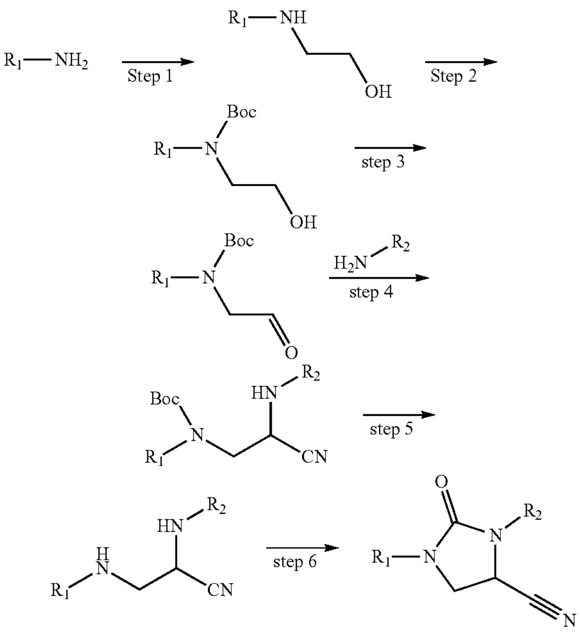

The alkylation of a primary alkyl, aryl or heteroaryl amine can be achieved using a suitable electrophile such as 2-bromoethanol in the presence of a base such as diisopropylethylamine in an organic solvent such as DMF. Protection of the amine with a suitable protecting group such as tert-butyl carbamate (Boc) can be achieved using standard conditions such as treatment with $Boc_2O$, with $Et_3N$ as a base in a solvent such as $CH_2Cl_2$. Oxidation of a primary alcohol to the corresponding aldehyde can be achieved using standard conditions with an oxidant such as Dess-Martin Reagent in a solvent such as $CH_2Cl_2$. An aldehyde can be transformed into an a-aminonitrile using a Strecker reaction, typically achieved using the desired amine, $R_1NH_2$ in the presence of a Lewis acid such as $Ti(OEt)_4$ in a non-polar organic solvent such as dichloroethane followed by treatment of the formed imine with a cyanide source such as TMSCN. Deprotection can be achieved using standard conditions, which for a Boc carbamate can include TFA in a solvent such as DCM. Cyclization of the diamine can be achieved using conditions such as triphosgene with an organic base such as $Et_3N$ in an organic solvent such as THF.

Scheme 2

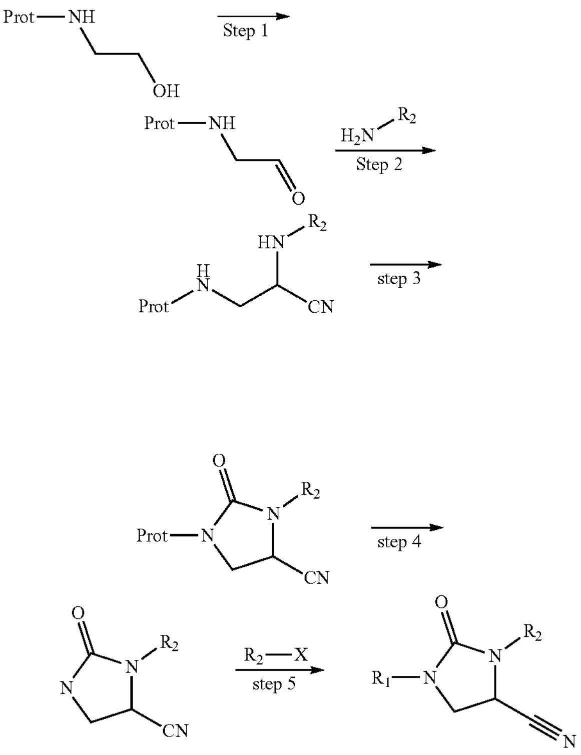

Oxidation of a primary alcohol to the corresponding aldehyde can be achieved using standard conditions with an oxidant such as Dess-Martin Reagent in a solvent such as $CH_2Cl_2$. An aldehyde can be transformed into an a-aminonitrile using a Strecker reaction, typically achieved using the desired amine, $R_1NH_2$ in the presence of a Lewis acid such as $Ti(OEt)_4$ in a non-polar organic solvent such as dichloroethane followed by treatment of the formed imine with a cyanide source such as TMSCN. Cyclization of the diamine can be achieved using conditions such as carbonyl diimidazole with an organic base such as diisopropylethylamine in an organic solvent such as THF. Deprotection can be achieved using standard conditions, which for a Boc carbamate can include HCl in a solvent such as EtOAc. Where $R_1$=Ar or Het-Ar, arylation can be achieved using a Buchwald-Hartwig coupling under typical conditions which can include using the required aryl or heteroaryl halide, $R_1$—X, a Cu (I) source such as $(Bu_4NICuI)_2$, a diamine ligand such as DMBACH in the presence of an inorganic base such as $Cs_2CO_3$, in an organic solvent such as 1,4-dioxane, typically requiring heating.

Scheme 3

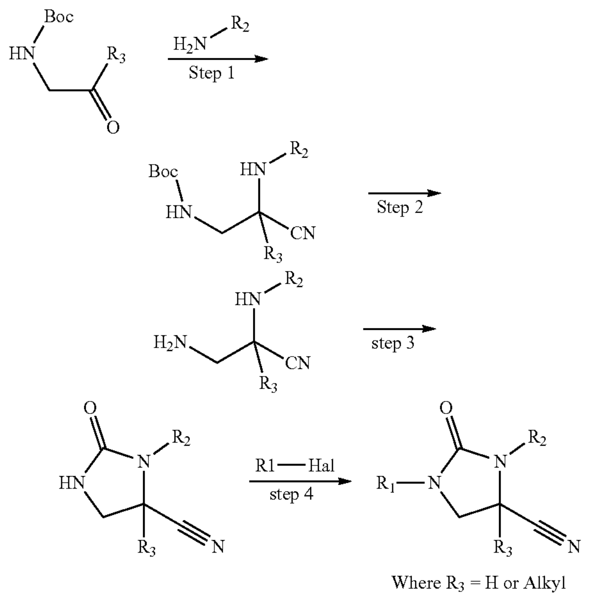

The formation of an a-aminonitrile using a Strecker reaction can typically be performed by treating the desired amine, $R_1NH_2$ and carbonyl compound in the presence of a Lewis acid such as $Ti(OEt)_4$ in a non-polar organic solvent such as dichloroethane followed by treatment of the intermediate with a cyanide source such as TMSCN. Deprotection can be achieved using standard conditions, which for a Boc carbamate can include TFA in a solvent such as DCM. Cyclization of the diamine can be achieved using conditions such as triphosgene with an organic base such as $Et_3N$ in an organic solvent such as THF. Alkylation of the cyclic urea can be achieved using the desired haloalkane $R_1$-Hal in the presence of an inorganic base such as $Cs_2CO_3$ in a polar aprotic solvent such as DMF. Where $R_1$=Ar or Het-Ar, arylation can be achieved using an Ullman-Goldberg coupling with typical conditions including using the required aryl or heteroaryl halide, $R_1$—X, a Cu (I) source such as $(Bu_4NICuI)_2$, a diamine ligand such as DMBACH in the presence of an inorganic base such as $Cs_2CO_3$, in an organic solvent such as 1,4-dioxane, typically requiring heating.

Scheme 4

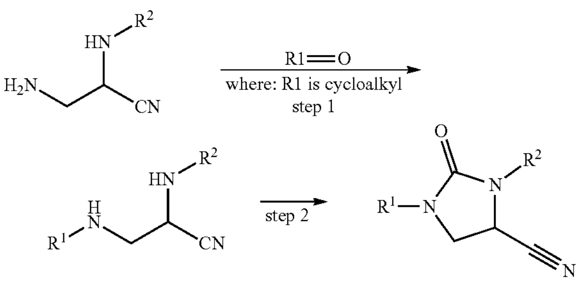

Alkylation of the primary amine can be achieved through a reductive amination using a suitable carbonyl $R^1$=O compound in the presence of a reductant such as $NaBH(OAc)_3$, with an optional acid catalyst such as AcOH in an organic solvent such as $CH_2Cl_2$. Cyclization of the diamine can be achieved using conditions such as triphosgene with an organic base such as $Et_3N$ in an organic solvent such as THE Scheme 5

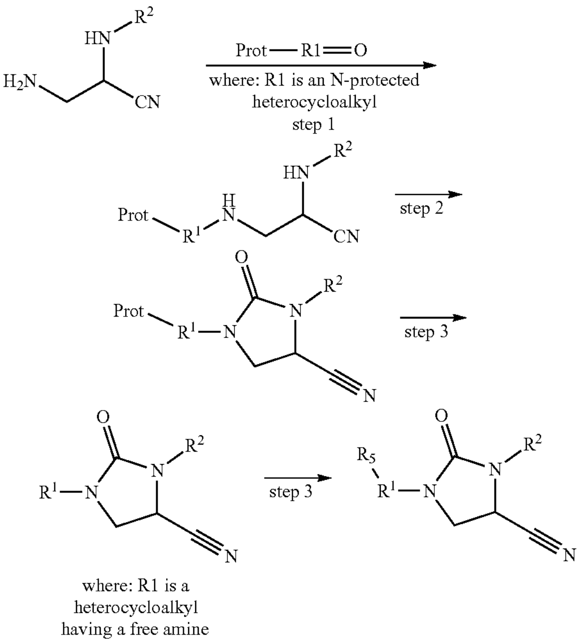

Alkylation of the primary amine can be achieved through a reductive amination using a suitable carbonyl $R^1$=O compound in the presence of a reductant such as $NaBH(OAc)_3$, with an optional acid catalyst such as AcOH in an organic solvent such as $CH_2Cl_2$. Cyclization of the diamine can be achieved using conditions such as triphosgene with an organic base such as $Et_3N$ in an organic solvent such as THF. Deprotection can be achieved using standard conditions, which for a Boc carbamate can include TFA in a solvent such as DCM. Functionalization of the deprotected amine can then be achieved using standard conditions.

Scheme 6

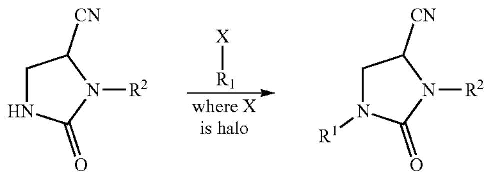

Arylation of the cyclic urea can be achieved using $S_NAr$ arylation conditions where $R^1$—X is a suitably electrophilic aryl- or heteroaryl-halide $R^1$-X in the presence of a base such as $Cs_2CO_3$ in a polar, aprotic solvent such as DMF, typically under heating.

Scheme 7

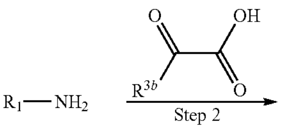

-continued

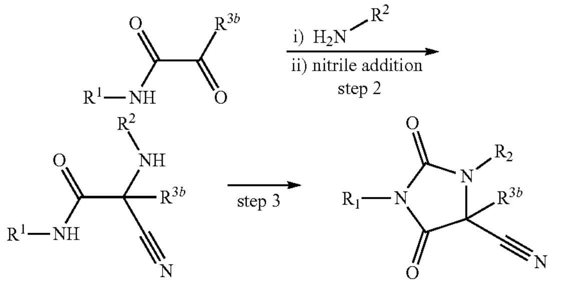

Amide formation can be achieved using standard conditions such as though using an amide coupling reagent such as N,N,N',N'-tetramethylchloroformamidinium hexafluorophosphate, in the presence of a base such as N-methylimidazole, in an organic solvent such as MeCN. The formation of an a-aminonitrile using a Strecker reaction can typically be performed by treating the desired amine, $R^2NH_2$ and carbonyl compound in the presence of a Lewis acid such as $Ti(OEt)_4$ in a non-polar organic solvent such as dichloroethane followed by treatment of the intermediate with a cyanide source such as TMSCN. Cyclization of the diamine can be achieved using conditions such as triphosgene with an organic base such as $Et_3N$ in an organic solvent such as THE Scheme 8

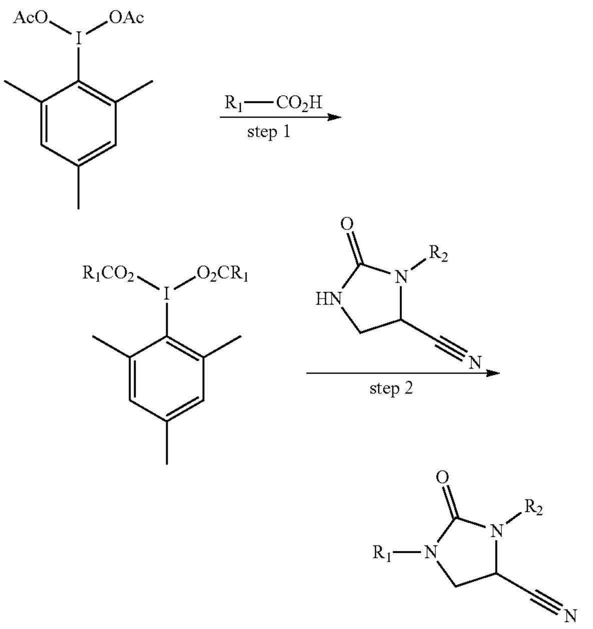

Alkylation of a cyclic urea can be achieved under photoredox conditions by first forming required activated hypervalent iodine reagent by heating the desired carboxylic acid with Diacetoxy(mesityl)-A3-iodane in toluene under reduced pressure. Alkylation can then be performed under decarboxylative photoredox catalysis conditions using a photoredox active catalyst such as $Ir(f\text{-}Meppy)_2(dtbbpy)PF_6$, with a Cu(I) salt such as Cu(I) thiophen-2-carboxylate (CuTC), a ligand such as bathophenanthroline, a base such as 2-tert-Butyl-1,1,3,3-tetramethylguanidine (BTMG) in an organic solvent such as 1,4-dioxane under blue light irradiation, typically provided by a source such as 34 W Blue LED lamps.

Administration and Pharmaceutical Compositions

For the therapeutic uses of compounds of the present invention, such compounds are administered either alone or as part of a pharmaceutical composition. Accordingly, in another aspect of the present invention provides a pharmaceutical composition, which comprises a compound of the present invention, or pharmaceutically acceptable salt or stereoisomer thereof, and one or more pharmaceutically acceptable carriers. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. In certain embodiments, the pharmaceutical composition comprising a compound of the present invention can be formulated for intramuscularly, intravenously, subcutaneously, orally, pulmonary, intrathecally, topically or intranasally administration.

The pharmaceutical compositions of the present invention can be made up in a solid form (including without limitation capsules, tablets, pills, granules, powders or suppositories), or in a liquid form (including without limitation solutions, suspensions or emulsions). Tablets may be either film coated or enteric coated according to methods known in the art.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Suitable compositions for oral administration include a compound of the present invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable carriers/excipients which are suitable for the manufacture of tablets. These carriers/excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g, intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compound of the present invention or pharmaceutical composition thereof for use in a subject (e.g., human) is typically administered orally or parenterally at a therapeutic dose of less than or equal to about 100 mg/kg. When administered intravenously via infusion, the dosage may depend upon the infusion rate at which an iv formulation is administered. In general, the therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

Certain aspects and examples of the pharmaceutical compositions of the present invention are provided in the following listing of enumerated embodiments. It will be recognized that features specified in each embodiment may be combined with other specified features to provide further embodiments of the present invention.

Embodiment 225. A pharmaceutical composition comprising a compound of Formula (I) or any one of Embodiments 1 to 224, a stereoisomer thereof, or a pharmaceutically acceptable salt thereof, and one or more pharmaceutically acceptable carriers.

Embodiment 226. A pharmaceutical composition comprising a compound of Embodiment 225, a stereoisomer thereof, or a pharmaceutically acceptable salt thereof, and one or more pharmaceutically acceptable carriers.

Embodiment 227. The pharmaceutical composition of Embodiment 225 or Embodiment 226 comprising one or more additional therapeutic agents.

Pharmacology and Utility

The compounds of the invention, in free form or in pharmaceutically acceptable salt form, exhibit valuable pharmacological properties, e.g. inhibition of SARS-CoV-2 main protease ($M^{pro}$), as indicated by the in vitro tests provided herein, and are therefore indicated for therapy or for use as research chemicals, e.g. as tool compounds. Accordingly, the compounds of the invention may generally be useful in the treatment, management and/or prevention of a coronaviral-related disease.

Certain aspects and examples of the use of compounds of the present invention and pharmaceutical compositions of the present invention are provided in the following listing of enumerated embodiments. It will be recognized that features specified in each embodiment may be combined with other specified features to provide further embodiments of the present invention.

Embodiment 228. A method for treating a disease or disorder associated with the activity of SARS-CoV-2 main protease ($M^{pro}$), wherein the method comprises administering to a subject in need of such treatment a therapeutically effective amount of a compound of any one of Embodiments 1 to 224, a stereoisomer thereof, or a pharmaceutically acceptable salt thereof.

Embodiment 229. A method for treating a disease or disorder associated with the activity of SARS-CoV-2 main protease ($M^{pro}$), wherein the method comprises administering to a subject in need of such treatment a compound of any one of Embodiments 1 to 224, a stereoisomer thereof, or a pharmaceutically acceptable salt thereof.

Embodiment 230. Use of a compound of any one of Embodiments 1 to 224, a stereoisomer thereof, or a pharmaceutically acceptable salt thereof, in the manufacture of a medicament for the treatment of a disease or disorder associated with the activity of SARS-CoV-2 main protease ($M^{pro}$)

Embodiment 231. Use of a compound of any one of Embodiments 1 to 224, a stereoisomer thereof, or a pharmaceutically acceptable salt thereof, in the treatment of a disease or disorder associated with the activity of SARS-CoV-2 main protease ($M^{pro}$)

Embodiment 232. A compound of any one of Embodiments 1 to 224, a stereoisomer thereof, or a pharmaceutically acceptable salt thereof, for use in the treatment of a disease or disorder associated with the activity of SARS-CoV-2 main protease ($M^{pro}$)

Embodiment 233. A method for treating, managing and/or preventing a coronaviral-related disease in a subject in need thereof, wherein the method comprises administering to the subject a therapeutically effective amount of a compound of any one of Embodiments 1 to 224, a stereoisomer thereof, or a pharmaceutically acceptable salt thereof.

Embodiment 234. A method for treating, managing and/or preventing a coronaviral-related disease in a subject in need thereof, wherein the method comprises administering to the subject a compound of any one of Embodiments 1 to 224, a stereoisomer thereof, or a pharmaceutically acceptable salt thereof.

Embodiment 235. Use of a compound of any one of Embodiments 1 to 224, a stereoisomer thereof, or a pharmaceutically acceptable salt thereof, in the manufacture of a medicament for the treatment, management and/or prevention of a coronaviral-related disease.

Embodiment 236. Use of a compound of any one of Embodiments 1 to 224, a stereoisomer thereof, or a pharmaceutically acceptable salt thereof, in the treatment, management and/or prevention of a coronaviral-related disease.

Embodiment 237. A compound of any one of Embodiments 1 to 224, a stereoisomer thereof, or a pharmaceutically acceptable salt thereof, for use in the treatment, management and/or prevention of a coronaviral-related disease.

Embodiment 238. A method for treating a coronaviral-related disease in a subject in need thereof, wherein the method comprises administering to the subject a therapeutically effective amount of a compound of any one of Embodiments 1 to 224, a stereoisomer thereof, or a pharmaceutically acceptable salt thereof.

Embodiment 239. A method for treating a coronaviral-related disease in a subject in need thereof, wherein the method comprises administering to the subject a compound of any one of Embodiments 1 to 224, a stereoisomer thereof, or a pharmaceutically acceptable salt thereof.

Embodiment 240. Use of a compound of any one of Embodiments 1 to 224, a stereoisomer thereof, or a pharmaceutically acceptable salt thereof, in the manufacture of a medicament for the treatment a coronaviral-related disease.

Embodiment 241. Use of a compound of any one of Embodiments 1 to 224, a stereoisomer thereof, or a pharmaceutically acceptable salt thereof, in the treatment of a coronaviral-related disease.

Embodiment 242. A compound of any one of Embodiments 1 to 224, a stereoisomer thereof, or a pharmaceutically acceptable salt thereof, for use in the treatment of a coronaviral-related disease.

Embodiment 243. A method for treating, managing and/or preventing COVID-19 disease in a subject in need thereof, wherein the method comprises administering to the subject a therapeutically effective amount of a compound of any one of Embodiments 1 to 224, a stereoisomer thereof, or a pharmaceutically acceptable salt thereof.

Embodiment 244. A method for treating, managing and/or preventing COVID-19 disease in a subject in need thereof, wherein the method comprises administering to the subject a compound of any one of Embodiments 1 to 224, a stereoisomer thereof, or a pharmaceutically acceptable salt thereof.

Embodiment 245. Use of a compound of any one of Embodiments 1 to 224, a stereoisomer thereof, or a pharmaceutically acceptable salt thereof, in the manufacture of a medicament for the treatment, management and/or prevention of COVID-19 disease.

Embodiment 246. Use of a compound of any one of Embodiments 1 to 224, a stereoisomer thereof, or a pharmaceutically acceptable salt thereof, in the treatment, management and/or prevention of COVID-19 disease.

Embodiment 247. A compound of any one of Embodiments 1 to 224, a stereoisomer thereof, or a pharmaceutically acceptable salt thereof, for use in the treatment, management and/or prevention of COVID-19 disease.

Embodiment 248. A method for treating COVID-19 disease in a subject in need thereof, wherein the method comprises administering to the subject a therapeutically effective amount of a compound of any one of Embodiments 1 to 224, a stereoisomer thereof, or a pharmaceutically acceptable salt thereof.

Embodiment 249. A method for treating COVID-19 disease in a subject in need thereof, wherein the method comprises administering to the subject a compound of any one of Embodiments 1 to 224, a stereoisomer thereof, or a pharmaceutically acceptable salt thereof.

Embodiment 250. Use of a compound of any one of Embodiments 1 to 224, a stereoisomer thereof, or a pharmaceutically acceptable salt thereof, in the manufacture of a medicament for the treatment of COVID-19 disease.

Embodiment 251. Use of a compound of any one of Embodiments 1 to 224, a stereoisomer thereof, or a pharmaceutically acceptable salt thereof, in the treatment of COVID-19 disease.

Embodiment 252. A compound of any one of Embodiments 1 to 224, a stereoisomer thereof, or a pharmaceutically acceptable salt thereof, for use in the treatment of COVID-19 disease.

Embodiment 253. The method of any one of Embodiments 233, 234, 238 and 239, wherein the coronaviral-related disease is COVID-19.

Embodiment 254. The use of a compound of any one of Embodiments 235, 236, 240 and 241, wherein the coronaviral-related disease is COVID-19.

Embodiment 255. The compound for the use in treatment of any one of Embodiments 237 and 242, wherein the coronaviral-related disease is COVID-19.

Embodiment 256. A method for inhibiting the activity of SARS-CoV-2 main protease ($M^{pro}$), wherein the method comprises administering to a subject in need of such treatment a therapeutically effective amount of a compound of any one of Embodiments 1 to 224, a stereoisomer thereof, or a pharmaceutically acceptable salt thereof.

Embodiment 257. A method for inhibiting the activity of SARS-CoV-2 main protease ($M^{pro}$), wherein the method comprises administering to a subject in need of such treatment a compound of any one of Embodiments 1 to 224, a stereoisomer thereof, or a pharmaceutically acceptable salt thereof.

Embodiment 258. Use of a compound of any one of Embodiments 1 to 224, a stereoisomer thereof, or a pharmaceutically acceptable salt thereof, in the inhibition of the activity of SARS-CoV-2 main protease ($M^{pro}$)

Embodiment 259. A compound of any one of Embodiments 1 to 224, a stereoisomer thereof, or a pharmaceutically acceptable salt thereof, for use in the inhibition of the activity of SARS-CoV-2 main protease ($M^{pro}$)

Combination Therapy

In certain instances, it may be advantageous to administer a compound of the present invention in combination with one or more additional therapeutic agents. A therapeutic agent is, for example, a chemical compound, peptide, antibody, antibody fragment or nucleic acid, which is therapeutically active or enhances the therapeutic activity when administered to a patient in combination with a compound of the present invention.

Compounds of the invention may be administered as the sole active ingredient or together with other active agents useful against a coronaviral-related disease. Accordingly, another aspect of the invention are combination for use in the treatment, prevention and/or management of a coronaviral related disease, wherein a compound of the invention is used in combination with one or more other active agents. In certain embodiments the active agent(s) is selected from neutralizing antibody and an antiviral agent. In certain embodiments the active agent(s) is selected from neutralizing antibody, an antiviral agent and other agents selected from alvelestat, Lenzilumab, Octagam, Remestemcel-L, RPH-104+olokizumab, Bucillamine, CD24FC (MK-7110), Tradipitant, Ifenprodil, Tocilizumab, Leronlimab, Fenretinide, ATYR-1923, CYTO-205, APN-01, and Ampion. In certain embodiments, the neutralizing antibody is selected from Bamlanivimab, bamlanivimab+etesevimab, bamlanivimab+VIR-7831, REGN-COV2, VIR-7831, AZD7442, Regdanvimab/CT-P59, ABP 300, COVI-AM/STI-2020, VIR-7832, SAB-185, JS016/etesevimab, C-135LS/C-144LS, BRII-196, BRII-198, SCTA-01, MW-33, DXP593, HFB-30132A, ADG20, COVI-GUARD (STI-1499) and convalescent plasma, and the antiviral agents is selected from remdesivir, Avigan/favipiravir, EIDD-2801/molnupiravir, AT-527, PF-00835231, PF-07321332, Ensovibep/DARPins, galidesivir, lopinavir-ritonavir, Virazole (ribavirin), levovir, elsulfavirine, thimerosal, UNI91103, silmitasertib/CX-4945, RBT-9, AT-301, Traneurocin/Neurosivir, Opaganib, ABX-464, SNG001, alisporivir, nafamostat mesylate, Vidofludimus/IMU-838, Emvododstat/PTC299, Brequinar, ATR-002, maraviroc.

In another aspect, the invention provides combinations for the treatment, prevention and/or management of a coronaviral related disease, wherein a compound of the invention is used in combination with remdesivir (also known as 2-ethylbutyl((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate).

EXAMPLES

The compounds of the present invention can be produced as shown in the following examples. The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art or are listed below.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art or can be produced by organic synthesis methods as described herein.

For illustrative purposes, the general reaction schemes depicted herein provide potential routes for synthesizing the compounds of the present invention as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Abbreviations

ACN acetonitrile
abs absolute
AcOH acetic acid
aq. aqueous
br. s broad singlet
BuLi n-Butyl lithium
CDI Carbonyldiimidazole (CDI)
$Cs_2CO_3$ cesium carbonate
CO carbon monoxide
CuBr copper(I) bromide
d doublet
DCE dichloroethane
DMBNH 2 2,4-dimethoxybenzylamine
DMEA N,N'-dimethylethylenediamine
DMF dimethylformamide
DMSO dimethylsulfoxide
$Et_3N$ triethylamine
EtOAc ethyl acetate
EtOH ethanol
h hour(s)
HATU O-(7-azabenzotriazol-1-yl)-N,N,N',N'-tetramethyluroniumhexafluorophosphonate
HCl hydrochloric acid
HPLC High Performance Liquid Chromatography
L liter(s)
LCMS Liquid Chromatography/Mass Spectrometry
LiOH lithium hydroxide
M molar (mol/L)
Me methyl
Mel methyl iodide
MeOH methanol
min minute(s)
mL milliliter
mm millimeter
MHz megaHertz
MS Mass Spectrometry
μm micrometer
NaCl sodium chloride
$NaHCO_3$ sodium bicarbonate
NaOH sodium hydroxide
$Na_2SO_4$ sodium sulfate
$NH_4Cl$ ammonium chloride
NMM 4-methylmorpholine
NMR Nuclear Magnetic Resonance
Pd/C palladium on charcoal
Prep Preparative
q Quartet
rt room temperature
$t_R$ retention time
s singlet
sat. saturated
t triplet
TEA triethylamine
TFA trifluoroacetic acid
THE tetrahydrofuran LCMS Methods:

LCMS Method 1: Instrument: Agilent 1200 & 6110, ESI; Column: Kinetex C18 50 mm×2.1 mm, 5 μm; Gradient: mobile phase A: 0.04% trifluoroacetic acid in water, B: 0.02% trifluoroacetic acid in acetonitrile; 5% B for 0.4 min, 5-95% B over 2.6 min, 95% B for 1.0 min, 95-5% B over 0.01 min; Flow rate: 1.0 mL/min; UV detection 215 nm and 254 nm; Mass detection MS range 100-1000 Da (ESI); Column temperature: 40° C.

LCMS Method 2: Instrument: Agilent 1260 & 6120, ESI; Column: Xbridge Shield RP18 50 mm×2.1 mm, 5 μm; Gradient: mobile phase A: 10 mM $NH_4HCO_3$ in water, B: acetonitrile; 15% B for 0.4 min, 15-90% B over 3 min, 90-100% B over 0.45 min, 100-15% B over 0.01 min; Flow rate: 0.8 mL/min; UV detection 215 nm and 254 nm; Mass detection MS range 100-1000 Da (ESI); Column temperature: 40° C.

LCMS Method 3: Instrument: Agilent 1260 & 6120, ESI; Column: Luna LC-C18 50 mm×2 mm, 5 μm; Gradient: mobile phase A: 0.05% trifluoroacetic acid in water, B: 0.05% trifluoroacetic acid in acetonitrile; 10% B for 0.4 min, 10-100% B over 3.0 min, 100% B for 0.45 min, 100-10% B over 0.01 min; Flow rate: 0.8 mL/min; UV detection 215 nm and 254 nm; Mass detection MS range 100-1000 Da (ESI); Column temperature: 40° C.

LCMS Method 4: Instrument: Agilent 1260 & 6120, ESI; Column: Luna LC-C18 50 mm×2 mm, 5 μm; Gradient: mobile phase A: 0.05% trifluoroacetic acid in water, B: 0.05% trifluoroacetic acid in acetonitrile; 1% B for 0.4 min, 1-90% B over 3.0 min, 90-100% B over 0.45 min, 100-1% B over 0.01 min; Flow rate: 0.8 mL/min; UV detection 215 nm and 254 nm; Mass detection MS range 100-1000 Da (ESI); Column temperature: 40° C.

LCMS Method 5: Instrument: Agilent 1260 & 6125B, ESI; Column: Agilent Poroshell SB-C18 30 mm×3.0 mm, 2.7 μm; Gradient: mobile phase A: 0.04% trifluoroacetic acid in water, B: 0.02% trifluoroacetic acid in acetonitrile; 5-95% B over 0.8 min, 95% B for 0.41 min, 95-5% B over 0.01 min; Flow rate: 2.0 mL/min; UV detection 220 nm; Mass detection MS range 100-1000 Da (ESI); Column temperature: 40° C.

LCMS Method 6: Instrument: Agilent 1260 & 6125B, ESI; Column: Agilent Poroshell SB-C18 30 mm×3.0 mm, 2.7 μm; Gradient: mobile phase A: 0.04% trifluoroacetic acid in water, B: 0.02% trifluoroacetic acid in acetonitrile; 5-95% B over 3 min, 95% B for 0.5 min, 95-5% B over 0.01 min; Flow rate: 1.5 mL/min; UV detection 220 nm; Mass detection MS range 100-1000 Da (ESI); Column temperature: 40° C.

LCMS Method 7: Instrument: Agilent 1200 & G6120B, ESI; Column: Kinetex EVO C18 100A 30 mm×2.1 mm, 5 μm; Gradient: mobile phase A: 0.04% trifluoroacetic acid in water, B: 0.02% trifluoroacetic acid in acetonitrile; 5-95% B over 0.69 min, 95% B for 0.45 min, 95-5% B over 0.01 min; Flow rate: 1.5 mL/min; UV detection 220 and 254 nm; Mass detection MS range 100-1000 Da (ESI); Column temperature: 40° C.

LCMS Method 8: Instrument: Agilent 1260 & 6125B, ESI; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5-95% B over 0.8 min, 95% B for 0.4 min, 95-5% B over 0.01 min; Flow rate: 2.0 mL/min; UV detection 220 nm; Mass detection MS range 100-1000 Da (ESI); Column temperature: 40° C.

LCMS Method 9: Instrument: Agilent 1200 & 6110, ESI; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5-95% B over 1.0 min, 95-100% B over 0.8 min, 100-5% over 0.01 min; Flow rate: 1.0 mL/min; UV detection 220 and 254 nm; Mass detection MS range 100-1000 Da (ESI); Column temperature: 40° C.

LCMS Method 10: Instrument: Shimadzu LC-20AD&MS 2020, ESI; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5% B for 0.01 min, 5-95% B over 0.69 min, 95% B for 0.46 min, 95-5% over 0.34 min; Flow rate: 1.5 mL/min; UV detection 220 and 254 nm; Mass detection MS range 100-1000 Da (ESI); Column temperature: 40° C.

LCMS Method 11: Instrument: Shimadzu LC-20AD&MS 2020, ESI; Column: Halo C18 30 mm×3.0 mm, 2.7 μm; Gradient: mobile phase A: 0.04% trifluoroacetic acid in water, B: 0.02% trifluoroacetic acid in acetonitrile; 5% B over 0.01 min., 5-95% B over 0.69 min, 95% B for 0.46 min, 95-5% over 0.34 min; Flow rate: 1.5 mL/min; UV detection 220 and 254 nm; Mass detection MS range 100-1000 Da (ESI); Column temperature: 40° C.

LCMS Method 12: Instrument: Shimadzu LC-20AB&MS 2010, ESI; Column: Xbridge C18 50 mm×2.1 mm, 5 μm; Gradient: mobile phase A: 10 mM $NH_4HCO_3$ in water, B: acetonitrile; 5% B for 0.01 min., 5-95% B over 0.69 min, 95% B for 0.46 min, 95-5% over 0.34 min; Flow rate: 1.5 mL/min; UV detection 220 and 254 nm; Mass detection MS range 100-1000 Da (ESI); Column temperature: 40° C.

LCMS Method 13: Instrument: Agilent 1260 & 6120, ESI; Column: Luna LC-C18 50 mm×2 mm, 5 μm; Gradient: mobile phase A: 0.04% trifluoroacetic acid in water, B: 0.02% trifluoroacetic acid in acetonitrile; 5% B for 0.4 min, 5-95% B over 2.6 min, 95% B over 1.0 min, 95-5% B over 0.01 min., 5% B over 0.49 min.; Flow rate: 1.0 mL/min; UV detection 215 nm and 254 nm; Mass detection MS range 100-1000 Da (ESI); Column temperature: 40° C.

LCMS Method 14: Instrument: Shimadzu LC-20AD&MS 2020, ESI; Column: InfinityLab Poroshell SB-C18 30 mm×3.0 mm 2.7 μm; Gradient: mobile phase A: 0.04% trifluoroacetic acid in water, B: 0.02% trifluoroacetic acid in acetonitrile; 5-95% B over 0.89 min, 95% B for 0.26 min, 95-5% over 0.44 min; Flow rate: 1.5 mL/min; UV detection 220 and 254 nm; Mass detection MS range 100-1000 Da (ESI); Column temperature: 40° C.

LCMS Method 15: Instrument: Shimadzu LC-20ADXR&MS 2020, ESI; Column: Shim-pack *Velox* SP-C18 30 mm×2.1 mm 2.7 μm; Gradient: mobile phase A: 0.04% trifluoroacetic acid in water, B: 0.02% trifluoroacetic acid in acetonitrile; 5% B for 0.01 min., 5-95% B over 0.69 min, 95% B for 0.46 min, 95-5% over 0.34 min; Flow rate: 1.5 mL/min; UV detection 220 and 254 nm; Mass detection MS range 100-1000 Da (ESI); Column temperature: 40° C.

LCMS Method 16: Instrument: Agilent 1260 & 6120, ESI; Column: Kinetex LC-C18 50 mm×2.1 mm, 5 μm; Gradient: mobile phase A: 0.04% trifluoroacetic acid in water, B: 0.02% trifluoroacetic acid in acetonitrile; 5% B for 0.4 min, 5-95% B over 3.0 min, 95% B over 1.0 min, 95-5% B over 0.5 min; Flow rate: 1.0 mL/min; UV detection 215 nm and 254 nm; Mass detection MS range 100-1000 Da (ESI); Column temperature: 40° C.

LCMS Method 17: Instrument: Agilent 1200 & 6120, ESI; Column: XBridge C18 50 mm×2.1 mm, 5 μm; Gradient: mobile phase A: 10 mM $NH_4HCO_3$ in water, B: acetonitrile; 5-95% B over 3.4 min, 95% B for 0.45 min, 95-5% B over 0.01 min, 5% B for 0.64 min; Flow rate: 0.8 mL/min; UV detection 215 nm and 254 nm; Mass detection MS range 100-1000 Da (ESI); Column temperature: 40° C.

LCMS Method 18: Instrument: Shimadzu LC-20AB&MS 2010, ESI; Column: Xbridge C18 50 mm×2.1 mm, 5 μm; Gradient: mobile phase A: 10 mM $NH_4HCO_3$ in water, B: acetonitrile; 5% B for 0.01 min., 5-95% B over 2.99 min, 95% B for 0.50 min, 95-5% over 0.01 min; 5% B for 0.79 min., Flow rate: 1.0 mL/min; UV detection 220 and 254 nm; Mass detection MS range 100-1000 Da (ESI); Column temperature: 40° C.

LCMS Method 19: Instrument: Agilent 1200 & 6130, MSD; Column: XBridge C18 50 mm×2.1 mm, 5 μm; Gradient: mobile phase A: 10 mM $NH_4HCO_3$ in water, B: acetonitrile; 5% B for 0.4 min., 5-95% B over 3.0 min, 95% B for 0.45 min, 95-5% B over 0.01 min, 5% B for 0.64 min; Flow rate: 0.8 mL/min; UV detection 215 nm and 254 nm; Mass detection MS range 100-1000 Da (ESI); Column temperature: 40° C.

LCMS Method 20: Instrument: Shimadzu LC-20AB&MS 2010, ESI; Column: Kinetex C18 50 mm×2.1 mm, 5 μm; Gradient: mobile phase A: 10 mM $NH_4HCO_3$ in water, B: acetonitrile; 5% B for 0.01 min., 5-95% B over 0.69 min, 95% B for 0.46 min, 95-5% over 0.34 min; Flow rate: 1.5 mL/min; UV detection 220 and 254 nm; Mass detection MS range 100-1000 Da (ESI); Column temperature: 40° C.

LCMS Method 21: Instrument: Shimadzu LC-20AD&MS 2020, ESI; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5% B over 0.0.01 min., 5-95% B over 0.69 min, 95% B for 0.50 min, 95-5% over 0.01 min; 5% B for 0.29 min Flow rate: 1.5 mL/min; UV detection 220 and 254 nm; Mass detection MS range 100-1000 Da (ESI); Column temperature: 40° C.

LCMS Method 22: Instrument: Shimadzu LC-20AD&MS 2020, ESI; Column: Xbridge C18 50 mm×2.1 mm, 5 μm; Gradient: mobile phase A: 10 mM $NH_4HCO_3$ in water, B: acetonitrile; 10% B for 0.01 min., 10-80% B over 3.49 min, 80% B for 0.30 min, 80-10% B over 0.01 min; 10% B for 0.49 min.; Flow rate: 0.8 mL/min; UV detection 220 and 254 nm; Mass detection MS range 100-1000 Da (ESI); Column temperature: 40° C.

LCMS Method 23: Instrument: Shimadzu LC-20AD&MS 2020, ESI; Column: Xbridge Shield RPC18 50 mm×2.1, 5 μm; Gradient: mobile phase A: 10 mM $NH_4HCO_3$ in water, B: acetonitrile; 5% B for 0.01 min., 5-95% B over 0.99 min, 95-100% B over 0.80 min, 100-5% B % over 0.0.01 min; 5% B for 0.39 min.; Flow rate: 1.0 mL/min (0.01-1.8 min) and 1.2 mL/min (1.81-2.20 min); Diode array detection; Mass detection MS range 100-1000 Da (ESI); Column temperature: 40° C.

LCMS Method 24: Instrument: Agilent 1200 & 1956A, ESI; Column: Xbridge Shield RPC18 50 mm×2.1, 5 μm; Gradient: mobile phase A: 10 mM $NH_4HCO_3$ in water, B: acetonitrile; 10-80% B over 2.00 min, 80% B for 0.48 min, 80-10% B over 0.02 min; 10% B for 1.50 min.; Flow rate: 1.0 mL/min (0.00-2.48 min) and 1.2 mL/min (2.50-3.00 min); Diode array detection; Mass detection MS range 100-1000 Da (ESI); Column temperature: 40° C.

LCMS Method 25: Instrument: Agilent 1200 & 6120, ESI; Column: Kinetex C18 30 mm×2.1 mm, μm; Gradient: mobile phase A: 0.04% trifluoroacetic acid in water, B: 0.02% trifluoroacetic acid in acetonitrile; 5-95% B over 1.00 min, 95-100% B over 0.8 min, 100-5% B over 0.01 min, 5% B for 0.19 min; Flow rate: 1.0 mL/min(0-1.80 min) and 1.2 ml/min (1.81-2.00); Diode array detection; Mass detection MS range 100-1000 Da (ESI); Column temperature: 40° C.

LCMS Method 26: Instrument: Shimadzu LC-20AD&MS 2020, ESI; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5% B over 0.01 min., 5-95% B over 2.99 min, 95% B for 0.50 min, 95-5% over 0.50 min, 5% B for 0.30 min; Flow rate: 1.0 mL/min; Diode array detection; Mass detection MS range 100-1000 Da (ESI); Column temperature: 40° C.

LCMS Method 27: Instrument: Shimadzu LC-20AB MSD: LCMS-2010, ESI; Column: Shim-pack Scepter C18 33 mm×3.0 mm 3 μm; Gradient: mobile phase A: 10 mM $NH_4HCO$ in water, B: ACN; 0-60% B over 3.5 min., 60% B for 0.30 min, 60-0% B over 0.50 min; Flow rate: 0.8 mL/min 0.01 to 3.8 min. and 1.0 mL/min 3.81 to 4.3 min; UV detection 220 and 254 nm; Mass detection MS range 100-1000 Da (ESI); Column temperature: 40° C.

LCMS Method 28: Instrument: Agilent 1200, MSD 6150; Column: Kinetex EVO C18 30 mm×2.1 mm, 5 μm; Gradient: mobile phase A: 0.04% trifluoroacetic acid in water, B: 0.02% trifluoroacetic acid in acetonitrile; 5% B for 0.01 min., 5-95% B over 3.49 min, 95% B for 0.30 min, 95-5% B over 0.01 min., 5% B for 0.49 min.; Flow rate: 1.0 mL/min; UV detection 220 and 254 nm; Mass detection MS range 100-1000 Da (ESI); Column temperature: 40° C.

LCMS Method 29: Instrument: Shimadzu LC-20AD&MS 2020, ESI; Column: Kinetex EVO 5 μm C18 30×2.1 mm; Gradient: mobile phase A-0.04% trifluoroacetic acid in water, B-0.02% trifluoroacetic acid in acetonitrile; 0-60% B over 0.79 min, hold 60% B for 0.4 min, 0% B over 0.01 min and hold 0% B for 0.29 min; Flow rate: 1.5 mL/min; UV detection 220 and 254 nm; Mass detection MS range 100-1000 Da (ESI); Column temperature: 40° C.

LCMS Method 30: Instrument: Shimadzu LC-20AD&MS 2020, ESI; Column: Poroshell SB-C18 mm×3.0 mm, 2.7 μm; Gradient: mobile phase A: 0.04% trifluoroacetic acid in water, B: 0.02% trifluoroacetic acid in acetonitrile; 5-95% B over 0.69 min, 95% B for 0.5 min, 95-5% over 0.01 min, 5% B for 0.29 min; Flow rate: 1.0 mL/min; UV detection 220 and 254 nm; Mass detection MS range 100-1000 Da (ESI); Column temperature: 40° C.

LCMS Method 31: Instrument: Agilent 1200 & 6120B, ESI; Column: XBridge RP18 50 mm×2.1 mm, 5 μm; Gradient: mobile phase A: 10 mM $NH_4HCO_3$ in water, B: acetonitrile; 5% B for 0.4 min, 5-95% B over 3.0 min, 95% B for 0.45 min, 95-5% B over 0.01 min, 5% B for 0.64 min; Flow rate: 0.8 mL/min; UV detection 215 nm and 254 nm; Mass detection MS range 100-1000 Da (ESI); Column temperature: 40° C.

LCMS Method 32: Instrument: Shimadzu LC-20AB&MS 2010, ESI; Column: Shim-Pack Scepter C18 33 mm×3.0 mm, 3 μm; Gradient: mobile phase A: 10 mM $NH_4HCO_3$ in water, B: acetonitrile; 0% B for 0.01 min, 0-60% B over 0.79 min, 60% B for 0.4 min, 60-0% B over 0.01 min, 0% B for 0.29 min; Flow rate: 1.5 mL/min; Diode array detection; Mass detection MS range 100-1000 Da (ESI); Column temperature: 40° C.

LCMS Method 33: Instrument: Shimadzu LC-20AB&MS 2010, ESI; Column: Shim-Pack Scepter C18 33 mm×3.0 mm, 3 μm; Gradient: mobile phase A: 10 mM $NH_4HCO_3$ in water, B: acetonitrile; 5% B for 0.01 min, 5-95% B over 0.69 min, 95% B for 0.46 min, 95-5% B over 0.34 min, 5% B for 0.29 min; Flow rate: 1.5 mL/min; Diode array detection; Mass detection MS range 100-1000 Da (ESI); Column temperature: 40° C.

LCMS Method 34: Instrument: Shimadzu LC-20AB&MS 2010, ESI; Column: Luna-C18 50 mm×2.0 mm, 5 μm; Gradient: mobile phase A: 0.04% trifluoroacetic acid in water, B: 0.02% trifluoroacetic acid in acetonitrile; 5%

B for 0.01 min, 5-95% B over 2.99 min, 95% B for 0.50 min, 95-5% B over 0.0.01 min, 5% B for 0.79 min; Flow rate: 1.0 mL/min; Diode array detection; Mass detection MS range 100-1000 Da (ESI); Column temperature: 40° C.

LCMS Method 35: Instrument: Shimadzu LC-20AD&MS 2020, ESI; Column: XBridge C18 50 mm×2.1 mm, 5 μm; Gradient: mobile phase A: 10 mM $NH_4COOCH_3$ in water, B: acetonitrile; 5% B for 0.01 min 5-95% B over 0.69 min. 95% B for 0.45 min, 95-5% B over 0.01 min. 5% B for 0.34 min; Flow rate: 1.5 mL/min; UV detection 220 and 254 nm; Mass detection MS range 100-1000 Da (ESI); Column temperature: 40° C.

LCMS Method 36: Instrument: Agilent 1200 & G6110A, ESI; Column: Xbridge Shield RPC18 50 mm×2.1, 5 μm; Gradient: mobile phase A: 10 mM $NH_4HCO_3$ in water, B: acetonitrile; 5-95% B over 3.00 min, 95% B for 0.50 min, 95-5% B over 0.01 min; 5% B for 0.80 min.; Flow rate: 1.0 mL/min; Diode array detection; Mass detection MS range 100-1000 Da (ESI); Column temperature: 40° C.

LCMS Method 37: Instrument: Agilent 1260 & 6120, ESI; Column: Xbridge Shield RP18 50 mm×2.1 mm, 5 μm; Gradient: mobile phase A: 10 mM $NH_4HCO_3$ in water, B: acetonitrile; 5% B for 0.4 min, 5-90% B over 3 min, 90-95% B over 0.45 min, 95-5% B over 0.01 min, 5% B for 0.64 min; Flow rate: 0.8 mL/min; UV detection 215 nm and 254 nm; Mass detection MS range 100-1000 Da (ESI); Column temperature: 40° C.

LCMS Method 38: Instrument: Shimadzu LC-20AD&MS 2020, ESI; Column: XBridge C18 50 mm×2.1 mm, 5 μm; Gradient: mobile phase A: 10 mM $NH_4HCO_3$ in water, B: acetonitrile; 0-60% B over 2.49 min, 60% B for 0.50 min, 60-0% B over 0.01 min; 0% B for 0.49 min.; Flow rate: 1.0 mL/min from 0.01 to 3.00 min and 1.2 mL/min from 3.01 to 3.50 min; UV detection 220 and 254 nm; Mass detection MS range 50-2000 Da (ESI); Column temperature: 40° C.

SFC Methods

SFC Method 1: Instrument: Waters UPCC with PDA; Chiralpak AD-3, 50×4.6 mm I.D., 3 μm; Gradient: mobile phase A-$CO_2$, B-IPA(0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 2: Instrument: Waters UPCC with PDA; Chiralcel OJ-3, 50×4.6 mm I.D., 3 μm; Gradient: mobile phase A-$CO_2$, B-ACN (0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 3: Instrument: Waters UPCC with PDA; Chiralpak OD-3, 150×4.6 mm I.D., 3 μm; Gradient: mobile phase A-$CO_2$, B-EtOH (0.1% IPAm, v/v); 10% B for 0.5 min; 10-50% B over 3.0 min, 50% B for 1.0 min, 50-10% B over 0.5 min, Flow rate: 2.5 mL/min; Column temperature: 35° C.

SFC Method 4: Instrument: Waters UPCC with SQ Detector 2; Chiralpak AD-3, 50×4.6 mm I.D., 3 μm; Gradient: mobile phase A-$CO_2$, B-EtOH (0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 5: Instrument: Waters UPCC with PDA; Lux Cellulose-2, 100×4.6 mm I.D., 3 μm; Gradient: mobile phase A-$CO_2$, B-ACN (0.1% IPAm, v/v); 5% B for 0.2 min; 5-50% B over 1.0 min, 50% B for 1.0 min, 50-5% B over 0.4 min, 5% B for 0.4 min; Flow rate: 4 mL/min; Column temperature: 35° C.

SFC Method 6: Instrument: Waters UPCC with PDA; Chiralpak IH, 50×4.6 mm I.D., 3 μm; Gradient: mobile phase A-$CO_2$, B-ACN (0.1% IPAm, v/v); 10% B for 0.2 min; 10-50% B over 2.2 min, 50-10% B over 1.6 min; Flow rate: 3.4 mL/min; Column temperature: 35° C.

SFC Method 7: Instrument: Waters UPCC with PDA; (S,S)-WHELK-01, 50×4.6 mm I.D., 3.5 μm; Gradient: mobile phase A-$CO_2$, B-ACN (0.1% IPAm, v/v); 5% B for 0.2 min; 5-50% B over 1.0 min, 50% B for 1.0 min, 50-5% B over 0.4 min; Flow rate: 3.4 mL/min; Column temperature: 35° C.

SFC Method 8: Instrument: Waters UPCC with PDA; Chiralpak IG-3, 100×4.6 mm I.D., 3 μm; Gradient: mobile phase A-$CO_2$, B-IPA (0.1% IPAm, v/v); 5% B for 0.2 min; 5-50% B over 1.0 min, 50% B for 1.0 min, 50-5% B over 0.4 min; Flow rate: 3.4 mL/min; Column temperature: 35° C.

SFC Method 9: Instrument: Waters UPCC with PDA; Chiralpak IH-3, 100×4.6 mm I.D., 3 μm; Gradient: mobile phase A-$CO_2$, B-IPA (0.1% IPAm, v/v); 10% B for 0.2 min; 10-50% B over 2.2 min, 50-10% B over 1.6 min; Flow rate: 3.4 mL/min; Column temperature: 35° C.

SFC Method 10: Instrument: Waters UPCC with PDA; Lux Cellulose-2, 50×4.6 mm I.D., 3 μm; Gradient: mobile phase A-$CO_2$, B-EtOH (0.1% IPAm, v/v); 5% B for 0.2 min; 5-50% B over 1.0 min, 50% B for 1.0 min, 50-5% B over 0.4 min, 5% B for 0.4 min; Flow rate: 4 mL/min; Column temperature: 35° C.

SFC Method 11: Instrument: Waters UPCC with PDA; Chiralcel OD-3, 150×4.6 mm I.D., 3 μm; Gradient: mobile phase A-$CO_2$, B-IPA (0.1% IPAm, v/v); 10% B for 0.5 min; 10-50% B over 3.0 min, 50% B for 1.0 min, 50-10% B over 0.5 min; Flow rate: 2.5 mL/min; Column temperature: 35° C.

SFC Method 12: Instrument: Waters UPCC with PDA; Chiralcel IG-3, 100×4.6 mm I.D., 3 μm; Gradient: mobile phase A-$CO_2$, B-EtOH (0.1% IPAm, v/v); 10% B for 0.2 min; 10-50% B over 2.2 min, 50% B for 1.0 min, 50-10% B over 0.6 min; Flow rate: 3.4 mL/min; Column temperature: 35° C.

SFC Method 13: Instrument: Waters UPCC with PDA; Chiralpak IH-3, 100×4.6 mm I.D., 3 μm; Gradient: mobile phase A-$CO_2$, B-ACN (0.1% IPAm, v/v); 10% B for 0.2 min; 10-50% B over 2.2 min, 50% B for 1.0 min, 50-10% B over 0.6 min; Flow rate: 3.4 mL/min; Column temperature: 35° C.

SFC Method 14: Instrument: Waters UPCC with PDA; Chiralpak AD-3, 150×4.6 mm I.D., 3 μm; Gradient: mobile phase A-$CO_2$, B-EtOH (0.1% IPAm, v/v); 10% B for 0.2 min; 10-50% B over 2.2 min, 50-10% B over 1.6 min; Flow rate: 2.5 mL/min; Column temperature: 35° C.

SFC Method 15: Instrument: Waters UPCC with PDA; Chiralpak AD-3, 50×4.6 mm I.D., 3 μm; Gradient: mobile phase A-$CO_2$, B-EtOH (0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 16: Instrument: Waters UPCC with QDA; Chiralpak OD-3, 150×4.6 mm I.D., 3 μm; Gradient: mobile phase A-$CO_2$, B-EtOH (0.1% IPAm, v/v); 10% B for 0.5 min; 10-50% B over 3.0 min, 50% B for 1.0 min, 50-10% B over 0.5 min, Flow rate: 2.5 mL/min; Column temperature: 35° C.

SFC Method 17: Instrument: Waters UPCC with PDA; (S,S)-WHELK-01, 50×4.6 mm I.D., 3.5 μm; Gradient: mobile phase A-$CO_2$, B-IPA (0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 18: Instrument: Waters UPCC with PDA; Chiralpak IG-3, 100×4.6 mm I.D., 3 μm; Gradient: mobile phase A-$CO_2$, B-IPA (0.1% IPAm, v/v); 10% B for 0.2 min; 10-50% B over 2.2 min, 50% B for 1.0 min, 50-10% B over 0.6 min, Flow rate: 3.4 mL/min; Column temperature: 35° C.

SFC Method 19: Instrument: Waters UPCC with PDA; Chiralpak IG-3, 100×4.6 mm I.D., 3 μm; Gradient: mobile phase A-$CO_2$, B-IPA (0.1% IPAm, v/v); 5% B for 3.2 min; 5-40% B over 3.0 min, 40% B for 3.0 min, 40-5% B over 0.4 min, 5% B for 0.40 min; Flow rate: 3.4 mL/min; Column temperature: 35° C.

SFC Method 20: Instrument: Waters UPCC with SQ Detector; Lux Cellulose-2, 50×4.6 mm I.D., 3 μm; Gradient: mobile phase A-$CO_2$, B-MeOH (0.1% IPAm, v/v); 5% B for 3.2 min; 5-40% B over 3.0 min, 40% B for 3.0 min, 40-5% B over 0.4 min, 5% B for 0.4 min; Flow rate: 4 mL/min; Column temperature: 35° C.

SFC Method 21: Instrument: Waters UPCC with PDA; Chiralpak IG-3, 50×4.6 mm I.D., 3 μm; Gradient: mobile phase A-$CO_2$, B-EtOH (0.1% IPAm, v/v); 5% B for 0.2 min; 5-50% B over 1.0 min, 50% B for 1.0 min, 50-5% B over 0.4 min, 5% B for 0.4 min; Flow rate: 3.4 mL/min; Column temperature: 35° C.

SFC Method 22: Instrument: Waters UPCC with PDA; Column: Chiralpak AD-3, 150×4.6 mm, I.D., 3 μm; Mobile phase A: $CO_2$; Mobile phase B: IPA(0.1% IPAm); 40% B: isocratic elution; Flow rate: 2.5 mL/min; Column temperature: 35° C.

SFC Method 23: Instrument: Waters UPCC with PDA; Column: Chiralpak AD-3, 50×4.6 mm I.D., 3 μm; Mobile phase A: $CO_2$; Mobile phase B: MeOH(0.1% IPAm, v/v); Gradient: 5% B for 0.2 min, 5-50% B over 1.0 min, 50% B for 2.2 min, 50-5% B over 0.40 min, 5% B for 3.00 min; Flow rate: 3.4 mL/min; Column temperature: 35° C.

SFC Method 24: Instrument: Waters UPCC with SQ Detector; Column: (S,S)-WHELK-01, 50×4.6 mm I.D., 3.5 μm; Mobile phase A:$CO_2$; Mobile phase B: EtOH (0.1% IPAm, v/v); Gradient: 5% B for 0.2 min, 5-50% B over 1.0 min, 50% B for 2.20 min, 50-5% B in 0.40 min, 5% B for 3.0 min; Flow rate: 3.4 mL/min, Column temperature: 35° C.

SFC Method 25: Instrument: Waters UPCC with QDa Detector; Column: Chiralpak IG-3, 50×4.6 mm I.D., 3 μm; Mobile phase A: $CO_2$; Mobile phase B: IPA(0.1% IPAm, v/v); Gradient 5% B for 0.20 min, 5-50% B over 1.00 min, 50% B for 2.20 min, 50-5% B over 0.40 min, 5% B for 3.00 min; Flow rate: 3.4 mL/min; Column temperature: 35° C.

SFC Method 26: Instrument: Waters UPCC with QDA; Column:(S,S)-WHELK-01,50×4.6 mm I.D., 3.5 μm; Mobile phase A: $CO_2$; Mobile phase B: IPA(0.1% IPAm, v/v); Gradient: 5% B for 0.20 min, 5-50% B over 1.00 min, 50% B for 2.20 min, 50-5% B over 0.40 min, 5% B for 3.00 min; Flow rate: 4.0 mL/min; Column temperature: 35° C.

SFC Method 27: Instrument: Waters UPCC with PDA; Column: Chiralpak AD-3, 50×4.6 mm I.D., 3 μm; Mobile phase A: $CO_2$; Mobile phase B: IPA (0.1% IPAm, v/v); Gradient: 5% B for 0.20 min, 5-50% B over 1.00 min, 50% B for 2.20 min, 50-5% B over 0.40 min, 5% B for 3.00 min; Flow rate: 3.4 mL/min, Column temperature: 35° C.

SFC Method 28: Instrument: Waters UPCC with PDA; Column: Chiralpak AD-3, 150×4.6 mm, I.D., 3 μm; Mobile phase A: $CO_2$; Mobile phase B: IPA (0.1% IPAm); isocratic elution, 50% B; Flow rate: 2.5 mL/min; Column temperature: 35° C.

SFC Method 29: Instrument: Waters UPCC with SQ Detector; Column: Lux Cellulose-2, 50×4.6 mm I.D., 3 μm; Mobile phase A: $CO_2$; Mobile phase B: MeOH (0.1% IPAm, v/v); Gradient: 5% B for 0.20 min, 5-50% B over 1.00 min, 50% B for 2.20 min, 50-5% B over 0.40 min, 5% B for 3.00 min; Flow rate: 3.4 mL/min; Column temperature: 35° C.

SFC Method 30: Instrument: Waters UPCC with PDA Column: Chiralcel OJ-3, 50×4.6 mm I.D., 3 μm; Mobile phase A: $CO_2$; Mobile phase B: EtOH(0.1% IPAm, v/v); Gradient: 5% B for 0.20 min, 5-50% B over 1.00 min, 50% B for 2.20 min, 50-5% B over 0.40 min, 5% B for 3.00 min; Flow rate: 3.4 mL/min; Column temperature: 35° C.

SFC Method 31: Instrument: Waters UPCC with PDA; Column: Chiralcel OD-3, 50×4.6 mm I.D., 3 μm; Mobile phase A: $CO_2$; Mobile phase B: IPA(0.1% IPAm, v/v); isocratic elution at 50% B; Flow rate: 4.0 mL/min; Column temperature: 35° C.

SFC Method 32: Instrument: Waters UPCC with PDA; Column: Chiralpak OJ-3, 150×4.6 mm, I.D., 3 μm; Mobile phase A: $CO_2$; Mobile phase B: EtOH (0.1% IPAm); Gradient: 5% B for 0.20 min, 5-40% B over 1.00 min, 40-60% B over 1.00 min, 60-5% B over 0.40 min, 5% B for 3.00 min; Flow rate: 2.5 mL/min; Column temperature: 35° C.

SFC Method 33: Instrument: Waters UPCC with PDA; Column: Chiralpak OJ-3,150×4.6 mm I.D., 3 μm; Mobile phase A: $CO_2$; Mobile phase B: IPA(0.1% IPAm, v/v); Gradient 10% B for 0.50 min, 10-50% B over 3.00 min, 50% B for 1.00 min; 50-10% B over 0.50 min; Flow rate: 2.5 mL/min; Column temperature: 35° C.

SFC Method 34: Instrument: Waters UPCC with PDA; Column: Chiralpak OJ-3,150×4.6 mm I.D., 3 μm; Mobile phase A: $CO_2$; Mobile phase B: MeOH(0.1% IPAm, v/v); Gradient 10% B for 0.50 min, 10-50% B over 3.00 min, 50% B for 1.00 min; 50-10% B over 0.50 min; Flow rate: 2.5 mL/min; Column temperature: 35° C.

SFC Method 35: Waters UPCC with PDA; Column: Chiralpak AD-3,150×4.6 mm I.D., 3 μm; Mobile phase A: $CO_2$; Mobile phase B: IPA (0.1% IPAm, v/v); Gradient 10% B for 0.50 min, 10-50% B over 3.00 min, 50% B for 1.00 min; 50-10% B over 0.50 min; Flow rate: 2.5 mL/min; Column temperature: 35° C.

SFC Method 36: Instrument: Waters UPCC with PDA; Column: Chiralpak IC-3, 50×4.6 mm I.D., 3 μm; Mobile phase A: $CO_2$; Mobile phase B: MeOH(0.1% IPAm, v/v); Gradient: 5% B for 0.20 min, 5-50% B over 1.00 min, 50% B for 1.00 min, 50-5% B over 0.40 min, 5% B for 0.40 min, Flow rate: 3.4 mL/min; Column temperature: 35° C.

SFC Method 37: Instrument: Waters UPCC with SQ Detector 2; Column: Chiralcel OJ-3, 50×4.6 mm I.D., 3 μm; Mobile phase A: $CO_2$; Mobile phase B: ACN (0.1% IPAm, v/v); 5% B for 0.20 min, 5-50% B over 1.00 min, 50% B for 2.20 min, 50-5% B over 0.40 min, 5% B for 3.00 min; Flow rate: 3.4 mL/min; Column temperature: 35° C.

SFC Method 38: Instrument: Waters UPCC with PDA; Column: Chiralpak IC-3, 50×4.6 mm I.D., 3 μm; Mobile phase A: $CO_2$; Mobile phase B: IPA(0.1% IPAm, v/v); 5% B for 0.20 min, 5-50% B over 1.00 min, 50% B for 1.00 min, 50-5% B over 0.40 min, 5% B for 0.4 min; Flow rate: 3.4 mL/min; Column temperature: 35° C.

SFC Method 39: Instrument: Waters UPCC with QDA; Column: WK, 100×4.6 mm I.D., 3 μm; Mobile phase A: $CO_2$; Mobile phase B: EtOH(0.1% IPAm, v/v); 10% B for 0.20 min, 10-50% B over 2.20 min, 50% B for 1.00 min, 50-10% B over 0.60 min; Flow rate: 3.4 mL/min; Column temperature: 35° C.

SFC Method 40: Instrument: Waters UPCC with PDA; Column: (S,S)-WHELK-01, 50×4.6 mm I.D., 3.5 μm; Mobile phase A: $CO_2$; Mobile phase B: EtOH(0.1% IPAm, v/v); 5% B for 0.20 min, 5-50% B over 1.00 min, 50% B for 1.00 min, 50-5% B over 0.40 min, 5% B for 0.4 min; Flow rate: 3.4 mL/min; Column temperature: 35° C.

SFC Method 41: Instrument: Waters UPCC with PDA; Column: Chiralpak IF-3, 50×4.6 mm I.D., 3 μm; Mobile phase A: $CO_2$; Mobile phase B: EtOH(0.1% IPAm, v/v); 5% B for 0.20 min, 5-50% B over 1.00 min, 50% B for 1.00 min, 50-5% B over 0.40 min, 5% B for 0.4 min; Flow rate: 3.4 mL/min; Column temperature: 35° C.

SFC Method 42: Instrument: Waters UPCC with PDA; Column: Chiralpak AS-3, 50×4.6 mm I.D., 3 μm; Mobile phase A: $CO_2$; Mobile phase B: EtOH(0.1% IPAm, v/v); 5% B for 0.20 min, 5-50% B over 1.00 min, 50% B for 1.00 min, 50-5% B over 0.40 min, 5% B for 0.4 min; Flow rate: 3.4 mL/min; Column temperature: 35° C.

SFC Method 43: Instrument: Waters UPCC with PDA; Column: Chiralpak IG-3, 100×4.6 mm I.D., 3 μm; Mobile phase A: $CO_2$; Mobile phase B: EtOH(0.1% IPAm, v/v); 10% B for 0.20 min, 10-50% B over 2.20 min, 50% B for 1.00 min, 50-10% B over 0.60 min; Flow rate: 3.4 mL/min; Column temperature: 35° C.

SFC Method 44: Instrument: Waters UPCC with SQ Detector 2; Column: Chiralpak AS-3, 50×4.6 mm I.D., 3 μm; Mobile phase A: $CO_2$; Mobile phase B: MeOH (0.1% IPAm, v/v); 5% B for 0.20 min, 5-50% B over 1.00 min, 50% B for 1.00 min, 50-5% B over 0.40 min, 5% B for 0.4 min; Flow rate: 3.4 mL/min; Column temperature: 35° C.

SFC Method 45: Instrument: Waters UPCC with PDA; Chiralpak OD-3, 150×4.6 mm I.D., 3 μm; Gradient: mobile phase A-$CO_2$, B-IPA (0.1% IPAm, v/v); Isocratic elution; 50% B for 4.0 min; Flow rate: 2.5 mL/min; Column temperature: 35° C.

SFC Method 46: Instrument: Waters UPCC with PDA; Column: Chiralcel OD-3,150×4.6 mm I.D., 3 um; mobile phase A: $CO_2$, mobile phase B: ACN(0.1% IPAm, v/v); Gradient 10% B for 0.50 min, 10-50% B over 3.00 min, 50% B for 1.00 min; 50-10% B over 0.50 min; flow rate: 2.5 mL/min; column temperature: 35° C.

SFC Method 47: Instrument: Waters UPCC with PDA; Column: Chiralcel OD-3,150×4.6 mm I.D., 3 um; Gradient: mobile phase A-$CO_2$, B-ACN (0.1% IPAm, v/v); 10% B for 0.2 min; 10-50% B over 2.2 min, 50% B for 1.0 min, 50-10% B over 0.6 min; Flow rate: 3.4 mL/min; Column temperature: 35° C.

XRPD method

X-ray powder diffraction (XRPD) patterns were obtained using a Bruker Advance D8 in reflection geometry. Powders were analyzed using a zero background Si flat sample holder. The radiation was Cu Kα (λ=1.5418 Å). Patterns were measured between 2° and 400 2theta.

Sample amount: 5-10 mg

Sample holder: zero background Si flat sample holder

XRPD parameter

| | |
|---|---|
| Instrument | Bruker D8 Advance |
| Detector | LYNXEYE (1D mode), open angle: 2.948°, scan mode: continuous scan |
| Radiation | CuKα (0.15418 nm) |
| Monochromator | Nickel filter |
| X-ray generator power | 40 kV, 40 mA |
| Goniometer radius | 280 mm |
| Step size | 0.0164°(2-theta value) |
| Time per step | 0.3 second per step |
| Scan range | 2° to 40° (2-theta value) |
| Scan time | About 768 seconds |
| Slits | Primary: fixed illuminated sample size 10 mm; secondary: open angle 2.2°, axial soller: 2.5° |

Assignment of Stereochemistry

Verification of the R-isomer was obtained by crystallization with the SARS-CoV-2 Main Protease protein described below. The R-isomer has been observed to be the more active isomer (see Example 11). Accordingly, unless indicated otherwise, the more active isomers of the Examples below have been assigned as (R). In addition, for examples in which cis/trans configurations can occur, confirmation of cis and trans was obtained by 2D NMR.

Synthesis of Intermediates

Synthesis of 3-(isoquinolin-4-yl)-2-oxoimidazolidine-4-carbonitrile (Int-1)

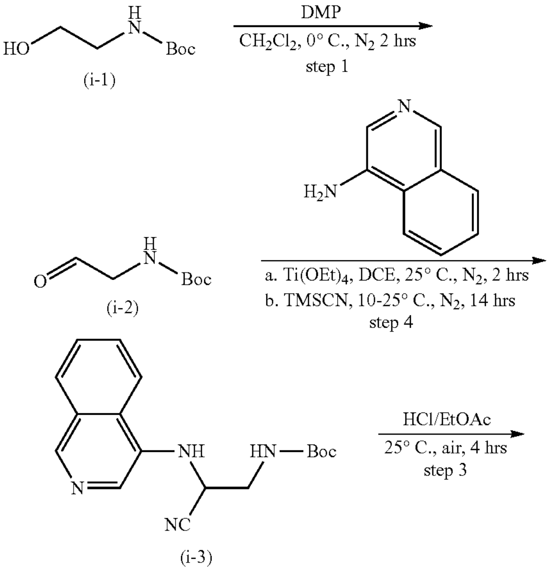

(i-1)

(i-2)

(i-3)

-continued

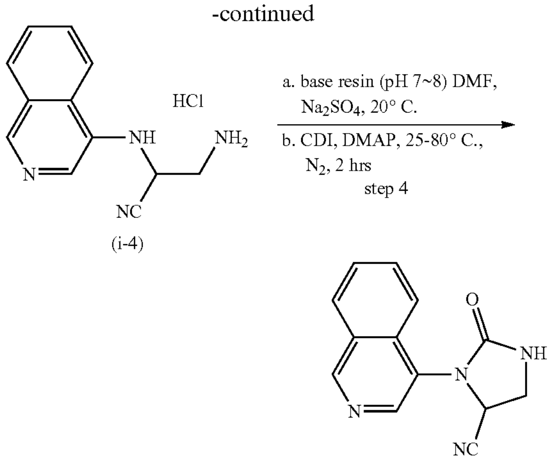

(i-4)

(Int-1)

Step 1: Under $N_2$ flow and at 0° C., DMP (138.2 g, 325 mmol, 1.05 eq.) was added in one portion to a solution of tert-butyl(2-hydroxyethyl)carbamate (i-1) (50.0 g, 310 mmol, 1.0 eq.) in $CH_2Cl_2$ (680 mL). The reaction mixture was stirring at 0° C. for 2 hrs. The mixture was quenched with saturated aqueous $NaHCO_3/Na_2S_2O_3$ (1:1, 3 L) and stirred at 25° C. for 30 min. The aqueous layer was separated from the organic and extracted with TBME (1L×3). The combined organic solutions were washed with $H_2O$ (1 L) and brine (500 mL), dried ($MgSO_4$), filtered and concentrated under reduced pressure. The crude mixture was purified by silica gel chromatography (petroleum ether/EtOAc=5/1 to 1/1) to give tert-butyl(2-oxoethyl)carbamate (i-2). $^1H$ NMR (400 MHz, $CDCl_3$): δ=9.65 (s, 1H), 4.10-4.04 (m, 2H), 1.45 (s, 9H).

Step 2: To a mixture of tert-butyl(2-oxoethyl)carbamate (i-2) (55.0 g, 345 mmol, 1.0 eq.) in DCE (1 L) was added isoquinolin-4-amine (40.0 g, 277 mmol, 0.8 eq.) and $Ti(OEt)_4$ (209.2 g, 918 mmol, 2.0 eq.) at 25° C. under $N_2$. The solution was stirred at 25° C. for 2 hrs under $N_2$. TMSCN (136.5 g, 1375 mmol, 3.0 eq.) was added into the reaction at 10° C. Then the solution was stirred at 25° C. for 14 hrs under $N_2$, whereupon the reaction was quenched with $H_2O$ (2 L) and filtered. The filter cake was washed with $CH_2Cl_2$ (500 mL×5). Then the filtrate was extracted with $CH_2Cl_2$ (500 mL×2). The combined organic layers were dried over $Na_2SO_4$, filtered and concentrated under reduced pressure to give a residue. The residue was purified by silica gel chromatography (petroleum ether/ethyl acetate=5/1 to 1/1) to give tert-butyl(2-cyano-2-(isoquinolin-4-ylamino)ethyl)carbamate (i-3). $^1H$ NMR (400 MHz, $CDCl_3$): δ=8.81 (s, 1H), 7.97-7.92 (m, 2H), 7.89 (d, J=8.4 Hz, 1H), 7.69 (ddd, J=1.3, 7.0, 8.3 Hz, 1H), 7.65-7.59 (m, 1H), 6.16-6.07 (m, 1H), 6.12 (br d, J=5.5 Hz, 1H), 5.48 (br s, 1H), 4.52 (dt, J=3.5, 6.2 Hz, 1H), 3.94 (ddd, J=3.2, 6.5, 14.9 Hz, 1H), 3.85-3.75 (m, 1H), 1.51 (s, 9H).

Step 3: To a mixture of tert-butyl(2-cyano-2-(isoquinolin-4-ylamino)ethyl)carbamate (i-3) (50.0 g, 160 mmol, 1.0 eq.) was added HCl/EtOAc (4 M, 500 mL) at 25° C. and the mixture was stirred for 4 hrs. The mixture was concentrated to give 3-amino-2-(isoquinolin-4-ylamino)propanenitrile hydrochloride (i-4). LCMS (Method 35): $t_R$=0.53 min. $[M+1]^+$ 213.2.

Step 4: 3-amino-2-(isoquinolin-4-ylamino)propanenitrile hydrochloride (i-4) (45.0 g, 212 mmol, 1.0 eq.) was dissolved in DMF (200 mL) and basified with basic resin (Amberlyst® A-21) to pH=7 to 8. $Na_2SO_4$ (50 g) was added into the mixture. The mixture was filtered and the filter cake was washed with DMF (100 mL×2). The combined filtrate was dried over and filtered to give a solution. To this solution was added CDI (68.7 g, 424 mmol, 2.0 eq.), DMAP (2.5 g, 21.2 mmol, 0.1 eq.) and 4A molecular sieves (25 g) at 25° C. The mixture was stirred at 80° C. for 2 hrs under $N_2$. The mixture was filtered and the filtrate concentrated under reduced pressure to give a residue which was purified by silica gel chromatography (petroleum ether/ethyl acetate=5/1 to 1/1) to give the crude product. The crude product was triturated by MeOH (50 mL) to give 3-(isoquinolin-4-yl)-2-oxoimidazolidine-4-carbonitrile (Int-1). LCMS (Method 1): $t_R$=0.76, $[M+1]^+$239.1. $^1H$ NMR: (400 MHz, $CD_3OD$) δ=9.31 (s, 1H), 8.54 (s, 1H), 8.23 (d, J=8.3 Hz, 1H), 8.05 (d, J=8.5 Hz, 1H), 7.91 (ddd, J=1.1, 7.0, 8.4 Hz, 1H), 7.82-7.75 (m, 1H), 5.39 (dd, J=4.2, 9.1 Hz, 1H), 4.13 (t, J=9.4 Hz, 1H), 3.90 (dd, J=4.3, 9.8 Hz, 1H).

Alternative Synthesis of 3-(isoquinolin-4-yl)-2-oxoimidazolidine-4-carbonitrile (Int-1)

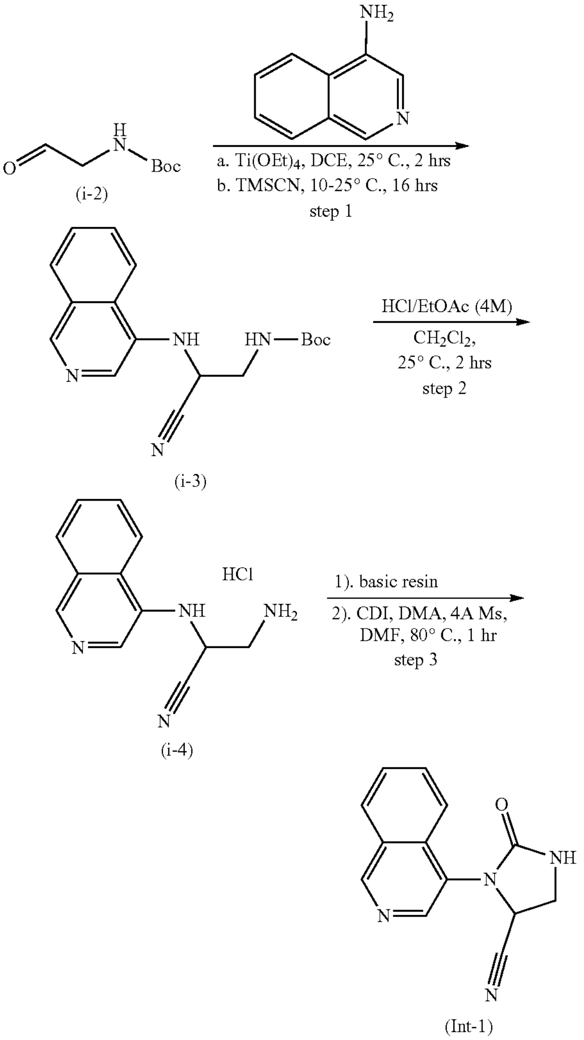

(i-2)

(i-3)

(i-4)

(Int-1)

Step1: To a solution of tert-butyl(2-oxoethyl)carbamate (i-2) (20.0 g, 125.64 mmol, 1.0 eq.) in DCE (300 mL) was added isoquinolin-4-amine (18.1 g, 125.64 mmol, 1.0 eq.) and $Ti(OEt)_4$ (57.32 g, 251.28 mmol, 2.0 eq.) at 25° C. under $N_2$. The solution was stirred at 25° C. for 2 h under $N_2$. TMSCN (37.40 g, 376.92 mmol, 3.0 eq.) was added into the reaction at 10° C. Then the solution was stirred at 25° C. for 16 hrs under $N_2$, whereupon the reaction was quenched with $H_2O$ (800 mL) and filtered. The filter cake was washed with $CH_2Cl_2$ (500 mL×5). Then the aqueous layer was extracted with $CH_2Cl_2$ and the organic layer dried over $Na_2SO_4$, filtered and concentrated under reduced pressure to give a residue. The residue was purified by flash silica gel chromatography (330 g, eluent of 60% ethyl acetate/petroleum ether, 200 mL/min) to give tert-butyl(2-cyano-2-(isoquinolin-4-ylamino)ethyl)carbamate (i-3). $^1$H NMR: (400 MHz, $CDCl_3$, 296 K) δ=8.81 (s, 1H), 7.98-7.93 (m, 2H), 7.89 (d, J=8.4 Hz, 1H), 7.71 (dt, J=1.1, 7.6 Hz, 1H), 7.62 (dt, J=1.1, 7.6 Hz, 1H), 6.13 (br d, J=5.7 Hz, 1H), 5.40 (br t, J=6.1 Hz, 1H), 4.53 (dt, J=3.2, 6.1 Hz, 1H), 4.01-3.90 (m, 1H), 3.85-3.76 (m, 1H), 1.51 (s, 9H).

Step 2: To a mixture of tert-butyl(2-cyano-2-(isoquinolin-4-ylamino)ethyl)carbamate (i-3) (23.0 g, 73.72 mmol, 1.0 eq.) in $CH_2Cl_2$ (30 mL) was added HCl/EtOAc (4 M, 150 mL) at 25° C. The mixture was stirred at 25° C. for 2 h under $N_2$. The mixture was concentrated to give 3-amino-2-(isoquinolin-4-ylamino)propanenitrile hydrochloride (i-4) which would be used without further purification.

Step 3: 3-amino-2-(isoquinolin-4-ylamino)propanenitrile hydrochloride (i-4) (37.0 g, crude, 149.19 mmol, 1.0 eq.) was dissolved in DMF (200 mL) and basified with basic resin to pH=7 to 8. The mixture was filtered and the filter cake was washed with DMF (30 mL×4). The combined filtrate was dried over $Na_2SO_4$ and filtered to give a solution. To this solution was added CDI (48.3 g, 298.38 mmol, 2.0 eq.), DMAP (1.8 g, 14.92 mmol, 0.1 eq.) and 4A molecular seives (15 10 g) at 25° C. The mixture was stirred at 80° C. for 1 h under $N_2$ and then filtered. The filtrate was concentrated under reduced pressure to give a residue which was purified by flash silica gel chromatography (220 g, eluent of 50-60% MeOH/ethyl acetate, 200 mL/min) to give crude product. The crude product was further purified by RP-MPLC (FA-MeOH) to give 3-(isoquinolin-4-yl)-2-oxoimidazolidine-4-carbonitrile (Int-1). LCMS (Method 29): $t_R$=0.51 min, $[M+1]^+$=239.1 $^1$H NMR (400 MHz, $CD_3OD$, 298 K) δ=9.31 (s, 1H), 8.54 (s, 1H), 8.23 (d, J=8.3 Hz, 1H), 8.04 (d, J=8.4 Hz, 1H), 7.91 (dt, J=1.0, 7.7 Hz, 1H), 7.78 (dt, J=1.0, 7.7 Hz, 1H), 5.38 (dd, J=4.2, 9.1 Hz, 1H), 4.12 (t, J=9.4 Hz, 1H), 3.90 (dd, J=4.1, 9.8 Hz, 1H).

Alternative Synthesis of 3-(isoquinolin-4-yl)-2-oxoimidazolidine-4-carbonitrile (Int-1)

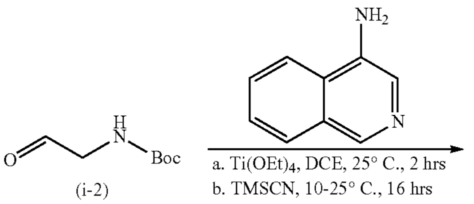

(i-2)

-continued

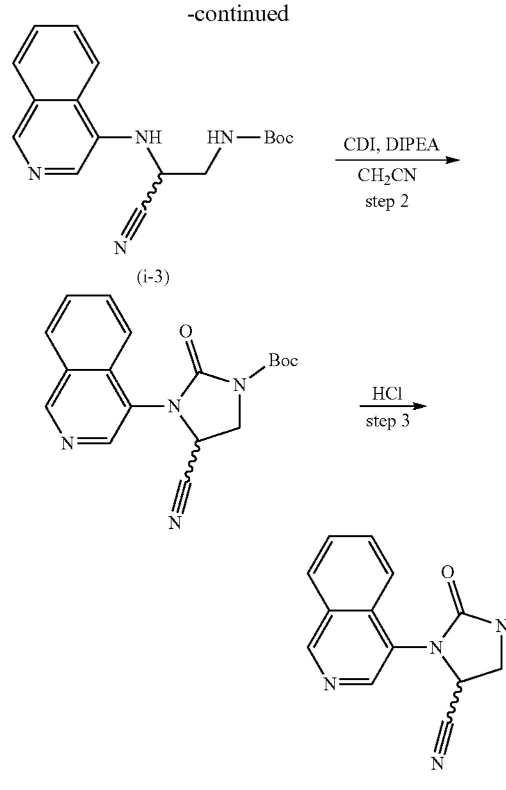

(i-3)

(Int-1)

Step1: To a solution of tert-butyl(2-oxoethyl)carbamate (i-2) (20.0 g, 125.64 mmol, 1.0 eq.) in DCE (300 mL) was added isoquinolin-4-amine (18.1 g, 125.64 mmol, 1.0 eq.) and $Ti(OEt)_4$ (57.32 g, 251.28 mmol, 2.0 eq.) at 25° C. under $N_2$. The solution was stirred at 25° C. for 2 h under $N_2$. TMSCN (37.40 g, 376.92 mmol, 3.0 eq.) was added into the reaction at 10° C. Then the solution was stirred at 25° C. for 16 hrs under $N_2$, whereupon the reaction was quenched with $H_2O$ (800 mL) and filtered. The filter cake was washed with $CH_2Cl_2$ (500 mL×5). Then the aqueous layer was extracted with $CH_2Cl_2$ and the organic layer dried over $Na_2SO_4$, filtered and concentrated under reduced pressure to give a residue. The residue was purified by flash silica gel chromatography (330 g, eluent of 60% ethyl acetate/petroleum ether, 200 mL/min) to give tert-butyl(2-cyano-2-(isoquinolin-4-ylamino)ethyl)carbamate (i-3). $^1$H NMR: (400 MHz, $CDCl_3$, 296 K) δ=8.81 (s, 1H), 7.98-7.93 (m, 2H), 7.89 (d, J=8.4 Hz, 1H), 7.71 (dt, J=1.1, 7.6 Hz, 1H), 7.62 (dt, J=1.1, 7.6 Hz, 1H), 6.13 (br d, J=5.7 Hz, 1H), 5.40 (br t, J=6.1 Hz, 1H), 4.53 (dt, J=3.2, 6.1 Hz, 1H), 4.01-3.90 (m, 1H), 3.85-3.76 (m, 1H), 1.51 (s, 9H).

Step 2: To a solution of tert-butyl(2-cyano-2-(isoquinolin-4-ylamino)ethyl)carbamate (i-3) (23.0 g, 73.6 mmol, 1.0 eq.) in MeCN (173 mL) was added DIPEA (25.4 g, 196.5 mmol, 2.67 eq) and CDI (31.9 g, 196.5 mmol, 2.67 eq) at 25° C., and the mixture was stirred at 25° C. for 16 h while solid was precipitated. The mixture was poured into $H_2O$ (200 mL) while solid was precipitated, stirred for 15 min and filtered. The wet cake was dried under reduced pressure to give tert-butyl 4-cyano-3-(isoquinolin-4-yl)-2-oxoimidazolidine-1-carboxylate.

Step 3: To a solution of tert-butyl 4-cyano-3-(isoquinolin-4-yl)-2-oxoimidazolidine-1-carboxylate (20.2 g, 59.7 mmol, 1.0 eq) in THE (100 mL) was added 4.5 N HCl aqueous (100 mL) dropwise at 0-5° C., and the mixture was warmed to 25° C. and stirred for 16 h. The mixture was cooled to 0° C., and 1 N NaOH aqueous was added dropwise to adjust the pH to 8-9 while solid precipitated. The mixture was stirred for 15 min and filtered. The filter cake was washed with $H_2O$ (100 mL), collected and dried under reduced pressure to 3-(isoquinolin-4-yl)-2-oxoimidazolidine-4-carbonitrile (Int-1). LCMS (Method 29): $t_R$=0.51 min, $[M+1]^+$=239.1 $^1H$ NMR (400 MHz, $CD_3OD$, 298 K) δ=9.31 (s, 1H), 8.54 (s, 1H), 8.23 (d, J=8.3 Hz, 1H), 8.04 (d, J=8.4 Hz, 1H), 7.91 (dt, J=1.0, 7.7 Hz, 1H), 7.78 (dt, J=1.0, 7.7 Hz, 1H), 5.38 (dd, J=4.2, 9.1 Hz, 1H), 4.12 (t, J=9.4 Hz, 1H), 3.90 (dd, J=4.1, 9.8 Hz, 1H).

Synthesis of 5-chloro-3-(trifluoromethyl)pyridazine (Int-2)

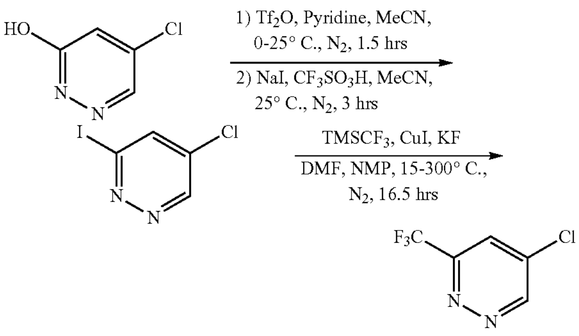

(Int-2)

Step 1. To a solution of 5-chloropyridazin-3-ol (2.5 g, 19.23 mmol, 1.0 eq.) and pyridine (1.8 g, 23.08 mmol, 1.2 eq.) in MeCN (17 mL) was added $Tf_2O$ (7.6 g, 26.92 mmol, 1.4 eq.) at 0° C. under $N_2$. The solution was stirred at 25° C. for 1.5 hrs. Then NaI (3.5 g, 23.08 mmol, 1.2 eq.) and $CF_3SO_3H$ (3.2 g, 21.15 mmol, 1.1 eq.) were added to the mixture at 25° C. and the solution was stirred at 25° C. for 3 hrs. The reaction mixture was quenched with $H_2O$ (50 mL) and adjusted to pH=10.0 with 1 M NaOH aqueous. Saturated $Na_2CO_3$ aqueous (50 mL) and saturated $Na_2S_2O_3$ aqueous (150 mL) were added to the mixture. Then the mixture was extracted with EtOAc (250 mL×2). The combined organic layers were washed with brine (250 mL), dried over $Na_2SO_4$, filtered and the filtrate was concentrated to give crude product. The crude was purified by MPLC (petroleum ether/EtOAc=100%-0%) to give 5-chloro-3-iodopyridazine LCMS (Method 15): $t_R$=0.64 min. $[M+1]^+$ 240.9.

Step 2. CuI (874 mg, 4.59 mmol, 1.1 eq.) and KF (267 mg, 4.59 mmol, 1.1 eq.) were thoroughly mixed and the mixture was heated 300° C. under reduced pressure for 30 min until a greenish color appeared. Then the mixture was cooled to 15° C. 5-chloro-3-iodopyridazine (1.0 g, 4.17 mmol, 1.0 eq.), anhydrous DMF (5 mL), NMP (5 mL) and $TMSCF_3$ (3.0 g, 20.5 mmol, 5.0 eq.) were added and the mixture was stirred vigorously for 16 hrs at 25° C. The reaction mixture was poured into water (10 mL) slowly and extracted with $CH_2Cl_2$ (10 mL×2). The combined organic layers were washed with brine (10 mL×2), dried over $Na_2SO_4$, filtered and concentrated to give 5-chloro-3-(trifluoromethyl) pyridazine (Int-2). LCMS (Method 30): $t_R$=1.39 min, $[M+1]^+$ 182.9.

Synthesis of 4-bromo-5-methoxy-2-(trifluoromethyl)pyridine (Int-3)

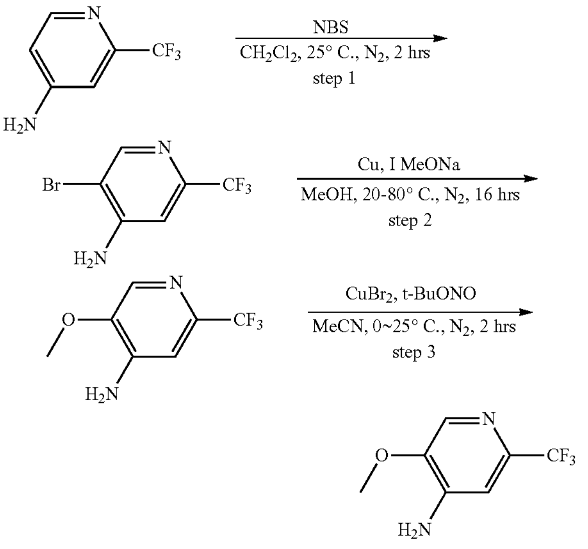

(Int-3)

Step 1. To a mixture of 2-(trifluoromethyl)pyridin-4-amine (1.0 g, 6.17 mmol, 1.0 eq.) in $CH_2Cl_2$ (25 mL) was added NBS (1.1 g, 11.28 mmol, 2.0 eq.) at 25° C. under $N_2$. The mixture was stirred at 25° C. for 2 hrs under $N_2$. The reaction mixture was quenched with water (50 mL) and extracted with $CH_2Cl_2$ (25 mL×2). The combined organic layers were washed with brine (50 mL), dried over $Na_2SO_4$, filtered and concentrated under reduced pressure to give crude product. The crude was purified by column (petroleum ether/EtOAc=10/1 to 5/1) to give 5-bromo-2-(trifluoromethyl)pyridin-4-amine.

Step 2. To a mixture of 5-bromo-2-(trifluoromethyl)pyridin-4-amine (2.5 g, 15.32 mmol, 1.0 eq.) and CuI (2.1 g, 15.32 mmol, 1.0 eq.) in MeOH (25 mL) was added (2.2 g, 15.32 mmol, 1.0 eq.) at 20° C. The mixture was stirred at 80° C. for 16 hrs under $N_2$. The reaction mixture was concentrated and extracted with EtOAc (30 mL×2). The combined organic layers were washed with brine (50 mL), dried over $Na_2SO_4$, filtered and concentrated under reduced pressure to give the crude product. The crude product was purified by column (petroleum ether/EtOAc=4/1 to 3/1) to give 5-methoxy-2-(trifluoromethyl)pyridin-4-amine.

Step 3. To a mixture of 5-methoxy-2-(trifluoromethyl) pyridin-4-amine (500 mg, 2.60 mmol, 1.0 eq.) in MeCN (10 mL) was added $CuBr_2$ (1.2 g, 5.20 mmol, 2.0 eq.) at 0° C. The mixture was stirred at 0° C. for 0.5 hrs under $N_2$. To the mixture was added t-BuONO (335 mg, 2.86 mmol, 1.1 eq.) at 0° C. under $N_2$. The mixture was stirred at 25° C. for 2 hrs under $N_2$. The reaction mixture was quenched into water (20 mL) and extracted with EtOAc (15 mL×2). The combined organic layers were washed with brine (30 mL), dried over $Na_2SO_4$, filtered and concentrated under reduced pressure to give the crude product. The crude product was purified by column (petroleum ether/EtOAc=10/1) to give 4-bromo-5-methoxy-2-(trifluoromethyl)pyridine (Int-3). $^1H$ NMR (400 MHz, CHLOROFORM-d) δ=8.30 (s, 1H), 7.88 (s, 1H), 4.08 (s, 3H).

Synthesis of 2-(tert-butyldiphenylsilyl)acetic acid (Int-4)

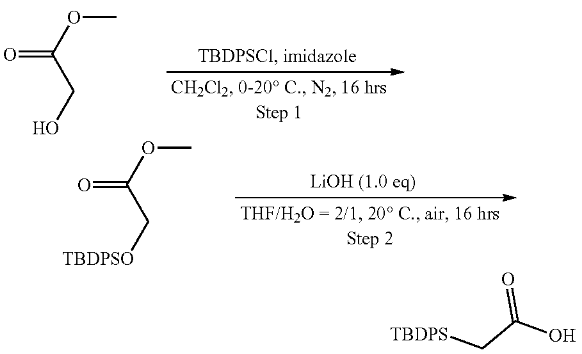

(Int-4)

Step 1: To a mixture of methyl 2-hydroxyacetate (5.0 g, 55.51 mmol, 1.0 eq.) in $CH_2Cl_2$ (50 mL) was added imidazole (7.6 g, 111.01 mmol, 2.0 eq.) at 20° C. TBDPSCl (18.3 g, 66.61 mmol, 1.2 eq.) was added into the reaction at 0° C. Then the reaction was stirred at 20° C. for 16 hrs under $N_2$. The reaction was quenched with $H_2O$ (100 mL) and extracted with $CH_2Cl_2$ (50 mL×3). The combined organic layers were dried over $Na_2SO_4$, filtered and concentrated under reduced pressure to give a residue. The residue was purified by MPLC (Eluent of Ethyl acetate/Petroleum ether=4/1 to 7/3, 80 mL/min) to give methyl 2-((tert-butyldiphenylsilyl)oxy)acetate. $^1H$ NMR (400 MHz, CHLOROFORM-d) δ=7.76-7.66 (m, 4H), 7.49-7.35 (m, 6H), 4.26 (s, 2H), 3.70 (s, 3H), 1.11 (s, 9H)

Step 2: To a solution of methyl 2-((tert-butyldiphenylsilyl)oxy)acetate (5.8 g, 17.66 mmol, 1.0 eq.) in THF/$H_2O$ (60 mL) was added LiOH·$H_2O$ (737 mg, 17.66 mmol, 1.0 eq.) at 20° C. The reaction was stirred at 20° C. for 16 hrs. The reaction was concentrated, quenched with $H_2O$ (20 mL) and acidified to pH 3-4 with aq. HCl solution (0.5 M). The mixture was extracted with EtOAc (20 mL×2). The combined organic layers were washed with brine (50 mL), dried over $Na_2SO_4$, filtered and concentrated under reduced pressure to give a residue. The residue was purified by MPLC (Eluent of Ethyl acetate/Petroleum ether=3/17 to 1/4, 80 mL/min) to give 2-(tert-butyldiphenylsilyl)acetic acid (Int-4). $^1H$ NMR (400 MHz, CHLOROFORM-d) δ=7.66 (dd, J=1.3, 7.9 Hz, 4H), 7.52-7.39 (m, 6H), 4.24 (s, 2H), 1.12 (s, 9H)

Synthesis of 6-(methylsulfonyl)isoquinolin-4-amine (Int-5)

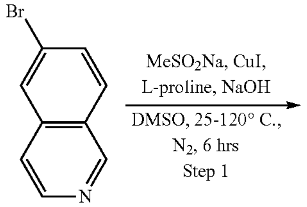

-continued

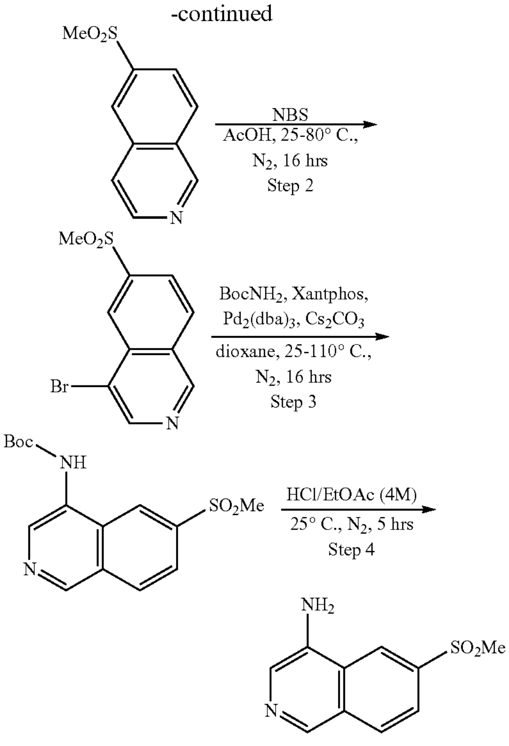

(Int-5)

Step 1: To a mixture of 6-bromoisoquinoline (5.0 g, 24.03 mmol, 1.0 eq.) in DMSO (60 mL) was added $MeSO_2Na$ (6.1 g, 60.08 mmol, 2.5 eq.), CuI (915 mg, 4.81 mmol, 0.2 eq.), L-proline (830 mg, 7.21 mmol, 0.3 eq.) and NaOH (288 mg, 7.21 mmol, 0.3 eq.) at 25° C. The mixture was stirred at 120° C. for 6 hrs. The mixture was quenched with water 100 mL and extracted with EtOAc (80 mL×2). The organic layers were washed with aq. NaCl (100 mL), dried over $Na_2SO_4$, filtered and concentrated to give crude product. The crude was purified by column (Petroleum ether/Ethyl acetate=100/1-1/1) to give 6-(methylsulfonyl)isoquinoline. $^1H$ NMR: (400 MHz, CHLOROFORM-d) δ=9.41 (s, 1H), 8.72 (d, J=5.6 Hz, 1H), 8.53 (s, 1H), 8.19 (d, J=8.7 Hz, 1H), 8.06 (dd, J=1.6, 8.7 Hz, 1H), 7.82 (d, J=5.8 Hz, 1H), 3.15 (s, 3H).

Step 2: To a mixture of 6-(methylsulfonyl)isoquinoline (3.5 g, 16.89 mmol, 1.0 eq.) in AcOH (50 mL) was added NBS (4.5 g, 25.34 mmol, 1.5 eq.) at 25° C. and the mixture was stirred at 80° C. for 16 hrs. The mixture was diluted with iced water (50 mL), adjusted to pH=7 with saturated $NaHCO_3$ aqueous at 0° C. and extracted with EtOAc (60 mL×2). The combined organic layers were washed with brine (120 mL), dried over $Na_2SO_4$, filtered and concentrated to give crude product. The crude was purified by column (Petroleum ether/Ethyl acetate=100/1-3/1) to give 4-bromo-6-(methylsulfonyl)isoquinoline.

Step 3: To a mixture of 4-bromo-6-(methylsulfonyl)isoquinoline (4.0 g, 13.94 mmol, 1.0 eq.) and $BocNH_2$ (3.3 g, 27.88 mmol, 2.0 eq.) in dioxane (50 mL) was added $Pd_2(dba)_3$ (570 mg, 0.70 mmol, 0.05 eq.), Xantphos (804 mg, 1.39 mmol, 0.1 eq.) and $Cs_2CO_3$ (13.6 g, 41.82 mmol, 3.0 eq.) at 25° C. under $N_2$ and the mixture was stirred at 120° C. for 16 hrs. The reaction was quenched with $H_2O$ (50 mL) and extracted with EtOAc (80 mL×2). The combined organic layers were washed with brine (200 mL×2), dried over $Na_2SO_4$, filtered and concentrated under reduced pressure to give crude product which was purified by column chromatography ($SiO_2$, Petroleum ether/Ethyl acetate=100/1 to 1/1) to give tert-butyl(6-(methylsulfonyl) isoquinolin-4-yl)carbamate.

Step 4: A mixture of tert-butyl(6-(methylsulfonyl)isoquinolin-4-yl)carbamate (3.0 g, 9.31 mmol, 1.0 eq.) in HCl/EtOAc (50 mL, 4M) was stirred at 25° C. under $N_2$ for 5 hrs. The mixture was diluted with iced water (30 mL), adjusted to pH=7 with saturated $NaHCO_3$ aqueous at 0° C. and extracted with EtOAc (60 mL×2). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate=10/1 to 1/1) to give 6-(methylsulfonyl)isoquinolin-4-amine (Int-5). $^1$H NMR: (400 MHz, DMSO-$d_6$) δ=8.79 (s, 1H), 8.60 (s, 1H), 8.16 (d, J=8.6 Hz, 1H), 8.03 (s, 1H), 7.98 (dd, J=1.6, 8.6 Hz, 1H), 6.33 (s, 2H), 3.31 (s, 3H).

Synthesis of 3-(6-(methylsulfonyl)isoquinolin-4-yl)-2-oxoimidazolidine-4-carbonitrile (Int-6)

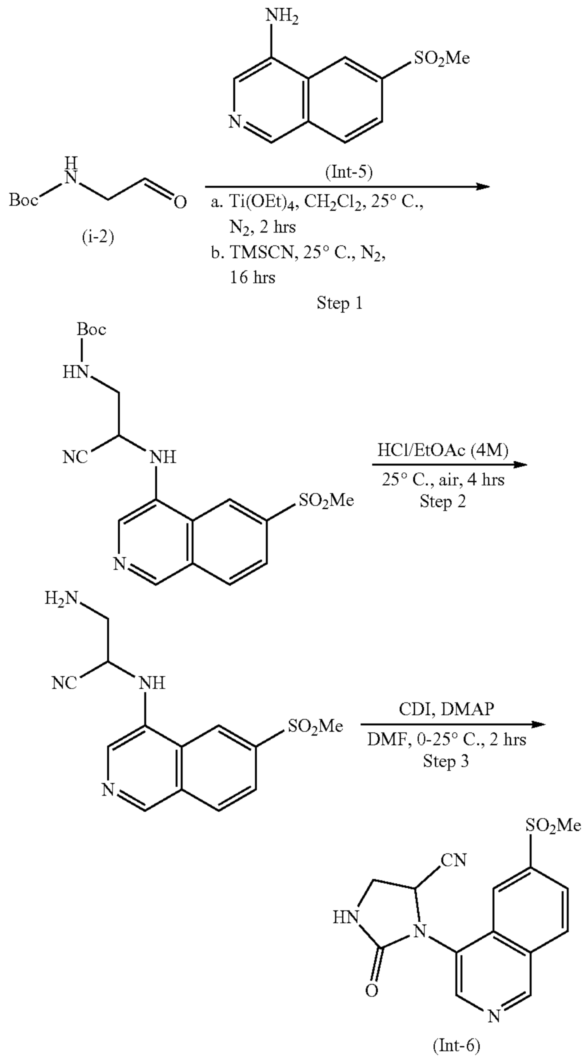

(Int-6)

Step 1: To a solution of tert-butyl(2-oxoethyl)carbamate (i-2) (10.7 g, 56.24 mmol, 2.5 eq.) in $CH_2Cl_2$ (90 mL) was added 6-(methylsulfonyl)isoquinolin-4-amine (Int-5), (5.0 g, 22.49 mmol, 1.0 eq.) and $Ti(OEt)_4$ (10.3 g, 44.98 mmol, 2.0 eq.) at 25° C. under $N_2$ and the mixture was stirred at 25° C. for 2 hrs. Then TMSCN (6.7 g, 67.47 mmol, 3.0 eq.) was added at 25° C. under $N_2$ and the mixture was stirred at 25° C. for 14 hrs. The reaction was quenched with $H_2O$ (150 mL) and filtered. The filtrate was extracted with EtOAc (80 mL×2). The combined organic layers were washed with brine (200 mL×2), dried over $Na_2SO_4$, filtered and concentrated under reduced pressure to give crude product which was purified by column chromatography ($SiO_2$, Petroleum ether/Ethyl acetate=100/1 to 0/1) to give tert-butyl(2-cyano-2-((6-(methylsulfonyl)isoquinolin-4-yl)amino)ethyl)carbamate. LCMS (Method 5): $t_R$=0.759 min, $[M+1]^+$ 391.1

Step 2: A solution of tert-butyl(2-cyano-2-((6-(methylsulfonyl)isoquinolin-4-yl)amino)ethyl)carbamate (5.8 g, 14.85 mmol, 1.0 eq.) in HCl/EtOAC (70 Ml, 4M) was stirred at 25° C. for 4 hrs. The reaction was concentrated under reduced pressure to give crude product. The crude product was diluted with DMF (10 mL) and adjusted pH to 8 using alkaline resin. The solution was concentrated to give 3-amino-2-((6-(methylsulfonyl)isoquinolin-4-yl)amino)propanenitrile which was used without further purification.

Step 3: To a solution of 3-amino-2-((6-(methylsulfonyl) isoquinolin-4-yl)amino)propanenitrile (4.0 g, 13.79 mol, 1.0 eq.) in DMF (30 mL) was added CDI (4.5 g, 27.58 mmol, 2.0 eq.) and DMAP (169 mg, 1.38 mmol, 0.1 eq.) at 25° C. under $N_2$ and the mixture stirred at 80° C. for 1 hr. The reaction was concentrated under reduced pressure to give crude product which was purified by column chromatography ($SiO_2$, Petroleum ether/Ethyl acetate=100/1 to 0/1) to give 3-(6-(methylsulfonyl)isoquinolin-4-yl)-2-oxoimidazolidine-4-carbonitrile (Int-6). $^1$H NMR: (400 MHz, DMSO-$d_6$) δ=9.54 (s, 1H), 8.75 (s, 1H), 8.53 (d, J=8.6 Hz, 1H), 8.49 (s, 1H), 8.22 (dd, J=1.6, 8.6 Hz, 1H), 7.77 (s, 1H), 5.62 (dd, J=4.8, 8.9 Hz, 1H), 4.05-4.00 (m, 1H), 3.86 (dd, J=4.8, 9.6 Hz, 1H), 3.35 (s, 3H).

Synthesis of 4-aminoisoquinoline-6-carbonitrile (Int-7)

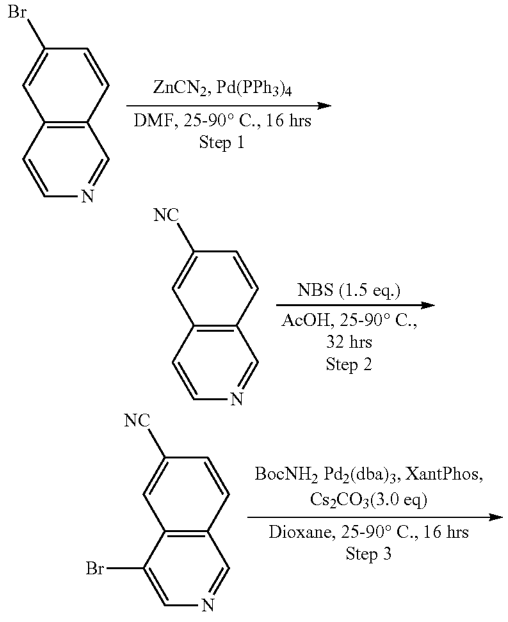

-continued

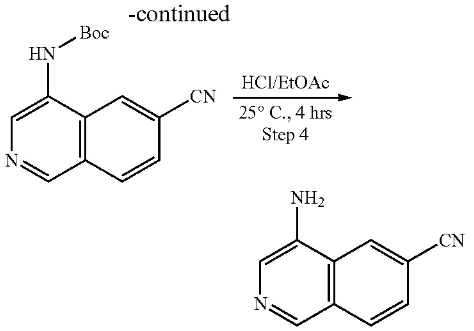

Step 1: To a solution of 6-bromoisoquinoline (5.0 g, 24.03 mmol, 1.0 eq.) in DMF (50 mL) was added $ZnCN_2$ (1.7 g, 14.40 mmol, 0.6 eq.) at 25° C. under $N_2$ and $Pd(PPh_3)_4$(1.4 g, 1.20 mmol, 0.05 eq.) at 25° C. The reaction was stirred at 90° C. for 16 hrs. The reaction mixture was filtered and the filtrate was quenched with $H_2O$ (100 mL) and extracted with ethyl acetate (100 mL×3).

The combined organic layers were washed with brine (100 mL), dried over $Na_2SO_4$, filtered and concentrated under reduced pressure to give a residue which was purified by column (Petroleum ether/EtOAc=100/1-1/1) to give isoquinoline-6-carbonitrile. $^1H$ NMR: (400 MHz, CHLOROFORM-d) δ=9.37 (s, 1H), 8.69 (d, J=5.6 Hz, 1H), 8.24 (s, 1H), 8.10 (d, J=8.5 Hz, 1H), 7.77 (d, J=8.4 Hz, 1H), 7.73 (d, J=5.8 Hz, 1H).

Step 2: To a solution of isoquinoline-6-carbonitrile (4.7 g, 30.49 mmol, 1.0 eq.) in AcOH (50 mL) was added NBS (6.5 g, 36.58 mmol, 1.5 eq.) at 25° C. under $N_2$ and the reaction stirred at 90° C. for 32 hrs. The reaction mixture was concentrated to give crude product which was purified by column (Petroleum ether/EtOAc=100/1-1/1) to give 4-bromoisoquinoline-6-carbonitrile. $^1H$ NMR: (400 MHz, CHLOROFORM-d) δ=9.26 (s, 1H), 8.85 (s, 1H), 8.55 (s, 1H), 8.11 (d, J=8.4 Hz, 1H), 7.83 (dd, J=1.3, 8.4 Hz, 1H).

Step 3: To a solution of 4-bromoisoquinoline-6-carbonitrile (4.0 g, 17.16 mmol, 1.0 eq.) and $BocNH_2$ (3.6 g, 34.32 mmol, 2.0 eq.) in Dioxane (40 mL) was added $Pd_2(dba)_3$ (450 mg, 0.85 mmol, 0.05 eq.), XantPhos (640 mg, 1.70 mmol, 0.1 eq.) and $Cs_2CO_3$ (15.3 g, 51.48 mmol, 3.0 eq.) at 250 C under $N_2$ and the mixture stirred at 900 C for 16 hrs. The reaction was quenched with $H_2O$ (50 mL) and extracted with EtOAc (80 mL×2). The combined organic layers were washed with brine (50 mL×2), dried over $Na_2SO_4$, filtered and concentrated under reduced pressure to give crude product which was purified by column chromatography ($SiO_2$, Petroleum ether/Ethyl acetate=100/1 to 3/1) to give the product tert-butyl(6-cyanoisoquinolin-4-yl)carbamate. $^1H$ NMR: (400 MHz, CHLOROFORM-d) δ=9.19-9.08 (m, 1H), 8.96 (s, 1H), 8.36 (s, 1H), 8.09 (d, J=8.5 Hz, 1H), 7.76 (dd, J=1.3, 8.4 Hz, 1H), 1.57 (s, 9H).

Step 4: A mixture of tert-butyl(6-cyanoisoquinolin-4-yl) carbamate (500 mg, 1.86 mmol 1.0 eq.) 30 in HCl/EtOAc (5 mL, 4 N) was stirred at 25° C. for 16 hrs. The mixture was diluted with iced water (1 mL), adjusted to pH=7 with saturated $NaHCO_3$ aqueous at 0° C. and extracted with EtOAc (5 mL×2). The combined organic layers were washed with brine (5 mL), dried over $Na_2SO_4$, filtered and concentrated to give 4-aminoisoquinoline-6-carbonitrile (Int-7). LCMS (Method 5): $t_R$=0.512 min, $[M+1]^+$ 170.1.

Synthesis of 3-iodo-2-methoxy-6-(trifluoromethyl) pyridine (Int-8) and 3-iodo-1-methyl-6-(trifluoromethyl)pyridin-2(1H)-one (Int-9)

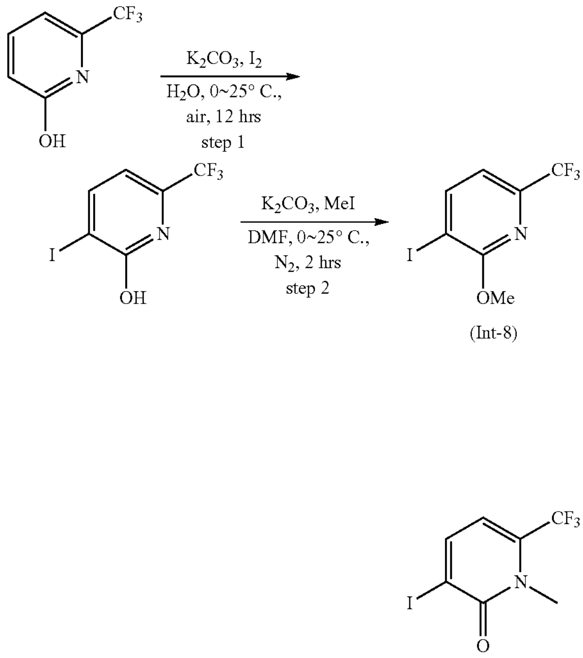

(Int-8)

(Int-9)

Step 1: To a mixture of $K_2CO_3$ (5.1 g, 36.79 mmol, 3.0 eq.) in $H_2O$ (50 mL) was added 6-(trifluoromethyl)pyridin-2-ol (2.0 g, 12.26 mmol, 1.0 eq.) and $I_2$ (4.7 g, 18.39 mmol, 1.5 eq.) at 0° C. and the mixture was stirred at 25° C. for 12 hrs under $N_2$. The reaction mixture was quenched with $H_2O$ (40 mL), filtered and the filtrate was extracted with EtOAc (50 mL×2). The combined organic layers were washed with brine (80 mL), dried over $Na_2SO_4$, filtered and concentrated under reduced pressure to give a residue. The residue was purified by flash silica gel chromatography (Petroleum ether/EtOAc=100/1-0/1) to give 3-iodo-6-(trifluoromethyl)pyridin-2-ol. $^1H$ NMR: (400 MHz, CHLOROFORM-d) δ=11.39 (br s, 1H), 8.20 (d, J=7.4 Hz, 1H), 6.59 (d, J=7.4 Hz, 1H).

Step 2: To a mixture of 3-iodo-6-(trifluoromethyl)pyridin-2-ol (1.7 g, 5.88 mmol, 1.0 eq.) in DMF (15 mL) was added $K_2CO_3$ (1.6 g, 11.76 mmol, 2.0 eq.) at 0° C. and dropwise MeI (1.3 g, 8.82 mmol, 1.5 eq.) in DMF (4 mL) at 0° C., the mixture was stirred at 25° C. for 2 hrs under $N_2$. The reaction mixture was quenched with $H_2O$ (50 mL), filtered and the filtrate was extracted with EtOAc (50 mL×2). The combined organic layers were washed with brine (80 mL), dried over $Na_2SO_4$, filtered and concentrated under reduced pressure to give a residue. The residue was purified by MPLC ($SiO_2$, petroleum ether/ethyl acetate=10/1 to 0/1) to give 3-iodo-2-methoxy-6-(trifluoromethyl)pyridine (Int-8) and 3-iodo-1-methyl-6-(trifluoromethyl)pyridin-2(1H)-one (Int-9). 3-iodo-2-methoxy-6-(trifluoromethyl)pyridine (Int-8): $^1H$ NMR: (400 MHz, CHLOROFORM-d) 6 25=8.18 (d, J=7.6 Hz, 1H), 7.02 (d, J=7.6 Hz, 1H), 4.05 (d, J=0.8 Hz, 3H). 3-iodo-1-methyl-6-(trifluoromethyl)pyridin-2(1H)-one (Int-9): $^1H$ NMR: (400 MHz, CHLOROFORM-d) δ=8.05 (d, J=7.5 Hz, 1H), 6.42 (d, J=7.5 Hz, 1H), 3.70 (s, 3H).

Synthesis of 1-(azetidin-3-yl)-3-(isoquinolin-4-yl)-2-oxoimidazolidine-4-carbonitrile (Int-10)

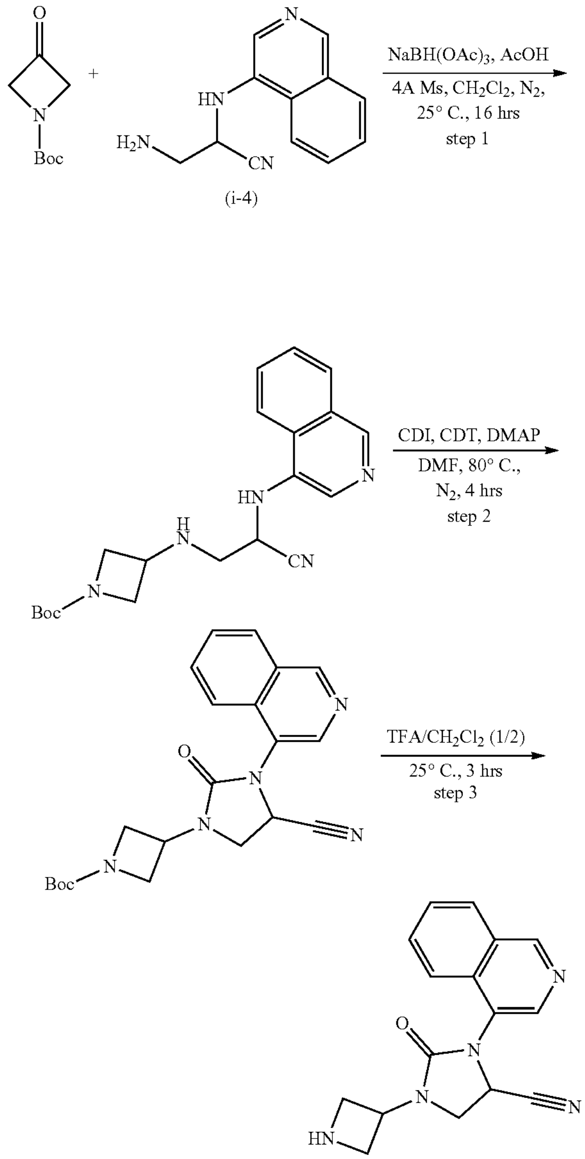

(i-4)

(Int-10)

Steps 1-2: Tert-butyl 3-(4-cyano-3-(isoquinolin-4-yl)-2-oxoimidazolidin-1-yl)azetidine-1-carboxylate was prepared in a manner similar to Example 120, using tert-butyl 3-oxoazetidine-1-carboxylate in place of 3-methylcyclobutan-1-one.

Step 3: To a mixture of tert-butyl 3-(4-cyano-3-(isoquinolin-4-yl)-2-oxoimidazolidin-1-yl)azetidine-1-carboxylate (1.6 g, 4.07 mmol, 1.0 eq.) in $CH_2Cl_2$ (24 mL) was added TFA (12 mL) at 25° C. Then the reaction was stirred at 25° C. for 3 hrs. The reaction mixture was concentrated to give a residue. The residue was dissolved with $H_2O$ (10 mL) and lyophilized to obtain 1-(azetidin-3-yl)-3-(isoquinolin-4-yl)-2-oxoimidazolidine-4-carbonitrile (Int-10). LCMS (Method 18): $t_R$=0.431 min, $[M+1]^+$ 293.9.

Alternative Synthesis of 1-(azetidin-3-yl)-3-(isoquinolin-4-yl)-2-oxoimidazolidine-4-carbonitrile (Int-10)

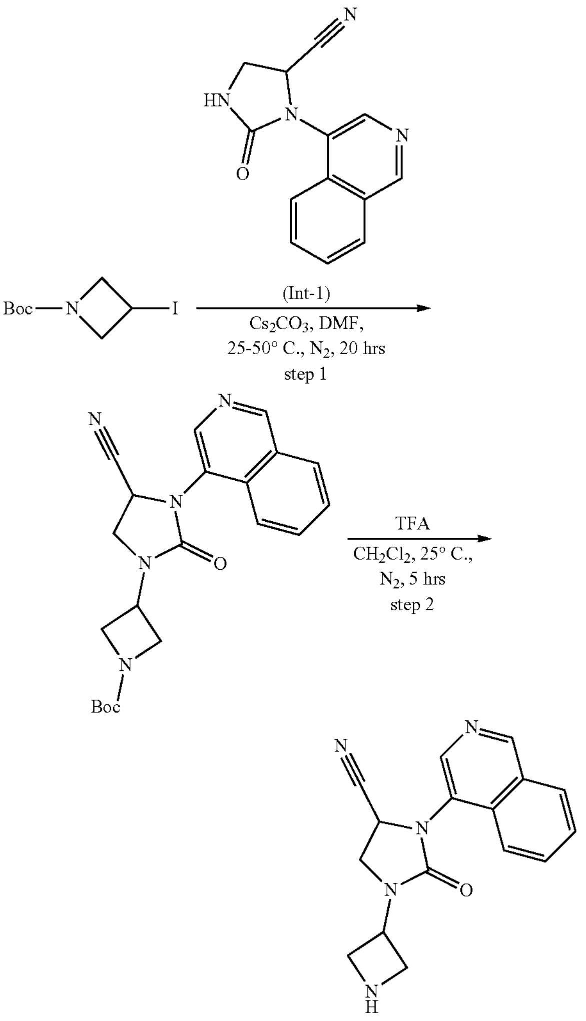

(Int-10)

Step 1: To a mixture of tert-butyl 3-iodoazetidine-1-carboxylate (1.2 g, 4.15 mmol, 3.0 eq.) and 3-(isoquinolin-4-yl)-2-oxoimidazolidine-4-carbonitrile (Int-1) (330 mg, 1.39 mmol, 1.0 eq.) in DMF (5 mL) was added $Cs_2CO_3$ (903 mg, 2.77 mmol, 2.0 eq.) at 25° C. The reaction was stirred at 50° C. for 20 hrs under $N_2$. The reaction mixture was poured into water (30 mL) and extracted with EtOAc (10 mL×3). The combined organic phases were washed with brine (30 mL), dried over $Na_2SO_4$, filtered and concentrated to give crude product. The crude product was purified by column chromatography on silica gel (petroleum ether/THF=100/0 to 60/40) to obtain tert-butyl 3-(4-cyano-3-(isoquinolin-4-yl)-2-oxoimidazolidin-1-yl)azetidine-1-carboxylate.

Step 2: To a mixture of tert-butyl 3-(4-cyano-3-(isoquinolin-4-yl)-2-oxoimidazolidin-1-yl)azetidine-1-carboxylate (260 mg, 0.66 mmol, 1.0 eq.) in $CH_2Cl_2$ (2.5 mL) was added TFA (1 mL) at 25° C. Then the reaction was stirred at 25° C. for 5 hrs under $N_2$. The reaction mixture was concentrated to give a residue which was dissolved with $H_2O$ (5 mL), ACN (2 mL) and lyophilized to give crude product. The crude product was purified by prep-HPLC (column: Waters Xbridge BEH C18 100 mm×25 mm, 5 μm; liquid phase: [A-10 mM $NH_4HCO_3$ in $H_2O$; B-ACN]B %: 5%-35%, 10 min]) to obtain 1-(azetidin-3-yl)-3-(isoquinolin-4-yl)-2-oxo-imidazolidine-4-carbonitrile (Int-10). LCMS (Method 36): $t_R$=1.150 min, $[M+1]^+$ 294.2. $^1H$ NMR: (400 MHz, METHANOL-$d_4$) δ=9.32 (s, 1H), 8.53 (s, 1H), 8.24 (d, J=8.2 Hz, 1H), 8.03 (d, J=8.4 Hz, 1H), 7.93-7.88 (m, 1H), 7.82-7.77 (m, 1H), 5.39 (dd, J=4.3, 9.0 Hz, 1H), 4.91-4.86 (m, 1H), 4.27 (t, J=9.3 Hz, 1H), 4.16-4.10 (m, 3H), 3.94-3.82 (m, 2H).

Synthesis of (R)-3-(isoquinolin-4-yl)-2-oxoimidazolidine-4-carbonitrile (Int-11) and (S)-3-(isoquinolin-4-yl)-2-oxoimidazolidine-4-carbonitrile (Int-12)

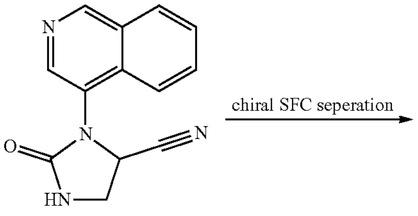

(Int-1)

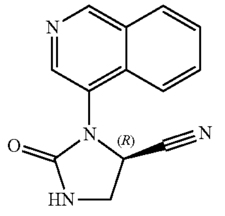

+

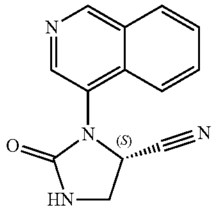

(Int-11) (Int-12)

3-(isoquinolin-4-yl)-2-oxoimidazolidine-4-carbonitrile (Int-1) (20 g, 83.65 mmol, 1.0 eq.) was separated by chiral SFC (column: ChiralPak IH, 250 mm×50 mm, 10 μm; liquid phase: [A-C02; B-ACN]B %: 60%-60%, 20 min]) to give two peaks. $t_R1$=1.333 min; $t_{R2}$=2.762 min.

Peak 1: (R)-3-(isoquinolin-4-yl)-2-oxoimidazolidine-4-carbonitrile (Int-11). LCMS (Method 32): $t_R$=0.603 min, $[M+1]^+$ 239.0. $^1H$ NMR: (400 MHz, CHLOROFORM-d) δ=9.32 (s, 1H), 8.64 (s, 1H), 8.10 (d, J=8.1 Hz, 1H), 7.91 (br d, J=8.3 Hz, 1H), 7.83 (br t, J=7.4 Hz, 1H), 7.77-7.66 (m, 1H), 6.57 (br s, 1H), 5.00 (dd, J=4.9, 9.0 Hz, 1H), 4.05 (t, J=9.3 Hz, 1H), 3.93 (dd, J=4.8, 9.4 H z, 1H). SFC: Instrument: Waters UPCC with PDA; Chiralpak IH-3, 100 mm×4.6 mm, 3 μm; Gradient: mobile phase A-$CO_2$, B-IPA (0.1% IPAm, v/v); 60% A for 4.0 min; Flow rate: 3.4 25 mL/min; Column temperature: 35° C.: $t_R$=1.323 min, 99.9%.

Peak 2: (S)-3-(isoquinolin-4-yl)-2-oxoimidazolidine-4-carbonitrile (Int-12). LCMS (Method 32): $t_R$=0.606 min, $[M+1]^+$ 239.0. $^1H$ NMR: (400 MHz, CHLOROFORM-d) δ=9.33 (s, 1H), 8.64 (s, 1H), 8.10 (d, J=8.3 Hz, 1H), 7.97-7.88 (m, 1H), 7.87-7.80 (m, 1H), 7.75-7.68 (m, 1H), 6.51 (s, 1H), 5.00 (dd, J=4.9, 9.0 Hz, 1H), 4.06 (t, J=9.3 Hz, 1H), 3.94 (dd, J=4.9, 9.5 Hz, 1H). SFC: Instrument: Waters UPCC with PDA; Chiralpak IH-3, 100 mm×4.6 mm, 3 μm; Gradient: mobile phase A-$CO_2$, B-IPA (0.1% IPAm, v/v); 60% A for 4.0 min; Flow rate: 3.4 mL/min; Column temperature: 35° C.: $t_R$=2.658 min, 99.7%.

Synthesis of 4-iodoisoquinoline (Int-13)

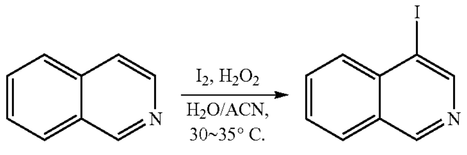

(Int-13)

To a 1 L reactor was added water (100 mL), acetonitrile (50 mL), isoquinoline (25 g, 1.0 equiv.) and iodine (29.5 g, 0.6 equiv.) under $N_2$ atmosphere. $H_2O_2$(65.8 g, 3.0 equiv., 30% in water) was added dropwise over 2 h at 30-35° C. The reaction mixture was stirred at 30-35° C. for 4-6 h. Then, the reaction was cooled to 20~25° C. 40% aq. $Na_2SO_3$ (160 mL) was added to quench the reaction, followed by addition of ethyl acetate (375 mL). Organic phase was separated and washed with water (100 mL), dried by anhydrous $Na_2SO_4$ (5 g), concentrated to give crude product (48.1 g). To the crude product was added n-heptane (125 mL). Heated to 70-75° C., and stirred for 30 min. Cooled down to 60-65° C., and stirred at this temperature for 1 h. Cooled down to 0-5° C. slowly, and stirred at 0-5° C. for another 1 h. Filtered and rinsed the wetcake with n-heptane. The wetcake was dried under reduced pressure at 50° C. for 16 h to give 4-iodo-isoquinoline (Int-13). $^1H$ NMR (400 MHz, DMSO-$d_6$): δ7.79 (ddd, 1H), 7.94 (m, 2H), 8.13 (d, 1H), 8.93 (s, 1H), 9.28 (s, 1H). HRMS: calculated for $CH_6IN$ $[M+H]^+$ 255.9623, found 255.9605.

Synthesis of Example Compounds

Example 1: Synthesis of 3-(isoquinolin-4-yl)-2-oxo-1-phenylimidazolidine-4-carbonitrile (1), (R)-3-(isoquinolin-4-yl)-2-oxo-1-phenylimidazolidine-4-carbonitrile (1a) and (S)-3-(isoquinolin-4-yl)-2-oxo-1-phenylimidazolidine-4-carbonitrile (1b)

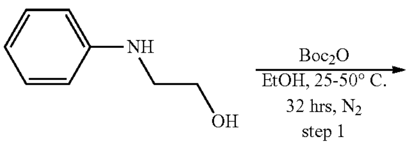

1-1

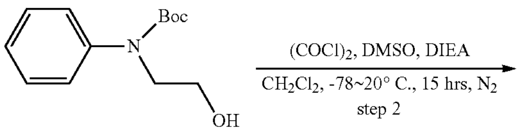

1-2

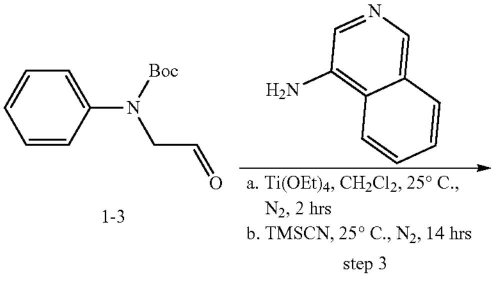

1-3

-continued

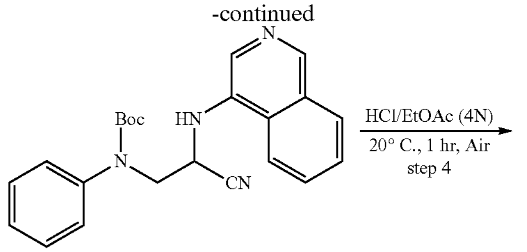

1-4

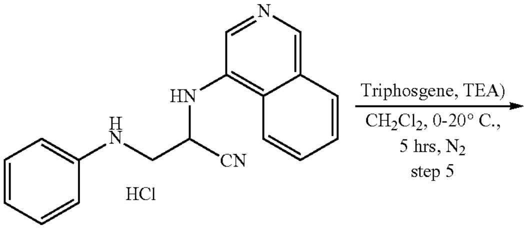

1-5

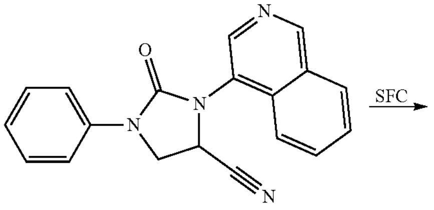

(1)

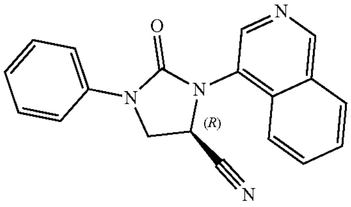

(1a)

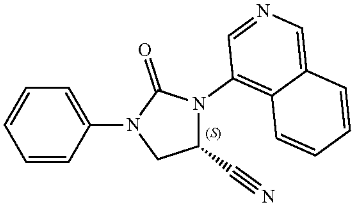

(1b)

Step 1: To a mixture of 2-(phenylamino)ethan-1-ol (1-1) (12.5 g, 91.12 mmol, 1.0 eq.) in EtOH (150 mL) was added $Boc_2O$ (20.0 g, 91.12 mmol, 1.0 eq.) at 25° C. The mixture was stirred at 50° C. for 32 h. The reaction mixture was concentrated under reduced pressure to give a residue that was purified by column chromatography ($SiO_2$, petroleum ether/ethyl acetate=10/1 to 0/1) to give tert-butyl(2-hydroxyethyl)(phenyl)carbamate (1-2). $^1H$ NMR (400 MHz, CHLOROFORM-d) δ=7.37-7.30 (m, 2H), 7.24-7.17 (m, 3H), 3.82-3.74 (m, 4H), 2.84 (br s, 1H), 1.41 (s, 9H).

Step 2: To a solution of $(COCl)_2$ (12.0 g, 63.21 mmol, 1.0 eq.) in $CH_2Cl_2$ (540 mL) was added dropwise a solution of DMSO (14.8 g, 189.64 mmol, 3.0 eq.) in $CH_2Cl_2$ (30 mL) at −78° C. under $N_2$. The reaction solution was stirred at −78° C. over 0.5 h. A solution of tert-butyl(2-hydroxyethyl)(phenyl)carbamate (1-2) (3.1 g, 13.1 mmol, 1.0 eq.) in $CH_2Cl_2$ (30 mL) was added dropwise at −78° C. under $N_2$. The solution was stirred at −78° C. for 0.5 hrs. DIEA (52.2 mL) was added dropwise at −78° C. under $N_2$. Then the mixture was stirred at −78~20° C. for 15 hrs. The mixture was diluted with $H_2O$ (400 mL), extracted with $CH_2Cl_2$ (300 mL×2). The organic layers were washed with brine (300 mL) and concentrated to give crude product which was purified by column chromatography ($SiO_2$, petroleum ether/EtOAc=10/1-5/1) to give tert-butyl(2-oxoethyl)(phenyl)carbamate (1-3). $^1H$ NMR (400 MHz, CHLOROFORM-d) δ=9.79 (s, 1H), 7.44-7.38 (m, 2H), 7.34-7.28 (m, 3H), 4.40 (s, 2H), 1.51 (s, 9H).

Step 3: To a mixture of tert-butyl(2-oxoethyl)(phenyl)carbamate (1-3) (4.7 g, 19.98 mmol, 1.0 eq.) in $CH_2Cl_2$ (100 mL) was added $Ti(OEt)_4$ (9.1 g, 39.96 mmol, 2.0 eq.) and isoquinolin-4-amine (2.8 g, 19.98 mmol, 1.0 eq.) in turn at 25° C., and the mixture then stirred at 25° C. for 2 h. TMSCN (5.9 g, 59.94 mmol, 3.0 eq.) was added into the reaction. The mixture was stirred at 25° C. for 14 h. The reaction mixture was quenched with $H_2O$ (500 mL), extracted with $CH_2Cl_2$ (300 mL×2) and the combined organic layers washed with brine (300 mL), dried over $Na_2SO_4$, filtered and concentrated under reduced pressure to give a residue. The residue was purified by column chromatography ($SiO_2$, petroleum ether/ethyl acetate=10/1 to 0/1) to give tert-butyl(2-cyano-2-(isoquinolin-4-ylamino)ethyl)(phenyl)carbamate (1-4). $^1H$ NMR (400 MHz, CHLOROFORM-d) δ=8.77 (s, 1H), 7.90 (d, J=7.7 Hz, 1H), 7.86 (s, 1H), 7.80 (br s, 1H), 7.64 (dt, J=1.3, 7.6 Hz, 1H), 7.60-7.54 (m, 1H), 7.32-7.26 (m, 2H), 7.25-7.19 (m, 1H), 7.06 (br d, J=7.1 Hz, 2H), 5.93 (br s, 1H), 4.76-4.58 (m, 1H), 4.54-4.45 (m, 1H), 3.94 (br d, J=13.7 Hz, 1H), 1.33 (br s, 9H).

Step 4: A mixture of tert-butyl(2-cyano-2-(isoquinolin-4-ylamino)ethyl)(phenyl)carbamate (1-4) (7.0 g, 18.02 mmol, 1.0 eq.) in 4M HCl in EtOAc (300 mL) was stirred at 20° C. for 1 hr. The reaction mixture was concentrated under reduced pressure to give a residue. The residue was triturated with EtOH (50 mL) at 70° C. for 5 minutes. The resulting solid was filtered, rinsed with EtOH and collected to give 2-(isoquinolin-4-ylamino)-3-(phenylamino)propanenitrile hydrochloride (1-5). $^1H$ NMR (400 MHz, DMSO-$d_6$) δ=9.25 (s, 1H), 8.83 (brd, J=8.6 Hz, 1H), 8.44 (br d, J=8.2 Hz, 1H), 8.21-8.07 (m, 3H), 7.99 (br t, J=7.5 Hz, 1H), 7.55-7.39 (m, 1H), 7.15-7.05 (m, 2H), 6.76 (br d, J=7.8 Hz, 2H), 6.62 (br t, J=7.2 Hz, 1H), 5.19 (br d, J=6.7 Hz, 1H), 4.01-3.79 (m, 2H).

Step 5: To a mixture of 2-(isoquinolin-4-ylamino)-3-(phenylamino)propanenitrile hydrochloride (1-5) (3.5 g, 10.78 mmol, 1.0 eq.) in $CH_2Cl_2$ (50 mL) was added TEA (5.4 g, 53.90 mmol, 5.0 eq.) and triphosgene (3.2 g, 10.78 mmol, 1.0 eq.) in turn at 0° C. The mixture was stirred at 20° C. for 5 h. The reaction mixture was quenched with $H_2O$ (30 mL), extracted with $CH_2Cl_2$ (30 mL×2). The combined organic layers were washed with brine (50 mL), dried over $Na_2SO_4$, filtered and concentrated under reduced pressure to give a residue. The residue was purified by prep-HPLC (column: Phenomenex luna C18 (250 mm×70 mm, 15 μm); liquid phase: [A-$H_2O$ (0.1% FA); B-ACN]B %: 20%-50%, 20 min]) to give the racemate 3-(isoquinolin-4-yl)-2-oxo-1-phenylimidazolidine-4-carbonitrile (1). LCMS (Method 1): $t_R$=2.08 min, $[M+1]^+$ 315.1. $^1H$ NNR (400 MHz, CHLOROFORM-d) δ=9.35 (s, 1H), 8.71 (s, 1H), 8.13 (d, J=8.3 Hz, 1H), 7.95 (br d, J=8.4 Hz, 1H), 7.84 (t, J=7.6 Hz, 1H), 7.77-7.70 (m, 1H), 7.60 (d, J=7.8 Hz, 2H), 7.44 (t, J=8.0 Hz, 2H), 7.23-7.17 (m, 1H), 5.12 (dd, J=4.7, 9.1 Hz, 1H), 4.54 (t, J=9.4 Hz, 1H), 4.41 (dd, J=4.8, 9.6 Hz, 1H).

The racemate was separated by SFC (column: DAICEL CHIRALPAK AD (250 mm×30 mm, 10 μm); mobile phase: [Neu-IP]; B %: 55%-55%, 12 min) to give two peaks.

Peak 1: (R)-3-(naphthalen-1-yl)-2-oxo-1-phenylimidazolidine-4-carbonitrile (47a) LCMS (Method 3): $t_R$=2.67 min, $[M+1]^+$ 315.1. SFC (Method 1): $t_R$=1.43 min, ee %=99.3%. $^1H$ NMR (400 MHz, CHLOROFORM-d) δ=9.34 (s, 1H), 8.70 (s, 1H), 8.11 (d, J=8.1 Hz, 1H), 7.93 (br d, J=8.4 Hz, 1H), 7.82 (dt, J=1.1, 7.7 Hz, 1H), 7.75-7.67 (m, 1H), 7.63-7.56 (m, 2H), 7.47-7.40 (m, 2H), 7.23-7.17 (m, 1H), 5.09 (dd, J=4.8, 9.1 Hz, 1H), 4.51 (t, J=9.4 Hz, 1H), 4.37 (dd, J=4.7, 9.7 Hz, 1H).

Peak 2: (S)-3-(naphthalen-1-yl)-2-oxo-1-phenylimidazolidine-4-carbonitrile (47b) LCMS (Method 3): $t_R$=2.67 min, $[M+1]^+$ 315.1. SFC (Method 1): $t_R$=1.73 min, ee %=99.5%. $^1H$ NMR (400 MHz, CHLOROFORM-d) δ=9.34 (s, 1H), 8.70 (s, 1H), 8.11 (d, J=8.3 Hz, 1H), 7.94 (br d, J=8.4 Hz, 1H), 7.82 (dt, J=1.1, 7.7 Hz, 1H), 7.76-7.67 (m, 1H), 7.59 (d, J=7.9 Hz, 2H), 7.47-7.38 (m, 2H), 7.24-7.16 (m, 1H), 5.10 (dd, J=4.8, 9.1 Hz, 1H), 4.52 (t, J=9.4 Hz, 1H), 4.38 (dd, J=4.7, 9.7 Hz, 1H).

Example 2: Synthesis of 1-(3-chlorophenyl)-3-(isoquinolin-4-yl)-2-oxoimidazolidine-4-carbonitrile (2), (R)-1-(3-chlorophenyl)-3-(isoquinolin-4-yl)-2-oxoimidazolidine-4-carbonitrile (2a) and (R)-1-(3-chlorophenyl)-3-(isoquinolin-4-yl)-2-oxoimidazolidine-4-carbonitrile (2b)

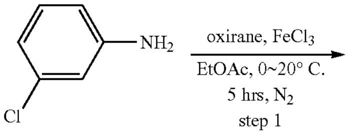

2-1

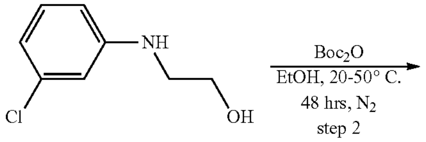

2-2

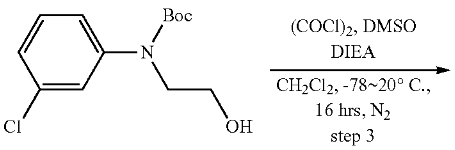

2-3

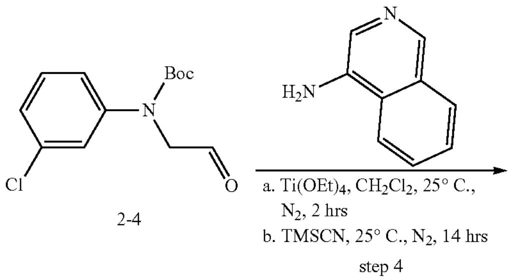

2-4

-continued

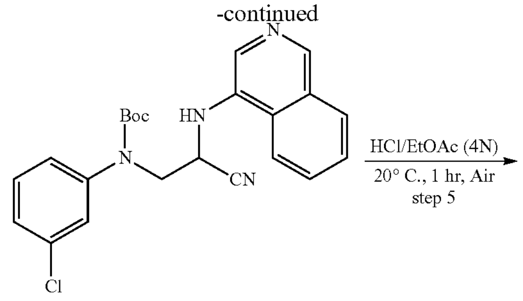

2-5

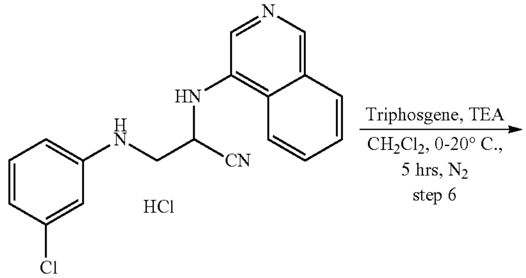

2-6

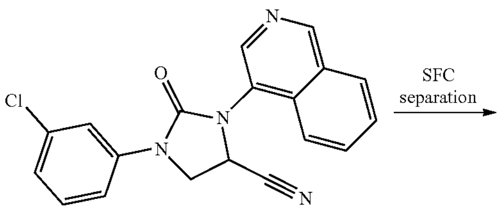

(2)

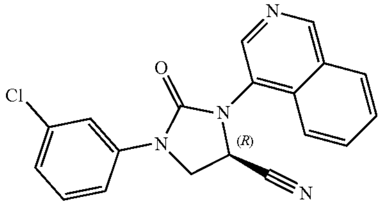

(2a)

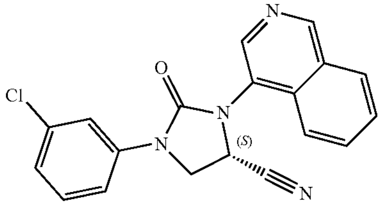

(2b)

Step 1: To a mixture of 3-chloroaniline (2-1) (12.5 g, 91.12 mmol, 1.0 eq.) in EtOAc (500 mL) was added $FeCl_3$ (625 mg, 3.88 mmol, 0.04 eq.) at 0° C. Oxirane (10.8 g, 244.96 mmol, 2.5 eq.) was added dropwise at 0° C. and the mixture stirred at 20° C. for 5 hrs. The reaction mixture was quenched with $H_2O$ (500 mL), extracted with EtOAc (300 mL×2). The combined organic layers were washed with brine (300 mL), dried over $Na_2SO_4$, filtered and concentrated under reduced pressure to give a residue. The residue was purified by column chromatography ($SiO_2$, petroleum ether/ethyl acetate=10/1 to 0/1) to give 2-((3-chlorophenyl)amino)ethan-1-ol (2-2). $^1H$ NMR (400 MHz, CHLOROFORM-d) δ=7.08 (t, J=8.1 Hz, 1H), 6.72-6.67 (m, 1H), 6.63

(t, J=2.1 Hz, 1H), 6.55-6.49 (m, 1H), 3.86-3.80 (m, 2H), 3.32-3.24 (m, 2H), 2.97 (br s, 1H).

Step 2: To a mixture of 2-((3-chlorophenyl)amino)ethan-1-ol (2-2) (15.5 g, 90.31 mmol, 1.0 eq.) in EtOH (200 mL) was added $Boc_2O$ (19.7 g, 90.31 mmol, 1.0 eq.) at 20° C. The mixture was stirred at 50° C. for 48 hrs. The reaction mixture was concentrated under reduced pressure to give a residue which was purified by column chromatography ($SiO_2$, petroleum ether/ethyl acetate=10/1 to 0/1) to give tert-butyl(3-chlorophenyl)(2-hydroxyethyl)carbamate (2-3). $^1H$ NMR (400 MHz, CHLOROFORM-d) δ=7.34-7.29 (m, 2H), 7.28-7.23 (m, 1H), 7.18 (br d, J=8.2 Hz, 1H), 3.88-3.79 (m, 4H), 1.49 (s, 9H).

Step 3: To a solution of $(COCl)_2$ (10.5 g, 82.80 mmol, 1.5 eq.) in $CH_2Cl_2$ (540 mL) was added dropwise DMSO (13.0 g, 165.60 mmol, 3.0 eq.) in $CH_2Cl_2$ (30 mL) at −78° C. The reaction solution was stirred at −78° C. for 0.5 h. tert-butyl (3-chlorophenyl)(2-hydroxyethyl)carbamate (2-3) (15.0 g, 55.20 mmol, 1.0 eq.) in $CH_2Cl_2$ (30 mL) was added dropwise at −78° C. The solution was stirred at −78° C. for 0.5 h. Then DIEA (45.5 mL) was added at −78° C. and the mixture warmed to 20° C. and stirred at 20° C. for 15 h. The mixture was diluted with $H_2O$ (150 mL) and extracted with $CH_2Cl_2$ (200 mL×2). The combined organic layers were washed with brine (100 mL) and concentrated to give crude product which was purified by silica gel column chromatography (petroleum ether/EtOAc=10/1-5/1) to give tert-butyl(3-chlorophenyl)(2-oxoethyl)carbamate (2-4). $^1H$ NMR: (400 MHz, CHLOROFORM-d) δ=9.70 (s, 1H), 7.30-7.24 (m, 2H), 7.22-7.18 (m, 1H), 7.14 (br d, J=7.9 Hz, 1H), 4.38-4.28 (m, 2H), 1.45 (s, 9H).

Step 4: To a mixture of tert-butyl(3-chlorophenyl)(2-oxoethyl)carbamate (2-4) (6.0 g, 22.24 mmol, 1.0 eq.) in $CH_2Cl_2$ (100 mL) was added isoquinolin-4-amine (3.2 g, 22.24 mmol, 1.0 eq.) and $Ti(OEt)_4$ (10.1 g, 44.48 mmol, 2.0 eq.) in turn at 25° C. The mixture was stirred at 25° C. for 2 h. TMSCN (6.6 g, 66.72 mmol, 3.0 eq.) was added and the mixture stirred at 25° C. for 14 h. The reaction mixture was quenched with $H_2O$ (500 mL) and extracted with $CH_2Cl_2$ (300 mL×2). The combined organic layers were washed with brine (300 mL), dried over $Na_2SO_4$, filtered and concentrated under reduced pressure to give a residue. The residue was purified by column chromatography ($SiO_2$, petroleum ether/ethyl acetate=10/1 to 0/1) to give tert-butyl (3-chlorophenyl)(2-cyano-2-(isoquinolin-4-ylamino)ethyl) carbamate (2-5). $^1H$ NMR (400 MHz, CHLOROFORM-d) δ=8.85 (s, 1H), 7.98 (d, J=7.8 Hz, 1H), 7.95 (s, 1H), 7.83 (br d, J=8.1 Hz, 1H), 7.74-7.68 (m, 1H), 7.67-7.61 (m, 1H), 7.29-7.27 (m, 2H), 7.18 (s, 1H), 7.03 (br d, J=2.8 Hz, 1H), 5.78 (br s, 1H), 4.71-4.62 (m, 1H), 4.60-4.52 (m, 1H), 4.04 (br d, J=11.4 Hz, 1H), 1.42 (s, 9H).

Step 5: A mixture of tert-butyl(3-chlorophenyl)(2-cyano-2-(isoquinolin-4-ylamino)ethyl)carbamate (2-5) (8.0 g, 18.90 mmol, 1.0 eq.) in 4M HCl in EtOAc (100 mL) was stirred at 20° C. for 1 h. The reaction mixture was concentrated under reduced pressure to give a residue which was triturated with EtOH (60 mL) at 70° C. for 5 min. The resulting solid was filtered, rinsed with EtOH, collected and dried to give the 3-((3-chlorophenyl)amino)-2-(isoquinolin-4-ylamino)propanenitrile hydrochloride (2-6). $^1H$ NMR (400 MHz, DMSO-$d_6$) δ=9.25 (s, 1H), 8.77 (d, J=8.6 Hz, 1H), 8.45 (d, J=8.0 Hz, 1H), 8.19-8.07 (m, 3H), 8.03-7.97 (m, 1H), 7.08 (t, J=8.0 Hz, 1H), 6.77 (t, J=2.0 Hz, 1H), 6.67 (dd, J=1.5, 8.3 Hz, 1H), 6.57 (dd, J=1.3, 7.9 Hz, 1H), 5.17 (q, J=7.1 Hz, 1H), 3.98-3.80 (m, 2H).

Step 6: To a mixture of 3-((3-chlorophenyl)amino)-2-(isoquinolin-4-ylamino)propanenitrile hydrochloride (2-6) (4.0 g, 12.39 mmol, 1.0 eq.) in $CH_2Cl_2$ (40 mL) was added TEA (6.3 g, 61.96 mmol, 5.0 eq.) and Triphosgene (3.6 g, 12.39 mmol, 1.0 eq.) in turn at 0° C. The mixture was stirred at 20° C. for 5 hrs. The reaction mixture was quenched with $H_2O$ (30 mL) and extracted with $CH_2Cl_2$ (30 mL×2). The combined organic layers were washed with brine (50 mL), dried over $Na_2SO_4$, filtered and concentrated under reduced pressure to give a residue. The residue was purified by prep-HPLC (column: Phenomenex luna C18 (250×70 mm, 15 μm); liquid phase: [A-$H_2O$(0.1% FA); B-ACN]B %: 30%-60%, 20 min]) to give the racemate 1-(3-chlorophenyl)-3-(isoquinolin-4-yl)-2-oxoimidazolidine-4-carbonitrile (2). The racemate was resolved by SFC (column: DAICEL CHIRALPAK AD (250 mm×30 mm, 10 μm); mobile phase: 0.1% $NH_3H_2O$ IPA; B %: 55%-55%, 13 min) to give enantiomer 1 and enantiomer 2.

Racemate 1-(3-chlorophenyl)-3-(isoquinolin-4-yl)-2-oxoimidazolidine-4-carbonitrile (2) LCMS (Method 1): $t_R$=2.32 min, $[M+1]^+$ 349.0. $^1H$ NMR (400 MHz, CHLOROFORM-d) δ=9.35 (s, 1H), 8.71 (s, 1H), 8.13 (d, J=8.3 Hz, 1H), 7.95 (br d, J=8.4 Hz, 1H), 7.84 (t, J=7.6 Hz, 1H), 7.77-7.70 (m, 1H), 7.60 (d, J=7.8 Hz, 2H), 7.44 (t, J=8.0 Hz, 2H), 7.23-7.17 (m, 1H), 5.12 (dd, J=4.7, 9.1 Hz, 1H), 4.54 (t, J=9.4 Hz, 1H), 4.41 (dd, J=4.8, 9.6 Hz, 1H).

Enantiomer 1: (R)-1-(3-chlorophenyl)-3-(isoquinolin-4-yl)-2-oxoimidazolidine-4-carbonitrile (2a) LCMS (Method 3): $t_R$=2.50 min, $[M+1]^+$ 349.0. SFC (Method 1): $t_R$=1.42 min, ee %=99.5%. $^1H$ NMR (400 MHz, CHLOROFORM-d) δ=9.37 (s, 1H), 8.82 (s, 1H), 8.17 (d, J=8.2 Hz, 1H), 8.02-7.94 (m, 1H), 7.90 (t, J=7.3 Hz, 1H), 7.80-7.74 (m, 1H), 7.66 (t, J=2.0 Hz, 1H), 7.49 (dd, J=1.6, 8.3 Hz, 1H), 7.36 (t, J=8.1 Hz, 1H), 7.17 (dd, J=1.0, 7.9 Hz, 1H), 5.28 (br d, J=4.4 Hz, 1H), 4.56 (t, J=9.4 Hz, 1H), 4.38 (dd, J=4.6, 9.6 Hz, 1H).

Enantiomer 2: (S)-1-(3-chlorophenyl)-3-(isoquinolin-4-yl)-2-oxoimidazolidine-4-carbonitrile (2b) LCMS (Method 3): $t_R$=2.54 min, $[M+1]^+$ 349.0. SFC (Method 1): $t_R$=1.65 min, ee %=99.8%. $^1H$ NMR (400 MHz, CHLOROFORM-d) δ=9.36 (s, 1H), 8.78 (s, 1H), 8.16 (d, J=8.3 Hz, 1H), 7.99-7.93 (m, 1H), 7.91-7.85 (m, 1H), 7.80-7.73 (m, 1H), 7.66 (t, J=2.1 Hz, 1H), 7.50 (dd, J=1.5, 8.3 Hz, 1H), 7.36 (t, J=8.2 Hz, 1H), 7.27 (s, 1H), 7.17 (dd, J=1.1, 7.9 Hz, 1H), 5.23 (br dd, J=4.4, 8.9 Hz, 1H), 4.55 (t, J=9.4 Hz, 1H), 4.38 (dd, J=4.6, 9.6 Hz, 1H).

Example 3: Synthesis of 3-(isoquinolin-4-yl)-2-oxo-1-(5-(trifluoromethyl)pyridin-2-yl)imidazolidine-4-carbonitrile (3)

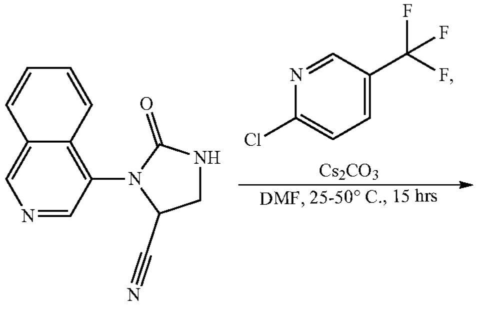

(Int-1)

-continued

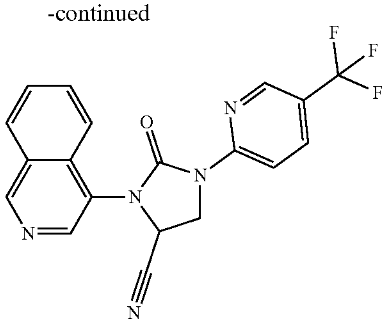

(3)

To the solution of 3-(isoquinolin-4-yl)-2-oxoimidazolidine-4-carbonitrile (Int-1) (100 mg, 0.42 mmol, 1.0 eq.) in DMF (2 mL) was added 2-chloro-5-(trifluoromethyl)pyridine (92 mg, 0.50 mmol, 1.2 eq.) and $Cs_2CO_3$ (205 mg, 4.24 mmol, 3.0 eq.) at 25° C. The solution was stirred at 50° C. under $N_2$ for 15 h. The mixture was then filtered and the filtrate was concentrated to give crude product. The crude product was purified by prep-HPLC (column: Waters Xbridge BEH C18 100×30 mm×10 μm; liquid phase: [A-10 mM $NH_4HCO_3$ in $H_2O$; B-ACN]B %: 35%-55%, 8 min]) to give 3-(isoquinolin-4-yl)-2-oxo-1-(5-(trifluoromethyl)pyridin-2-yl)imidazolidine-4-carbonitrile (3). LCMS (Method 3): $t_R$=3.1 min, $[M+1]^+$ 384.1. $^1H$ NMR (400 MHz, CHLOROFORM-d) δ=9.38 (s, 1H), 8.77-8.61 (m, 2H), 8.42 (d, J=8.8 Hz, 1H), 8.15 (d, J=8.2 Hz, 1H), 7.95 (dd, J=2.3, 8.9 Hz, 1H), 7.92-7.80 (m, 2H), 7.78-7.71 (m, 1H), 5.12 (t, J=6.8 Hz, 1H), 4.75 (d, J=6.8 Hz, 2H).

Example 4: Synthesis of 3-(isoquinolin-4-yl)-2-oxo-1-(4-(trifluoromethyl)phenyl)imidazolidine-4-carbonitrile (4)

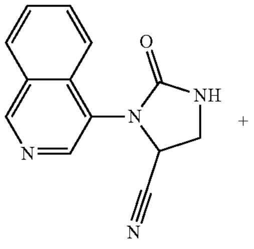

(Int-1)

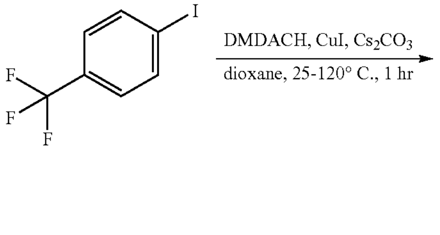

-continued

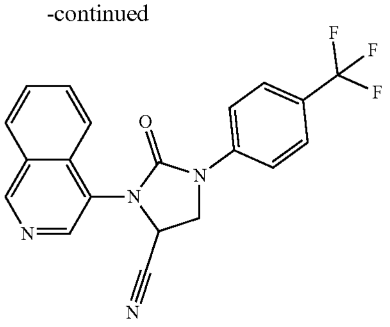

(4)

A mixture of 3-(isoquinolin-4-yl)-2-oxoimidazolidine-4-carbonitrile (Int-1) (250 mg, 1.05 mmol, 1.0 eq.), 4-trifluoromethyl-iodobenzene (285 mg, 1.05 mmol, 1.0 eq.), trans-N,N'-dimethyl-1,2-diaminocyclohexane (DMDACH, 60 mg, 0.40 mmol, 0.4 eq.), CuI (40 mg, 0.20 mmol, 0.2 eq.) and $Cs_2CO_3$ (585 mg, 2.10 mmol, 2.0 eq.) in dioxane (3 mL) was stirred at 120° C. under $N_2$ for 1 h. Thiourea resin (LS-2000, 500 mg) was added and the reaction mixture was stirred at 20° C. for 2 h. The mixture was filtered and the filtrate was concentrated under reduced pressure to give crude product. The crude product was purified by prep-HPLC (column: Phenomenex Luna C 18 75 mm×30 mm×3 μm; liquid phase: [A-FA/$H_2O$=0.1% v/v; B-ACN]B %: 40%-70%, 8 min]) to give 3-(isoquinolin-4-yl)-2-oxo-1-(4-(trifluoromethyl)phenyl)imidazolidine-4-carbonitrile (4). LCMS (Method 1): $t_R$=2.47 min, $[M+1]^+$ 383.2. $^1H$ NMR (400 MHz, DMSO-$d_6$) δ=9.44 (s, 1H), 8.70 (s, 1H), 8.29 (d, J=8.2 Hz, 1H), 8.14 (d, J=8.4 Hz, 1H), 7.93-7.89 (m, 1H), 7.87-7.83 (m, 2H), 7.82-7.76 (m, 3H), 5.71 (dd, J=4.8, 9.4 Hz, 1H), 4.68-4.59 (m, 1H), 4.53 (dd, J=4.8, 9.7 Hz, 1H).

Example 5: Synthesis of 1-(4-chlorophenyl)-3-(isoquinolin-4-yl)-2-oxoimidazolidine-4-carbonitrile (5)

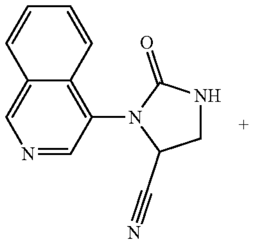

(Int-1)

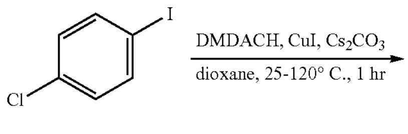

-continued

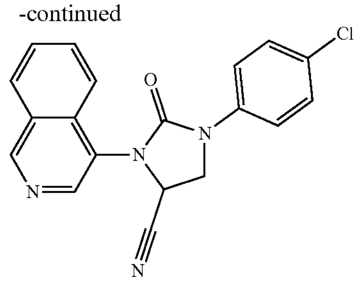

(5)

1-(4-chlorophenyl)-3-(isoquinolin-4-yl)-2-oxoimidazolidine-4-carbonitrile (5) was prepared in a manner similar to Example 4, using 4-iodo-chlorobenzene in place of 4-trifluoromethyl-iodobenzene. The crude product obtained was purified by prep-HPLC (column: Phenomenex Luna C18 75 mm×30 mm×3 μm; liquid phase: [A-FA/$H_2O$=0.1% v/v; B-ACN]B %: 30%-60%, 8 min]) to give 1-(4-chlorophenyl)-3-(isoquinolin-4-yl)-2-oxoimidazolidine-4-carbonitrile (5). LCMS (Method 1): $t_R$=2.32 min, $[M+1]^+$ 349.2. $^1$H NMR (400 MHz, DMSO-$d_6$) δ=9.42 (s, 1H), 8.68 (s, 1H), 8.28 (d, J=8.2 Hz, 1H), 8.11 (d, J=8.6 Hz, 1H), 7.92-7.87 (m, 1H), 7.83-7.78 (m, 1H), 7.67 (d, J=9.0 Hz, 2H), 7.48 (d, J=8.9 Hz, 2H), 5.68 (dd, J=4.6, 9.3 Hz, 1H), 4.60-4.53 (m, 1H), 4.46 (dd, J=4.7, 9.7 Hz, 1H).

Example 6: Synthesis of 1-(4-fluorophenyl)-3-(isoquinolin-4-yl)-2-oxoimidazolidine-4-carbonitrile (6)

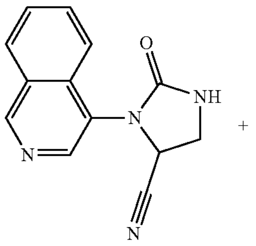

(int-1)

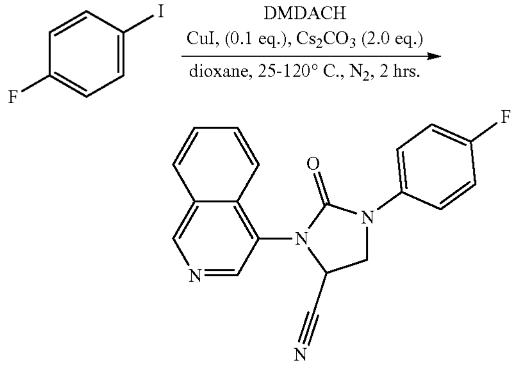

(6)

Racemic 1-(4-fluorophenyl)-3-(isoquinolin-4-yl)-2-oxoimidazolidine-4-carbonitrile (6) was prepared in a manner similar to Example 4, using 4-iodo-fluorobenzene in place of 4-trifluoromethyl-iodobenzene. The crude product obtained was purified by prep-HPLC (column: Phenomenex Luna C18 75 mm×30 mm×3 μm; liquid phase: [A-FA/$H_2O$=0.1% v/v; B-ACN]B %: 15%-45%, 8 min]) to give 1-(4-fluorophenyl)-3-(isoquinolin-4-yl)-2-oxoimidazolidine-4-carbonitrile (6). LCMS (Method 1): $t_R$=2.15 min, $[M+1]^+$ 384.2. $^1$H NMR (400 MHz, DMSO-$d_6$) δ=9.42 (s, 1H), 8.68 (s, 1H), 8.28 (d, J=8.4 Hz, 1H), 8.11 (d, J=8.5 Hz, 1H), 7.93-7.87 (m, 1H), 7.83-7.77 (m, 1H), 7.69-7.62 (m, 2H), 7.31-7.23 (m, 2H), 5.67 (dd, J=4.6, 9.2 Hz, 1H), 4.57 (t, J=9.4 Hz, 1H), 4.45 (dd, J=4.7, 9.7 Hz, 1H).

Example 7: Synthesis of 1-(3-fluorophenyl)-3-(isoquinolin-4-yl)-2-oxoimidazolidine-4-carbonitrile (7)

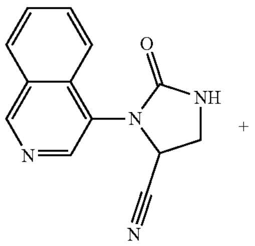

Intermediate 1

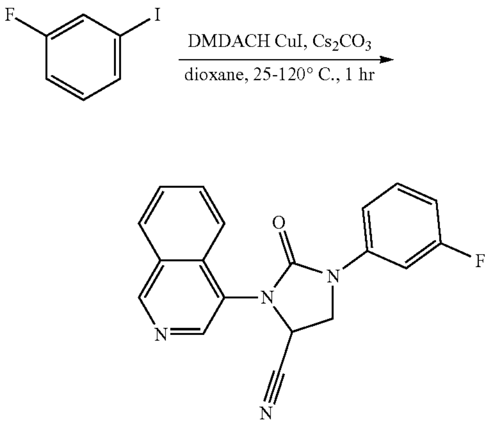

(7)

1-(3-fluorophenyl)-3-(isoquinolin-4-yl)-2-oxoimidazolidine-4-carbonitrile (7) was prepared in a manner similar to Example 4, using 3-iodo-fluorobenzene in place of 4-trifluoromethyl-iodobenzene. The crude product obtained was purified by prep-HPLC (column: Phenomenex Luna C18 200 mm×40 mm×10 μm; liquid phase: [A-$H_2O$ (0.1% HCOOH); B-ACN]B %: 10%-50%, 20 min]) to give 1-(3-fluorophenyl)-3-(isoquinolin-4-yl)-2-oxoimidazolidine-4-carbonitrile (7). LCMS (Method 2): $t_R$=2.82 min, $[M+1]^+$ 333.1. $^1$H NMR: (400 MHz, CHLOROFORM-d) δ=9.35 (s, 1H), 8.69 (s, 1H), 8.12 (d, J=8.1 Hz, 1H), 7.95-7.86 (m, 1H), 7.83 (dt, J=1.1, 7.6 Hz, 1H), 7.75-7.70 (m, 1H), 7.50 (td, J=2.3, 11.2 Hz, 1H), 7.39 (dt, J=6.5, 8.3 Hz, 1H), 7.30-7.27 (m, 1H), 6.93-6.86 (m, 1H), 5.11 (dd, J=4.6, 9.3 Hz, 1H), 4.51 (t, J=9.4 Hz, 1H), 4.38 (dd, J=4.7, 9.7 Hz, 1H).

Example 8: Synthesis of 1-(5-fluoropyridin-2-yl)-3-(isoquinolin-4-yl)-2-oxoimidazolidine-4-carbonitrile (8)

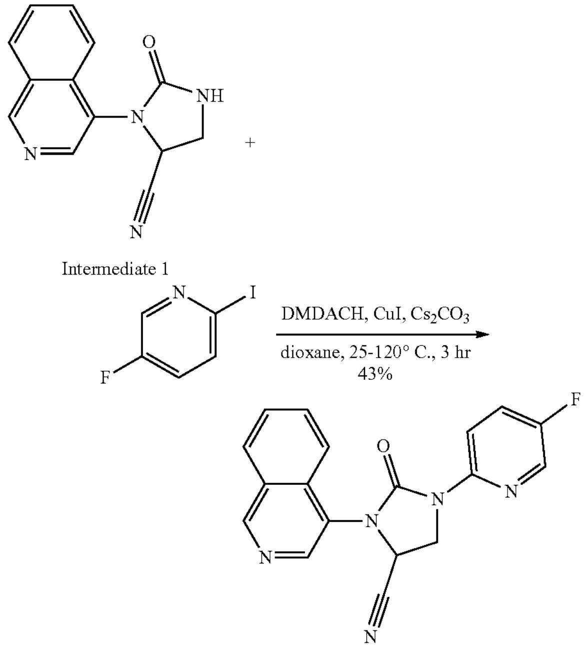

Intermediate 1

(7)

1-(5-fluoropyridin-2-yl)-3-(isoquinolin-4-yl)-2-oxoimidazolidine-4-carbonitrile (8) was prepared in a manner similar to Example 4, using 5-fluoro-2-iodopyridine in place of 4-trifluoromethyl-iodobenzene. The crude product obtained was purified by prep-HPLC (column: Phenomenex C18 75 mm×30 mm×3 μm; liquid phase: [A-$H_2O$ (0.1% HCOOH); B-ACN]B %: 20%-50%, 8 min]) to give 1-(5-fluoropyridin-2-yl)-3-(isoquinolin-4-yl)-2-oxoimidazolidine-4-carbonitrile (8).

LCMS (Method 3): $t_R$=2.73 min, $[M+1]^+$ 334.0. $^1$H NMR: (400 MHz, CHLOROFORM-d) δ=9.36 (s, 1H), 8.71 (s, 1H), 8.27 (dd, J=3.9, 9.3 Hz, 1H), 8.23 (d, J=3.0 Hz, 1H), 8.13 (d, J=8.3 Hz, 1H), 7.95-7.87 (m, 1H), 7.87-7.80 (m, 1H), 7.76-7.70 (m, 1H), 7.49 (ddd, J=3.0, 7.6, 9.3 Hz, 1H), 5.08 (dd, J=5.1, 8.8 Hz, 1H), 4.73-4.62 (m, 2H).

Example 9: Synthesis of 3-(isoquinolin-4-yl)-2-oxo-1-(6-(trifluoromethyl)pyridin-3-yl)imidazolidine-4-carbonitrile (9)

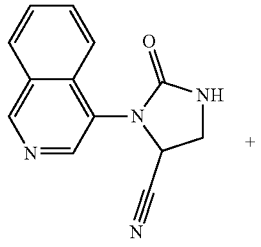

Intermediate 1

-continued

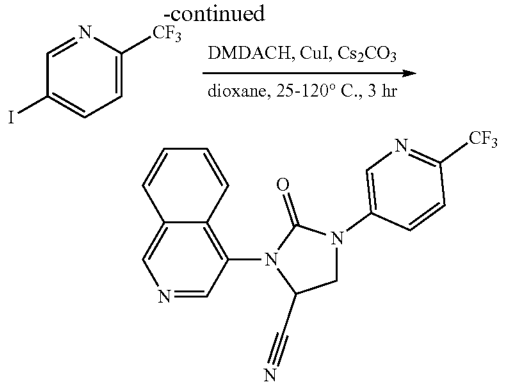

(9)

3-(isoquinolin-4-yl)-2-oxo-1-(6-(trifluoromethyl)pyridin-3-yl)imidazolidine-4-carbonitrile (9) was prepared in a manner similar to Example 4, using 5-iodo-2-(trifluoromethyl) pyridine in place of 4-trifluoromethyl-iodobenzene. The crude product obtained was purified by prep-HPLC (column: Phenomenex C18 75 mm×30 mm×3 μm; liquid phase: [A-$H_2O$ (0.1% HCOOH); B-ACN]B %: 15%-45%, 8 min]) to give 3-(isoquinolin-4-yl)-2-oxo-1-(6-(trifluoromethyl) pyridin-3-yl)imidazolidine-4-carbonitrile (9). LCMS (Method 3): $t_R$=2.86 min, $[M+1]^+$ 384.1. $^1$H NMR: (400 MHz, CHLOROFORM-d) δ=9.38 (s, 1H), 8.79 (d, J=2.6 Hz, 1H), 8.71 (s, 1H), 8.42 (dd, J=2.4, 8.7 Hz, 1H), 8.14 (d, J=8.1 Hz, 1H), 7.92-7.82 (m, 2H), 7.81-7.69 (m, 2H), 5.18 (dd, J=4.4, 9.1 Hz, 1H), 4.62 (t, J=9.4 Hz, 1H), 4.49 (dd, J=4.4, 9.6 Hz, 1H).

Example 10: Synthesis of 1-(5-chloropyridin-2-yl)-3-(isoquinolin-4-yl)-2-oxoimidazolidine-4-carbonitrile (10)

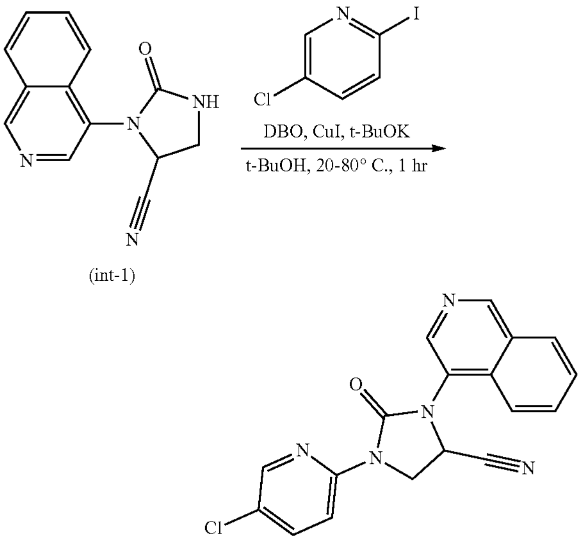

(int-1)

(10)

To the solution of 3-(isoquinolin-4-yl)-2-oxoimidazolidine-4-carbonitrile (Int-1) (100 mg, 0.42 mmol, 1.0 eq.) in t-BuOH (2 mL) was added 5-chloro-2-iodopyridine (100 mg, 0.42 mmol, 1.0 eq.), DBO (45 mg, 0.17 mmol, 0.4 eq.), CuI (1 mg, 0.004 mmol, 0.01 eq.) and t-BuOK (94 mg, 0.84 mmol, 2.0 eq.) at 20° C. under $N_2$. Then the solution was stirred at 80° C. under $N_2$ for 1 h. Thiourea resin (LS_2000, 300 mg) was added and the mixtures was stirred at 25° C. for 2 h. The mixture was filtered and the filtrate was concentrated to give crude product which was purified by prep-HPLC (column: Phenomenex Luna C18 100 mm×30 mm×5 μm; liquid phase: [A-FA/$H_2O$=0.1% v/v; B-ACN]B %: 25%-60%, 8 min]) to give 1-(5-chloropyridin-2-yl)-3-(isoquinolin-4-yl)-2-oxoimidazolidine-4-carbonitrile (10). LCMS (Method 3): $t_R$=2.93 min, [M+1]$^+$ 350.1. $^1$H NMR (400 MHz, CHLOROFORM-d) δ=9.36 (s, 1H), 8.70 (s, 1H), 8.33 (dd, J=0.6, 2.6 Hz, 1H), 8.24 (dd, J=0.6, 8.9 Hz, 1H), 8.13 (d, J=8.2 Hz, 1H), 7.95-7.88 (m, 1H), 7.84 (dt, J=1.2, 7.6 Hz, 1H), 7.76-7.72 (m, 1H), 7.70 (dd, J=2.6, 9.0 Hz, 1H), 5.09 (dd, J=5.5, 8.3 Hz, 1H), 4.71-4.65 (m, 2H).

Example 11-1: Synthesis of (R)-3-(isoquinolin-4-yl)-2-oxo-1-(6-(trifluoromethyl)pyridin-3-yl)imidazolidine-4-carbonitrile (11a) and (S)-3-(isoquinolin-4-yl)-2-oxo-1-(6-(trifluoromethyl)pyridin-3-yl)imidazolidine-4-carbonitrile (11b)

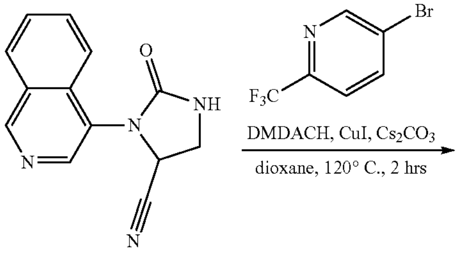

(int-1)

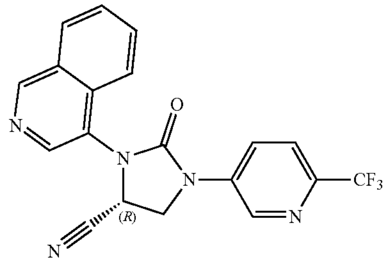

(11a)

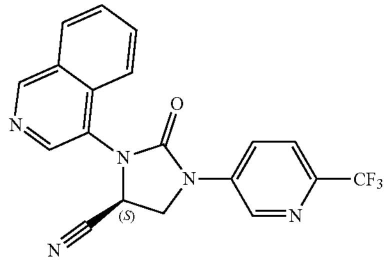

(11b)

A mixture of 3-(isoquinolin-4-yl)-2-oxoimidazolidine-4-carbonitrile (Int-1) (3.5 g, 14.69 mmol, 1.0 eq.), 5-bromo-2-(trifluoromethyl)pyridine (5.0 g, 22.03 mmol, 1.5 eq.), DMDACH (840 mg, 5.87 mmol, 0.4 eq.), CuI (560 mg, 2.94 mmol, 0.2 eq.), $Cs_2CO_3$ (9.6 g, 29.38 mmol, 2.0 eq.) and 4A molecular sieves (1.0 g) in dioxane (50 mL) was stirred at 120° C. under $N_2$ for 2 hrs. Thiourea resin (LS-2000, 4 g) was added and the mixture was stirred at 25° C. for 2 hrs. The mixture was filtered and concentrated to give crude product to which water (200 mL) was added and the mixture then extracted with $CH_2Cl_2$ (150 mL×2). The combined organic layers was washed with brine (100 mL×2), dried over $Na_2SO_4$, filtered and concentrated under reduced pressure to give crude product which was purified by column (petroleum ether/EtOAc=1/2 to 1/3) to give racemic 3-(isoquinolin-4-yl)-2-oxo-1-(6-(trifluoromethyl)pyridin-3-yl)imidazolidine-4-carbonitrile (9). The racemate was resolved by chiral SFC (DAICEL CHIRALCEL OJ (250 mm×50 mm, μm); liquid phase: [0.1% $NH_3H_2O$ EtOH]B %: 35%-35%, 20 min]) to give two peaks.

Peak 1: The compound obtained from peak 1 was further purified by prep-HPLC (column: Agela DuraShell C18 250×70 mm×10 μm; liquid phase: [A-$H_2O$ (10 mM $NH_4HCO_3$); B-ACN]B %: 30%-60%, 20 min]); B-ACN]B %: 10%-40%, 20 min]) to give (R)-3-(isoquinolin-4-yl)-2-oxo-1-(6-(trifluoromethyl)pyridin-3-yl)imidazolidine-4-carbonitrile (11a). Verification of the R-isomer was obtained by crystallization with the SARS-CoV-2 Main Protease protein described below. LCMS (Method 13): $t_R$=2.19 min, [M+1]$^+$ 384.0. SFC (Method 2): $t_R$=1.17 min, ee %=100.0%. $^1$H NMR: (400 MHz, $CDCl_3$) δ=9.38 (s, 1H), 8.80 (d, J=2.4 Hz, 1H), 8.74 (s, 1H), 8.42 (dd, J=2.4, 8.8 Hz, 1H), 8.16 (d, J=8.2 Hz, 1H), 7.95-7.82 (m, 2H), 7.80-7.73 (m, 2H), 5.23 (br dd, J=4.2, 9.0 Hz, 1H), 4.64 (t, J=9.5 Hz, 1H), 4.50 (dd, J=4.3, 9.7 Hz, 1H).

Peak 2: The compound obtained from peak 2 was further purified by prep-HPLC (column: Agela DuraShell C18 250×70 mm×10 um; liquid phase: [A-$H_2O$ (10 mM $NH_4HCO_3$); B-ACN]B %: 30%-60%, 20 min]); B-ACN]B %: 10%-40%, 20 min]) to give (S)-3-(isoquinolin-4-yl)-2-oxo-1-(6-(trifluoromethyl)pyridin-3-yl)imidazolidine-4-carbonitrile (11b).

LCMS (Method 13): $t_R$=2.19 min, [M+1]$^+$ 384.0. SFC (Method 2): $t_R$=1.29 min, ee %=96.5%. $^1$H NMR: (400 MHz, $CDCl_3$) δ=9.38 (br s, 1H), 8.80 (d, J=2.4 Hz, 1H), 8.78-8.71 (m, 1H), 8.42 (br dd, J=1.7, 8.6 Hz, 1H), 8.16 (br d, J=7.9 Hz, 1H), 7.98-7.84 (m, 2H), 7.82-7.70 (m, 2H), 5.23 (br d, J=5.1 Hz, 1H), 4.64 (br t, J=9.4 Hz, 1H), 4.50 (br dd, J=4.3, 9.5 Hz, 1H).

Example 11-2: Alternative Synthesis of (R)-3-(isoquinolin-4-yl)-2-oxo-1-(6-(trifluoromethyl)pyridin-3-yl)imidazolidine-4-carbonitrile (11a)

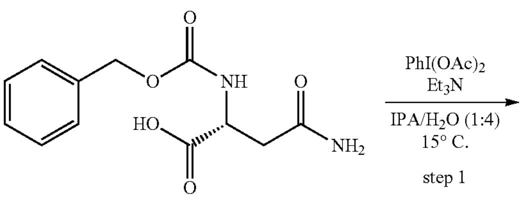

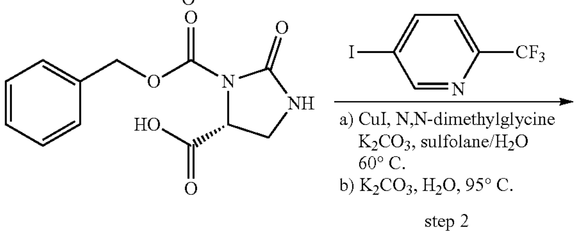

-continued

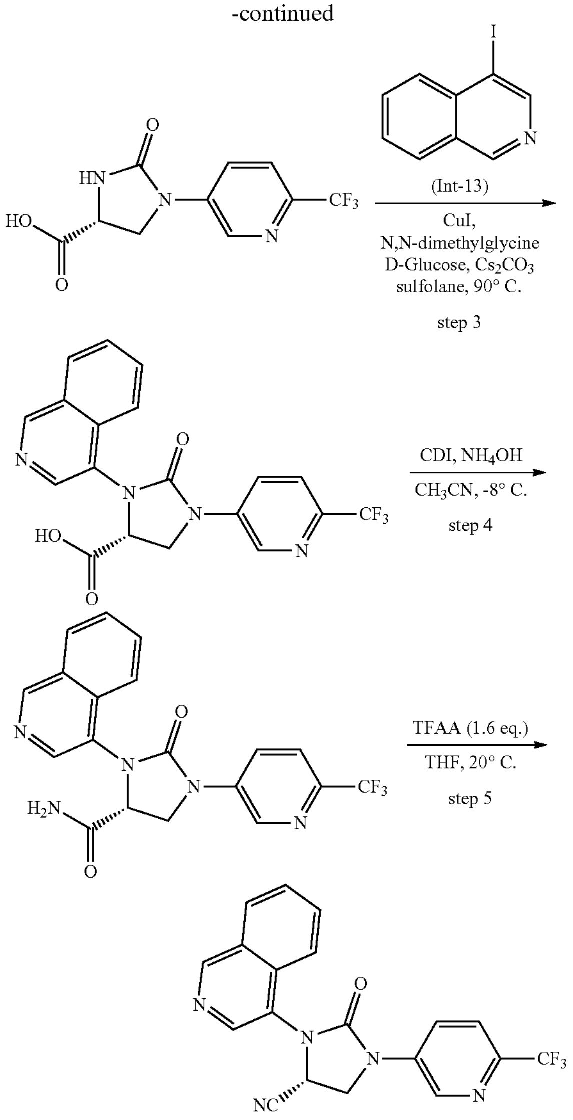

(11a)

Step 1: To a 1000 mL reactor was added ((benzyloxy) carbonyl)-D-asparagine (102 g, 1.0 equiv.), water (654 mL), isopropanol (163 mL) and triethylamine (136 g, 3.6 equiv.). The resulting mixture was stirred at 20~25° C. to form a clear solution and then cooled to 15° C. (Diacetoxyiodo) benzene (102 g, 1.2 equiv.) was added into the reactor at 15° C. in five portions over 80 mins. The mixture was stirred at 15° C. for another 2 hours, then warmed to 25° C. and stirred overnight. The mixture was washed with MTBE (400 mL) (2 x) and the aqueous phase collected and charged with 31% HCl solution to adjust the pH to 1. The mixture was stirred at 15° C. for 2 hours and then cooled to −5° C. After stirring at −5° C. for another 16 hours, the suspension was filtered. The wet cake was washed with water (200 mL) and dried under reduced pressure at 60° C. for 24 hours to give (R)-3-((benzyloxy)carbonyl)-2-oxoimidazolidine-4-carboxylic acid. $^1H$ NMR (400 MHz, DMSO-$d_6$): δ13.26 (s, 1H), 7.57 (s, 1H), 7.36 (m, 5H), 5.17 (s, 2H), 4.68 (dd, 1H), 3.65 (t, 1H), 3.22 (dd, 1H). HRMS: calculated for $C_{12}H_{12}N_2O_5$ $[M+H]^+$ 265.0819, found 265.0811. Chiral HPLC conditions: CHIRALPAK AY-3 (150 mm×4. mm, 3 μm); Heptane/EtOH=70/30, 40° C.; flow rate=0.8 mL/min; 214 nm UV detector; $t_R$ (major)=5.15 min and $t_R$ (minor)=8.56 min.

Step 2: To a 500 mL reactor was added sulfolane (180 mL) and water (23 mL), the mixture was degassed with $N_2$. (R)-3-((benzyloxy)carbonyl)-2-oxoimidazolidine-4-carboxylic acid (20 g, 1.0 equiv.), 5-iodo-2-(trifluoromethyl)pyridine (22.72 g, 1.15 equiv.), dimethylglycine (3.12 g, 0.4 equiv.) and potassium carbonate (41.84 g, 4.0 equiv.) were sequentially added at 20~25° C. The reaction mixture was heated to 30-38° C. and CuI (2.16 g, 0.2 equiv.) was charged in four portions with each interval of 2 hours. The resulting mixture was then stirred at 38° C. under nitrogen for 12 hours. Water (160 mL) and toluene (200 mL) were added. The resulting mixture was stirred at 50° C. for 30 minutes and formed two layers. The top layer was then separated and discarded. Potassium carbonate (31 g, 3.0 equiv.) was then added. The mixture was degassed with nitrogen, heated to 90° C. and stirred at 90° C. under nitrogen for 12 hours. After cooling to 60° C., EDTA-4Na (20 g) was charged. The resulting mixture was stirred at 60° C. for 30 minutes to form two layers. The bottom layer (salt) was separated and discarded. The upper layer was then charged with MIBK (200 mL) and 10% brine (100 g) at 25° C. the mixture was stirred and separated to remove the top layer. MIBK (200 mL) was then charged at 25° C. the mixture was stirred and separated to remove the top layer. The mixture was then charged with EDTA-4Na (10 g) and stirred at 25° C. for 30 minutes. MeTHF (200 mL) was charged, followed by dropwise addition of 31% HCl until pH was adjusted to 3.5. the mixture was then charged with $NaHSO_3$ (8g) and stirred at 25° C. for 5 minutes before the bottom layer was separated and removed. The organic layer was washed twice with 10% brine (200 g) and then distilled under reduced pressure (JTh 45° C., endpoint: residue=100 g). toluene (100 mL) was charged dropwise. The resulting organic layer was then distilled under reduced pressure (JTh 45° C., endpoint: residue=120 g). toluene (100 mL) was charged dropwise. The resulting organic layer was then distilled under reduced pressure (JT<45° C., endpoint: residue=140 g). the mixture after distillation was cooled to 20° C. and stirred for 30 minutes. Toluene (100 mL) was charged at 20° C. dropwise for 1 hour. After the completion of addition, the mixture was stirred at 20° C. for another 1 hour. Filtered, the wet cake was sequentially washed with toluene (40 mL) and water (2×40 mL), then dried under reduced pressure at 50° C. to give (R)-2-oxo-1-(6-(trifluoromethyl)pyridin-3-yl)imidazolidine-4-carboxylic acid. $^1H$ NMR (400 MHz, DMSO-$d_6$): δ 13.23 (s, 1H), 8.91 (d, 1H), 8.25 (dd, 1H), 7.97 (s, 1H), 7.82 (d, 1H), 4.39 (d, 1H), 4.23 (t, 1H), 4.02 (dd, 1H). HRMS: calculated for $C_{10}H_9F_3N_3O_3$ $[M+H]^+$ 276.0591, found 276.0584. Chiral HPLC conditions: Chiralpak IG-3 (150 mm×4.6 mm, 3 μm); Water/ACN, 40° C.; flow rate=0.8 mL/min; 254 nm UV detector; $t_R$ (major)=8.42 min and $t_R$ (minor)=6.58 min.

Step 3: To a 100 mL reactor was added (R)-2-oxo-1-(6-(trifluoromethyl)pyridin-3-yl)imidazolidine-4-carboxylic acid (10.0 g, 1.0 equiv.), 4-iodoisoquinoline (Int-13) (12.05 g, 1.3 equiv.), dimethylglycine (0.75 g, 0.2 equiv.), D-glucose monohydrate (0.33 g, 0.05 equiv.) and sulfolane (100 mL) under $N_2$ atmosphere, the resulting mixture was stirred at 35° C. for half an hour. $Cs_2CO_3$ (47.4 g, 4.0 equiv.) was then added to the reaction mixture followed by CuI (0.7 g, 0.1 equiv.), the mixture was heated to 90° C. and stirred at this temperature for 18 hours. After that, the mixture was cooled down to 40° C. Water (100 mL) and toluene (100 mL) were added, phases separated. To the aqueous phase was added N-acetyl-L-cysteine (5.9 g), stirred at 20~25° C.

to get a clear solution. 36% HCl solution was added to adjust the pH to 5.0, then 5 mg B6 seed was added. The mixture was stirred at 20° C. for an hour to get a brown suspension. Keep adjusting the pH to 4.0 and stirring for another hour. 100 ml water was then added and keep stirring for another hour. Filter, the wet cake was sequentially washed with water (100 mL) twice, then dried under reduced pressure at 70° C. to give (R)-3-(isoquinolin-4-yl)-2-oxo-1-(6-(trifluoromethyl)pyridin-3-yl)imidazolidine-4-carboxylic acid. $^1H$ NMR (400 MHz, DMSO-$d_6$): δ 13.47 (s, 1H), 9.34 (s, 1H), 9.03 (d, J=2.6 Hz, 2H), 8.67 (s, 1H), 8.34 (dd, J=8.8, 2.6 Hz, 1H), 8.23 (d, J=8.2 Hz, 2H), 8.10 (d, J=8.4 Hz, 2H), 7.92 (d, J=8.8 Hz, 2H), 7.84 (t, J=7.6 Hz, 2H), 7.75 (t, J=7.6 Hz, 2H), 5.19 (dd, J=9.9, 5.2 Hz, 1H), 4.62 (t, J=9.9 Hz, 1H), 4.30 (dd, J=9.9, 5.2 Hz, 2H). HRMS: calculated for $C_{19}H_{14}F_3N_4O_3[M+1]^+$ 403.1018, found: 403.1003. Chiral HPLC conditions: Chiralpak IG-3 (150 mm×4.6 mm, 3 μm); Water/ACN, 40° C.; flow rate=0.5 mL/min; 230 nm UV detector; $t_R$ (major)=5.81 min and $t_R$ (minor)=6.25 min.

Step 4: To a 400 mL reactor was added CDI (20.6 g, 1.7 equiv.) and acetonitrile (240 mL), the resulting suspension was cooled to −10° C. Then (R)-3-(isoquinolin-4-yl)-2-oxo-1-(6-(trifluoromethyl)pyridin-3-yl)imidazolidine-4-carboxylic acid (30 g, 1.0 equiv.) was added at −10° C. in three portions with 40 min interval. The mixture was stirred at this temperature for 18 hours. Then, the reaction mixture was added into another 1000 mLRedlay rector containing 25-28 wt % aqueous ammonia solution (97.6 g, 20 equiv.), acetonitrile (60 mL) and water (60 mL), while maintaining the internal temperature at −5° C. The mixture was stirred at the same temperature for 1 hour, then warmed up to 40° C. Water (480 mL) was added dropwise at this temperature and stirred for 2 hours. Slowly cooled to −5° C. over 1 hour and aged for another 2 hours. The suspension was filtered and the wet cake was washed with cold water (90×2 mL), then dried under reduced pressure at 55° C. for 20 hours to give (R)-3-(isoquinolin-4-yl)-2-oxo-1-(6-(trifluoromethyl)pyridin-3-yl)imidazolidine-4-carboxamide. $^1H$ NMR (400 MHz, DMSO-$d_6$): δ 9.35 (s, 1H), 9.04 (d, 1H), 8.59 (s, 1H), 8.36 (dd, 1H), 8.24 (d, 1H), 8.13 (d, 1H), 7.93 (d, 1H), 7.86 (ddd, 1H), 7.77 (dd, 2H), 7.35 (s, 1d), 4.95 (dd, 1H), 4.54 (t, 1H), 4.13 (dd, 1H). HRMS: calculated for $C_{19}H_{14}F_3N_5O_2[M+H]^+$ 402.1172, found 402.1159. Chiral HPLC conditions: Chiralpak IG-3 (150 mm×4.6 mm, 3 μm); Water/ACN, 40° C.; flow rate=1.0 mL/min; 260 nm UV detector; $t_R$ (major)=7.53 min and $t_R$ (minor)=6.73 min.

Step 5: To a 100 ml reactor was added (R)-3-(isoquinolin-4-yl)-2-oxo-1-(6-(trifluoromethyl)pyridin-3-yl)imidazolidine-4-carboxamide (5 g, 1.0 equiv.) and THE (50 mL) at 15° C. To the suspension was added trifluoroacetic anhydride (TFAA) (4.2 g, 1.6 equiv.) over 15-20 min (exothermic). After addition, the suspension was stirred at 15° C. for additional 2 hrs to give almost clear solution. A solution of $NaHCO_3$ (3.66 g, 3.5 equiv.) in water (50 mL) was added to the reaction mixture over 10 min (gas evolved and exothermic) to give almost a clear solution (pH=8-9). Stirred for 30 min at 15° C. and added seed (2-3 mg). Stirred for 2 hrs at 15° C. to give suspension. Added additional water (50 mL) over 30 min (exothermic). Stirred for additional 2 hrs at 15° C. and cooled to 5° C. over 2 hrs. Stirred for further 4 hrs at 5° C., followed by filtration (8 um PTFE). Washed with THF/$H_2O$ (1/2 V/V, 5 mL) and water (10 mL). The wet cake was collected and dried at 55° C. for 20 hrs under reduced pressure to give (R)-3-(isoquinolin-4-yl)-2-oxo-1-(6-(trifluoromethyl)pyridin-3-yl)imidazolidine-4-carbonitrile (11a). $^1H$ NMR (400 MHz, DMSO-$d_6$): δ9.46 (s, 1H), 6 9.02 (d, J=8 Hz, 1H), 6 8.73 (s, 1H), 6 8.29-8.33 (m, 2H), 6 8.17 (d, J=8 Hz, 1H), 6 7.97 (d, J=8 Hz, 1H), 6 7.92 (t, J=8 Hz, 1H), 6 7.82 (t, J=, 1H), 6 5.77 (dd, J=4 Hz, 8 Hz, 1H), 6 4.69 (t, J=8 Hz, 1H), 6 4.61 (dd, J=4 Hz, 8 Hz, 1H). HRMS: calculated for $C_{19}H_{13}F_3N_5O$ $[M+1]^+$ 384.1067, found: 384.1052. Chiral HPLC conditions: Chiralpak IG-3 (150 mm×4.6 mm, 3 μm); Water/ACN, 40° C.; flow rate=1.0 mL/min; 254 nm UV detector; $t_R$(major)=12.56 min and $t_R$ (minor)=11.77 min.

Example 12: Synthesis of 3-(isoquinolin-4-yl)-1-(2-methoxy-4-(trifluoromethyl)phenyl)-2-oxoimidazolidine-4-carbonitrile (12); (R)-3-(isoquinolin-4-yl)-1-(2-methoxy-4-(trifluoromethyl)phenyl)-2-oxoimidazolidine-4-carbonitrile (12a), and (S)-3-(isoquinolin-4-yl)-1-(2-methoxy-4-(trifluoromethyl)phenyl)-2-oxoimidazolidine-4-carbonitrile (12b)

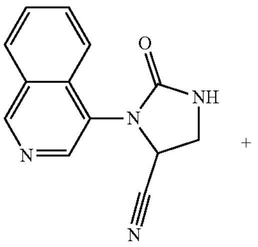

(Int-1)

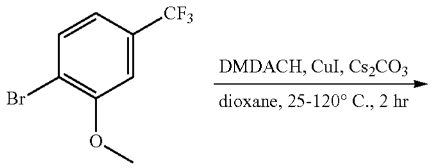

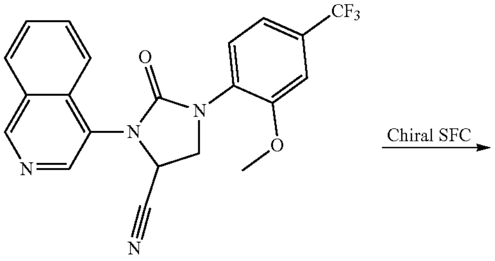

(12)

-continued

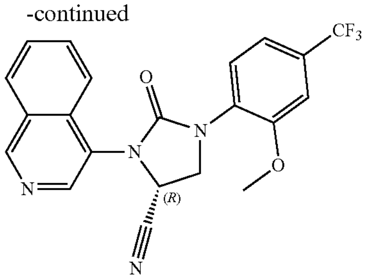

(12a)

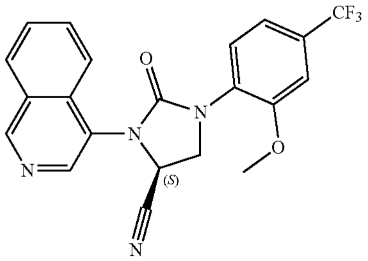

(12b)

3-(isoquinolin-4-yl)-1-(2-methoxy-4-(trifluoromethyl)phenyl)-2-oxoimidazolidine-4-carbonitrile (12) was prepared in a manner similar to Example 4, using 1-bromo-2-methoxy-4-(trifluoromethyl)benzene in place of 4-trifluoromethyl-iodobenzene. The crude product was purified by prep-HPLC (column: Waters Xbridge BEH C18 100×25 mm, 5 μm; liquid phase: water ($NH_4HCO_3$)-ACN B %: 35%-55%, 10 min) to give racemic product. LCMS (Method 1): $t_R$=2.34 min, $[M+1]^+$ 413.1. $^1H$ NMR: (400 MHz, CHLOROFORM-d) δ=9.35 (s, 1H), 8.73 (s, 1H), 8.13 (d, J=8.1 Hz, 1H), 7.99 (br d, J=8.4 Hz, 1H), 7.85 (t, J=7.6 Hz, 1H), 7.77-7.70 (m, 1H), 7.66 (d, J=8.1 Hz, 1H), 7.35 (br d, J=8.1 Hz, 1H), 7.30 (s, 1H), 5.10 (dd, J=4.4, 8.8 Hz, 1H), 4.52 (t, J=9.3 Hz, 1H), 4.38 (dd, J=4.5, 9.6 Hz, 1H), 4.05 (s, 3H).

Racemic 3-(isoquinolin-4-yl)-1-(2-methoxy-4-(trifluoromethyl)phenyl)-2-oxoimidazolidine-4-carbonitrile (12) was purified by preparative SFC (column: DAICEL CHIRALPAK IC (250 mm×30 mm, 10 μm); liquid phase: 0.1% $NH_3H_2O$ IPA B %: 55%-55%, 10 min) to give two peaks.

Peak 1: (R)-3-(isoquinolin-4-yl)-1-(2-methoxy-4-(trifluoromethyl)phenyl)-2-oxoimidazolidine-4-carbonitrile (12a). LCMS (Method 1): $t_R$=2.33 min, $[M+1]^+$ 413.1. SFC (Method 1): $t_R$=1.49 min, 100%. $^1H$ NMR: (400 MHz, CHLOROFORM-d) δ=9.34 (s, 1H), 8.71 (s, 1H), 8.12 (d, J=8.2 Hz, 1H), 7.97 (d, J=8.3 Hz, 1H), 7.84 (t, J=7.6 Hz, 1H), 7.75-7.69 (m, 1H), 7.65 (d, J=8.2 Hz, 1H), 7.33 (d, J=8.2 Hz, 1H), 7.25 (s, 1H), 5.08 (dd, J=4.5, 8.9 Hz, 1H), 4.51 (t, J=9.3 Hz, 1H), 4.37 (dd, J=4.5, 9.7 Hz, 1H), 4.04 (s, 3H)

Peak 2: (S)-3-(isoquinolin-4-yl)-1-(2-methoxy-4-(trifluoromethyl)phenyl)-2-oxoimidazolidine-4-carbonitrile (12b). LCMS (Method 1): $t_R$=2.37 min. $[M+1]^+$ 413.0. SFC (Method 1): $t_R$=1.78 min, 99.9%. $^1H$ NMR: (400 MHz, CHLOROFORM-d) δ=9.34 (s, 1H), 8.71 (s, 1H), 8.11 (d, J=8.1 Hz, 1H), 7.97 (d, J=8.3 Hz, 1H), 7.84 (dt, J=1.0, 7.7 Hz, 1H), 7.75-7.69 (m, 1H), 7.64 (d, J=8.2 Hz, 1H), 7.33 (d, J=8.2 Hz, 1H), 7.25 (s, 1H), 5.08 (dd, J=4.5, 8.9 Hz, 1H), 4.50 (t, J=9.3 Hz, 1H), 4.37 (dd, J=4.5, 9.7 Hz, 1H), 4.03 (s, 3H)

Example 13: Synthesis of 3-(isoquinolin-4-yl)-2-oxo-1-(6-(trifluoromethyl)pyridazin-4-yl)imidazolidine-4-carbonitrile (13); (R)-3-(isoquinolin-4-yl)-2-oxo-1-(6-(trifluoromethyl)pyridazin-4-yl)imidazolidine-4-carbonitrile (13a) and (S)-3-(isoquinolin-4-yl)-2-oxo-1-(6-(trifluoromethyl)pyridazin-4-yl)imidazolidine-4-carbonitrile (13b)

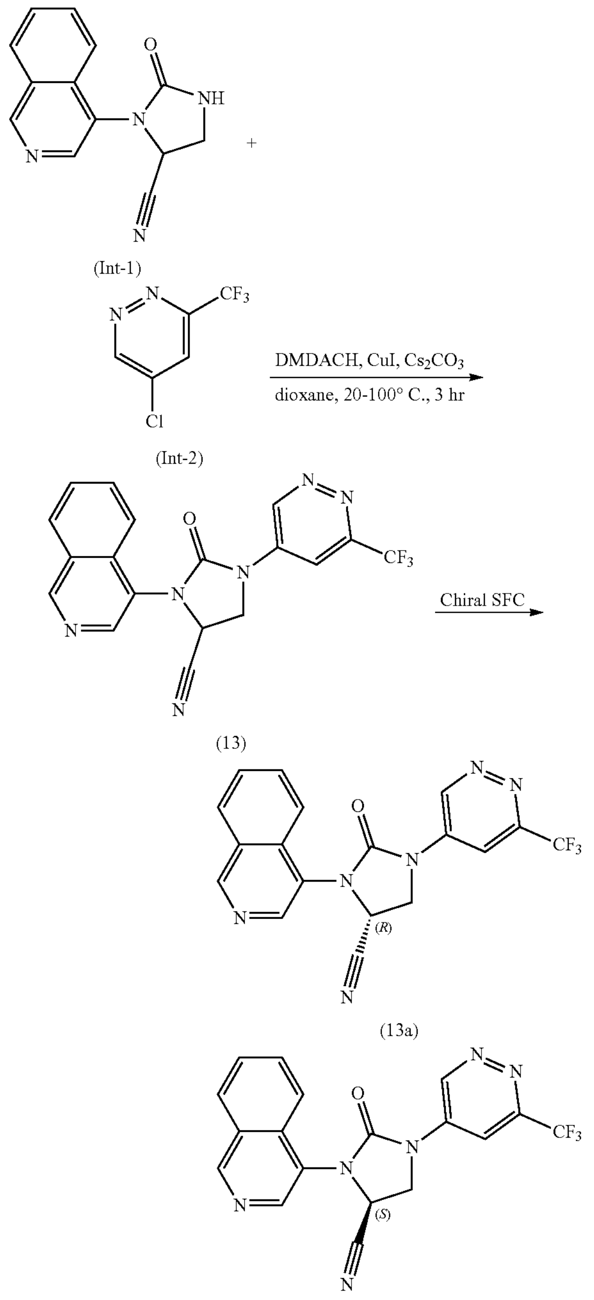

(Int-1)

(Int-2)

(13)

(13a)

(13b)

3-(isoquinolin-4-yl)-2-oxo-1-(6-(trifluoromethyl)pyridazin-4-yl)imidazolidine-4-carbonitrile (13) was prepared in a manner similar to Example 4, using 5-chloro-3-(trifluoromethyl)pyridazine (Int-2) in place of 4-trifluoromethyl-iodobenzene. The crude product was purified by prep-HPLC (column: Phenomenex Luna C18 75 mm×30 mm, 3 μm; liquid phase: [A-$H_2O$ (0.1% FA); B-ACN]B %: 10%-40%, 8 min) to give racemic product. The racemic product was purified by preparative SFC (Column: Phenomenex-Cellulose-2 (250 mm×30 mm, 10 μm)); Mobile phase: A for $H_2O$ (10 mm $NH_4HCO_3$) and B for ACN; Gradient: B %=50% isocratic elution mode; Flow rate: 80 g/min; Wavelength: 220 nm; Column temperature: 35° C.; System back pressure: 120 bar) to give two peaks.

Peak 1: (R)-3-(isoquinolin-4-yl)-2-oxo-1-(6-(trifluoromethyl)pyridazin-4-yl)imidazolidine-4-carbonitrile (13a). LCMS (Method 17): $t_R$=2.50 min, $[M+1]^+$ 385.1. SFC (Method 5): $t_R$=0.90 min, 100%. $^1$H NMR: (400 MHz, CHLOROFORM-d) δ=9.66 (d, J=2.6 Hz, 1H), 9.41 (s, 1H), 8.73 (s, 1H), 8.32-8.10 (m, 2H), 7.98-7.82 (m, 2H), 7.82-7.75 (m, 1H), 5.37-5.17 (m, 1H), 4.72-4.62 (m, 1H), 4.60-4.51 (m, 1H).

Peak 2: (S)-3-(isoquinolin-4-yl)-2-oxo-1-(6-(trifluoromethyl)pyridazin-4-yl)imidazolidine-4-carbonitrile (13b). LCMS (Method 17): $t_R$=2.50 min, $[M+1]^+$ 413.0. SFC (Method 5): $t_R$=1.34 min, 99.7%. $^1$H NMR: (400 MHz, CHLOROFORM-d) δ=9.66 (d, J=2.5 Hz, 1H), 9.42 (s, 1H), 8.73 (s, 1H), 8.29-8.12 (m, 2H), 7.93-7.82 (m, 2H), 7.82-7.75 (m, 1H), 5.28 (br dd, J=4.1, 9.2 Hz, 1H), 4.72-4.62 (m, 1H), 4.56 (dd, J=4.4, 9.9 Hz, 1H).

Example 14: Synthesis of 3-(isoquinolin-4-yl)-1-(5-methoxy-2-(trifluoromethyl)pyridin-4-yl)-2-oxoimidazolidine-4-carbonitrile (14); (R)-3-(isoquinolin-4-yl)-1-(5-methoxy-2-(trifluoromethyl)pyridin-4-yl)-2-oxoimidazolidine-4-carbonitrile (14a), and (S)-3-(isoquinolin-4-yl)-1-(5-methoxy-2-(trifluoromethyl)pyridin-4-yl)-2-oxoimidazolidine-4-carbonitrile (14b)

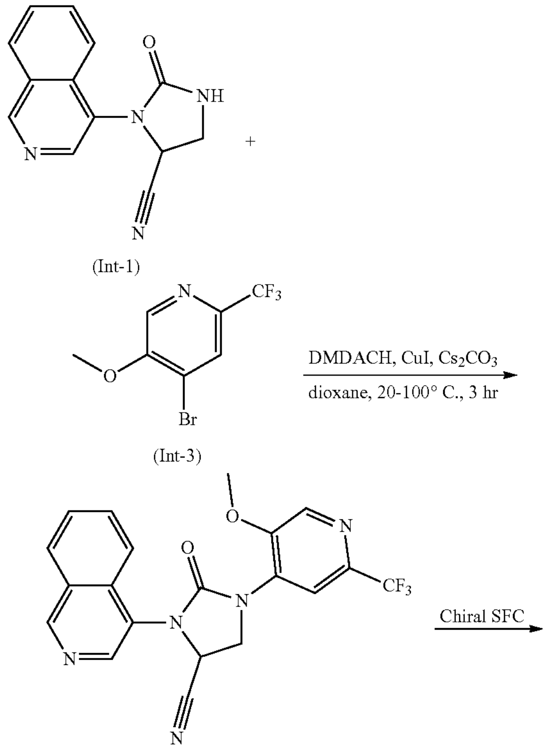

(Int-1)

(Int-3)

(14)

-continued

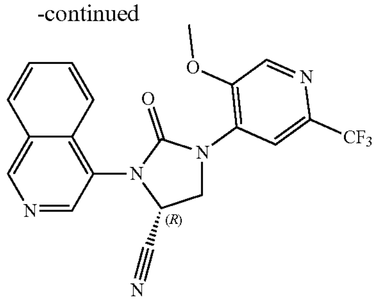

(14a)

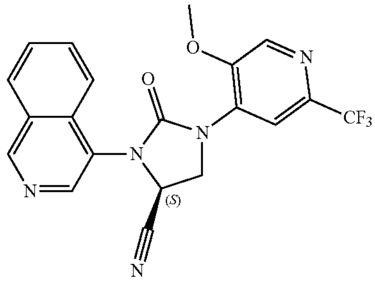

(14b)

3-(isoquinolin-4-yl)-1-(5-methoxy-2-(trifluoromethyl)pyridin-4-yl)-2-oxoimidazolidine-4-carbonitrile (14) was prepared in a manner similar to Example 4, using 4-bromo-5-methoxy-2-(trifluoromethyl)pyridine (Int-3) in place of 4-trifluoromethyl-iodobenzene. The crude product was purified by column (petroleum ether/EtOAc=1/2 to 1/3) to give racemic product. The racemic product was purified by chiral SFC (DAICEL CHIRALCEL OJ (250 mm*50 mm, 10 μm); liquid phase: [0.1% $NH_3H_2O$ EtOH]B %: 35%-35%, 20 min]) to give two peaks.

Peak 1: (R)-3-(isoquinolin-4-yl)-1-(5-methoxy-2-(trifluoromethyl)pyridin-4-yl)-2-oxoimidazolidine-4-carbonitrile (14a). LCMS (Method 17): $t_R$=2.17 min, $[M+1]^+$ 414.2. SFC (Method 2): $t_R$=1.16 min, 96.2%. $^1$H NMR: (400 MHz, CHLOROFORM-d) δ=9.37 (s, 1H), 8.73 (s, 1H), 8.48 (s, 1H), 8.15 (d, J=8.2 Hz, 1H), 8.09 (s, 1H), 7.97-7.84 (m, 2H), 7.78-7.72 (m, 1H), 5.12 (dd, J=4.7, 8.6 Hz, 1H), 4.71-4.55 (m, 2H), 4.15 (s, 3H)

Peak 2: (S)-3-(isoquinolin-4-yl)-1-(5-methoxy-2-(trifluoromethyl)pyridin-4-yl)-2-oxoimidazolidine-4-carbonitrile (14b). LCMS (Method 17): $t_R$=2.16 min, $[M+1]^+$ 414.2. SFC (Method 2): $t_R$=1.26 min, 99.7%. $^1$H NMR: (400 MHz, CHLOROFORM-d) δ=9.38 (s, 1H), 8.75 (s, 1H), 8.48 (s, 1H), 8.16 (d, J=8.2 Hz, 1H), 8.09 (s, 1H), 7.97-7.86 (m, 2H), 7.80-7.74 (m, 1H), 5.15 (dd, J=4.7, 8.6 Hz, 1H), 4.70-4.57 (m, 2H), 4.15 (s, 3H)

Example 15: Synthesis of 1-(5-cyano-2-methoxyphenyl)-3-(isoquinolin-4-yl)-2-oxoimidazolidine-4-carbonitrile (15), (R)-1-(5-cyano-2-methoxyphenyl)-3-(isoquinolin-4-yl)-2-oxoimidazolidine-4-carbonitrile (15a), (S)-1-(5-cyano-2-methoxyphenyl)-3-(isoquinolin-4-yl)-2-oxoimidazolidine-4-carbonitrile (15b)

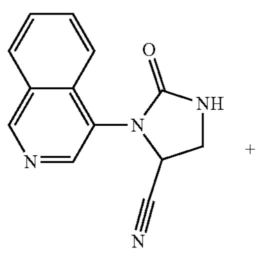

(Int-1)

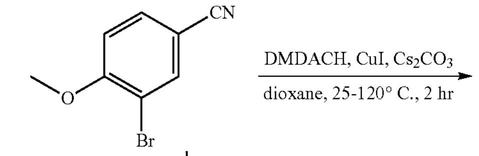

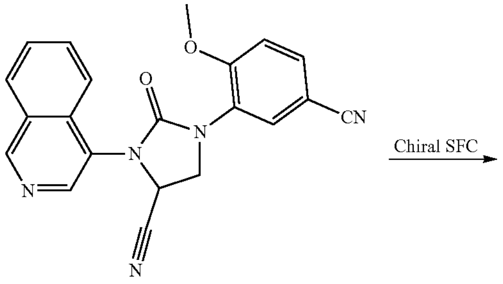

(15)

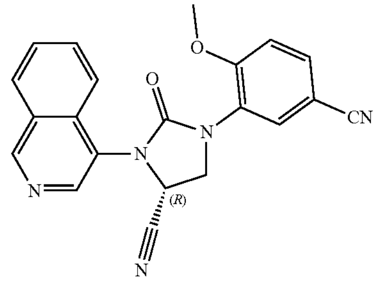

(15a)

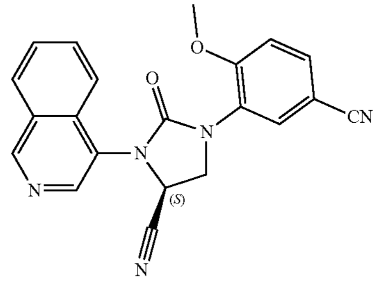

(15b)

1-(5-cyano-2-methoxyphenyl)-3-(isoquinolin-4-yl)-2-oxoimidazolidine-4-carbonitrile (15) was prepared in a manner similar to Example 4, using 3-bromo-4-methoxybenzonitrile (1.5 eq) in place of 4-trifluoromethyl-iodobenzene. The crude product was purified by MPLC (ethyl acetate/petroleum ether=7/3 to 0/1, 50 mL/min) to give racemic product, which was further purified by prep-HPLC (column: Waters Xbridge BEH C18 100 mm×30 mm, 10 μm; liquid phase: [A-10 mM $NH_4HCO_3$ in $H_2O$; B-ACN]B %: 30%-50%, 8 min]). LCMS (Method 2): $t_R$=2.58 min, $[M+1]^+$ 370.1. $^1$H NMR: (400 MHz, DMSO-$d_6$) δ=9.41 (s, 1H), 8.67 (s, 1H), 8.28 (d, J=8.1 Hz, 1H), 8.09 (d, J=8.4 Hz, 1H), 7.99 (d, J=2.0 Hz, 1H), 7.94 (ddd, J=1.2, 7.0, 8.3 Hz, 1H), 7.86 (dd, J=2.2, 8.7 Hz, 1H), 7.83-7.79 (m, 1H), 7.37 (d, J=8.6 Hz, 1H), 5.68 (dd, J=4.3, 9.1 Hz, 1H), 4.45 (t, J=9.3 Hz, 1H), 4.23 (dd, J=4.4, 9.5 Hz, 1H), 4.01 (s, 3H).

The racemic product was purified by chiral SFC (column: DAICEL CHIRALPAK AD (250 mm*30 mm, 10 μm); liquid phase: [A for $CO_2$ and B for EtOH (0.1% $NH_3H_2O$)]B %: 50%-50%, 6 min]) to give two peaks.

Peak 1: (S)-1-(5-cyano-2-methoxyphenyl)-3-(isoquinolin-4-yl)-2-oxoimidazolidine-4-carbonitrile (15b). LCMS (Method 2): $t_R$=2.58 min, $[M+1]^+$ 370.1. SFC (Method 1): $t_R$=1.63 min, 100%. $^1$H NMR: (400 MHz, DMSO-$d_6$) δ=9.41 (s, 1H), 8.67 (s, 1H), 8.28 (d, J=8.1 Hz, 1H), 8.09 (dd, J=0.7, 8.4 Hz, 1H), 7.99 (d, J=2.1 Hz, 1H), 7.94 (ddd, J=1.2, 7.0, 8.3 Hz, 1H), 7.86 (dd, J=2.2, 8.7 Hz, 1H), 7.81 (dt, J=0.9, 7.5 Hz, 1H), 7.37 (d, J=8.8 Hz, 1H), 5.68 (dd, J=4.4, 9.1 Hz, 1H), 4.45 (t, J=9.3 Hz, 1H), 4.23 (dd, J=4.4, 9.6 Hz, 1H), 4.01 (s, 3H)

Peak 2: (R)-1-(5-cyano-2-methoxyphenyl)-3-(isoquinolin-4-yl)-2-oxoimidazolidine-4-carbonitrile (15a). LCMS (Method 2): $t_R$=2.58 min, $[M+1]^+$ 370.1. SFC (Method 1): $t_R$=1.99 min, 98.8%. $^1$H NMR: (400 MHz, DMSO-$d_6$) δ=9.41 (s, 1H), 8.67 (s, 1H), 8.28 (d, J=8.0 Hz, 1H), 8.06 (d, J=8.0 Hz, 1H), 7.99 (d, J=2.1 Hz, 1H), 7.94 (ddd, J=1.2, 7.0, 8.3 Hz, 1H), 7.86 (dd, J=2.1, 8.7 Hz, 1H), 7.81 (dt, J=0.9, 7.5 Hz, 1H), 7.37 (d, J=8.8 Hz, 1H), 5.68 (dd, J=4.4, 9.0 Hz, 1H), 4.45 (t, J=9.3 Hz, 1H), 4.23 (dd, J=4.4, 9.5 Hz, 1H), 4.01 (s, 3H)

Example 16: Synthesis of 1-(5-chloropyrimidin-2-yl)-3-(isoquinolin-4-yl)-2-oxoimidazolidine-4-carbonitrile (16), (R)-1-(5-chloropyrimidin-2-yl)-3-(isoquinolin-4-yl)-2-oxoimidazolidine-4-carbonitrile (16a), and (S)-1-(5-chloropyrimidin-2-yl)-3-(isoquinolin-4-yl)-2-oxoimidazolidine-4-carbonitrile (16b)

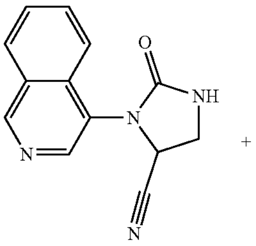

(Int-1)

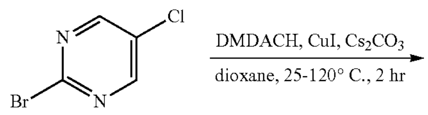

-continued

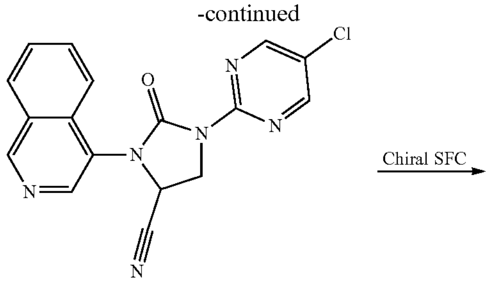

(16)

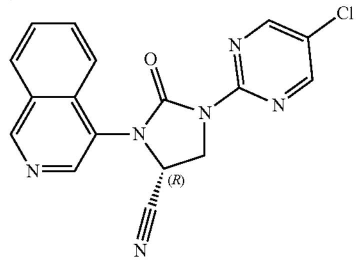

(16a)

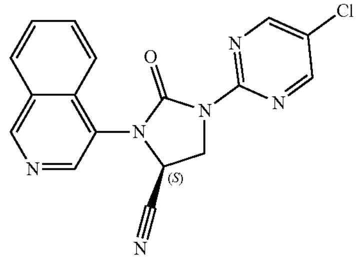

(16b)

1-(5-chloropyrimidin-2-yl)-3-(isoquinolin-4-yl)-2-oxoimidazolidine-4-carbonitrile (16) was prepared in a manner similar to Example 4, using 2-bromo-5-chloropyrimidine (1.2 eq) in place of 4-trifluoromethyl-iodobenzene. The crude product was purified by MPLC (petroleum ether/EtOAc=100%-0%) to give racemic product, which was further purified by prep-HPLC (column: Welch Xtimate C18 250 mm×70 mm, 10 μm; mobile phase: [water ($NH_4HCO_3$)-ACN]; B %: 20%-50%, 5 min). The racemic product was purified by chiral SFC (Column: DAICEL CHIRALPAK IG (250 mm×50 mm, 10 μm); Mobile phase: A for $CO_2$ and B for EtOH (0.1% $NH_3H_2O$); Gradient: B %=60% isocratic elution mode; Flow rate: 70 g/min; Wavelength: 220 nm; Column temperature: 35° C.; System back pressure: 120 bar.) to give two peaks.

Peak 1: (R)-1-(5-chloropyrimidin-2-yl)-3-(isoquinolin-4-yl)-2-oxoimidazolidine-4-carbonitrile (16a). LCMS (Method 31): $t_R$=2.19 min, $[M+1]^+$ 351.2. SFC (Method 6): $t_R$=2.76 min, 100%. $^1$H NMR: (400 MHz, CHLOROFORM-d) δ=9.35 (s, 1H), 8.70 (s, 1H), 8.65 (s, 2H), 8.12 (d, J=8.1 Hz, 1H), 7.91 (br d, J=8.2 Hz, 1H), 7.81 (t, J=7.3 Hz, 1H), 7.76-7.63 (m, 1H), 5.07 (dd, J=4.1, 8.9 Hz, 1H), 4.73-4.58 (m, 2H)

Peak 2: (S)-1-(5-chloropyrimidin-2-yl)-3-(isoquinolin-4-yl)-2-oxoimidazolidine-4-carbonitrile (16b). LCMS (Method 31): $t_R$=2.18 min, $[M+1]^+$ 351.2. SFC (Method 6): $t_R$=3.31 min, 100%. $^1$H NMR: (400 MHz, CHLOROFORM-d) δ=9.35 (s, 1H), 8.71 (br s, 1H), 8.66 (s, 2H), 8.13 (d, J=8.1 Hz, 1H), 7.92 (br d, J=8.0 Hz, 1H), 7.82 (t, J=7.4 Hz, 1H), 7.76-7.68 (m, 1H), 5.08 (br dd, J=3.5, 8.6 Hz, 1H), 4.75-4.56 (m, 2H)

Example 17: Synthesis of 3-(isoquinolin-4-yl)-1-(2-methoxy-5-(trifluoromethyl)phenyl)-2-oxoimidazolidine-4-carbonitrile (17); (R)-3-(isoquinolin-4-yl)-1-(2-methoxy-5-(trifluoromethyl)phenyl)-2-oxoimidazolidine-4-carbonitrile (17a), and (S)-3-(isoquinolin-4-yl)-1-(2-methoxy-5-(trifluoromethyl)phenyl)-2-oxoimidazolidine-4-carbonitrile (17b)

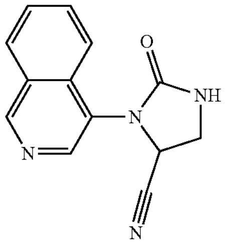

(Int-1)

+

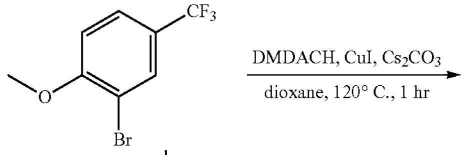

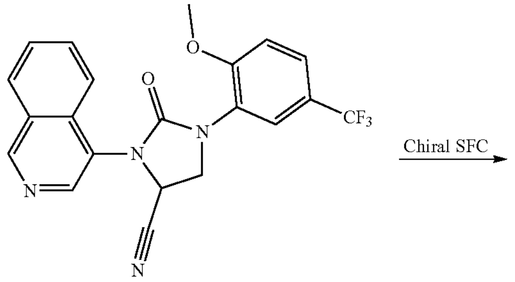

(17)

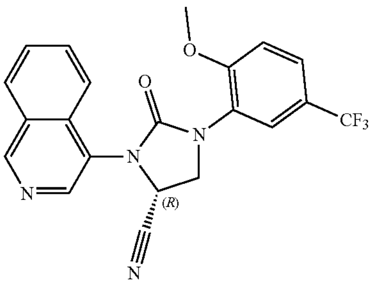

(17a)

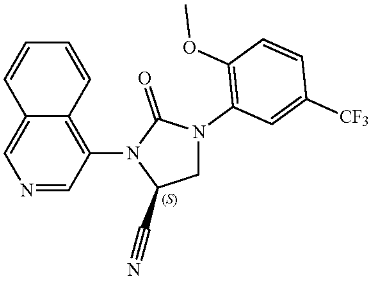

(17b)

3-(isoquinolin-4-yl)-1-(2-methoxy-5-(trifluoromethyl)phenyl)-2-oxoimidazolidine-4-carbonitrile (17) was prepared in a manner similar to Example 4, using 2-bromo-1-methoxy-4-trifluoromethyl)benzene in place of 4-trifluoromethyl-iodobenzene. The crude product was purified by MPLC (petroleum ether/EtOAc=100%-0%) to give racemic product, which was further purified by prep-HPLC (column: Phenomenex Luna C18 75 mm×30 mm, 3 μm; liquid phase: [A-FA/$H_2O$=0.1% v/v; B-ACN]B %: 35%-65%, 8 min]). The racemic product was purified by chiral SFC (column: REGIS(S, S) WHELK-01 (250 mm×25 mm, 10 μm; mobile phase: 0.1% $NH_3H_2O$ IPA; B % 45%-45%, 15 min]) to give two peaks.

Peak 1: (S)-3-(isoquinolin-4-yl)-1-(2-methoxy-5-(trifluoromethyl)phenyl)-2-oxoimidazolidine-4-carbonitrile (17b). LCMS (Method 1): $t_R$=2.34 min, $[M+1]^+$ 412.1. SFC (Method 7): $t_R$=1.57 min, 99.9%. $^1H$ NMR: (400 MHz, METHANOL-$d_4$) δ=9.35 (s, 1H), 8.65 (s, 1H), 8.27 (d, J=8.4 Hz, 1H), 8.14 (d, J=7.9 Hz, 1H), 7.97 (t, J=7.7 Hz, 1H), 7.85-7.78 (m, 2H), 7.71 (dd, J=1.7, 8.8 Hz, 1H), 7.35 (d, J=8.8 Hz, 1H), 5.52 (dd, J=4.3, 9.1 Hz, 1H), 4.51 (t, J=9.4 Hz, 1H), 4.32 (dd, J=4.3, 9.6 Hz, 1H), 4.07 (s, 3H).

Peak 2: (R)-3-(isoquinolin-4-yl)-1-(2-methoxy-5-(trifluoromethyl)phenyl)-2-oxoimidazolidine-4-carbonitrile (17b). LCMS (Method 1): $t_R$=2.34 min, $[M+1]^+$ 412.1. SFC (Method 7): $t_R$=1.73 min, 99.6%. $^1H$ NMR: (400 MHz, METHANOL-$d_4$) δ=9.35 (s, 1H), 8.65 (s, 1H), 8.27 (d, J=8.3 Hz, 1H), 8.14 (d, J=8.5 Hz, 1H), 7.97 (dt, J=1.2, 7.7 Hz, 1H), 7.86-7.78 (m, 2H), 7.71 (dd, J=1.9, 8.8 Hz, 1H), 7.35 (d, J=8.8 Hz, 1H), 5.52 (dd, J=4.4, 9.1 Hz, 1H), 4.51 (t, J=9.4 Hz, 1H), 4.32 (dd, J=4.4, 9.6 Hz, 1H), 4.07 (s, 3H).

Example 18: Synthesis of 5-(4-cyano-3-(isoquinolin-4-yl)-2-oxoimidazolidin-1-yl)-2-(trifluoromethyl)isonicotinonitrile (18); (R)-5-(4-cyano-3-(isoquinolin-4-yl)-2-oxoimidazolidin-1-yl)-2-(trifluoromethyl)isonicotinonitrile (18a), and (S)-5-(4-cyano-3-(isoquinolin-4-yl)-2-oxoimidazolidin-1-yl)-2-(trifluoromethyl)isonicotinonitrile (18b)

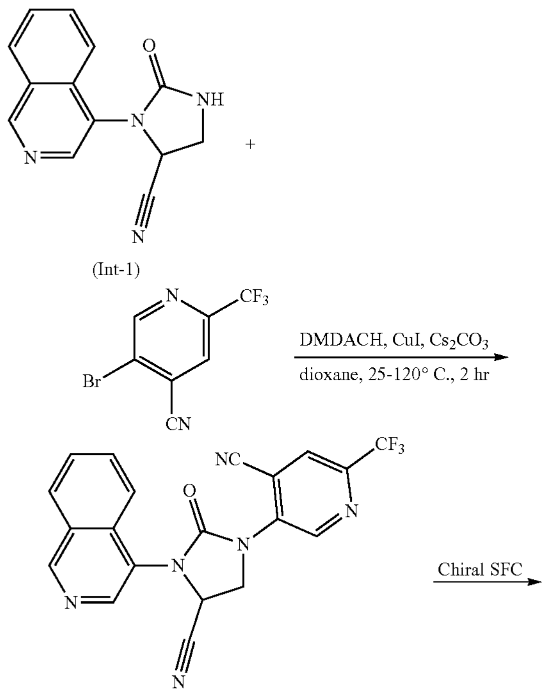

(Int-1)
(18)

-continued

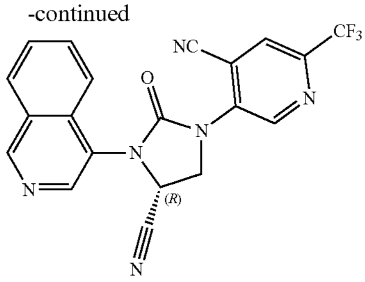
(18a)

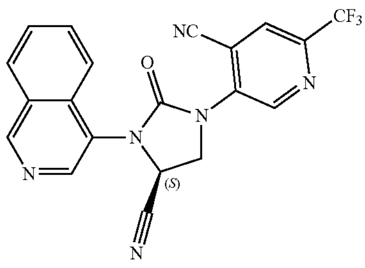
(18b)

5-(4-cyano-3-(isoquinolin-4-yl)-2-oxoimidazolidin-1-yl)-2-(trifluoromethyl)isonicotinonitrile (18) was prepared in a manner similar to Example 4, using 5-bromo-2-(trifluoromethyl)isonicotinonitrile in place of 4-trifluoromethyl-iodobenzene. The crude product was purified by MPLC (petroleum ether/EtOAc=100%-0%) to give racemic product, which was further purified by prep-HPLC (column: Phenomenex Luna C18 75 mm×30 mm, 3 μm; liquid phase: water (HCOOH)-ACN B %: 25%-65%, 8 min]). The racemic product was purified by chiral SFC (column: DAICEL CHIRALPAK AD (250 mm×30 mm, 10 μm); Mobile phase: A for $CO_2$ and B for i-PrOH (0.1% $NH_3H_2O$); Gradient: B %=44, 10 min) to give two peaks.

Peak 1: (R)-5-(4-cyano-3-(isoquinolin-4-yl)-2-oxoimidazolidin-1-yl)-2-(trifluoromethyl)isonicotinonitrile (18a). LCMS (Method 1): $t_R$=2.23 min, $[M+1]^+$ 409.1. SFC (Method 7): $t_R$=1.23 min, 99.6%. $^1H$ NMR: (400 MHz, CHLOROFORM-d) δ=9.39 (s, 1H), 9.18 (s, 1H), 8.74 (s, 1H), 8.15 (d, J=8.1 Hz, 1H), 8.01 (s, 1H), 7.94 (s, 1H), 7.92-7.86 (m, 1H), 7.80-7.73 (m, 1H), 5.21 (dd, J=4.2, 8.7 Hz, 1H), 4.91 (t, J=9.1 Hz, 1H), 4.61 (dd, J=4.1, 9.5 Hz, 1H)

Peak 2: (S)-5-(4-cyano-3-(isoquinolin-4-yl)-2-oxoimidazolidin-1-yl)-2-(trifluoromethyl)isonicotinonitrile (18b). LCMS (Method 1): $t_R$=2.24 min, $[M+1]^+$ 409.0. SFC (Method 7): $t_R$=1.42 min, 99.7%. $^1H$ NMR: (400 MHz, CHLOROFORM-d) δ=9.39 (s, 1H), 9.18 (s, 1H), 8.74 (s, 1H), 8.15 (d, J=8.1 Hz, 1H), 8.01 (s, 1H), 7.94 (s, 1H), 7.92-7.86 (m, 1H), 7.80-7.73 (m, 1H), 5.21 (dd, J=4.2, 8.7 Hz, 1H), 4.91 (t, J=9.1 Hz, 1H), 4.61 (dd, J=4.1, 9.5 Hz, 1H)

Example 19: Synthesis of 1-(4-cyano-2-methoxyphenyl)-3-(isoquinolin-4-yl)-2-oxoimidazolidine-4-carbonitrile (19); (R)-1-(4-cyano-2-methoxyphenyl)-3-(isoquinolin-4-yl)-2-oxoimidazolidine-4-carbonitrile and (S)-1-(4-cyano-2-methoxyphenyl)-3-(isoquinolin-4-yl)-2-oxoimidazolidine-4-carbonitrile

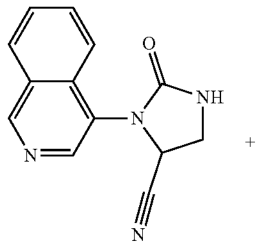

(Int-1)

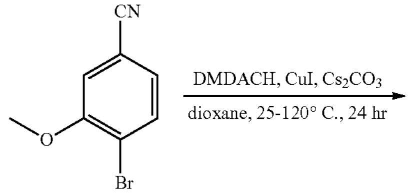

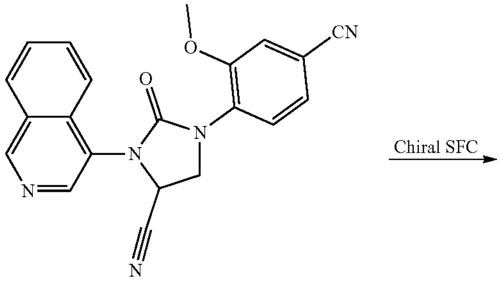

(19)

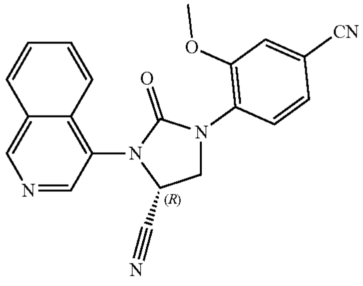

(19a)

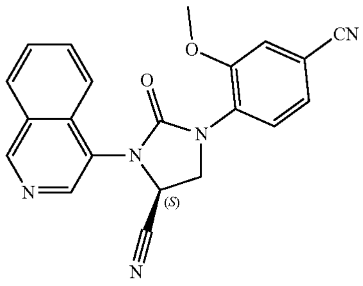

(19b)

1-(4-cyano-2-methoxyphenyl)-3-(isoquinolin-4-yl)-2-oxoimidazolidine-4-carbonitrile (19) was prepared in a manner similar to Example 4, using 4-bromo-3-methoxybenzonitrile in place of 4-trifluoromethyl-iodobenzene. The crude product was purified by MPLC (petroleum ether/EtOAc=100%-0%) to give racemic product, which was further purified by prep-HPLC (column: Phenomenex Luna C18 75 mm×30 mm, 3 μm; liquid phase: water (HCOOH)-ACN B %: 25%-65%, 8 min]). LCMS (Method 1): $t_R$=2.05 min, $[M+1]^+$ 370.0. $^1H$ NMR: (400 MHz, CHLOROFORM-d) δ=9.37 (br s, 1H), 8.75 (br s, 1H), 8.12 (d, J=8.1 Hz, 1H), 7.96-7.92 (m, 1H), 7.84 (dt, J=1.1, 7.7 Hz, 1H), 7.76-7.70 (m, 1H), 7.67 (d, J=8.1 Hz, 1H), 7.37 (dd, J=1.8, 8.1 Hz, 1H), 7.28-7.27 (m, 1H), 5.09 (dd, J=4.4, 8.9 Hz, 1H), 4.57-4.50 (m, 1H), 4.41 (dd, J=4.5, 9.8 Hz, 1H), 4.02 (s, 3H).

The racemic product was purified by chiral SFC (column: DAICEL CHIRALPAK AD (250 mm×30 mm, 10 μm); Mobile phase: A for $CO_2$ and B for i-PrOH (0.1% $NH_3H_2O$); Gradient: B %=44%, 10 min) to give two peaks.

Peak 1: (S)-1-(4-cyano-2-methoxyphenyl)-3-(isoquinolin-4-yl)-2-oxoimidazolidine-4-carbonitrile (19b). LCMS (Method 1): $t_R$=2.05 min, $[M+1]^+$ 370.0. SFC (Method 1): $t_R$=1.53 min, 98.9%. $^1H$ NMR: (400 MHz, CHLOROFORM-d) δ=9.37 (br s, 1H), 8.75 (br s, 1H), 8.15 (br d, J=8.1 Hz, 1H), 7.98 (br d, J=8.4 Hz, 1H), 7.88 (br t, J=7.5 Hz, 1H), 7.81-7.72 (m, 1H), 7.67 (d, J=8.3 Hz, 1H), 7.38 (dd, J=1.6, 8.1 Hz, 1H), 7.28 (s, 1H), 5.14 (br dd, J=4.1, 8.0 Hz, 1H), 4.60-4.49 (m, 1H), 4.42 (br dd, J=4.3, 9.8 Hz, 1H), 4.02 (s, 3H)

Peak 2: (R)-1-(4-cyano-2-methoxyphenyl)-3-(isoquinolin-4-yl)-2-oxoimidazolidine-4-carbonitrile (19a). LCMS (Method 17): $t_R$=2.52 min, $[M+1]^+$ 370.2. SFC (Method 1): $t_R$=1.65 min, 99.5%. $^1H$ NMR: (400 MHz, CHLOROFORM-d) δ=9.35 (s, 1H), 8.71 (s, 1H), 8.13 (d, J=8.1 Hz, 1H), 7.95 (d, J=8.4 Hz, 1H), 7.88-7.81 (m, 1H), 7.76-7.72 (m, 1H), 7.67 (d, J=8.3 Hz, 1H), 7.37 (dd, J=1.8, 8.1 Hz, 1H), 7.28-7.27 (m, 1H), 5.10 (dd, J=4.4, 8.9 Hz, 1H), 4.54 (t, J=9.4 Hz, 1H), 4.41 (dd, J=4.4, 9.8 Hz, 1H), 4.02 (s, 3H)

Example 20: Synthesis of 1-(5-chloro-2-cyanophenyl)-3-(isoquinolin-4-yl)-2-oxoimidazolidine-4-carbonitrile (20), (R)-1-(5-chloro-2-cyanophenyl)-3-(isoquinolin-4-yl)-2-oxoimidazolidine-4-carbonitrile (20a) and (S)-1-(5-chloro-2-cyanophenyl)-3-(isoquinolin-4-yl)-2-oxoimidazolidine-4-carbonitrile(20b)

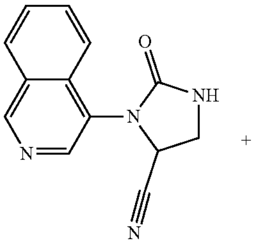

(Int-1)

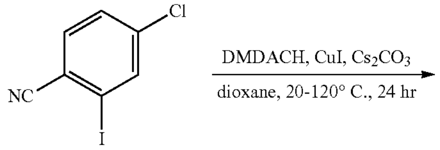

-continued

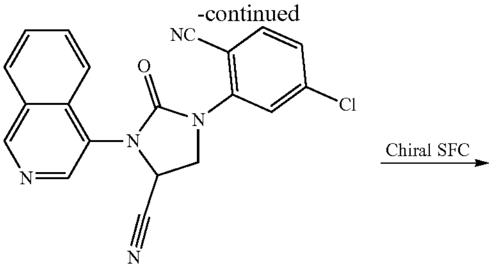

(20)

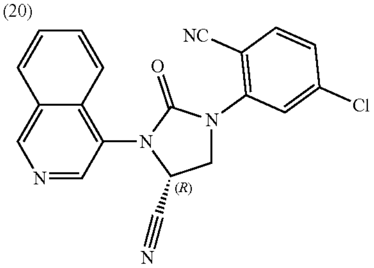

(20a)

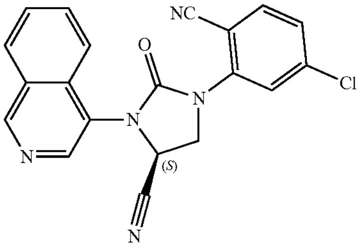

(20b)

1-(5-chloro-2-cyanophenyl)-3-(isoquinolin-4-yl)-2-oxo-imidazolidine-4-carbonitrile (20) was prepared in a manner similar to Example 4, using 4-chloro-2-iodobenzonitrile (1.5 eq) in place of 4-trifluoromethyl-iodobenzene. The crude product was purified by MPLC (petroleum ether/EtOAc=100%-0%) to give racemic product, which was further purified by column chromatography ($SiO_2$, petroleum ether/ethyl acetate=10:1 to 0:1) to give the racemate (20). $^1$H NMR: (400 MHz, CHLOROFORM-d) δ=9.36 (s, 1H), 8.72 (s, 1H), 8.13 (d, J=8.1 Hz, 1H), 7.98 (br d, J=8.4 Hz, 1H), 7.88 (dt, J=1.1, 7.7 Hz, 1H), 7.80-7.65 (m, 3H), 7.43 (dd, J=1.9, 8.4 Hz, 1H), 5.15 (dd, J=4.8, 8.8 Hz, 1H), 4.76 (t, J=9.2 Hz, 1H), 4.45 (dd, J=4.8, 9.5 Hz, 1H)

The racemic product was purified by chiral SFC (column: DAICEL CHIRALPAK IG (250 mm×30 mm, 10 μm); mobile phase: 0.1% $NH_3H_2O$ IPA; B %: 60%-60%, 7 min) to give two peaks.

Peak 1: (R)-1-(5-chloro-2-cyanophenyl)-3-(isoquinolin-4-yl)-2-oxoimidazolidine-4-carbonitrile (20a). LCMS (Method 13): $t_R$=2.18 min, [M+1]$^+$ 374.1. SFC (Method 8): $t_R$=1.76 min, 100%. $^1$H NMR: (400 MHz, CHLOROFORM-d) δ=9.36 (s, 1H), 8.72 (s, 1H), 8.13 (d, J=8.2 Hz, 1H), 7.99 (br d, J=8.3 Hz, 1H), 7.88 (t, J=7.6 Hz, 1H), 7.79-7.66 (m, 3H), 7.46-7.38 (m, 1H), 5.15 (dd, J=4.6, 8.7 Hz, 1H), 4.76 (t, J=9.1 Hz, 1H), 4.45 (dd, J=4.6, 9.4 Hz, 1H).

Peak 2: (S)-1-(5-chloro-2-cyanophenyl)-3-(isoquinolin-4-yl)-2-oxoimidazolidine-4-carbonitrile (20b). LCMS (Method 13): $t_R$=2.18 min, [M+1]$^+$ 374.1. SFC (Method 8): $t_R$=2.17 min, 99.9%. $^1$H NMR: (400 MHz, CHLOROFORM-d) 9.35 (s, 1H), 8.71 (s, 1H), 8.12 (br d, J=8.2 Hz, 1H), 7.98 (br d, J=8.3 Hz, 1H), 7.87 (br t, J=7.6 Hz, 1H), 7.79-7.63 (m, 3H), 7.41 (br d, J=8.3 Hz, 1H), 5.15 (br dd, J=4.3, 8.2 Hz, 1H), 4.74 (br t, J=9.0 Hz, 1H), 4.44 (br dd, J=4.5, 9.2 Hz, 1H).

Example 21: Synthesis of 1-(5-fluoro-2-methylphenyl)-3-(isoquinolin-4-yl)-2-oxoimidazolidine-4-carbonitrile (21), (R)-1-(5-fluoro-2-methylphenyl)-3-(isoquinolin-4-yl)-2-oxoimidazolidine-4-carbonitrile (21a) and (S)-1-(5-fluoro-2-methylphenyl)-3-(isoquinolin-4-yl)-2-oxoimidazolidine-4-carbonitrile (21b)

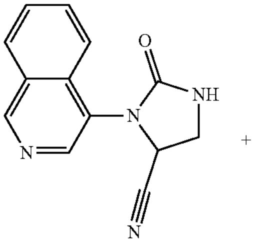

(Int-1)

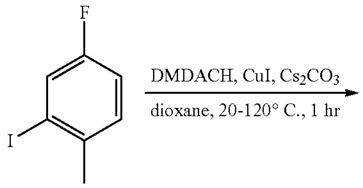

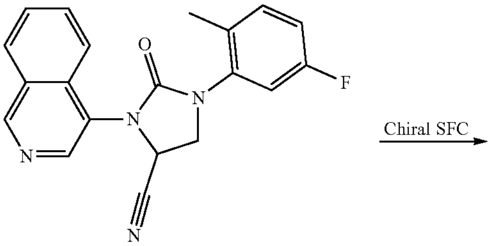

(21)

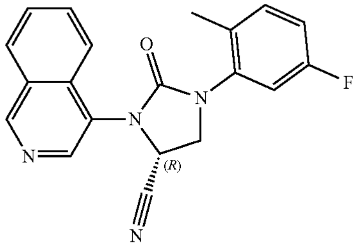

(21a)

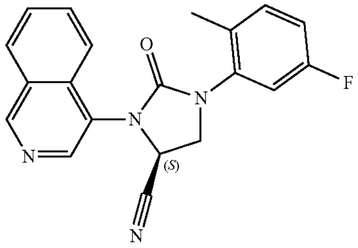

(21b)

1-(5-fluoro-2-methylphenyl)-3-(isoquinolin-4-yl)-2-oxo-imidazolidine-4-carbonitrile (21) was prepared in a manner similar to Example 4, using 4-fluoro-2-iodo-1-methylbenzene in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 15%-55%, 20 min] to give racemic product. The racemic product was purified by chiral SFC (column: Phenomenex Luna C18 200 mm×40 mm, 10 μm; liquid phase: water (FA)-ACN B %: 15%-55%, 8 min); Mobile phase: A for $CO_2$ and B for i-PrOH (0.1% $NH_3H_2O$); Gradient: B %=44%, 10 min) to give two peaks.

Peak 1: (S)-1-(5-fluoro-2-methylphenyl)-3-(isoquinolin-4-yl)-2-oxoimidazolidine-4-carbonitrile (21b). LCMS (Method 3): $t_R$=0.65 min, $[M+1]^+$ 347.3. SFC (Method 15): $t_R$=1.67 min, 100%. $^1$H NMR: (400 MHz, CHLOROFORM-d) δ=9.34 (s, 1H), 8.71 (s, 1H), 8.12 (d, J=8.3 Hz, 1H), 7.95 (d, J=8.5 Hz, 1H), 7.85 (ddd, J=8.3, 7.0, 1.19 Hz, 1H), 7.70-7.75 (ddd, J=8.3, 7.0, 1.2 Hz, 1H), 7.31 (dd, J=8.3, 6.3 Hz, 1H), 7.09 (dd, J=9.1, 2.6 Hz, 1H), 7.03 (td, J=8.3, 2.7 Hz, 1H), 5.08 (dd, J=8.6, 3.8 Hz, 1H), 4.41 (t, J=9.1 Hz, 1H), 4.21 (dd, J=9.6, 3.8 Hz, 1H), 2.43 (s, 3H)

Peak 2: (R)-1-(5-fluoro-2-methylphenyl)-3-(isoquinolin-4-yl)-2-oxoimidazolidine-4-carbonitrile (21a). LCMS (Method 3): $t_R$=0.65 min, $[M+1]^+$ 347.3. SFC (Method 15): $t_R$=1.88 min, 96.9%, $^1$H NMR: (400 MHz, CHLOROFORM-d) δ=9.32 (s, 1H), 8.69 (s, 1H), 8.10 (d, J=8.2 Hz, 1H), 7.93 (d, J=8.0 Hz, 1H), 7.83 (ddd, J=8.3, 7.0, 1.2 Hz, 1H), 7.70-7.75 (ddd, J=8.3, 7.0, 1.2 Hz, 1H), 7.29 (dd, J=8.6, 6.4 Hz, 1H), 7.07 (dd, J=9.1, 2.6 Hz, 1H), 7.01 (td, J=8.3, 2.8 Hz, 1H), 5.06 (dd, J=8.5, 3.9 Hz, 1H), 4.39 (t, J=9.1 Hz, 1H), 4.20 (dd, J=9.6, 3.8 Hz, 1H), 2.41 (s, 3H)

Example 22: Synthesis of 1-(3-(difluoromethyl)phenyl)-3-(isoquinolin-4-yl)-2-oxoimidazolidine-4-carbonitrile (22), (R)-1-(3-(difluoromethyl)phenyl)-3-(isoquinolin-4-yl)-2-oxoimidazolidine-4-carbonitrile (22a) and (S)-1-(3-(difluoromethyl)phenyl)-3-(isoquinolin-4-yl)-2-oxoimidazolidine-4-carbonitrile (22b)

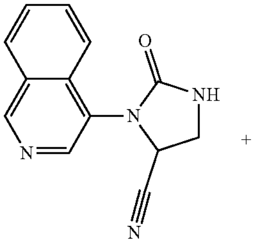

(Int-1)

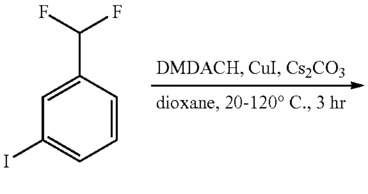

-continued

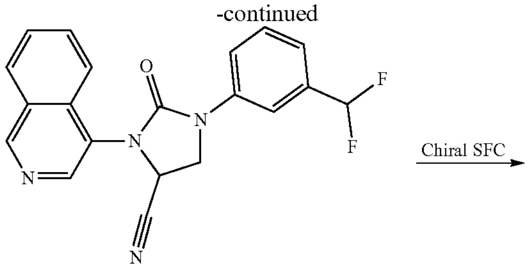

(22)

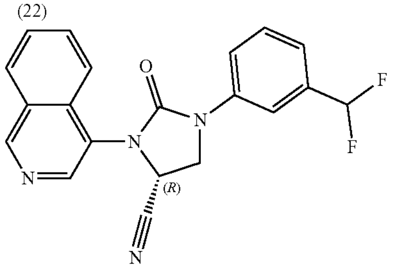

(22a)

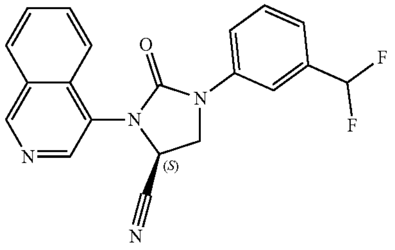

(22b)

1-(3-(difluoromethyl)phenyl)-3-(isoquinolin-4-yl)-2-oxoimidazolidine-4-carbonitrile (22) was prepared in a manner similar to Example 4, using 1-(difluoromethyl)-3-iodobenzene (1.5 eq) in place of 4-trifluoromethyl-iodobenzene. The crude product was purified by flash silica gel chromatography (4 g SepaFlash® Silica Flash Column, eluent of 50-100% ethyl acetate/petroleum ether gradient at 75 mL/min) to give racemic product. The racemic product was purified by chiral SFC (column: DAICEL CHIRALPAK AD (250 mm×30 mm, 10 μm); mobile phase: [0.1% $NH_3H_2O$ in ETOH]; B %: 50%-50%, 12 min); Mobile phase: A for $CO_2$ and B for i-PrOH (0.1% $NH_3H_2O$); Gradient: B %=44%, 10 min) to give two peaks.

Peak 1: (R)-1-(3-(difluoromethyl)phenyl)-3-(isoquinolin-4-yl)-2-oxoimidazolidine-4-carbonitrile (22a). LCMS (Method 31): $t_R$=2.71 min, $[M+1]^+$ 365.1. SFC (Method 15): $t_R$=1.49 min, 99.5%. $^1$H NMR: (400 MHz, CHLOROFORM-d) 9.36 (s, 1H), 8.71 (s, 1H), 8.13 (d, J=8.2 Hz, 1H), 7.92 (br d, J=8.3 Hz, 1H), 7.84 (t, J=7.6 Hz, 1H), 7.79-7.71 (m, 3H), 7.53 (t, J=8.2 Hz, 1H), 7.34 (br d, J=7.9 Hz, 1H), 6.68 (t, J=56.3 Hz, 1H), 5.14 (dd, J=4.7, 9.1 Hz, 1H), 4.58 (t, J=9.3 Hz, 1H), 4.44 (dd, J=4.6, 9.6 Hz, 1H).

Peak 2: (S)-1-(3-(difluoromethyl)phenyl)-3-(isoquinolin-4-yl)-2-oxoimidazolidine-4-carbonitrile (22b). LCMS (Method 31): $t_R$=2.79 min, $[M+1]^+$ 365.1. SFC (Method 15): $t_R$=1.86 min, 99.8%. $^1$H NMR: (400 MHz, CHLOROFORM-d) 9.36 (s, 1H), 8.71 (s, 1H), 8.14 (d, J=8.2 Hz, 1H), 7.97-7.89 (m, 1H), 7.88-7.82 (m, 1H), 7.79-7.71 (m, 3H), 7.54 (t, J=8.3 Hz, 1H), 7.35 (d, J=7.6 Hz, 1H), 6.83-6.52 (m, 1H), 5.14 (dd, J=4.5, 9.1 Hz, 1H), 4.58 (t, J=9.4 Hz, 1H), 4.44 (dd, J=4.6, 9.6 Hz, 1H).

Example 23: Synthesis of 3-(isoquinolin-4-yl)-1-(2-methoxypyridin-4-yl)-2-oxoimidazolidine-4-carbonitrile (23), (R)-3-(isoquinolin-4-yl)-1-(2-methoxypyridin-4-yl)-2-oxoimidazolidine-4-carbonitrile (23a) and (S)-3-(isoquinolin-4-yl)-1-(2-methoxypyridin-4-yl)-2-oxoimidazolidine-4-carbonitrile (23b)

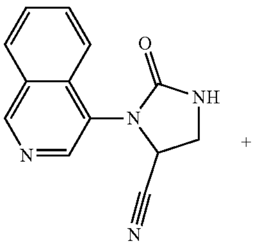

(Int-1)

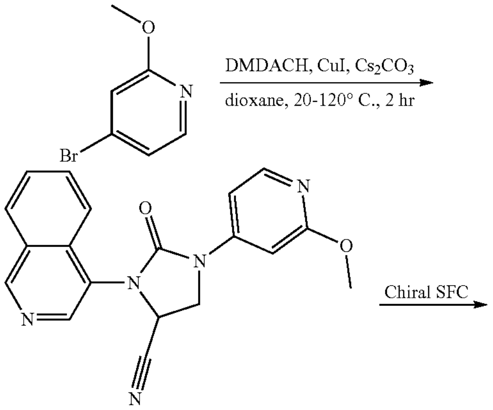

(23)

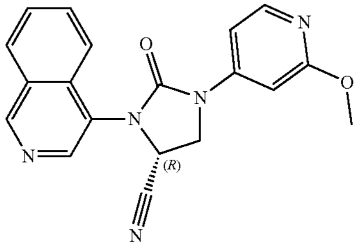

(23a)

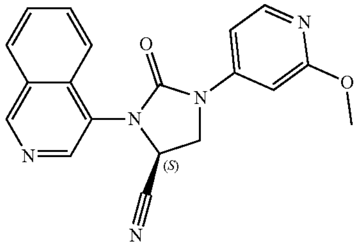

(23b)

3-(isoquinolin-4-yl)-1-(2-methoxypyridin-4-yl)-2-oxoimidazolidine-4-carbonitrile (23) was prepared in a manner similar to Example 4, using 4-bromo-2-methoxypyridine (1.2 eq) in place of 4-trifluoromethyl-iodobenzene. The crude product was purified by MPLC (petroleum ether/EtOAc, 50 to 70%) to give racemic product. The racemic product was purified by chiral SFC (Column: Chiralpak AD-3, 150 mm×4.6 mm, 3 μm); Mobile phase: A for $CO_2$ and B for IPA (0.1% IPAm); Gradient: B %=40% isocratic elution mode; Flow rate: 2.5 mL/min; Wavelength: 220 nm; Column temperature: 35° C.; System back pressure: 138 bar) to give two peaks.

Peak 1: (R)-3-(isoquinolin-4-yl)-1-(2-methoxypyridin-4-yl)-2-oxoimidazolidine-4-carbonitrile (23a) LCMS (Method 1): $t_R$=1.65 min, $[M+1]^+$ 346.1. SFC (Method 22): $t_R$=2.18 min, 100%. $^1$H NMR: (400 MHz, CHLOROFORM-d) 9.37 (s, 1H), 8.69 (br s, 1H), 8.20-8.10 (m, 2H), 7.93-7.80 (m, 2H), 7.78-7.71 (m, 1H), 7.39 (br dd, J=1.8, 5.9 Hz, 1H), 6.78 (d, J=1.5 Hz, 1H), 5.12 (br dd, J=4.4, 9.1 Hz, 1H), 4.49 (br t, J=9.6 Hz, 1H), 4.38 (dd, J=4.6, 9.8 Hz, 1H), 3.97 (s, 3H).

Peak 2: (S)-3-(isoquinolin-4-yl)-1-(2-methoxypyridin-4-yl)-2-oxoimidazolidine-4-carbonitrile (23b) LCMS (Method 1): $t_R$=1.68 min, $[M+1]^+$ 346.1. SFC (Method 22): $t_R$=3.65 min, 99.7%. $^1$H NMR: (400 MHz, CHLOROFORM-d) 9.35 (s, 1H), 8.68 (s, 1H), 8.17-8.09 (m, 2H), 7.91-7.79 (m, 2H), 7.77-7.69 (m, 1H), 7.37 (dd, J=1.9, 5.9 Hz, 1H), 6.77 (d, J=1.9 Hz, 1H), 5.11 (dd, J=4.6, 9.3 Hz, 1H), 4.48 (t, J=9.6 Hz, 1H), 4.36 (dd, J=4.6, 9.9 Hz, 1H), 3.97 (s, 3H)

Example 24: Synthesis of 3-(isoquinolin-4-yl)-1-(2-methyl-5-(trifluoromethyl)phenyl)-2-oxoimidazolidine-4-carbonitrile (24), (R)-3-(isoquinolin-4-yl)-1-(2-methyl-5-(trifluoromethyl)phenyl)-2-oxoimidazolidine-4-carbonitrile (24a) and (S)-3-(isoquinolin-4-yl)-1-(2-methyl-5-(trifluoromethyl)phenyl)-2-oxoimidazolidine-4-carbonitrile (24b)

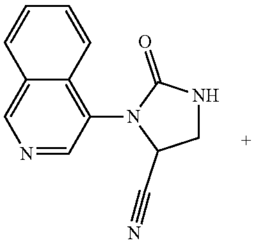

(Int-1)

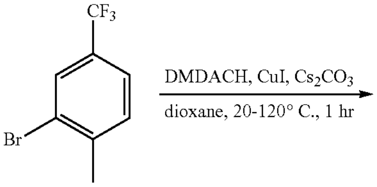

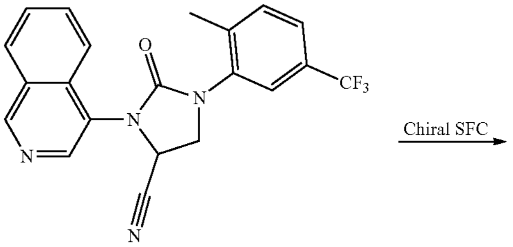

(24)

-continued

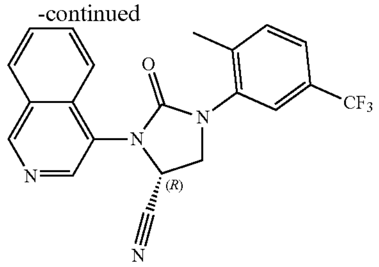

(24a)

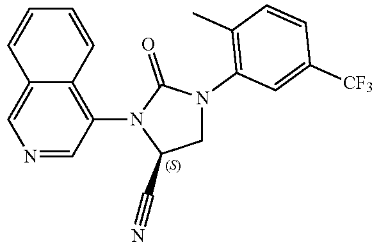

(24b)

3-(isoquinolin-4-yl)-1-(2-methyl-5-(trifluoromethyl)phenyl)-2-oxoimidazolidine-4-carbonitrile (24) was prepared in a manner similar to Example 4, using 2-bromo-1-methyl-4-(trifluoromethyl)benzene (1.5 eq) in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 30%-70%, 20 min] to give racemic product. The racemic product was purified by chiral SFC (DAICEL CHIRALPAK IG (250 mm×30 mm, 10 μm); Mobile phase: A for $CO_2$ and B for 0.1% $NH_3H_2O$ ETOH; Gradient: B %=45% isocratic elution mode; Flow rate: 70 mL/min; Wavelength: 220 nm; Column temperature: 35° C.; System back pressure: 120 bar) to give two peaks.

Peak 1: (R)-3-(isoquinolin-4-yl)-1-(2-methyl-5-(trifluoromethyl)phenyl)-2-oxoimidazolidine-4-carbonitrile (24a). LCMS (Method): $t_R$=2.63 min, $[M+1]^+$ 397.1. SFC (Method 21): $t_R$=1.37 min, 100%. $^1$H NMR: (400 MHz, CHLOROFORM-d) δ=9.35 (s, 1H), 8.72 (s, 1H), 8.13 (d, J=8.3 Hz, 1H), 7.95 (d, J=8.3 Hz, 1H), 7.86 (dt, J=1.1, 7.7 Hz, 1H), 7.78-7.70 (m, 1H), 7.61 (s, 1H), 7.58-7.53 (m, 1H), 7.51-7.46 (m, 1H), 5.11 (dd, J=3.8, 8.5 Hz, 1H), 4.48 (t, J=9.1 Hz, 1H), 4.25 (dd, J=3.8, 9.5 Hz, 1H), 2.54 (s, 3H)

Peak 2: (S)-3-(isoquinolin-4-yl)-1-(2-methyl-5-(trifluoromethyl)phenyl)-2-oxoimidazolidine-4-carbonitrile (24b). LCMS (Method): $t_R$=2.63 min, $[M+1]^+$ 397.1. SFC (Method 21): $t_R$=1.61 min, 100%. $^1$H NMR: (400 MHz, CHLOROFORM-d) 9.37 (s, 1H), 8.74 (s, 1H), 8.15 (d, J=8.2 Hz, 1H), 8.01-7.96 (m, 1H), 7.88 (dt, J=0.9, 7.7 Hz, 1H), 7.76 (t, J=7.8 Hz, 1H), 7.64 (s, 1H), 7.61-7.57 (m, 1H), 7.54-7.50 (m, 1H), 5.14 (dd, J=3.7, 8.6 Hz, 1H), 4.51 (t, J=9.0 Hz, 1H), 4.28 (dd, J=3.7, 9.6 Hz, 1H), 2.56 (s, 3H)

Example 25: Synthesis of 1-((R)-1-(2-hydroxyacetyl)pyrrolidin-3-yl)-3-(isoquinolin-4-yl)-2-oxoimidazolidine-4-carbonitrile (25), (R)-1-((R)-1-(2-hydroxyacetyl)pyrrolidin-3-yl)-3-(isoquinolin-4-yl)-2-oxoimidazolidine-4-carbonitrile (25a) and (S)-1-((R)-1-(2-hydroxyacetyl)pyrrolidin-3-yl)-3-(isoquinolin-4-yl)-2-oxoimidazolidine-4-carbonitrile (25b)

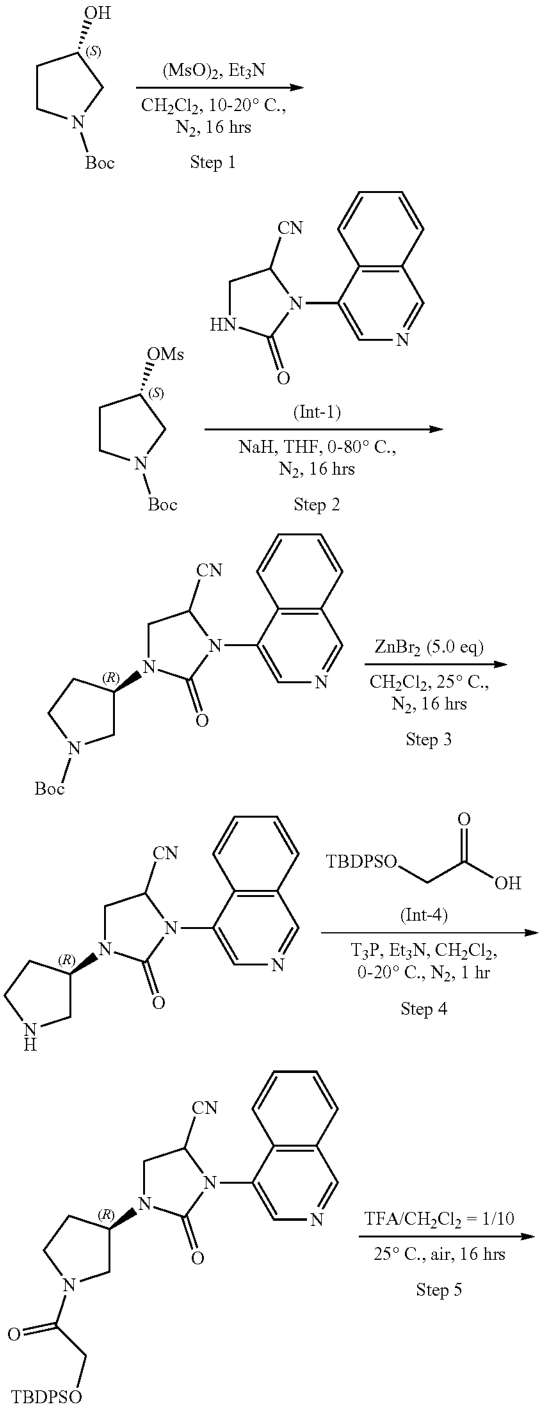

-continued

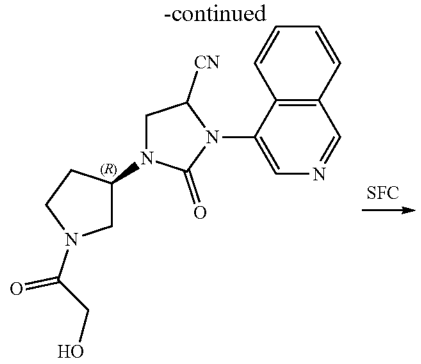

(25)

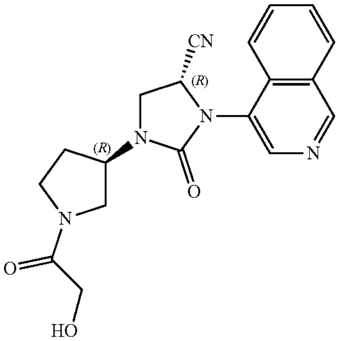

(25a)

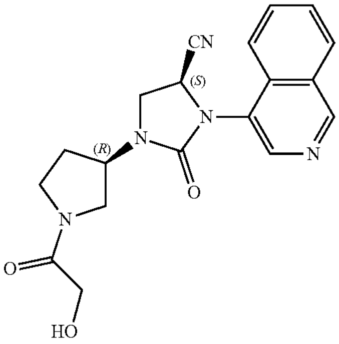

(25b)

Step 1: To a mixture of tert-butyl(S)-3-hydroxypyrrolidine-1-carboxylate (30.0 g, 160.23 mmol, 1.0 eq.) in $CH_2Cl_2$ (200 mL) was added $Et_3N$ (62 mL, 480.69 mmol, 3.0 eq.) and $Ms_2O$ (41.8 g, 240.34 mmol, 1.5 eq.) at 10° C. The reaction was stirred at 20° C. for 16 hrs under $N_2$. The reaction was quenched with $H_2O$ (500 mL) and extracted with $CH_2Cl_2$ (150 mL×3). The combined organic layers were washed with HCl (300 mL×2, 0.5M) and brine (300 mL), dried over $Na_2SO_4$, filtered and concentrated under reduced pressure to give a residue. The residue was purified by MPLC (Eluent of Ethyl acetate/Petroleum ether=1/1 to 3/2, 200 mL/min) to give tert-butyl(S)-3-((methylsulfonyl)oxy)pyrrolidine-1-carboxylate. H NMR (400 MHz, CHLOROFORM-d) δ=5.27 (br s, 1H), 3.80-3.40 (m, 4H), 3.06 (s, 3H), 2.38-2.22 (m, 1H), 2.20-2.08 (m, 1H), 1.48 (s, 9H).

Step 2: To a mixture of 3-(isoquinolin-4-yl)-2-oxoimidazolidine-4-carbonitrile (Int-1) (5.0 g, 20.99 mmol, 1.0 eq.) in THE (50 mL) was added NaH (1.3 g, 31.48 mmol, 1.5 eq.) at 0° C. under $N_2$.

The reaction was stirred at 0° C. for 1 hr. A solution of tert-butyl(S)-3-((methylsulfonyl)oxy)pyrrolidine-1-carboxylate (8.4 g, 31.48 mmol, 1.5 eq.) in THE (50 mL) was added into the reaction. The reaction was stirred at 80° C. for 16 hrs under $N_2$. The reaction was quenched with AcOH (1.9 mL) and filtered, the filtrate was concentrated under reduced pressure to give a residue. The residue was purified by MPLC (Eluent of THE/Petroleum ether=3/2 to 7/3, 120 mL/min) to give tert-butyl(3R)-3-(4-cyano-3-(isoquinolin-4-yl)-2-oxoimidazolidin-1-yl)pyrrolidine-1-carboxylate. $^1$H NMR (400 MHz, CHLOROFORM-d) δ=9.31 (s, 1H), 8.62 (s, 1H), 8.10 (d, J=8.3 Hz, 1H), 7.82 (br d, J=5.6 Hz, 2H), 7.74-7.67 (m, 1H), 5.00-4.89 (m, 1H), 4.71 (br d, J=6.3 Hz, 1H), 4.05 (t, J=9.1 Hz, 1H), 3.89 (br s, 1H), 3.71-3.57 (m, 2H), 3.54-3.34 (m, 2H), 2.38-2.26 (m, 1H), 2.24-2.09 (m, 1H), 1.50 (s, 9H).

Step 3: To a mixture of tert-butyl(3R)-3-(4-cyano-3-(isoquinolin-4-yl)-2-oxoimidazolidin-1-yl)pyrrolidine-1-carboxylate (200 mg, 0.49 mmol, 1.0 eq.) in $CH_2Cl_2$ (5 mL) was added $ZnBr_2$ (553 mg, 2.45 mmol, 5.0 eq.) at 25° C. The reaction was stirred at 25° C. for 16 hrs under $N_2$. The mixture was filtered and the filter cake was dried under vacuum to give 3-(isoquinolin-4-yl)-2-oxo-1-((R)-pyrrolidin-3-yl)imidazolidine-4-carbonitrile which was used without further purification.

Step 4: To a solution of 3-(isoquinolin-4-yl)-2-oxo-1-((R)-pyrrolidin-3-yl)imidazolidine-4-carbonitrile (1.6 g crude, 1.01 mmol, 1.0 eq.) in $CH_2Cl_2$ (15 mL) was added 2-(tert-butyldiphenylsilyl)oxy)acetic acid (Int-4) (317 mg, 1.01 mmol, 1.0 eq.), $Et_3N$ (0.42 mL, 3.03 mmol, 3.0 eq.) and $T_3P$ (960 mg, 1.51 mmol, 1.5 eq.) in turn at 0° C. under $N_2$ and the reaction was stirred at 20° C. for 1 hr. The reaction was quenched with $H_2O$ (20 mL) and extracted with $CH_2Cl_2$ (10 mL×3). The combined organic layers were dried over $Na_2SO_4$, filtered and concentrated under reduced pressure to give a residue. The residue was purified by MPLC (Eluent of THE/Petroleum ether=7/3 to I/O, 50 mL/min) to give 1-((R)-1-(2-((tert-butyldiphenylsilyl)oxy)acetyl)pyrrolidin-3-yl)-3-(isoquinolin-4-yl)-2-oxoimidazolidine-4-carbonitrile. LCMS (Method 33): $t_R$=0.900 min, $[M+1]^+$=604.1.

Step 5: A solution of 1-((R)-1-(2-((tert-butyldiphenylsilyl)oxy)acetyl)pyrrolidin-3-yl)-3-(isoquinolin-4-yl)-2-oxoimidazolidine-4-carbonitrile (160 mg, 0.26 mmol, 1.0 eq.) in TFA/$CH_2Cl_2$ (4 mL) was stirred at 25° C. for 16 hrs. The reaction was concentrated under reduced pressure to give a residue. The residue was purified by prep-HPLC (column: Waters Xbridge Prep OBD C18 150 mm×40 mm, 10 um; liquid phase: [A-10 mM $NH_4HCO_3$ in $H_2O$; B-ACN]B %: 1%-30%, 8 min]) to give 1-((R)-1-(2-hydroxyacetyl)pyrrolidin-3-yl)-3-(isoquinolin-4-yl)-2-oxoimidazolidine-4-carbonitrile (25) as a diastereomeric mixture which was separated by SFC (column: DAICEL CHIRALPAK IC (250 mm×30 mm, 10 um); liquid phase: ACN/EtOH (0.1% $NH_3H_2O$) B %: 60%-60%, 15 min]) to give two peaks.

Peak 1: (S)-1-((R)-1-(2-hydroxyacetyl)pyrrolidin-3-yl)-3-(isoquinolin-4-yl)-2-oxoimidazolidine-4-carbonitrile (25b). LCMS (Method 31): $t_R$=1.886 min, $[M+1]^+$=366.2. SFC: (Method 12), $t_R$=0.825 min, 100.0% $^1$H NMR: (400 MHz, DMSO-d6) δ=9.38 (s, 1H), 8.55 (s, 1H), 8.26 (d, J=8.1 Hz, 1H), 7.99 (d, J=8.4 Hz, 1H), 7.89 (t, J=7.6 Hz, 1H), 7.77 (t, J=7.6 Hz, 1H), 5.60-5.45 (m, 1H), 4.54-4.40 (m, 1H), 4.11-4.01 (m, 3H), 3.98-3.89 (m, 1H), 3.69 (dd, J=7.4, 11.1 Hz, 1H), 3.62-3.52 (m, 2H), 3.45-3.35 (m, 1H), 2.17 (q, J=7.0 Hz, 1H), 2.10-2.02 (m, 1H).

Peak 2: (R)-1-((R)-1-(2-hydroxyacetyl)pyrrolidin-3-yl)-3-(isoquinolin-4-yl)-2-oxoimidazolidine-4-carbonitrile (25b). LCMS (Method 31): $t_R$=1.930 min, $[M+1]^+$=366.2. SFC: (Method 12): $t_R$=1.105 min, 100.0% $^1$H NMR: (400 MHz, DMSO-d6) δ=9.38 (s, 1H), 8.55 (s, 1H), 8.26 (d, J=8.3 Hz, 1H), 7.99 (dd, J=1.6, 8.4 Hz, 1H), 7.89 (t, J=7.6 Hz, 1H), 7.77 (t, J=7.6 Hz, 1H), 5.50 (dd, J=4.5, 8.9 Hz, 1H), 4.65-4.57 (m, 1H), 4.56-4.40 (m, 1H), 4.13-3.99 (m, 3H), 3.93 (dd, J=4.3, 9.2 Hz, 1H), 3.66-3.55 (m, 2H), 3.53-3.47 (m, 1H), 3.46-3.35 (m, 1H), 2.29-2.18 (m, 1H), 2.17-2.06 (m, 1H).

Example 26: Synthesis of 3-(isoquinolin-4-yl)-2-oxo-1-((R)-1-(3,3,3-trifluoropropyl)pyrrolidin-3-yl)imidazolidine-4-carbonitrile (26), (R)-3-(isoquinolin-4-yl)-2-oxo-1-((R)-1-(3,3,3-trifluoropropyl)pyrrolidin-3-yl)imidazolidine-4-carbonitrile (26a) and (S)-3-(isoquinolin-4-yl)-2-oxo-1-((R)-1-(3,3,3-trifluoropropyl)pyrrolidin-3-yl)imidazolidine-4-carbonitrile (26b)

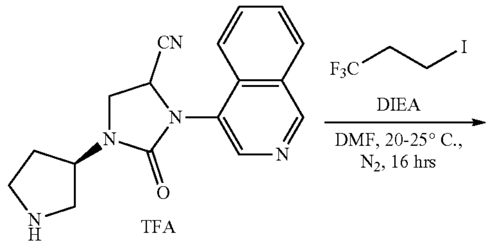

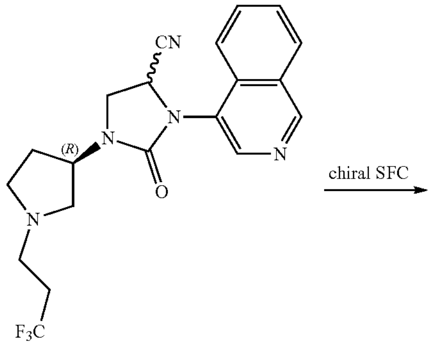

(26)

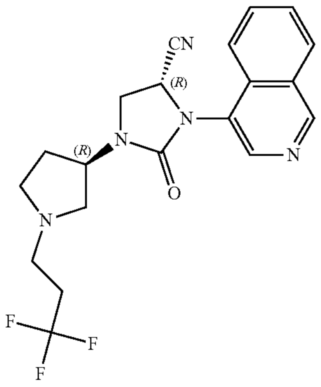

(26a)

-continued

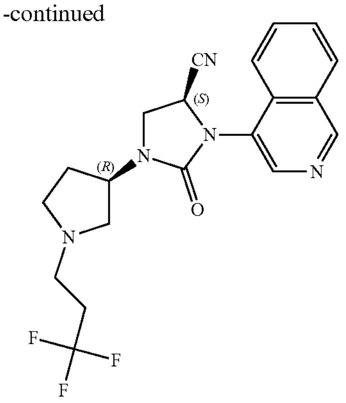

(26b)

To a mixture of tert-butyl(3R)-3-(4-cyano-3-(isoquinolin-4-yl)-2-oxoimidazolidin-1-yl)pyrrolidine-1-carboxylate (see Example 25) (500 mg, 1.63 mmol, 1.0 eq.) in DMF (6 mL) was added DIEA (1.6 mL, 9.78 mmol, 6.0 eq.) and 1,1,1-trifluoro-3-iodopropane (911 mg, 4.07 mmol, 2.5 eq.) at 20° C. The reaction was stirred at 250 C for 16 hrs under $N_2$. The mixture was concentrated to give a residue. The residue was purified by prep-HPLC (column: Waters Xbridge BEH C18 250 mm×50 mm, 10 μm; liquid phase: [A-$H_2O$ (10 mm $NH_4HCO_3$); B-ACN]B %: 25%-45%, 20 min]) to give 3-(isoquinolin-4-yl)-2-oxo-1-((R)-1-(3,3,3-trifluoropropyl)pyrrolidin-3-yl)imidazolidine-4-carbonitrile (26). The mixture of diastereoisomers was separated by SFC (column: ChiralPak IH, 250 mm×30 mm, 10 μm; liquid phase: Neu-ACN B %: 35%-35%, 10 min]) to give two peaks.

Peak 1: (R)-3-(isoquinolin-4-yl)-2-oxo-1-((R)-1-(3,3,3-trifluoropropyl)pyrrolidin-3-yl)imidazolidine-4-carbonitrile (26a). LCMS (Method 31): $t_R$=2.640 min, $[M+1]^+$=404.2 SFC (Method 13): $t_R$=1.622 min, 100.0% $^1H$ NMR: $^1H$ NMR (400 MHz, CHLOROFORM-d) δ=9.30 (br s, 1H), 8.61 (s, 1H), 8.09 (d, J=8.1 Hz, 1H), 7.90-7.76 (m, 2H), 7.74-7.64 (m, 1H), 4.90 (dd, J=4.5, 8.8 Hz, 1H), 4.75 (br m, 1H), 4.13 (t, J=9.5 Hz, 1H), 3.95 (dd, J=4.5, 10.1 Hz, 1H), 3.20-3.09 (m, 1H), 2.95 (br d, J=9.9 Hz, 1H), 2.74 (br t, J=7.3 Hz, 2H), 2.48 (br dd, J=6.9, 9.7 Hz, 1H), 2.43-2.31 (m, 3H), 2.23 (q, J=8.6 Hz, 1H), 2.04-1.91 (m, 1H).

Peak 2: (S)-3-(isoquinolin-4-yl)-2-oxo-1-((R)-1-(3,3,3-trifluoropropyl)pyrrolidin-3-yl)imidazolidine-4-carbonitrile (26b). LCMS (Method 31): $t_R$=2.638 min, $[M+1]^+$=404.2 SFC (Method 13): $t_R$=2.434 min, 100.0% $^1H$ NMR: $^1H$ NMR (400 MHz, CHLOROFORM-d) δ=9.30 (s, 1H), 8.61 (s, 1H), 8.09 (d, J=8.1 Hz, 1H), 7.89-7.76 (m, 2H), 7.73-7.66 (m, 1H), 4.90 (dd, J=4.8, 8.5 Hz, 1H), 4.75 (br m, 1H), 4.12-3.96 (m, 2H), 3.10 (br t, J=7.6 Hz, 1H), 3.02 (br d, J=9.9 Hz, 1H), 2.82-2.69 (m, 2H), 2.56 (br dd, J=7.3, 9.5 Hz, 1H), 2.44-2.27 (m, 3H), 2.27-2.19 (m, 1H), 1.95-1.80 (m, 1H).

Example 27: Synthesis of 1-(3,3-difluorocyclobutyl)-3-(isoquinolin-4-yl)-2-oxoimidazolidine-4-carbonitrile (27)

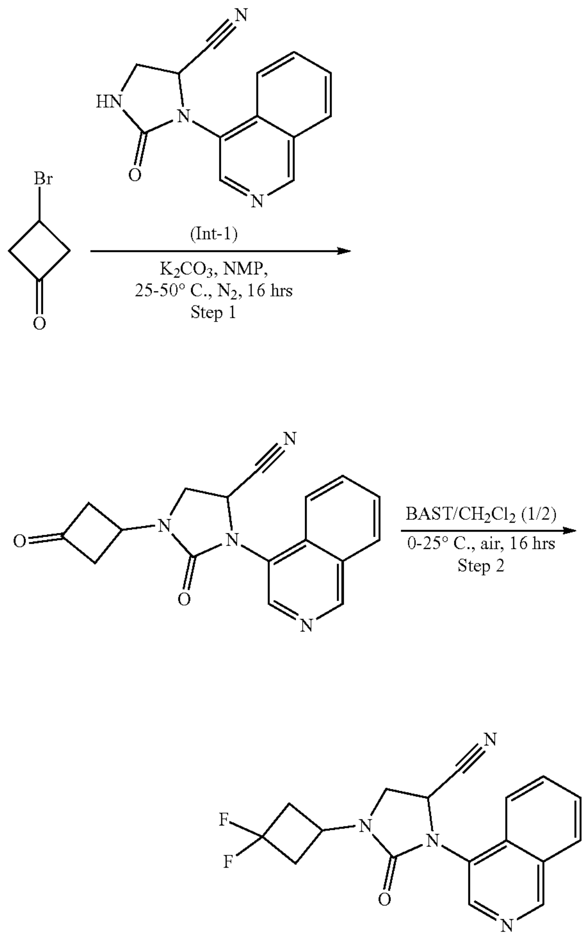

(27)

Step 1: To a mixture of 3-bromocyclobutan-1-one (250 mg, 1.68 mmol, 2.0 eq.) and 3-(isoquinolin-4-yl)-2-oxoimidazolidine-4-carbonitrile (Int-1) (200 mg, 0.84 mmol, 1.0 eq.) in NMP (2 mL) was added $K_2CO_3$ (232 mg, 1.68 mmol, 2.0 eq.) at 25° C. and the reaction stirred at 50° C. for 16 hrs under $N_2$. The reaction mixture was poured into water (5 mL) and extracted with EtOAc (3 mL×3). The combined organic phases were washed with brine (10 mL), dried over $Na_2SO_4$, filtered and concentrated to give crude product. The crude was purified by column chromatography on silica gel (petroleum ether/THF=100/0 to 60/40) to give 3-(isoquinolin-4-yl)-2-oxo-1-(3-oxocyclobutyl)imidazolidine-4-carbonitrile which was used without further purification.

Step 2: To a mixture of 3-(isoquinolin-4-yl)-2-oxo-1-(3-oxocyclobutyl)imidazolidine-4-carbonitrile (90 mg, crude) in $CH_2Cl_2$ (1 mL) was added bis(2-methoxyethyl)arninosulfur trifluoride (BAST) (0.5 mL) at 0° C. under $N_2$ and the reaction stirred at 25° C. for 16 hrs under $N_2$. The reaction mixture was quenched with sat. $NaHCO_3$ (5 mL) and extracted with $CH_2Cl_2$ (3 mL×3). The combined organic phases were washed with brine (50 mL), dried over $Na_2SO_4$, filtered and concentrated to give crude product. The crude product was purified by prep-HPLC (column: Phenomenex C18 75 mm×30 mm, 3 μm; liquid phase: [A-10 mM $NH_4HCO_3$ in $H_2O$; B-ACN]B %: 5%-35%, 8 min]) to give racemic 1-(3,3-difluorocyclobutyl)-3-(isoquinolin-4-yl)-2-oxoimidazolidine-4-carbonitrile (27). LCMS (Method 19): $t_R$=2.302 min, $[M+1]^+$ 329.1 $^1H$ NMR: (400 MHz, CHLOROFORM-d) δ=9.32 (s, 1H), 8.60 (s, 1H), 8.10 (d, J=8.1 Hz, 1H), 7.87-7.78 (m, 2H), 7.75-7.68 (m, 1H), 4.98 (dd, J=4.5, 8.8 Hz, 1H), 4.56-4.44 (m, 1H), 4.11-4.04 (m, 1H), 3.96 (dd, J=4.5, 9.3 Hz, 1H), 3.13-2.83 (m, 4H).

Example 28: Synthesis of 1-(3-hydroxy-3-(trifluoromethyl)cyclobutyl)-3-(isoquinolin-4-yl)-2-oxoimidazolidine-4-carbonitrile (28)

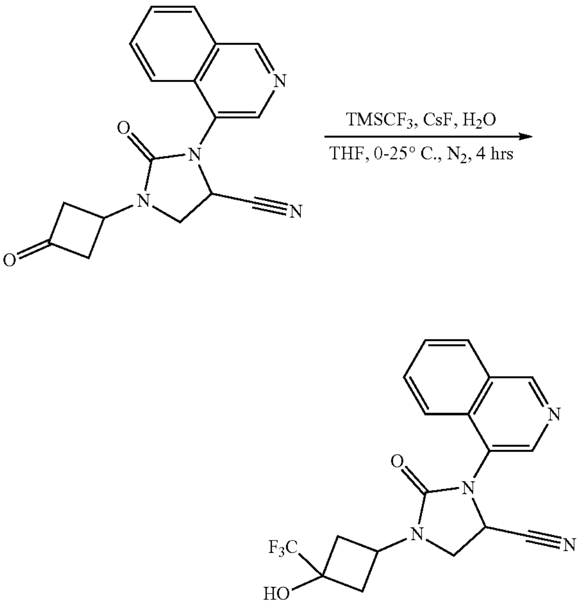

(28)

To a mixture of 3-(isoquinolin-4-yl)-2-oxo-1-(3-oxocyclobutyl)imidazolidine-4-carbonitrile (from Step 1, Example 32) (300 mg, 0.98 mmol, 1.0 eq.) and CsF (223 mg, 1.47 mmol, 1.5 eq.) in THE (3 mL) was added $TMSCF_3$ (182 mg, 1.96 mmol, 2.0 eq.) dropwised at 0° C. and the reaction stirred at 25° C. for 2 hrs under $N_2$. To the mixture was added $H_2O$ (35 mg, 1.96 mmol, 2.0 eq.) at 25° C. and the mixture was stirred at 25° C. for 2 hrs under $N_2$. The reaction mixture was poured into water (10 mL) and extracted with EtOAc (3 mL×3). The combined organic phases were washed with brine (10 mL), dried over $Na_2SO_4$, filtered and concentrated to give crude product. The crude was purified by prep-HPLC (column: Phenomenex C18 75 mm×30 mm, 3 μm; liquid phase: [A-10 mM $NH_4HCO_3$ in $H_2O$; B-ACN]B %: 20%-50%, 8 min]) to give racemic 1-(3-hydroxy-3-(trifluoromethyl)cyclobutyl)-3-(isoquinolin-4-yl)-2-oxoimidazolidine-4-carbonitrile (28). LCMS (Method 1): $t_R$=1.808 min, $[M+1]^+$ 377.1 $^1H$ NMR: (400 MHz, CHLOROFORM-d) δ=9.32 (s, 1H), 8.64-8.59 (m, 1H), 8.11 (d, J=8.2 Hz, 1H), 7.88-7.80 (m, 2H), 7.73 (ddd, J=2.0, 6.1, 8.1 Hz, 1H), 4.98 (dd, J=4.5, 8.8 Hz, 1H), 4.20 (t, J=8.1 Hz, 1H), 4.15-4.08 (m, 1H), 4.00 (dd, J=4.5, 9.4 Hz, 1H), 3.08-2.95 (m, 2H), 2.66 (dt, J=7.5, 13.2 Hz, 2H).

Example 29: Synthesis of 1-(3,3-difluorocyclohexyl)-3-(isoquinolin-4-yl)-2-oxoimidazolidine-4-carbonitrile (29)

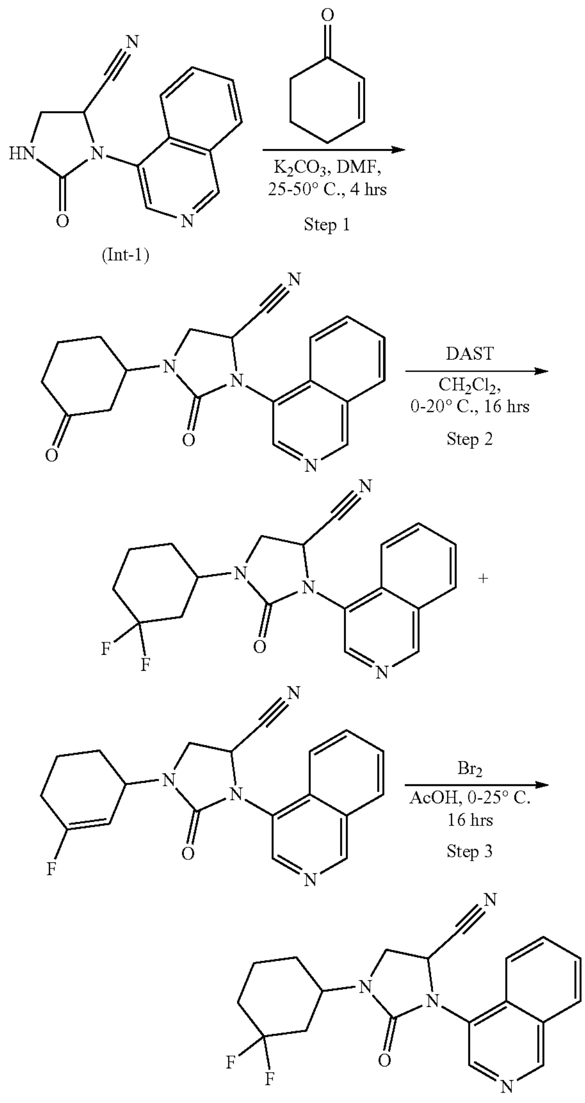

(Int-1)

(29)

Step 1: To the solution of 3-(isoquinolin-4-yl)-2-oxoimidazolidine-4-carbonitrile (Int-1) (200 mg, 0.84 mmol, 1.0 eq.) and cyclohex-2-en-1-one (161 mg, 1.68 mmol, 2.0 eq.) in DMF (4 mL) was added $K_2CO_3$ (460 mg, 3.36 mmol, 4.0 eq.) at 25° C. under $N_2$ and the mixture was stirred at 50° C. for 4 hrs. The reaction mixture was quenched with $H_2O$ (10 mL), extracted with EtOAc (20 mL×2). The combined organic layers were washed with brine (10 mL), dried over $Na_2SO_4$, filtered and concentrated to give crude product. The crude product was purified by column (Petroleum ether/EtOAc=100/1-1/1) to give 3-(isoquinolin-4-yl)-2-oxo-1-(3-oxocyclohexyl)imidazolidine-4-carbonitrile. $^1$H NMR: (400 MHz, CHLOROFORM-d) δ=9.31 (s, 1H), 8.61 (d, J=4.0 Hz, 1H), 8.09 (d, J=8.1 Hz, 1H), 7.86-7.77 (m, 2H), 7.74-7.65 (m, 1H), 4.96 (td, J=4.5, 8.8 Hz, 1H), 4.33-4.14 (m, 1H), 4.04 (td, J=9.0, 18.2 Hz, 1H), 3.95-3.85 (m, 1H), 2.79-2.57 (m, 2H), 2.53-2.46 (m, 1H), 2.37-2.26 (m, 1H), 2.25-2.12 (m, 2H), 2.03-1.91 (m, 1H), 1.83-1.68 (m, 1H).

Step 2: To the solution of 3-(isoquinolin-4-yl)-2-oxo-1-(3-oxocyclohexyl)imidazolidine-4-carbonitrile (200 mg, 0.60 mmol, 1.0 eq.) in $CH_2Cl_2$ (2 mL) was added and DAST (529 mg, 2.40 mmol, 4.0 eq.) at 0° C. under $N_2$. The mixture was stirred at 20° C. for 16 hrs. The reaction mixture was quenched with saturated aqueous $NaHCO_3$ (5 mL), extracted with $CH_2Cl_2$ (10 mL×2). The combined organic layers were washed with brine (5 mL), dried over $Na_2SO_4$, filtered and concentrated to give crude product which was purified by column chromatography ($SiO_2$, Petroleum ether/Ethyl acetate=100/1, 50/1 to 0/1) to give a mixture of 1-(3,3-difluorocyclohexyl)-3-(isoquinolin-4-yl)-2-oxoimidazolidine-4-carbonitrile and 1-(3-fluorocyclohex-2-en-1-yl)-3-(isoquinolin-4-yl)-2-oxoimidazolidine-4-carbonitrile.

Step 3: To a solution of the mixture from step 2 (190 mg, 0.53 mmol, 1.0 eq.) in AcOH (2 mL) was added $Br_2$ (126 mg, 0.80 mmol, 1.5 eq.) at 0° C. under $N_2$. The mixture was stirred at 25° C. for 16 hrs. The reaction mixture was concentrated to give crude product which was purified by prep-HPLC (column: Phenomenex Luna C18 75 mm×30 mm, 3 μm; liquid phase: [A-FA/$H_2O$=0.1% v/v; B-ACN]B %: 10%-40%, 8 min]) to give 1-(3,3-difluorocyclohexyl)-3-(isoquinolin-4-yl)-2-oxoimidazolidine-4-carbonitrile (29). LCMS (Method 1): $t_R$=2.098 min, $[M+1]^+$ 357.1 $^1$H NMR: (400 MHz, METHANOL-$d_4$) δ=9.32 (s, 1H), 8.54 (s, 1H), 8.24 (d, J=8.3 Hz, 1H), 8.06-7.98 (m, 1H), 7.91 (dt, J=0.8, 7.7 Hz, 1H), 7.79 (dt, J=1.0, 7.6 Hz, 1H), 5.35 (ddd, J=3.1, 4.3, 9.0 Hz, 1H), 4.12 (dt, J=6.7, 9.3 Hz, 1H), 4.08-3.99 (m, 1H), 3.95 (dd, J=4.3, 9.6 Hz, 1H), 2.40-2.25 (m, 1H), 2.25-2.11 (m, 1H), 2.11-2.02 (m, 1H), 2.01-1.87 (m, 2H), 1.85-1.72 (m, 1H), 1.71-1.58 (m, 2H).

Example 30: Synthesis of 3-(isoquinolin-4-yl)-2-oxo-1-(5-(trifluoromethyl)pyridazin-3-yl)imidazolidine-4-carbonitrile (30), (R)-3-(isoquinolin-4-yl)-2-oxo-1-(5-(trifluoromethyl)pyridazin-3-yl) imidazolidine-4-carbonitrile (30a) and (S)-3-(isoquinolin-4-yl)-2-oxo-1-(5-(trifluoromethyl) pyridazin-3-yl)imidazolidine-4-carbonitrile (30b)

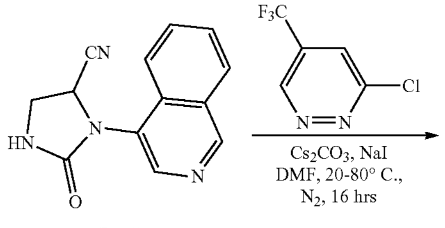

(Int-1)

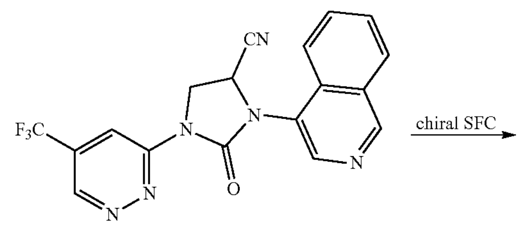

(30)

-continued

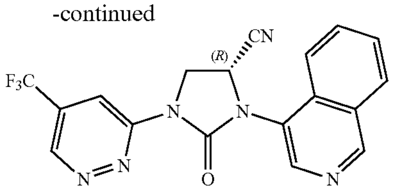

(30a)

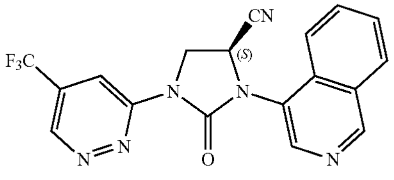

(30b)

To a solution of 3-(isoquinolin-4-yl)-2-oxoimidazolidine-4-carbonitrile (Int-1) (200 mg, 0.84 mmol, 1.0 eq.) and 3-chloro-5-(trifluoromethyl)pyridazine (200 mg, 1.09 mmol, 1.3 eq.) in DMF (5 mL) was added NaI (13 mg, 0.08 mmol, 0.1 eq.) and $Cs_2CO_3$ (547 mg, 1.68 mmol, 2.0 eq.) at 20° C. The solution was stirred at 80° C. for 16 hrs under $N_2$. The reaction mixture was poured into water (10 mL) slowly and extracted with $CH_2Cl_2$ (10 mL×2). The combined organic layers were washed with brine (10 mL×2), dried over $Na_2SO_4$, filtered and concentrated to give crude product. The crude product was purified by MPLC (Petroleum ether/EtOAc=1/1, $R_f$=0.10, Petroleum ether/EtOAc=100%-0%) to give racemic 3-(isoquinolin-4-yl)-2-oxo-1-(5-(trifluoromethyl)pyridazin-3-yl)imidazolidine-4-carbonitrile (30). The racemate was separated by SFC (Column: DAICEL CHIRALPAK IG (250 mm×30 mm, 10 μm); Mobile phase: A for $CO_2$ and B for EtOH (0.1% $NH_3H_2O$); Gradient: B %=45% isocratic elution mode; Flow rate: 80 g/min; Wavelength: 220 nm; Column temperature: 35° C.; System back pressure: 120 bar.) to give two peaks.

Peak 1: (R)-3-(isoquinolin-4-yl)-2-oxo-1-(5-(trifluoromethyl)pyridazin-3-yl)imidazolidine-4-carbonitrile (30a). LCMS (Method 1): $t_R$=2.214 min, $[M+1]^+$ 385.0 LCMS (Method 14): $t_R$=1.542 min, 99.9% $^1H$ NMR: (400 MHz, CHLOROFORM-d) δ=9.41 (s, 1H), 9.22 (d, J=1.4 Hz, 1H), 8.86 (s, 1H), 8.73 (s, 1H), 8.17 (d, J=8.3 Hz, 1H), 7.93-7.84 (m, 2H), 7.81-7.73 (m, 1H), 5.21 (t, J=6.7 Hz, 1H), 4.93 (d, J=7.1 Hz, 2H).

Peak 2: (S)-3-(isoquinolin-4-yl)-2-oxo-1-(5-(trifluoromethyl)pyridazin-3-yl)imidazolidine-4-carbonitrile (30b). LCMS (Method 1): $t_R$=2.211 min, $[M+1]^+$ 385.1 LCMS (Method 14): $t_R$=2.167 min, 98.7% $^1H$ NMR: (400 MHz, CHLOROFORM-d) δ=9.41 (br s, 1H), 9.22 (d, J=1.1 Hz, 1H), 8.86 (s, 1H), 8.73 (br s, 1H), 8.17 (d, J=8.1 Hz, 1H), 7.94-7.84 (m, 2H), 7.81-7.72 (m, 1H), 5.21 (br t, J=6.7 Hz, 1H), 4.93 (d, J=6.6 Hz, 2H).

Example 31: Synthesis of 3-(isoquinolin-4-yl)-1-(5-methoxy-2-(trifluoromethyl)pyrimidin-4-yl)-2-oxoimidazolidine-4-carbonitrile (31), (R)-3-(isoquinolin-4-yl)-1-(5-methoxy-2-(trifluoromethyl)pyrimidin-4-yl)-2-oxoimidazolidine-4-carbonitrile (31a) and (S)-3-(isoquinolin-4-yl)-1-(5-methoxy-2-(trifluoromethyl)pyrimidin-4-yl)-2-oxoimidazolidine-4-carbonitrile (31b)

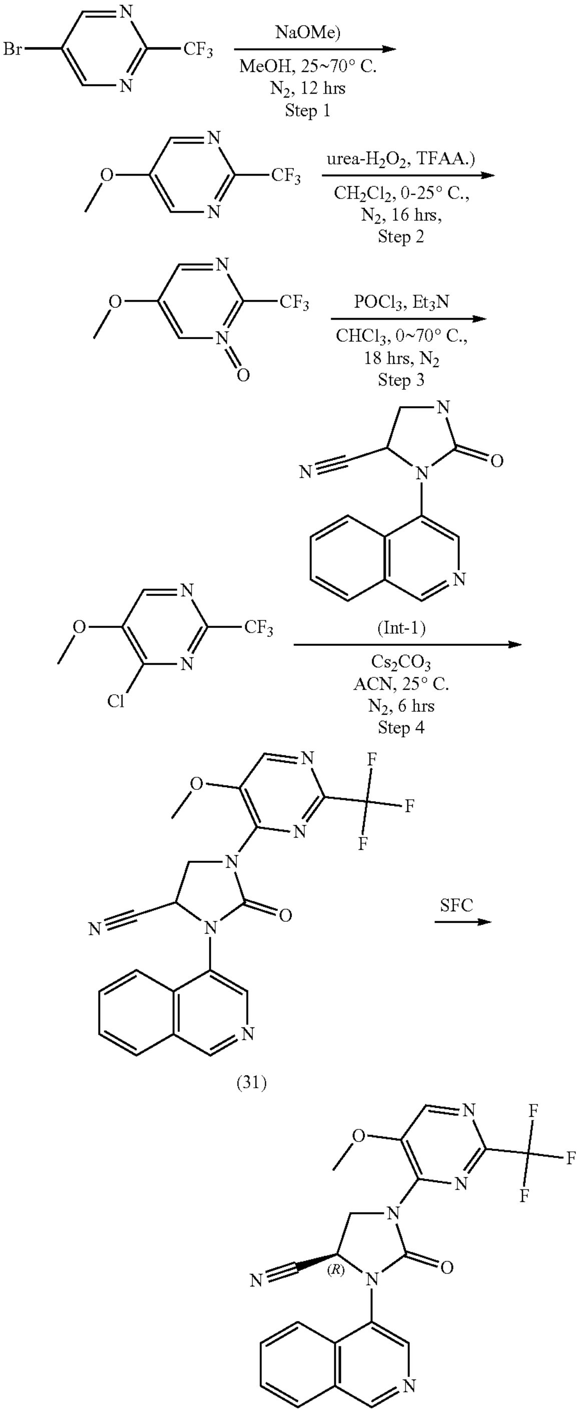

(31)

(31a)

-continued

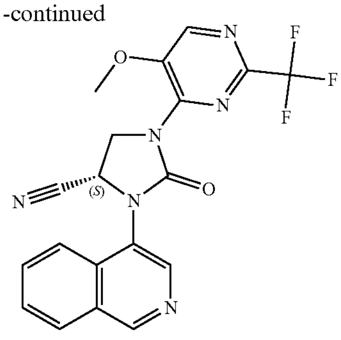

(31b)

Step 1: To a solution of 5-bromo-2-(trifluoromethyl) pyrimidine (5.0 g, 22.03 mmol, 1.0 eq.) in MeOH (50 mL) was added NaOMe (1.4 g, 26.43 mmol, 1.2 eq.) at 25° C. under $N_2$ and the mixture stirred at 70° C. for 12 hrs. The mixture was concentrated, diluted with $H_2O$ (100 mL), and extracted with MTBE (60 mL×2). The organic layer was washed with brine (100 mL), dried over $Na_2SO_4$, filtered and concentrated to give a residue. The residue was purified by column (petroleum ether/THF=20/1) to give 5-methoxy-2-(trifluoromethyl)pyrimidine. $^1$H NMR: (400 MHz, CHLOROFORM-d) δ=8.52 (s, 2H), 4.02 (s, 3H).

Step 2: To a mixture of 5-methoxy-2-(trifluoromethyl) pyrimidine (1.5 g, 8.42 mmol, 1.0 eq.) and urea-$H_2O_2$(1.2 g, 12.63 mmol, 1.5 eq.) in $CH_2Cl_2$ (25 mL) was added dropwise a solution of TFAA (3.5 g, 16.84 mmol, 2.0 eq.) in $CH_2Cl_2$ (5 mL) at 0° C. under $N_2$. The mixture was stirred at 25° C. for 16 hrs under $N_2$. The mixture was diluted with $CH_2Cl_2$ (50 mL), washed with aq·$Na_2SO_3$ (100 mL), aq·$NaHCO_3$ (100 mL), brine (100 mL), dried over $Na_2SO_4$, filtered and concentrated to give a residue. The residue was purified by column (petroleum ether/THF=5/1-3/1) to give 5-methoxy-2-(trifluoromethyl)pyrimidine 1-oxide. $^1$H NMR: (400 MHz, CHLOROFORM-d) δ=8.21 (d, J=2.3 Hz, 1H), 8.05 (d, J=2.4 Hz, 1H), 3.98 (s, 3H).

Step 3: To a mixture of $Et_3N$ (886 mg, 8.76 mmol, 2.0 eq.) in $CHCl_3$ (15 mL) was added $POCl_3$ (1.34 g, 8.76 mmol, 2.0 eq.) at 0° C. under $N_2$. A solution of 5-methoxy-2-(trifluoromethyl)pyrimidine 1-oxide (850 mg, 4.38 mmol, 1.0 eq.) in $CHCl_3$ (5 mL) at 0° C. was then added dropwise under $N_2$ and the mixture stirred at 70° C. for 18 hrs. The mixture was diluted with $CH_2Cl_2$ (30 mL), washed with aq·$NaHCO_3$ (50 mL), brine (50 mL), dried over $Na_2SO_4$, filtered and concentrated to give 4-chloro-5-methoxy-2-(trifluoromethyl) pyrimidine which was used directly without purification. $^1$H NMR: (400 MHz, CHLOROFORM-d) δ=8.40 (s, 1H), 4.11 (s, 3H).

Step 4: To a mixture of 4-chloro-5-methoxy-2-(trifluoromethyl)pyrimidine (400 mg, 1.88 mmol, 1.0 eq.) in ACN (6 mL) was added 3-(isoquinolin-4-yl)-2-oxoimidazolidine-4-carbonitrile (Int-1) (373 mg, 1.57 mmol, 0.8 eq.) and $Cs_2CO_3$ (995 mg, 3.06 mmol, 1.6 eq.) at 25° C., and the mixture was stirred at 25° C. for 6 hrs. The mixture was diluted with $H_2O$ (20 mL) and extracted with EtOAc (10 mL×2). The organic layer was washed with brine (20 mL), dried over $Na_2SO_4$, filtered and concentrated to give a residue. The residue was purified by column (petroleum ether/THF=4/1-3/1) to give racemic 3-(isoquinolin-4-yl)-1-(5-methoxy-2-(trifluoromethyl)pyrimidin-4-yl)-2-oxoimidazolidine-4-carbonitrile (38). The racemate was separated by SFC (column: DAICEL CHIRALPAK IG (250 mm×30 mm, 10 μm); IPA (0.1% $NH_3$—$H_2O$); 27%, 10 min) to give two peaks.

Peak 1: (R)-3-(isoquinolin-4-yl)-1-(5-methoxy-2-(trifluoromethyl)pyrimidin-4-yl)-2-oxoimidazolidine-4-carbonitrile (31a). LCMS (Method 17): $t_R$=2.674 min, $[M+1]^+$ 415.1 LCMS (Method 1): $t_R$=1.104 min, 100.0% $^1$H NMR: $^1$H NMR (400 MHz, CHLOROFORM-d) δ=9.36 (s, 1H), 8.73 (s, 1H), 8.49 (s, 1H), 8.13 (d, J=8.3 Hz, 1H), 7.93-7.89 (m, 1H), 7.88-7.83 (m, 1H), 7.77-7.72 (m, 1H), 5.11 (dd, J=3.4, 8.5 Hz, 1H), 4.88 (dd, J=8.6, 10.6 Hz, 1H), 4.45 (dd, J=3.4, 10.6 Hz, 1H), 4.09 (s, 3H).

Peak 2: (S)-3-(isoquinolin-4-yl)-1-(5-methoxy-2-(trifluoromethyl)pyrimidin-4-yl)-2-oxoimidazolidine-4-carbonitrile (31b). LCMS (Method 17): $t_R$=2.665 min, $[M+1]^+$ 415.1 LCMS (Method 1): $t_R$=1.216 min, 99.7% $^1$H NMR: $^1$H NMR (400 MHz, CHLOROFORM-d) δ=9.36 (s, 1H), 8.73 (s, 1H), 8.49 (s, 1H), 8.13 (d, J=8.3 Hz, 1H), 7.93-7.89 (m, 1H), 7.88-7.83 (m, 1H), 7.77-7.71 (m, 1H), 5.11 (dd, J=3.4, 8.4 Hz, 1H), 4.87 (dd, J=8.6, 10.6 Hz, 1H), 4.44 (dd, J=3.4, 10.6 Hz, 1H), 4.09 (s, 3H).

Example 32: Synthesis of 3-(isoquinolin-4-yl)-2-oxo-1-(5-(trifluoromethyl)pyrazin-2-yl)imidazolidine-4-carbonitrile (32), (R)-3-(isoquinolin-4-yl)-2-oxo-1-(5-(trifluoromethyl)pyrazin-2-yl) imidazolidine-4-carbonitrile (32a) and (S)-3-(isoquinolin-4-yl)-2-oxo-1-(5-(trifluoromethyl) pyrazin-2-yl)imidazolidine-4-carbonitrile (32b)

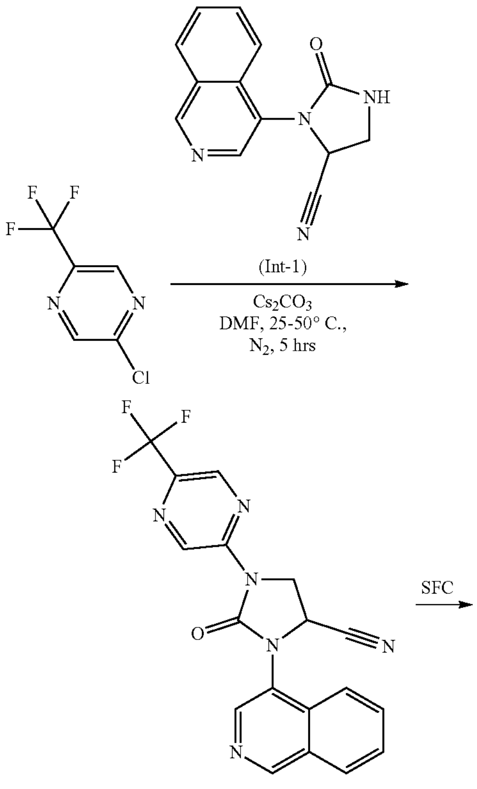

(32)

-continued

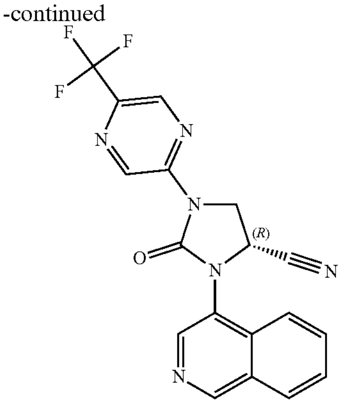

(32a)

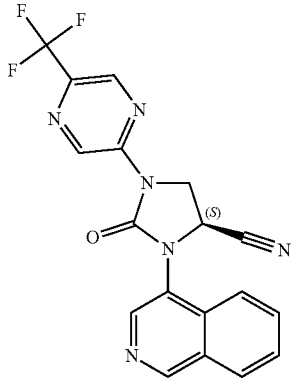

(32b)

To a mixture of 2-chloro-5-(trifluoromethyl)pyrazine (200 mg, 0.8 mmol, 1.0 eq.) in DMF (5 mL) was added 3-(isoquinolin-4-yl)-2-oxoimidazolidine-4-carbonitrile (Int-1) (150 mg, 0.8 mmol, 1.0 eq.) and $Cs_2CO_3$ (550 mg, 1.6 mmol, 2.0 eq.) at 25° C., and the mixture stirred at 50° C. for 5 hrs under $N_2$. The reaction mixture was quenched with $H_2O$ (20 mL). The reaction mixture was extracted with ethyl acetate (20 mL×3). The combined organic layers were washed with brine (20 mL×3), dried over $Na_2SO_4$, filtered and concentrated under reduced pressure to give a residue. The residue was purified by MPLC (Eluent of Ethyl acetate/Petroleum ether=3/1 to 2/1, 40 mL/min) to give 3-(isoquinolin-4-yl)-2-oxo-1-(5-(trifluoromethyl)pyrazin-2-yl)imidazolidine-4-carbonitrile (39). The racemate was separated by SFC (column: DAICEL CHIRALCEL OJ (250 mm×30 mm, 10 μm); liquid phase: [0.1% $NH_3H_2O$ IPA]B %: 46%-46%, 12 min]) to give two peaks.

Peak 1: (S)-3-(isoquinolin-4-yl)-2-oxo-1-(5-(trifluoromethyl)pyrazin-2-yl)imidazolidine-4-carbonitrile (32b) LCMS (Method 13): $t_R$=2.372 min, $[M+1]^+$ 385.0 SFC (Method 45): $t_R$=1.446 min, 100.0% $^1H$ NMR: (400 MHz, CHLOROFORM-d) δ=9.73 (s, 1H), 9.40 (s, 1H), 8.79-8.62 (m, 2H), 8.17 (d, J=8.1 Hz, 1H), 7.89 (br d, J=5.7 Hz, 2H), 7.78 (br d, J=8.1 Hz, 1H), 5.31-5.09 (m, 1H), 4.84-4.65 (m, 2H).

Peak 2: (R)-3-(isoquinolin-4-yl)-2-oxo-1-(5-(trifluoromethyl)pyrazin-2-yl)imidazolidine-4-carbonitrile (32a) LCMS (Method 13): $t_R$=2.372 min, $[M+1]^+$ 385.0 SFC (Method 45): $t_R$=2.791 min, 100.0% $^1H$ NMR: (400 MHz, CHLOROFORM-d) δ=9.73 (s, 1H), 9.40 (s, 1H), 8.79-8.63 (m, 2H), 8.16 (d, J=8.3 Hz, 1H), 7.88 (br d, J=5.5 Hz, 2H), 7.83-7.67 (m, 1H), 5.18 (dd, J=5.6, 8.0 Hz, 1H), 4.84-4.59 (m, 2H).

Example 33: Synthesis of 4-(3-(3-chlorophenyl)-5-cyano-2-oxoimidazolidin-1-yl)isoquinoline-6-carboxylic acid (33), (R)-4-(3-(3-chlorophenyl)-5-cyano-2-oxoimidazolidin-1-yl)isoquinoline-6-carboxylic acid (33a) and (S)-4-(3-(3-chlorophenyl)-5-cyano-2-oxoimidazolidin-1-yl)isoquinoline-6-carboxylic acid (33b)

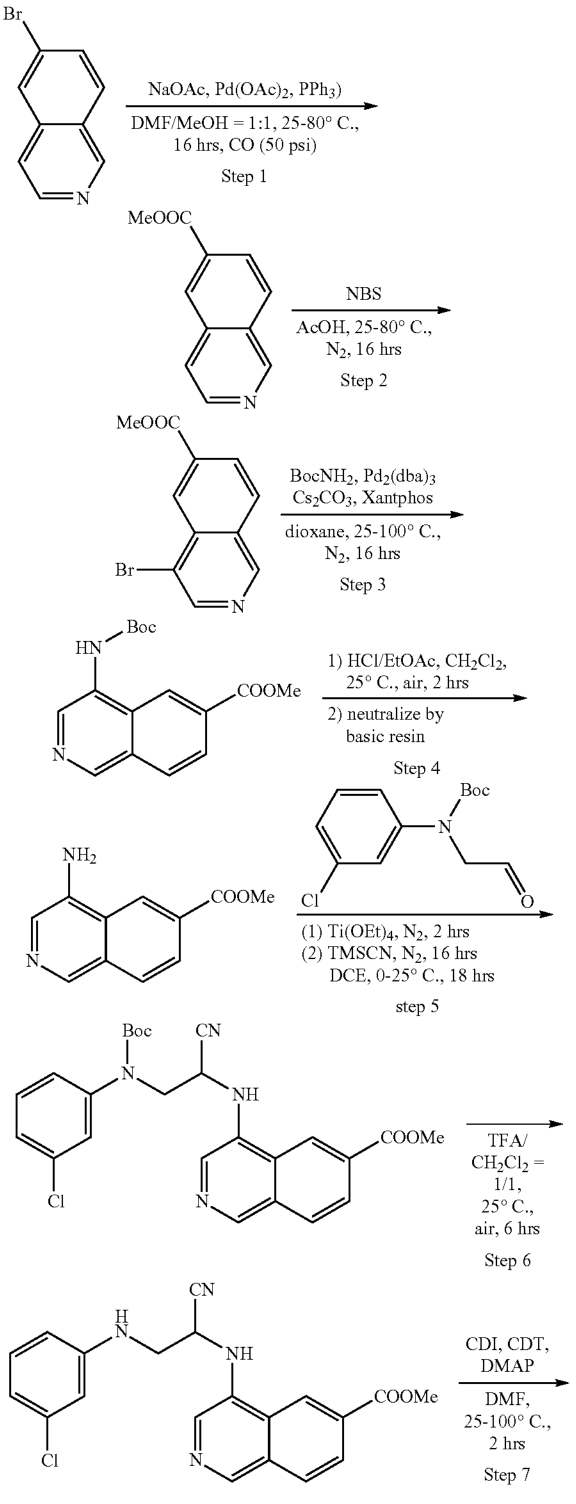

-continued

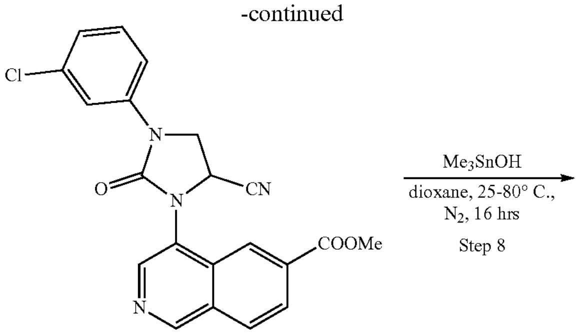

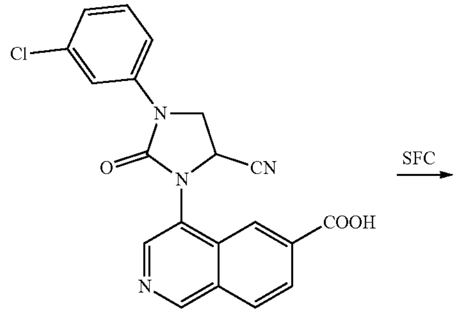

(33)

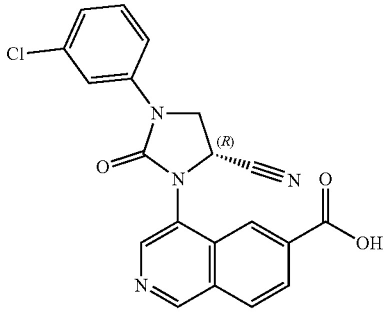

(33a)

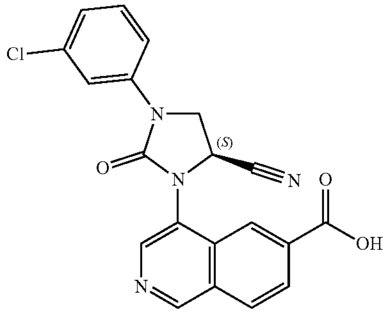

(33b)

Step 1: To a mixture of 6-bromoisoquinoline (35.0 g, 168.23 mmol, 1.0 eq.) and NaOAc (18.0 g, 218.69 mmol, 1.3 eq.) in DMF/MeOH (1.5 L, V/V=1/1) was added $PPh_3$ (7.6 g, 33.65 mmol, 0.2 eq.) and $Pd(OAc)_2$ (8.8 g, 33.65 mmol, 0.2 eq.) at 25° C. under $N_2$. The reaction mixture was stirred at 80° C. under CO (50 Psi) for 16 hrs. The mixture was filtered and the filtrated was concentrated. The mixture was added the water (1.0 L) and extracted with EtOAc (300 mL×3). The combined organic layers were washed with brine (1.0 L), dried over $Na_2SO_4$, filtered and concentrated under reduced pressure to give crude product. The crude product was purified by silica gel column (petroleum ether/EtOAc=I/O to 0/1) to give methyl isoquinoline-6-carboxylate.

Step 2: To a mixture of methyl isoquinoline-6-carboxylate (10.0 g, 53.42 mmol, 1.0 eq.) in AcOH (200 mL) was added NBS (12.4 g, 69.45 mmol, 1.3 eq.) at 25° C. under $N_2$. The reaction mixture was stirred at 80° C. for 16 hrs. The mixture was concentrated and added the water (500 mL) and extracted with EtOAc (200 mL×3). The combined organic layers were washed with brine (500 mL), dried over $Na_2SO_4$, filtered and concentrated under reduced pressure to give crude product. The crude product was purified by silica gel column (petroleum ether/EtOAc=I/O to 0/1) to give methyl 4-bromoisoquinoline-6-carboxylate. LCMS (Method 15): $t_R$=0.826 min, $[M+1]^+$ 266.0.

Step 3: To a mixture of methyl 4-bromoisoquinoline-6-carboxylate (25.0 g, 93.95 mmol, 1.0 eq.) and $BocNH_2$ (14.3 g, 122.14 mmol, 1.3 eq.) in dioxane (1.5 L) was added $Cs_2CO_3$ (60.0 g, 187.90 mmol, 2.0 eq.), $Pd_2(dba)_3$ (2.5 g, cat.) and Xantphos (2.5 g, cat.) at 25° C. under $N_2$. The reaction mixture was stirred at 100° C. for 16 hrs. The mixture was concentrated, added to water (500 mL) and extracted with EtOAc (200 mL×3). The combined organic layers were washed with brine (500 mL), dried over $Na_2SO_4$, filtered and concentrated under reduced pressure to give crude product. The crude product was purified by silica gel column (petroleum ether/EtOAc=I/O to 0/1) to give methyl 4-((tert-butoxycarbonyl)amino)isoquinoline-6-carboxylate. $^1H$ NMR: (400 MHz, CHLOROFORM-d) δ=9.11 (s, 1H) 9.03 (br s, 1H) 8.67 (s, 1H) 8.19 (dd, J=8.50, 1.25 Hz, 1H) 8.05 (d, J=8.50 Hz, 1H) 7.00 (br s, 1H) 4.02 (s, 3H) 1.58 (s, 9H)

Step 4: To a mixture of methyl 4-((tert-butoxycarbonyl)amino)isoquinoline-6-carboxylate (25.0 g, 82.75 mmol, 1.0 eq.) in $CH_2Cl_2$ (300 mL) was added HCl/EtOAc (300 mL, 4 N) at 25° C. and the reaction mixture stirred at 25° C. for 2 hrs. The mixture was concentrated to give crude product. MeOH (20 mL) was added to the crude product and the mixture neutralized to pH=7 using basic resin. The mixture was filtered and the filtrate was concentrated to give methyl 4-aminoisoquinoline-6-carboxylate. LCMS (Method 35): $t_R$=0.578 min, $[M+1]^+$ 203.1

Step 5: To a solution of methyl 4-aminoisoquinoline-6-carboxylate (3.0 g, 14.84 mmol, 1.0 eq.) in DCE (30 mL) was added tert-butyl(3-chlorophenyl)(2-oxoethyl)carbamate (2-4) (6.0 g, 22.25 mmol, 1.5 eq.) and $Ti(OEt)_4$ (6.8 g, 29.67 mmol, 2.0 eq.) at 25° C. under $N_2$ and the reaction mixture was stirred at 25° C. under $N_2$ for 2 hrs. TMSCN (4.4 g, 44.51 mmol, 3.0 eq.) was dropwise added at 0° C. and the reaction mixture stirred at 25° C. under $N_2$ for 14 hrs. The reaction mixture was poured into water (50 mL) and filtered. The filter cake was washed with EtOAc (50 mL×5). The aqueous phase was extracted with EtOAc (40 mL×2). The combined organic layers were washed with brine (40 mL×2), dried over $Na_2SO_4$, filtered and concentrated under reduced pressure to give crude product. The crude product was purified by column (petroleum ether/EtOAc=100/0 to 70/30) to give methyl 4-((2-((tert-butoxycarbonyl)(3-chlorophenyl)amino)-1-cyanoethyl)amino)isoquinoline-6-carboxylate. $^1H$ NMR: (400 MHz, CHLOROFORM-d) δ=8.88 (s, 1H) 8.64 (br s, 1H) 8.24 (d, J=8.56 Hz, 1H) 7.99-8.05 (m, 2H) 7.28-7.31 (m, 2H) 7.20 (s, 1H) 7.05-7.10 (m, 1H) 6.18-6.46 (m, 1H) 4.62 (br d, J=6.11 Hz, 2H) 4.12-4.18 (m, 1H) 4.02 (s, 3H) 1.44 (s, 9H).

Step 6: A solution of methyl 4-((2-((tert-butoxycarbonyl)(3-chlorophenyl)amino)-1-cyanoethyl)amino)isoquinoline-6-carboxylate (3.4 g, 9.15 mmol, 1.0 eq.) in $THF/CH_2Cl_2$ (V/V=1/1, 30 mL) was stirred at 25° C. for 6 hrs. The reaction was poured into aq. $NaHCO_3$ (50 mL) and extracted with $CH_2Cl_2$ (20 mL×3). The combined organic layers were washed with brine (50 mL), dried over $Na_2SO_4$, filtered and concentrated under reduced pressure to give methyl 4-((2-((3-chlorophenyl)amino)-1-cyanoethyl)amino)isoquinoline-6-carboxylate. LCMS (Method 35): $t_R$=0.777 min, $[M+1]^+$ 381.1

Step 7: To the mixture of methyl 4-((2-((3-chlorophenyl)amino)-1-cyanoethyl)amino)isoquinoline-6-carboxylate (2.6 g, 6.84 mmol, 1.0 eq.) in DMF (30 mL) was added CDI (2.2 g, 13.68 mmol, 2.0 eq.), CDT (2.2 g, 13.68 mmol, 2.0 eq.) and DMAP (835 mg, 6.84 mmol, 1.0 eq.) at 25° C.

The mixture was stirred at 100° C. for 2 hrs. The mixture was poured into water (150 mL) and extracted with EtOAc (50 mL×3). The combined organic layers were washed with brine (150 mL), dried over $Na_2SO_4$, filtered and concentrated under reduced pressure to give crude product. The crude product was purified by column (petroleum ether/EtOAc=I/O to 0/1) to give methyl 4-(3-(3-chlorophenyl)-5-cyano-2-oxoimidazolidin-1-yl)isoquinoline-6-carboxylate.

Step 8: To a solution of methyl 4-(3-(3-chlorophenyl)-5-cyano-2-oxoimidazolidin-1-yl)isoquinoline-6-carboxylate (1.0 g, 2.46 mmol, 1.0 eq.) in dioxane (20 mL) was added $Me_3SnOH$ (886 mg, 4.90 mmol, 2.0 eq.) at 25° C. and the reaction mixture stirred at 80° C. under $N_2$ for 16 hrs. The mixture was poured into water (100 mL) and extracted with EtOAc (30 mL×3). The combined organic layers were washed with brine (100 mL), dried over $Na_2SO_4$, filtered and concentrated under reduced pressure to give crude product. The crude product was purified by prep-HPLC (column: Phenomenex luna C18 (250 mm×70 mm, 15 μm); liquid phase: [A-$NH_4HCO_3$; B-ACN]B %: 2%-45%, 20 min]) to give racemic 4-(3-(3-chlorophenyl)-5-cyano-2-oxoimidazolidin-1-yl)isoquinoline-6-carboxylic acid (33). LCMS (Method 17): $t_R$=2.716 min, $[M-1]^-$ 391.1 $^1H$ NMR: (400 MHz, DMSO-$d_6$) δ=9.47-9.49 (m, 1H), 8.73-8.79 (m, 1H), 8.55 (s, 1H), 8.28-8.35 (m, 1H), 8.20-8.25 (m, 1H), 7.80 (t, J=2.02 Hz, 1H), 7.56 (dd, J=8.31, 1.34 Hz, 1H), 7.42-7.48 (m, 1H), 7.18-7.22 (m, 1H), 5.71-5.80 (m, 1H), 4.53-4.62 (m, 2H). The racemate (40) was separated by prep-SFC (column: DAICEL CHIRALCEL OJ (250 mm×30 mm, 10 μm); liquid phase: [A-EtOH; B-ACN]B %: 15%, 12 min]) to give two peaks.

Peak 1: (R)-4-(3-(3-chlorophenyl)-5-cyano-2-oxoimidazolidin-1-yl)isoquinoline-6-carboxylic acid (33a). LCMS (Method 17): $t_R$=2.155 min, $[M+1]^+$ 393.1 SFC (Method 14): $t_R$=1.328 min, 100.0% $^1H$ NMR: (400 MHz, DMSO-d6) δ=13.69 (br d, J=16.14 Hz, 1H) 9.52 (s, 1H) 8.81 (s, 1H) 8.60 (s, 1H) 8.35-8.40 (m, 1H) 8.23 (d, J=8.44 Hz, 1H) 7.79 (t, J=1.96 Hz, 1H) 7.56 (dd, J=8.56, 1.83 Hz, 1H) 7.43-7.48 (m, 1H) 7.19-7.23 (m, 1H) 5.75-5.80 (m, 1H) 4.55-4.60 (m, 2H).

Peak 2: (S)-4-(3-(3-chlorophenyl)-5-cyano-2-oxoimidazolidin-1-yl)isoquinoline-6-carboxylic acid (33b). LCMS (Method 17): $t_R$=2.156 min, $[M+1]^+$ 393.1 SFC (Method 14): $t_R$=3.406 min, 100.0% $^1H$ NMR: (400 MHz, DMSO-d6) δ=13.69 (br d, J=16.14 Hz, 1H) 9.52 (s, 1H) 8.81 (s, 1H) 8.60 (s, 1H) 8.35-8.40 (m, 1H) 8.23 (d, J=8.44 Hz, 1H) 7.79 (t, J=1.96 Hz, 1H) 7.56 (dd, J=8.56, 1.83 Hz, 1H) 7.43-7.48 (m, 1H) 7.19-7.23 (m, 1H) 5.75-5.80 (m, 1H) 4.55-4.60 (m, 2H).

Example 34: Synthesis of 1-(3-chlorophenyl)-3-(6-(2-hydroxypropan-2-yl)isoquinolin-4-yl)-2-oxoimidazolidine-4-carbonitrile (34)

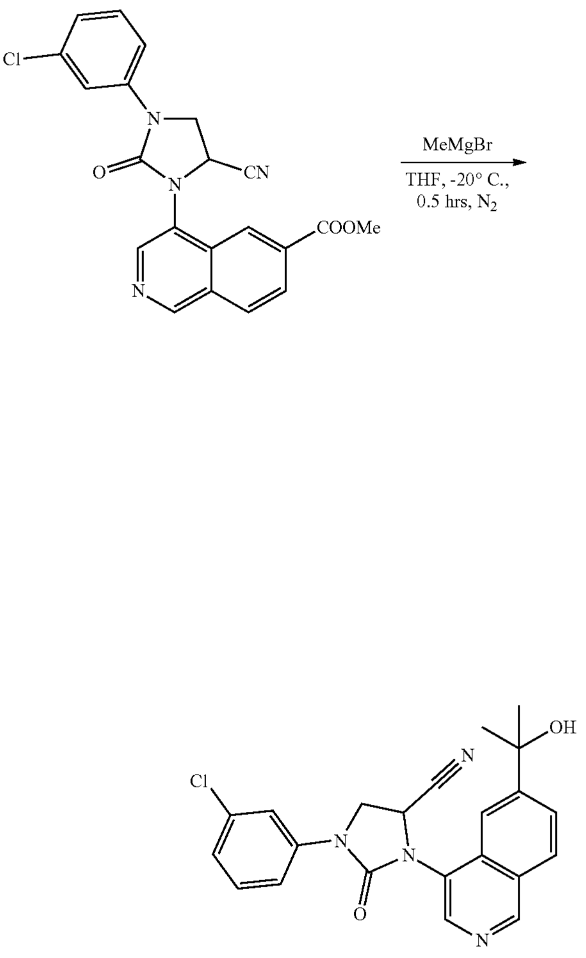

(34)

To the solution of methyl 4-(3-(3-chlorophenyl)-5-cyano-2-oxoimidazolidin-1-yl)isoquinoline-6-carboxylate, (from step 7 Example 40), (400 mg, 0.98 mmol, 1.0 eq.) in THE (2 mL) was added MeMgBr (0.7 mL, 3 M, 1.97 mmol, 2.0 eq.) dropwise at −20° C. and the mixture stirred at −20° C. for 0.5 hrs. The reaction mixture was quenched with water (10 mL) and extracted with EtOAc (5 mL×2). The combined organic layers were washed with brine (10 mL×2), dried over $Na_2SO_4$, filtered and concentrated under reduced pressure to give crude product. The crude product was purified twice by prep-HPLC (column: Waters Xbridge Prep OBD C18 150 mm×40 mm, 10 μm; liquid phase: [A-$H_2O$ (10 mM $NH_4HCO_3$); B-ACN]B %: 35%-65%, 20 min]) to give the product 1-(3-chlorophenyl)-3-(6-(2-hydroxypropan-2-yl)isoquinolin-4-yl)-2-oxoimidazolidine-4-carbonitrile (34). LCMS (Method 17): $t_R$=2.716 min, $[M+1]^+$ 407.2 $^1H$ NMR: (400 MHz, CHLOROFORM-d) δ=9.31 (s, 1H), 8.67 (s, 1H), 8.05-8.15 (m, 2H), 7.74-7.81 (m, 1H), 7.63-7.67 (m, 1H), 7.47-7.52 (m, 1H), 7.33-7.39 (m, 1H), 7.15-7.19 (m, 1H), 5.08-5.14 (m, 1H), 4.50-4.58 (m, 1H), 4.35-4.41 (m, 1H), 1.62 (br s, 6H).

Example 35: Synthesis of 4-(3-(3-chlorophenyl)-5-cyano-2-oxoimidazolidin-1-yl)isoquinoline-6-carboxamide

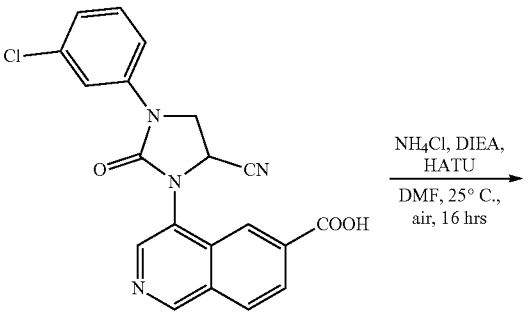

(33)

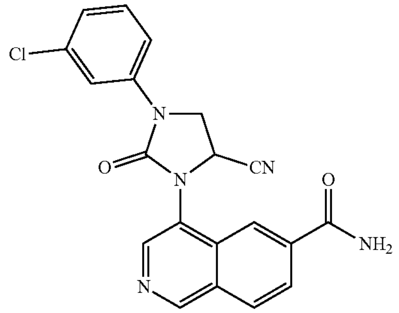

(35)

To a solution of 4-(3-(3-chlorophenyl)-5-cyano-2-oxoimidazolidin-1-yl)isoquinoline-6-carboxylic acid (33) (100 mg, 0.25 mmol, 1.0 eq.) in DMF (2 mL) was added and HATU (145 mg, 0.38 mmol, 1.5 eq.), DIEA (100 mg, 0.75 mmol, 3.0 eq.) $NH_4Cl$ (40 mg, 0.75 mmol, 3.0 eq.) at 25° C. and the mixture stirred at 25° C. for 16 hrs. The mixture was purified by prep-HPLC (column: Phenomenex Luna C18 75 mm×30 mm, 3 μm; liquid phase: [A-$H_2O$ (10 mM FA); B-ACN]B %: 20%-50%, 8 min]) to give 4-(3-(3-chlorophenyl)-5-cyano-2-oxoimidazolidin-1-yl)isoquinoline-6-carboxamide (35). LCMS (Method 17): $t_R$=2.472 min, $[M+1]^+$ 392.1 $^1H$ NMR: (400 MHz, CHLOROFORM-d) δ=9.41 (s, 1H), 8.76 (s, 1H), 8.40 (s, 1H), 8.21 (d, J=8.46 Hz, 1H), 8.04-8.08 (m, 1H), 7.65 (t, J=1.91 Hz, 1H), 7.49 (dd, J=8.34, 1.43 Hz, 1H), 7.37 (t, J=8.17 Hz, 1H), 7.19 (br d, J=8.94 Hz, 1H), 6.31 (br s, 1H), 5.75 (br s, 1H), 5.13 (dd, J=9.12, 4.59 Hz, 1H), 4.56 (t, J=9.42 Hz, 1H), 4.38-4.45 (m, 1H).

Example 36: Synthesis of 4-(3-(3-chlorophenyl)-5-cyano-2-oxoimidazolidin-1-yl)-N-(2-methoxyethyl)isoquinoline-6-carboxamide (36)

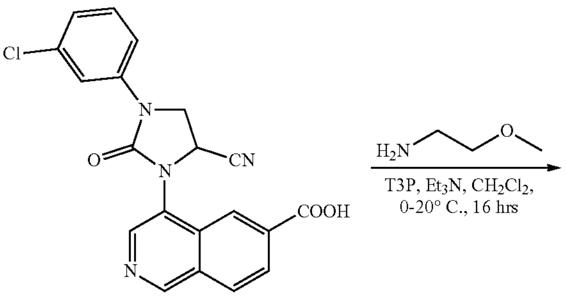

(33)

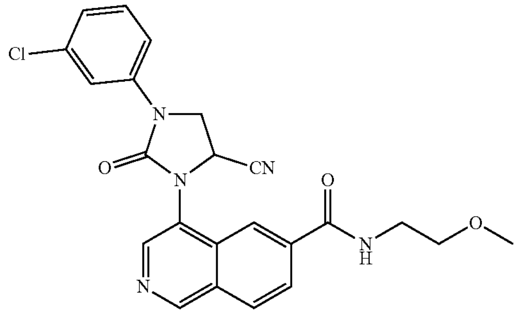

(36)

To a mixture of 4-(3-(3-chlorophenyl)-5-cyano-2-oxoimidazolidin-1-yl)isoquinoline-6-carboxylic acid (33) (100 mg, 0.26 mmol, 1.0 eq.), 2-methoxyethan-1-amine (23 mg, 0.31 mmol, 1.2 eq.) and $Et_3N$ (105 mg, 1.04 mmol, 4.0 eq.) in $CH_2Cl_2$ (1 mL) was added T3P (248 mg, 0.39 mmol, 1.5 eq.) at 0° C. The mixture was stirred at 20° C. for 16 hrs. The mixture was purified by prep-HPLC (column: Waters Xbridge BEH C18 100 mm×30 mm, 10 μm; liquid phase: [A-$H_2O$ (10 mM $NH_4HCO_3$); B-ACN]B %: 25%-55%, 10 min]) to give 4-(3-(3-chlorophenyl)-5-cyano-2-oxoimidazolidin-1-yl)-N-(2-methoxyethyl)isoquinoline-6-carboxamide (36). LCMS (Method 26): $t_R$=1.515 min, $[M+1]^+$ 450.2 $^1H$ NMR: (400 MHz, CHLOROFORM-d) δ=9.38 (s, 1H), 8.76 (s, 1H), 8.38 (s, 1H), 8.18 (d, J=8.56 Hz, 1H), 8.02 (d, J=8.80 Hz, 1H), 7.64 (s, 1H), 7.47 (dd, J=8.25, 1.16 Hz, 1H), 7.35 (t, J=8.13 Hz, 1H), 7.17 (d, J=7.82 Hz, 1H), 6.81-6.87 (m, 1H), 5.14-5.21 (m, 1H), 4.56 (t, J=9.35 Hz, 1H), 4.38 (dd, J=9.78, 4.28 Hz, 1H), 3.68-3.73 (m, 2H), 3.57-3.62 (m, 2H), 3.38 (s, 3H).

Example 37: Synthesis of 1-(3-chlorophenyl)-3-(6-(methylsulfonyl)isoquinolin-4-yl)-2-oxoimidazolidine-4-carbonitrile (37), (R)-1-(3-chlorophenyl)-3-(6-(methylsulfonyl)isoquinolin-4-yl)-2-oxoimidazolidine-4-carbonitrile (37a) and (S)-1-(3-chlorophenyl)-3-(6-(methylsulfonyl)isoquinolin-4-yl)-2-oxoimidazolidine-4-carbonitrile (37b)

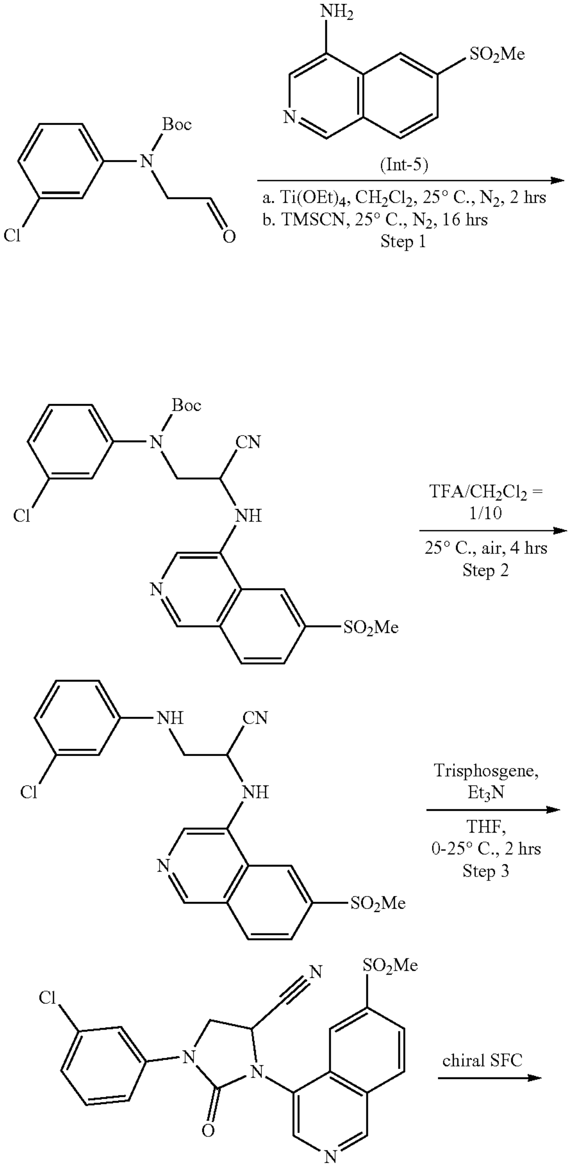

(37)

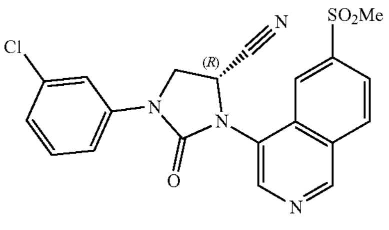

(37a)

-continued

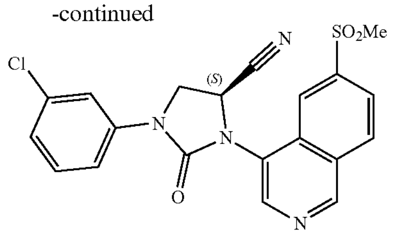

(37b)

Step 1: To a solution of tert-butyl(3-chlorophenyl)(2-oxoethyl)carbamate (2-4) (1.8 g, 6.75 mmol, 1.0 eq.) in $CH_2Cl_2$ (20 mL) was added 6-(methylsulfonyl)isoquinolin-4-amine (Int-5) (1.2 g, 5.40 mmol, 0.8 eq.) and $Ti(OEt)_4$ (3.1 g, 13.50 mmol, 2.0 eq.) at 25° C. under $N_2$ and the mixture was stirred at 25° C. for 2 hrs. TMSCN (2.0 g, 20.25 mmol, 3.0 eq.) was added at 25° C. under $N_2$ and the mixture was stirred at 25° C. for 16 hrs. The reaction was quenched with $H_2O$ (50 mL) and extracted with EtOAc (40 mL×2). The combined organic layers were washed with brine (100 mL×2), dried over $Na_2SO_4$, filtered and concentrated under reduced pressure to give crude product which was purified by column chromatography ($SiO_2$, Petroleum ether/Ethyl acetate=100/1 to 1/1) to give tert-butyl(3-chlorophenyl)(2-cyano-2-((6-(methylsulfonyl)isoquinolin-4-yl)amino)ethyl) carbamate. $^1H$ NMR: (400 MHz, CHLOROFORM-d) δ=8.91 (d, J=4.1 Hz, 1H), 8.18-8.13 (m, 1H), 8.11-8.05 (m, 1H), 7.32-7.25 (m, 2H), 7.22-7.20 (m, 2H), 7.12-7.09 (m, 1H), 4.34-4.28 (m, 1H), 4.04-3.99 (m, 2H), 3.20-3.11 (m, 3H), 1.41 (s, 9H).

Step 2: A solution of tert-butyl(3-chlorophenyl)(2-cyano-2-((6-(methylsulfonyl)isoquinolin-4-yl)amino)ethyl)carbamate (1.4 g, 2.79 mmol, 1.0 eq.) in TFA/$CH_2Cl_2$ (15 mL, 1:10) was stirred at 25° C. for 4 hrs. The reaction was quenched with sat. $NaHCO_3$ solution (50 mL) and extracted with EtOAc (80 mL×2). The combined organic layers were washed with brine (100 mL×2), dried over $Na_2SO_4$, filtered and concentrated under reduced pressure to give 3-((3-chlorophenyl)amino)-2-((6-(methylsulfonyl)isoquinolin-4-yl)amino)propanenitrile.

Step 3: To a solution of 3-((3-chlorophenyl)amino)-2-((6-(methylsulfonyl)isoquinolin-4-yl)amino)propanenitrile (1.4 g, 3.49 mol, 1.0 eq.) in THE (20 mL) was added $Et_3N$ (1.1 g, 10.47 mmol, 3.0 eq.) at 25° C. and triphosgene (1.1 g, 3.49 mmol, 1.0 eq.) in THE (10 mL) was dropwise to the above solution at 0° C. under $N_2$ and the mixture stirred at 25° C. for 16 hrs. The reaction was quenched with sat. $NH_4Cl$ (50 mL) and extracted with EtOAc (40 mL×2). The combined organic layers were washed with brine (80 mL×2), dried over $Na_2SO_4$, filtered and concentrated under reduced pressure to give crude product which was purified by prep-HPLC (column: Phenomenex Luna C 18 150 mm×30 mm, 5 μm; liquid phase: [A-$NaHCO_3$/$H_2O$=0.075% v/v; B-ACN]B %: 25%-55%, 8 min]) to give racemic 1-(3-chlorophenyl)-3-(6-(methylsulfonyl)isoquinolin-4-yl)-2-oxoimidazolidine-4-carbonitrile (37). LCMS (Method 17): $t_R$=2.690 min, $[M+1]^+$ 427.1 $^1H$ NMR: (400 MHz, CHLOROFORM-d) δ=9.50 (s, 1H), 8.87 (s, 1H), 8.58 (s, 1H), 8.35 (d, J=8.6 Hz, 1H), 8.18 (dd, J=1.6, 8.6 Hz, 1H), 7.64 (t, J=2.0 Hz, 1H), 7.48 (dd, J=2.2, 8.3 Hz, 1H), 7.38 (t, J=8.2 Hz, 1H), 7.20 (dd, J=1.0, 8.0 Hz, 1H), 5.16 (dd, J=4.9, 9.0 Hz, 1H), 4.57 (t, J=9.3 Hz, 1H), 4.43 (dd, J=4.9, 9.6 Hz, 1H), 3.15 (s, 3H).

The racemate was separated by prep-SFC (column: REGIS(S, S) WHELK-O (250 mm×25 mm, μm; mobile phase: 0.1% $NH_3H_2O$ EtOH; B % 35%-35%, 20 min]) to give two peaks.

Peak 1: (R)-1-(3-chlorophenyl)-3-(6-(methylsulfonyl)isoquinolin-4-yl)-2-oxoimidazolidine-4-carbonitrile (37a). LCMS (Method 31): $t_R$=2.690 min, $[M+1]^+$ 427.1 SFC Method 15): $t_R$=1.399 min, 100.0% $^1$H NMR: (400 MHz, CHLOROFORM-d) δ=9.50 (s, 1H), 8.88 (s, 1H), 8.59 (s, 1H), 8.35 (d, J=8.6 Hz, 1H), 8.19 (dd, J=1.6, 8.6 Hz, 1H), 7.64 (t, J=2.0 Hz, 1H), 7.48 (dd, J=1.8, 8.1 Hz, 1H), 7.38 (t, J=8.1 Hz, 1H), 7.20 (br d, J=8.0 Hz, 1H), 5.17 (dd, J=4.9, 9.0 Hz, 1H), 4.61-4.54 (m, 1H), 4.44 (dd, J=4.9, 9.6 Hz, 1H), 3.15 (s, 3H)

Peak 2: (S)-1-(3-chlorophenyl)-3-(6-(methylsulfonyl)isoquinolin-4-yl)-2-oxoimidazolidine-4-carbonitrile (37b). LCMS (Method 31): $t_R$=2.684 min, $[M+1]^+$ 427.1 SFC Method 15): $t_R$=1.914 min, 98.5% $^1$H NMR: (400 MHz, CHLOROFORM-d) δ=9.50 (br s, 1H), 8.88 (br s, 1H), 8.60 (s, 1H), 8.36 (d, J=8.4 Hz, 1H), 8.19 (d, J=8.6 Hz, 1H), 7.64 (d, J=1.4 Hz, 1H), 7.48 (br d, J=8.4 Hz, 1H), 7.38 (t, J=8.2 Hz, 1H), 7.20 (br d, J=8.3 Hz, 1H), 5.18 (dd, J=4.8, 9.3 Hz, 1H), 4.61-4.54 (m, 1H), 4.44 (dd, J=4.6, 9.8 Hz, 1H), 3.15 (d, J=1.3 Hz, 3H)

Example 38: Synthesis of 1-(2-methoxy-5-(trifluoromethyl)phenyl)-3-(6-(methylsulfonyl)isoquinolin-4-yl)-2-oxoimidazolidine-4-carbonitrile (38), (R)-1-(2-methoxy-5-(trifluoromethyl)phenyl)-3-(6-(methylsulfonyl)isoquinolin-4-yl)-2-oxoimidazolidine-4-carbonitrile (38a) and (S)-1-(2-methoxy-5-(trifluoromethyl)phenyl)-3-(6-(methylsulfonyl)isoquinolin-4-yl)-2-oxoimidazolidine-4-carbonitrile (38b)

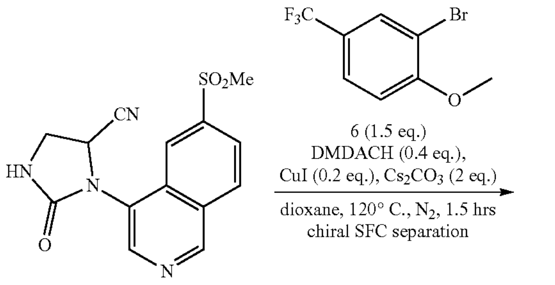

(Int-6)

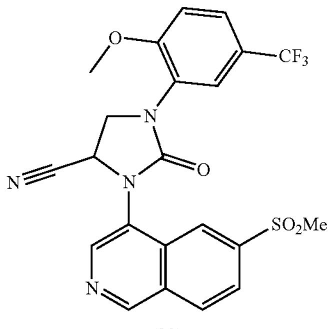

(38)

-continued

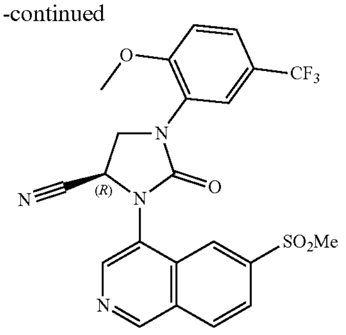

(38a)

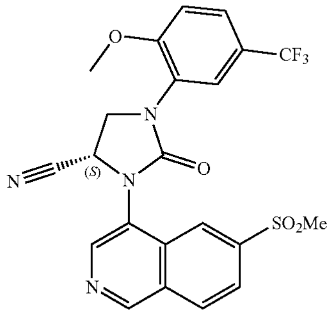

(38b)

A mixture of 3-(6-(methylsulfonyl)isoquinolin-4-yl)-2-oxoimidazolidine-4-carbonitrile (Int-6) (250 mg, 0.79 mmol, 1.0 eq.), 2-bromo-1-methoxy-4-(trifluoromethyl) benzene (302 mg, 1.19 mmol, 1.5 eq.), DMDACH (46 mg, 0.32 mmol, 0.4 eq.), CuI (30 mg, 0.16 mmol, 0.2 eq.) and $Cs_2CO_3$(470 mg, 1.58 mmol, 2.0 eq.) in dioxane (4 mL) was stirred at 120° C. under $N_2$ for 1 hr. The mixture was stirred with LS_2000 thiourea resin (1.0 g) at 25° C. for 2 hrs to remove the Cu catalyst and then filtered. The filtrate was concentrated to give crude product which was purified by column chromatography ($SiO_2$, Petroleum ether/Ethyl acetate=100/1 to 0/1) to give racemic 1-(2-methoxy-5-(trifluoromethyl)phenyl)-3-(6-(methylsulfonyl)isoquinolin-4-yl)-2-oxoimidazolidine-4-carbonitrile (45). The racemate was separated by prep-SFC (column: DAICEL CHIRALPAK AD (250 mm×25 mm, 10 μm; mobile phase: 0.1% $NH_3H_2O$ IPA; B % 32%-32%, 14 min]) to give two peaks.

Peak 1: (R)-1-(2-methoxy-5-(trifluoromethyl)phenyl)-3-(6-(methylsulfonyl)isoquinolin-4-yl)-2-oxoimidazolidine-4-carbonitrile (38a). LCMS (Method 17): $t_R$=2.733 min, $[M+1]^+$ 491.1 SFC Method 33): $t_R$=3.611 min, 99.9% $^1$H NMR: (400 MHz, CHLOROFORM-d) δ=9.47 (s, 1H), 8.89 (s, 1H), 8.65 (s, 1H), 8.33 (d, J=8.6 Hz, 1H), 8.17 (dd, J=1.4, 8.6 Hz, 1H), 7.75 (d, J=1.9 Hz, 1H), 7.65 (dd, J=1.7, 8.7 Hz, 1H), 7.14 (d, J=8.8 Hz, 1H), 5.14 (dd, J=5.1, 8.7 Hz, 1H), 4.49 (t, J=9.1 Hz, 1H), 4.34 (dd, J=5.1, 9.4 Hz, 1H), 4.09 (s, 3H), 3.15 (s, 3H).

Peak 2: (S)-1-(2-methoxy-5-(trifluoromethyl)phenyl)-3-(6-(methylsulfonyl)isoquinolin-4-yl)-2-oxoimidazolidine-4-carbonitrile (38b). LCMS (Method 17): $t_R$=2.733 min, $[M+1]^+$ 491.1 SFC Method 33): $t_R$=4.172 min, 99.8% $^1$H NMR: (400 MHz, CHLOROFORM-d) δ=9.47 (br s, 1H), 8.89 (br s, 1H), 8.65 (s, 1H), 8.33 (d, J=8.6 Hz, 1H), 8.17 (dd, J=1.4, 8.6 Hz, 1H), 7.75 (d, J=2.0 Hz, 1H), 7.65 (dd, J=1.9, 8.8 Hz, 1H), 7.14 (d, J=8.6 Hz, 1H), 5.14 (dd, J=5.1, 8.8 Hz, 1H), 4.49 (t, J=9.1 Hz, 1H), 4.34 (dd, J=5.1, 9.6 Hz, 1H), 4.09 (s, 3H), 3.15 (s, 3H).

Example 39: Synthesis of 4-(3-(3-chlorophenyl)-5-cyano-2-oxoimidazolidin-1-yl)isoquinoline-6-carbonitrile (39), (R)-4-(3-(3-chlorophenyl)-5-cyano-2-oxoimidazolidin-1-yl)isoquinoline-6-carbonitrile (39a) and (S)-4-(3-(3-chlorophenyl)-5-cyano-2-oxoimidazolidin-1-yl)isoquinoline-6-carbonitrile (39b)

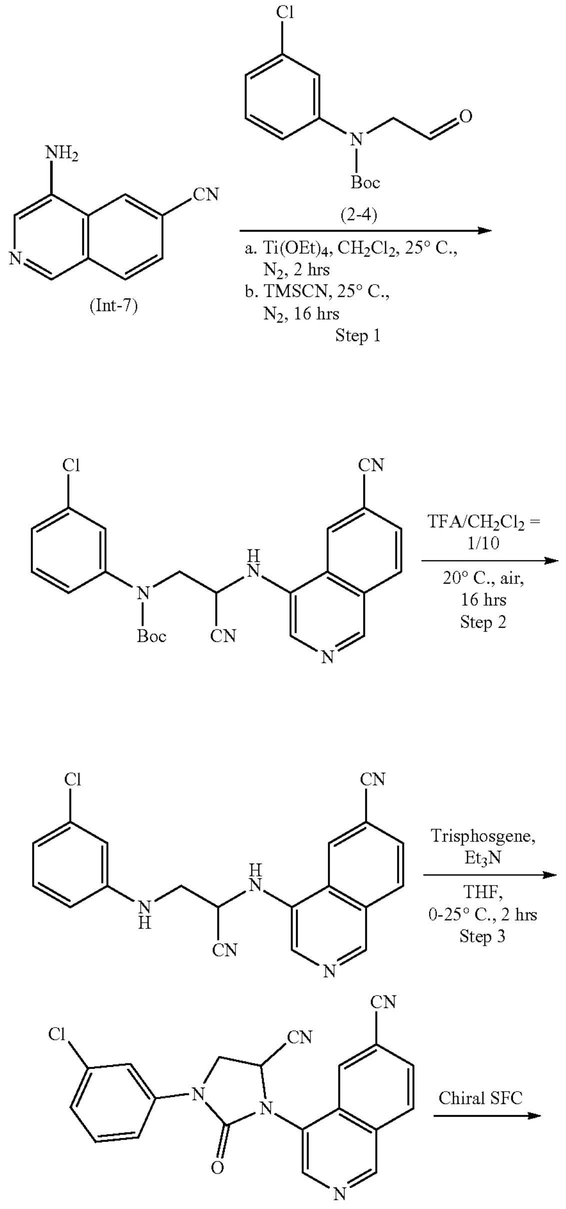

(39)

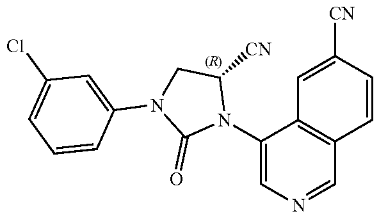

(39a)

-continued

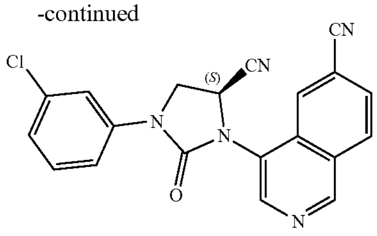

(39b)

Step 1: To a solution of tert-butyl(3-chlorophenyl)(2-oxoethyl)carbamate (2-4) (1.2 g, 4.33 mmol, 1.0 eq.) in $CH_2Cl_2$ (15 mL) was added 4-aminoisoquinoline-6-carbonitrile (Int-7) (600 mg, 3.55 mmol, 0.8 eq.) and $Ti(OEt)_4$ (3.6 g, 8.86 mmol, 2.0 eq.) at 25° C. under $N_2$ and the mixture was stirred at 25° C. for 2 hrs. Then TMSCN (1.3 g, 13.29 mmol, 3.0 eq.) was added to the above mixture at 25° C. under $N_2$ and the mixture was stirred at 25° C. for 16 hrs. The reaction was quenched with $H_2O$ (15 mL) and extracted with EtOAc (30 mL×2). The combined organic layers were washed with brine (10 mL×2), dried over $Na_2SO_4$, filtered and concentrated under reduced pressure to give crude product which was purified by column chromatography ($SiO_2$, Petroleum ether/Ethyl acetate=100/1 to 3/1) to give tert-butyl(3-chlorophenyl)(2-cyano-2-((6-cyanoisoquinolin-4-yl)amino)ethyl)carbamate.

Step 2: A mixture of tert-butyl(3-chlorophenyl)(2-cyano-2-((6-cyanoisoquinolin-4-yl)amino)ethyl)carbamate (400 mg, 1.86 mmol 1.0 eq.) in TFA/$CH_2Cl_2$ (5 mL) was stirred at 20° C. for 16 hrs. The mixture was diluted with iced water (2 mL), adjusted to pH=7 with saturated $NaHCO_3$ aqueous at 0° C. and extracted with EtOAc (15 mL×2). The combined organic layers were washed with brine (15 mL), dried over $Na_2SO_4$, filtered and concentrated to give 4-((2-((3-chlorophenyl)amino)-1-cyanoethyl)amino)isoquinoline-6-carbonitrile (760 mg, crude). LCMS (Method 15): $t_R$=0.644 min, $[M+1]^+$ 348.1.

Step 3: To a solution of 4-((2-((3-chlorophenyl)amino)-1-cyanoethyl)amino)isoquinoline-6-carbonitrile (760 mg, 2.19 mmol, 1.0 eq.) in THF (6 mL) was added $Et_3N$ (880 mg, 8.74 mmol, 4.0 eq.) and a solution of triphosgene (518 mg, 1.75 mmol, 0.8 eq.) in THF (1 mL) at 0° C. under $N_2$ and the mixture was stirred at 25° C. for 2 hrs. The reaction mixture was quenched with $H_2O$ (10 mL) and extracted with EtOAc (10 mL×2). The combined organic layers were washed with brine (10 mL), dried over $Na_2SO_4$, filtered and concentrated to give crude product. The crude product was purified by prep-HPLC (column: Waters Xbridge BEH C18 100 mm×30 mm, 10 μm; liquid phase: [A-10 mM $NH_4HCO_3$ in $H_2O$; B-ACN]B %: 30%-60%, 8 min]) to give racemic 4-(3-(3-chlorophenyl)-5-cyano-2-oxoimidazolidin-1-yl)isoquinoline-6-carbonitrile (39).

The racemate was separated by prep-SFC (column: DAICEL CHIRALPAK AD (250 mm×30 mm, 10 μm; mobile phase A: $CO_2$; mobile phase B: 0.1% $NH_3H_2O$ IPA; B % 42%-42%, 20 min]) to give two peaks.

Peak 1: (R)-4-(3-(3-chlorophenyl)-5-cyano-2-oxoimidazolidin-1-yl)isoquinoline-6-carbonitrile (39a). LCMS (Method 1): $t_R$=2.552 min, $[M+1]^+$ 374.0 SFC (Method 1): $t_R$=1.270 min, 99.6% $^1H$ NMR: (400 MHz, CHLOROFORM-d) δ=9.44 (s, 1H), 8.83 (s, 1H), 8.32 (s, 1H), 8.27-8.21 (m, 1H), 7.87 (dd, J=1.3, 8.4 Hz, 1H), 7.64 (t, J=1.9 Hz, 1H), 7.50 (dd, J=1.5, 8.3 Hz, 1H), 7.38 (t, J=8.1 Hz, 1H), 7.23-7.18 (m, 1H), 5.21-5.11 (m, 1H), 4.56 (t, J=9.4 Hz, 1H), 4.44 (dd, J=4.9, 9.7 Hz, 1H).

Peak 2: (S)-4-(3-(3-chlorophenyl)-5-cyano-2-oxoimidazolidin-1-yl)isoquinoline-6-carbonitrile (39b). LCMS (Method 1): $t_R$=2.551 min, $[M+1]^+$ 374.0 SFC (Method 1): $t_R$=1.421 min, 99.4% $^1H$ NMR: (400 MHz, CHLOROFORM-d) δ=9.45 (bs, 1H), 8.84 (bs, 1H), 8.32 (s, 1H), 8.24 (d, J=8.5 Hz, 1H), 7.88 (d, J=8.9 Hz, 1H), 7.65 (s, 1H), 7.50 (dd, J=1.7, 8.2 Hz, 1H), 7.38 (t, J=8.1 Hz, 1H), 7.21 (d, J=7.9 Hz, 1H), 5.18-5.12 (m, 1H), 4.60-4.53 (m, 1H), 4.47-4.42 (m, 1H).

Example 40: Synthesis of 1-(3-chlorophenyl)-3-(isoquinolin-4-yl)-4-methyl-2-oxoimidazolidine-4-carbonitrile (40), (R)-1-(3-chlorophenyl)-3-(isoquinolin-4-yl)-4-methyl-2-oxoimidazolidine-4-carbonitrile (40a) and (S)-1-(3-chlorophenyl)-3-(isoquinolin-4-yl)-4-methyl-2-oxoimidazolidine-4-carbonitrile (40b)

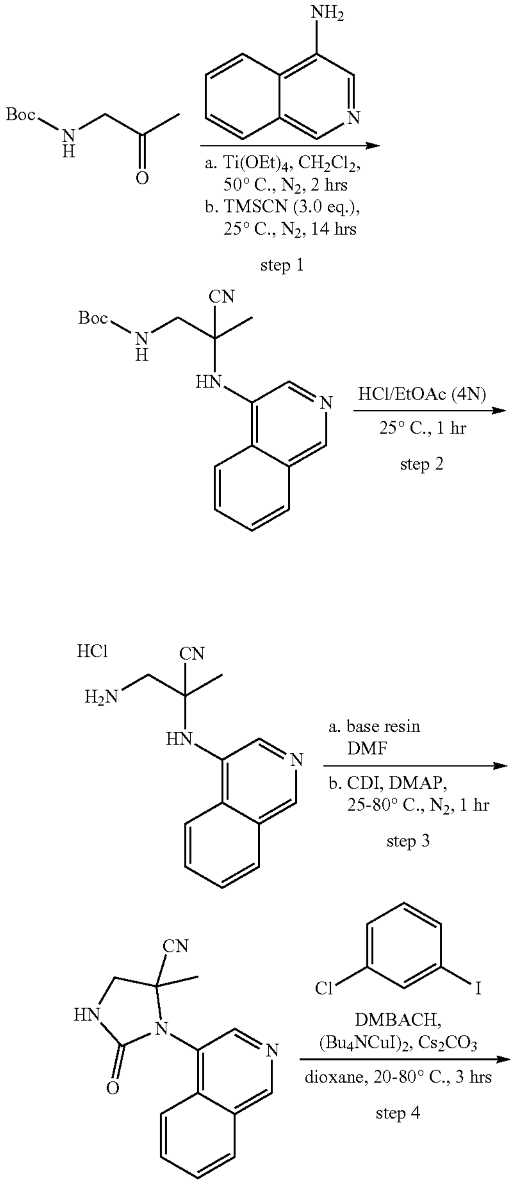

-continued

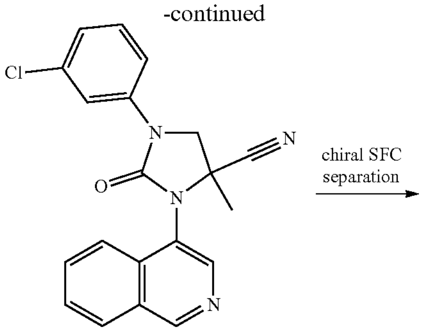

(40)

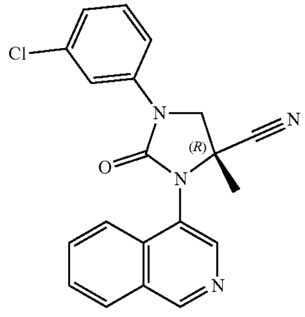

(40a)

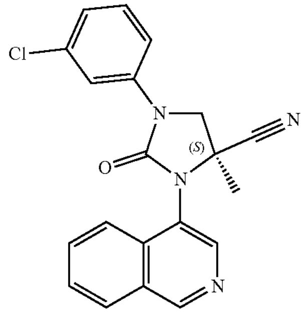

(40b)

Step 1: To a mixture of tert-butyl(2-oxopropyl)carbamate (1.5 g, 8.66 mmol, 1.0 eq.) in $CH_2Cl_2$ (100 mL) was added isoquinolin-4-amine (1.2 g, 8.66 mmol, 1.0 eq.) and $Ti(OEt)_4$ (3.9 g, 17.32 mmol, 2.0 eq.) in turn at 50° C. under $N_2$. The mixture was stirred at 50° C. for 2 hrs. TMSCN (2.5 g, 25.98 mmol, 3.0 eq.) was added into the reaction and the mixture stirred at 25° C. for 14 hrs The reaction mixture was quenched with $H_2O$ (100 mL) and extracted with $CH_2Cl_2$ (100 mL×2). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate=10/1 to 0/1) to give tert-butyl (2-cyano-2-(isoquinolin-4-ylamino)propyl)carbamate. $^1H$ NMR: (400 MHz, CHLOROFORM-d) δ=8.80 (s, 1H), 8.22 (s, 1H), 7.95 (dd, J=8.3, 16.5 Hz, 2H), 7.68 (dt, J=1.3, 7.7 Hz, 1H), 7.64-7.58 (m, 1H), 6.21 (s, 1H), 5.66 (br t, J=6.4 Hz, 1H), 3.96 (dd, J=7.9, 14.8 Hz, 1H), 3.54 (dd, J=5.9, 14.8 Hz, 1H), 1.50 (s, 9H).

Step 2: A mixture of tert-butyl(2-cyano-2-(isoquinolin-4-ylamino)propyl)carbamate (1.8 g, 5.52 mmol, 1.0 eq.) in HCl/EtOAc (4 N) (30 mL) was stirred at 25° C. for 1 hr. The reaction mixture was concentrated under reduced pressure to give 3-amino-2-(isoquinolin-4-ylamino)-2-methylpropanenitrile hydrochloride.

Step 3: 3-amino-2-(isoquinolin-4-ylamino)-2-methylpropanenitrile hydrochloride (1.4 g, 5.32 mmol, 1.0 eq.) was dissolved in DMF (10 mL) and the pH adjusted to pH 7-8 using basic resin. The mixture was stirred, filtered and the filter cake was washed with DMF (5 mL×4). The combined filtrate was dried over $Na_2SO_4$ and filtered to give a solution. To the solution was added CDI (1.7 g, 10.64 mmol, 1.0 eq.) and DMAP (65 mg, 0.53 mmol, 0.1 eq.) at 25° C. The mixture was stirred at 80° C. for 1 hr. The reaction mixture was concentrated under reduced pressure to give a residue which was purified by RP-MPLC to give 3-(isoquinolin-4-yl)-4-methyl-2-oxoimidazolidine-4-carbonitrile. LCMS (Method 27): $t_R$=2.34 min, $[M+1]^+$ 253.1. $^1$H NMR: (400 MHz, CHLOROFORM-d) δ=9.34 (d, J=11.1 Hz, 1H), 8.86 (s, 0.5H), 8.41 (s, 0.5H), 8.14-8.03 (m, 1.5H), 7.92-7.84 (m, 1H), 7.81 (dt, J=1.1, 7.7 Hz, 0.5H), 7.74-7.67 (m, 1H), 6.65-6.41 (m, 1H), 4.18-4.01 (m, 1H), 3.75-3.61 (m, 1H), 1.82 (s, 1.5H), 1.58 (s, 1.5H).

Step 4: To a mixture of 3-(isoquinolin-4-yl)-4-methyl-2-oxoimidazolidine-4-carbonitrile (300 mg, 1.19 mmol, 1.0 eq.) in dioxane (10 mL) was added 1-chloro-3-iodobenzene (285 mg, 1.19 mmol, 1.0 eq.), DMBACH (68 mg, 0.48 mmol, 0.4 eq.), $(Bu_4NCuI)_2$ (134 mg, 0.12 mmol, 0.1 eq.) and $Cs_2CO_3$ (773 mg, 2.38 mmol, 2.0 eq.) at 20° C. under $N_2$. The reaction was stirred at 80° C. for 3 hrs. The mixture was then stirred with LS_2000 thiourea resin (500 mg) at 25° C. for 2 hrs to remove Cu catalyst. The mixture was filtered and the filtrate was concentrated to give crude product which was purified by prep-HPLC (column: Phenomenex Luna C18 75 mm×30 mm, 3 μm; liquid phase: water (HCOOH)-ACN]B %: 40%-65%, 8 min]) to give racemic 1-(3-chlorophenyl)-3-(isoquinolin-4-yl)-4-methyl-2-oxoimidazolidine-4-carbonitrile (47).

The racemate was separated by SFC (column: DAICEL CHIRALPAK AD (250 mm×30 mm, 10 μm); mobile phase: 0.1% $NH_3H_2O$ IPA; B %: 40%-40%, 15 min) to give two peaks.

Peak 1: (R)-1-(3-chlorophenyl)-3-(isoquinolin-4-yl)-4-methyl-2-oxoimidazolidine-4-carbonitrile (40a). LCMS (Method 1): $t_R$=2.426 min, $[M+1]^+$ 363.0 SFC (Method 1): $t_R$=1.306 min, 100.0% $^1$H NMR: (400 MHz, DMSO-$d_6$) δ=9.51-9.44 (m, 1H), 8.67 (s, 0.5H), 8.57 (s, 0.5H), 8.29 (br d, J=8.1 Hz, 0.5H), 8.20 (d, J=8.4 Hz, 0.5H), 8.09 (d, J=8.4 Hz, 1H), 7.93-7.86 (m, 1H), 7.81 (d, J=8.0 Hz, 1H), 7.78-7.73 (m, 1H), 7.56-7.50 (m, 1H), 7.49-7.42 (m, 1H), 7.20 (br d, J=7.9 Hz, 1H), 4.81-4.69 (m, 1H), 4.43-4.28 (m, 1H), 1.89 (s, 1H), 1.63 (s, 2H). Peak 2: (S)-1-(3-chlorophenyl)-3-(isoquinolin-4-yl)-4-methyl-2-oxoimidazolidine-4-carbonitrile (40b). LCMS (Method 1): $t_R$=2.428 min, $[M+1]^+$ 363.0 SFC (Method 1): $t_R$=1.515 min, 99.9% $^1$H NMR: (400 MHz, DMSO-$d_6$) δ=9.48 (d, J=4.0 Hz, 1H), 8.68 (s, 0.5H), 8.57 (s, 0.5H), 8.29 (br d, J=8.0 Hz, 1H), 8.20 (br d, J=8.4 Hz, 0.5H), 8.09 (br d, J=8.5 Hz, 0.5H), 7.93-7.85 (m, 1H), 7.79 (br dd, J=7.0, 16.1 Hz, 2H), 7.57-7.51 (m, 1H), 7.45 (dt, J=2.1, 8.1 Hz, 1H), 7.20 (br d, J=7.8 Hz, 1H), 4.84-4.66 (m, 1H), 4.46-4.23 (m, 1H), 1.89 (s, 1H), 1.63 (s, 2H).

Example 41: Synthesis of (R)-1-(5-chloropyridin-2-yl)-3-(isoquinolin-4-yl)-2-oxoimidazolidine-4-carbonitrile (41a) and (R)-1-(5-chloropyridin-2-yl)-3-(isoquinolin-4-yl)-2-oxoimidazolidine-4-carbonitrile (41b)

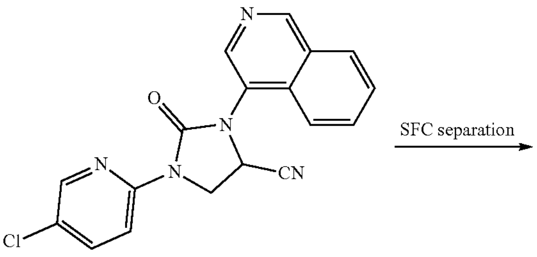

(10)

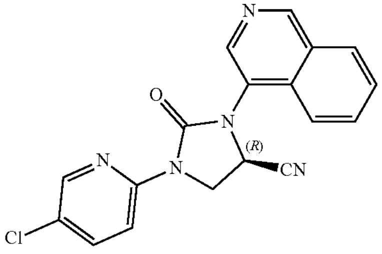

(41a)

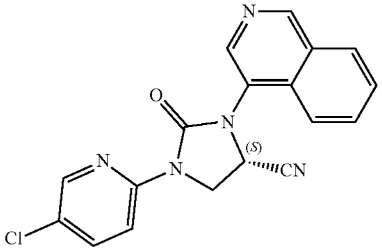

(41b)

Racemic 1-(5-chloropyridin-2-yl)-3-(isoquinolin-4-yl)-2-oxoimidazolidine-4-carbonitrile (10) was separated by SFC (DAICEL CHIRALPAK AD (250 mm×30 mm, 10 μm); Mobile phase: A for $CO_2$ and B for 0.1% $NH_3H_2O$ i-PrOH; Gradient: B %=46% isocratic elution mode; Flow rate: 77 5 mL/min; Wavelength: 220 nm; Column temperature: 35° C.; System back pressure: 120 bar) to give two peaks.

Peak 1: (R)-1-(5-chloropyridin-2-yl)-3-(isoquinolin-4-yl)-2-oxoimidazolidine-4-carbonitrile (41a). LCMS (Method 1): $t_R$=2.830 min, $[M+1]^+$ 350.1 SFC (Method 1): $t_R$=1.599 min, 100.0% $^1$H NMR: (400 MHz, CHLOROFORM-d) δ=9.37 (s, 1H), 8.70 (s, 1H), 8.33 (d, J=2.5 Hz, 1H), 8.24 (d, J=9.0 Hz, 1H), 8.14 (d, J=8.1 Hz, 1H), 7.95-7.88 (m, 1H), 7.87-7.81 (m, 1H), 7.78-7.67 (m, 2H), 5.09 (dd, J=5.4, 8.4 Hz, 1H), 4.73-4.64 (m, 2H).

Peak 2: (S)-1-(5-chloropyridin-2-yl)-3-(isoquinolin-4-yl)-2-oxoimidazolidine-4-carbonitrile (41b). LCMS (Method 1): $t_R$=2.840 min, $[M+1]^+$ 350.1 SFC (Method 1): $t_R$=1.882 min, 99.8% $^1$H NMR: (400 MHz, CHLOROFORM-d) δ=9.36 (s, 1H), 8.70 (s, 1H), 8.33 (d, J=2.0 Hz, 1H), 8.24 (d, J=9.0 Hz, 1H), 8.14 (d, J=8.1 Hz, 1H), 7.94-7.87 (m, 1H), 7.84 (t, J=7.6 Hz, 1H), 7.76-7.68 (m, 2H), 5.09 (dd, J=5.4, 8.4 Hz, 1H), 4.73-4.64 (m, 2H).

Example 42: Synthesis of 3-(isoquinolin-4-yl)-2-oxo-1-(5-(trifluoromethyl)pyrimidin-2-yl)imidazolidine-4-carbonitrile (42), (R)-3-(isoquinolin-4-yl)-2-oxo-1-(5-(trifluoromethyl)pyrimidin-2-yl)imidazolidine-4-carbonitrile (42a) and (S)-3-(isoquinolin-4-yl)-2-oxo-1-(5-(trifluoromethyl)pyrimidin-2-yl)imidazolidine-4-carbonitrile (42b)

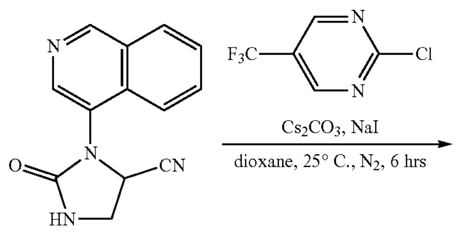

(Int-1)

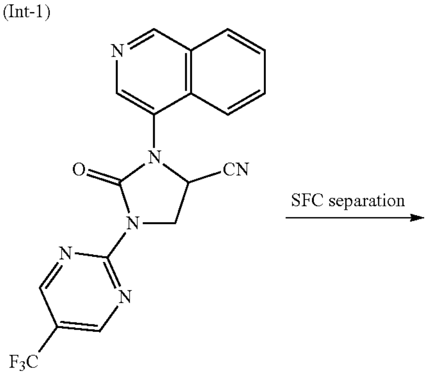

(42)

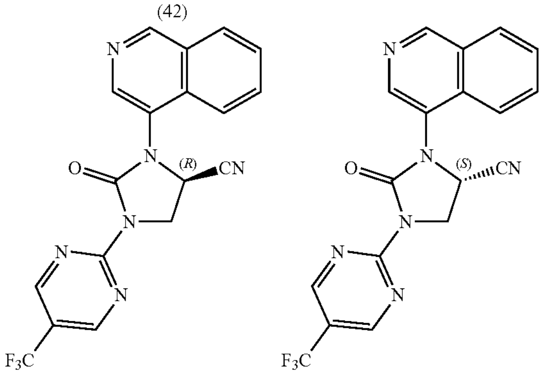

(42a) (42b)

Step 1: To a mixture of 3-(isoquinolin-4-yl)-2-oxoimidazolidine-4-carbonitrile (Int-1) (300 mg, 1.26 mmol, 1.0 eq.) in dioxane (6 mL) was added 2-chloro-5-(trifluoromethyl)pyrimidine (241 mg, 1.32 mmol, 1.05 eq.), $Cs_2CO_3$ (821 mg, 2.52 mmol, 2.0 eq.) and NaI (19 mg, 0.13 mmol, 0.1 eq.) in turn at 25° C. under $N_2$ and the reaction stirred for 6 hrs at 25° C. under $N_2$. The reaction was filtered and quenched with $H_2O$ (6 mL) and extracted with EtOAc (6 mL×2). The combined organic layers were washed with brine (5 mL×3), dried over $Na_2SO_4$, filtered and concentrated under reduced pressure to give crude product which was purified by flash silica gel chromatography (4 g SepaFlash® Silica Flash Column, Eluent of 0-100% Ethyl acetate/Petroleum ether 60 mL/min) to give racemic 3-(isoquinolin-4-yl)-2-oxo-1-(5-(trifluoromethyl)pyrimidin-2-yl)imidazolidine-4-carbonitrile (42). LCMS (Method 34): $t_R$=1.596 min, $[M+1]^+$ 385. $^1H$ NMR: (400 MHz, CHLOROFORM-d), δ=4.67-4.80 (m, 3H), 5.11 (m, 1H), 7.69-7.76 (m, 1H), 7.78-7.85 (m, 1H), 7.90 (br d, J=8.38 Hz, 1H), 8.12 (d, J=8.26 Hz, 1H), 8.70 (s, 1H), 8.93 (s, 2H), 9.36 (s, 1H).

The racemic mixture was further purified by prep-HPLC (column: waters Xbridge prep OBD C18 250 mm×50 mm, 10 μm; mobile phase: [water(10 mM $NH_4CO_3$)-ACN]; B %: 25%-50%, 10 min).

The racemate was then separated by chiral SFC (REGIS (s,s) DAICEL CHIRALPAK IG (250 mm×30 mm, 10 μm); mobile phase: 0.1% $NH_3H_2O$ IPA; B %: 45%-45%, 7 min]) to give two peaks.

Peak 1: (R)-3-(isoquinolin-4-yl)-2-oxo-1-(5-(trifluoromethyl)pyrimidin-2-yl)imidazolidine-4-carbonitrile (42a). LCMS (Method 17): $t_R$=2.545 min, $[M+1]^+$ 385.1 SFC (Method 8): $t_R$=1.328 min, 100% $^1H$ NMR: (400 MHz, CHLOROFORM-d), δ=9.36 (s, 1H), 8.93 (s, 2H), 8.71 (s, 1H), 8.12 (d, J=8.13 Hz, 1H), 7.90 (br d, J=8.13 Hz, 1H), 7.82 (br t, J=7.63 Hz, 1H), 7.69-7.76 (m, 1H), 5.10 (m, 1H), 4.67-4.78 (m, 2H).

Peak 2: (S)-3-(isoquinolin-4-yl)-2-oxo-1-(5-(trifluoromethyl)pyrimidin-2-yl)imidazolidine-4-carbonitrile (42b). LCMS (Method 17): $t_R$=2.545 min, $[M+1]^+$ 385.1 SFC (Method 8): $t_R$=1.734 min, 100% $^1H$ NMR: (400 MHz, CHLOROFORM-d), δ=9.37 (br s, 1H), 8.94 (br s, 2H), 8.65-8.78 (m, 1H), 8.13 (br d, J=7.38 Hz, 1H), 7.90 (br s, 1H), 7.83 (br t, J=6.82 Hz, 1H), 7.70-7.77 (m, 1H), 5.01-5.18 (m, 1H), 4.67-4.79 (m, 2H).

Example 43: Synthesis of (5S)-1-(3-chlorophenyl)-3-(isoquinolin-4-yl)-5-methyl-2-oxoimidazolidine-4-carbonitrile (43), (4R,5S)-1-(3-chlorophenyl)-3-(isoquinolin-4-yl)-5-methyl-2-oxoimidazolidine-4-carbonitrile (43a) and (4S,5S)-1-(3-chlorophenyl)-3-(isoquinolin-4-yl)-5-methyl-2-oxoimidazolidine-4-carbonitrile (43b)

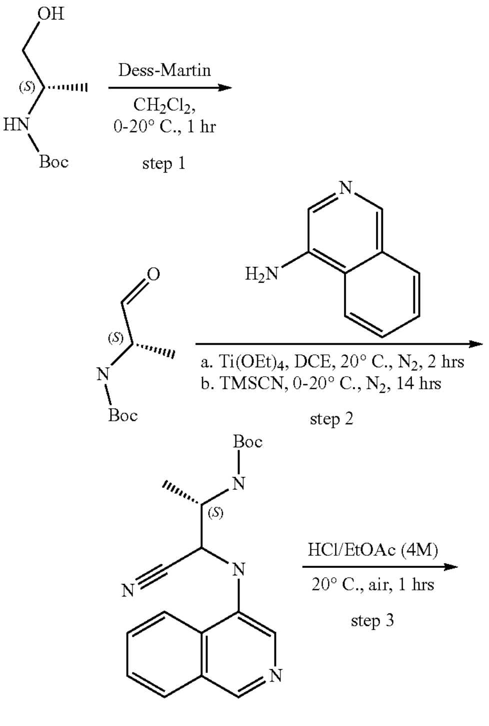

-continued

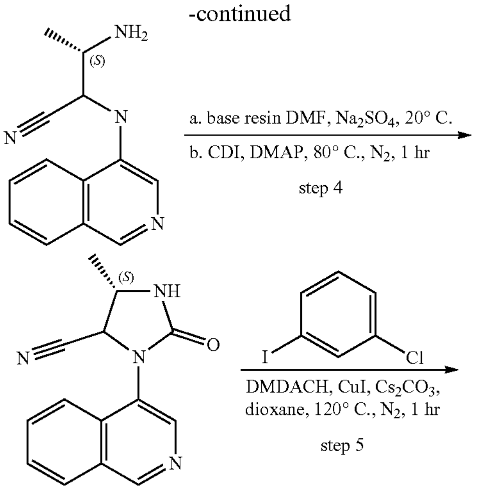

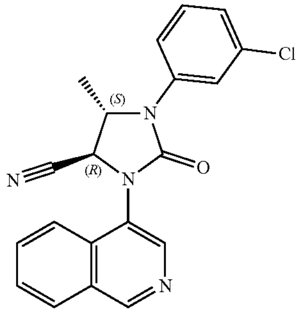

(43a)

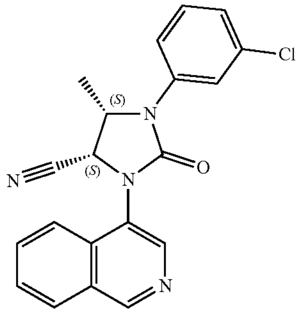

(43b)

Step 1: To a mixture of tert-butyl (S)-(1-hydroxypropan-2-yl)carbamate (25.0 g, 142.65 mmol, 1.0 eq.) in $CH_2Cl_2$ (150 mL) was added a solution of Dess-Martin (60.3 g, 142.65 mmol, 1.0 eq.) in $CH_2Cl_2$ (100 mL) dropwised at 0° C. and the mixture was stirred at 20° C. for 1 hr. A 10% sodium thiosulfate solution (100 mL) was added and the mixture was stirred for 30 min. The organic layers was separated, washed with saturated $NaHCO_3$ (100 mL) solution, dried on a Phase separator cartridge and evaporated under reduce pressure to give tert-butyl (S)-(1-oxopropan-2-yl)carbamate. $^1$H NMR: (400 MHz, CHLOROFORM-d) δ=9.57 (s, 1H), 5.12 (br s, 1H), 4.33-4.14 (m, 1H), 1.47-1.44 (m, 12H).

Step 2: To a solution of tert-butyl (S)-(1-oxopropan-2-yl) carbamate (25.0 g, 144.41 mmol, 1.0 eq.) and isoquinolin-4-amine (17.7 g, 123.00 mmol, 0.9 eq.) in DCE (200 mL) was added $Ti(OEt)_4$ (66.0 g, 288.82 mmol, 2.0 eq.) at 20° C. The mixture was stirred at 20° C. for 2 hrs. TMSCN (43.0 g, 433.23 mmol, 3.0 eq.) was added into the reaction dropwised at 0° C. and the mixture stirred at 20° C. for 14 hrs under $N_2$. The reaction was quenched with $H_2O$ (200 mL) and filtered. The filter cake was washed with $CH_2Cl_2$ (100 mL×5) and the filtrate extracted with $CH_2Cl_2$ (100 mL×2). The combined organic layers were dried over $Na_2SO_4$, filtered and concentrated under reduced pressure to give a residue which was purified by column (Petroleum ether/EtOAc=3/2 to 1/1) to give tert-butyl ((2S)-1-cyano-1-(isoquinolin-4-ylamino)propan-2-yl)carbamate. $^1$H NMR: (400 MHz, CHLOROFORM-d) δ=8.83-8.79 (m, 1H), 8.00-7.87 (m, 3H), 7.72-7.59 (m, 2H), 5.76 (br s, 1H), 4.83 (br d, J=7.1 Hz, 1H), 4.53-4.41 (m, 1H), 4.32-4.25 (m, 1H), 1.56-1.54 (m, 3H), 1.45 (s, 9H).

Step 3: A mixture of tert-butyl ((2S)-1-cyano-1-(isoquinolin-4-ylamino)propan-2-yl)carbamate (32.1 g, 98.34 mmol, 1.0 eq.) in HCl/EtOAc (200 mL, 4 M) was stirred at 20° C. for 1 hr. The mixture was then concentrated to give (3S)-3-amino-2-(isoquinolin-4-ylamino)butanenitrile hydrochloride which was used directly without purification.

Step 4: (3S)-3-Amino-2-(isoquinolin-4-ylamino)butanenitrile hydrochloride (22.0 g, crude, 97.22 mmol, 1.0 eq.) was dissolved in DMF (120 mL) and the pH adjusted to pH 7-8 using basic resin. The mixture was stirred, filtered and the filter cake washed with DMF (20 mL×4). The combined filtrate was dried over $Na_2SO_4$ and filtered to give a solution. To this solution was added CDI (31.5 g, 194.44 mmol, 2.0 eq.), DMAP (2.0 g, Cat.) and 4A Ms (10 g) at 25° C. The mixture was stirred at 80° C. for 1 hrs under $N_2$ and then filtered. The filtrate was concentrated under reduced pressure to give crude product which was purified by RP-MPLC (HCOOH-MeOH) to give (5S)-3-(isoquinolin-4-yl)-5-methyl-2-oxoimidazolidine-4-carbonitrile. LCMS (Method 31): $t_R$=0.539 min, $[M+1]^+$ 253.1

Step 5: A mixture of (5S)-3-(isoquinolin-4-yl)-5-methyl-2-oxoimidazolidine-4-carbonitrile (300 mg, 1.20 mmol, 1.0 eq.), 1-chloro-3-iodobenzene (314 mg, 1.32 mmol, 1.32 eq.), DMDACH (70 mg, 0.48 mmol, 0.4 eq.), CuI (45 mg, 0.24 mmol, 0.2 eq.), $Cs_2CO_3$ (780 mg, 2.40 mmol, 2.0 eq.) and 4A Ms (200 mg) in dioxane (5 mL) was stirred at 120° C. under $N_2$for 1 hr. The reaction mixture was filtered and the filtrate concentrated to give crude residue. The residue was purified by column (petroleum ether/EtOAc=3/7 to 2/8) to give racemic (5S)-1-(3-chlorophenyl)-3-(isoquinolin-4-yl)-5-methyl-2-oxoimidazolidine-4-carbonitrile (43). The racemate was purified by SFC (prep-HPLC (column: Chiralpak AD-3, 50 mm×4.6 mm, 3 μm; A: $CO_2$ B: EtOH(0.1% IPAm, v/v), 3.0 mins) to give two peaks.

Peak 1: (4R,5S)-1-(3-chlorophenyl)-3-(isoquinolin-4-yl)-5-methyl-2-oxoimidazolidine-4-carbonitrile (43a). LCMS (Method 17): $t_R$=2.366 min, $[M+1]^+$ 363.2 SFC (Method 33): $t_R$=3.153 min, 99.4% $^1$H NMR: (400 MHz, DMSO-$d_6$) δ=9.43 (s, 1H), 8.68 (s, 1H), 8.29 (d, J=8.1 Hz, 1H), 8.04-7.97 (m, 1H), 7.94-7.89 (m, 1H), 7.85-7.78 (m, 2H), 7.59 (dd, J=1.4, 8.3 Hz, 1H), 7.46 (t, J=8.1 Hz, 1H), 7.26-7.23 (m, 1H), 5.43 (d, J=3.9 Hz, 1H), 5.20-5.13 (m, 1H), 1.54 (d, J=6.3 Hz, 3H).

Peak 2: (4S,5S)-1-(3-chlorophenyl)-3-(isoquinolin-4-yl)-5-methyl-2-oxoimidazolidine-4-carbonitrile (43b). LCMS (Method 17): $t_R$=2.331 min, $[M+1]^+$ 363.2 SFC (Method 33): $t_R$=3.394 min, 100% $^1$H NMR: (400 MHz, DMSO-$d_6$) δ=9.41 (s, 1H), 8.68 (s, 1H), 8.27 (d, J=8.1 Hz, 1H), 8.09 (d, J=8.3 Hz, 1H), 7.91 (dt, J=1.1, 7.7 Hz, 1H), 7.83-7.77 (m, 1H), 7.69 (s, 1H), 7.48-7.45 (m, 2H), 7.30-7.25 (m, 1H), 5.85 (d, J=8.3 Hz, 1H), 5.15-5.07 (m, 1H), 1.51 (d, J=6.3 Hz, 3H).

Example 44: Synthesis of 3-(isoquinolin-4-yl)-1-(2-methylpyridin-4-yl)-2-oxoimidazolidine-4-carbonitrile (44), (R)-3-(isoquinolin-4-yl)-1-(2-methylpyridin-4-yl)-2-oxoimidazolidine-4-carbonitrile (44a) and (S)-3-(isoquinolin-4-yl)-1-(2-methylpyridin-4-yl)-2-oxoimidazolidine-4-carbonitrile (44b)

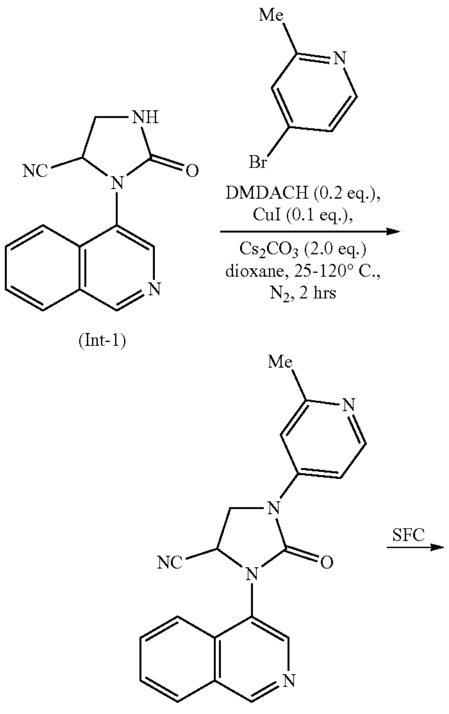

(Int-1)

(44)

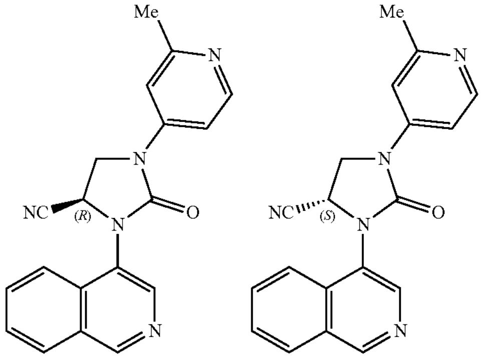

(44a) (44b)

Racemic 3-(isoquinolin-4-yl)-1-(2-methylpyridin-4-yl)-2-oxoimidazolidine-4-carbonitrile (44) was synthesized in a manner similar to Example 4 using 4-bromo-2-methylpyridine in place of 4-trifluoromethyl-iodobenzene. Achiral purification of the racemate of the crude product was achieved using by MPLC (Petroleum ether/EtOAc=50%-70%). Chiral purification of the racemate by SFC (Instrument: Waters UPCC with PDA; Column: Chiralpak AD-3, 150×4.6 mm, 3 um; Mobile phase: A for $CO_2$ and B for IPA (0.1% IPAm); Gradient: B %=40% isocratic elution mode; Flow rate: 2.5 mL/min; Wavelength: 220 nm; Column temperature: 35° C.; System back pressure: 138 bar.) gave 2 peaks.

Peak 1 was assigned as (R)-3-(isoquinolin-4-yl)-1-(2-methylpyridin-4-yl)-2-oxoimidazolidine-4-carbonitrile (44a); LCMS (Method 13): $t_R$=1.49 min, M+1 (330.1); SFC (22): $t_R$=1.63 min, 99.8%; $^1$H NMR: (400 MHz, CHLOROFORM-d) δ=9.36 (s, 1H), 8.69 (s, 1H), 8.47 (d, J=5.7 Hz, 1H), 8.13 (d, J=8.2 Hz, 1H), 7.92-7.81 (m, 2H), 7.78-7.69 (m, 1H), 7.45 (d, J=1.7 Hz, 1H), 7.34 (dd, J=5.7, 2.1 Hz, 1H), 5.14 (dd, J=9.3, 4.5, Hz, 1H), 4.56-4.47 (m, 1H), 4.40 (dd, J=9.9, 4.6 Hz, 1H), 2.59 (s, 3H).

Peak 2 was assigned as (S)-3-(isoquinolin-4-yl)-1-(2-methylpyridin-4-yl)-2-oxoimidazolidine-4-carbonitrile (44b); LCMS (Method 13): $t_R$=1.49 min, M+1 (330.1); SFC (22): $t_R$=2.33 min, 99.4%; $^1$H NMR: (400 MHz, CHLOROFORM-d) δ=9.36 (s, 1H), 8.69 (s, 1H), 8.47 (d, J=5.7 Hz, 1H), 8.13 (d, J=8.2 Hz, 1H), 7.92-7.81 (m, 2H), 7.78-7.69 (m, 1H), 7.45 (d, J=1.7 Hz, 1H), 7.34 (dd, J=5.7, 2.1 Hz, 1H), 5.14 (dd, J=9.3, 4.5, Hz, 1H), 4.56-4.47 (m, 1H), 4.40 (dd, J=9.9, 4.6 Hz, 1H), 2.59 (s, 3H).

Example 45: Synthesis of (R)-3-(isoquinolin-4-yl)-2-oxo-1-(3-(trifluoromethyl)cyclobutyl)imidazolidine-4-carbonitrile (45), (R)-3-(isoquinolin-4-yl)-2-oxo-1-((1 r,3R)-3-(trifluoromethyl)cyclobutyl)imidazolidine-4-carbonitrile (45a) and (R)-3-(isoquinolin-4-yl)-2-oxo-1-((1s,3S)-3-(trifluoromethyl)cyclobutyl)imidazolidine-4-carbonitrile (45b)

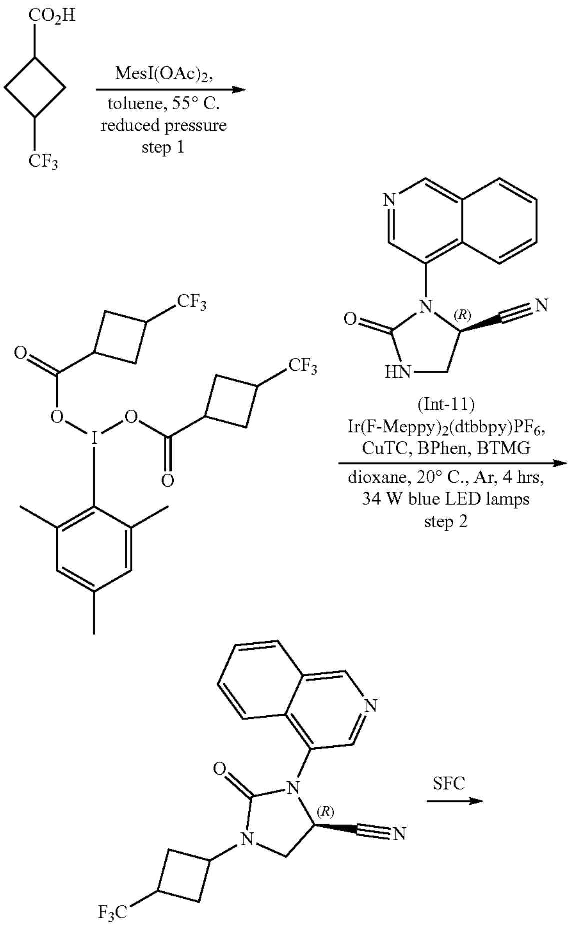

(45)

-continued

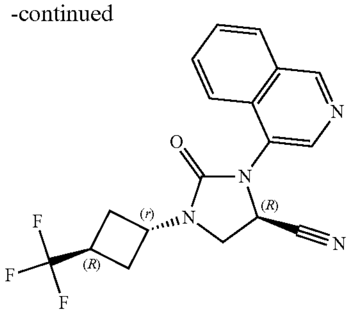

(45a)

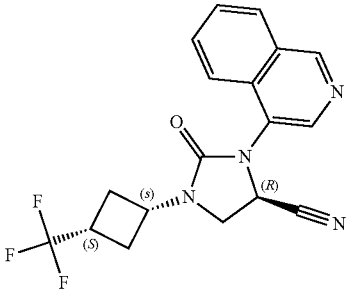

(45b)

Step 1: A flask was charged with Mesl$(OAc)_2$ (21.1 g, 58.03 mmol, 1.0 eq.), 3-(trifluoromethyl)cyclobutane-1-carboxylic acid (20.0 g, 118.97 mmol, 2.05 eq.) and toluene (500 mL). The flask was attached to a rotary evaporator with the water bath heated to 55° C. and the solvent (and the generated acetic acid) was removed over a time period of approximately 10 mins. A second 400 mL aliquot of toluene was added to the flask and the evaporation step was repeated. This was repeated an additional two times with 300 mL toluene each time. After further removal of residual toluene under high-vacuum, mesityl-$\lambda^3$-iodanediyl bis(3-(trifluoromethyl)cyclobutane-1-carboxylate) was obtained which was used without purification. $^1$H NMR: (400 MHz, CHLOROFORM-d) δ=7.11 (s, 2H), 3.18-3.03 (m, 1H), 3.03-2.86 (m, 2H), 2.85-2.65 (m, 7H), 2.54-2.24 (m, 11H).

Step 2: A solution of (R)-3-(isoquinolin-4-yl)-2-oxoimidazolidine-4-carbonitrile (Int-11) (500 mg, 2.10 mmol, 1.0 eq.), mesityl-$\lambda^3$-iodanediyl bis(3-(trifluoromethyl)cyclobutane-1-carboxylate) (2.4 g, 4.20 mmol, 2.0 eq.), Ir(F-Meppy)$_2$ (dtbbpy)$PF_6$ (41 mg, 0.04 mmol, 0.02 eq.), Copper (I) thiophene-2-carboxylate (CuTC) (80 mg, 0.42 mmol, 0.5 eq.), BPhen (209 mg, 0.63 mmol, 0.3 eq.), dioxane (34 mL) and BTMG (1.1 g, 6.30 mmol, 3.0 eq.) at 20° C. was degassed by sparging with nitrogen for 5 minutes and irradiated using 34 W blue LED lamps (3 cm away, with cooling fan to keep the reaction at 20° C.) for 4 hrs while stirring. The reaction was quenched with $H_2O$ (800 mL) and separated. The aqueous layer was extracted with EtOAc (200 mL×2). The combined organic layers were washed with brine (200 mL), dried over $Na_2SO_4$, filtered and concentrated under reduced pressure to give crude product. The crude product was dissolved in EtOAc (200 mL) and thiol resin LS-2000 (5 g) and $Na_2SO_4$ (10 g) were added. The mixture was stirred at 25° C. for 2 hrs. The mixture was filtered and the filtrate was concentrated to dryness to give crude product. The crude product was purified by column (petroleum ether/EtOAc=10/1 to 0/1) to give racemic (R)-3-(isoquinolin-4-yl)-2-oxo-1-(3-(trifluoromethyl)cyclobutyl)imidazolidine-4-carbonitrile (45). LCMS (Method 32): $t_R$=0.639 min, $[M+1]^+$ 361.1.

The racemate was separated by chiral SFC (column: Phenomenex-Cellulose-2 (250 mm×50 mm, 10 μm); liquid phase: [A-$CO_2$; B-ACN]B %: 55%-55%, 20 min]) to give two peaks. $t_{R1}$=0.731 min., $t_R2$=1.165 min.

Peak 1: (R)-3-(isoquinolin-4-yl)-2-oxo-1-((1 r,3R)-3-(trifluoromethyl)cyclobutyl)imidazolidine-4-carbonitrile (45a). LCMS (Method 13): $t_R2$=2.145 min, $[M+1]^+$ 361.1. $^1$H NMR: (400 MHz, CHLOROFORM-d) δ=9.32 (br s, 1H), 8.61 (br s, 1H), 8.09 (br d, J=8.3 Hz, 1H), 7.97-7.76 (m, 2H), 7.75-7.64 (m, 1H), 4.96 (dd, J=4.4, 8.7 Hz, 1H), 4.67 (quin, J=8.4 Hz, 1H), 4.21-4.01 (m, 1H), 3.95 (dd, J=4.5, 9.1 Hz, 1H), 3.04-2.83 (m, 1H), 2.82-2.65 (m, 2H), 2.65-2.48 (m, 2H). SFC: Instrument: Waters UPCC with PDA; Column: Lux-Cellulose-2 (100 mm×4.6 mm, 3 μm); Gradient: mobile phase A-$CO_2$, B-ACN (0.1% IPAm, v/v); B %: 50%-50%, 4 min]), Flow rate: 4 mL/min; Column temperature: 35° C.: $t_R$=0.722 min, 100%. SFC (Method 13): $t_R$=1.846 min., 99.4%, Peak 2 was triturated with hexane/EtOAc (5/1, 20 mL) to give (R)-3-(isoquinolin-4-yl)-2-oxo-1-((1s,3S)-3-(trifluoromethyl)cyclobutyl)imidazolidine-4-carbonitrile (45b). LCMS (Method 13): 2.158 min, $[M+1]^+$ 361.1, 99.8%. $^1$H NMR: (400 MHz, CHLOROFORM-d) 6=9.31 (br s, 1H), 8.60 (br s, 1H), 8.09 (d, J=8.2 Hz, 1H), 7.89-7.76 (m, 2H), 7.74-7.66 (m, 1H), 4.97 (dd, J=4.6, 8.9 Hz, 1H), 4.64 (quin, J=8.9 Hz, 1H), 4.15-4.04 (m, 1H), 3.98 (dd, J=4.6, 9.3 Hz, 1H), 2.87-2.66 (m, 1H), 2.63-2.54 (m, 1H), 2.53 (br s, 3H).

SFC: Instrument: Waters UPCC with PDA; Column: Lux-Cellulose-2 (100 mm×4.6 mm, 3 μm); Gradient: mobile phase A-$CO_2$, B-ACN (0.1% IPAm, v/v); B %: 50%-50%, 4 min]), Flow rate: 4 mL/min; Column temperature: 35° C.: $t_R$=1.166 min., 99.2%. SFC (Method 13): $t_R$=1.686 min., 99.7%.

Example 46: Synthesis of 1-((R)-1-(2-hydroxyethyl)pyrrolidin-3-yl)-3-(isoquinolin-4-yl)-2-oxoimidazolidine-4-carbonitrile (46), (R)-1-((R)-1-(2-hydroxyethyl)pyrrolidin-3-yl)-3-(isoquinolin-4-yl)-2-oxoimidazolidine-4-carbonitrile (46a) and (S)-1-((R)-1-(2-hydroxyethyl)pyrrolidin-3-yl)-3-(isoquinolin-4-yl)-2-oxoimidazolidine-4-carbonitrile (46b)

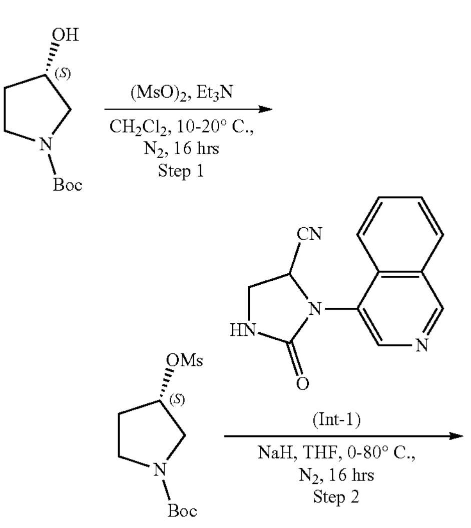

-continued

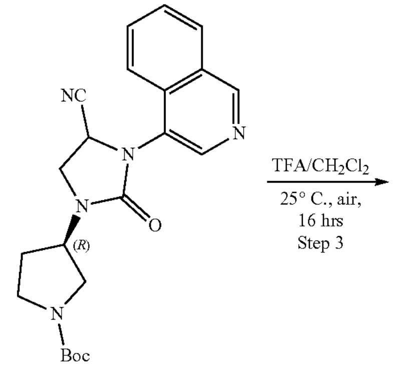

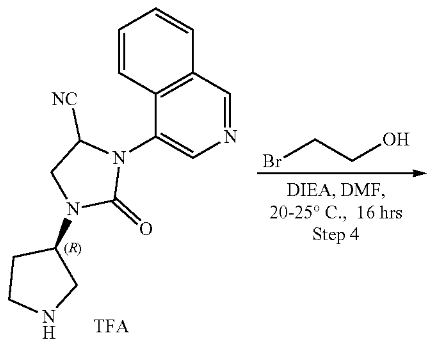

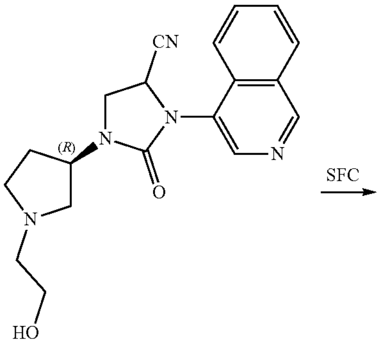

(46)

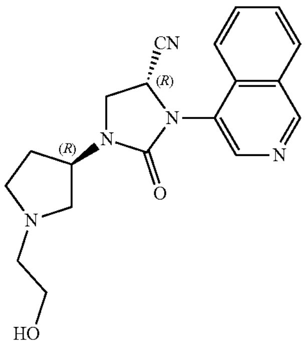

(46a)

-continued

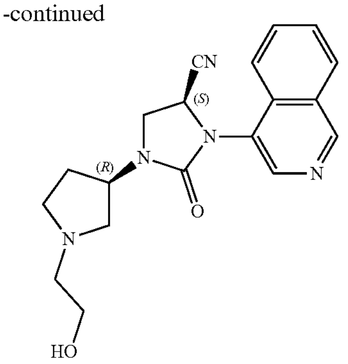

(46b)

Step 1. To a mixture of tert-butyl(S)-3-hydroxypyrrolidine-1-carboxylate (30.0 g, 160.23 mmol, 1.0 eq.) in $CH_2Cl_2$ (200 mL) was added $Et_3N$ (62 mL, 480.69 mmol, 3.0 eq.) and $Ms_2O$ (41.8 g, 240.34 mmol, 1.5 eq.) at 10° C. The reaction was stirred at 20° C. for 16 hrs under $N_2$. The reaction was quenched with $H_2O$ and extracted with $CH_2Cl_2$. The combined organic layers were washed with 0.5M aqueous HCl and brine, dried over $Na_2SO_4$, filtered and concentrated under reduced pressure to give a residue. The residue was purified by MPLC (eluent of ethyl acetate/petroleum ether=1/1 to 3/2, 200 mL/min) to give tert-butyl (S)-3-((methylsulfonyl)oxy)pyrrolidine-1-carboxylate. H NMR: (400 MHz, CHLOROFORM-d) δ=5.27 (br s, 1H), 3.80-3.40 (m, 4H), 3.06 (s, 3H), 2.38-2.22 (m, 1H), 2.20-2.08 (m, 1H), 1.48 (s, 9H)

Step 2. To a mixture of 3-(isoquinolin-4-yl)-2-oxoimidazolidine-4-carbonitrile (Int-1) (5.0 g, 20.99 mmol, 1.0 eq.) in THE (50 mL) was added NaH (1.3 g, 31.48 mmol, 1.5 eq.) at 0° C. under $N_2$.

The reaction was stirred at 0° C. for 1 hr. A solution of tert-butyl(S)-3-((methylsulfonyl)oxy)pyrrolidine-1-carboxylate (8.4 g, 31.48 mmol, 1.5 eq.) in THE (50 mL) was added into the reaction. The reaction was stirred at 80° C. for 16 hrs under $N_2$. The reaction was then quenched with AcOH (1.9 mL) and filtered. The filtrate was concentrated under reduced pressure to give a residue. The residue was purified by MPLC (eluent of THE/Petroleum ether=3/2 to 7/3, 120 mL/min) to give tert-butyl(3R)-3-(4-cyano-3-(isoquinolin-4-yl)-2-oxoimidazolidin-1-yl)pyrrolidine-1-carboxylate. $^1$H NMR: (400 MHz, CHLOROFORM-d) δ=9.31 (s, 1H), 8.62 (s, 1H), 8.10 (d, J=8.3 Hz, 1H), 7.82 (br d, J=5.6 Hz, 2H), 7.74-7.67 (m, 1H), 5.00-4.89 (m, 1H), 4.62-4.73 (m, 1H), 4.05 (t, J=9.1 Hz, 1H), 3.93-3.80 (m, 1H), 3.71-3.57 (m, 2H), 3.54-3.34 (m, 2H), 2.38-2.26 (m, 1H), 2.24-2.09 (m, 1H), 1.50 (s, 9H)

Step 3. A solution of tert-butyl(3R)-3-(4-cyano-3-(isoquinolin-4-yl)-2-oxoimidazolidin-1-yl)pyrrolidine-1-carboxylate (800 mg, 1.96 mmol, 1.0 eq.) in $TFA/CH_2Cl_2$=1/10 (20 mL) was stirred at 25° C. for 16 hrs, then concentrated and lyophilized to give 3-(isoquinolin-4-yl)-2-oxo-1-((R)-pyrrolidin-3-yl)imidazolidine-4-carbonitrile as a TFA salt which was used without further purification.

Step 4. To a mixture of 3-(isoquinolin-4-yl)-2-oxo-1-((R)-pyrrolidin-3-yl)imidazolidine-4-carbonitrile (400 mg, 1.30 mmol, 1.0 eq.) in DMF (6 mL) was added DIEA (1.28 mL, 7.80 mmol, 6.0 eq.) and 2-bromoethanol (406 mg, 3.25 mmol, 2.5 eq.) at 20° C. The reaction was stirred at 25° C. for 16 hrs under $N_2$. The mixture was concentrated to give a residue that was purified by prep-HPLC (column: Waters Xbridge BEH C18 250 mm×50 mm, 10 μm; liquid phase:

[A-$H_2O$ (10 mM $NH_4HCO_3$); B-ACN]B %: 5%-25%, 20 min]) to give 1-((R)-1-(2-hydroxyethyl)pyrrolidin-3-yl)-3-(isoquinolin-4-yl)-2-oxoimidazolidine-4-carbonitrile (46). 1-((R)-1-(2-hydroxyethyl)pyrrolidin-3-yl)-3-(isoquinolin-4-yl)-2-oxoimidazolidine-4-carbonitrile was resolved by chiral SFC (column: ChiralPak IH, 250 mm×30 mm, 10 μm; liquid phase: Neu-ACN B %: 50%-50%, 10 min]) to give 2 peaks.

Peak 1: (R)-1-((R)-1-(2-hydroxyethyl)pyrrolidin-3-yl)-3-(isoquinolin-4-yl)-2-oxoimidazolidine-4-carbonitrile (46a). LCMS (Method 31): $t_R$=1.96 min, $[M+1]^+$ 352.2. SFC (Method 13): $t_R$=2.56 min, 100%. $^1H$ NMR: (400 MHz, CHLOROFORM-d) δ=9.30 (s, 1H), 8.60 (s, 1H), 8.08 (d, J=8.1 Hz, 1H), 7.89-7.75 (m, 2H), 7.74-7.63 (m, 1H), 4.91 (dd, J=4.4, 8.8 Hz, 1H), 4.82-4.71 (m, 1H), 4.10 (t, J=9.3 Hz, 1H), 3.97 (dd, J=4.4, 9.8 Hz, 1H), 3.77-3.66 (m, 2H), 3.10 (dd, J=6.6, 7.9 Hz, 1H), 2.97 (dd, J=2.6, 10.3 Hz, 1H), 2.77-2.65 (m, 2H), 2.61 (dd, J=7.2, 10.3 Hz, 1H), 2.44-2.27 (m, 3H), 2.03-1.90 (m, 1H).

Peak 2: (S)-1-((R)-1-(2-hydroxyethyl)pyrrolidin-3-yl)-3-(isoquinolin-4-yl)-2-oxoimidazolidine-4-carbonitrile (46b). LCMS (Method 31): $t_R$=1.93 min, $[M+1]^+$ 352.2. SFC (Method 13): $t_R$=3.26 min, 99.8%. $^1H$ NMR: (400 MHz, CHLOROFORM-d) δ=9.29 (s, 1H), 8.60 (s, 1H), 8.08 (d, J=8.1 Hz, 1H), 7.91-7.75 (m, 2H), 7.72-7.63 (m, 1H), 4.91 (dd, J=4.5, 8.8 Hz, 1H), 4.79-4.67 (m, 1H), 4.11-4.04 (m, 1H), 4.00-3.94 (m, 1H), 3.72 (t, J=5.4 Hz, 2H), 3.09-2.97 (m, 2H), 2.76-2.67 (m, 3H), 2.43-2.25 (m, 3H), 1.87 (dtd, J=4.8, 8.2, 13.3 Hz, 1H).

Example 47: Synthesis of 3-(isoquinolin-4-yl)-1-(3-methoxy-6-(trifluoromethyl)pyridin-2-yl)-2-oxoimidazolidine-4-carbonitrile (47), (R)-3-(isoquinolin-4-yl)-1-(3-methoxy-6-(trifluoromethyl)pyridin-2-yl)-2-oxoimidazolidine-4-carbonitrile (47a) and (S)-3-(isoquinolin-4-yl)-1-(3-methoxy-6-(trifluoromethyl)pyridin-2-yl)-2-oxoimidazolidine-4-carbonitrile (47b)

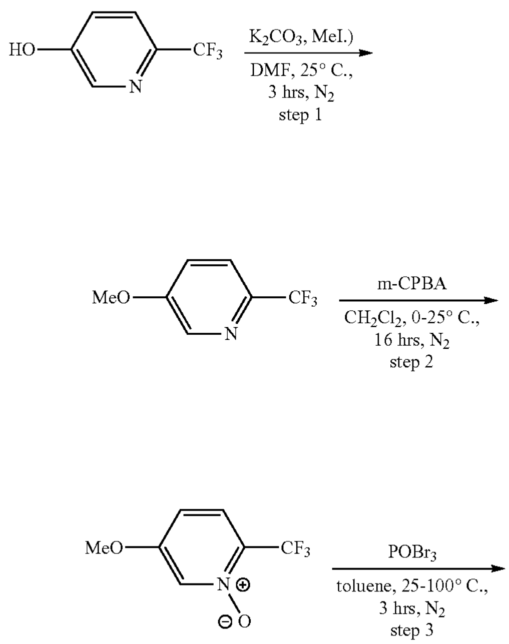

-continued

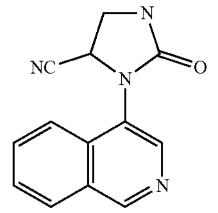

(Int-1)

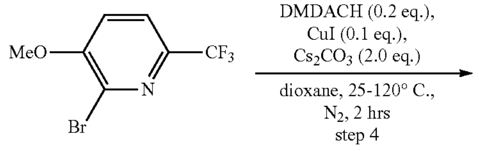

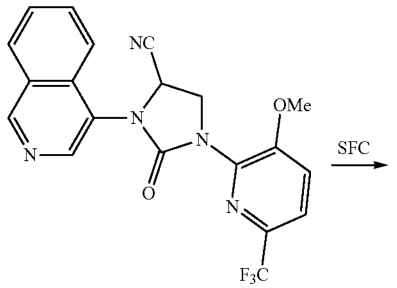

(47)

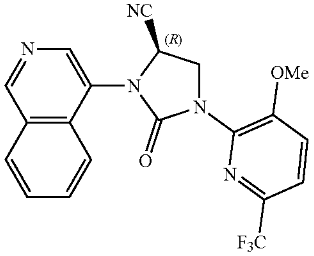

(47a)

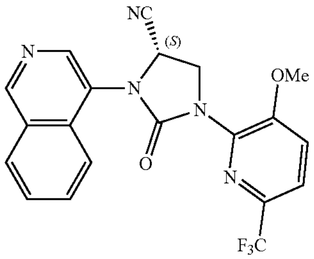

(47b)

Step 1: To a mixture of 6-(trifluoromethyl)pyridin-3-ol (2.0 g, 12.28 mmol, 1.0 eq.) in DMF (20 mL) was added $K_2CO_3$ (1.7 g, 12.28 mmol, 1.0 eq.) and $CH_3I$ (1.7 g, 12.28 mmol, 1.0 eq.) in turn at 25° C. under $N_2$ and the mixture was stirred at 25° C. for 3 hrs under $N_2$. The reaction was quenched with $H_2O$ (100 mL) and extracted with EtOAc (20 mL×3). The combined organic layers were washed with brine (100 mL×5), dried over $Na_2SO_4$, filtered and concentrated under reduced pressure to give a residue. The residue was purified by MPLC (Eluent of Ethyl acetate/Petroleum ether=2/23 to 1/9, 36 mL/min) to give 5-methoxy-2-(trifluoromethyl)pyridine.

Step 2: To a mixture of 5-methoxy-2-(trifluoromethyl) pyridine (1.0 g, 5.65 mmol, 1.0 eq.) in $CH_2Cl_2$ (20 mL) was added m-CPBA (1.7 g, 8.47 mmol, 1.5 eq.) at 0° C. under $N_2$. The mixture was stirred at 25° C. for 16 hrs under $N_2$. The reaction was quenched with $H_2O$ (100 mL) and extracted with EtOAc (50 mL×3). The combined organic layers were washed with $Na_2SO_3$ (100 mL) and $NaHCO_3$ (100 mL), dried over $Na_2SO_4$, filtered and concentrated under reduced pressure to give a residue. The residue was purified by MPLC (Eluent of Ethyl acetate/Petroleum ether=1/2 to 1/1, 50 mL/min) to give 5-methoxy-2-(trifluoromethyl)pyridine 1-oxide. $^1H$ NMR (400 MHz, CHLOROFORM-d) δ=8.06 (d, J=2.0 Hz, 1H), 7.58 (d, J=9.0 Hz, 1H), 6.91 (dd, J=2.0, 9.0 Hz, 1H), 3.91 (s, 3H).

Step 3: To a solution of 5-methoxy-2-(trifluoromethyl) pyridine 1-oxide (1.0 g, 5.18 mmol, 1.0 eq.) in toluene (10 mL) was added $POBr_3$ (1.5 g, 5.18 mmol, 1.0 eq.) at 25° C. The reaction was stirred at 100° C. for 3 hrs under $N_2$. The reaction was quenched with $H_2O$ (50 mL) and extracted with EtOAc (20 mL×3). The combined organic layers were washed with brine (100 mL), dried over $Na_2SO_4$, filtered and concentrated under reduced pressure to give a residue. The residue was purified by MPLC (Eluent of Ethyl acetate/Petroleum ether=1/5 to 3/7, 50 mL/min) to give 2-bromo-3-methoxy-6-(trifluoromethyl)pyridine.

Step 4: Racemic 3-(isoquinolin-4-yl)-1-(3-methoxy-6-(trifluoromethyl)pyridin-2-yl)-2-oxoimidazolidine-4-carbonitrile (47) was synthesized in a manner similar to Example 4 using 2-bromo-3-methoxy-6-(trifluoromethyl)pyridine in place of 4-trifluoromethyl-iodobenzene. Achiral purification of the racemate of the racemate was achieved using MPLC (Eluent of Ethyl acetate/Petroleum ether=1/1 to 7/3, 50 mL/min). Chiral separation of the racemate using SFC (column: DAICEL CHIRALPAK AD (250 mm×30 mm, 10 μm); liquid phase: [0.1% $NH_3H_2O$ in EtOH]B %: 20%-20%, 16 min) gave two peaks. Peak 1 was assigned as (R)-3-(isoquinolin-4-yl)-1-(3-methoxy-6-(trifluoromethyl)pyridin-2-yl)-2-oxoimidazolidine-4-carbonitrile (47a). LCMS (Method 2): $t_R$=2.84 min, M+1(414.1); SFC (Method 23): $t_R$=1.05 min, 100.0%; $^1H$ NMR: (400 MHz, DMSO-$d_6$) δ=9.42 (s, 1H), 8.68 (s, 1H), 8.29 (d, J=8.1 Hz, 1H), 8.06 (d, J=8.4 Hz, 1H), 7.95 (ddd, J=1.2, 7.0, 8.3 Hz, 1H), 7.92-7.87 (m, 1H), 7.85-7.78 (m, 2H), 5.70 (dd, J=3.3, 8.7 Hz, 1H), 4.70 (dd, J=9.9, 8.7 Hz, 1H), 4.31 (dd, J=3.4, 9.9 Hz, 1H), 4.00 (s, 3H).

Peak 2 was assigned as (S)-3-(isoquinolin-4-yl)-1-(3-methoxy-6-(trifluoromethyl)pyridin-2-yl)-2-oxoimidazolidine-4-carbonitrile (47b). LCMS (Method 2): $t_R$=2.84 min, M+1(414.1); SFC (Method 23): $t_R$=1.14 min, 99.7%; $^1H$ NMR: (400 MHz, DMSO-$d_6$) δ=9.42 (s, 1H), 8.68 (s, 1H), 8.29 (d, J=8.1 Hz, 1H), 8.06 (d, J=8.4 Hz, 1H), 7.95 (ddd, J=1.2, 7.0, 8.3 Hz, 1H), 7.92-7.88 (m, 1H), 7.85-7.78 (m, 2H), 5.70 (dd, J=3.4, 8.8 Hz, 1H), 4.70 (dd, J=8.8, 9.8 Hz, 1H), 4.31 (dd, J=3.5, 9.9 Hz, 1H), 4.00 (s, 3H).

Example 48: Synthesis of 3-(isoquinolin-4-yl)-1-(3-(methylsulfonyl)phenyl)-2-oxoimidazolidine-4-carbonitrile (48), (R)-3-(isoquinolin-4-yl)-1-(3-(methylsulfonyl)phenyl)-2-oxoimidazolidine-4-carbonitrile (48a) and (S)-3-(isoquinolin-4-yl)-1-(3-(methylsulfonyl)phenyl)-2-oxoimidazolidine-4-carbonitrile (48b)

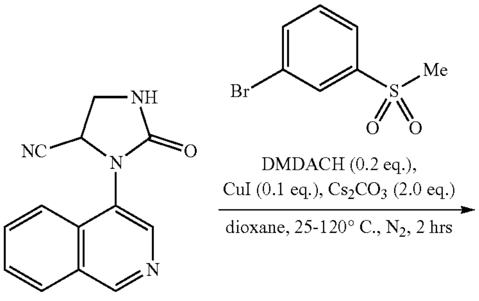

(Int-1)

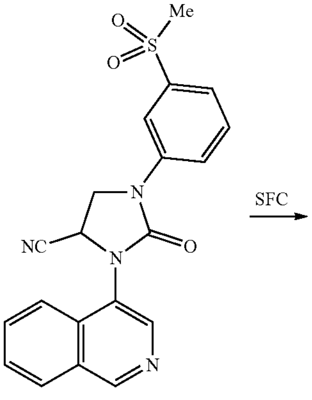

(48)

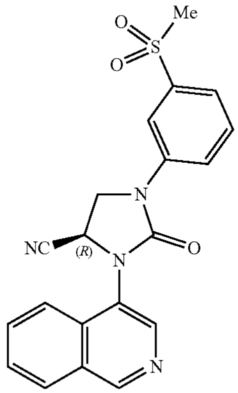

(48a)

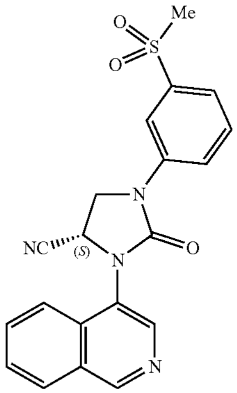

(48b)

Racemic 3-(isoquinolin-4-yl)-1-(3-(methylsulfonyl)phenyl)-2-oxoimidazolidine-4-carbonitrile (48) was synthesized in a manner similar to Example 4 using 1-bromo-3-(methylsulfonyl)benzene in place of 4-trifluoromethyl-iodobenzene. Achiral purification of the racemate of the racemate was achieved using prep-HPLC (column: Phenomenex Luna C18 75 mm×30 mm, 3 μm; liquid phase:

[A-$NH_4HCO_3/H_2O$=0.1% v/v; B-ACN]B %: 25%-55%, 8 min]). Chiral separation of the racemate by SFC (Instrument: Waters UPCC with SQ Detector 2; column: DAICEL CHIRALCEL OJ (250 mm×30 mm, 10 μm; mobile phase: 0.1% $NH_3$—$H_2O$ IPA; B % 20-50%, flow rate: 3.4 mL/min, column temp: 35 C, 25 min) gave 2 peaks.

Peak 1 was assigned as (R)-3-(isoquinolin-4-yl)-1-(3-(methylsulfonyl)phenyl)-2-oxoimidazolidine-4-carbonitrile (48a). LCMS (Method 1): $t_R$=2.40 min, M+1 (393.2); SFC (Method 2): $t_R$=1.55 min, 99.8%; $^1$H NMR: (400 MHz, DMSO-$d_6$) δ=9.44 (s, 1H), 8.70 (s, 1H), 8.29 (d, J=8.1 Hz, 1H), 8.25 (s, 1H), 8.13 (d, J=8.4 Hz, 1H), 7.94-7.87 (m, 2H), 7.84-7.78 (m, 1H), 7.73-7.65 (m, 2H), 5.72 (dd, J=4.7, 9.2 Hz, 1H), 4.69-4.62 (m, 1H), 4.59-4.54 (m, 1H), 3.24 (s, 3H). Peak 2 was assigned as (S)-3-(isoquinolin-4-yl)-1-(3-(methylsulfonyl)phenyl)-2-oxoimidazolidine-4-carbonitrile (48b). LCMS (Method 1): $t_R$=2.40 min, M+1 (393.2); SFC (Method 2): $t_R$=1.71 min, 99.8%; $^1$H NMR: (400 MHz, DMSO-$d_6$) δ=9.44 (s, 1H), 8.70 (s, 1H), 8.29 (d, J=8.1 Hz, 1H), 8.25 (s, 1H), 8.14 (d, J=8.4 Hz, 1H), 7.94-7.88 (m, 2H), 7.83-7.78 (m, 1H), 7.73-7.66 (m, 2H), 5.72 (dd, J=4.8, 9.3 Hz, 1H), 4.69-4.62 (m, 1H), 4.59-4.54 (m, 1H), 3.24 (s, 3H).

Example 49: Synthesis of 3-(isoquinolin-4-yl)-2-oxo-1-(4-(trifluoromethyl)pyrimidin-2-yl)imidazolidine-4-carbonitrile (49), (R)-3-(isoquinolin-4-yl)-2-oxo-1-(4-(trifluoromethyl)pyrimidin-2-yl) imidazolidine-4-carbonitrile (49a) and (S)-3-(isoquinolin-4-yl)-2-oxo-1-(4-(trifluoromethyl) pyrimidin-2-yl)imidazolidine-4-carbonitrile (49b)

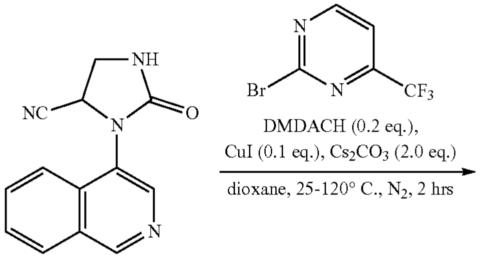

(Int-1)

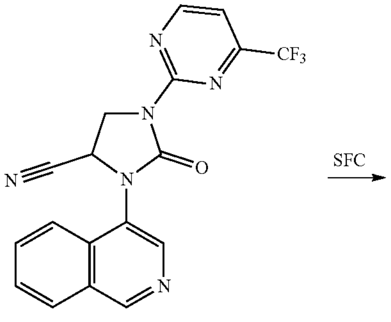

(49)

-continued

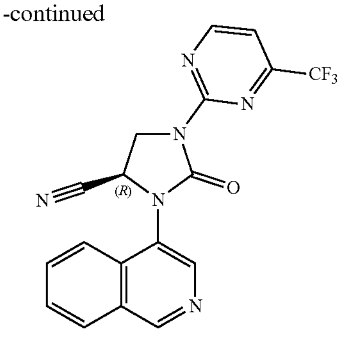

(49a)

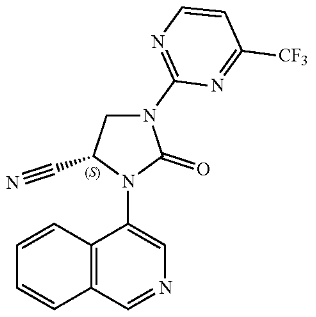

49b)

Racemic 3-(isoquinolin-4-yl)-2-oxo-1-(4-(trifluoromethyl)pyrimidin-2-yl)imidazolidine-4-carbonitrile (49) was synthesized in a manner similar to Example 4 using 2-bromo-4-(trifluoromethyl)pyrimidine in place of 4-trifluoromethyl-iodobenzene. Achiral purification of the racemate of the racemate was achieved by prep-HPLC (column: Phenomenex Luna C18 200 mm×40 mm, 10 μm; mobile phase: [water (HCOOH)-CAN]; B %: 15%-45%, 8 min). Chiral separation of the racemate by SFC (Instrument: Waters UPCC with SQ Detector 2; column: WHELK-01 (250 mm*30 mm, 5 um); mobile phase: 0.1% $NH_3H_2O$ MeOH; B %: 50%13 min) gave 2 peaks. The enantiopure material was repurified by prep-HPLC (column: Waters Xbridge BEH C18 100*30 mm*10 um); mobile phase: water ($NH_4HCO_3$)-ACN; B %: 30%-60%, 8 min).

Peak 1 was assigned as (R)-3-(isoquinolin-4-yl)-2-oxo-1-(4-(trifluoromethyl)pyrimidin-2-yl)imidazolidine-4-carbonitrile (49a). LCMS (Method 13): $t_R$=2.13 min, M+1(385.1); SFC (Method 24): $t_R$=1.75 min, 99.9%; $^1$H NMR: (400 MHz, CHLOROFORM-d) δ=9.37 (s, 1H), 9.01 (d, J=4.9 Hz, 1H), 8.72 (s, 1H), 8.13 (d, J=8.1 Hz, 1H), 7.91 (br d, J=7.7 Hz, 1H), 7.83 (t, J=7.7 Hz, 1H), 7.76-7.70 (m, 1H), 7.42 (d, J=4.9 Hz, 1H), 5.14-5.06 (m, 1H), 4.80-4.69 (m, 2H).

Peak 2 was assigned as (S)-3-(isoquinolin-4-yl)-2-oxo-1-(4-(trifluoromethyl)pyrimidin-2-yl)imidazolidine-4-carbonitrile (49b). LCMS (Method 13): $t_R$=2.13 min, M+1(385.1); SFC (Method 24): $t_R$=1.91 min, 98.6%. $^1$H NMR: (400 MHz, CHLOROFORM-d) δ=9.37 (s, 1H), 9.01 (d, J=4.9 Hz, 1H), 8.72 (s, 1H), 8.13 (d, J=8.3 Hz, 1H), 7.91 (br d, J=8.1 Hz, 1H), 7.83 (s, 1H), 7.74 (d, J=7.3 Hz, 1H), 7.42 (d, J=4.9 Hz, 1H), 5.10 (dd, J=4.3, 8.8 Hz, 1H), 4.82-4.67 (m, 2H).

Example 50: Synthesis of 1-(4-cyanophenyl)-3-(isoquinolin-4-yl)-2-oxoimidazolidine-4-carbonitrile (50), (R)-1-(4-cyanophenyl)-3-(isoquinolin-4-yl)-2-oxoimidazolidine-4-carbonitrile (50a) and (S)-1-(4-cyanophenyl)-3-(isoquinolin-4-yl)-2-oxoimidazolidine-4-carbonitrile (50b)

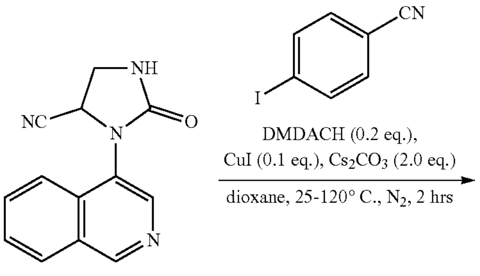

(Int-1)

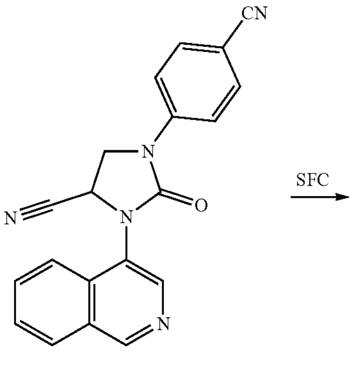

(50)

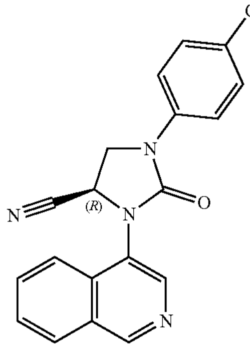

(50a)

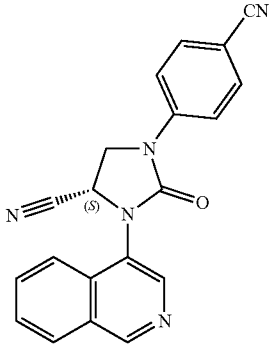

(50b)

Racemic 1-(4-cyanophenyl)-3-(isoquinolin-4-yl)-2-oxoimidazolidine-4-carbonitrile (50) was synthesized in a manner similar to Example 4 using 4-iodobenzonitrile in place of 4-trifluoromethyl-iodobenzene. Achiral purification of the racemate of the racemate was achieved by prep-HPLC (column: Phenomenex Luna C18 75 mm×30 mm, 3 μm; liquid phase: water (HCOOH)-ACN]B %: 25%-50%, 8 min]. Chiral separation of the racemate by SFC (Instrument: Waters UPCC with SQ Detector; column: DAICEL CHIRALPAK AD (250 mm×30 mm, 10 μm); mobile phase: 0.1% $NH_3H_2O$ EtOH; B %: 55%-55%, 7 min).

Peak 1 was assigned as (R)-1-(4-cyanophenyl)-3-(isoquinolin-4-yl)-2-oxoimidazolidine-4-carbonitrile (50a). LCMS (Method 1): $t_R$=2.09 min, M+1(340.1); SFC (Method 15): $t_R$=1.69 min, 100.0%; $^1$H NMR: (400 MHz, CHLOROFORM-d) δ=9.37 (s, 1H), 8.69 (s, 1H), 8.14 (d, J=8.1 Hz, 1H), 7.93-7.81 (m, 2H), 7.77-7.68 (m, 5H), 5.14 (dd, J=4.4, 9.2 Hz, 1H), 4.55 (dd, J=9.2, 9.8 Hz, 1H), 4.42 (dd, J=4.5, 9.8 Hz, 1H).

Peak 2 was assigned as (S)-1-(4-cyanophenyl)-3-(isoquinolin-4-yl)-2-oxoimidazolidine-4-carbonitrile (50b). LCMS (Method 1): $t_R$=2.09 min, M+1(340.1); SFC (Method 15): $t_R$=1.97 min, 99.2%; $^1$H NMR: (400 MHz, CHLOROFORM-d) δ=9.37 (s, 1H), 8.70 (s, 1H), 8.14 (d, J=8.1 Hz, 1H), 7.93-7.83 (m, 2H), 7.77-7.70 (m, 5H), 5.15 (dd, J=4.4, 9.2 Hz, 1H), 4.56 (dd, J=9.8, 9.2 Hz, 1H), 4.43 (dd, J=4.5, 9.8 Hz, 1H).

Example 51: Synthesis of 3-(isoquinolin-4-yl)-2-oxo-1-(6-(trifluoromethyl)pyridin-2-yl)imidazolidine-4-carbonitrile (51), (R)-3-(isoquinolin-4-yl)-2-oxo-1-(6-(trifluoromethyl)pyridin-2-yl)imidazolidine-4-carbonitrile (51a) and (S)-3-(isoquinolin-4-yl)-2-oxo-1-(6-(trifluoromethyl)pyridin-2-yl)imidazolidine-4-carbonitrile (51b)

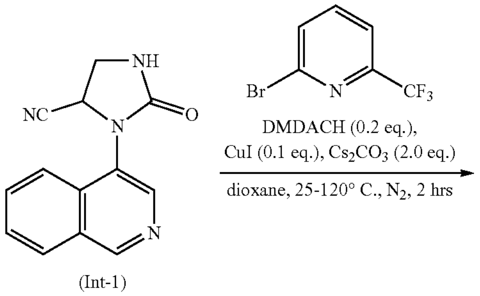

(Int-1)

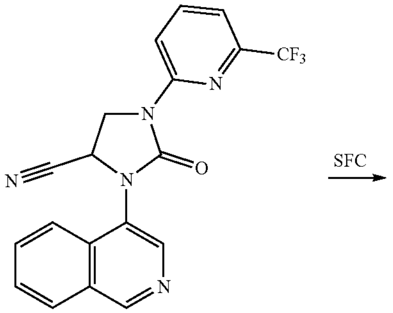

(51)

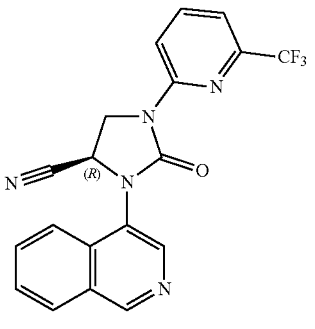

(51a)

-continued

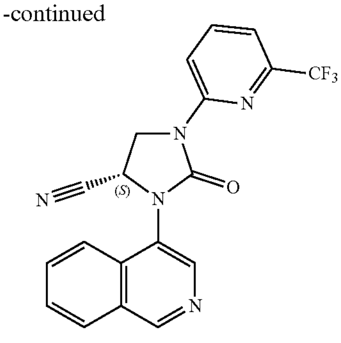

(51b)

Racemic 3-(isoquinolin-4-yl)-2-oxo-1-(6-(trifluoromethyl)pyridin-2-yl)imidazolidine-4-carbonitrile (51) was synthesized in a manner similar to Example 4 using 2-bromo-6-(trifluoromethyl)pyridine in place of 4-trifluoromethyl-iodobenzene. Achiral purification of the racemate of the racemate was achieved by prep-HPLC (column: Phenomenex C18 75 mm×30 mm, 3 μm; liquid phase: [A-$H_2O$ (0.1% FA); B-ACN]B %: 5%-50%, 20 min]). Chiral separation of the racemate by SFC (column: DAICEL CHIRALPAK IG [250 mm×30 mm, 10 μm; 0.1% $NH_3H_2O$ IPA; B % 45%-45%, 8 min]) gave 2 peaks.

Peak 1 was assigned as (R)-3-(isoquinolin-4-yl)-2-oxo-1-(6-(trifluoromethyl)pyridin-2-yl)imidazolidine-4-carbonitrile (51a); LCMS (Method 3): $t_R$=3.13 min, M+1 (384.1); SFC (Method 25): $t_R$=1.35 min, 100.0%; $^1$H NMR: (400 MHz, CHLOROFORM-d) δ=9.37 (s, 1H), 8.71 (s, 1H), 8.47 (d, J=8.6 Hz, 1H), 8.14 (d, J=8.1 Hz, 1H), 7.93-7.82 (m, 3H), 7.77-7.72 (m, 1H), 7.46 (d, J=7.5 Hz, 1H), 5.11 (br dd, J=8.3, 5.1 Hz, 1H), 4.81-4.71 (m, 2H).

Peak 2 was assigned as (S)-3-(isoquinolin-4-yl)-2-oxo-1-(6-(trifluoromethyl)pyridin-2-yl)imidazolidine-4-carbonitrile (51b); LCMS (Method 3): $t_R$=3.13 min, M+1 (384.1); SFC (Method 25): $t_R$=1.59 min, 100.0%; $^1$H NMR: (400 MHz, CHLOROFORM-d) δ=9.37 (s, 1H), 8.71 (s, 1H), 8.47 (d, J=8.6 Hz, 1H), 8.14 (d, J=8.2 Hz, 1H), 7.93-7.82 (m, 3H), 7.77-7.71 (m, 1H), 7.46 (d, J=7.5 Hz, 1H), 5.10 (dd, J=8.3, 5.1 Hz, 1H), 4.81-4.71 (m, 2H).

Example 52: Synthesis of 1-(3-cyanophenyl)-3-(isoquinolin-4-yl)-2-oxoimidazolidine-4-carbonitrile (52), (R)-1-(3-cyanophenyl)-3-(isoquinolin-4-yl)-2-oxoimidazolidine-4-carbonitrile (52a) and (S)-1-(3-cyanophenyl)-3-(isoquinolin-4-yl)-2-oxoimidazolidine-4-carbonitrile (52b)

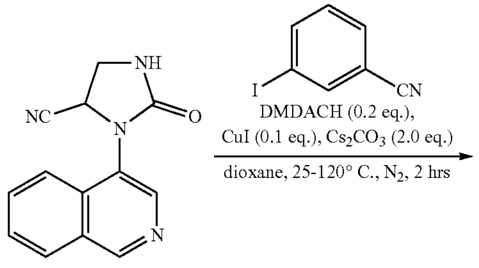

(Int-1)

-continued

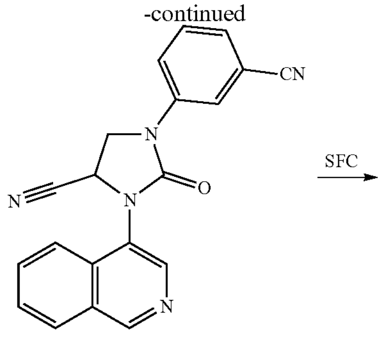

(52)

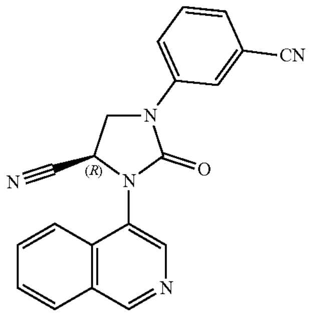

(52a)

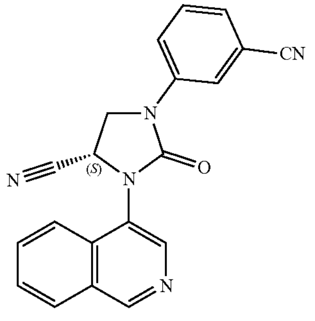

(52b)

Racemic 1-(3-cyanophenyl)-3-(isoquinolin-4-yl)-2-oxoimidazolidine-4-carbonitrile (52) was synthesized in a manner similar to Example 4 using 3-iodobenzonitrile in place of 4-trifluoromethyl-iodobenzene. Achiral purification of the racemate was achieved by prep-HPLC (column: Phenomenex Luna C18 75 mm×30 mm, 3 μm; liquid phase: [A-FA/$H_2O$=0.1% v/v; B-ACN]B %: 20%-50%, 8 min]). Chiral separation of the racemate by SFC (DAICEL CHIRALPAK AD (250 mm×30 mm, 10 um); Mobile phase: A for $CO_2$ and B for 0.1% $NH_3H_2O$ EtOH; Gradient: B %=50% isocratic elution mode; Flow rate: 70 mL/min; Wavelength: 220 nm; Column temperature: 35° C.; System back pressure: 120 bar) gave 2 peaks Peak 1 was assigned as (R)-1-(3-cyanophenyl)-3-(isoquinolin-4-yl)-2-oxoimidazolidine-4-carbonitrile (52a). LCMS (Method 32): $t_R$=2.59 min, M+1 (340.1); SFC (Method 15): $t_R$=1.71 min, 100.0%; $^1$H NMR: (400 MHz, CHLOROFORM-d) δ=9.37 (s, 1H), 8.70 (s, 1H), 8.14 (d, J=8.1 Hz, 1H), 7.95-7.87 (m, 3H), 7.87-7.82 (m, 1H), 7.77-7.72 (m, 1H), 7.58-7.53 (m, 1H), 7.51-7.45 (m, 1H), 5.15 (dd, J=4.5, 9.1 Hz, 1H), 4.55 (dd, J=9.6, 9.1 Hz, 1H), 4.41 (dd, J=4.4, 9.6 Hz, 1H).

Peak 2 was assigned as (s)-1-(3-cyanophenyl)-3-(isoquinolin-4-yl)-2-oxoimidazolidine-4-carbonitrile (52b). LCMS (Method 32): $t_R$=2.59 min, M+1 (340.1); SFC (Method 15):

$t_R$=2.16 min, 99.1%; $^1$H NMR: (400 MHz, CHLOROFORM-d) δ=9.37 (s, 1H), 8.70 (s, 1H), 8.14 (d, J=8.1 Hz, 1H), 7.96-7.87 (m, 3H), 7.87-7.83 (m, 1H), 7.77-7.72 (m, 1H), 7.58-7.53 (m, 1H), 7.51-7.46 (m, 1H), 5.15 (dd, J=4.4, 9.2 Hz, 1H), 4.55 (dd, J=9.6, 9.2 Hz, 1H), 4.42 (dd, J=4.4, 9.6 Hz, 1H).

Example 53: Synthesis of 3-(isoquinolin-4-yl)-1-(4-methylpyrimidin-2-yl)-2-oxoimidazolidine-4-carbonitrile (53), (R)-3-(isoquinolin-4-yl)-1-(4-methylpyrimidin-2-yl)-2-oxoimidazolidine-4-carbonitrile (53a) and (S)-3-(isoquinolin-4-yl)-1-(4-methylpyrimidin-2-yl)-2-oxoimidazolidine-4-carbonitrile (53b)

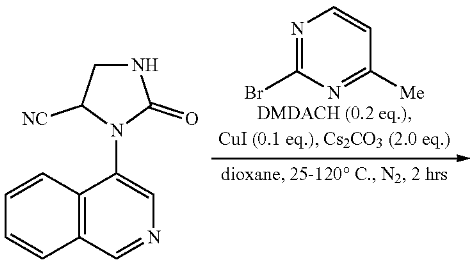

(Int-1)

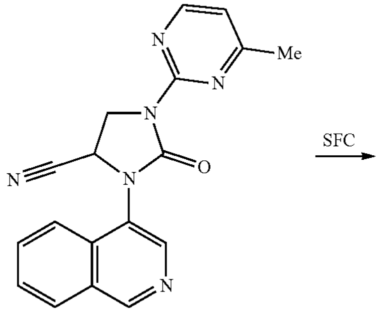

(53)

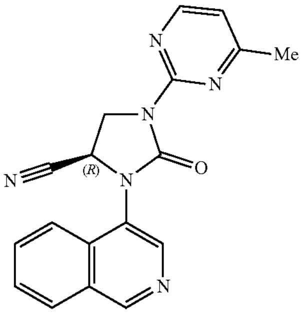

(53a)

-continued

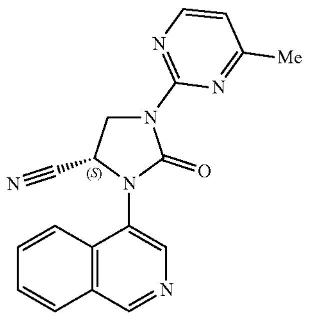

(53b)

Racemic 3-(isoquinolin-4-yl)-1-(4-methylpyrimidin-2-yl)-2-oxoimidazolidine-4-carbonitrile (53) was synthesized in a manner similar to Example 4 using 2-bromo-4-methylpyrimidine in place of 4-trifluoromethyl-iodobenzene. Achiral purification of the racemate was achieved by prep-HPLC (column: Waters Xbridge BEH C18 100 mm×30 mm, 10 μm; liquid phase: [A-10 mM $NH_4HCO_3$ in $H_2O$; B-ACN]B %: 20%-50%, 8 min]). Chiral separation of the racemate by SFC (column: REGIS (S, S) WHELK-01 (250 mm*25 mm, 10 um); mobile phase: 0.1% $NH_3H_2O$ IPA; B % 70%-70%, 15 min]) gave 2 peaks.

Peak 1 was assigned as (R)-3-(isoquinolin-4-yl)-1-(4-methylpyrimidin-2-yl)-2-oxoimidazolidine-4-carbonitrile (53a). LCMS (Method 31): $t_R$=2.24 min, M+1 (331.2); SFC (Method 26): $t_R$=2.22 min, 100.0%; $^1$H NMR: (400 MHz, DMSO-$d_6$) δ=9.43 (s, 1H), 8.68 (s, 1H), 8.59 (d, J=5.0 Hz, 1H), 8.29 (d, J=8.1 Hz, 1H), 8.11 (d, J=8.3 Hz, 1H), 7.90 (dt, J=1.1, 7.7 Hz, 1H), 7.84-7.78 (m, 1H), 7.14 (d, J=5.0 Hz, 1H), 5.58 (dd, J=4.2, 9.1 Hz, 1H), 4.70 (dd, J=9.1, 10.8 Hz, 1H), 4.47 (dd, J=4.3, 10.8 Hz, 1H), 2.46 (s, 3H).

Peak 2 was assigned as (S)-3-(isoquinolin-4-yl)-1-(4-methylpyrimidin-2-yl)-2-oxoimidazolidine-4-carbonitrile (53b). LCMS (Method 31): $t_R$=2.23 min, M+1 (331.2); SFC (Method 26): $t_R$=3.37 min, 99.7%; $^1$H NMR: (400 MHz, DMSO-$d_6$) δ=9.43 (s, 1H), 8.68 (s, 1H), 8.58 (d, J=5.0 Hz, 1H), 8.29 (d, J=8.1 Hz, 1H), 8.11 (d, J=8.3 Hz, 1H), 7.93-7.87 (m, 1H), 7.84-7.77 (m, 1H), 7.14 (d, J=5.0 Hz, 1H), 5.58 (dd, J=4.2, 9.2 Hz, 1H), 4.74-4.67 (m, 1H), 4.47 (dd, J=4.3, 11.0 Hz, 1H), 2.46 (s, 3H).

Example 54: Synthesis of 1-(5-chloropyridazin-3-yl)-3-(isoquinolin-4-yl)-2-oxoimidazolidine-4-carbonitrile (54), (R)-1-(5-chloropyridazin-3-yl)-3-(isoquinolin-4-yl)-2-oxoimidazolidine-4-carbonitrile (54a) and (S)-1-(5-chloropyridazin-3-yl)-3-(isoquinolin-4-yl)-2-oxoimidazolidine-4-carbonitrile (54b)

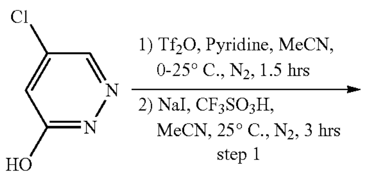

-continued

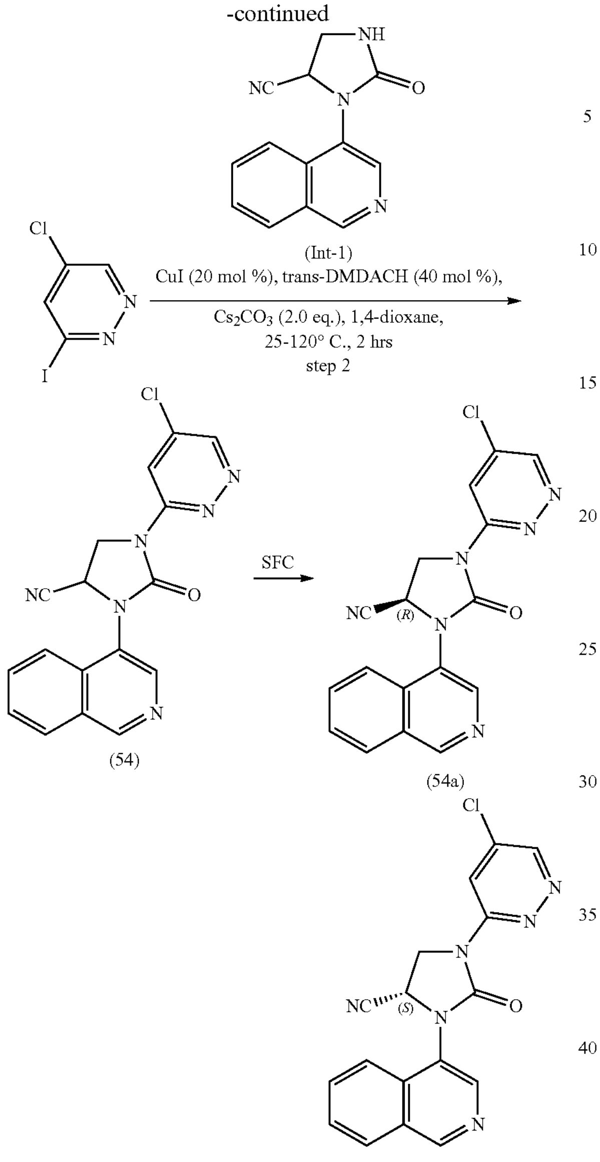

(Int-1)

(54)

(54a)

(54b)

Step 1: To a solution of 5-chloropyridazin-3-ol (1.0 g, 7.69 mmol, 1.0 eq.) and pyridine (730 mg, 9.23 mmol, 1.2 eq.) in MeCN (7 mL) was added $Tf_2O$ (3.0 g, 10.77 mmol, 1.4 eq.) at 0° C. under $N_2$. The solution was stirred at 25° C. for 1.5 hrs. Then NaI (1.4 g, 9.23 mmol, 1.2 eq.) and $CF_3SO_3H$ (1.3 g, 8.46 mmol, 1.1 eq.) were added to the mixture at 25° C. and the solution was stirred at 25° C. for 3 hrs. The reaction mixture was quenched with $H_2O$ (10 mL) and adjusted to pH=10.0 with 1M NaOH (aq). $Na_2CO_3$ aqueous (10 mL) and saturated $Na_2S_2O_3$ aqueous (30 25 mL) were added to the mixture and the mixture was extracted with EtOAc (50 mL×2). The combined organic layers were washed with brine (50 mL), dried over $Na_2SO_4$, filtered and the filtrate was concentrated to give crude product. The crude was purified by MPLC (Petroleum ether/EtOAc=3/1, $R_f$=0.70, Petroleum ether/EtOAc=100%-0%) to give 5-chloro-3-iodopyridazine. $^1$H NMR: (400 MHz, CHLOROFORM-d) δ=9.15 (d, J=2.1 Hz, 1H), 7.96 (d, J=2.1 Hz, 1H).

Step 2: Racemic 1-(5-chloropyridazin-3-yl)-3-(isoquinolin-4-yl)-2-oxoimidazolidine-4-carbonitrile (54) was synthesized in a manner similar to Example 4 using 5-chloro-3-iodopyridazine in place of 4-trifluoromethyl-iodobenzene. Achiral purification of the racemate was achieved by MPLC (EtOAc, $R_f$=0.40, Petroleum ether/EtOAc=100%-0%). Chiral separation of the racemate by SFC (Column: DAICEL CHIRALPAK IG (250 mm×30 mm, 10 μm); Mobile phase: A for $CO_2$ and B for IPA (0.1% $NH_3H_2O$); Gradient: B %=45% isocratic elution mode; Flow rate: 70 g/min; Wavelength: 220 nm; Column temperature: 35° C.; System back pressure: 120 bar.) gave 2 peaks.

Peak 1 was assigned as (R)-1-(5-chloropyridazin-3-yl)-3-(isoquinolin-4-yl)-2-oxoimidazolidine-4-carbonitrile (54a). LCMS (Method 31): $t_R$=2.51 min, M+1 (351.1); SFC (Method 27): $t_R$=2.53 min, 100%; $^1$H NMR: (400 MHz, CHLOROFORM-d) δ=9.39 (s, 1H), 8.97 (d, J=2.0 Hz, 1H), 8.71 (s, 1H), 8.65 (d, J=2.0 Hz, 1H), 8.15 (d, J=8.3 Hz, 1H), 7.98-7.79 (m, 2H), 7.79-7.69 (m, 1H), 5.17 (dd, J=5.6, 7.9 Hz, 1H), 5.01-4.69 (m, 2H).

Peak 2 was assigned as (S)-1-(5-chloropyridazin-3-yl)-3-(isoquinolin-4-yl)-2-oxoimidazolidine-4-carbonitrile (54b). LCMS (Method 31): $t_R$=2.506 min, M+1 (351.1); SFC (Method 27): $t_R$=3.53 min, 98.6%; $^1$H NMR: (400 MHz, CHLOROFORM-d) δ=9.39 (s, 1H), 8.97 (d, J=1.9 Hz, 1H), 8.72 (s, 1H), 8.66 (d, J=1.9 Hz, 1H), 8.16 (d, J=8.1 Hz, 1H), 7.96-7.80 (m, 2H), 7.80-7.72 (m, 1H), 5.24-5.09 (m, 1H), 4.96-4.78 (m, 2H).

Example 55: Synthesis of 1-(6-fluoropyridin-3-yl)-3-(isoquinolin-4-yl)-2-oxoimidazolidine-4-carbonitrile (55), (R)-1-(6-fluoropyridin-3-yl)-3-(isoquinolin-4-yl)-2-oxoimidazolidine-4-carbonitrile (55a) and (S)-1-(6-fluoropyridin-3-yl)-3-(isoquinolin-4-yl)-2-oxoimidazolidine-4-carbonitrile (55b)

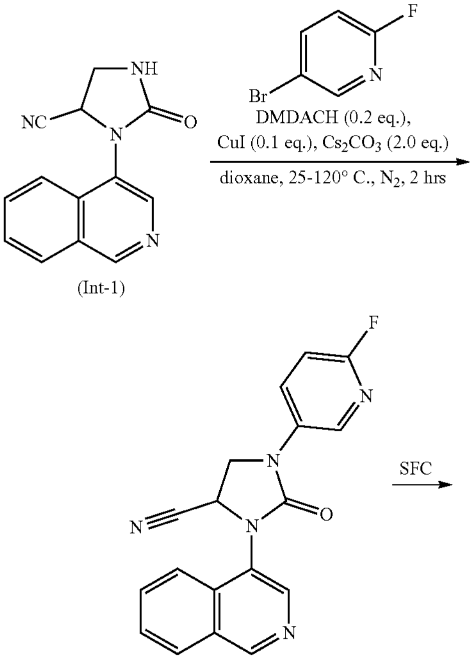

(Int-1)

(55)

-continued

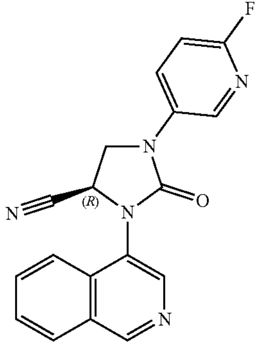

(55a)

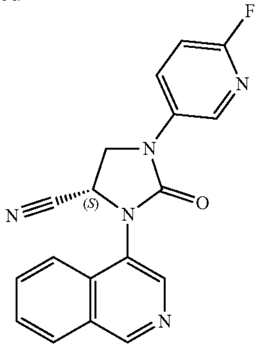

(55b)

Racemic 1-(6-fluoropyridin-3-yl)-3-(isoquinolin-4-yl)-2-oxoimidazolidine-4-carbonitrile (55) was synthesized in a manner similar to Example 4 using 5-bromo-2-fluoropyridine in place of 4-trifluoromethyl-iodobenzene. Achiral purification of the racemate was achieved flash column chromatography (Petroleum ether/EtOAc=1/1 to 1/3). Chiral separation of the racemate by SFC (column: DAICEL CHIRALCEL OJ (250 mm×30 mm, 10 μm); liquid phase: 0.1% $NH_3H_2O$ IPA B %: 55%-55%, 15 min]) gave 2 peaks.

Peak 1 was assigned as (R)-1-(6-fluoropyridin-3-yl)-3-(isoquinolin-4-yl)-2-oxoimidazolidine-4-carbonitrile (55a). LCMS (Method 1): $t_R$=1.88 min, M+1 (334.1); SFC (Method 28): $t_R$=1.69 min, 99.9%; $^1$H NMR: (400 MHz, METHANOL-$d_4$) δ=9.37 (s, 1H), 8.66 (s, 1H), 8.43 (s, 1H), 8.33 (ddd, J=2.9, 6.7, 9.1 Hz, 1H), 8.27 (d, J=8.3 Hz, 1H), 8.14 (d, J=8.4 Hz, 1H), 7.97-7.91 (m, 1H), 7.85-7.79 (m, 1H), 7.14 (dd, J=3.0, 8.9 Hz, 1H), 5.56 (dd, J=4.6, 9.4 Hz, 1H), 4.67-4.61 (m, 1H), 4.50 (dd, J=4.5, 9.6 Hz, 1H).

Peak 2 was assigned as (S)-1-(6-fluoropyridin-3-yl)-3-(isoquinolin-4-yl)-2-oxoimidazolidine-4-carbonitrile (55b). LCMS (Method 1): $t_R$=1.89 min, M+1 (334.1); SFC (Method 28): $t_R$=2.13 min, 98.9%; $^1$H NMR: (400 MHz, METHANOL-$d_4$) δ=9.37 (s, 1H), 8.66 (s, 1H), 8.44 (s, 1H), 8.33 (ddd, J=2.9, 6.6, 9.1 Hz, 1H), 8.27 (d, J=8.1 Hz, 1H), 8.14 (d, J=8.5 Hz, 1H), 7.96-7.91 (m, 1H), 7.85-7.79 (m, 1H), 7.14 (dd, J=3.0, 8.9 Hz, 1H), 5.56 (dd, J=4.6, 9.4 Hz, 1H), 4.64 (dd, J=9.7, 9.4 Hz, 1H), 4.50 (dd, J=4.6, 9.7 Hz, 1H).

Example 56: Synthesis of 1-(2-fluorophenyl)-3-(isoquinolin-4-yl)-2-oxoimidazolidine-4-carbonitrile (56), (R)-1-(2-fluorophenyl)-3-(isoquinolin-4-yl)-2-oxoimidazolidine-4-carbonitrile (56a) and (S)-1-(2-fluorophenyl)-3-(isoquinolin-4-yl)-2-oxoimidazolidine-4-carbonitrile (56b)

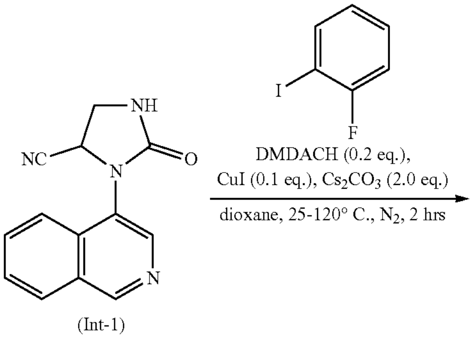

(Int-1)

-continued

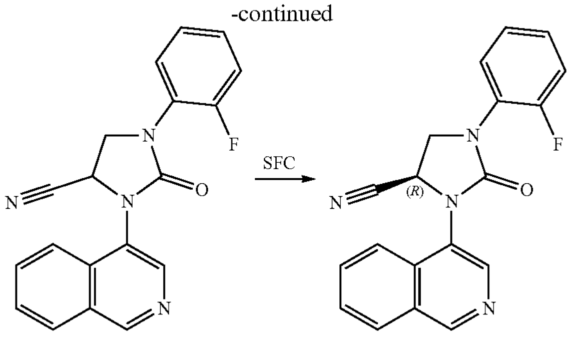

(56) (56a)

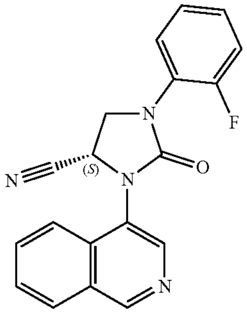

(56b)

Racemic 1-(2-fluorophenyl)-3-(isoquinolin-4-yl)-2-oxo-imidazolidine-4-carbonitrile (56) was synthesized in a manner similar to Example 4 using 1-fluoro-2-iodobenzene in place of 4-trifluoromethyl-iodobenzene. Achiral purification of the racemate was achieved using prep-HPLC (column: Phenomenex Luna C18 200 mm×40 mm, 10 μm; liquid phase: [A-$H_2O$ (0.1% HCOOH); B-ACN]B %: 20%-50%, 20 min]). LCMS (Method 2): $t_R$=2.05, M+1 (333.0); SFC (Method 29): Peak 1 $R_t$=1.39 min, peak 2 $R_t$=1.54 min, $^1$H NMR: (400 MHz, DMSO-d6) δ=9.41 (s, 1H), 8.66 (s, 1H), 8.28 (d, J=8.1 Hz, 1H), 8.08 (d, J=8.4 Hz, 1H), 7.96-7.88 (m, 1H), 7.84-7.76 (m, 1H), 7.65 (t, J=8.0 Hz, 1H), 7.41-7.34 (m, 2H), 7.32-7.23 (m, 1H), 5.69 (dd, J=4.2, 8.9 Hz, 1H), 4.56 (dd, J=9.6, 8.9 Hz, 1H), 4.33 (dd, J=4.2, 9.6 Hz, 1H).

Chiral separation of the racemate by SFC (DAICEL CHIRALPAK IC (250 mm×30 mm, 10 μm); mobile phase: A: $CO_2$ B:IPA; B % 45%-45%, 15 min]) gave 2 peaks.

Peak 1 was assigned as (R)-1-(2-fluorophenyl)-3-(isoquinolin-4-yl)-2-oxoimidazolidine-4-carbonitrile (56a). LCMS (Method 2): $t_R$=2.05 min. M+1 (333.0); SFC (Method 29): $t_R$=1.40 min, 100.0%; $^1$H NMR: (400 MHz, DMSO-$d_6$) δ=9.41 (s, 1H), 8.66 (s, 1H), 8.28 (d, J=8.1 Hz, 1H), 8.10-8.06 (m, 1H), 7.92 (ddd, J=8.4, 7.0, 1.1, Hz, 1H), 7.80 (ddd, J=8.1, 7.0, 1.0, Hz 1H), 7.68-7.62 (m, 1H), 7.40-7.35 (m, 2H), 7.32-7.27 (m, 1H), 5.69 (dd, J=8.9, 4.2 Hz, 1H), 4.57 (dd, J=9.5, 8.9 Hz, 1H), 4.33 (dd, J=9.5, 4.1, 1H).

Peak 2 was assigned as (S)-1-(2-fluorophenyl)-3-(isoquinolin-4-yl)-2-oxoimidazolidine-4-carbonitrile (56b). LCMS (Method 2): $t_R$=2.05 min, M+1 (333.0); SFC (Method 29): $t_R$=1.86 min, 98.1%; $^1$H NMR: (400 MHz, DMSO-$d_6$) δ=9.43 (s, 1H), 8.68 (s, 1H), 8.29 (d, J=8.1 Hz, 1H), 8.10 (dd, J=0.7, 8.4 Hz, 1H), 7.94 (ddd, J=8.4, 7.0, 1.1, Hz, 1H), 7.82 (ddd, J=8.1, 7.0, 1.0, Hz 1H), 7.67 (dd, J=8.4, 7.5 Hz, 1H), 7.42-7.36 (m, 2H), 7.34-7.28 (m, 1H), 5.71 (dd, J=8.9, 4.2 Hz, 1H), 4.58 (dd, J=9.5, 8.9 Hz, 1H), 4.35 (dd, J=9.5, 4.1, 1H).

Example 57: Synthesis of 3-(isoquinolin-4-yl)-2-oxo-1-(2-(trifluoromethyl)pyridin-4-yl)imidazolidine-4-carbonitrile (57), (R)-3-(isoquinolin-4-yl)-2-oxo-1-(2-(trifluoromethyl)pyridin-4-yl) imidazolidine-4-carbonitrile (57a) and (S)-3-(isoquinolin-4-yl)-2-oxo-1-(2-(trifluoromethyl) pyridin-4-yl)imidazolidine-4-carbonitrile (57b)

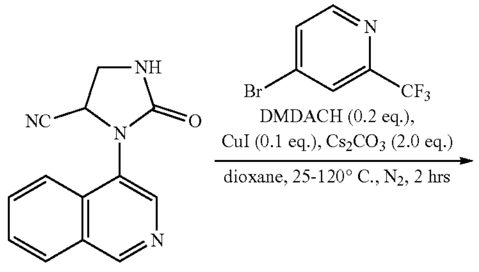

(Int-1)

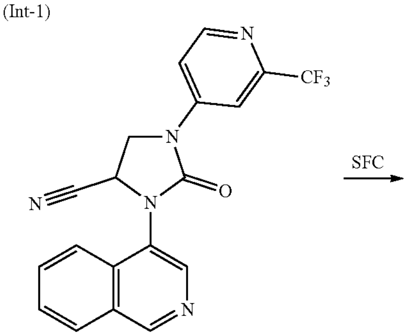

(57)

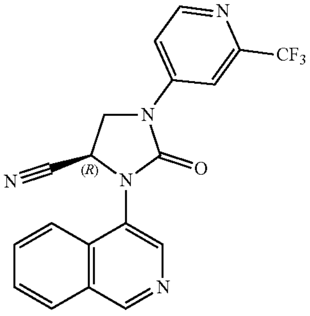

(57a)

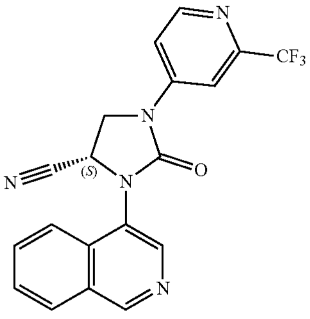

(57b)

Racemic 3-(isoquinolin-4-yl)-2-oxo-1-(2-(trifluoromethyl)pyridin-4-yl)imidazolidine-4-carbonitrile (57) was synthesized in a manner similar to Example 4 using 4-bromo-2-(trifluoromethyl)pyridine in place of 4-trifluoromethyl-iodobenzene. Achiral purification of the racemate was achieved using prep-HPLC (column: Phenomenex Luna C18 75 mm×30 mm, 3 μm; liquid phase: [A-FA/$H_2O$=0.1% v/v; B-ACN]B %: 25%-65%, 8 min]). LCMS (Method 31): $t_R$=2.67 min, M+1 (384.1); SFC (Method 15): peak 1 $R_t$=1.28 min, peak 2 $R_t$=1.42 min; $^1H$ NMR: (400 MHz, CHLOROFORM-d) δ=9.39 (s, 1H), 8.76-8.65 (m, 2H), 8.16 (d, J=8.3 Hz, 1H), 7.98 (d, J=2.1 Hz, 1H), 7.87 (br d, J=4.1 Hz, 2H), 7.79-7.73 (m, 2H), 5.19 (dd, J=4.4, 9.3 Hz, 1H), 4.61-4.56 (dd, J=9.9, 9.3 Hz, 1H), 4.48 (dd, J=4.5, 9.9 Hz, 1H).

Chiral separation of the racemate by SFC (DAICEL CHIRALPAK AD (250 mm×30 mm, 10 μm)); Mobile phase: A for $CO_2$ and B for 0.1% $NH_3H_2O$ EtOH; Gradient: B %=50% isocratic elution mode; Flow rate: 60 mL/min; Wavelength: 220 nm; Column temperature: 35° C.; System back pressure: 120 bar) gave 2 peaks.

Peak 1 was assigned as (R)-3-(isoquinolin-4-yl)-2-oxo-1-(2-(trifluoromethyl)pyridin-4-yl)imidazolidine-4-carbonitrile (57a). LCMS (Method 1): $t_R$=2.18 min, M+1 (384.1); SFC (Method 15): $t_R$=1.25 min, 99.8%; $^1H$ NMR: (400 MHz, CHLOROFORM-d) δ ppm 9.39 (1H, s) 8.64-8.77 (2H, m) 8.16 (1H, d, J=8.2 Hz) 7.98 (1H, d, J=2.0 Hz) 7.83-7.91 (2H, m) 7.73-7.79 (2H, m) 5.19 (1H, dd, J=9.4, 4.5 Hz) 4.55-4.63 (dd, J=9.9, 9.4 Hz, 1H) 4.45-4.51 (dd, J=9.9, 4.5 Hz, 1H).

Peak 2 was assigned as (S)-3-(isoquinolin-4-yl)-2-oxo-1-(2-(trifluoromethyl)pyridin-4-yl)imidazolidine-4-carbonitrile (57b). LCMS (Method 1): $t_R$=2.18 min, M+1 (384.1); SFC (Method 15): $t_R$=1.41 min, 99.1%; $^1H$ NMR: (400 MHz, CHLOROFORM-d) δ ppm 9.39 (1H, s) 8.63-8.78 (2H, m) 8.16 (1H, d, J=8.2 Hz) 7.98 (1H, d, J=1.9 Hz) 7.87 (2H, br d, J=4.1 Hz) 7.72-7.79 (2H, m) 5.19 (1H, dd, J=9.3, 4.5 Hz) 4.55-4.64 (dd, J=9.9, 9.3 Hz, 1H) 4.45-4.51 (dd, J=9.9, 4.5 Hz, 1H).

Example 58: Synthesis of 1-(5-chloro-3-methoxypyridin-2-yl)-3-(isoquinolin-4-yl)-2-oxoimidazolidine-4-carbonitrile (58), (R)-1-(5-chloro-3-methoxypyridin-2-yl)-3-(isoquinolin-4-yl)-2-oxoimidazolidine-4-carbonitrile (58a) and (S)-1-(5-chloro-3-methoxypyridin-2-yl)-3-(isoquinolin-4-yl)-2-oxoimidazolidine-4-carbonitrile (58b)

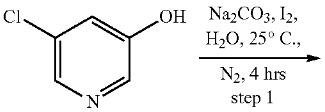

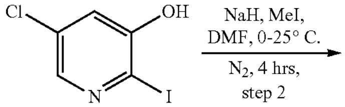

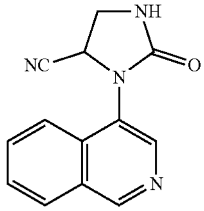

(Int-1)

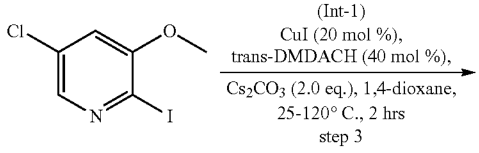

-continued

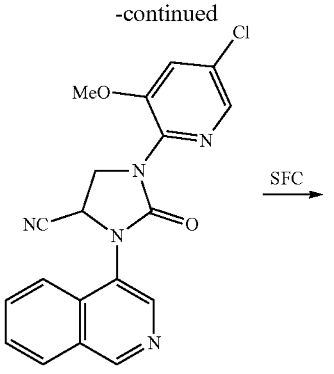

(58)

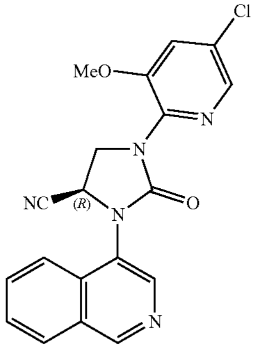

(58a)

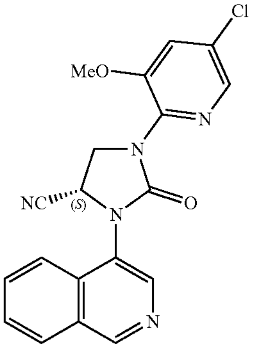

(58b)

Step 1: To a mixture of 5-chloropyridin-3-ol (2.0 g, 15.50 mmol, 1.0 eq.) in $H_2O$ (20 mL) was added $Na_2CO_3$ (3.3 g, 31.01 mmol, 2.0 eq.) and $I_2$ (3.9 g, 15.50 mmol, 1.0 eq.) at 25° C. Then the mixture was stirred at 25° C. for 4 hrs. The mixture was diluted with iced water (5 mL), adjusted to pH=7 with 1 M HCl at 0° C. The mixture was extracted with EtOAc (20 mL×3). The combined organic layers were washed with brine (10 mL), dried over $Na_2SO_4$, filtered and concentrated under reduced pressure to give crude product. The crude product was purified by MPLC (Petroleum ether/EtOAc=100%-75%) to give 5-chloro-2-iodopyridin-3-ol. $^1H$ NMR: (400 MHz, DMSO-$d_6$) δ=7.92 (d, J=2.3 Hz, 1H), 7.15 (d, J=2.3 Hz, 1H).

Step 2: To a solution of 5-chloro-2-iodopyridin-3-ol (500 mg, 1.96 mmol, 1.0 eq.) in DMF (5 mL) was added NaH (126 mg, 3.14 mmol, 1.6 eq.) at 0° C. and the mixture stirred at 25° C. for 30 25 mins. To the mixture was added MeI (557 mg, 3.92 mmol, 2.0 eq.) at 0° C. and the mixture stirred at 25° C. for 4 hrs. The reaction was quenched with ice $H_2O$ (5 mL), extracted with EtOAc (10 mL×2). The combined organic phase was washed with brine (25 mL×2), dried over $Na_2SO_4$, filtered and concentrated to give crude product. The crude product was purified by MPLC (Petroleum ether/EtOAc=100%-0%) to give 5-chloro-2-iodo-3-methoxypyridine. $^1H$ NMR: (400 MHz, CHLOROFORM-d) δ=8.02 (d, J=2.1 Hz, 1H), 7.00 (d, J=2.1 Hz, 1H), 3.92 (s, 3H).

Step 3: Racemic 1-(5-chloro-3-methoxypyridin-2-yl)-3-(isoquinolin-4-yl)-2-oxoimidazolidine-4-carbonitrile (58) was synthesized in a manner similar to Example 4 using 5-chloro-2-iodo-3-methoxypyridine in place of 4-trifluoromethyl-iodobenzene. Achiral purification of the racemate was achieved using prep-HPLC (column: Phenomenex C18 75 mm×30 mm, 3 μm; liquid phase: water ($NH_4HCO_3$)-ACN B %: 10%-40%, 8 min]). LCMS (Method 31): $t_R$=2.51 min, M+1 (380.1); SFC (Method 1): peak 1 $R_t$=1.54 min, peak 2 $R_t$=2.00 min; $^1H$ NMR: (400 MHz, CHLOROFORM-d) δ=9.33 (s, 1H), 8.71 (s, 1H), 8.10 (d, J=8.1 Hz, 1H), 8.06 (d, J=2.0 Hz, 1H), 7.97 (d, J=8.5 Hz, 1H), 7.83 (dt, J=7.7, 1.0 Hz, 1H), 7.74-7.68 (m, 1H), 7.34 (d, J=2.0 Hz, 1H), 5.10 (dd, J=8.8, 4.5 Hz, 1H), 4.66 (dd, J=9.8, 8.8 Hz, 1H), 4.37 (dd, J=9.8, 4.5 Hz, 1H), 3.96 (s, 3H). Chiral separation of the racemate by SFC (column: DAICEL CHIRALPAK AD (250 mm×30 mm, 10 μm); liquid phase: 0.1% $NH_3H_2O$ IPA B %: 50%-50%, 10 min]) gave 2 peaks.

Peak 1 was assigned as (R)-1-(5-chloro-3-methoxypyridin-2-yl)-3-(isoquinolin-4-yl)-2-oxoimidazolidine-4-carbonitrile (58a). LCMS (Method 31): $t_R$=2.507 min, M+1 (380.1); SFC (Method 1): $t_R$=1.51 min, 100.0%; $^1H$ NMR: (400 MHz, CHLOROFORM-d) δ=9.32 (s, 1H), 8.71 (s, 1H), 8.10 (d, J=8.2 Hz, 1H), 8.06 (d, J=2.0 Hz, 1H), 7.97 (d, J=8.5 Hz, 1H), 7.83 (dt, J=7.7,1.0 Hz, 1H), 7.74-7.68 (m, 1H), 7.34 (d, J=2.0 Hz, 1H), 5.10 (dd, J=8.8, 4.5 Hz, 1H), 4.66 (dd, J=9.8, 8.8 Hz, 1H), 4.37 (dd, J=9.8, 4.5 Hz, 1H), 3.96 (s, 3H).

Peak 2 was assigned as (S)-1-(5-chloro-3-methoxypyridin-2-yl)-3-(isoquinolin-4-yl)-2-oxoimidazolidine-4-carbonitrile (58b). LCMS (Method 31): $t_R$=2.51 min, M+1 (380.1); SFC (Method 1): $t_R$=1.82 min, 99.9%; $^1H$ NMR: (400 MHz, CHLOROFORM-d) δ=9.32 (s, 1H), 8.71 (s, 1H), 8.10 (d, J=8.2 Hz, 1H), 8.06 (d, J=2.0 Hz, 1H), 7.97 (d, J=8.5 Hz, 1H), 7.83 (dt, J=7.7,1.0 Hz, 1H), 7.74-7.68 (m, 1H), 7.34 (d, J=2.0 Hz, 1H), 5.10 (dd, J=8.8, 4.5 Hz, 1H), 4.66 (dd, J=9.8, 8.8 Hz, 1H), 4.37 (dd, J=9.8, 4.5 Hz, 1H), 3.96 (s, 3H).

Example 59: Synthesis of 1-(5-(difluoromethoxy)-2-fluorophenyl)-3-(isoquinolin-4-yl)-2-oxoimidazolidine-4-carbonitrile (59), (R)-1-(5-(difluoromethoxy)-2-fluorophenyl)-3-(isoquinolin-4-yl)-2-oxoimidazolidine-4-carbonitrile (59a) and (S)-1-(5-(difluoromethoxy)-2-fluorophenyl)-3-(isoquinolin-4-yl)-2-oxoimidazolidine-4-carbonitrile (59b)

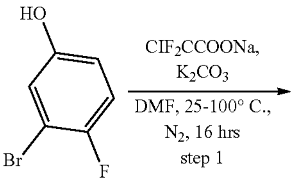

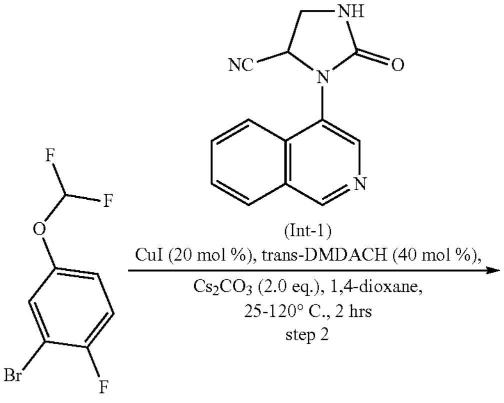

-continued

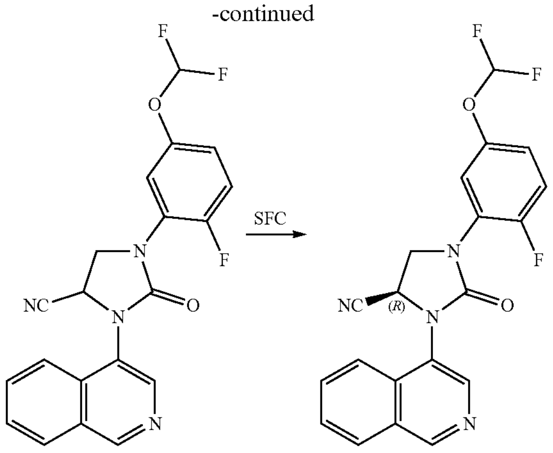

(59) (59a)

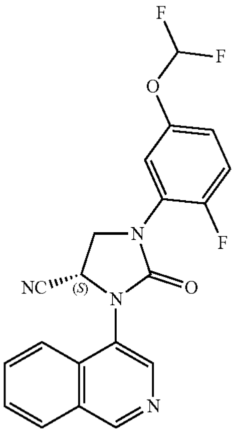

(59b)

Step 1: To a solution of 3-bromo-4-fluorophenol (4.0 g, 20.94 mmol, 1.0 eq.) in DMF (40 mL) was added $ClF_2OOOONa$ (4.8 g, 31.42 mmol, 1.5 eq.) and $K_2CO_3$ (3.2 g, 23.04 mmol, 1.1 eq.) at 25° C. under $N_2$ and the reaction stirred at 100° C. under $N_2$ for 16 hrs. The solution was adjusted to pH=6 with 1 M HCl at 0° C. The reaction was quenched with $H_2O$ (120 mL) and extracted with n-Pentane (60 mLx3). The combined organic layers were washed with $NaHCO_3$ (60 mLx3), dried over $Na_2SO_4$, filtered and concentrated under reduced pressure to give crude product. The crude product was purified by flash column chromatography (Petroleum ether/EtOAc=100/1-1/1), 80 mL/min) to give 2-bromo-4-(difluoromethoxy)-1-fluorobenzene. $^1$H NMR: (400 MHz, CHLOROFORM-d) δ=7.38 (dd, J=2.6, 5.6 Hz, 1H), 7.16-7.06 (m, 2H), 6.47 (t, J=73.0 Hz, 1H).

Step 2: Racemic 1-(5-(difluoromethoxy)-2-fluorophenyl)-3-(isoquinolin-4-yl)-2-oxoimidazolidine-4-carbonitrile (59) was synthesized in a manner similar to Example 4 using 2-bromo-4-(difluoromethoxy)-1-fluorobenzene in place of 4-trifluoromethyl-iodobenzene. Achiral purification of the racemate was achieved using prep-HPLC (column: Waters Xbridge BEH C18 100 mmx30 mm, 10 μm; liquid phase: [A-10 mM $NH_4HCO_3$ in $H_2O$; B-ACN]B %: 40%-60%, 8 min]). Chiral separation of the racemate by SFC (column: DAICEL CHIRALCEL OJ (250 mmx30 mm, 10 μm); mobile phase: A: $CO_2$ B: EtOH (0.1% IPA)) gave 2 peaks Peak 1 was assigned as (R)-1-(5-(difluoromethoxy)-2-fluorophenyl)-3-(isoquinolin-4-yl)-2-oxoimidazolidine-4-carbonitrile (59a). LCMS (Method 31): $t_R$=2.77 min, M+1 (399.1); SFC (Method 30): $t_R$=1.01 min, 99.8%; $^1$H NMR: (400 MHz, DMSO-d6) δ=9.43 (s, 1H), 8.68 (s, 1H), 8.29 (d, J=8.3 Hz, 1H), 8.10 (d, J=8.5 Hz, 1H), 7.93 (ddd, J=8.3, 7.1, 1.1 Hz, 1H), 7.85-7.78 (m, 1H), 7.63-7.54 (m, 1H), 7.49-7.43 (m, 1H), 7.42-7.05 (m, 2H), 5.71 (dd, J=9.0, 4.3 Hz, 1H), 4.60 (dd, J=9.5, 9.0 Hz, 1H), 4.39 (dd, J=9.5, 4.3, Hz, 1H).

Peak 2 was assigned as (S)-1-(5-(difluoromethoxy)-2-fluorophenyl)-3-(isoquinolin-4-yl)-2-oxoimidazolidine-4-carbonitrile (59b). LCMS (Method 31): $t_R$=2.77 min, M+1 (399.1); SFC (Method 30): $t_R$=1.10 min, 99.6%; $^1$H NMR: (400 MHz, DMSO-d6) δ=9.43 (s, 1H), 8.68 (s, 1H), 8.29 (d, J=8.3 Hz, 1H), 8.10 (d, J=8.5 Hz, 1H), 7.93 (ddd, J=8.3, 7.1, 1.1 Hz, 1H), 7.85-7.78 (m, 1H), 7.63-7.54 (m, 1H), 7.49-7.43 (m, 1H), 7.42-7.05 (m, 2H), 5.71 (dd, J=9.0, 4.3 Hz, 1H), 4.60 (dd, J=9.5, 9.0 Hz, 1H), 4.39 (dd, J=9.5, 4.3, Hz, 1H).

Example 60: Synthesis of 1-(4-chloro-2-cyanophenyl)-3-(isoquinolin-4-yl)-2-oxoimidazolidine-4-carbonitrile (60), (R)-1-(4-chloro-2-cyanophenyl)-3-(isoquinolin-4-yl)-2-oxoimidazolidine-4-carbonitrile (60a) and (S)-1-(4-chloro-2-cyanophenyl)-3-(isoquinolin-4-yl)-2-oxoimidazolidine-4-carbonitrile (60b)

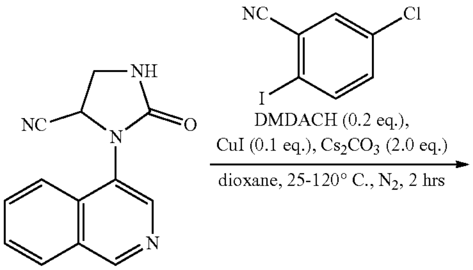

(Int-1)

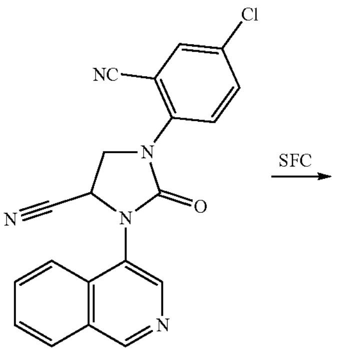

(60)

-continued

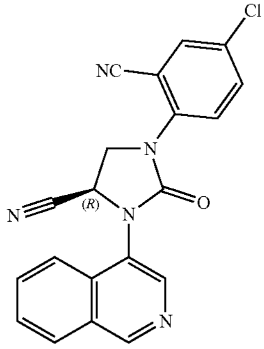

(60a)

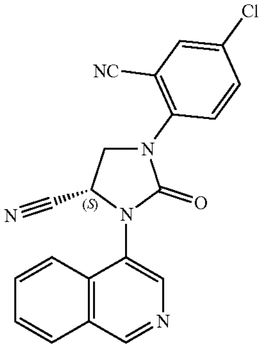

(60b)

Racemic 1-(4-chloro-2-cyanophenyl)-3-(isoquinolin-4-yl)-2-oxoimidazolidine-4-carbonitrile (60) was synthesized in a manner similar to Example 4 using 2-bromo-5-chlorobenzonitrile in place of 4-trifluoromethyl-iodobenzene. Achiral purification of the racemate was achieved using flash column chromatography ($SiO_2$, petroleum ether/ethyl acetate=10/1 to 0/1). LCMS (Method 13): $t_R$=2.20 min, M+1(374.1); SFC (Method 15): peak 1 $R_t$=1.88 min, peak 2 $R_t$=2.09 min; $^1H$ NMR: (400 MHz, CHLOROFORM-d) δ=9.35 (s, 1H), 8.71 (s, 1H), 8.12 (d, J=8.1 Hz, 1H), 7.98 (br d, J=8.6 Hz, 1H), 7.87 (t, J=7.6 Hz, 1H), 7.77-7.71 (m, 2H), 7.70-7.65 (m, 1H), 7.63-7.59 (m, 1H), 5.14 (dd, J=8.8, 4.8 Hz, 1H), 4.72 (dd, J=9.4, 8.8 Hz, 1H), 4.42 (dd, J=9.4, 8.8 Hz, 1H).

Chiral separation of the racemate by SFC (column: DAICEL CHIRALPAK AD (250 mm×30 mm, μm); mobile phase: 0.1% $NH_3H_2O$ IPA; B %: 55%-55%, 13 min) gave 2 peaks.

Peak 1 was assigned as (R)-1-(4-chloro-2-cyanophenyl)-3-(isoquinolin-4-yl)-2-oxoimidazolidine-4-carbonitrile (60a). LCMS (Method 13): $t_R$=2.20 min, M+1(374.1); SFC (Method 15): $t_R$=1.86 min, 99.7%; $^1H$ NMR: (400 MHz, CHLOROFORM-d) δ=9.35 (s, 1H), 8.71 (s, 1H), 8.12 (d, J=8.1 Hz, 1H), 7.98 (br d, J=8.6 Hz, 1H), 7.87 (t, J=7.6 Hz, 1H), 7.77-7.71 (m, 2H), 7.70-7.65 (m, 1H), 7.63-7.59 (m, 1H), 5.14 (dd, J=8.8, 4.8 Hz, 1H), 4.72 (dd, J=9.4, 8.8 Hz, 1H), 4.42 (dd, J=9.4, 8.8 Hz, 1H).

Peak 2 was assigned as (S)-1-(4-chloro-2-cyanophenyl)-3-(isoquinolin-4-yl)-2-oxoimidazolidine-4-carbonitrile (60b). LCMS (Method 13): $t_R$=2.20 min, M+1(374.1); SFC (Method 15): $t_R$=2.08 min, 96.4%; $^1H$ NMR: (400 MHz, CHLOROFORM-d) δ=9.35 (s, 1H), 8.71 (s, 1H), 8.12 (d, J=8.1 Hz, 1H), 7.98 (br d, J=8.6 Hz, 1H), 7.87 (t, J=7.6 Hz, 1H), 7.77-7.71 (m, 2H), 7.70-7.65 (m, 1H), 7.63-7.59 (m, 1H), 5.14 (dd, J=8.8, 4.8 Hz, 1H), 4.72 (dd, J=9.4, 8.8 Hz, 1H), 4.42 (dd, J=9.4, 8.8 Hz, 1H).

Example 61: Synthesis of 1-(6-fluoropyridin-3-yl)-3-(isoquinolin-4-yl)-2-oxoimidazolidine-4-carbonitrile (61), (R)-1-(6-fluoropyridin-2-yl)-3-(isoquinolin-4-yl)-2-oxoimidazolidine-4-carbonitrile (61a) and (S)-1-(6-fluoropyridin-3-yl)-3-(isoquinolin-4-yl)-2-oxoimidazolidine-4-carbonitrile (61b)

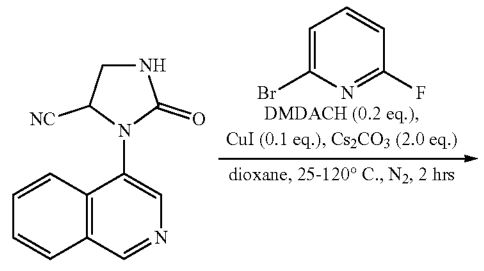

(Int-1)

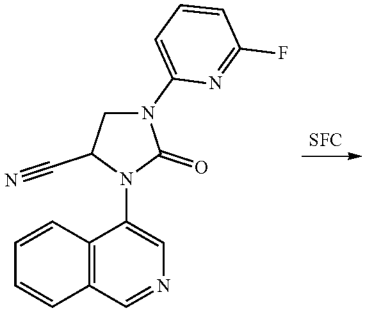

(61)

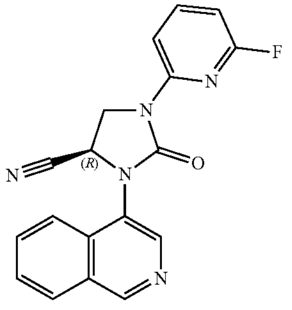

(61a)

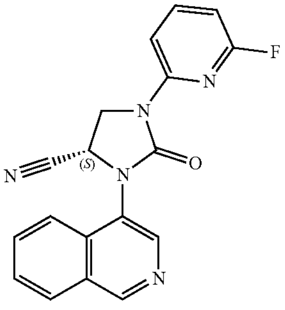

(61b)

Racemic 1-(6-fluoropyridin-3-yl)-3-(isoquinolin-4-yl)-2-oxoimidazolidine-4-carbonitrile (61) was synthesized in a manner similar to Example 4 using 3-bromo-5-fluoropyridine in place of 4-trifluoromethyl-iodobenzene. Achiral purification of the racemate was achieved using prep-HPLC (column: Phenomenex Luna C18 75 mm×30 mm, 3 μm; liquid phase: [A-$H_2O$ (0.1% FA); B-ACN]B %: 20%-60%, 8 min]). Chiral separation of the racemate by SFC (column: DAICEL CHIRALPAK AD (250 mm×30 mm, 10 μm); liquid phase: 0.1% $NH_3H_2O$ IPA B %: 35%-35%, 12 min]) gave 2 peaks.

Peak 1 was assigned as (R)-1-(6-fluoropyridin-2-yl)-3-(isoquinolin-4-yl)-2-oxoimidazolidine-4-carbonitrile (61a). LCMS (Method 4): $t_R$=2.45 min, M+1 (334.1); SFC (Method 1): $t_R$=1.32 min, 99.7%; $^1H$ NMR: (400 MHz, CHLOROFORM-d) δ=9.37 (s, 1H), 8.69 (s, 1H), 8.43 (s, 1H), 8.33 (d, J=2.5 Hz, 1H), 8.21-8.16 (m, 1H), 8.14 (d, J=8.6 Hz, 1H), 7.92-7.82 (m, 2H), 7.78-7.71 (m, 1H), 5.16 (dd, J=9.2, 4.4 Hz, 1H), 4.58 (dd, J=9.6, 9.2 Hz, 1H), 4.45 (dd, J=9.6, 4.4 Hz, 1H).

Peak 2 was assigned as (S)-1-(6-fluoropyridin-2-yl)-3-(isoquinolin-4-yl)-2-oxoimidazolidine-4-carbonitrile (61b). LCMS (Method 4): $t_R$=2.45 min, M+1 (334.1); SFC (Method 1): $t_R$=1.44 min, 97.6%; $^1H$ NMR: (400 MHz, CHLOROFORM-d) δ=9.37 (s, 1H), 8.69 (s, 1H), 8.43 (s, 1H), 8.33 (d, J=2.5 Hz, 1H), 8.21-8.16 (m, 1H), 8.14 (d, J=8.6 Hz, 1H), 7.92-7.82 (m, 2H), 7.78-7.71 (m, 1H), 5.16 (dd, J=9.2, 4.4 Hz, 1H), 4.58 (dd, J=9.6, 9.2 Hz, 1H), 4.45 (dd, J=9.6, 4.4 Hz, 1H).

Example 62: Synthesis of 3-(isoquinolin-4-yl)-1-(5-methyl-2-(trifluoromethyl)pyrimidin-4-yl)-2-oxoimidazolidine-4-carbonitrile (62), (R)-3-(isoquinolin-4-yl)-1-(5-methyl-2-(trifluoromethyl)pyrimidin-4-yl)-2-oxoimidazolidine-4-carbonitrile (62a) and (S)-3-(isoquinolin-4-yl)-1-(5-methyl-2-(trifluoromethyl)pyrimidin-4-yl)-2-oxoimidazolidine-4-carbonitrile (62b)

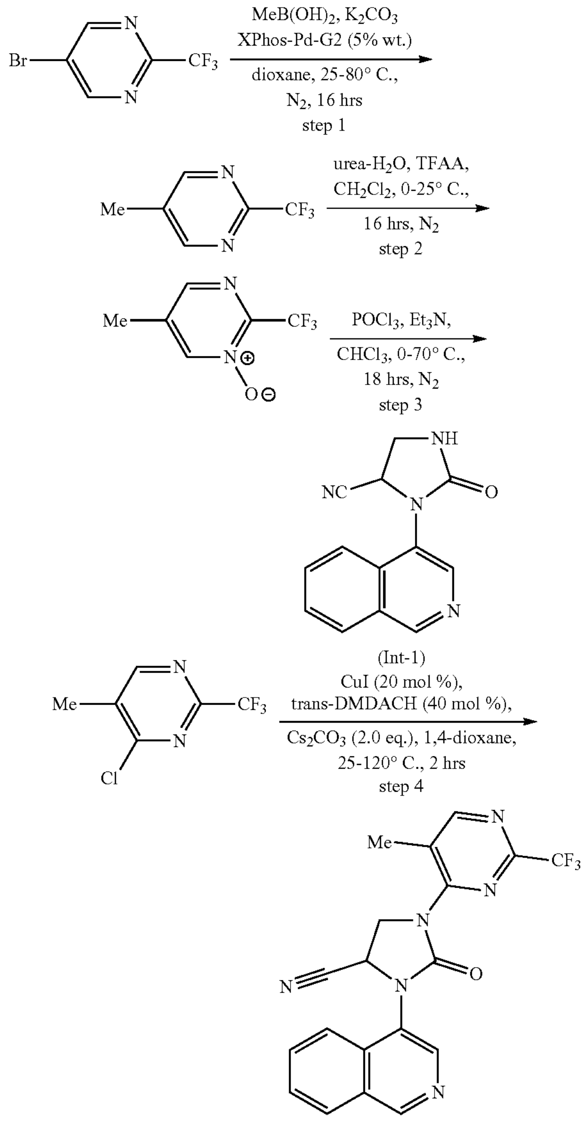

(62)

-continued

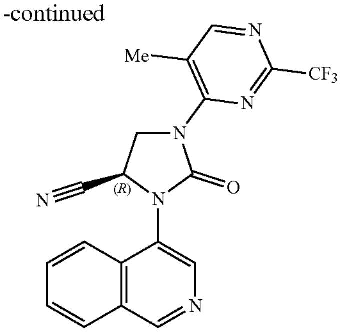

(62a)

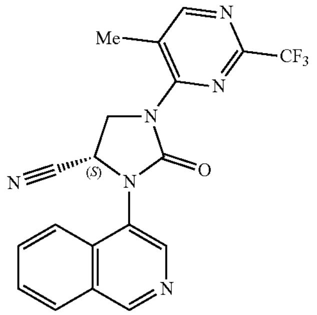

(62b)

Step 1: To a solution of 5-bromo-2-(trifluoromethyl) pyrimidine (8.0 g, 35.24 mmol, 1.0 eq.), methylboronic acid (4.2 g, 70.48 mmol, 2.0 eq.) and $K_2CO_3$ (9.7 g, 70.48 mmol, 2.0 eq.) in dioxane (100 mL) was added XPhos-Pd-G2 (400 mg, 5% wt.) at 25° C. under $N_2$. The mixture was stirred at 80° C. under $N_2$ for 16 hrs. The mixture was concentrated, diluted with $H_2O$ (100 mL), extracted with MTBE (60 mL×2). The organic layer was washed with brine (100 mL), dried over $Na_2SO_4$, filtered and concentrated to give a residue. The residue was purified by flash column chromatogrpahy (petroleum ether/THF=20/1) to give 5-methyl-2-(trifluoromethyl)pyrimidine. $^1H$ NMR: (400 MHz, CHLOROFORM-d) δ=8.74 (s, 2H), 2.45 (s, 3H).

Step 2: To a mixture of 5-methyl-2-(trifluoromethyl) pyrimidine (1.0 g, 6.17 mmol, 1.0 eq.) and urea-$H_2O_2$(870 mg, 9.25 mmol, 1.5 eq.) in $CH_2Cl_2$ (15 mL) was added drop wise a solution of TFAA (2.6 g, 12.34 mmol, 2.0 eq.) in $CH_2Cl_2$ (5 mL) at 0° C. under $N_2$. The mixture was stirred at 25° C. for 16 hrs. The combined mixtures were diluted with $CH_2Cl_2$ (50 mL), washed with aq·$Na_2SO_3$ (50 mL), aq·$NaHCO_3$ (50 mL), brine (30 mL), dried over $Na_2SO_4$, filtered and concentrated to give a residue. The residue was purified by flash column chromatography (petroleum ether/THF=5/1-3/1) to give 5-methyl-2-(trifluoromethyl)pyrimidine 1-oxide. $^1H$ NMR: (400 MHz, CHLOROFORM-d) δ=8.34 (s, 1H), 8.15 (s, 1H), 2.41 (s, 3H).

Step 3: To a solution of $Et_3N$ (451 mg, 4.50 mmol, 2.0 eq.) in $CHCl_3$ (8 mL) was added dropwise $POCl_3$ (689 mg, 4.50 mmol, 2.0 eq.) at 0° C. under $N_2$. Then the mixture was cooled to 0° C. and added dropwise to a solution of 5-methyl-2-(trifluoromethyl)pyrimidine 1-oxide (400 mg, 2.25 mmol, 1.0 eq.) in $CHCl_3$ (2 mL) at 0° C. under $N_2$. The mixture was stirred at 70° C. for 18 hrs. The mixture was diluted with $CH_2Cl_2$ (30 mL), washed with aq·$NaHCO_3$ (50 mL), brine (50 mL), dried over $Na_2SO_4$, filtered and concentrated to give a residue. The residue was purified by flash column chromatograhy (petroleum ether/THF=5/1) to give 4-chloro-5-methyl-2-(trifluoromethyl)pyrimidine. $^1$H NMR: (400 MHz, CHLOROFORM-d) δ=8.40 (s, 1H), 4.11 (s, 3H).

Step 4: Racemic 3-(isoquinolin-4-yl)-1-(5-methyl-2-(trifluoromethyl)pyrimidin-4-yl)-2-oxoimidazolidine-4-carbonitrile (62) was synthesized in a manner similar to Example 4 using 4-chloro-5-methyl-2-(trifluoromethyl)pyrimidine in place of 4-trifluoromethyl-iodobenzene. Achiral purification of the racemate was achieved using flash chromatography column (petroleum ether/THF=4/1-3/1). Chiral separation of the racemate by SFC column: DAICEL CHIRALPAK IG (250 mm×30 mm, 10 μm); IPA (0.1% $NH_3$—$H_2O$); 50%, 8 min) gave 2 peaks.

Peak 1 was assigned as (R)-3-(isoquinolin-4-yl)-1-(5-methyl-2-(trifluoromethyl)pyrimidin-4-yl)-2-oxoimidazolidine-4-carbonitrile (62a). LCMS (Method 31): $t_R$=2.81 min, M+1 (399.1); SFC (Method 25): $t_R$=1.18 min, 100.0%; $^1$H NMR: (400 MHz, CHLOROFORM-d) δ=9.37 (s, 1H), 8.73 (d, J=8.3 Hz, 2H), 8.15 (d, J=8.3 Hz, 1H), 7.88 (d, J=4.0 Hz, 2H), 7.80-7.72 (m, 1H), 5.11 (dd, J=8.4, 2.9 Hz, 1H), 5.00 (dd, J=10.6, 8.4 Hz, 1H), 4.45 (dd, J=10.6, 2.4 Hz, 1H), 2.55 (s, 3H).

Peak 2 was assigned as (S)-3-(isoquinolin-4-yl)-1-(5-methyl-2-(trifluoromethyl)pyrimidin-4-yl)-2-oxoimidazolidine-4-carbonitrile (62b). LCMS (Method 31): $t_R$=2.81 min, M+1 (399.1); SFC (Method 25): $t_R$=1.49 min, 100.0%; $^1$H NMR: (400 MHz, CHLOROFORM-d) δ=9.37 (s, 1H), 8.73 (d, J=8.3 Hz, 2H), 8.15 (d, J=8.3 Hz, 1H), 7.88 (d, J=4.0 Hz, 2H), 7.80-7.72 (m, 1H), 5.11 (dd, J=8.4, 2.9 Hz, 1H), 5.00 (dd, J=10.6, 8.4 Hz, 1H), 4.45 (dd, J=10.6, 2.4 Hz, 1H), 2.55 (s, 3H).

Example 63: Synthesis of 1-(1H-indazol-7-yl)-3-(isoquinolin-4-yl)-2-oxoimidazolidine-4-carbonitrile (63), (R)-1-(1H-indazol-7-yl)-3-(isoquinolin-4-yl)-2-oxoimidazolidine-4-carbonitrile (63a) and (S)-1-(1H-indazol-7-yl)-3-(isoquinolin-4-yl)-2-oxoimidazolidine-4-carbonitrile (63b)

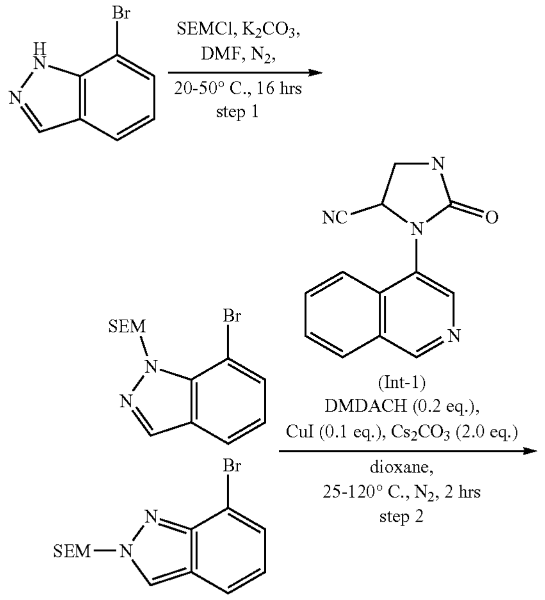

-continued

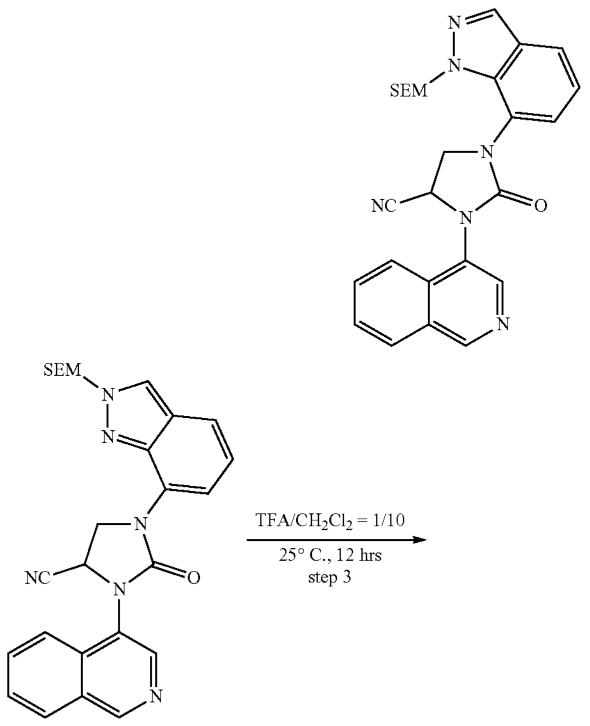

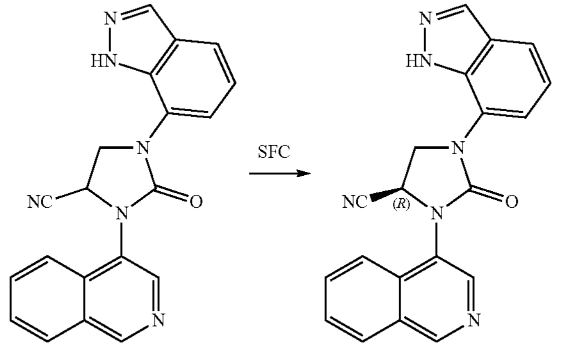

(63) (63a)

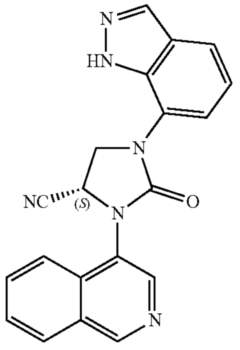

(63b)

Step 1: To a mixture of 7-bromo-1H-indazole (3.0 g, 15.23 mmol, 1.0 eq.) and $K_2CO_3$ (3.2 g, 22.84 mmol, 1.5 eq.) in DMF (60 mL) was added SEMCI (3.1 g, 18.27 mmol, 1.2 eq.) at 2° C. and the reaction mixture stirred at 50° C. under $N_2$ for 16 hrs. The reaction mixture was quenched with $H_2O$ and extracted with ethyl acetate. The combined organic layers were washed with brine, dried over $Na_2SO_4$, filtered and concentrated to give crude product. The crude product was purified by MPLC (Petroleum ether/EtOAc=10%-15%) to give a mixture of 7-bromo-1-((2-(trimethylsilyl)ethoxy)methyl)-1H-indazole and 7-bromo-2-((2-(trimethylsilyl)ethoxy)methyl)-2H-indazole. LCMS (Method 15): $t_R$=0.97 min, M+1 (329.1).

Step 2: A mixture of rac-3-(isoquinolin-4-yl)-2-oxo-1-(1-((2-(trimethylsilyl)ethoxy)methyl)-1H-indazol-7-yl)imidazolidine-4-carbonitrile and rac-3-(isoquinolin-4-yl)-2-oxo-1-(2-((2-(trimethylsilyl)ethoxy)methyl)-2H-indazol-7-yl) imidazolidine-4-carbonitrile was synthesized in a manner similar to Example 4 using a mixture of 7-bromo-1-((2-(trimethylsilyl)ethoxy)methyl)-1H-indazole and 7-bromo-2-((2-(trimethylsilyl)ethoxy)methyl)-2H-indazole in place of 4-trifluoromethyl-iodobenzene. Achiral purification of the racemate was achieved using MPLC (Petroleum ether/EtOAc=50%-70%). LCMS (Method 15): $t_R$=0.84 min, M+1 (485.2).

Step 3: The mixture of rac-3-(isoquinolin-4-yl)-2-oxo-1-(1-((2-(trimethylsilyl)ethoxy)methyl)-1H-indazol-7-yl)imidazolidine-4-carbonitrile and rac-3-(isoquinolin-4-yl)-2-oxo-1-(2-((2-(trimethylsilyl)ethoxy)methyl)-2H-indazol-7-yl)imidazolidine-4-carbonitrile (500 mg, 0.41 mmol) in TFA and $CH_2Cl_2$ (2.0 mL, 1/10) was stirred at 25° C. under $N_2$ for 12 hrs. The mixture was concentrated to give crude product. Achiral purification of the crude product by prep-HPLC (Instrument: Gilson 281 semi-preparative HPLC system, Mobile phase: A: 10 mM $NH_4HCO_3$ in $H_2O$; B: ACN, Column: Waters Xbridge BEH C18 100 mm×30 mm, 10 μm, Flow rate: 25 mL/min, Monitor wavelength: 220 & 254 nm) gave racemic 1-(1H-indazol-7-yl)-3-(isoquinolin-4-yl)-2-oxoimidazolidine-4-carbonitrile (63). Chiral separation of the racemate by SFC (Column: Chiralcel OD-3, 50 mm×4.6 mm, 3 μm; Mobile phase: A for $CO_2$ and B for IPA (0.1% IPAm, V/V); Gradient: B %=50% isocratic elution mode; Flow rate: 4.0 mL/min; Wavelength: 220 nm; Column temperature: 35° C.; System back pressure: 125 bar.) gave 2 peaks.

Peak 1 was assigned as (R)-1-(1H-indazol-7-yl)-3-(isoquinolin-4-yl)-2-oxoimidazolidine-4-carbonitrile (63a). LCMS (Method 1): $t_R$=1.93 min, M+1 (355.1); SFC (Method 31): $t_R$=0.64 5 min, 100.0%; $^1H$ NMR: (400 MHz, CHLOROFORM-d) δ=9.37 (s, 1H), 8.77 (s, 1H), 8.17-8.07 (m, 2H), 7.97 (br d, J=8.1 Hz, 1H), 7.89-7.84 (m, 1H), 7.80-7.70 (m, 1H), 7.65 (d, J=8.0 Hz, 1H), 7.19 (t, J=7.8 Hz, 1H), 6.95 (d, J=7.6 Hz, 1H), 5.26 (br dd, J=9.0, 4.9 Hz, 1H), 4.68 (dd, J=9.7, 9.0 Hz, 1H), 4.53 (dd, J=9.7, 4.9 Hz, 1H).

Peak 2 was assigned as (S)-1-(1H-indazol-7-yl)-3-(isoquinolin-4-yl)-2-oxoimidazolidine-4-carbonitrile (63b). LCMS (Method 1): $t_R$=1.93 min, M+1 (355.1), SFC (Method 31): $t_R$=1.79 min, 99.8%; $^1H$ NMR: (400 MHz, CHLOROFORM-d) δ=9.37 (s, 1H), 8.77 (s, 1H), 8.17-8.07 (m, 2H), 7.97 (br d, J=8.1 Hz, 1H), 7.89-7.84 (m, 1H), 7.80-7.70 (m, 1H), 7.65 (d, J=8.0 Hz, 1H), 7.19 (t, J=7.8 Hz, 1H), 6.95 (d, J=7.6 Hz, 1H), 5.26 (br dd, J=9.0, 4.9 Hz, 1H), 4.68 (dd, J=9.7, 9.0 Hz, 1H), 4.53 (dd, J=9.7, 4.9 Hz, 1H).

Example 64: Synthesis of 1-(1-isopropyl-1H-pyrazol-4-yl)-3-(isoquinolin-4-yl)-2-oxoimidazolidine-4-carbonitrile (64), (R)-1-(1-isopropyl-1H-pyrazol-4-yl)-3-(isoquinolin-4-yl)-2-oxoimidazolidine-4-carbonitrile (64a) and (S)-1-(1-isopropyl-1H-pyrazol-4-yl)-3-(isoquinolin-4-yl)-2-oxoimidazolidine-4-carbonitrile (64b)

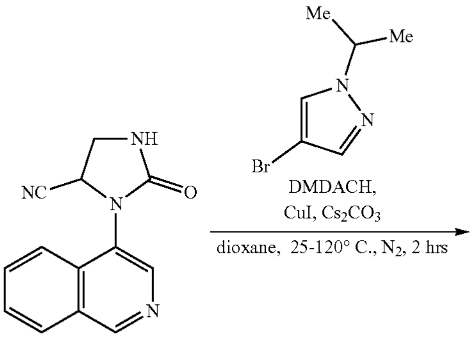

(Int-1)

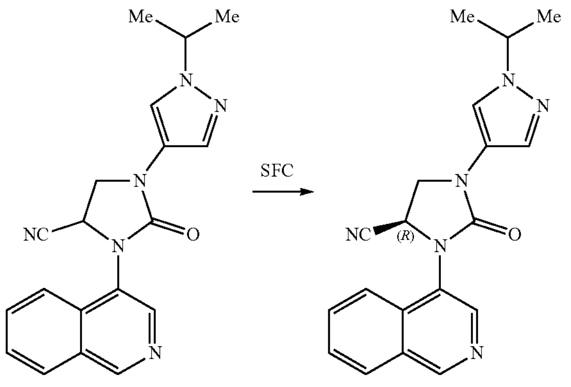

(64) (64a)

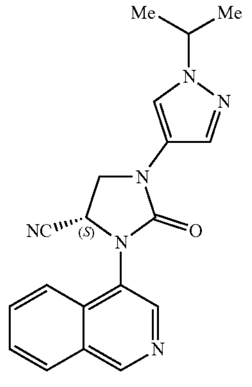

(64b)

Racemate 1-(1-isopropyl-1H-pyrazol-4-yl)-3-(isoquinolin-4-yl)-2-oxoimidazolidine-4-carbonitrile (64) was synthesized in a manner similar to Example 4 using 4-bromo-1-isopropyl-1H-pyrazole in place of 4-trifluoromethyl-iodobenzene. Achiral purification of the racemate was achieved using flash column chromatography ($SiO_2$, Petroleum ether/Ethyl acetate=100/1 to 0/1). LCMS (Method 31): $t_R$=2.39 min, M+1 (347.2); SFC (Method 1): Peak 1 $R_t$=1.29 min, peak 2 $R_t$=1.40 min; $^1$H NMR: (400 MHz, DMSO-$d_6$) δ=9.41 (s, 1H), 8.62 (s, 1H), 8.27 (d, J=8.1 Hz, 1H), 8.06 (d, J=8.6 Hz, 1H), 7.93 (s, 1H), 7.89 (dt, J=7.7, 1.2 Hz, 1H), 7.82-7.77 (m, 1H), 7.61 (s, 1H), 5.67 (dd, J=9.2, 4.4 Hz, 1H), 4.49 (hept, J=6.6 Hz, 1H), 4.43-4.35 (m, 1H), 4.29 (dd, J=4.4, 9.7 Hz, 1H), 1.41 (d, J=6.6 Hz, 6H).

Chiral separation of the racemate by SFC (column: REGIS(S, S) WHELK-01 (250 mm×25 mm, μm); mobile phase: 0.1% $NH_3H_2O$ IPA; B % 35%-35%, 20 min]) gave 2 peaks Peak 1 was assigned as (R)-1-(1-isopropyl-1H-pyrazol-4-yl)-3-(isoquinolin-4-yl)-2-oxoimidazolidine-4-carbonitrile (64a). LCMS (Method 31): $t_R$=2.38 min, M+1 (347.2); SFC (Method 1): $t_R$=1.30 min, 99.8%; $^1$H NMR: (400 MHz, DMSO-$d_6$) δ=9.41 (s, 1H), 8.62 (s, 1H), 8.27 (d, J=8.1 Hz, 1H), 8.06 (d, J=8.6 Hz, 1H), 7.93 (s, 1H), 7.89 (dt, J=7.7, 1.2 Hz, 1H), 7.82-7.77 (m, 1H), 7.61 (s, 1H), 5.67 (dd, J=9.2, 4.4 Hz, 1H), 4.49 (hept, J=6.6 Hz, 1H), 4.43-4.35 (m, 1H), 4.29 (dd, J=4.4, 9.7 Hz, 1H), 1.41 (d, J=6.6 Hz, 6H).

Peak 2 was assigned as (S)-1-(1-isopropyl-1H-pyrazol-4-yl)-3-(isoquinolin-4-yl)-2-oxoimidazolidine-4-carbonitrile (64b). LCMS (Method 31): $t_R$=2.38 min, M+1 (347.2); SFC (Method 1): $t_R$=1.40 min, 99.3%; $^1$H NMR: (400 MHz, DMSO-$d_6$) δ=9.41 (s, 1H), 8.62 (s, 1H), 8.27 (d, J=8.1 Hz, 1H), 8.06 (d, J=8.6 Hz, 1H), 7.93 (s, 1H), 7.89 (dt, J=7.7, 1.2 Hz, 1H), 7.82-7.77 (m, 1H), 7.61 (s, 1H), 5.67 (dd, J=9.2, 4.4 Hz, 1H), 4.49 (hept, J=6.6 Hz, 1H), 4.43-4.35 (m, 1H), 4.29 (dd, J=4.4, 9.7 Hz, 1H), 1.41 (d, J=6.6 Hz, 6H).

Example 65: Synthesis of 3-(isoquinolin-4-yl)-1-(1-methyl-1H-pyrazol-4-yl)-2-oxoimidazolidine-4-carbonitrile (65), (R)-3-(isoquinolin-4-yl)-1-(1-methyl-1H-pyrazol-4-yl)-2-oxoimidazolidine-4-carbonitrile (65a) and (S)-3-(isoquinolin-4-yl)-1-(1-methyl-1H-pyrazol-4-yl)-2-oxoimidazolidine-4-carbonitrile (65b)

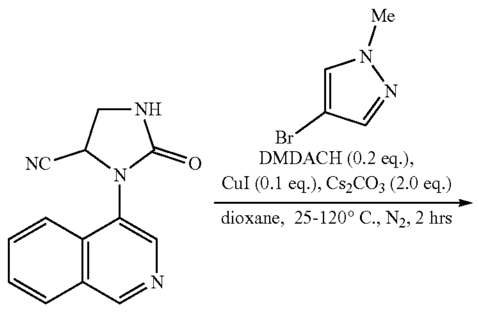

(Int-1)

-continued

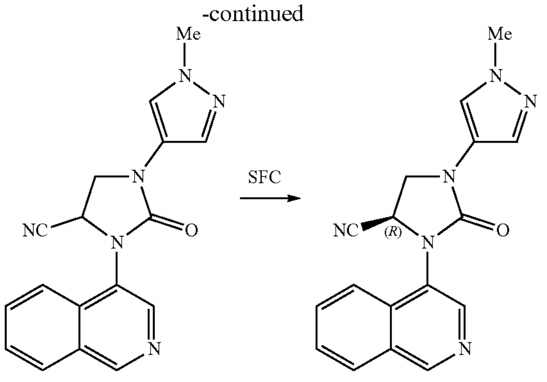

(65) (65a)

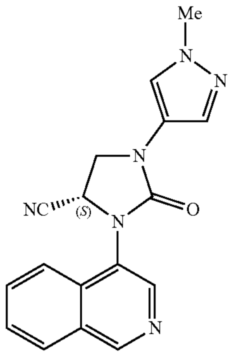

(65b)

Racemic 3-(isoquinolin-4-yl)-1-(1-methyl-1H-pyrazol-4-yl)-2-oxoimidazolidine-4-carbonitrile (65) was synthesized in a manner similar to Example 4 using 4-bromo-1-methyl-1H-pyrazole in place of 4-trifluoromethyl-iodobenzene. Achiral purification of the racemate was achieved using prep-HPLC (column: Phenomenex C18 75 mm×30 mm, 3 μm; liquid phase: [A-FA/$H_2O$=0.1% v/v; B-ACN]B %: 1%-40%, 8 min]). LCMS (Method 31): $t_R$=2.14 min, M+1 (319.1); SFC (Method 15): Peak 1 $R_t$=1.61 min, peak 2 $R_t$=2.22 min; $^1$H NMR (400 MHz, CHLOROFORM-d) δ=9.33 (s, 1H), 8.65 (s, 1H), 8.11 (d, J=8.2 Hz, 1H), 7.94-7.86 (m, 1H), 7.85-7.78 (m, 2H), 7.75-7.68 (m, 1H), 7.47 (s, 1H), 5.12 (dd, J=9.2, 4.8 Hz, 1H), 4.41-4.34 (m, 1H), 4.26 (dd, J=9.4, 4.8 Hz, 1H), 3.92 (s, 3H).

Chiral separation of the racemate using SFC (DAICEL CHIRALPAK AD (250 mm×30 mm, 10 μm); Mobile phase: A for $CO_2$ and B for EtOH (0.1% $NH_3H_2O$); Gradient: B %=50% isocratic elution mode; Flow rate: 70 g/min; Wavelength: 220 nm; Column temperature: 35° C.; System back pressure: 120 bar.) gave 2 peaks Peak 1 was assigned as (R)-3-(isoquinolin-4-yl)-1-(1-methyl-1H-pyrazol-4-yl)-2-oxoimidazolidine-4-carbonitrile (65a). LCMS (Method 1): $t_R$=1.64 min, M+1 (319.1); SFC (Method 15): $t_R$=1.61 min, 100.0%; $^1$H NMR (400 MHz, CHLOROFORM-d) δ=9.33 (s, 1H), 8.65 (s, 1H), 8.11 (d, J=8.2 Hz, 1H), 7.94-7.86 (m, 1H), 7.85-7.78 (m, 2H), 7.75-7.68 (m, 1H), 7.47 (s, 1H), 5.12 (dd, J=9.2, 4.8 Hz, 1H), 4.41-4.34 (m, 1H), 4.26 (dd, J=9.4, 4.8 Hz, 1H), 3.92 (s, 3H)

Peak 2 was assigned as (S)-3-(isoquinolin-4-yl)-1-(1-methyl-1H-pyrazol-4-yl)-2-oxoimidazolidine-4-carbonitrile (65b). LCMS (Method 1): $t_R$=1.64 min, M+1 (319.1); SFC (Method 15): $t_R$=2.25 min, 99.7%; $^1$H NMR (400 MHz, CHLOROFORM-d) δ=9.33 (s, 1H), 8.65 (s, 1H), 8.11 (d, J=8.2 Hz, 1H), 7.94-7.86 (m, 1H), 7.85-7.78 (m, 2H), 7.75-7.68 (m, 1H), 7.47 (s, 1H), 5.12 (dd, J=9.2, 4.8 Hz, 1H), 4.41-4.34 (m, 1H), 4.26 (dd, J=9.4, 4.8 Hz, 1H), 3.92 (s, 3H).

Example 66: Synthesis of 1-(2,4-difluorophenyl)-3-(isoquinolin-4-yl)-2-oxoimidazolidine-4-carbonitrile (66), (R)-1-(2,4-difluorophenyl)-3-(isoquinolin-4-yl)-2-oxoimidazolidine-4-carbonitrile (66a) and (S)-1-(2,4-difluorophenyl)-3-(isoquinolin-4-yl)-2-oxoimidazolidine-4-carbonitrile (66b)

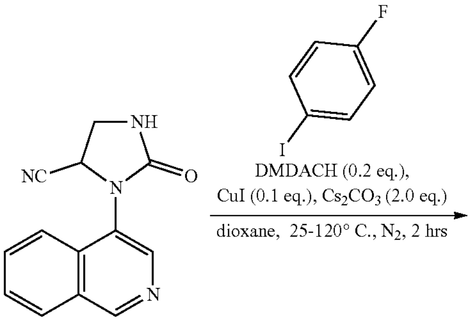

(Int-1)

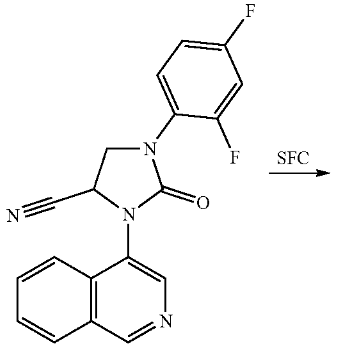

(66)

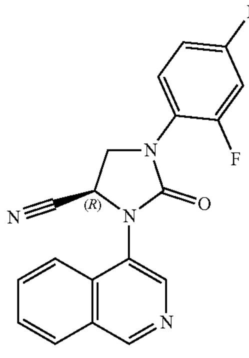

(66a)

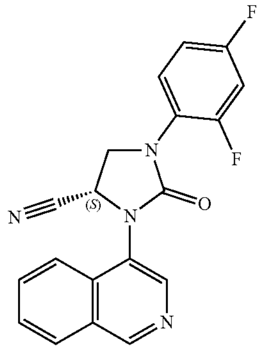

(66b)

Racemic 1-(2,4-difluorophenyl)-3-(isoquinolin-4-yl)-2-oxoimidazolidine-4-carbonitrile (66) was synthesized in a manner similar to Example 4 using 2,4-difluoro-1-iodobenzene in place of 4-trifluoromethyl-iodobenzene. Achiral purification of the racemate was achieved using prep-HPLC ((column: Phenomenex Luna C18 75 mm×30 mm, 3 μm; liquid phase: [A-FA/$H_2O$=0.1% v/v; B-ACN]B %: 20%-60%, 8 min]). LCMS (Method 31): $t_R$=2.62 min, M+1 (351.1); SFC (Method 21): peak 1 $R_t$=1.69 min, peak 2 $R_t$=2.10 min; $^1$H NMR: (400 MHz, CHLOROFORM-d) δ=9.34 (s, 1H), 8.71 (s, 1H), 8.12 (d, J=8.3 Hz, 1H), 7.98-7.91 (m, 1H), 7.85 (td, J=7.7,1.1 Hz, 1H), 7.76-7.70 (m, 1H), 7.64-7.57 (m, 1H), 7.04-6.93 (m, 2H), 5.10 (dd, J=9.0, 4.5, Hz, 1H), 4.52 (dd, J=9.6, 9.0 Hz, 1H), 4.33 (dd, J=9.6, 4.5 Hz, 1H).

Chiral purification of the racemate using SFC (Column: DAICEL CHIRALPAK IG (250 mm×30 mm, 10 μm); Mobile phase: A for $CO_2$ and B for EtOH (0.1% $NH_3H_2O$); Gradient: B %=50% isocratic elution mode; Flow rate: 70 mL/min; Wavelength: 220 nm; Column temperature: 35° C.; System back pressure: 120 bar.) gave 2 peaks.

Peak 1 was assigned as (R)-1-(2,4-difluorophenyl)-3-(isoquinolin-4-yl)-2-oxoimidazolidine-4-carbonitrile (66a). LCMS (Method 1): $t_R$=2.07 min. M+1 (351.1); SFC (Method 21): $t_R$=1.70 min, 99.8%; $^1$H NMR: (400 MHz, CHLOROFORM-d) δ=9.34 (s, 1H), 8.71 (s, 1H), 8.12 (d, J=8.3 Hz, 1H), 7.98-7.91 (m, 1H), 7.85 (td, J=7.7,1.1 Hz, 1H), 7.76-7.70 (m, 1H), 7.64-7.57 (m, 1H), 7.04-6.93 (m, 2H), 5.10 (dd, J=9.0, 4.5, Hz, 1H), 4.52 (dd, J=9.6, 9.0 Hz, 1H), 4.33 (dd, J=9.6, 4.5 Hz, 1H).

Peak 2 was assigned as (S)-1-(2,4-difluorophenyl)-3-(isoquinolin-4-yl)-2-oxoimidazolidine-4-carbonitrile (66b). LCMS (Method 1): $t_R$=2.02 min, M+1 (351.1); SFC (Method 21): $t_R$=2.12 min, 99.9%; $^1$H NMR: (400 MHz, CHLOROFORM-d) δ=9.34 (s, 1H), 8.71 (s, 1H), 8.12 (d, J=8.3 Hz, 1H), 7.98-7.91 (m, 1H), 7.85 (td, J=7.7,1.1 Hz, 1H), 7.76-7.70 (m, 1H), 7.64-7.57 (m, 1H), 7.04-6.93 (m, 2H), 5.10 (dd, J=9.0, 4.5, Hz, 1H), 4.52 (dd, J=9.6, 9.0 Hz, 1H), 4.33 (dd, J=9.6, 4.5 Hz, 1H).

Example 67: Synthesis of 3-(isoquinolin-4-yl)-1-(1-methyl-2-oxo-1,2-dihydropyridin-4-yl)-2-oxoimidazolidine-4-carbonitrile (67), (R)-3-(isoquinolin-4-yl)-1-(1-methyl-2-oxo-1,2-dihydropyridin-4-yl)-2-oxoimidazolidine-4-carbonitrile (67a) and (S)-3-(isoquinolin-4-yl)-1-(1-methyl-2-oxo-1,2-dihydropyridin-4-yl)-2-oxoimidazolidine-4-carbonitrile (67b) (KNA551 DAM569, no rac. Checked.)

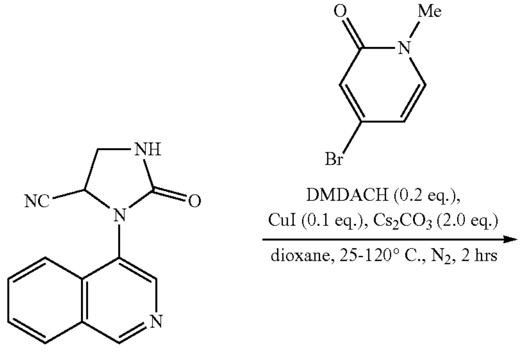

(Int-1)

-continued

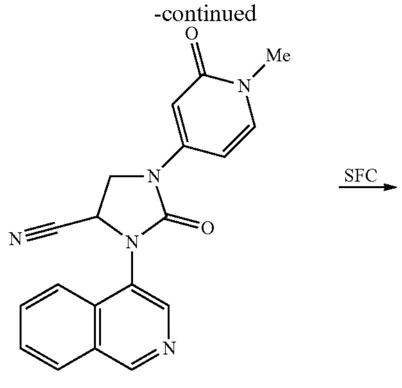

(67)

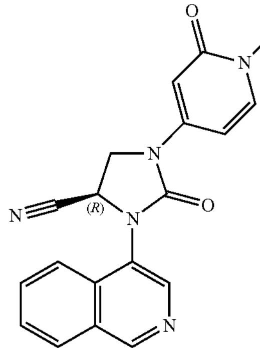

(67a)

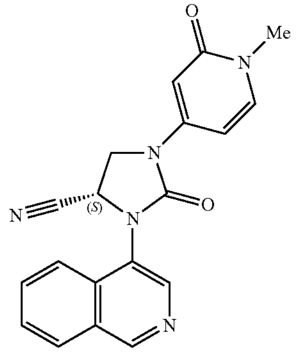

(67b)

Racemic 3-(isoquinolin-4-yl)-1-(1-methyl-2-oxo-1,2-dihydropyridin-4-yl)-2-oxoimidazolidine-4-carbonitrile (67) was synthesized in a manner similar to Example 4 using 4-bromo-1-methylpyridin-2(1H)-one in place of 4-trifluoromethyl-iodobenzene. Achiral purification of the racemate was achieved by MPLC ($SiO_2$, petroleum ether/ethyl acetate=10/1 to 0/1). Chiral separation of the racemate using SFC (column: DAICEL CHIRALCEL OJ (250 mm×30 mm, μm); mobile phase: 0.1% $NH_3H_2O$ EtOH: 50%-50%, 7 min) gave 2 peaks which were independently repurified by prep-HPLC (column: Phenomenex Luna C18 75 mm×30 mm, 3 μm; mobile phase: water (FA)-ACN: 1%-35%, 8 min) and chiral SFC (column: DAICEL CHIRALCEL OJ (250 mm×30 mm, 10 μm; mobile phase: Neu-EtOH: 50%-50%, 15 min).

Peak 1 was assigned as (R)-3-(isoquinolin-4-yl)-1-(1-methyl-2-oxo-1,2-dihydropyridin-4-yl)-2-oxoimidazolidine-4-carbonitrile (67a). LCMS (Method 1): $t_R$=1.64 min, M+1 (346.1); SFC (Method 32): $t_R$=1.66 min, 100%; $^1$H NMR: (400 MHz, CHLOROFORM-d) δ=9.37 (s, 1H), 8.68 (s, 1H), 8.10-8.19 (m, 1H), 7.82-7.90 (m, 2H), 7.70-7.79 (m, 1H), 7.40 (dd, J=7.7, 2.6 Hz, 1H), 7.29 (s, 1H), 6.02 (d, J=2.5 Hz, 1H), 5.10 (dd, J=9.2, 4.44 Hz, 1H), 4.41-4.49 (m, 1H), 4.30 (dd, J=10.1, 4.4 Hz, 1H), 3.56 (s, 3H)

Peak 2 was assigned as (S)-3-(isoquinolin-4-yl)-1-(1-methyl-2-oxo-1,2-dihydropyridin-4-yl)-2-oxoimidazolidine-4-carbonitrile (67b). LCMS (Method 1): $t_R$=1.63 min, M+1 (346.1); SFC (Method 32): $t_R$=2.08 min, 95.7%; $^1$H NMR: (400 MHz, CHLOROFORM-d) δ=9.37 (s, 1H), 8.68 (s, 1H), 8.10-8.19 (m, 1H), 7.82-7.90 (m, 2H), 7.70-7.79 (m, 1H), 7.40 (dd, J=7.7, 2.6 Hz, 1H), 7.29 (s, 1H), 6.02 (d, J=2.5 Hz, 1H), 5.10 (dd, J=9.2, 4.44 Hz, 1H), 4.41-4.49 (m, 1H), 4.30 (dd, J=10.1, 4.4 Hz, 1H), 3.56 (s, 3H).

Example 68: Synthesis of 3-(isoquinolin-4-yl)-2-oxo-1-(5-(trifluoromethyl)-1H-imidazol-2-yl)imidazolidine-4-carbonitrile (68), (R)-3-(isoquinolin-4-yl)-2-oxo-1-(5-(trifluoromethyl)-1H-imidazol-2-yl)imidazolidine-4-carbonitrile (68a) and (S)-3-(isoquinolin-4-yl)-2-oxo-1-(5-(trifluoromethyl)-1H-imidazol-2-yl)imidazolidine-4-carbonitrile (68b)

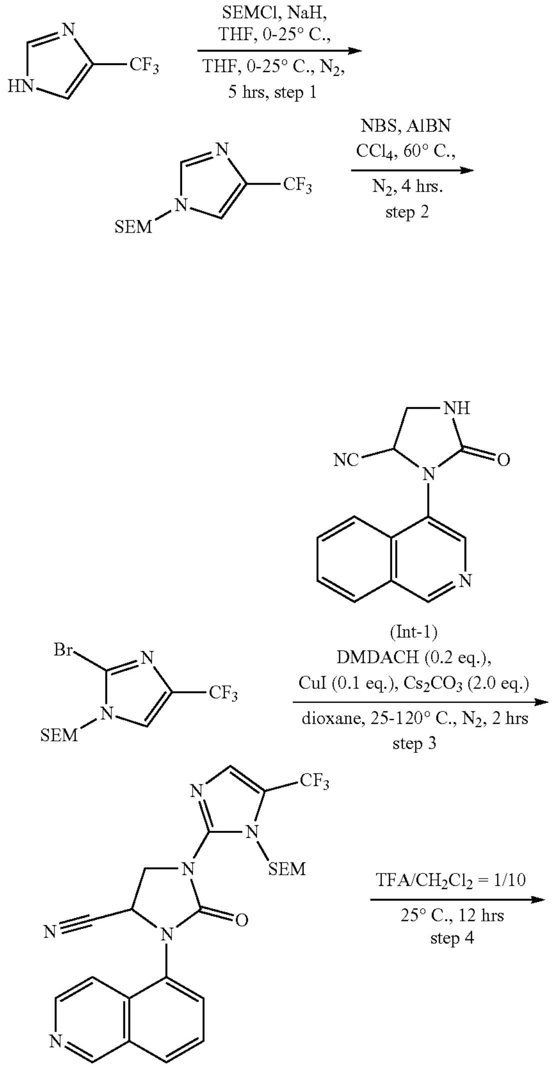

-continued

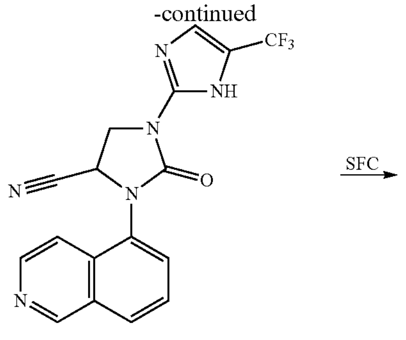

(68)

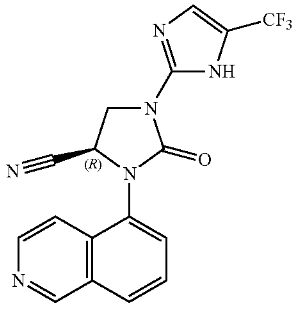

(68a)

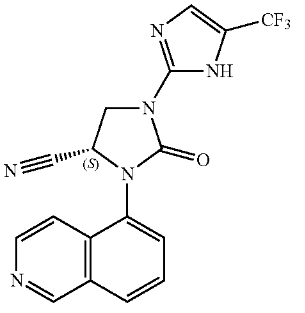

(68b)

Step 1: A mixture of NaH (647 mg, 16.17 mmol, 1.1 eq.) in THE (40 mL) was stirred at 0° C. under $N_2$. A solution of 4-(trifluoromethyl)-1H-imidazole (2.0 g, 14.70 mmol, 1.0 eq.) in THE (9 15 mL) was added dropwise. The solution was stirred at 25° C. for 1.5 hrs and SEMCI (3.2 g, 19.11 mmol, 1.3 eq.) was added. The mixture was stirred at 25° C. for 3.5 hrs. The reaction was quenched with $NaHCO_3$ (50 mL) and extracted with EtOAc (30 mL×3). The combined organic layers were washed with brine (30 mL×3), dried over $Na_2SO_4$, filtered and concentrated under reduced pressure to give a residue. The residue was purified by MPLC (petroleum ether/Ethyl acetate=100/0 to 0/100) to give 4-(trifluoromethyl)-1-((2-(trimethylsilyl)ethoxy)methyl)-1H-imidazole. $^1$H NMR: (400 MHz, CHLOROFORM-d) δ=7.64 (s, 1H), 7.39 (d, J=1.1 Hz, 1H), 5.30 (s, 2H), 3.54-3.49 (m, 2H), 0.97-0.90 (m, 2H), 0.01-0.01 (m, 9H).

Step 2: To a solution of 4-(trifluoromethyl)-1-((2-(trimethylsilyl)ethoxy)methyl)-1H-imidazole (2.9 g, 10.89 mmol, 1.0 eq.) in $CC_4$ (60 mL) was added NBS (2.5 g, 14.16 mmol, 1.3 eq.) and AIBN (358 mg, 2.18 mmol, 0.2 eq.) under $N_2$. The mixture was stirred at 60° C. for 4 hrs. The reaction was quenched with $NaHCO_3$ (60 mL) and extracted with $CH_2Cl_2$ (50 mL×3). The combined organic layers were washed with brine (50 mL×3), dried over $Na_2SO_4$, filtered and concentrated under reduced pressure to give a residue. The residue was purified by MPLC (petroleum ether/Ethyl acetate=100/0 to 0/100) to give 2-bromo-4-(trifluoromethyl)-1-((2-(trimethylsilyl)ethoxy)methyl)-1H-imidazole. $^1$H NMR: (400 MHz, CHLOROFORM-d) δ=7.45 (d, J=1.1 Hz, 1H), 5.31 (s, 2H), 3.60-3.55 (m, 2H), 0.97-0.92 (m, 2H), 0.03-0.00 (m, 9H).

Step 3: Racemic 3-(isoquinolin-4-yl)-2-oxo-1-(5-(trifluoromethyl)-1-((2-(trimethylsilyl)ethoxy)methyl)-1H-imidazol-2-yl)imidazolidine-4-carbonitrile was synthesized in a manner similar to Example 4 using 2-bromo-4-(trifluoromethyl)-1-((2-(trimethylsilyl)ethoxy)methyl)-1H-imidazole in place of 4-trifluoromethyl-iodobenzene. Achiral purification of the racemate was achieved using prep-HPLC (column: Phenomenex Luna C18 200 mm×40 mm, 10 μm; liquid phase: [A-$H_2O$ (0.1% FA); B-ACN]B %: 50%-90%, 20 min]). $^1$H NMR: (400 MHz, CHLOROFORM-d) δ=9.36 (s, 1H), 8.69 (s, 1H), 8.13 (d, J=8.2 Hz, 1H), 7.89-7.83 (m, 2H), 7.77-7.72 (m, 1H), 7.38 (s, 1H), 5.52-5.48 (m, 1H), 5.41-5.37 (m, 1H), 5.10 (dd, J=8.7, 3.5 Hz, 1H), 4.83 (t, J=9.4 Hz, 1H), 4.38 (dd, J=10.1, 3.4 Hz, 1H), 3.69-3.57 (m, 2H), 1.04-0.98 (m, 2H), 0.05 (s, 9H).

Step 4: A mixture of rac-3-(isoquinolin-4-yl)-2-oxo-1-(5-(trifluoromethyl)-1-((2-(trimethylsilyl)ethoxy)methyl)-1H-imidazol-2-yl)imidazolidine-4-carbonitrile (100 mg, 198.98 μmol, 1.0 eq.) in $CH_2Cl_2$/TFA=10/1 (2 mL) was stirred at 25° C. for 16 hrs. The reaction was concentrated under reduced pressure to give a crude product. The crude product was purified by prep-TLC (Petroleum ether/Ethyl acetate=1/1) to obtain the racemate 3-(isoquinolin-4-yl)-2-oxo-1-(5-(trifluoromethyl)-1H-imidazol-2-yl)imidazolidine-4-carbonitrile (68). Separation of racemic 3-(isoquinolin-4-yl)-2-oxo-1-(5-(trifluoromethyl)-1H-imidazol-2-yl) imidazolidine-4-carbonitrile (75) by prep-SFC (column: DAICEL CHIRALPAK IG [250 mm×30 mm, 10 μm; 0.1% $NH_3H_2O$ IPA; B % 40%-40%, 20 min]) gave two peaks.

Peak 1 was assigned as (R)-3-(isoquinolin-4-yl)-2-oxo-1-(5-(trifluoromethyl)-1H-imidazol-2-yl)imidazolidine-4-carbonitrile (68a). LCMS (Method 2): $t_R$=2.66 min, M+1 (373.0); SFC (Method 25): $t_R$=1.19 min, 100%; $^1$H NMR: (400 MHz, DMSO-$d_6$) δ=12.20 (brs, 1H), 9.44 (s, 1H), 8.71 (s, 1H), 8.29 (d, J=8.1 Hz, 1H), 8.20 (d, J=8.5 Hz, 1H), 7.97-7.94 (m, 1H), 7.83-7.79 (m, 1H), 7.47 (s, 1H), 5.69 (dd, J=4.7, 9.6 Hz, 1H), 4.62 (dd, J=10.1, 9.6 Hz, 1H), 4.42 (dd, J=4.7, 10.1 Hz, 1H).

Peak 2 was assigned as (S)-3-(isoquinolin-4-yl)-2-oxo-1-(5-(trifluoromethyl)-1H-imidazol-2-yl)imidazolidine-4-carbonitrile (68b). LCMS (Method 2): $t_R$=2.57 min, M+1 (373.1); SFC (Method 25): $t_R$=1.41 min, 100.0%; $^1$H NMR: (400 MHz, DMSO-$d_6$) δ=12.20 (brs, 1H), 9.44 (s, 1H), 8.71 (s, 1H), 8.29 (d, J=8.1 Hz, 1H), 8.20 (d, J=8.5 Hz, 1H), 7.97-7.94 (m, 1H), 7.83-7.79 (m, 1H), 7.47 (s, 1H), 5.69 (dd, J=4.7, 9.6 Hz, 1H), 4.62 (dd, J=10.1, 9.6 Hz, 1H), 4.42 (dd, J=4.7, 10.1 Hz, 1H).

Example 69: Synthesis of 1-(3-(2-hydroxypropan-2-yl)phenyl)-3-(isoquinolin-4-yl)-2-oxoimidazolidine-4-carbonitrile (69), (R)-1-(3-(2-hydroxypropan-2-yl)phenyl)-3-(isoquinolin-4-yl)-2-oxoimidazolidine-4-carbonitrile (69a) and (S)-1-(3-(2-hydroxypropan-2-yl)phenyl)-3-(isoquinolin-4-yl)-2-oxoimidazolidine-4-carbonitrile (69b)

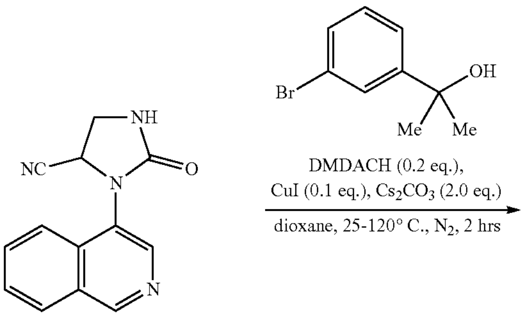

(Int-1)

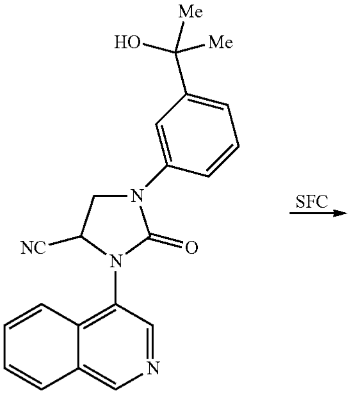

(69)

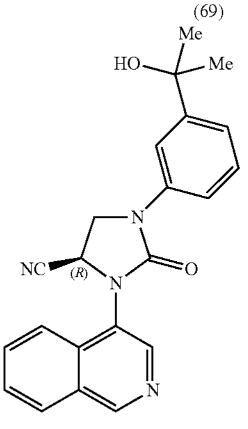

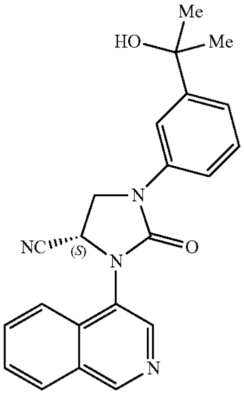

(69a) (69b)

Racemic 1-(3-(2-hydroxypropan-2-yl)phenyl)-3-(isoquinolin-4-yl)-2-oxoimidazolidine-4-carbonitrile (69) was synthesized in a manner similar to Example 4 using 2-(3-bromophenyl)propan-2-ol in place of 4-trifluoromethyl-iodobenzene. Achiral purification of the racemate was achieved using prep-HPLC (column: Phenomenex Luna C18 75 mm×30 mm, 3 μm; liquid phase: [A-$NH_4HCO_3$/$H_2O$=0.1% v/v; B-ACN]B %: 20%-40%, 8 min]). Chiral separation of the racemate by SFC (column: DAICEL CHIRALPAK AD (250 mm×30 mm, 10 μm; mobile phase: 0.1% $NH_3$—$H_2O$ MeOH; B % 55%-55%, 10 min]) gave 2 peaks.

Peak 1 was assigned as (R)-1-(3-(2-hydroxypropan-2-yl)phenyl)-3-(isoquinolin-4-yl)-2-oxoimidazolidine-4-carbonitrile (69a). LCMS (Method 1): $t_R$=2.50 min, M+1 (373.2); SFC (Method 23): $t_R$=1.58 min, 100.0%; $^1$H NMR: (400 MHz, DMSO-$d_6$) δ=9.42 (s, 1H), 8.67 (s, 1H), 8.28 (d, J=8.3 Hz, 1H), 8.10 (d, J=8.4 Hz, 1H), 7.93-7.87 (m, 1H), 7.82-7.78 (m, 1H), 7.74 (s, 1H), 7.44 (br d, J=8.0 Hz, 1H), 7.36-7.30 (m, 1H), 7.23 (br d, J=7.8 Hz, 1H), 5.66 (br dd, J=4.6, 9.1 Hz, 1H), 5.07 (s, 1H), 4.62-4.54 (m, 1H), 4.45 (br dd, J=4.6, 9.6 Hz, 1H), 1.44 (s, 6H).

Peak 2 was assigned as (S)-1-(3-(2-hydroxypropan-2-yl)phenyl)-3-(isoquinolin-4-yl)-2-oxoimidazolidine-4-carbonitrile (69b). LCMS (Method 1): $t_R$=2.50 min, M+1 (373.2); SFC (Method 23): $t_R$=1.81 min, 98.7%; $^1$H NMR: (400 MHz, DMSO-$d_6$) δ=9.42 (s, 1H), 8.67 (s, 1H), 8.28 (d, J=8.3 Hz, 1H), 8.10 (d, J=8.4 Hz, 1H), 7.93-7.87 (m, 1H), 7.82-7.78 (m, 1H), 7.74 (s, 1H), 7.44 (br d, J=8.0 Hz, 1H), 7.36-7.30 (m, 1H), 7.23 (br d, J=7.8 Hz, 1H), 5.66 (br dd, J=4.6, 9.1 Hz, 1H), 5.07 (s, 1H), 4.62-4.54 (m, 1H), 4.45 (br dd, J=4.6, 9.6 Hz, 1H), 1.44 (s, 6H).

Example 70: Synthesis of 1-(5-chloro-2-(trifluoromethyl)pyridin-4-yl)-3-(isoquinolin-4-yl)-2-oxoimidazolidine-4-carbonitrile (70-1), 3-(isoquinolin-4-yl)-1-(5-methyl-2-(trifluoromethyl)pyridin-4-yl)-2-oxoimidazolidine-4-carbonitrile (70-2), (R)-3-(isoquinolin-4-yl)-1-(5-methyl-2-(trifluoromethyl)pyridin-4-yl)-2-oxoimidazolidine-4-carbonitrile (70a) and (S)-3-(isoquinolin-4-yl)-1-(5-methyl-2-(trifluoromethyl)pyridin-4-yl)-2-oxoimidazolidine-4-carbonitrile (70b)

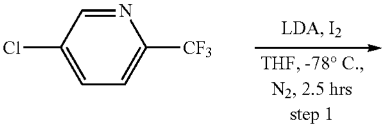

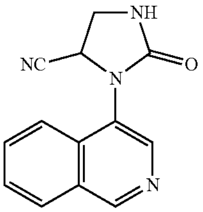

(Int-1)

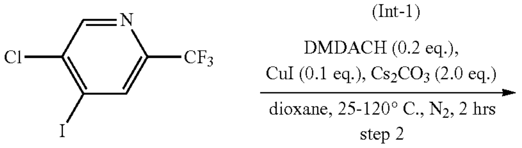

-continued

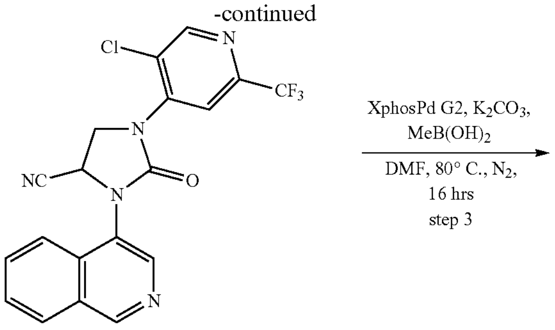

(70-1)

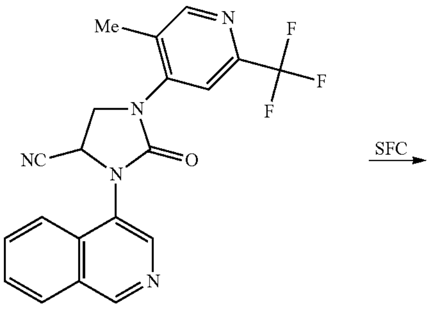

(70-2)

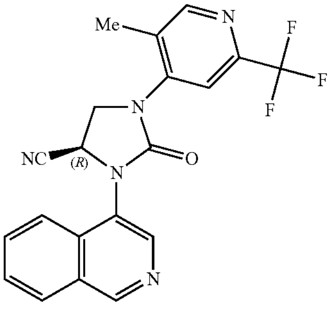

(70a)

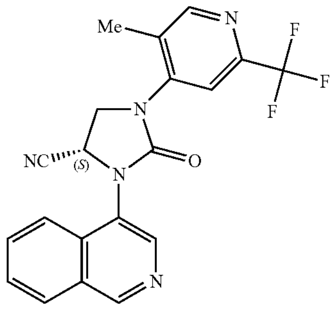

(70b)

Step 1: To a mixture of 5-chloro-2-(trifluoromethyl)pyridine (2.0 g, 11.0 mmol, 1.0 eq.) in THE (20 mL) was added LDA (5.5 mL, 11.01 mmol, 1.0 eq.) dropwise at −78° C. under $N_2$. The mixture was stirred at −78° C. for 0.5 hr under $N_2$. To the mixture was added a solution of $I_2$ (3.0 g, 11.82 mmol, 1.1 eq.) in THE (5 mL) at −78° C. The mixture was stirred at −78° C. for 2 hrs $N_2$. The reaction mixture was quenched with water (50 mL) and extracted with EtOAc (20 mL×2). The combined organic layers were washed with brine (50 mL×2), dried over $Na_2SO_4$, filtered and concentrated under reduced pressure to give crude product which was purified by flash column chromatography (Petroleum ether) to give 5-chloro-4-iodo-2-(trifluoromethyl)pyridine. H NMR: (400 MHz, CHLOROFORM-d) δ=8.64 (s, 1H), 8.16 (s, 1H).

Step 2: Racemic 1-(5-chloro-2-(trifluoromethyl)pyridin-4-yl)-3-(isoquinolin-4-yl)-2-oxoimidazolidine-4-carbonitrile (70-1) was synthesized in a manner similar to Example 4 using 5-chloro-4-iodo-2-(trifluoromethyl)pyridine in place of 4-trifluoromethyl-iodobenzene. Achiral purification of 1-(5-chloro-2-(trifluoromethyl)pyridin-4-yl)-3-(isoquinolin-4-yl)-2-oxoimidazolidine-4-carbonitrile (70-1) was achieved using flash column chromatogrpahy (Petroleum ether/EtOAc=1/1 to 1/2). LCMS (Method 31): $t_R$=2.28 min, M+1 (418.2); $^1H$ NMR: (400 MHz, CHLOROFORM-d) δ=9.38 (s, 1H), 8.82 (s, 1H), 8.73 (s, 1H), 8.15 (d, J=8.1 Hz, 1H), 8.01 (s, 1H), 7.95-7.85 (m, 2H), 7.80-7.73 (m, 1H), 5.15 (dd, J=4.1, 8.5 Hz, 1H), 4.72-4.66 (m, 1H), 4.63-4.57 (m, 1H).

Step 3: A mixture of 1-(5-chloro-2-(trifluoromethyl)pyridin-4-yl)-3-(isoquinolin-4-yl)-2-oxoimidazolidine-4-carbonitrile (70-1) (200 mg, 0.48 mmol, 1.0 eq.), $K_2CO_3$ (200 mg, 1.44 mmol, 3.0 eq.), $MeB(OH)_2$ (86 mg, 1.44 mmol, 3.0 eq.) and Xphos Pd G2 (20 mg, Cat.) in DMF (4 mL) was stirred at 80° C. under $N_2$ for 16 hrs. The reaction mixture was quenched with water (10 mL) and extracted with EtOAc (5 mL×3). The combined organic layers were washed with brine (20 25 mL), dried over $Na_2SO_4$, filtered and concentrated under reduced pressure to give crude product. The crude product was purified by column (petroleum ether/EtOAc=1/2 to 1/3) and then by prep-HPLC (column: Chiralcel OJ-3, 50 mm×4.6 mm, 3 um; liquid phase: [A-FA/$H_2O$=0.1% v/v; B-ACN]B %: 20%-60%, 8 min]) to give racemic 3-(isoquinolin-4-yl)-1-(5-methyl-2-(trifluoromethyl)pyridin-4-yl)-2-oxoimidazolidine-4-carbonitrile (70-2) which was separated by chiral SFC (column: DAICEL CHIRALCEL OJ (250 mm×30 mm, 10 μm); liquid phase: [A-$H_2O$ (0.1% $NH_3H_2O$ IPA); B-ACN]B %: 5%-30%, 20 min]) to obtain two peaks.

Peak 1 was assigned as (R)-3-(isoquinolin-4-yl)-1-(5-methyl-2-(trifluoromethyl)pyridin-4-yl)-2-oxoimidazolidine-4-carbonitrile (70a). LCMS (Method 31): $t_R$=2.16 min, M+1 (398.1); SFC (Method 2): $t_R$=1.01 min, 99.3%; $^1H$ NMR: (400 MHz, DMSO-$d_6$) δ=9.43 (s, 1H), 8.71 (s, 1H), 8.68 (s, 1H), 8.29 (d, J=8.1 Hz, 1H), 8.14 (d, J=7.9 Hz, 1H), 8.02 (s, 1H), 7.94 (td, J=7.7, 1.1 Hz, 1H), 7.84-7.79 (m, 1H), 5.74 (dd, J=8.8, 4.4 Hz, 1H), 4.72 (dd, J=9.4, 8.8 Hz, 1H), 4.48 (dd, J=9.4, 4.4 Hz, 1H), 2.44 (s, 3H).

Peak 2 was assigned as (S)-3-(isoquinolin-4-yl)-1-(5-methyl-2-(trifluoromethyl)pyridin-4-yl)-2-oxoimidazolidine-4-carbonitrile (70b). LCMS (Method 31): $t_R$=2.16 min, M+1 (398.1); SFC (Method 2): $t_R$=1.19 min, 99.5%; $^1H$ NMR: (400 MHz, DMSO-$d_6$) δ=9.43 (s, 1H), 8.71 (s, 1H), 8.68 (s, 1H), 8.29 (d, J=8.1 Hz, 1H), 8.14 (d, J=7.9 Hz, 1H), 8.02 (s, 1H), 7.94 (td, J=7.7, 1.1 Hz, 1H), 7.84-7.79 (m, 1H), 5.74 (dd, J=8.8, 4.4 Hz, 1H), 4.72 (dd, J=9.4, 8.8 Hz, 1H), 4.48 (dd, J=9.4, 4.4 Hz, 1H), 2.44 (s, 3H).

Example 71: Synthesis of 1-(4-(difluoromethoxy)phenyl)-3-(isoquinolin-4-yl)-2-oxoimidazolidine-4-carbonitrile (71), (R)-1-(4-(difluoromethoxy)phenyl)-3-(isoquinolin-4-yl)-2-oxoimidazolidine-4-carbonitrile (71a) and (S)-1-(4-(difluoromethoxy)phenyl)-3-(isoquinolin-4-yl)-2-oxoimidazolidine-4-carbonitrile (71 b)

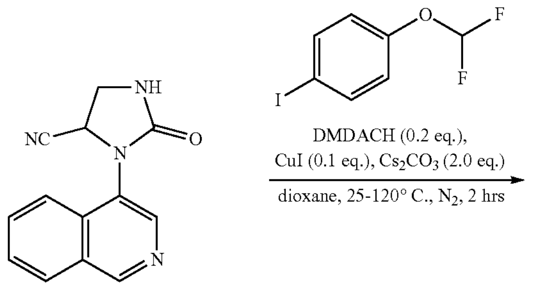

(Int-1)

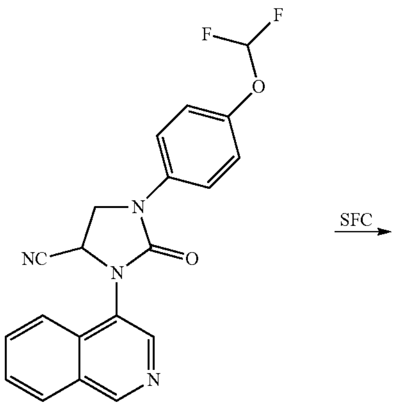

(71)

-continued

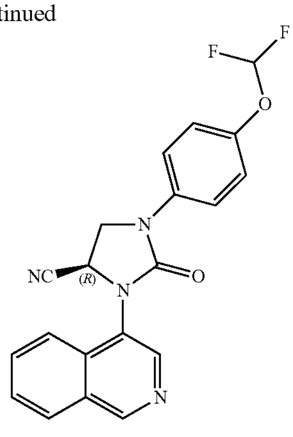

(71a)

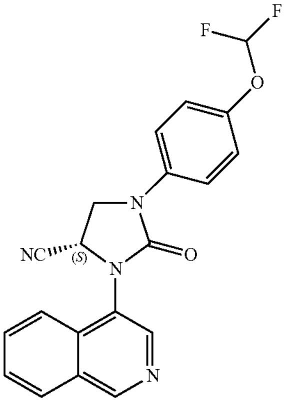

(71b)

Racemic 1-(4-(difluoromethoxy)phenyl)-3-(isoquinolin-4-yl)-2-oxoimidazolidine-4-carbonitrile (71) was synthesized in a manner similar to Example 4 using 1-(difluoromethoxy)-4-iodobenzene in place of 4-trifluoromethyl-iodobenzene. Achiral purification of the racemate was achieved using flash column chromatogrpahy ($SiO_2$, Petroleum ether/EtOAc=100%~35%).

Chiral purification of the racemate by SFC (column: DAICEL CHIRALCEL OJ (250 mm×30 mm, 10 μm); liquid phase: 0.1% $NH_3H_2O$ IPA B %: 35%-35%, 15 min]) gave 2 peaks.

Peak 1 was assigned as (R)-1-(4-(difluoromethoxy)phenyl)-3-(isoquinolin-4-yl)-2-oxoimidazolidine-4-carbonitrile (71a). LCMS (Method 1): $t_R$=2.26 min, M+1 (381.1); SFC (Method 33): $t_R$=3.64 min, 100.0%; $^1H$ NMR: (400 MHz, CHLOROFORM-d) δ=9.34 (s, 1H), 8.69 (s, 1H), 8.11 (d, J=8.1 Hz, 1H), 7.91 (br d, J=8.4 Hz, 1H), 7.82 (td, J=7.7,1.1 Hz, 1H), 7.75-7.69 (m, 1H), 7.61-7.59 (m, 1H), 7.58-7.56 (m, 1H), 7.23-7.20 (m, 1H), 7.20-7.17 (m, 1H), 6.71-6.31 (m, 1H), 5.09 (dd, J=9.1, 4.6 Hz, 1H), 4.50 (dd, J=9.6, 9.1 Hz, 1H), 4.36 (dd, J=9.6, 4.6 Hz, 1H)

Peak 2 was assigned as (S)-1-(4-(difluoromethoxy)phenyl)-3-(isoquinolin-4-yl)-2-oxoimidazolidine-4-carbonitrile (71b). LCMS (Method 1): $t_R$=2.26 min, M+1 (381.1); SFC (Method 33): $t_R$=4.08 min, 99.5%; $^1H$ NMR: (400 MHz, CHLOROFORM-d) δ=9.34 (s, 1H), 8.69 (s, 1H), 8.11 (d, J=8.1 Hz, 1H), 7.91 (br d, J=8.4 Hz, 1H), 7.82 (td, J=7.7,1.1 Hz, 1H), 7.75-7.69 (m, 1H), 7.61-7.59 (m, 1H), 7.58-7.56 (m, 1H), 7.23-7.20 (m, 1H), 7.20-7.17 (m, 1H), 6.71-6.31 (m, 1H), 5.09 (dd, J=9.1, 4.6 Hz, 1H), 4.50 (dd, J=9.6, 9.1 Hz, 1H), 4.36 (dd, J=9.6, 4.6 Hz, 1H).

Example 72: Synthesis of 1-(3,4-difluorophenyl)-3-(isoquinolin-4-yl)-2-oxoimidazolidine-4-carbonitrile (72), (R)-1-(3,4-difluorophenyl)-3-(isoquinolin-4-yl)-2-oxoimidazolidine-4-carbonitrile (72a) and (S)-1-(3,4-difluorophenyl)-3-(isoquinolin-4-yl)-2-oxoimidazolidine-4-carbonitrile (72b)

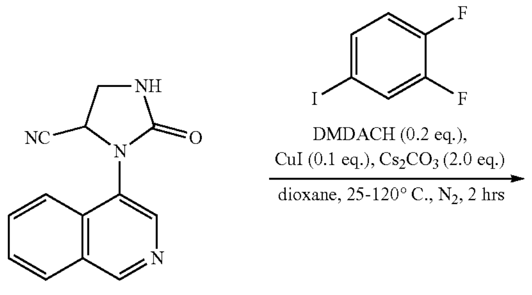

(Int-1)

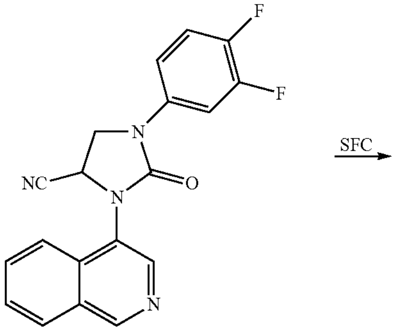

(72)

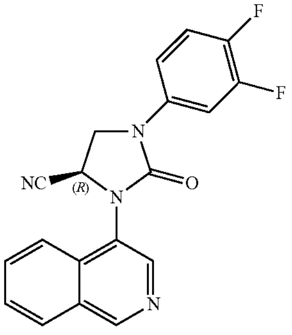

(72a)

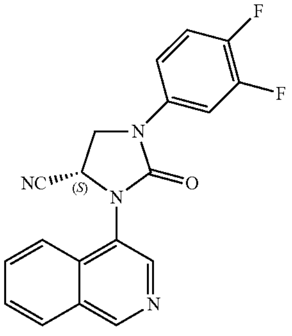

(72b)

Racemic 1-(3,4-difluorophenyl)-3-(isoquinolin-4-yl)-2-oxoimidazolidine-4-carbonitrile (72) was synthesized in a manner similar to Example 4 using 1,2-difluoro-4-iodobenzene in place of 4-trifluoromethyl-iodobenzene. Achiral purification of the racemate was achieved using MLPC (Petroleum ether/Ethyl acetate=1/0~0/1). LCMS (Method 15): $t_R$=0.65 min, M+1 (351.1); $^1$H NMR: (400 MHz, CHLOROFORM-d) δ=9.35 (br s, 1H), 8.68 (br s, 1H), 8.12 (d, J=8.1 Hz, 1H), 7.95-7.86 (m, 1H), 7.86-7.80 (m, 1H), 7.76-7.70 (m, 1H), 7.65 (ddd, J=12.4, 6.9, 2.3 Hz, 1H), 7.26-7.15 (m, 2H), 5.10 (dd, J=9.2, 4.6 Hz, 1H), 4.47 (dd, J=9.6, 9.2 Hz, 1H), 4.34 (dd, J=9.6, 4.6 Hz, 1H). Chiral separation of the racemate by SFC (column: DAICEL CHIRALPAK AD [250 mm×30 mm, 10 μm; 0.1% $NH_3H_2O$ IPA; B % 38%-38%, 6 min]) gave 2 peaks.

Peak 1 was assigned as ((R)-1-(3,4-difluorophenyl)-3-(isoquinolin-4-yl)-2-oxoimidazolidine-4-carbonitrile (72a). LCMS (Method 31): $t_R$=2.77 min, M+1 (351.2); SFC (Method 1): $t_R$=1.37 min, 99.7%; $^1$H NMR: (400 MHz, CHLOROFORM-d) δ=9.35 (br s, 1H), 8.68 (br s, 1H), 8.12 (d, J=8.1 Hz, 1H), 7.95-7.86 (m, 1H), 7.86-7.80 (m, 1H), 7.76-7.70 (m, 1H), 7.65 (ddd, J=12.4, 6.9, 2.3 Hz, 1H), 7.26-7.15 (m, 2H), 5.10 (dd, J=9.2, 4.6 Hz, 1H), 4.47 (dd, J=9.6, 9.2 Hz, 1H), 4.34 (dd, J=9.6, 4.6 Hz, 1H).

Peak 2 was assigned as (S)-1-(3,4-difluorophenyl)-3-(isoquinolin-4-yl)-2-oxoimidazolidine-4-carbonitrile (72b). LCMS (Method 31): $t_R$=2.77 min, M+1 (351.2); SFC (Method 1): $t_R$=1.46 min, 98.8%; $^1$H NMR: (400 MHz, CHLOROFORM-d) δ=9.35 (br s, 1H), 8.68 (br s, 1H), 8.12 (d, J=8.1 Hz, 1H), 7.95-7.86 (m, 1H), 7.86-7.80 (m, 1H), 7.76-7.70 (m, 1H), 7.65 (ddd, J=12.4, 6.9, 2.3 Hz, 1H), 7.26-7.15 (m, 2H), 5.10 (dd, J=9.2, 4.6 Hz, 1H), 4.47 (dd, J=9.6, 9.2 Hz, 1H), 4.34 (dd, J=9.6, 4.6 Hz, 1H).

Example 73: Synthesis of 1-(4-cyano-3-fluorophenyl)-3-(isoquinolin-4-yl)-2-oxoimidazolidine-4-carbonitrile (73), (R)-1-(4-cyano-3-fluorophenyl)-3-(isoquinolin-4-yl)-2-oxoimidazolidine-4-carbonitrile (73a) and (S)-1-(4-cyano-3-fluorophenyl)-3-(isoquinolin-4-yl)-2-oxoimidazolidine-4-carbonitrile (73b)

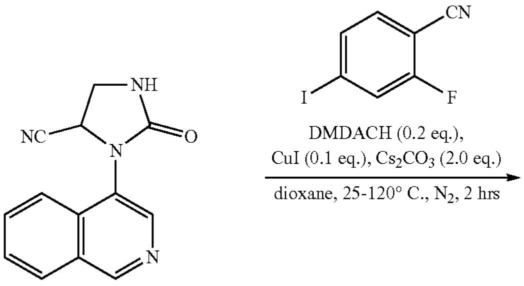

(Int-1)

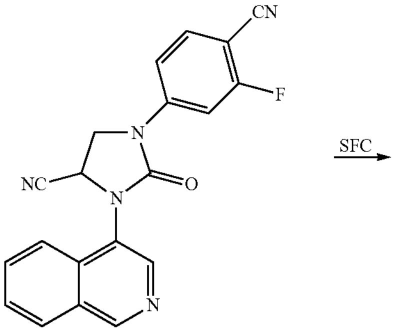

(73)

-continued

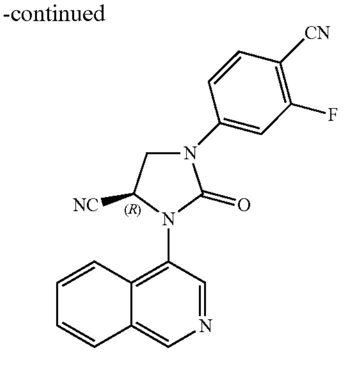

(73a)

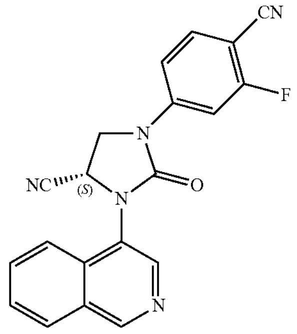

(73b)

Racemic 1-(4-cyano-3-fluorophenyl)-3-(isoquinolin-4-yl)-2-oxoimidazolidine-4-carbonitrile (73) was synthesized in a manner similar to Example 4 using 2-fluoro-4-iodobenzonitrile in place of 4-trifluoromethyl-iodobenzene. Achiral purification of the racemate was achieved using prep-HPLC (column: Phenomenex Luna C18 75 mm×30 mm, 3 μm; liquid phase: [A-FA/$H_2O$=0.1% v/v; B-ACN]B %: 25%-55%, 8 min]). Chiral purification of the racemate by SFC (DAICEL CHIRALPAK AD (250 mm×30 mm, 10 μm)); Mobile phase: A for $CO_2$ and B for 0.1% $NH_3H_2O$ EtOH; Gradient: B %=45% isocratic elution mode; Flow rate: 70 mL/min; Wavelength: 220 nm; Column temperature: 35° C.; System back pressure: 120 bar) gave 2 peaks.

Peak 1 was assigned as (R)-1-(4-cyano-3-fluorophenyl)-3-(isoquinolin-4-yl)-2-oxoimidazolidine-4-carbonitrile (73a). LCMS (Method 31): $t_R$=2.70 min, M+1 (358.1); SFC (Method 15): $t_R$=1.53 min, 99.1%; $^1$H NMR: (400 MHz, CHLOROFORM-d) δ=9.38 (s, 1H), 8.69 (s, 1H), 8.15 (d, J=8.1 Hz, 1H), 7.90-7.82 (m, 2H), 7.78-7.71 (m, 2H), 7.68 (dd, J=8.6, 7.3 Hz, 1H), 7.41 (dd, J=8.8, 2.1 Hz, 1H), 5.16 (dd, J=9.3, 4.4 Hz, 1H), 4.59-4.52 (m, 1H), 4.43 (dd, J=4.4, 9.8 Hz, 1H).

Peak 2 was assigned as (S)-1-(4-cyano-3-fluorophenyl)-3-(isoquinolin-4-yl)-2-oxoimidazolidine-4-carbonitrile (73b). LCMS (Method 31): $t_R$=2.70 min, M+1 (358.1); SFC (Method 15): $t_R$=1.78 min, 97.5%; $^1$H NMR: (400 MHz, CHLOROFORM-d) δ=9.38 (s, 1H), 8.69 (s, 1H), 8.15 (d, J=8.1 Hz, 1H), 7.90-7.82 (m, 2H), 7.78-7.71 (m, 2H), 7.68 (dd, J=8.6, 7.3 Hz, 1H), 7.41 (dd, J=8.8, 2.1 Hz, 1H), 5.16 (dd, J=9.3, 4.4 Hz, 1H), 4.59-4.52 (m, 1H), 4.43 (dd, J=4.4, 9.8 Hz, 1H).

Example 74: Synthesis of 3-(isoquinolin-4-yl)-1-(2-methylpyridin-3-yl)-2-oxoimidazolidine-4-carbonitrile (74), (R)-3-(isoquinolin-4-yl)-1-(2-methylpyridin-3-yl)-2-oxoimidazolidine-4-carbonitrile (74a) and (S)-3-(isoquinolin-4-yl)-1-(2-methylpyridin-3-yl)-2-oxoimidazolidine-4-carbonitrile (74b)

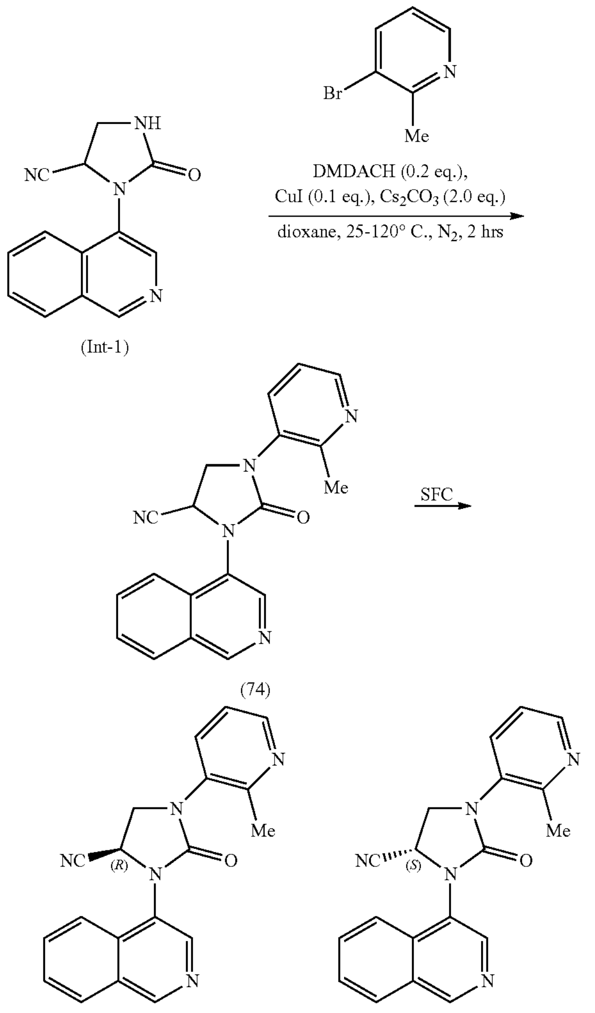

(Int-1)

(74)

(74a) (74b)

Racemic 3-(isoquinolin-4-yl)-1-(2-methylpyridin-3-yl)-2-oxoimidazolidine-4-carbonitrile (74) was synthesized in a manner similar to Example 4 using 3-bromo-2-methylpyridine in place of 4-trifluoromethyl-iodobenzene. Achiral purification of the racemate was achieved using MPLC (Petroleum ether/EtOAc=100%-0%). Chiral separation of the racemate by SFC ((DAICEL CHIRALPAK AD (250 mm×30 mm, 10 μm); Mobile phase: A for $CO_2$ and B for EtOH (0.1% $NH_3H_2O$) gave 2 peaks.

Peak 1 was assigned as (R)-3-(isoquinolin-4-yl)-1-(2-methylpyridin-3-yl)-2-oxoimidazolidine-4-carbonitrile (74a). LCMS (Method 1): $t_R$=1.36 min, M+1 (330.1); SFC (Method 15): $t_R$=1.53 min, 99.8%; $^1$H NMR: (400 MHz, CHLOROFORM-d) δ ppm 9.35 (s, 1H) 8.72 (s, 1H) 8.56 (dd, J=4.8, 1.4 Hz, 1H) 8.13 (d, J=8.2 Hz, 1H) 7.90-8.01 (m, 1H) 7.86 (td, J=7.7, 1.1 Hz, 1H) 7.66-7.77 (m, 2H) 7.27-7.31 (m, 1H) 5.11 (dd, J=8.5, 3.9 Hz, 1H) 4.42 (dd, J=9.5, 8.5 Hz, 1H) 4.25 (dd, J=9.5, 3.9 Hz, 1H) 2.71 (s, 3H).

Peak 2 was assigned as (S)-3-(isoquinolin-4-yl)-1-(2-methylpyridin-3-yl)-2-oxoimidazolidine-4-carbonitrile (74b). LCMS (Method 1): $t_R$=1.35 min, M+1 (330.1); SFC (Method 15): $t_R$=1.73 min, 99.3%; $^1$H NMR: (400 MHz, CHLOROFORM-d) δ ppm 9.35 (s, 1H) 8.72 (s, 1H) 8.56 (dd, J=4.8, 1.4 Hz, 1H) 8.13 (d, J=8.2 Hz, 1H) 7.90-8.01 (m, 1H) 7.86 (td, J=7.7, 1.1 Hz, 1H) 7.66-7.77 (m, 2H) 7.27-7.31 (m, 1H) 5.11 (dd, J=8.5, 3.9 Hz, 1H) 4.42 (dd, J=9.5, 8.5 Hz, 1H) 4.25 (dd, J=9.5, 3.9 Hz, 1H) 2.71 (s, 3H).

Example 75: Synthesis of 1-(6-(difluoromethyl)pyridin-3-yl)-3-(isoquinolin-4-yl)-2-oxoimidazolidine-4-carbonitrile (75), (R)-1-(6-(difluoromethyl)pyridin-3-yl)-3-(isoquinolin-4-yl)-2-oxoimidazolidine-4-carbonitrile (75a) and (S)-1-(6-(difluoromethyl)pyridin-3-yl)-3-(isoquinolin-4-yl)-2-oxoimidazolidine-4-carbonitrile (75b)

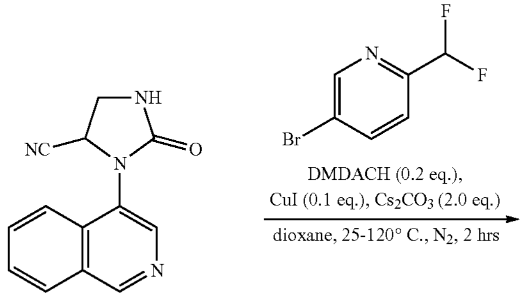

(Int-1)

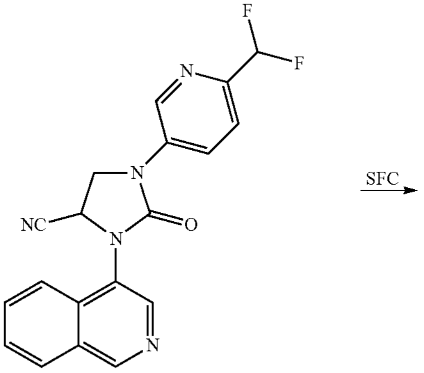

(75)

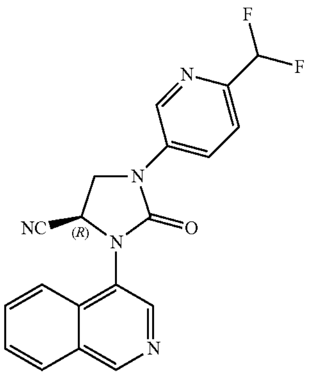

(75a)

-continued

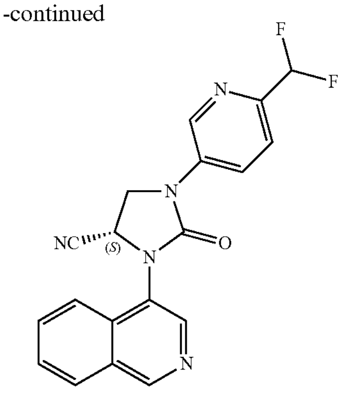

(75b)

Racemic 1-(6-(difluoromethyl)pyridin-3-yl)-3-(isoquinolin-4-yl)-2-oxoimidazolidine-4-carbonitrile (75) was synthesized in a manner similar to Example 4 using 5-bromo-2-(difluoromethyl)pyridine in place of 4-trifluoromethyl-iodobenzene. Achiral purification of the racemate was achieved using MPLC (Petroleum ether/EtOAc=100%-0%). Chiral separation of the racemate using SFC ((DAICEL CHIRALPAK AD (250 mm×30 mm, 10 μm); Mobile phase: A for $CO_2$ and B for EtOH (0.1% $NH_3H_2O$) to give 2 peaks.

Peak 1 was assigned as (R)-1-(6-(difluoromethyl)pyridin-3-yl)-3-(isoquinolin-4-yl)-2-oxoimidazolidine-4-carbonitrile (75a). LCMS (Method 1): $t_R$=2.05 min, M+1 (366.0); SFC (Method 34): $t_R$=3.24 min, 99.8%; $^1$H NMR: (400 MHz, CHLOROFORM-d) δ=9.38 (s, 1H), 8.77 (d, J=2.6 Hz, 1H), 8.71 (s, 1H), 8.35 (dd, J=8.7, 2.6 Hz, 1H), 8.14 (d, J=8.1 Hz, 1H), 7.93-7.82 (m, 2H), 7.78-7.69 (m, 2H), 6.82-6.51 (m, 1H), 5.18 (dd, J=9.1, 4.5 Hz, 1H), 4.61 (dd, J=9.7, 9.1 Hz, 1H), 4.48 (dd, J=9.7, 4.4 Hz, 1H).

Peak 2 was assigned as (S)-1-(6-(difluoromethyl)pyridin-3-yl)-3-(isoquinolin-4-yl)-2-oxoimidazolidine-4-carbonitrile (75b). LCMS (Method 1): $t_R$=2.06 min, M+1 (366.0); SFC (Method 34): $t_R$=3.73 min, 99.9%; $^1$H NMR: (400 MHz, CHLOROFORM-d) δ=9.38 (s, 1H), 8.77 (d, J=2.6 Hz, 1H), 8.71 (s, 1H), 8.35 (dd, J=8.7, 2.6 Hz, 1H), 8.14 (d, J=8.1 Hz, 1H), 7.93-7.82 (m, 2H), 7.78-7.69 (m, 2H), 6.82-6.51 (m, 1H), 5.18 (dd, J=9.1, 4.5 Hz, 1H), 4.61 (dd, J=9.7, 9.1 Hz, 1H), 4.48 (dd, J=9.7, 4.4 Hz, 1H).

Example 76: Synthesis of (R)-1-(3-fluorophenyl)-3-(isoquinolin-4-yl)-2-oxoimidazolidine-4-carbonitrile (76a) and (S)-1-(3-fluorophenyl)-3-(isoquinolin-4-yl)-2-oxoimidazolidine-4-carbonitrile (76b)

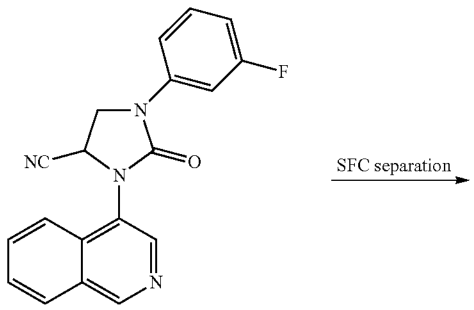

(7)

-continued

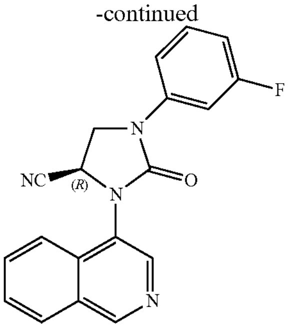

(76a)

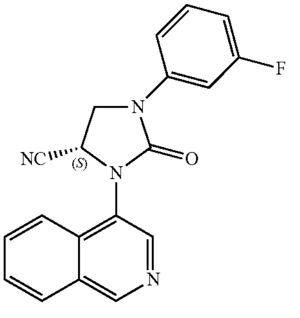

(76b)

Chiral separation of racemic 1-(3-fluorophenyl)-3-(isoquinolin-4-yl)-2-oxoimidazolidine-4-carbonitrile (7). SFC (column: DAICEL CHIRALPAK AD [250 mm×30 mm, 10 μm; 0.1% $NH_3H_2O$ IPA; B % 42%-42%, 8 min]) gave 2 peaks.

Peak 1 was assigned as (R)-1-(3-fluorophenyl)-3-(isoquinolin-4-yl)-2-oxoimidazolidine-4-carbonitrile (76a). LCMS (Method 3): $t_R$=2.83 min, M+1 (333.1); SFC (Method 35): $t_R$=3.95 min, 99.8%; $^1$H NMR: (400 MHz, CHLOROFORM-d) δ=9.35 (s, 1H), 8.69 (s, 1H), 8.12 (d, J=8.1 Hz, 1H), 7.95-7.86 (m, 1H), 7.83 (td, J=7.6, 1.1 Hz, 1H), 7.75-7.70 (m, 1H), 7.50 (dt, J=11.2, 2.3 Hz, 1H), 7.39 (td, J=8.3, 6.5 Hz, 1H), 7.30-7.27 (m, 1H), 6.93-6.86 (m, 1H), 5.11 (dd, J=9.3, 4.6 Hz, 1H), 4.51 (dd, J=9.7, 9.3 Hz, 1H), 4.38 (dd, J=9.7, 4.7 Hz, 1H).

Peak 2 was assigned as (S)-1-(3-fluorophenyl)-3-(isoquinolin-4-yl)-2-oxoimidazolidine-4-carbonitrile (76b). LCMS (Method 3): $t_R$=2.83 min, M+1 (333.1); SFC (Method 35): $t_R$=4.69 min, 100.0%; $^1$H NMR: (400 MHz, CHLOROFORM-d) δ=9.35 (s, 1H), 8.69 (s, 1H), 8.12 (d, J=8.1 Hz, 1H), 7.95-7.86 (m, 1H), 7.83 (td, J=7.6, 1.1 Hz, 1H), 7.75-7.70 (m, 1H), 7.50 (dt, J=11.2, 2.3 Hz, 1H), 7.39 (td, J=8.3, 6.5 Hz, 1H), 7.30-7.27 (m, 1H), 6.93-6.86 (m, 1H), 5.11 (dd, J=9.3, 4.6 Hz, 1H), 4.51 (dd, J=9.7, 9.3 Hz, 1H), 4.38 (dd, J=9.7, 4.7 Hz, 1H).

Example 77: Synthesis of 1-(5-fluoro-6-(trifluoromethyl)pyridin-3-yl)-3-(isoquinolin-4-yl)-2-oxoimidazolidine-4-carbonitrile (77), (R)-1-(5-fluoro-6-(trifluoromethyl)pyridin-3-yl)-3-(isoquinolin-4-yl)-2-oxoimidazolidine-4-carbonitrile (77a) and (S)-1-(5-fluoro-6-(trifluoromethyl)pyridin-3-yl)-3-(isoquinolin-4-yl)-2-oxoimidazolidine-4-carbonitrile (77b)

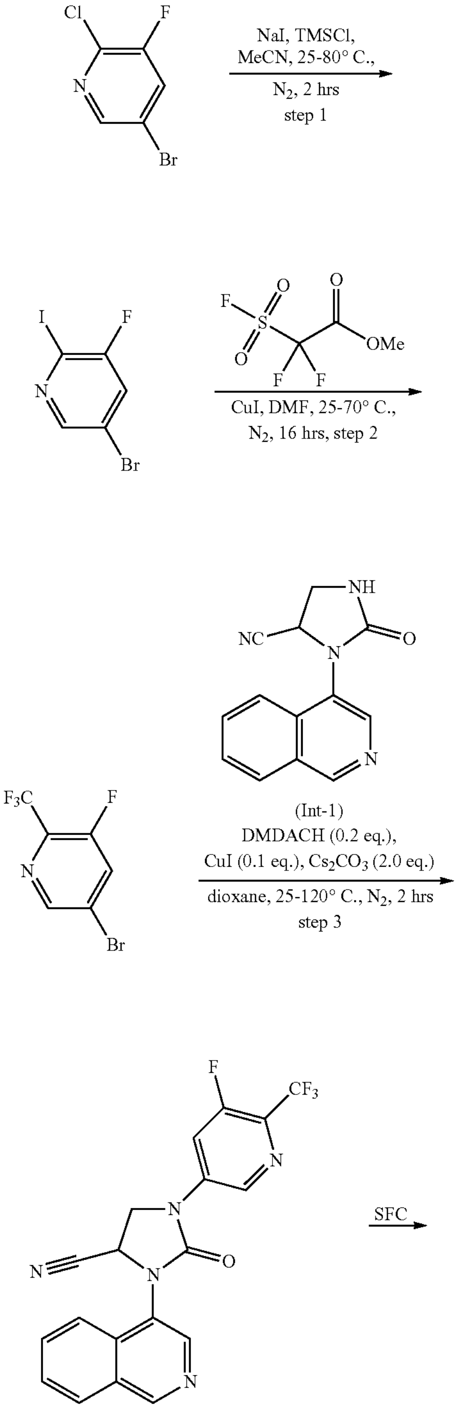

(77)

-continued

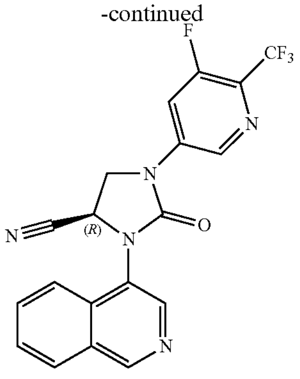

(77a)

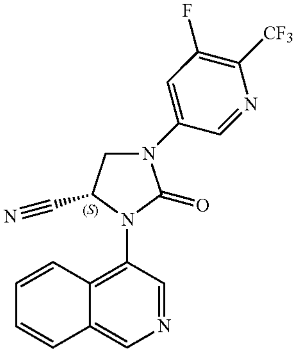

(77b)

Step 1: To a solution of 5-bromo-2-chloro-3-fluoropyridine (5.0 g, 23.76 mmol, 1.0 eq.) and TMSCl (2.6 g, 23.76 mmol, 1.0 eq.) in MeCN (50 mL) was added NaI (10.7 g, 71.28 mmol, 3.0 eq.) at 25° C. The reaction was stirred at 80° C. for 2 hrs. The reaction mixture was quenched with $H_2O$ (300 mL) and extracted with ethyl acetate (300 mL×3). The combined organic layers were washed with brine (600 mL), dried over $Na_2SO_4$, filtered and concentrated under reduced pressure to give crude product. The crude product was purified by column (Petroleum ether/EtOAc=I/O to 50/1) to give 5-bromo-3-fluoro-2-iodopyridine. LCMS (Method 2): $t_R$=0.74 min, M+1 (303.9).

Step 2: To a solution of 5-bromo-3-fluoro-2-iodopyridine (500 mg, 1.66 mmol, 1.0 eq.) and methyl 2,2-difluoro-2-(fluorosulfonyl)acetate (2.2 g, 11.59 mmol, 7.0 eq.) in DMF (10 mL) was added CuI (2.2 g, 11.59 mmol, 7.0 eq.) at 25° C. The reaction was stirred at 70° C. for 16 hrs under $N_2$. The reaction mixture was quenched with $H_2O$ (30 mL) and filtered. The filtrate was extracted with $CH_2Cl_2$ (30 mL×2). The combined organic layers were washed with brine (50 mL×3), dried over $Na_2SO_4$, filtered and concentrated under reduced pressure to give 5-bromo-3-fluoro-2-(trifluoromethyl)pyridine. LCMS (Method 26): $t_R$=1.65 min, M+1 (246.1).

Step 3: Racemic 1-(5-fluoro-6-(trifluoromethyl)pyridin-3-yl)-3-(isoquinolin-4-yl)-2-oxoimidazolidine-4-carbonitrile (77) was synthesized in a manner similar to Example 4 using 5-bromo-3-fluoro-2-(trifluoromethyl)pyridine in place of 4-trifluoromethyl-iodobenzene. Achiral purification of the racemate was achieved using prep-HPLC (column: Waters Xbridge BEH C18 100 mm×30 mm, 10 μm; liquid phase: [A-10 mM $NH_4HCO_3$ in $H_2O$; B-ACN]B %: 30%-50%, 8 min]). Chiral separation of the racemate by SFC (column: DAICEL CHIRALCEL OJ (250 mm×30 mm, 10 μm); liquid phase: 0.1% $NH_3H_2O$ IPA B %: 40%-40%, 10 min]) to give 2 peaks Peak 1 was assigned as (R)-1-(5-fluoro-6-(trifluoromethyl)pyridin-3-yl)-3-(isoquinolin-4-yl)-2-oxoimidazolidine-4-carbonitrile (77a). LCMS (Method 1): $t_R$=2.41 min, M+1 (402.0); SFC (Method 18): $t_R$=2.36 min, 99.9%; $^1$H NMR: (400 MHz, DMSO-$d_6$) δ=9.46 (s, 1H), 8.89 (s, 1H), 8.72 (s, 1H), 8.36-8.24 (m, 2H), 8.16 (d, J=8.4 Hz, 1H), 7.91 (td, J=7.7, 1.1 Hz, 1H), 7.84-7.78 (m, 1H), 5.79 (dd, J=9.4, 5.0 Hz, 1H), 4.70-4.57 (m, 2H)

Peak 2 was assigned as (S)-1-(5-fluoro-6-(trifluoromethyl)pyridin-3-yl)-3-(isoquinolin-4-yl)-2-oxoimidazolidine-4-carbonitrile (77b). LCMS (Method 1): $t_R$=2.41 min, M+1 (402.0); SFC (Method 18): $t_R$=2.621 min, 97.8%; $^1$H NMR: (400 MHz, DMSO-$d_6$) δ=9.46 (s, 1H), 8.89 (s, 1H), 8.72 (s, 1H), 8.36-8.24 (m, 2H), 8.16 (d, J=8.4 Hz, 1H), 7.91 (td, J=7.7, 1.1 Hz, 1H), 7.84-7.78 (m, 1H), 5.79 (dd, J=9.4, 5.0 Hz, 1H), 4.70-4.57 (m, 2H)

Example 78: Synthesis of 1-(5-(difluoromethyl)pyridin-2-yl)-3-(isoquinolin-4-yl)-2-oxoimidazolidine-4-carbonitrile (78), (R)-1-(5-(difluoromethyl)pyridin-2-yl)-3-(isoquinolin-4-yl)-2-oxoimidazolidine-4-carbonitrile (78a) and (S)-1-(5-(difluoromethyl)pyridin-2-yl)-3-(isoquinolin-4-yl)-2-oxoimidazolidine-4-carbonitrile (78b)

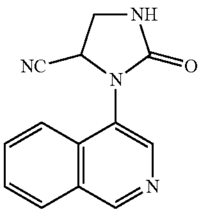

(Int-1)

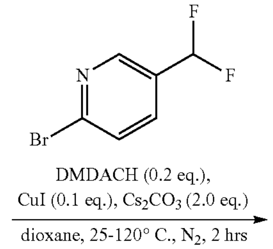

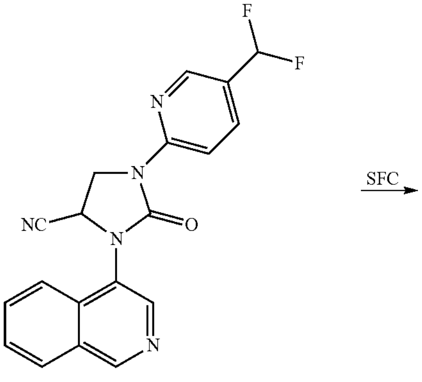

(78)

-continued

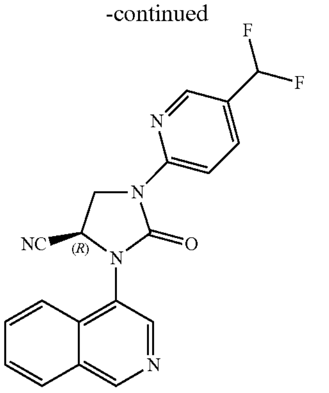

(78a)

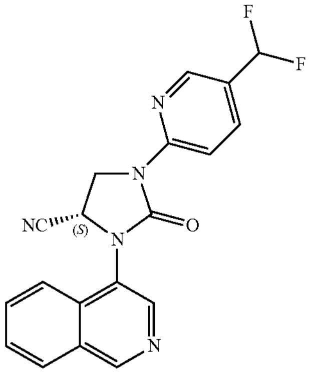

(78b)

Racemic 1-(5-(difluoromethyl)pyridin-2-yl)-3-(isoquinolin-4-yl)-2-oxoimidazolidine-4-carbonitrile (78) was synthesized in a manner similar to Example 4 using 2-bromo-5-(difluoromethyl)pyridine in place of 4-trifluoromethyl-iodobenzene. Achiral purification of the racemate was achieved using flash column chromatography (petroleum ether/EtOAc=100/0 to 10/90). Chiral separation of the racemateby SFC (Column: DAICEL CHIRALPAK AD (250 mm×30 mm, μm); mobile phase: 0.1% $NH_3H_2O$ IPA; B %: 50%-50%, 12 min]) gave 2 peaks.

Peak 1 was assigned as (R)-1-(5-(difluoromethyl)pyridin-2-yl)-3-(isoquinolin-4-yl)-2-oxoimidazolidine-4-carbonitrile (78a). LCMS (Method 31): $t_R$=2.74 min, M+1 (366.2); SFC (Method 1): $t_R$=1.44 min, 99.9%; $^1$H NMR: (400 MHz, METHANOL-$d_4$) δ=9.37 (s, 1H), 8.68 (s, 1H), 8.56 (d, J=1.3 Hz, 1H), 8.35 (d, J=8.9 Hz, 1H), 8.27 (d, J=8.3 Hz, 1H), 8.14 (d, J=8.5 Hz, 1H), 7.97-7.91 (m, 2H), 7.85-7.79 (m, 1H), 6.87 (t, J=55.5 Hz, 1H), 5.52 (dd, J=4.6, 9.5 Hz, 1H), 4.81-4.75 (m, 1H), 4.69-4.64 (m, 1H).

Peak 2 was assigned as (S)-1-(5-(difluoromethyl)pyridin-2-yl)-3-(isoquinolin-4-yl)-2-oxoimidazolidine-4-carbonitrile (78b). LCMS (Method 31): $t_R$=2.74 min, M+1 (366.1); SFC (Method 1): $t_R$=1.68 min, 99.7%; $^1$H NMR: (400 MHz, METHANOL-$d_4$) δ=9.37 (s, 1H), 8.68 (s, 1H), 8.56 (d, J=1.3 Hz, 1H), 8.35 (d, J=8.9 Hz, 1H), 8.27 (d, J=8.3 Hz, 1H), 8.14 (d, J=8.5 Hz, 1H), 7.97-7.91 (m, 2H), 7.85-7.79 (m, 1H), 6.87 (t, J=55.5 Hz, 1H), 5.52 (dd, J=4.6, 9.5 Hz, 1H), 4.81-4.75 (m, 1H), 4.69-4.64 (m, 1H).

Example 79: Synthesis of 3-(isoquinolin-4-yl)-1-(2-methylpyrimidin-5-yl)-2-oxoimidazolidine-4-carbonitrile (79), (R)-3-(isoquinolin-4-yl)-1-(2-methylpyrimidin-5-yl)-2-oxoimidazolidine-4-carbonitrile (79a) and (S)-3-(isoquinolin-4-yl)-1-(2-methylpyrimidin-5-yl)-2-oxoimidazolidine-4-carbonitrile (79b)

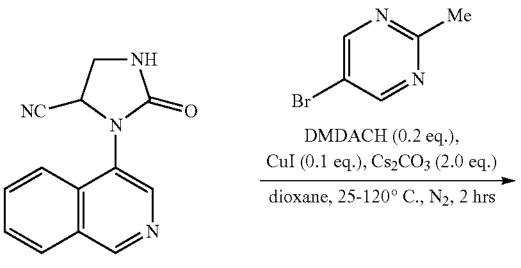

(Int-1)

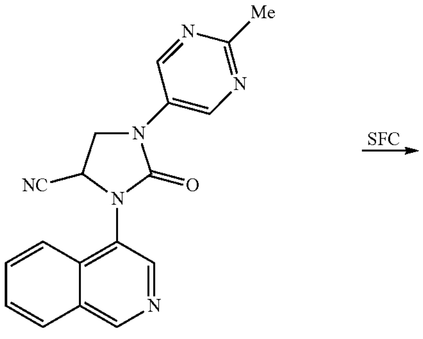

(79)

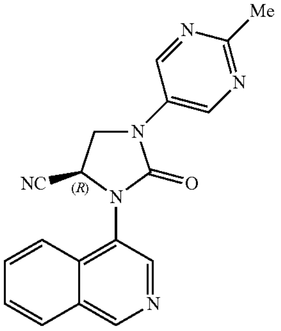

(79a)

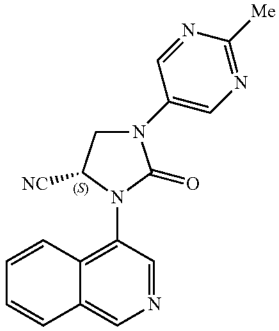

(79b)

Racemic 3-(isoquinolin-4-yl)-1-(2-methylpyrimidin-5-yl)-2-oxoimidazolidine-4-carbonitrile (79) was synthesized in a manner similar to Example 4 using 5-bromo-2-methylpyrimidine in place of 4-trifluoromethyl-iodobenzene. Achiral purification of the racemate was achieved using prep-HPLC (column: Waters Xbridge Prep OBD C18 150 mm×40 mm, 10 μm; mobile phase: [water ($NH_4HCO_3$)-ACN]; B %: 5%-35%, 8 min). Chiral separation of the racemate by SFC (Column: DAICEL CHIRALPAK IG (250 mm×30 mm, 10 μm); Mobile phase: A for $CO_2$ and B for EtOH (0.1% $NH_3H_2O$); Gradient: B %=25%) to give 2 peaks. Peak 1 was then repurified using prep HPLC (column: Phenomenex C18 75 mm×30 mm, 3 μm; liquid phase: [A-$H_2O$ (0.1% $NH_4HCO_3$); B-ACN]B %: 10%-30%, 8 min])

Peak 1 was assigned as (R)-3-(isoquinolin-4-yl)-1-(2-methylpyrimidin-5-yl)-2-oxoimidazolidine-4-carbonitrile (79a). LCMS: LCMS (Method 31): $t_R$=2.12 min, M+1 (331.2); SFC (Method 30): $t_R$=1.14 min, 99.2%; $^1$H NMR: (400 MHz, DMSO-d6) δ=9.43 (s, 1H), 8.96 (s, 2H), 8.69 (s, 1H), 8.29 (d, J=8.1 Hz, 1H), 8.14 (d, J=8.4 Hz, 1H), 7.94-7.87 (m, 1H), 7.83-7.75 (m, 1H), 5.75 (dd, J=9.3, 4.9 Hz, 1H), 4.65-4.57 (m, 1H), 4.56-4.50 (m, 1H), 2.61 (s, 3H)

Peak 2 was assigned as (S)-3-(isoquinolin-4-yl)-1-(2-methylpyrimidin-5-yl)-2-oxoimidazolidine-4-carbonitrile (79b). LCMS (Method 31): $t_R$=2.13 min, M+1 (331.1); SFC (Method 30): $t_R$=1.20 min, 97.4%; $^1$H NMR: (400 MHz, DMSO-d6) δ=9.43 (s, 1H), 8.96 (s, 2H), 8.69 (s, 1H), 8.29 (d, J=8.1 Hz, 1H), 8.14 (d, J=8.4 Hz, 1H), 7.94-7.87 (m, 1H), 7.83-7.75 (m, 1H), 5.75 (dd, J=9.3, 4.9 Hz, 1H), 4.65-4.57 (m, 1H), 4.56-4.50 (m, 1H), 2.61 (s, 3H).

Example 80: Synthesis of 1-(5-chloro-3-methylpyridin-2-yl)-3-(isoquinolin-4-yl)-2-oxoimidazolidine-4-carbonitrile (80), (R)-1-(5-chloro-3-methylpyridin-2-yl)-3-(isoquinolin-4-yl)-2-oxoimidazolidine-4-carbonitrile (80a) and (S)-1-(5-chloro-3-methylpyridin-2-yl)-3-(isoquinolin-4-yl)-2-oxoimidazolidine-4-carbonitrile (80b)

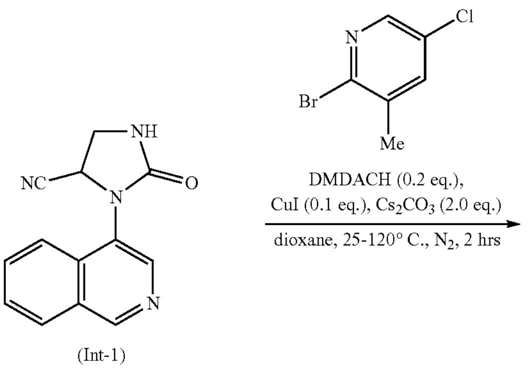

(Int-1)

-continued

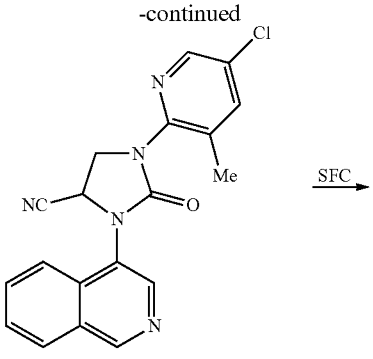

(80)

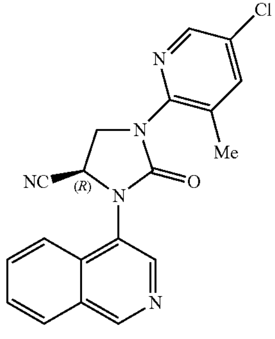

(80a)

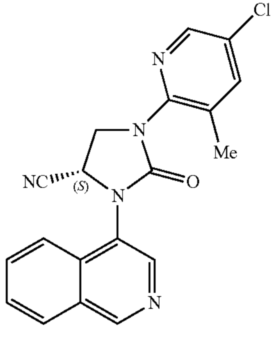

(80b)

1-(5-chloro-3-methylpyridin-2-yl)-3-(isoquinolin-4-yl)-2-oxoimidazolidine-4-carbonitrile (80) was synthesized in a manner similar to Example 4 using 2-bromo-5-chloro-3-methylpyridine in place of 4-trifluoromethyl-iodobenzene. Achiral purification of the racemate was achieved using prep-HPLC (column: Waters Xbridge Prep OBD C18 150 mm×40 mm, 10 μm; mobile phase: [water ($NH_4HCO_3$)-ACN]; B %: 5%-35%, 8 min). LCMS (Method 1): $t_R$=2.19 min, M+1 (364.0); SFC (Method 15): peak 1 $R_t$=1.62 min, peak 2 $R_t$=1.83 min; $^1$H NMR: (400 MHz, CHLOROFORM-d) δ=9.34 (s, 1H), 8.70 (s, 1H), 8.27 (d, J=2.4 Hz, 1H), 8.11 (d, J=8.1 Hz, 1H), 7.94-7.89 (m, 1H), 7.87-7.80 (m, 1H), 7.75-7.69 (m, 1H), 7.65 (dd, J=2.4, 0.6 Hz, 1H), 5.07 (dd, J=8.5, 3.5 Hz, 1H), 4.86 (dd, J=10.2, 8.5 Hz, 1H), 4.33 (dd, J=10.1, 3.5 Hz, 1H), 2.48 (s, 3H). Chiral separation of the racemate by SFC (Column: DAICEL CHIRALPAK IG (250 mm×30 mm, μm); Mobile phase: A for $CO_2$ and B for EtOH (0.1% $NH_3H_2O$); Gradient: B %=25%) gave 2 peaks.

Peak 1 was assigned as (R)-1-(5-chloro-3-methylpyridin-2-yl)-3-(isoquinolin-4-yl)-2-oxoimidazolidine-4-carbonitrile (80a). LCMS (Method 1): $t_R$=2.18 min, M+1 (364.1); SFC (Method 15): $t_R$=1.58 min, 100.0%; $^1$H NMR: (400 MHz, CHLOROFORM-d) δ=9.34 (s, 1H), 8.70 (s, 1H), 8.27 (d, J=2.4 Hz, 1H), 8.11 (d, J=8.1 Hz, 1H), 7.94-7.89 (m, 1H), 7.87-7.80 (m, 1H), 7.75-7.69 (m, 1H), 7.65 (dd, J=2.4, 0.6 Hz, 1H), 5.07 (dd, J=8.5, 3.5 Hz, 1H), 4.86 (dd, J=10.2, 8.5 Hz, 1H), 4.33 (dd, J=10.1, 3.5 Hz, 1H), 2.48 (s, 3H).

Peak 2 was assigned as (S)-1-(5-chloro-3-methylpyridin-2-yl)-3-(isoquinolin-4-yl)-2-oxoimidazolidine-4-carbonitrile (80b). LCMS (Method 1): $t_R$=2.18 min, M+1 (364.1); SFC (Method 15): $t_R$=1.79 min, 97.7%; $^1$H NMR: (400 MHz, CHLOROFORM-d) δ=9.34 (s, 1H), 8.70 (s, 1H), 8.27 (d, J=2.4 Hz, 1H), 8.11 (d, J=8.1 Hz, 1H), 7.94-7.89 (m, 1H), 7.87-7.80 (m, 1H), 7.75-7.69 (m, 1H), 7.65 (dd, J=2.4, 0.6 Hz, 1H), 5.07 (dd, J=8.5, 3.5 Hz, 1H), 4.86 (dd, J=10.2, 8.5 Hz, 1H), 4.33 (dd, J=10.1, 3.5 Hz, 1H), 2.48 (s, 3H).

Example 81: Synthesis of 3-(isoquinolin-4-yl)-2-oxo-1-(6-(trifluoromethyl)pyridazin-3-yl)imidazolidine-4-carbonitrile (81), (R)-3-(isoquinolin-4-yl)-2-oxo-1-(6-(trifluoromethyl)pyridazin-3-yl)imidazolidine-4-carbonitrile (81a) and (S)-3-(isoquinolin-4-yl)-2-oxo-1-(6-(trifluoromethyl)pyridazin-3-yl)imidazolidine-4-carbonitrile (81b)

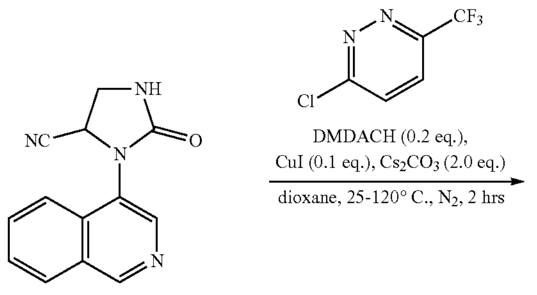

(Int-1)

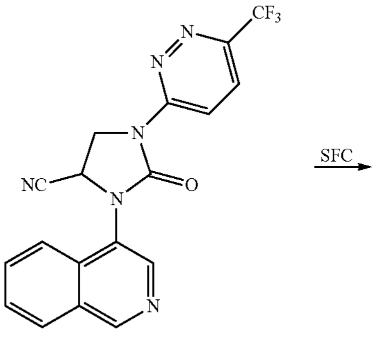

(81)

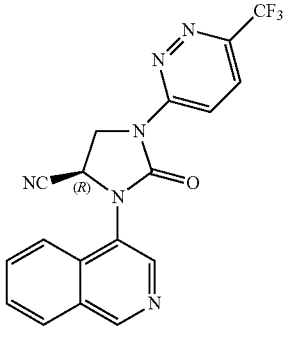

(81a)

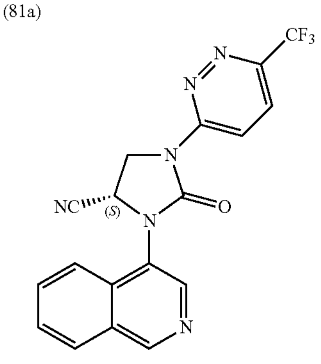

(81b)

Racemic 3-(isoquinolin-4-yl)-2-oxo-1-(6-(trifluoromethyl)pyridazin-3-yl)imidazolidine-4-carbonitrile (81) was synthesized in a manner similar to Example 4 using 3-chloro-6-(trifluoromethyl)pyridazine in place of 4-trifluoromethyl-iodobenzene. Achiral purification of the racemate was achieved using MPLC (Eluent of Ethyl acetate/Petroleum ether=1/90 to 90/1, 40 mL/min). Chiral separation of the racemate by SFC (DAICEL CHIRALPAK IG (250 mm×30 mm, μm); liquid phase: [0.1% $NH_3H_2O$ IPA]B %: 50%-50%, 11 min]) gave 2 peaks. Peak 1 was assigned as (R)-3-(isoquinolin-4-yl)-2-oxo-1-(6-(trifluoromethyl)pyridazin-3-yl)imidazolidine-4-carbonitrile (81a). LCMS (Method 1): $t_R$=2.31 min, M+1 (385.0); SFC (Method 18): $t_R$=2.47 min, 100.0%; $^1$H NMR: (400 MHz, DMSO-d6) δ=9.47 (s, 1H), 8.76 (s, 1H), 8.65 (d, J=9.5 Hz, 1H), 8.30 (d, J=8.2 Hz, 1H), 8.25-8.21 (m, 2H), 7.93-7.88 (m, 1H), 7.84-7.79 (m, 1H), 5.75 (dd, J=9.7, 4.8 Hz, 1H), 4.87 (dd J=11.1, 9.7, Hz, 1H), 4.70 (dd, J=11.1, 4.9, Hz, 1H);

Peak 2 was assigned as (S)-3-(isoquinolin-4-yl)-2-oxo-1-(6-(trifluoromethyl)pyridazin-3-yl)imidazolidine-4-carbonitrile (81b). LCMS (Method 1): $t_R$=2.30 min, M+1(385.0); SFC (Method 18): $t_R$=3.14 min, 99.9%; $^1$H NMR: (400 MHz, DMSO-d6) δ=9.47 (s, 1H), 8.76 (s, 1H), 8.65 (d, J=9.5 Hz, 1H), 8.30 (d, J=8.2 Hz, 1H), 8.25-8.21 (m, 2H), 7.93-7.88 (m, 1H), 7.84-7.79 (m, 1H), 5.75 (dd, J=9.7, 4.8 Hz, 1H), 4.87 (dd J=11.1, 9.7, Hz, 1H), 4.70 (dd, J=11.1, 4.9, Hz, 1H).

Example 82: Synthesis of 3-(isoquinolin-4-yl)-1-(3-methyl-6-(trifluoromethyl)pyridin-2-yl)-2-oxoimidazolidine-4-carbonitrile (82), (R)-3-(isoquinolin-4-yl)-1-(3-methyl-6-(trifluoromethyl)pyridin-2-yl)-2-oxoimidazolidine-4-carbonitrile (82a) and (S)-3-(isoquinolin-4-yl)-1-(3-methyl-6-(trifluoromethyl)pyridin-2-yl)-2-oxoimidazolidine-4-carbonitrile (82b)

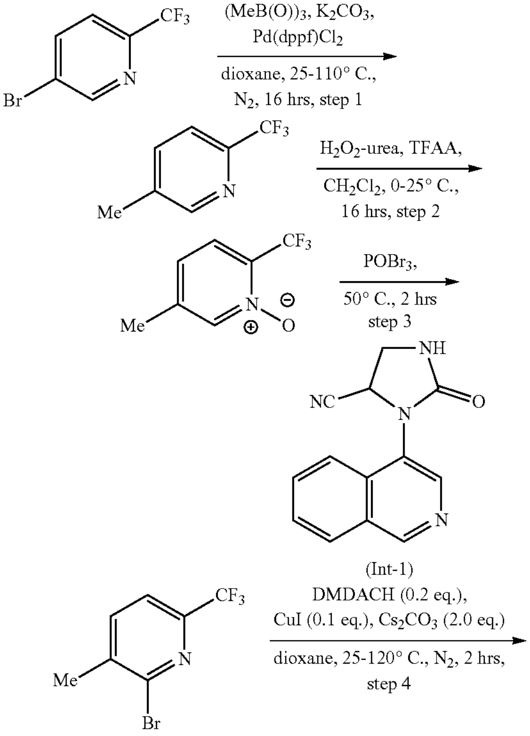

-continued

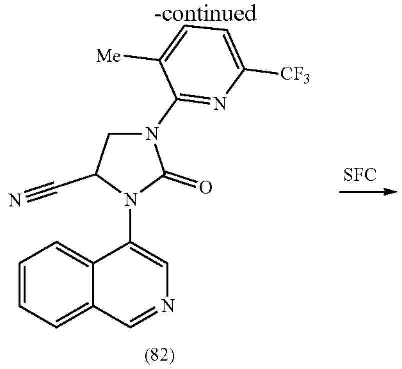

(82)

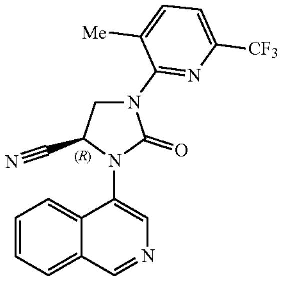

(82a)

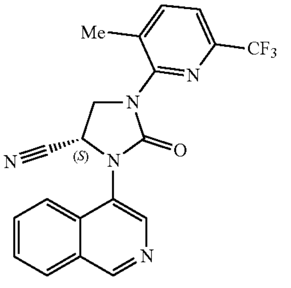

(82b)

Step 1: To a solution of 5-bromo-2-(trifluoromethyl)pyridine (5.0 g, 22.20 mmol, 1.0 eq.) in dioxane (55 mL) was added trimethylboroxime (6.6 g, 111.10 mmol, 5.0 eq.), $K_3CO_3$ (21.0 g, 66.60 mmol, 2.0 eq.) and Pd(dppf)$Cl_2$ (1.4 g, 2.20 mmol, 0.1 eq.) at 25° C. under $N_2$. The mixture was stirred at 110° C. for 16 hrs. The reaction was poured into water (100 mL) and extracted with n-heptane (50 mL×3). The combined organic phases were dried over $Na_2SO_4$, filtered and concentrated to give 5-methyl-2-(trifluoromethyl)pyridine). LCMS (Method 15): $t_R$=0.65 min, M+1 (162.4).

Step 2: A solution of 5-methyl-2-(trifluoromethyl)pyridine (3.0 g, 18.6 mmol, 1.0 eq.) in $CH_2Cl_2$ (50 mL) was cooled to 0° C. Then $H_2O_2$.urea (3.5 g, 37.3 mmol, 2.0 eq.) and TFAA (9.7 g, 46.6 mmol, 2.5 eq.) was added to the mixture at 0° C. The mixture was stirred at 25° C. for 16 hrs. The reaction was quenched with saturated $Na_2SO_3$ aq. (50 mL) and stirred for 15 mins. Then the solution was diluted with dichloromethane (50 mL) and made basic by the careful addition of saturated aqueous sodium bicarbonate solution. The organic layer was separated, and the aqueous layer was extracted with dichloromethane (50 mL×2). The combined organic layers were dried and concentrated to afford 5-methyl-2-(trifluoromethyl)pyridine 1-oxide which was used directly in the next step. LCMS (Method 15): $t_R$=0.44 min, M+1 (178.1).

Step 3: A solution of 5-methyl-2-(trifluoromethyl)pyridine 1-oxide (500 mg, 3.10 mmol, 1.0 eq.) in $POBr_3$ (6 mL) was stirred at 50° C. for 2 hrs. The reaction was quenched with ice water (10 mL) and stirred for 15 mins. Then the solution was extracted with dichloromethane (10 mL×2). The combined organic layers were dried over $Na_2SO_4$, filtered and concentrated to afford 2-bromo-3-methyl-6-(trifluoromethyl)pyridine which was used directly in the next step. $^1$H NMR: (400 MHz, CHLOROFORM-d) δ=7.69 (d, J=7.6 Hz, 1H), 7.56 (d, J=7.8 Hz, 1H), 2.49 (s, 3H)

Step 4: Racemic 3-(isoquinolin-4-yl)-1-(3-methyl-6-(trifluoromethyl)pyridin-2-yl)-2-oxoimidazolidine-4-carbonitrile (82) was synthesized in a manner similar to Example 4 using 2-bromo-3-methyl-6-(trifluoromethyl)pyridine in place of 4-trifluoromethyl-iodobenzene. Achiral purification of the racemate was achieved using MPLC (Eluent of Ethyl acetate/Petroleum ether=3/2 to 4/1, 50 mL/min). Chiral separation of the racemate by SFC (column: DAICEL CHIRALPAK AD (250 mm×30 mm, 10 μm); liquid phase: [0.1% $NH_3H_2O$ EtOH]B %: 38%-38%, 5 min]) gave 2 peaks.

Peak 1 was assigned as (R)-3-(isoquinolin-4-yl)-1-(3-methyl-6-(trifluoromethyl)pyridin-2-yl)-2-oxoimidazolidine-4-carbonitrile (82a). LCMS (Method 2): $t_R$=3.05 min, M+1(398.1); SFC (Method 15): $t_R$=1.16 min, 99.7%; $^1$H NMR: (400 MHz, DMSO-$d_6$) δ=9.43 (s, 1H), 8.71 (s, 1H), 8.29 (d, J=8.2 Hz, 1H), 8.14-8.03 (m, 2H), 7.94 (td, J=7.7, 1.0 Hz, 1H), 7.84-7.78 (m, 2H), 5.70 (dd, J=8.6, 3.2 Hz, 1H), 4.86 (dd, J=10.0, 8.6 Hz, 1H), 4.38 (dd, J=10.0, 3.3, Hz, 1H), 2.48 (br s, 3H).

Peak 2 was assigned as (S)-3-(isoquinolin-4-yl)-1-(3-methyl-6-(trifluoromethyl)pyridin-2-yl)-2-oxoimidazolidine-4-carbonitrile (82b). LCMS (Method 2): $t_R$=3.05 min, M+1(398.1); SFC (Method 15): $t_R$=1.29 min, 98.7%; $^1$H NMR: (400 MHz, DMSO-$d_6$) δ=9.43 (s, 1H), 8.71 (s, 1H), 8.29 (d, J=8.2 Hz, 1H), 8.14-8.03 (m, 2H), 7.94 (td, J=7.7, 1.0 Hz, 1H), 7.84-7.78 (m, 2H), 5.70 (dd, J=8.6, 3.2 Hz, 1H), 4.86 (dd, J=10.0, 8.6 Hz, 1H), 4.38 (dd, J=10.0, 3.3, Hz, 1H), 2.48 (br s, 3H).

Example 83: Synthesis of 1-(4-(difluoromethoxy)-2-fluorophenyl)-3-(isoquinolin-4-yl)-2-oxoimidazolidine-4-carbonitrile (83), (R)-1-(4-(difluoromethoxy)-2-fluorophenyl)-3-(isoquinolin-4-yl)-2-oxoimidazolidine-4-carbonitrile (83a) and (S)-1-(4-(difluoromethoxy)-2-fluorophenyl)-3-(isoquinolin-4-yl)-2-oxoimidazolidine-4-carbonitrile (83b)

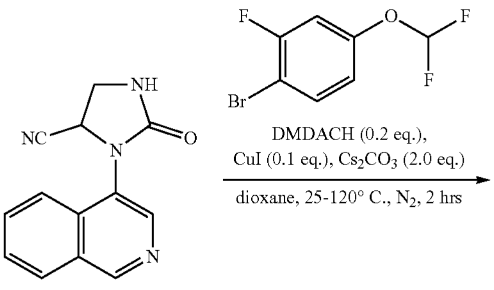

(Int-1)

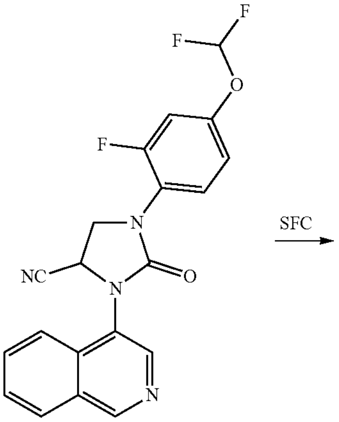

(83)

-continued

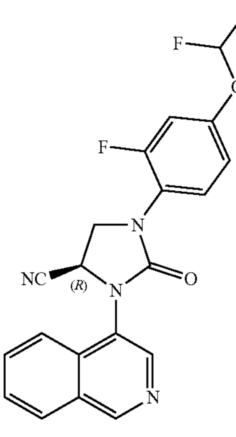

(83a)

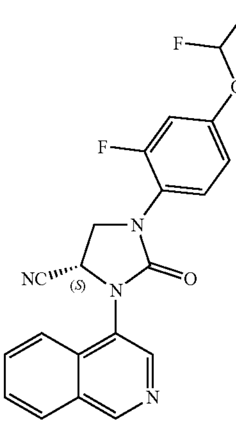

(83b)

Racemic 1-(4-(difluoromethoxy)-2-fluorophenyl)-3-(isoquinolin-4-yl)-2-oxoimidazolidine-4-carbonitrile (83) was synthesized in a manner similar to Example 4 using 1-bromo-4-(difluoromethoxy)-2-fluorobenzene in place of 4-trifluoromethyl-iodobenzene. Achiral purification of the racemate was achieved using MPLC (Petroleum ether/EtOAc=50%-70%). Chiral separation of the racemate by SFC (Column: Chiralpak AD-3, I.D. (50 mm×4.6 mm, 3 μm); Mobile phase: A for $CO_2$ and B for EtOH (0.1% IPA); Gradient: B %=50% isocratic elution mode; Flow rate: 3.4 mL/min; Wavelength: 220 nm; Column temperature: 35° C.; System back pressure: 124 bar.) gave 2 peaks.

Peak 1 was assigned as (R)-1-(4-(difluoromethoxy)-2-fluorophenyl)-3-(isoquinolin-4-yl)-2-oxoimidazolidine-4-carbonitrile (83a). LCMS (Method 1): $t_R$=2.22 min, M+1 (399.1); SFC (Method 15): $t_R$=1.44 min, 100.0%; $^1$H NMR: (400 MHz, CHLOROFORM-d) δ=9.34 (s, 1H), 8.71 (s, 1H), 8.12 (d, J=8.1 Hz, 1H), 7.93 (br d, J=8.5 Hz, 1H), 7.84 (t, J=7.7 Hz, 1H), 7.75-7.70 (m, 1H), 7.64 (t, J=9.0 Hz, 1H), 7.08-7.01 (m, 2H), 6.54 (t, J=72.8 Hz, 1H), 5.10 (dd, J=8.9, 4.5 Hz, 1H), 4.53 (dd, J=9.6, 8.9 Hz, 1H), 4.35 (dd, J=9.6, 4.5 Hz, 1H);

Peak 2 was assigned as (S)-1-(4-(difluoromethoxy)-2-fluorophenyl)-3-(isoquinolin-4-yl)-2-oxoimidazolidine-4-carbonitrile (83b). LCMS (Method 1): $t_R$=2.22 min, M+1 (399.1); SFC (Method 15): $t_R$=1.59 min, 98.9%; $^1$H NMR: (400 MHz, CHLOROFORM-d) δ=9.34 (s, 1H), 8.71 (s, 1H), 8.12 (d, J=8.1 Hz, 1H), 7.93 (br d, J=8.5 Hz, 1H), 7.84 (t, J=7.7 Hz, 1H), 7.75-7.70 (m, 1H), 7.64 (t, J=9.0 Hz, 1H), 7.08-7.01 (m, 2H), 6.54 (t, J=72.8 Hz, 1H), 5.10 (dd, J=8.9, 4.5 Hz, 1H), 4.53 (dd, J=9.6, 8.9 Hz, 1H), 4.35 (dd, J=9.6, 4.5 Hz, 1H);

Example 84: Synthesis of 1-(4-(2-hydroxypropan-2-yl)phenyl)-3-(isoquinolin-4-yl)-2-oxoimidazolidine-4-carbonitrile (84), (R)-1-(4-(2-hydroxypropan-2-yl)phenyl)-3-(isoquinolin-4-yl)-2-oxoimidazolidine-4-carbonitrile (84a) and (S)-1-(4-(2-hydroxypropan-2-yl)phenyl)-3-(isoquinolin-4-yl)-2-oxoimidazolidine-4-carbonitrile (84b)

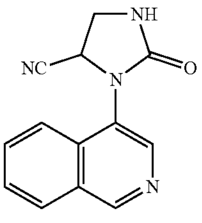

(Int-1)

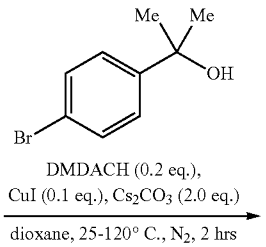

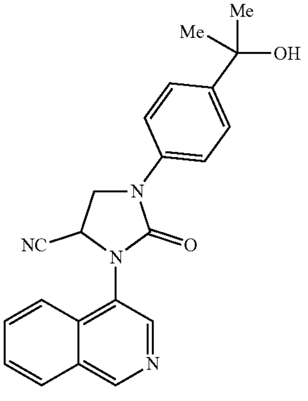

(84)

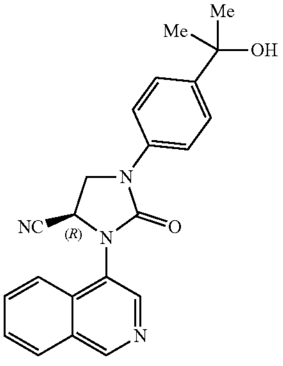

(84a)

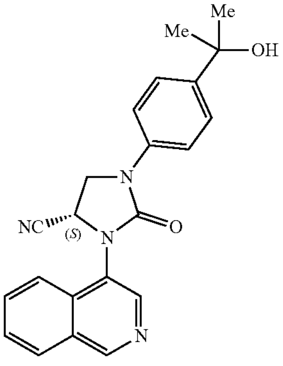

(84b)

Racemic 1-(4-(2-hydroxypropan-2-yl)phenyl)-3-(isoquinolin-4-yl)-2-oxoimidazolidine-4-carbonitrile (84) was synthesized in a manner similar to Example 4 using 2-(4-bromophenyl)propan-2-ol in place of 4-trifluoromethyl-iodobenzene. Achiral purification of the racemate was achieved using prep-HPLC (column: Phenomenex Luna C18 75 mm×30 mm, 3 μm; liquid phase: [A-$NH_4HCO_3$/$H_2O$=0.1% v/v; B-ACN]B %: 20%-40%, 8 min]). Chiral separation of the racemate by SFC (column: DAICEL CHIRALPAK IC (250 mm*30 mm, 10 um; mobile phase: 0.1% $NH_3$—$H_2O$ MeOH; B % 60%-60%, 10 min]) gave 2 peaks.

Peak 1 was assigned as (R)-1-(4-(2-hydroxypropan-2-yl) phenyl)-3-(isoquinolin-4-yl)-2-oxoimidazolidine-4-carbonitrile (84a). LCMS (Method 1): $t_R$=3.50 min, M+1 (373.2); SFC (Method 36): $t_R$=1.72 min, 99.8%; $^1$H NMR: (400 MHz, DMSO-$d_6$) δ=9.42 (s, 1H), 8.67 (s, 1H), 8.28 (d, J=7.9 Hz, 1H), 8.09 (d, J=8.6 Hz, 1H), 7.90 (t, J=7.4 Hz, 1H), 7.84-7.77 (m, 1H), 7.56-7.52 (m, 2H), 7.51-7.46 (m, 2H), 5.67 (dd, J=9/0, 4.4, Hz, 1H), 5.00 (s, 1H), 4.57 (dd, J=9.9, 9.0 Hz, 1H), 4.43 (dd, J=9.9, 4.6 Hz, 1H), 1.43 (s, 6H).

Peak 2 was assigned as (S)-1-(4-(2-hydroxypropan-2-yl) phenyl)-3-(isoquinolin-4-yl)-2-oxoimidazolidine-4-carbonitrile (84b). LCMS (Method 1): $t_R$=2.46 min, M+1 (373.2); SFC (Method 36): $t_R$=1.99 min, 99.8%; $^1$H NMR: (400 MHz, DMSO-$d_6$) δ=9.42 (s, 1H), 8.67 (s, 1H), 8.28 (d, J=7.9 Hz, 1H), 8.09 (d, J=8.6 Hz, 1H), 7.90 (t, J=7.4 Hz, 1H), 7.84-7.77 (m, 1H), 7.56-7.52 (m, 2H), 7.51-7.46 (m, 2H), 5.67 (dd, J=9/0, 4.4, Hz, 1H), 5.00 (s, 1H), 4.57 (dd, J=9.9, 9.0 Hz, 1H), 4.43 (dd, J=9.9, 4.6 Hz, 1H), 1.43 (s, 6H).

Example 85: Synthesis of 1-(3,4-difluorophenyl)-3-(6-(methylsulfonyl)isoquinolin-4-yl)-2-oxoimidazolidine-4-carbonitrile (85), (R)-1-(3,4-difluorophenyl)-3-(6-(methylsulfonyl)isoquinolin-4-yl)-2-oxoimidazolidine-4-carbonitrile (85a) and (S)-1-(3,4-difluorophenyl)-3-(6-(methylsulfonyl)isoquinolin-4-yl)-2-oxoimidazolidine-4-carbonitrile (85b)

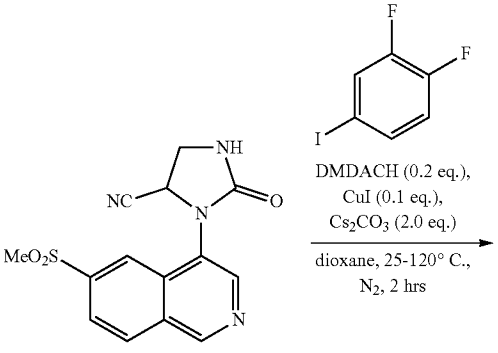

(Int-6)

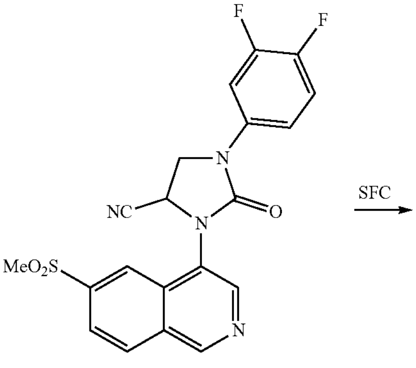

(85)

-continued

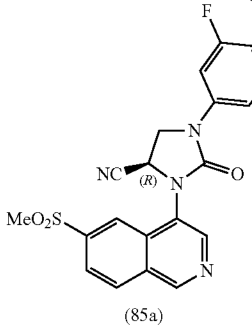

(85a)

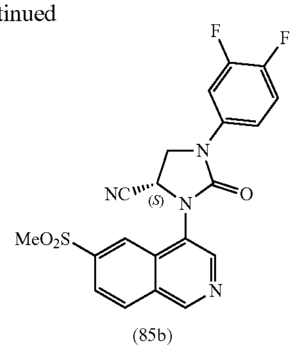

(85b)

Racemic 1-(3,4-difluorophenyl)-3-(6-(methylsulfonyl) isoquinolin-4-yl)-2-oxoimidazolidine-4-carbonitrile (85) was synthesized in a manner similar to Example 4 using 1,2-difluoro-4-iodobenzene in place of 4-trifluoromethyl-iodobenzene, and using 3-(6-(methylsulfonyl)isoquinolin-4-yl)-2-oxoimidazolidine-4-carbonitrile (Int-6) in place of 3-(isoquinolin-4-yl)-2-oxoimidazolidine-4-carbonitrile (Int-1). Achiral purification of the racemate was achieved using flash column chromatography ($SiO_2$, Petroleum ether/Ethyl acetate=100/1 to 0/1). Chiral separation of the racemate by SFC (column: DAICEL CHIRALPAK AD (250 mm×25 mm, 10 μm; mobile phase: 0.1% IPAm ACN; B % 32%-32%, 14 min]) gave 2 peaks.

Peak 1 was assigned as (R)-1-(3,4-difluorophenyl)-3-(6-(methylsulfonyl)isoquinolin-4-yl)-2-oxoimidazolidine-4-carbonitrile (85a). LCMS (Method 31): $t_R$=2.63 min, M+1 (429.1); SFC (Method 37): $t_R$=0.00 min, 100.0%; $^1$H NMR: (400 MHz, CHLOROFORM-d) δ=9.50 (brs, 1H), 8.86 (br s, 1H), 8.58 (s, 1H), 8.35 (d, J=8.5 Hz, 1H), 8.18 (d, J=8.5 Hz, 1H), 7.62 (ddd, J=12.2, 6.9, 2.7 Hz, 1H), 7.26-7.17 (m, 2H), 5.15 (dd, J=8.9, 4.8 Hz, 1H), 4.58-4.48 (m, 1H), 4.40 (dd, J=9.6, 4.9 Hz, 1H), 3.14 (s, 3H)

Peak 2 was assigned as (S)-1-(3,4-difluorophenyl)-3-(6-(methylsulfonyl)isoquinolin-4-yl)-2-oxoimidazolidine-4-carbonitrile (85b). LCMS (Method 31): $t_R$=2.62 min, M+1 (429.1); SFC (Method 37): $t_R$=1.09 min, 100.0%; $^1$H NMR: (400 MHz, CHLOROFORM-d) δ=9.50 (br s, 1H), 8.86 (br s, 1H), 8.58 (s, 1H), 8.35 (d, J=8.5 Hz, 1H), 8.18 (d, J=8.5 Hz, 1H), 7.62 (ddd, J=12.2, 6.9, 2.7 Hz, 1H), 7.26-7.17 (m, 2H), 5.15 (dd, J=8.9, 4.8 Hz, 1H), 4.58-4.48 (m, 1H), 4.40 (dd, J=9.6, 4.9 Hz, 1H), 3.14 (s, 3H).

Example 86: Synthesis of 1-(3,5-difluorophenyl)-3-(6-(methylsulfonyl)isoquinolin-4-yl)-2-oxoimidazolidine-4-carbonitrile (86), (R)-1-(3,5-difluorophenyl)-3-(6-(methylsulfonyl)isoquinolin-4-yl)-2-oxoimidazolidine-4-carbonitrile (86a) and (S)-1-(3,5-difluorophenyl)-3-(6-(methylsulfonyl)isoquinolin-4-yl)-2-oxoimidazolidine-4-carbonitrile (86b)

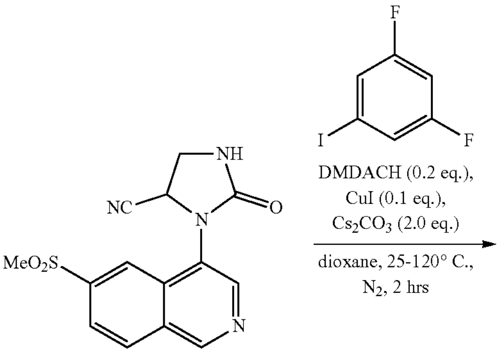

(Int-6)

-continued

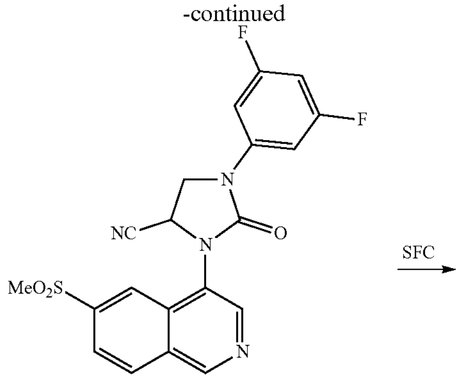

(86)

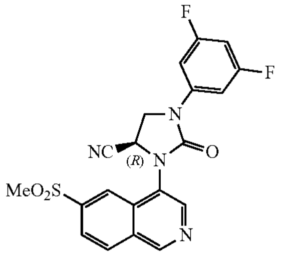

(86a)

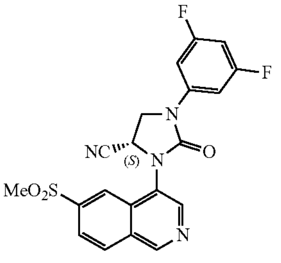

(86b)

1-(3,5-difluorophenyl)-3-(6-(methylsulfonyl)isoquinolin-4-yl)-2-oxoimidazolidine-4-carbonitrile (86) was synthesized in a manner similar to Example 4 using 1,3-difluoro-5-iodobenzene in place of 4-trifluoromethyl-iodobenzene, and using 3-(6-(methylsulfonyl)isoquinolin-4-yl)-2-oxoimidazolidine-4-carbonitrile (Int-6) in place of 3-(isoquinolin-4-yl)-2-oxoimidazolidine-4-carbonitrile (Int-1). Achiral purification of the racemate was achieved using flash column chromatography column chromatography ($SiO_2$, Petroleum ether/Ethyl acetate=100/1 to 0/1). Hiral separation of the racemate by SFC (column: REGIS(S, S) WHELK-O (250 mm×25 mm, μm; mobile phase: 0.1% $NH_3H_2O$ EtOH; B % 35%-35%, 20 min]) gave 2 peaks Peak 1 was assigned as (R)-1-(3,5-difluorophenyl)-3-(6-(methylsulfonyl)isoquinolin-4-yl)-2-oxoimidazolidine-4-carbonitrile (86a). LCMS (Method 2): $t_R$=0.90 min, M+1 (429.2); SFC (Method 15): $t_R$=1.19 min, 99.5%; $^1H$ NMR: (400 MHz, CHLOROFORM-d) δ=9.50 (s, 1H), 8.86 (s, 1H), 8.57 (s, 1H), 8.35 (d, J=8.5 Hz, 1H), 8.21-8.16 (m, 1H), 7.22-7.16 (m, 2H), 6.70-6.62 (m, 1H), 5.16 (dd, J=9.1, 4.8 Hz, 1H), 4.57-4.49 (m, 1H), 4.40 (dd, J=9.6, 4.9 Hz, 1H), 3.15 (s, 3H).

Peak 2 was assigned as (S)-1-(3,5-difluorophenyl)-3-(6-(methylsulfonyl)isoquinolin-4-yl)-2-oxoimidazolidine-4-carbonitrile (86b). LCMS (Method 2): $t_R$=0.90 min, M+1 (429.2); SFC (Method 15): $t_R$=1.43 min, 98.9%; $^1H$ NMR: (400 MHz, CHLOROFORM-d) δ=9.50 (s, 1H), 8.86 (s, 1H), 8.57 (s, 1H), 8.35 (d, J=8.5 Hz, 1H), 8.21-8.16 (m, 1H), 7.22-7.16 (m, 2H), 6.70-6.62 (m, 1H), 5.16 (dd, J=9.1, 4.8 Hz, 1H), 4.57-4.49 (m, 1H), 4.40 (dd, J=9.6, 4.9 Hz, 1H), 3.15 (s, 3H).

Example 87: Synthesis of 1-(3-chloro-4-fluorophenyl)-3-(isoquinolin-4-yl)-2-oxoimidazolidine-4-carbonitrile (87), (R)-1-(3-chloro-4-fluorophenyl)-3-(isoquinolin-4-yl)-2-oxoimidazolidine-4-carbonitrile (87a) and (S)-1-(3-chloro-4-fluorophenyl)-3-(isoquinolin-4-yl)-2-oxoimidazolidine-4-carbonitrile (87b)

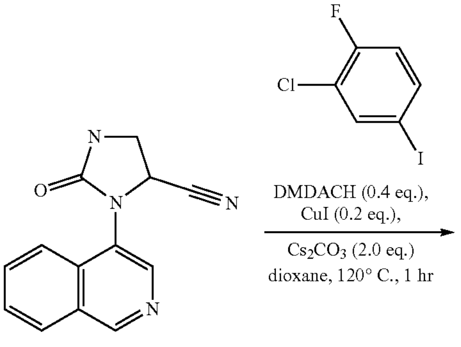

(Int-1)

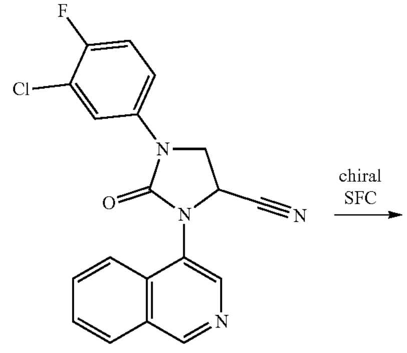

(87)

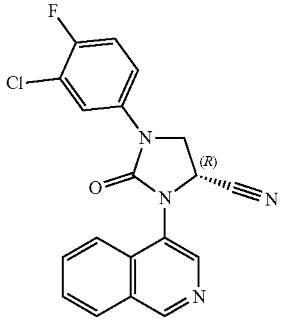

(87a)

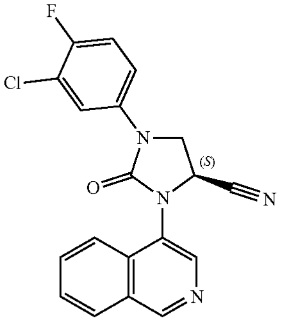

(87b)

Racemic 1-(3-chloro-4-fluorophenyl)-3-(isoquinolin-4-yl)-2-oxoimidazolidine-4-carbonitrile (87) was prepared in a manner similar to Example 4, using 2-chloro-1-fluoro-4-iodobenzene (1.2 eq) in place of 4-trifluoromethyl-iodobenzene. The crude product was purified by prep-HPLC (column: Phenomenex Luna C18 75 mm×30 mm, 3 μm; liquid phase: [A-HCOOH/$H_2O$=0.1% v/v; B-ACN]B %: 35%-65%, 8 min]). LCMS (Method 31): $t_R$=2.88 min, $[M+1]^+$ 367.2. $^1H$ NMR: (400 MHz, DMSO-$d_6$) δ=9.43 (s, 1H), 8.68 (s, 1H), 8.28 (d, J=8.1 Hz, 1H), 8.11 (d, J=8.1 Hz, 1H), 7.93-7.87 (m, 2H), 7.83-7.77 (m, 1H), 7.64-7.57 (m, 1H), 7.54-7.45 (m, 1H), 5.69 (dd, J=9.1, 4.9 Hz, 1H), 4.60-4.54 (m, 1H), 4.51-4.45 (m, 1H).

The racemic product was resolved by preparative SFC (column: REGIS (S, S) WHELK-01 (250 mm×25 mm, 10 μm); mobile phase: 0.1% $NH_3H_2O$ IPA; B % 35%-35%, 20 min]) to give two peaks.

Peak 1: (R)-1-(3-chloro-4-fluorophenyl)-3-(isoquinolin-4-yl)-2-oxoimidazolidine-4-carbonitrile (87a). LCMS (Method 31): $t_R$=2.87 min, $[M+1]^+$ 367.2; SFC (Method 1): $t_R$=1.41 min, 99.9%; $^1H$ NMR: (400 MHz, DMSO-$d_6$) δ=9.43 (s, 1H), 8.68 (s, 1H), 8.28 (d, J=8.2 Hz, 1H), 8.11 (d, J=8.4 Hz, 1H), 7.94-7.86 (m, 2H), 7.84-7.77 (m, 1H), 7.63-7.57 (m, 1H), 7.53-7.45 (m, 1H), 5.69 (dd, J=9.2, 4.8 Hz, 1H), 4.60-4.53 (m, 1H), 4.51-4.46 (m, 1H).

Peak 2: (S)-1-(3-chloro-4-fluorophenyl)-3-(isoquinolin-4-yl)-2-oxoimidazolidine-4-carbonitrile (87b). LCMS (Method 2): $t_R$=2.33 min; SFC (Method 1): $t_R$=1.53 min, 99.4%; $^1H$ NMR: (400 MHz, DMSO-$d_6$) δ=9.43 (s, 1H), 8.68 (s, 1H), 8.28 (d, J=8.2 Hz, 1H), 8.11 (d, J=8.4 Hz, 1H), 7.94-7.86 (m, 2H), 7.84-7.77 (m, 1H), 7.63-7.57 (m, 1H), 7.53-7.45 (m, 1H), 5.69 (dd, J=9.2, 4.8 Hz, 1H), 4.60-4.53 (m, 1H), 4.51-4.46 (m, 1H).

Example 88: Synthesis of 3-(isoquinolin-4-yl)-1-(2-methyl-5-(trifluoromethyl)pyridin-3-yl)-2-oxoimidazolidine-4-carbonitrile (88), (R)-3-(isoquinolin-4-yl)-1-(2-methyl-5-(trifluoromethyl)pyridin-3-yl)-2-oxoimidazolidine-4-carbonitrile (88a) and (S)-3-(isoquinolin-4-yl)-1-(2-methyl-5-(trifluoromethyl)pyridin-3-yl)-2-oxoimidazolidine-4-carbonitrile (88b)

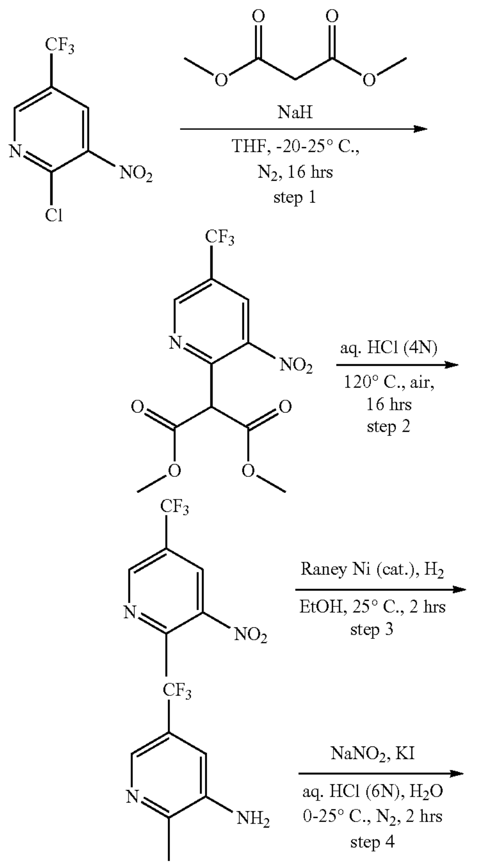

-continued

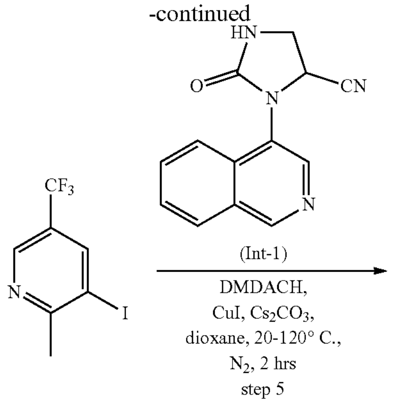

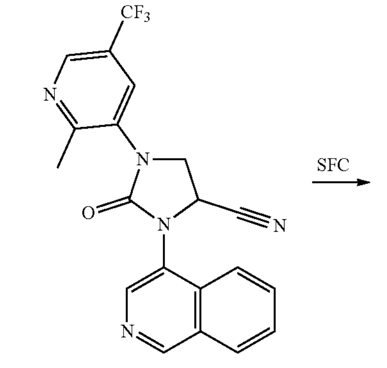

(88)

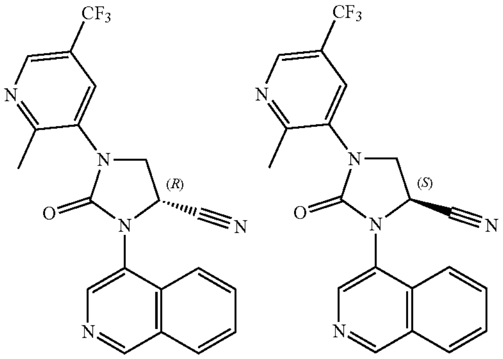

(88a) (88b)

Step 1: To a mixture of 2-chloro-3-nitro-5-(trifluoromethyl)pyridine (5.0 g, 22.13 mmol, 1.0 eq.) and dimethyl malonate (5.2 g, 39.83 mmol, 1.8 eq.) in THE (50 mL) was added NaH (1.6 g, 39.83 mmol, 1.8 eq.) at −20° C. under $N_2$. The reaction mixture was stirred at 25° C. under $N_2$ for 16 hrs. The reaction was quenched with sat. $NH_4Cl$ (150 mL) and extracted with ethyl acetate (50 mL×3). The combined organic layers were washed with brine (50 mL), dried over $Na_2SO_4$, filtered and concentrated under reduced pressure to give dimethyl 2-(3-nitro-5-(trifluoromethyl)pyridin-2-yl) malonate. LCMS (Method 35): $t_R$=0.75 min, $[M+1]^+$ 323.1

Step 2: A solution of dimethyl 2-(3-nitro-5-(trifluoromethyl)pyridin-2-yl)malonate (10.0 g, crude) 25 in aq. HCl (4 N, 100 mL) was stirred at 120° C. for 16 hrs. The reaction was extracted with ethyl acetate (50 mL×3). The combined organic layers were washed with brine (50 mL), dried over $Na_2SO_4$, filtered and concentrated under reduced pressure to give 2-methyl-3-nitro-5-(trifluoromethyl)pyridine. LCMS (Method 10): $t_R$=0.68 min, $[M+1]^+$ 386.2. $^1$H NMR: (400 MHz, CHLOROFORM-d) δ=8.99 (s, 1H) 8.53 (d, J=1.1 Hz, 1H) 2.96 (s, 3H).

Step 3: To a mixture of 2-methyl-3-nitro-5-(trifluoromethyl)pyridine (4.2 g, 20.4 mmol, 1.0 eq.) in EtOH (100 mL) was added Raney Ni (10.0 g, cat.) at 25° C. under $H_2$ (15 Psi). The mixture was stirred at 25° C. for 2 hrs. The reaction was filtered, and the filtrate concentrated under reduced pressure to give 2-methyl-5-(trifluoromethyl)pyridin-3-amine. LCMS (Method 15): $t_R$=0.31 min, $[M+1]^+$ 177.1. $^1$H NMR: (400 MHz, CHLOROFORM-d) δ=8.19 (s, 1H) 7.09 (d, J=1.8 Hz, 1H) 3.86 (br s, 2H) 2.47 (s, 3H).

Step 4: To the mixture of 2-methyl-5-(trifluoromethyl) pyridin-3-amine (3.8 g, 21.6 mmol, 1.0 eq.) in aq. HCl (6 N, 50 mL) was added a solution of $NaNO_2$ (2.2 g, 32.4 mmol, 1.5 eq.) in $H_2O$ (10 mL) under $N_2$ at 0° C. The mixture was stirred at 0° C. for 0.5 hrs. Then KI (7.2 g, 43.2 mmol, 2.0 eq.) was added at 0° C. The mixture was stirred at 20° C. for 1.5 hrs. The mixture was poured into aq. $Na_2S_2O_3$ (30 mL) and extracted with ethyl acetate (10 mL×3). The combined organic layers were washed with brine (20 mL), dried over $Na_2SO_4$, filtered and concentrated under reduced pressure to give the crude product. The crude product was purified by silica gel column (petroleum ether/EtOAc=I/O to 3/1) to give 3-iodo-2-methyl-5-(trifluoromethyl)pyridine. $^1$H NMR: (400 MHz, CHLOROFORM-d) δ=8.71 (s, 1H) 8.27 (d, J=1.6 Hz, 1H) 2.81 (s, 3H).

Step 5: Racemic 3-(isoquinolin-4-yl)-1-(2-methyl-5-(trifluoromethyl)pyridin-3-yl)-2-oxoimidazolidine-4-carbonitrile (88) was prepared in a manner similar to Example 4, using 3-iodo-2-methyl-5-(trifluoromethyl)pyridine in place of 4-trifluoromethyl-iodobenzene. The crude product was purified by silica gel column (petroleum ether/EtOAc=I/O to 1/2). The racemic product was resolved by prep-SFC (column: REGIS(S, S) WHELK-O (250 mm×30 mm, 10 μm; mobile phase: 0.1% $NH_3H_2O$ IPA; B % 15%-15%, 12 min]) to give two peaks.

Peak 1: (R)-3-(isoquinolin-4-yl)-1-(2-methyl-5-(trifluoromethyl)pyridin-3-yl)-2-oxoimidazolidine-4-carbonitrile (88a). LCMS (Method 31): $t_R$=2.61 min, $[M+1]^+$ 398.2. SFC (Method 33): $t_R$=2.42 min, 100.0%. $^1$H NMR: (400 MHz, CHLOROFORM-d) δ=9.37 (s, 1H) 8.81 (s, 1H) 8.75 (s, 1H) 8.15 (d, J=8.1 Hz, 1H) 7.93 (s, 3H) 7.76 (s, 1H) 5.17 (dd, J=8.4, 3.7 Hz, 1H) 4.55-4.42 (m, 1H) 4.33-4.21 (m, 1H) 2.79 (s, 3H).

Peak 2: (S)-3-(isoquinolin-4-yl)-1-(2-methyl-5-(trifluoromethyl)pyridin-3-yl)-2-oxoimidazolidine-4-carbonitrile (88b). LCMS (Method 31): $t_R$=2.60 min, $[M+1]^+$ 398.2. SFC (Method 33): $t_R$=2.70 min, 99.7%. $^1$H NMR: (400 MHz, CHLOROFORM-d) δ=9.37 (s, 1H) 8.81 (s, 1H) 8.75 (s, 1H) 8.15 (d, J=8.1 Hz, 1H) 7.93 (s, 3H) 7.76 (s, 1H) 5.17 (dd, J=8.4, 3.7 Hz, 1H) 4.55-4.42 (m, 1H) 4.33-4.21 (m, 1H) 2.79 (s, 3H).

Example 89: Synthesis of 1-(3-(difluoromethoxy) phenyl)-3-(isoquinolin-4-yl)-2-oxoimidazolidine-4-carbonitrile (89), (R)-1-(3-(difluoromethoxy)phenyl)-3-(isoquinolin-4-yl)-2-oxoimidazolidine-4-carbonitrile (89a), and (S)-1-(3-(difluoromethoxy) phenyl)-3-(isoquinolin-4-yl)-2-oxoimidazolidine-4-carbonitrile (89b)

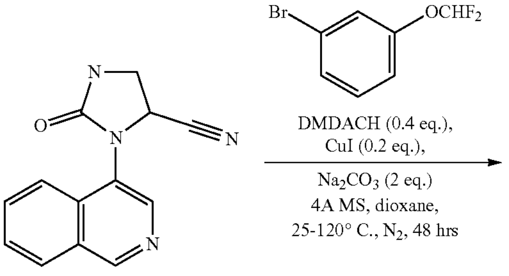

(Int-1)

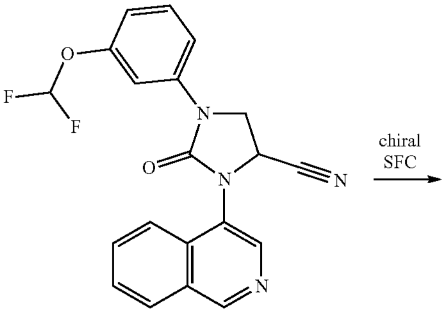

(89)

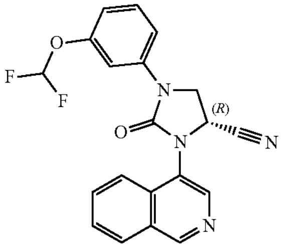

(89a)

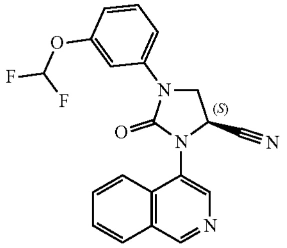

(89b)

Racemic 1-(3-(difluoromethoxy)phenyl)-3-(isoquinolin-4-yl)-2-oxoimidazolidine-4-carbonitrile (89) was prepared in a manner similar to Example 4, using 1-bromo-3-(difluoromethoxy)benzene (2.0 eq) in place of 4-trifluoromethyl-iodobenzene. The crude product was purified by prep-HPLC (column: Waters Xbridge BEH C18 100 mm×30 mm, 10 μm; liquid phase: [A-10 mM $NH_4HCO_3$ in $H_2O$; B-ACN]B %: 15%-55%, 8 min]). LCMS (Method 13): $t_R$=2.32 min, $[M+1]^+$ 381.0. $^1$H NMR: (400 MHz, DMSO-$d_6$) δ=9.44 (br s, 1H), 8.70 (br s, 1H), 8.29 (d, J=8.1 Hz, 1H), 8.12 (d, J=8.4 Hz, 1H), 7.90 (td, J=7.7, 1.1 Hz, 1H), 7.84-7.78 (m, 1H), 7.60-7.56 (m, 1H), 7.51-7.44 (m, 2H), 7.26 (s, 1H), 6.98-6.92 (m, 1H), 5.69 (dd, J=9.3, 4.8 Hz, 1H), 4.62-4.54 (m, 1H), 4.51-4.44 (m, 1H).

The racemic product was resolved by prep-SFC (DAICEL CHIRALPAK IC (250 mm×30 mm, μm); mobile phase: 0.1% $NH_3H_2O$ MeOH; B % 45%-45%, 8 min]) to give two peaks.

Peak 1: (R)-1-(3-(difluoromethoxy)phenyl)-3-(isoquinolin-4-yl)-2-oxoimidazolidine-4-carbonitrile (89a). LCMS (Method 13): $t_R$=2.28 min, $[M+1]^+$ 381.1. SFC (Method 15): $t_R$=1.52 min, 100.0%. $^1H$ NMR: (400 MHz, DMSO-$d_6$) δ=9.44 (br s, 1H), 8.70 (br s, 1H), 8.29 (d, J=8.1 Hz, 1H), 8.12 (d, J=8.4 Hz, 1H), 7.90 (td, J=7.7, 1.1 Hz, 1H), 7.84-7.78 (m, 1H), 7.60-7.56 (m, 1H), 7.51-7.44 (m, 2H), 7.26 (s, 1H), 6.98-6.92 (m, 1H), 5.69 (dd, J=9.3, 4.8 Hz, 1H), 4.62-4.54 (m, 1H), 4.51-4.44 (m, 1H)

Peak 2: (S)-1-(3-(difluoromethoxy)phenyl)-3-(isoquinolin-4-yl)-2-oxoimidazolidine-4-carbonitrile (89b). LCMS (Method 13): $t_R$=2.28 min, $[M+1]^+$ 381.1. SFC (Method 15): $t_R$=1.86 min, 99.7%. $^1H$ NMR: (400 MHz, DMSO-$d_6$) δ=9.44 (br s, 1H), 8.70 (br s, 1H), 8.29 (d, J=8.1 Hz, 1H), 8.12 (d, J=8.4 Hz, 1H), 7.90 (td, J=7.7, 1.1 Hz, 1H), 7.84-7.78 (m, 1H), 7.60-7.56 (m, 1H), 7.51-7.44 (m, 2H), 7.26 (s, 1H), 6.98-6.92 (m, 1H), 5.69 (dd, J=9.3, 4.8 Hz, 1H), 4.62-4.54 (m, 1H), 4.51-4.44 (m, 1H).

Example 90: Synthesis of 1-(2-cyano-5-(trifluoromethyl)phenyl)-3-(isoquinolin-4-yl)-2-oxoimidazolidine-4-carbonitrile (90), (R)-1-(2-cyano-5-(trifluoromethyl)phenyl)-3-(isoquinolin-4-yl)-2-oxoimidazolidine-4-carbonitrile (90a) and (S)-1-(2-cyano-5-(trifluoromethyl)phenyl)-3-(isoquinolin-4-yl)-2-oxoimidazolidine-4-carbonitrile (90b)

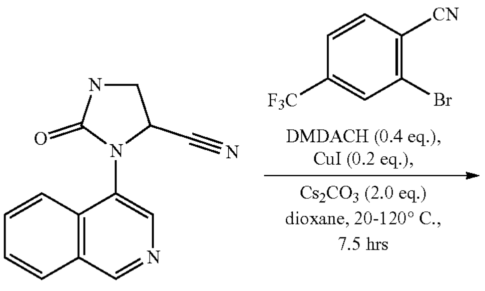

(Int-1)

-continued

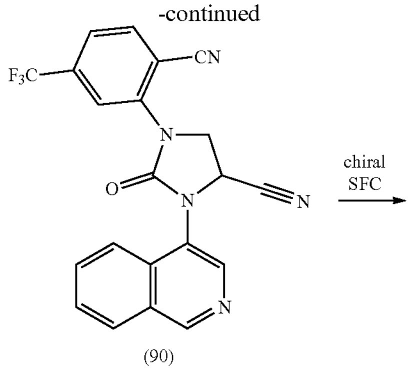

(90)

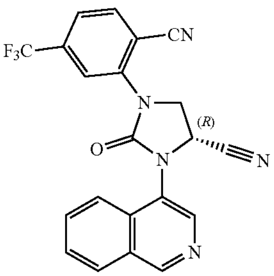

(90a)

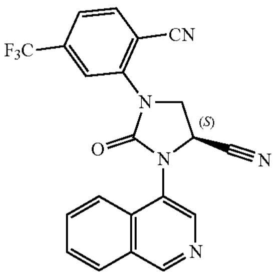

(90b)

Racemic 1-(2-cyano-5-(trifluoromethyl)phenyl)-3-(isoquinolin-4-yl)-2-oxoimidazolidine-4-carbonitrile (90) was prepared in a manner similar to Example 4, using 2-bromo-4-(trifluoromethyl)benzonitrile in place of 4-trifluoromethyl-iodobenzene. The crude product was purified by MPLC (Petroleum ether/EtOAc=100%-0%). LCMS (Method 31): $t_R$=2.78 min, $[M+1]^+$ 408.2. SFC (Method 4): peak 1 $t_R$=1.25 min, peak 2 $t_R$=1.35 min; $^1H$ NMR: (400 MHz, CHLOROFORM-d) δ=9.38 (br s, 1H), 8.74 (br. s, 1H), 8.14 (d, J=8.3 Hz, 1H), 8.00 (br d, J=8.5 Hz, 1H), 7.93 (br d, J=10.4 Hz, 2H), 7.89 (dt, J=1.1, 7.7 Hz, 1H), 7.78-7.73 (m, 1H), 7.70 (dd, J=0.9, 8.1 Hz, 1H), 5.19 (dd, J=4.6, 8.8 Hz, 1H), 4.80 (t, J=9.1 Hz, 1H), 4.52 (dd, J=4.6, 9.4 Hz, 1H).

The racemic product was resolved by prep-SFC (column: DAICEL CHIRALPAK IG (250 mm×30 mm, 10 μm)); Mobile phase: A for $CO_2$ and B for EtOH (0.1% $NH_3H_2O$); Gradient: B %=15%-15%, 10 min) to give two peaks.

Peak 1: (R)-1-(2-cyano-5-(trifluoromethyl)phenyl)-3-(isoquinolin-4-yl)-2-oxoimidazolidine-4-carbonitrile (90a). LCMS (Method 31): $t_R$=2.78 min, $[M+1]^+$ 408.1. SFC (Method 21): $t_R$=1.24 min, 100.0%. $^1H$ NMR: (400 MHz, CHLOROFORM-d) δ=9.37 (s, 1H), 8.73 (s, 1H), 8.14 (d, J=8.1 Hz, 1H), 8.00 (br d, J=8.1 Hz, 1H), 7.97-7.85 (m, 3H), 7.78-7.65 (m, 2H), 5.18 (dd, J=8.8, 4.6 Hz, 1H), 4.80 (dd, J=9.4, 8.8 Hz, 1H), 4.53 (dd, J=9.4, 4.6 Hz, 1H).

Peak 2: (S)-1-(2-cyano-5-(trifluoromethyl)phenyl)-3-(isoquinolin-4-yl)-2-oxoimidazolidine-4-carbonitrile (90b). LCMS (Method 31): $t_R$=2.78 min, $[M+1]^+$ 408.1. SFC (Method 21): $t_R$=1.34 min, 99.5%. $^1H$ NMR: (400 MHz, CHLOROFORM-d) δ=9.37 (s, 1H), 8.73 (s, 1H), 8.14 (d, J=8.1 Hz, 1H), 8.00 (br d, J=8.1 Hz, 1H), 7.97-7.85 (m, 3H), 7.78-7.65 (m, 2H), 5.18 (dd, J=8.8, 4.6 Hz, 1H), 4.80 (dd, J=9.4, 8.8 Hz, 1H), 4.53 (dd, J=9.4, 4.6 Hz, 1H).

Example 91: Synthesis of 3-(isoquinolin-4-yl)-2-oxo-1-(4-(trifluoromethoxy)phenyl)imidazolidine-4-carbonitrile (91), (R)-3-(isoquinolin-4-yl)-2-oxo-1-(4-(trifluoromethoxy)phenyl)imidazolidine-4-carbonitrile (91a) and (S)-3-(isoquinolin-4-yl)-2-oxo-1-(4-(trifluoromethoxy)phenyl)imidazolidine-4-carbonitrile (91 b)

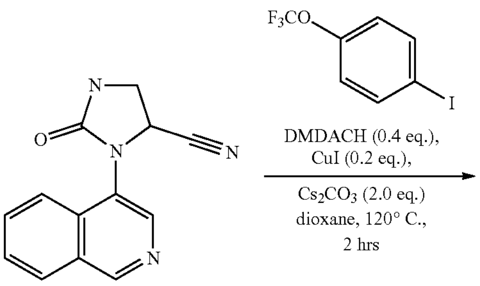

(Int-1)

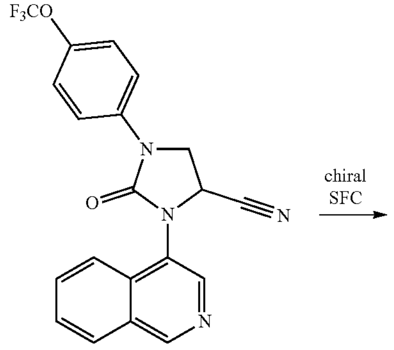

(91)

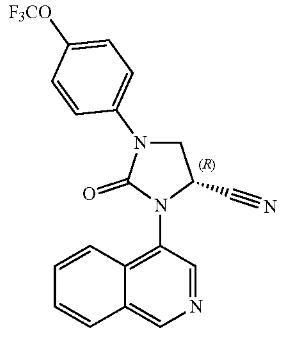

(91a)

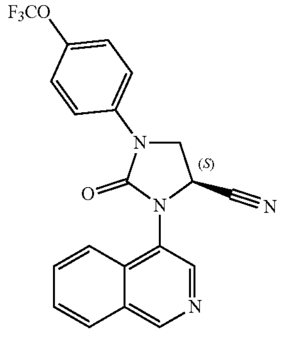

(91b)

Racemic 3-(isoquinolin-4-yl)-2-oxo-1-(4-(trifluoromethoxy)phenyl)imidazolidine-4-carbonitrile (91) was prepared in a manner similar to Example 4, using 1-iodo-4-(trifluoromethoxy)benzene in place of 4-trifluoromethyl-iodobenzene. The crude product was purified by column ($SiO_2$, Petroleum ether/EtOAc=100%~30%). The racemic product was resolved by SFC (column: DAICEL CHIRALPAK AD (250 mm×30 mm, 10 um); liquid phase: 0.1% $NH_3H_2O$ EtOH B %: 50%-50%, 10 min]) to give two peaks.

Peak 1: (R)-3-(isoquinolin-4-yl)-2-oxo-1-(4-(trifluoromethoxy)phenyl)imidazolidine-4-carbonitrile (91a). LCMS (Method 13): $t_R$=2.46 min, $[M+1]^+$ 399.0. SFC (Method 15): $t_R$=1.34 min, 99.9%. $^1$H NMR: (400 MHz, CHLOROFORM-d) δ=9.31 (s, 1H), 8.66 (s, 1H), 8.08 (d, J=8.1 Hz, 1H), 7.91-7.84 (m, 1H), 7.83-7.76 (m, 1H), 7.73-7.66 (m, 1H), 7.63-7.59 (m, 1H), 7.59-7.57 (m, 1H), 7.24 (m, 2H), 5.07 (dd, J=9.1, 4.6 Hz, 1H), 4.47 (dd, J=9.6, 9.1 Hz, 1H), 4.34 (dd, J=9.6, 4.6 Hz, 1H).

Peak 2: (S)-3-(isoquinolin-4-yl)-2-oxo-1-(4-(trifluoromethoxy)phenyl)imidazolidine-4-carbonitrile (91b). LCMS (Method 13): $t_R$=2.45 min, $[M+1]^+$ 399.1. SFC (Method 15): $t_R$=1.59 min, 99.9%. $^1$H NMR: (400 MHz, CHLOROFORM-d) δ=9.31 (s, 1H), 8.66 (s, 1H), 8.08 (d, J=8.1 Hz, 1H), 7.91-7.84 (m, 1H), 7.83-7.76 (m, 1H), 7.73-7.66 (m, 1H), 7.63-7.59 (m, 1H), 7.59-7.57 (m, 1H), 7.24 (m, 2H), 5.07 (dd, J=9.1, 4.6 Hz, 1H), 4.47 (dd, J=9.6, 9.1 Hz, 1H), 4.34 (dd, J=9.6, 4.6 Hz, 1H).

Example 92: Synthesis of 3-(isoquinolin-4-yl)-2-oxo-1-(3-(trifluoromethoxy)phenyl)imidazolidine-4-carbonitrile (92), (R)-3-(isoquinolin-4-yl)-2-oxo-1-(3-(trifluoromethoxy)phenyl)imidazolidine-4-carbonitrile (92a) and (S)-3-(isoquinolin-4-yl)-2-oxo-1-(3-(trifluoromethoxy)phenyl)imidazolidine-4-carbonitrile (92b)

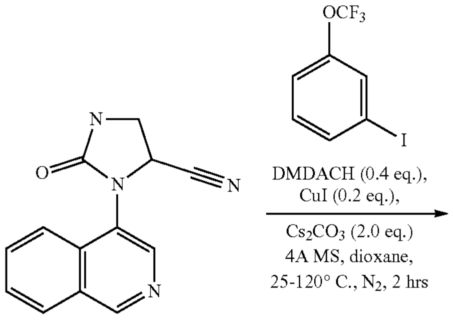

(Int-1)

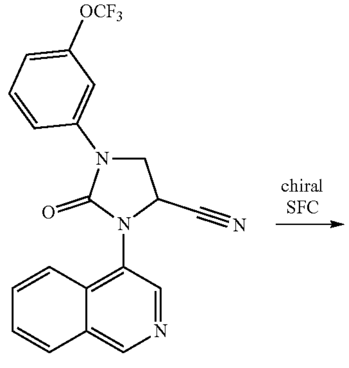

(92)

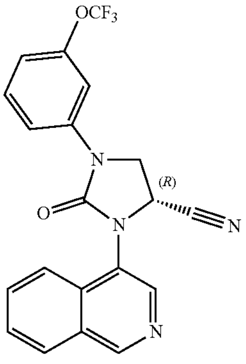

(92a)

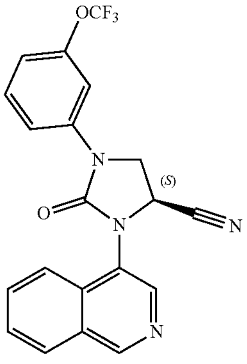

(92b)

Racemic 3-(isoquinolin-4-yl)-2-oxo-1-(3-(trifluoromethoxy)phenyl)imidazolidine-4-carbonitrile (92) was prepared in a manner similar to Example 4, using 1-iodo-3-(trifluoromethoxy)benzene in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 20%-50%, 20 min]). LCMS (Method 31): $t_R$=3.02 min, $[M+1]^+$ 399.1; $^1H$ NMR: (400 MHz, DMSO-$d_6$) δ=9.45 (s, 1H), 8.71 (s, 1H), 8.30 (d, J=8.1 Hz, 1H), 8.15 (d, J=8.4 Hz, 1H), 7.93-7.86 (m, 1H), 7.84-7.79 (m, 2H), 7.58-7.52 (m, 2H), 7.19-7.09 (m, 1H), 5.71 (dd, J=9.4, 9.4 Hz, 1H), 4.64-4.57 (m, 1H), 4.55-4.50 (m, 1H).

The racemic product was resolved by prep-SFC (DAICEL CHIRALPAK IC (250 mm×30 mm, μm); mobile phase: 0.1% $NH_3H_2O$ EtOH; B % 45%-45%, 15 min]) to give two peaks.

Peak 1: (R)-3-(isoquinolin-4-yl)-2-oxo-1-(3-(trifluoromethoxy)phenyl)imidazolidine-4-carbonitrile (92a). LCMS (Method 13): $t_R$=2.45 min, $[M+1]^+$ 399.1. SFC (Method 15): $t_R$=1.25 min, 100.0%. $^1H$ NMR: (400 MHz, DMSO-$d_6$) δ=9.45 (s, 1H), 8.71 (s, 1H), 8.30 (d, J=8.1 Hz, 1H), 8.15 (d, J=8.4 Hz, 1H), 7.93-7.86 (m, 1H), 7.84-7.79 (m, 2H), 7.58-7.52 (m, 2H), 7.19-7.09 (m, 1H), 5.71 (dd, J=9.4, 9.4 Hz, 1H), 4.64-4.57 (m, 1H), 4.55-4.50 (m, 1H).

Peak 2: (S)-3-(isoquinolin-4-yl)-2-oxo-1-(3-(trifluoromethoxy)phenyl)imidazolidine-4-carbonitrile (92b). LCMS (Method 13): $t_R$=2.45 min, $[M+1]^+$ 399.1. SFC (Method 15): $t_R$=1.46 min, 98.73%. $^1H$ NMR: (400 MHz, DMSO-$d_6$) δ=9.45 (s, 1H), 8.71 (s, 1H), 8.30 (d, J=8.1 Hz, 1H), 8.15 (d, J=8.4 Hz, 1H), 7.93-7.86 (m, 1H), 7.84-7.79 (m, 2H), 7.58-7.52 (m, 2H), 7.19-7.09 (m, 1H), 5.71 (dd, J=9.4, 9.4 Hz, 1H), 4.64-4.57 (m, 1H), 4.55-4.50 (m, 1H).

Example 93: Synthesis of 3-(isoquinolin-4-yl)-2-oxo-1-(2-(trifluoromethyl)pyrimidin-5-yl)imidazolidine-4-carbonitrile (93), (R)-3-(isoquinolin-4-yl)-2-oxo-1-(2-(trifluoromethyl)pyrimidin-5-yl)imidazolidine-4-carbonitrile (93a) and (S)-3-(isoquinolin-4-yl)-2-oxo-1-(2-(trifluoromethyl)pyrimidin-5-yl)imidazolidine-4-carbonitrile (93b)

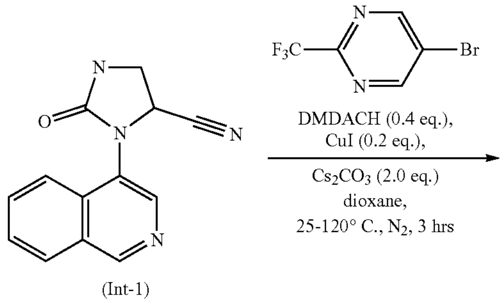

(Int-1)

-continued

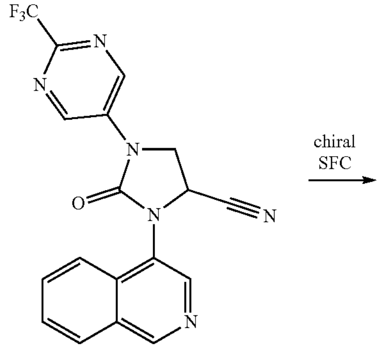

(93)

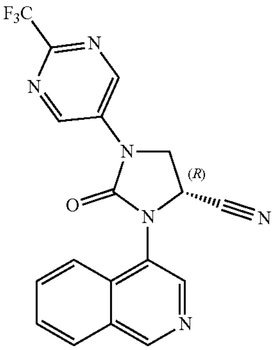

(93a)

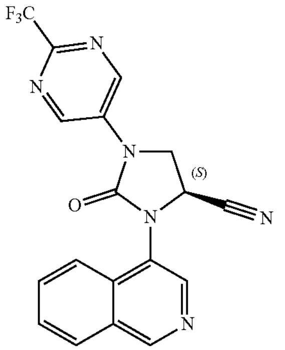

(93b)

Racemic 3-(isoquinolin-4-yl)-2-oxo-1-(2-(trifluoromethyl)pyrimidin-5-yl)imidazolidine-4-carbonitrile (93) was prepared in a manner similar to Example 4, using 5-bromo-2-(trifluoromethyl)pyrimidine in place of 4-trifluoromethyl-iodobenzene. The crude product was purified by flash silica gel chromatography (4 g SepaFlash® Silica Flash Column, Eluent of 50-100% Ethyl acetate/Petroleum ether gradient, 75 mL/min). The racemic product was resolved by SFC (column: DAICEL CHIRALPAK AD (250 mm×30 mm, 10 μm); liquid phase: [0.1% $NH_4HCO_3$ in EtOH]; B %: 50%-50%, 13 min]) to obtain two peaks.

Peak 1: (R)-3-(isoquinolin-4-yl)-2-oxo-1-(2-(trifluoromethyl)pyrimidin-5-yl)imidazolidine-4-carbonitrile (93a). LCMS (Method 31): $t_R$=2.67 min, $[M+1]^+$ 385.1. SFC (Method 15): $t_R$=1.51 5 min, 100.0%. $^1H$ NMR: (400 MHz, CHLOROFORM-d) δ=9.40 (s, 1H), 9.24 (s, 2H), 8.72 (brs, 1H), 8.17 (d, J=8.2 Hz, 1H), 7.94-7.83 (m, 2H), 7.82-7.68 (m, 1H), 5.24 (dd, J=9.1, 4.1 Hz, 1H), 4.64 (dd, J=9.5, 9.1 Hz, 1H), 4.51 (dd, J=9.5, 4.5 Hz, 1H)

Peak 2: (S)-3-(isoquinolin-4-yl)-2-oxo-1-(2-(trifluoromethyl)pyrimidin-5-yl)imidazolidine-4-carbonitrile (93b). LCMS (Method 31): $t_R$=2.67 min, $[M+1]^+$ 385.1. SFC (Method 15): $t_R$=2.10 10 min, 100.0%. $^1H$ NMR: (400 MHz, CHLOROFORM-d) δ=9.40 (s, 1H), 9.24 (s, 2H), 8.72 (brs, 1H), 8.17 (d, J=8.2 Hz, 1H), 7.94-7.83 (m, 2H), 7.82-7.68 (m, 1H), 5.24 (dd, J=9.1, 4.1 Hz, 1H), 4.64 (dd, J=9.5, 9.1 Hz, 1H), 4.51 (dd, J=9.5, 4.5 Hz, 1H)

Example 94: Synthesis of 1-(6-isopropylpyridin-3-yl)-3-(isoquinolin-4-yl)-2-oxoimidazolidine-4-carbonitrile (94), (R)-1-(6-isopropylpyridin-3-yl)-3-(isoquinolin-4-yl)-2-oxoimidazolidine-4-carbonitrile (94a) and (S)-1-(6-isopropylpyridin-3-yl)-3-(isoquinolin-4-yl)-2-oxoimidazolidine-4-carbonitrile (94b)

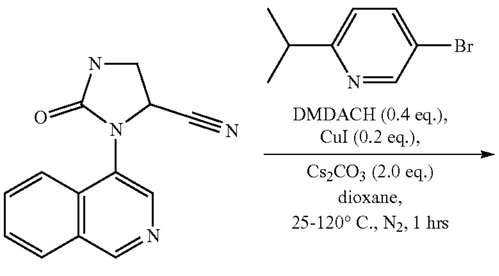

(Int-1)

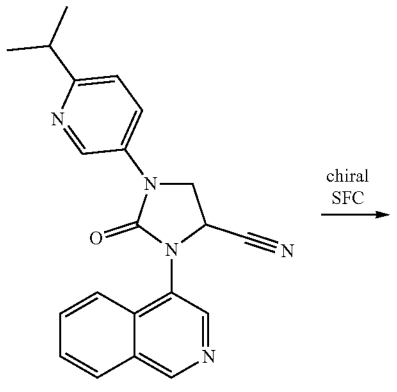

(94)

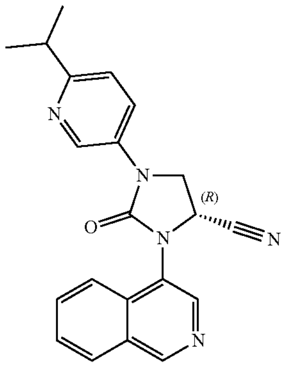

(94a)

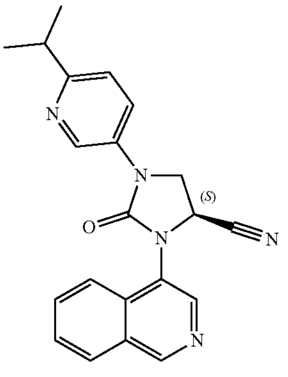

(94b)

Racemic 1-(6-isopropylpyridin-3-yl)-3-(isoquinolin-4-yl)-2-oxoimidazolidine-4-carbonitrile (94) was prepared in a manner similar to Example 4, using 5-bromo-2-isopropylpyridine in place of 4-trifluoromethyl-iodobenzene. The crude product was purified by column (petroleum ether/EtOAc=1/2 to 1/3). The racemic product was resolved by chiral SFC (prep-HPLC (column: DAICEL CHIRALPAK AD (250 mm×30 mm, 10 μm); liquid phase: [0.1% $NH_3H_2O$ IPA: 44%-44%, 20 min]) to obtain two peaks.

Peak 1: (R)-1-(6-isopropylpyridin-3-yl)-3-(isoquinolin-4-yl)-2-oxoimidazolidine-4-carbonitrile (94a). LCMS (Method 13): $t_R$=1.67 min, $[M+1]^+$ 358.1. SFC (Method 22): $t_R$=2.05 min, 100.0%. $^1H$ NMR: (400 MHz, DMSO-$d_6$) δ=9.43 (s, 1H), 8.71 (d, J=2.8 Hz, 1H), 8.69 (s, 1H), 8.28 (d, J=8.1 Hz, 1H), 8.11 (d, J=8.4 Hz, 1H), 7.99 (dd, J=8.5, 2.8 Hz, 1H), 7.90 (td, J=7.7, 1.1 Hz, 1H), 7.82-7.77 (m, 1H), 7.33 (d, J=8.5 Hz, 1H), 5.71 (dd, J=9.3, 4.8 Hz, 1H), 4.64-4.55 (m, 1H), 4.50 (dd, J=9.7, 4.8 Hz, 1H), 3.02 (hept, J=6.9 Hz, 1H), 1.24 (d, J=6.9 Hz, 6H).

Peak 2: (S)-1-(6-isopropylpyridin-3-yl)-3-(isoquinolin-4-yl)-2-oxoimidazolidine-4-carbonitrile (94b). LCMS (LCMS Method 13): $t_R$=1.67 min, $[M+1]^+$ 358.1. SFC (Method 22): $t_R$=3.41 min, 99.6%. $^1H$ NMR: (400 MHz, DMSO-$d_6$) δ=9.43 (s, 1H), 8.71 (d, J=2.8 Hz, 1H), 8.69 (s, 1H), 8.28 (d, J=8.1 Hz, 1H), 8.11 (d, J=8.4 Hz, 1H), 7.99 (dd, J=8.5, 2.8 Hz, 1H), 7.90 (td, J 5=7.7, 1.1 Hz, 1H), 7.82-7.77 (m, 1H), 7.33 (d, J=8.5 Hz, 1H), 5.71 (dd, J=9.3, 4.8 Hz, 1H), 4.64-4.55 (m, 1H), 4.50 (dd, J=9.7, 4.8 Hz, 1H), 3.02 (hept, J=6.9 Hz, 1H), 1.24 (d, J=6.9 Hz, 6H).

Example 95. Synthesis of 3-(isoquinolin-4-yl)-1-(2-methoxy-6-(trifluoromethyl)pyridin-3-yl)-2-oxoimidazolidine-4-carbonitrile (95), (R)-3-(isoquinolin-4-yl)-1-(2-methoxy-6-(trifluoromethyl)pyridin-3-yl)-2-oxoimidazolidine-4-carbonitrile (95a) and (S)-3-(isoquinolin-4-yl)-1-(2-methoxy-6-(trifluoromethyl)pyridin-3-yl)-2-oxoimidazolidine-4-carbonitrile (95b)

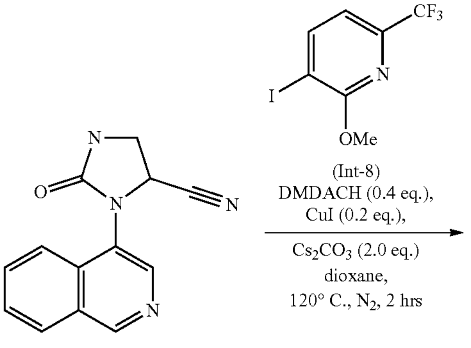

(Int-1)

-continued

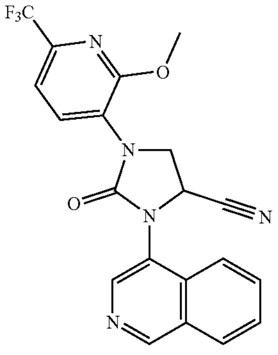

(95)

chiral
SFC

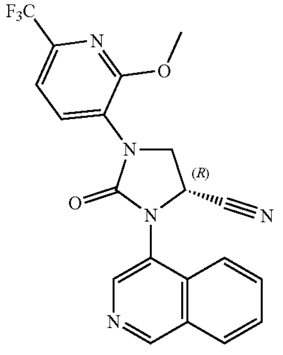

(95a)

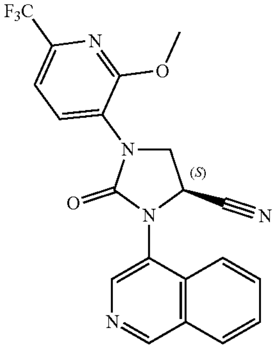

(95b)

Racemic 3-(isoquinolin-4-yl)-1-(2-methoxy-6-(trifluoromethyl)pyridin-3-yl)-2-oxoimidazolidine-4-carbonitrile (95) was prepared in a manner similar to Example 4, using 3-iodo-2-methoxy-6-(trifluoromethyl)pyridine (Int-8) in place of 4-trifluoromethyl-iodobenzene. The crude product was purified by MPLC ($SiO_2$, petroleum ether/ethyl acetate=10/1 to 0/1) to give racemic product. The racemic product was resolved using prep-SFC (column: DAICEL CHIRALPAK IC (250 mm×30 mm, 10 um); mobile phase: IPA; B %: 50%-50%, 9 min) to give two peaks.

Peak 1: (S)-3-(isoquinolin-4-yl)-1-(2-methoxy-6-(trifluoromethyl)pyridin-3-yl)-2-oxoimidazolidine-4-carbonitrile (95b). LCMS (Method 13): $t_R$=2.38 min, $[M+1]^+$ 414.1. SFC (Method 38): $t_R$=1.33 min, 100.0%. $^1H$ NMR: (400 MHz, CHLOROFORM-d) δ=9.35 (s, 1H), 8.71 (s, 1H), 8.13 (d, J=8.1 Hz, 1H), 8.05 (d, J=7.9 Hz, 1H), 7.93 (br d, J=8.4 Hz, 1H), 7.81-7.89 (m, 1H), 7.70-7.77 (m, 1H), 7.39 (d, J=7.9 Hz, 1H), 5.09 (dd, J=8.9, 4.5 Hz, 1H), 4.62 (dd, J=9.9, 8.9 Hz, 1 25 H), 4.46 (dd, J=9.9, 4.5 Hz, 1H), 4.16 (s, 3H).

Peak 2: (R)-3-(isoquinolin-4-yl)-1-(2-methoxy-6-(trifluoromethyl)pyridin-3-yl)-2-oxoimidazolidine-4-carbonitrile (95a). LCMS (Method 13): $t_R$=2.38 min, $[M+1]^+$ 414.1. SFC (Method 38): $t_R$=1.48 min, 99.9%. $^1H$ NMR: (400 MHz, CHLOROFORM-d) δ=9.35 (s, 1H), 8.71 (s, 1H), 8.13 (d, J=8.1 Hz, 1H), 8.05 (d, J=7.9 Hz, 1H), 7.93 (br d, J=8.4 Hz, 1H), 7.81-7.89 (m, 1H), 7.70 30-7.77 (m, 1H), 7.39 (d, J=7.9 Hz, 1H), 5.09 (dd, J=8.9, 4.5 Hz, 1H), 4.62 (dd, J=9.9, 8.9 Hz, 1H), 4.46 (dd, J=9.9, 4.5 Hz, 1H), 4.16 (s, 3H).

Example 96: Synthesis of 3-(isoquinolin-4-yl)-1-(1-methyl-2-oxo-6-(trifluoromethyl)-1,2-dihydropyridin-3-yl)-2-oxoimidazolidine-4-carbonitrile (96), (R)-3-(isoquinolin-4-yl)-1-(1-methyl-2-oxo-6-(trifluoromethyl)-1,2-dihydropyridin-3-yl)-2-oxoimidazolidine-4-carbonitrile (96a) and (S)-3-(isoquinolin-4-yl)-1-(1-methyl-2-oxo-6-(trifluoromethyl)-1,2-dihydropyridin-3-yl)-2-oxoimidazolidine-4-carbonitrile (96b)

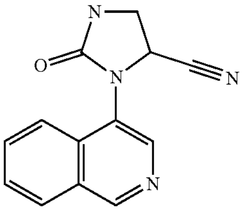

(Int-1)

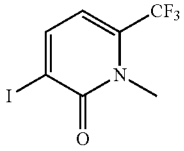

(Int-9)
DMDACH (0.4 eq.),
CuI (0.2 eq.),
$Cs_2CO_3$ (2.0 eq.)
dioxane,
120° C., $N_2$, 2 hrs

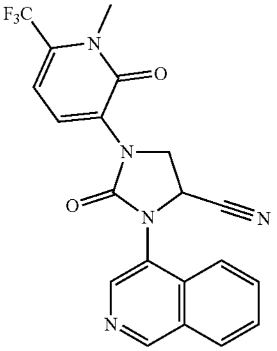

(96)

chiral
SFC

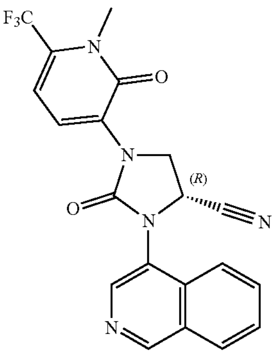

(96a)

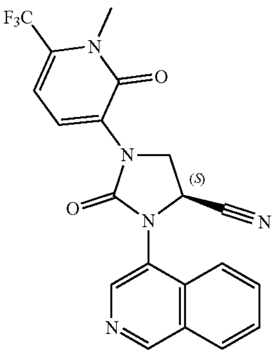

(96b)

Racemic 3-(isoquinolin-4-yl)-1-(1-methyl-2-oxo-6-(trifluoromethyl)-1,2-dihydropyridin-3-yl)-2-oxoimidazolidine-4-carbonitrile (96) was prepared in a manner similar to Example 4, using 3-iodo-1-methyl-6-(trifluoromethyl)pyridin-2(1H)-one (Int-9) in place of 4-trifluoromethyl-iodobenzene. The crude product was purified by MPLC ($SiO_2$, petroleum ether/ethyl acetate=10/1 to 0/1). The racemic product was separated by SFC (column: REGIS (s,s) WHELK-01 (250 mm×50 mm, 10 μm); mobile phase: 0.1% $NH_3H_2O$ EtOH; B %: 50%-50%, 16 min) to give two peaks.

Peak 1: (R)-3-(isoquinolin-4-yl)-1-(1-methyl-2-oxo-6-(trifluoromethyl)-1,2-dihydropyridin-3-yl)-2-oxoimidazolidine-4-carbonitrile (96a). LCMS (Method 13): $t_R$=1.95 min, $[M+1]^+$ 414.0. SFC (Method 40): $t_R$=1.73 min, 100.0%. $^1$H NMR: (400 MHz, CHLOROFORM-d) δ=9.34 (s, 1H), 8.70 (s, 1H), 8.11 (d, J=8.2 Hz, 1H), 7.90-7.96 (m, 1H), 7.79-7.88 (m, 2H), 7.67-7.76 (m, 1H), 6.81 (d, J=7.9 Hz, 1H), 5.03-5.09 (m, 1H), 4.95-5.03 (m, 1H), 4.53 (dd, J=9.9, 4.1 Hz, 1 20 H), 3.72 (s, 3H).

Peak 2: (S)-3-(isoquinolin-4-yl)-1-(1-methyl-2-oxo-6-(trifluoromethyl)-1,2-dihydropyridin-3-yl)-2-oxoimidazolidine-4-carbonitrile (96b). LCMS (Method 13): $t_R$=1.94 min, $[M+1]^+$ 414.0. SFC (Method 40): $t_R$=1.978 min, 99.3%. $^1$H NMR: (400 MHz, CHLOROFORM-d) δ=9.34 (s, 1H), 8.70 (s, 1H), 8.11 (d, J=8.2 Hz, 1H), 7.90-7.96 (m, 1H), 7.79-7.88 (m, 2H), 7.67-7.76 (m, 1H), 6.81 (d, J=7.9 Hz, 1H), 5.03-5.09 (m, 1H), 4.95-5.03 (m, 1H), 4.53 (dd, J=9.9, 4.1 Hz, 1H), 3.72 (s, 3H).

Example 97: Synthesis of 3-(isoquinolin-4-yl)-2-oxo-1-(5-(trifluoromethyl)pyridin-2-yl)imidazolidine-4-carbonitrile (3), (R)-3-(isoquinolin-4-yl)-2-oxo-1-(5-(trifluoromethyl)pyridin-2-yl)imidazolidine-4-carbonitrile (97a) and (S)-3-(isoquinolin-4-yl)-2-oxo-1-(5-(trifluoromethyl)pyridin-2-yl)imidazolidine-4-carbonitrile (79b)

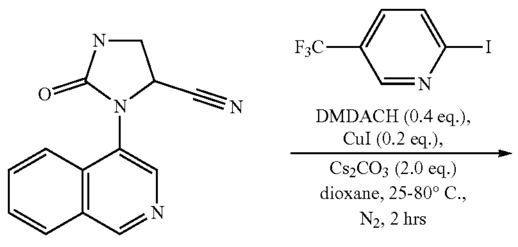

(Int-1)

-continued

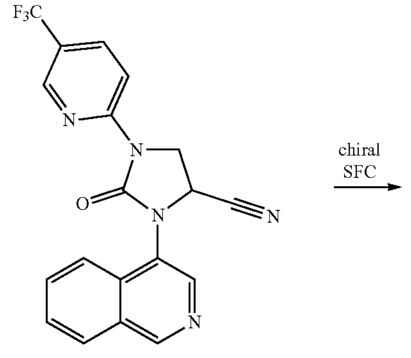

(3)

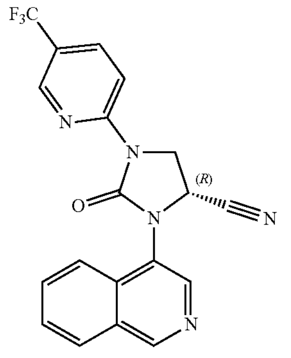

(97a)

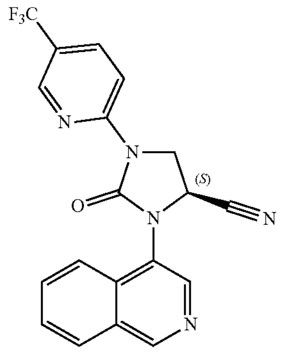

(97b)

Racemic 3-(isoquinolin-4-yl)-2-oxo-1-(5-(trifluoromethyl)pyridin-2-yl)imidazolidine-4-carbonitrile (3) was prepared in a manner similar to Example 4, using 2-iodo-5-(trifluoromethyl)pyridine in place of 4-trifluoromethyl-iodobenzene. The crude product was purified by MLPC (Petroleum ether/Ethyl acetate=1/0~0/1). LCMS (Method 15): $t_R$=0.70 min, $[M+1]^+$ 384.2. $^1$H NMR: (400 MHz, CHLOROFORM-d) δ=9.39 (s, 1H), 8.74 (s, 1H), 8.69-8.60 (m, 1H), 8.41 (d, J=8.9 Hz, 1H), 8.16 (d, J=8.1 Hz, 1H), 7.97-7.84 (m, 3H), 7.79-7.73 (m, 1H), 5.14 (t, J=6.9 Hz, 1H), 4.79-4.71 (m, 2H).

Racemic 3-(isoquinolin-4-yl)-2-oxo-1-(5-(trifluoromethyl)pyridin-2-yl)imidazolidine-4-carbonitrile (3) was resolved by prep-SFC (column: DAICEL CHIRALPAK IG [250 mm×30 mm, 10 μm; 0.1% $NH_3H_2O$ ETOH; B % 50%-50%, 15 min]) to give two peaks.

Peak 1: (R)-3-(isoquinolin-4-yl)-2-oxo-1-(5-(trifluoromethyl)pyridin-2-yl)imidazolidine-4-carbonitrile (97a). LCMS (Method 13): $t_R$=2.41 min, $[M+1]^+$ 384.0. SFC (Method 43): $t_R$=2.57 min, 100.0%. $^1$H NMR: (400 MHz, CHLOROFORM-d) δ=9.39 (s, 1H), 8.74 (s, 1H), 8.69-8.60 (m, 1H), 8.41 (d, J=8.9 Hz, 1H), 8.16 (d, J=8.1 Hz, 1H), 7.97-7.84 (m, 3H), 7.79-7.73 (m, 1H), 5.14 (t, J=6.9 Hz, 1H), 4.79-4.71 (m, 2H).

Peak 2: (S)-3-(isoquinolin-4-yl)-2-oxo-1-(5-(trifluoromethyl)pyridin-2-yl)imidazolidine-4-carbonitrile (97b). LCMS (Method 13): $t_R$=2.41 min, $[M+1]^+$ 384.1. SFC (Method 43): $t_R$=3.37 min, 99.9%. $^1$H NMR: (400 MHz, CHLOROFORM-d) δ=9.39 (s, 1H), 8.74 (s, 1H), 8.69-8.60 (m, 1H), 8.41 (d, J=8.9 Hz, 1H), 8.16 (d, J=8.1 Hz, 1H), 7.97-7.84 (m, 3H), 7.79-7.73 (m, 1H), 5.14 (t, J=6.9 Hz, 1H), 4.79-4.71 (m, 2H).

Example 98: Synthesis of 1-(5,6-dimethylpyridin-3-yl)-3-(isoquinolin-4-yl)-2-oxoimidazolidine-4-carbonitrile (98), (R)-1-(5,6-dimethylpyridin-3-yl)-3-(isoquinolin-4-yl)-2-oxoimidazolidine-4-carbonitrile (98a) and (S)-1-(5,6-dimethylpyridin-3-yl)-3-(isoquinolin-4-yl)-2-oxoimidazolidine-4-carbonitrile (98b)

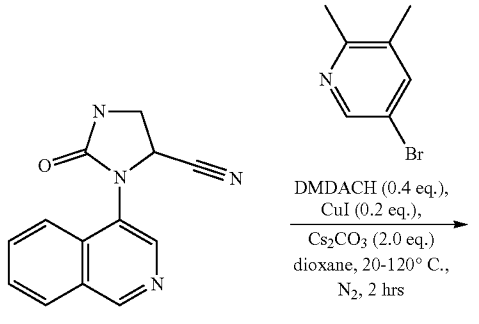

(Int-1)

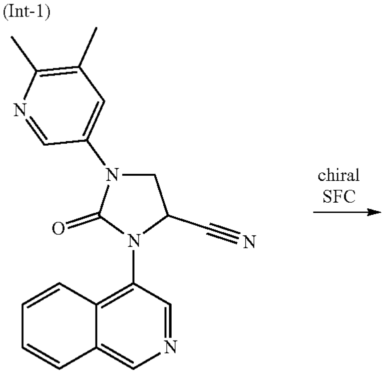

(98)

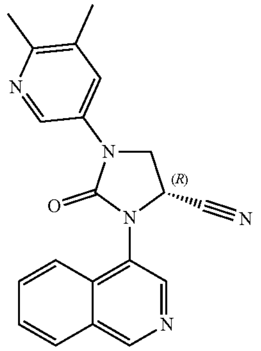

(98a)

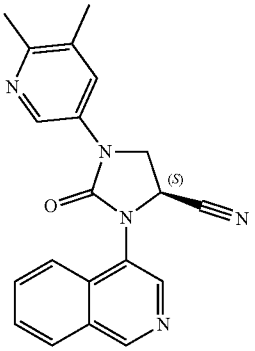

(98b)

Racemic 1-(5,6-dimethylpyridin-3-yl)-3-(isoquinolin-4-yl)-2-oxoimidazolidine-4-carbonitrile (98) was prepared in a manner similar to Example 4, using 5-bromo-2,3-dimethylpyridine in place of 4-trifluoromethyl-iodobenzene. The crude product was purified by MLPC (Petroleum ether/EtOAc=100%-0%). The racemic product was resolved by SFC (Column: DAICEL CHIRALPAK AD (250 mm×30 mm, 10 μm); Mobile phase: A for $CO_2$ and B for IPA(0.1% $NH_3H_2O$); B %=45%, 10 min) to give two peaks.

Peak 1: (R)-1-(5,6-dimethylpyridin-3-yl)-3-(isoquinolin-4-yl)-2-oxoimidazolidine-4-carbonitrile (98a). LCMS (Method 31): $t_R$=2.40 min, $[M+1]^+$ 344.2. SFC (Method 1): $t_R$=1.37 min, 100.0%, 10 $^1$H NMR: (400 MHz, CHLOROFORM-d) δ=9.35 (s, 1H), 8.70 (s, 1H), 8.34 (d, J=2.5 Hz, 1H), 8.13 (d, J=8.3 Hz, 1H), 8.00 (d, J=2.4 Hz, 1H), 7.95-7.89 (m, 1H), 7.86-7.81 (m, 1H), 7.76-7.70 (m, 1H), 5.13 (dd, J=9.1, 4.6 Hz, 1H), 4.55 (dd, J=9.6, 9.1 Hz, 1H), 4.40 (dd, J=9.6, 4.6 Hz, 1H), 2.52 (s, 3H), 2.33 (s, 3H).

Peak 2: (S)-1-(5,6-dimethylpyridin-3-yl)-3-(isoquinolin-4-yl)-2-oxoimidazolidine-4-carbonitrile (98b). LCMS (Method 31): $t_R$=2.40 min, $[M+1]^+$ 344.2. SFC (Method 1): $t_R$=1.58 min, 99.7%. $^1$H NMR: (400 MHz, CHLOROFORM-d) δ=9.35 (s, 1H), 8.70 (s, 1H), 8.34 (d, J=2.5 Hz, 1H), 8.13 (d, J=8.3 Hz, 1H), 8.00 (d, J=2.4 Hz, 1H), 7.95-7.89 (m, 1H), 7.86-7.81 (m, 1H), 7.76-7.70 (m, 1H), 5.13 (dd, J=9.1, 4.6 Hz, 1H), 4.55 (dd, J=9.6, 9.1 Hz, 1H), 4.40 (dd, J=9.6, 4.6 Hz, 1H), 2.52 (s, 3H), 2.33 (s, 3H).

Example 99: Synthesis of (R)-3-(isoquinolin-4-yl)-2-oxo-1-(4-(trifluoromethyl)phenyl)imidazolidine-4-carbonitrile (99a) and (S)-3-(isoquinolin-4-yl)-2-oxo-1-(4-(trifluoromethyl)phenyl)imidazolidine-4-carbonitrile (99b)

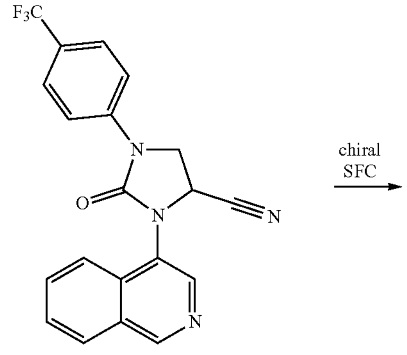

(4)

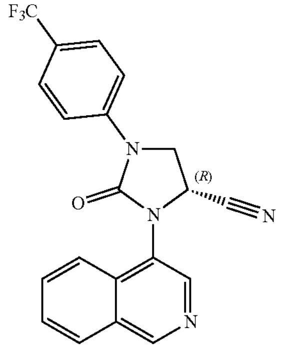

(99a)

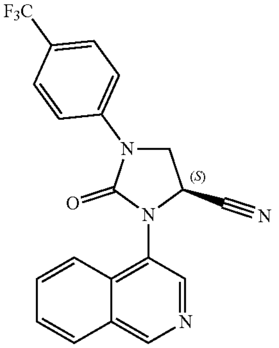

(99b)

Racemic 3-(isoquinolin-4-yl)-2-oxo-1-(4-(trifluoromethyl)phenyl)imidazolidine-4-carbonitrile (4) was resolved by prep-SFC (column: REGIS(S, S) WHELK-O (250 mm×25 mm, 10 μm; mobile phase: 0.1% $NH_3H_2O$ ETOH; B % 35%-55%, 16 min]) to give two peaks.

Peak 1: (R)-3-(isoquinolin-4-yl)-2-oxo-1-(4-(trifluoromethyl)phenyl)imidazolidine-4-carbonitrile (99a). LCMS (Method 31): $t_R$=2.974 min, $[M+1]^+$ 383.2. SFC (Method 15): $t_R$=1.452 min, 100.0%. $^1$H NMR: (400 MHz, DMSO-$d_6$) δ=9.44 (s, 1H), 8.70 (s, 1H), 8.29 (d, J=8.3 Hz, 1H), 8.13 (d, J=8.4 Hz, 1H), 7.90 (t, J=7.6 Hz, 1H), 7.86-7.75 (m, 5H), 5.70 (dd, J=4.7, 9.3 Hz, 1H), 4.66-4.61 (m, 1H), 4.53 (dd, J=4.8, 9.8 Hz, 1H).

Peak 2: (S)-3-(isoquinolin-4-yl)-2-oxo-1-(4-(trifluoromethyl)phenyl)imidazolidine-4-carbonitrile (99b). LCMS (Method 31): $t_R$=2.973 min, $[M+1]^+$ 383.2. SFC (Method 15): $t_R$=1.791 min, 99.2%. $^1H$ NMR: (400 MHz, DMSO-$d_6$) δ=9.44 (s, 1H), 8.71 (s, 1H), 8.29 (d, J=8.1 Hz, 1H), 8.14 (d, J=8.3 Hz, 1H), 7.91 (t, J=7.7 Hz, 1H), 7.87-7.76 (m, 5H), 5.71 (dd, J=4.8, 9.3 Hz, 1H), 4.67-4.61 (m, 1H), 4.53 (dd, J=4.8, 9.8 Hz, 1H).

Example 100: Synthesis of 3-(isoquinolin-4-yl)-1-(2-methoxy-5-(trifluoromethyl)pyridin-3-yl)-2-oxoimidazolidine-4-carbonitrile (100), (R)-3-(isoquinolin-4-yl)-1-(2-methoxy-5-(trifluoromethyl)pyridin-3-yl)-2-oxoimidazolidine-4-carbonitrile (100a) and (S)-3-(isoquinolin-4-yl)-1-(2-methoxy-5-(trifluoromethyl)pyridin-3-yl)-2-oxoimidazolidine-4-carbonitrile (100b)

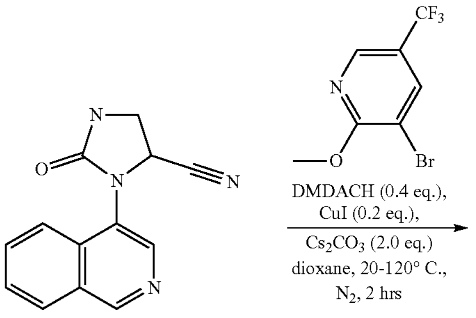

(Int-1)

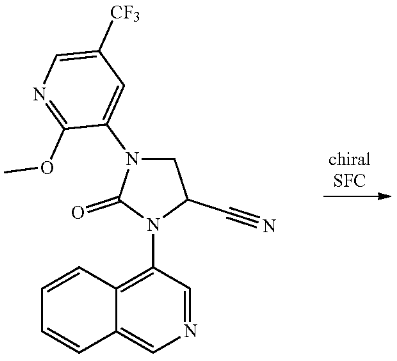

(100)

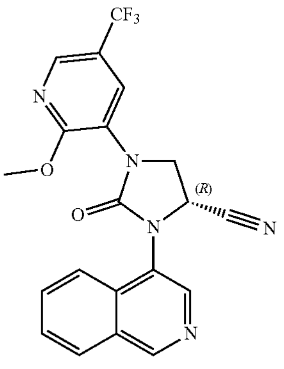

(100a)

-continued

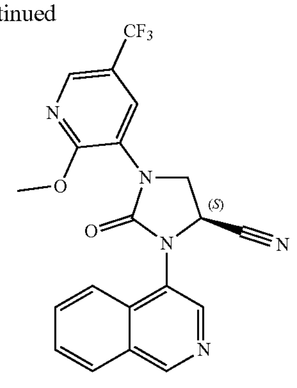

(100b)

Racemic 3-(isoquinolin-4-yl)-1-(2-methoxy-5-(trifluoromethyl)pyridin-3-yl)-2-oxoimidazolidine-4-carbonitrile (100) was prepared in a manner similar to Example 4, using 3-bromo-2-methoxy-5-(trifluoromethyl)pyridine (1.5 eq.) in place of 4-trifluoromethyl-iodobenzene. The crude product was purified by prep-HPLC (column: Phenomenex Luna C18 75 mm×30 mm, 3 μm; mobile phase: [water (HCOOH)-ACN]; B %: 20%-60%, 8 min). The racemic product was resolved by SFC (column: DAICEL CHIRALPAK AD (250 mm×30 mm, 10 μm); mobile phase: 0.1% $NH_3H_2O$ EtOH; B %: 28%-28%, 8 min) to give two peaks.

Peak 1: (R)-3-(isoquinolin-4-yl)-1-(2-methoxy-5-(trifluoromethyl)pyridin-3-yl)-2-oxoimidazolidine-4-carbonitrile (100a). LCMS (Method 13): $t_R$=2.33 min, $[M+1]^+$ 414.0. SFC (Method 41): $t_R$=1.12 min, 99.6%. $^1H$ NMR: (400 MHz, CHLOROFORM-d) δ=9.36 (s, 1H), 8.72 (s, 1H), 8.42 (d, J=1.0 Hz, 1H), 8.14 (d, J=8.2 Hz, 1H), 8.11 (d, J=2.2 Hz, 1H), 7.99-7.93 (m, 1H), 7.87 (t, J=7.6 Hz, 1H), 7.78-7.71 (m, 1H), 5.12 (dd, J=9.0, 4.6 Hz, 1H), 4.58-4.52 (m, 1H), 4.44 (dd, J=9.7, 4.5 Hz, 1H), 4.17 (s, 3H).

Peak 2: (S)-3-(isoquinolin-4-yl)-1-(2-methoxy-5-(trifluoromethyl)pyridin-3-yl)-2-oxoimidazolidine-4-carbonitrile (100b). LCMS (Method 13): $t_R$=2.33 min, $[M+1]^+$ 414.0. SFC (Method 41): $t_R$=1.20 min, 99.0%. $^1H$ NMR: (400 MHz, CHLOROFORM-d) δ=9.36 (s, 1H), 8.72 (s, 1H), 8.42 (d, J=1.0 Hz, 1H), 8.14 (d, J=8.2 Hz, 1H), 8.11 (d, J=2.2 Hz, 1H), 7.99-7.93 (m, 1H), 7.87 (t, J=7.6 Hz, 1H), 7.78-7.71 (m, 1H), 5.12 (dd, J=9.0, 4.6 Hz, 1H), 4.58-4.52 (m, 1H), 4.44 (dd, J=9.7, 4.5 Hz, 1H), 4.17 (s, 3H).

Example 101: Synthesis of 1-(5-(difluoromethoxy)-2-methylphenyl)-3-(isoquinolin-4-yl)-2-oxoimidazolidine-4-carbonitrile (101), (R)-1-(5-(difluoromethoxy)-2-methylphenyl)-3-(isoquinolin-4-yl)-2-oxoimidazolidine-4-carbonitrile (101a) and (S)-1-(5-(difluoromethoxy)-2-methylphenyl)-3-(isoquinolin-4-yl)-2-oxoimidazolidine-4-carbonitrile (101b)

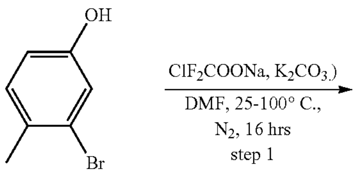

-continued

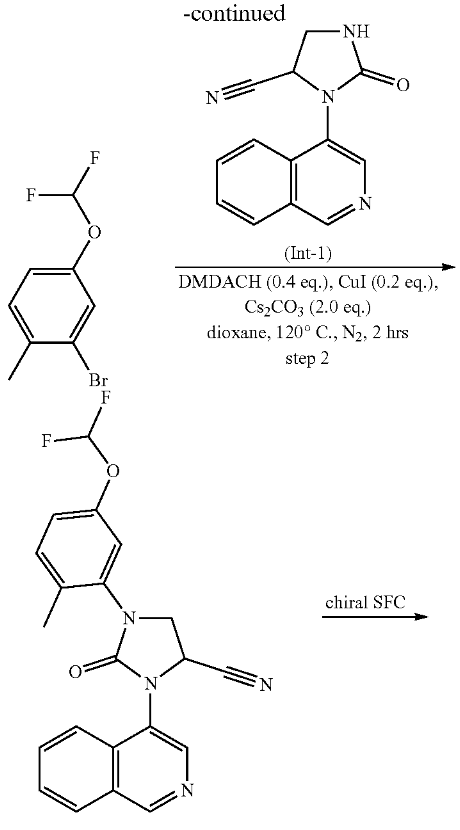

(101)

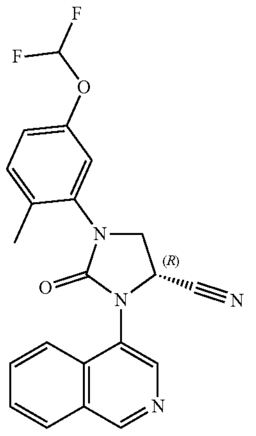

(101a)

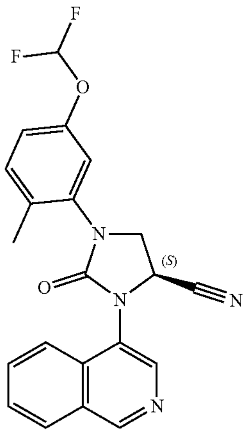

(101b)

Step 1: To a solution of 3-bromo-4-methylphenol (2.0 g, 10.75 mmol, 1.0 eq.) in DMF (20 mL) was added $ClF_2COONa$ (3.9 g, 16.13 mmol, 1.5 eq.) and $K_2CO_3$ (2.3 g, 16.13 mmol, 1.5 eq.) at 25° C. The mixture was heated to 100° C. and stirred at 100° C. for 16 hrs under $N_2$. The reaction mixture was cooled to 25° C. The mixture was poured into water (50 mL) and extracted with EtOAc (20 mL×3). The combined organic layers were washed with brine (20 mL×3), dried over $Na_2SO_4$, filtered and concentrated to give a residue. The residue was purified by flash silica gel chromatography (20 g SepaFlash® Silica Flash Column, Eluent of 0-20% Ethyl acetate/Petroleum ethergradient at 60 mL/min) to give 2-bromo-4-(difluoromethoxy)-1-methylbenzene. $^1$H NMR: (400 MHz, CHLOROFORM-d) δ=7.27 (s, 1H), 7.14 (d, J=8.4 Hz, 1H), 6.93 (dd, J=8.3, 2.4 Hz, 1H), 6.38 (t, J=73.6, 1H), 2.31 (s, 3H).

Step 2: Racemic 1-(5-(difluoromethoxy)-2-methylphenyl)-3-(isoquinolin-4-yl)-2-oxoimidazolidine-4-carbonitrile (101) was prepared in a manner similar to Example 4, using 2-bromo-4-(difluoromethoxy)-1-methylbenzene in place of 4-trifluoromethyl-iodobenzene. The racemate was purified by flash silica gel chromatography (12 g SepaFlash® Silica Flash Column, Eluent of 0-80% Ethyl acetate/Petroleum ethergradient at 100 mL/min). The racemic product was separated by prep-SFC (column: DAICEL CHIRALPAK AD (250 mm×30 mm, 10 μm); mobile phase: 0.1% $NH_3H_2O$ EtOH; B %: 44%-44%, 5 min) to give two peaks. Peak 1 was repurified by prep-SFC (column: DAICEL CHIRALPAK AD (250 mm×30 mm, 10 μm); mobile phase: 0.1% $NH_3H_2O$ EtOH; B %: 40%-40%, 10 min).

Peak 1: (S)-1-(5-(difluoromethoxy)-2-methylphenyl)-3-(isoquinolin-4-yl)-2-oxoimidazolidine-4-carbonitrile (101b). LCMS (Method 13): $t_R$=2.29 min, $[M+1]^+$ 395.0. SFC (Method 15): $t_R$=1.47 min, 100.0%. $^1$H NMR: (400 MHz, CHLOROFORM-d) δ=9.33 (s, 1H), 8.71 (s, 1H), 8.12 (d, J=8.3 Hz, 1H), 7.95 (d, J=8.4 Hz, 1H), 7.84 (td, J=7.6, 1.1 Hz, 1H), 7.76-7.70 (m, 1H), 7.34 (d, J=8.4 Hz, 1H), 7.15-7.07 (m, 2H), 6.52 (t, J=73.6 Hz, 1H), 5.08 (dd, J=8.5, 3.8 Hz, 1H), 4.41 (dd, J=9.6, 8.5 Hz, 1H), 4.21 (dd, J=9.6, 3.8 Hz, 1H), 2.44 (s, 3H).

Peak 2: (R)-1-(5-(difluoromethoxy)-2-methylphenyl)-3-(isoquinolin-4-yl)-2-oxoimidazolidine-4-carbonitrile (101a). LCMS (Method 13): $t_R$=2.30 min, $[M+1]^+$ 395.0. SFC (Method 15): $t_R$=1.58 min, 98.8%. $^1$H NMR: (400 MHz, CHLOROFORM-d) δ=9.33 (s, 1H), 8.71 (s, 1H), 8.12 (d, J=8.3 Hz, 1H), 7.95 (d, J=8.4 Hz, 1H), 7.84 (td, J=7.6, 1.1 Hz, 1H), 7.76-7.70 (m, 1H), 7.34 (d, J=8.4 Hz, 1H), 7.15-7.07 (m, 2H), 6.52 (t, J=73.6 Hz, 1H), 5.08 (dd, J=8.5, 3.8 Hz, 1H), 4.41 (dd, J=9.6, 8.5 Hz, 1H), 4.21 (dd, J=9.6, 3.8 Hz, 1H), 2.44 (s, 3H).

Example 102: Synthesis of 1-(2,6-dimethylpyridin-4-yl)-3-(isoquinolin-4-yl)-2-oxoimidazolidine-4-carbonitrile (102), (R)-1-(2,6-dimethylpyridin-4-yl)-3-(isoquinolin-4-yl)-2-oxoimidazolidine-4-carbonitrile (102a) and (S)-1-(2,6-dimethylpyridin-4-yl)-3-(isoquinolin-4-yl)-2-oxoimidazolidine-4-carbonitrile (102b)

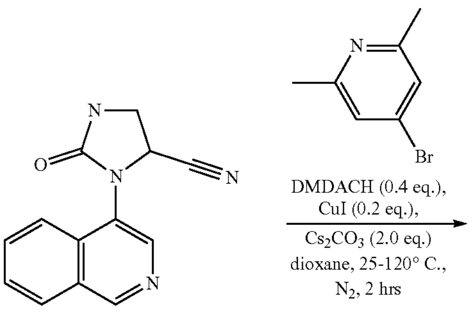

(Int-1)

-continued

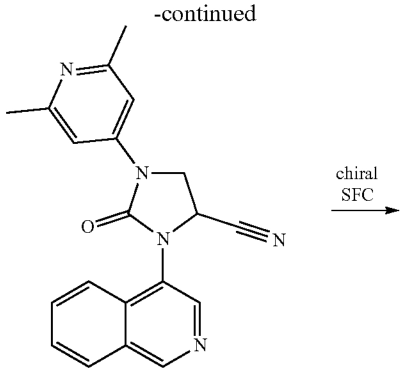

(102)

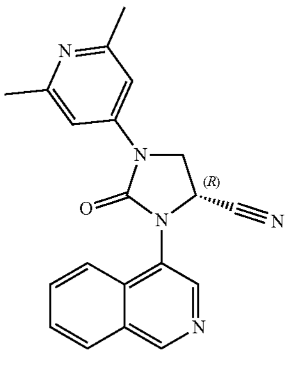

(102a)

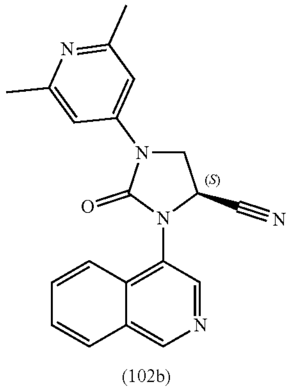

(102b)

Racemic 1-(2,6-dimethylpyridin-4-yl)-3-(isoquinolin-4-yl)-2-oxoimidazolidine-4-carbonitrile (102) was prepared in a manner similar to Example 4, using 4-bromo-2,6-dimethylpyridine (1.2 eq) in place of 4-trifluoromethyl-iodobenzene. The crude product was purified by MPLC (Petroleum ether/EtOAc=50%-70%). The racemic product was resolved by SFC (Column: Chiralcel OJ-3, 50 mm×4.6 mm, 3 μm); Mobile phase: A for $CO_2$ and B for IPA (0.1% IPAm); Gradient: B %=50% isocratic elution mode; Flow rate: 3.4 mL/min; Wavelength: 220 nm; Column temperature: 35° C.; System back pressure: 124 bar) to give two peaks.

Peak 1: (R)-1-(2,6-dimethylpyridin-4-yl)-3-(isoquinolin-4-yl)-2-oxoimidazolidine-4-carbonitrile (102a). LCMS (Method 13): $t_R$=1.56 min, $[M+1]^+$ 344.1. SFC (Method 2): $t_R$=1.20 min, 97.5%. $^1$H NMR: (400 MHz, CHLOROFORM-d) δ=9.36 (s, 1H), 8.68 (s, 1H), 8.13 (d, J=8.2 Hz, 1H), 7.91-7.81 (m, 2H), 7.78-7.69 (m, 1H), 7.32 (s, 2H), 5.17 (br dd, J=9.2, 4.3, Hz, 1H), 4.55 (dd, J=9.9, 9.2 Hz, 1H), 4.41 (dd, J=9.9, 4.4 Hz, 1H), 2.58 (s, 6H).

Peak 2: (S)-1-(2,6-dimethylpyridin-4-yl)-3-(isoquinolin-4-yl)-2-oxoimidazolidine-4-carbonitrile (102b). LCMS (Method 13): $t_R$=1.56 min, $[M+1]^+$ 344.1. SFC (Method 2): $t_R$=1.27 min, 97.6%. tH NMR: (400 MHz, CHLOROFORM-d) δ=9.36 (s, 1H), 8.68 (s, 1H), 8.13 (d, J=8.2 Hz, 1H), 7.91-7.81 (m, 2H), 7.78-7.69 (m, 1H), 7.32 (s, 2H), 5.17 (br dd, J=9.2, 4.3, Hz, 1H), 4.55 (dd, J=9.9, 9.2 Hz, 1H), 4.41 (dd, J=9.9, 4.4 Hz, 1H), 2.58 (s, 6H).

Example 103: Synthesis of 1-(4-chloro-2-methoxyphenyl)-3-(isoquinolin-4-yl)-2-oxoimidazolidine-4-carbonitrile (103), (R)-1-(4-chloro-2-methoxyphenyl)-3-(isoquinolin-4-yl)-2-oxoimidazolidine-4-carbonitrile (103a) and (S)-1-(4-chloro-2-methoxyphenyl)-3-(isoquinolin-4-yl)-2-oxoimidazolidine-4-carbonitrile (103b)

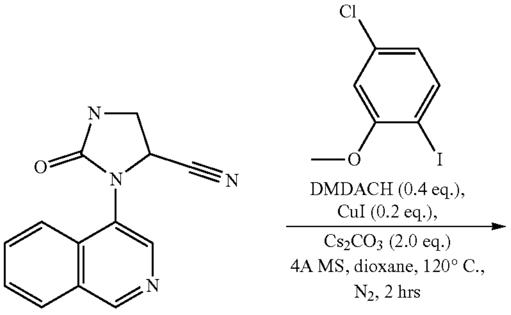

(Int-1)

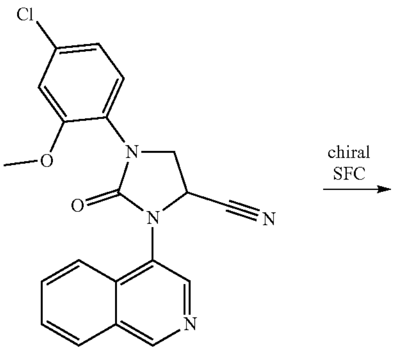

(103)

-continued

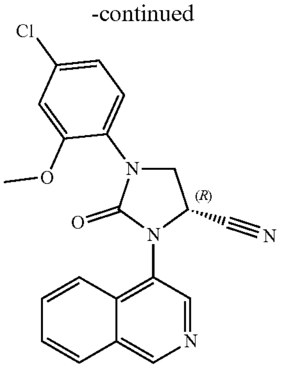

(103a)

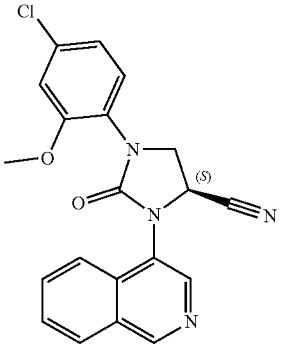

(103b)

Racemic 1-(4-chloro-2-methoxyphenyl)-3-(isoquinolin-4-yl)-2-oxoimidazolidine-4-carbonitrile (103) was prepared in a manner similar to Example 4, using 4-chloro-1-iodo-2-methoxybenzene in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 20%-50%, 20 min]). LCMS (Method 13): $t_R$=2.23 min, $[M+1]^+$ 379.0. SFC (Method 15): peak 1 $t_R$=1.68 min, peak 2 $t_R$=2.07 min; $^1H$ NMR: (400 MHz, DMSO-$d_6$) δ=9.40 (br s, 1H), 8.65 (s, 1H), 8.27 (d, J=8.1 Hz, 1H), 8.05 (d, J=8.4 Hz, 1H), 7.93 (t, J=7.3 Hz, 1H), 7.84-7.75 (m, 1H), 7.47 (d, J=8.4 Hz, 1H), 7.27 (d, J=2.1 Hz, 1H), 7.09 (dd, J=8.4, 2.2 Hz, 1H), 5.65 (dd, J=9.0, 4.3 Hz, 1H), 4.39 (dd, J=9.6, 9.0 Hz, 1H), 4.18 (dd, J=9.6, 4.3 Hz, 1H), 3.94 (s, 3H).

The racemic product was resolved by prep-SFC (DAICEL CHIRALPAK IC (250 mm×30 mm, 10 μm); mobile phase: 0.1% $NH_3H_2O$ IPA; B % 45%-45%, 8 min]) to give two peaks.

Peak 1: (S)-1-(4-chloro-2-methoxyphenyl)-3-(isoquinolin-4-yl)-2-oxoimidazolidine-4-carbonitrile (103b). LCMS (Method 13): $t_R$=2.24 min, $[M+1]^+$ 379.0. SFC (Method 15): $t_R$=1.68 min, 100.0%. $^1H$ NMR: (400 MHz, DMSO-$d_6$) δ=9.40 (br s, 1H), 8.65 (s, 1H), 8.27 (d, J=8.1 Hz, 1H), 8.05 (d, J=8.4 Hz, 1H), 7.93 (t, J=7.3 Hz, 1H), 7.84-7.75 (m, 1H), 7.47 (d, J=8.4 Hz, 1H), 7.27 (d, J=2.1 Hz, 1H), 7.09 (dd, J=8.4, 2.2 Hz, 1H), 5.65 (dd, J=9.0, 4.3 Hz, 1H), 4.39 (dd, J=9.6, 9.0 Hz, 1H), 4.18 (dd, J=9.6, 4.3 Hz, 1H), 3.94 (s, 3H).

Peak 2: (R)-1-(4-chloro-2-methoxyphenyl)-3-(isoquinolin-4-yl)-2-oxoimidazolidine-4-carbonitrile (103a). LCMS (Method 13): $t_R$=2.24 min, $[M+1]^+$ 379.0. SFC (Method 15): $t_R$=2.16 min, 99.7%. $^1H$ NMR: (400 MHz, DMSO-$d_6$) δ=9.40 (br s, 1H), 8.65 (s, 1H), 8.27 (d, J=8.1 Hz, 1H), 8.05 (d, J=8.4 Hz, 1H), 7.93 (t, J=7.3 Hz, 1H), 7.84-7.75 (m, 1H), 7.47 (d, J=8.4 Hz, 1H), 7.27 (d, J=2.1 Hz, 1H), 7.09 (dd, J=8.4, 2.2 Hz, 1H), 5.65 (dd, J=9.0, 4.3 Hz, 1H), 4.39 (dd, J=9.6, 9.0 Hz, 1H), 4.18 (dd, J=9.6, 4.3 Hz, 1H), 3.94 (s, 3H).

Example 104: Synthesis of 3-(isoquinolin-4-yl)-2-oxo-1-(5-(trifluoromethyl)pyridin-3-yl)imidazolidine-4-carbonitrile (104), (R)-3-(isoquinolin-4-yl)-2-oxo-1-(5-(trifluoromethyl)pyridin-3-yl)imidazolidine-4-carbonitrile (104a) and (S)-3-(isoquinolin-4-yl)-2-oxo-1-(5-(trifluoromethyl)pyridin-3-yl)imidazolidine-4-carbonitrile (104b)

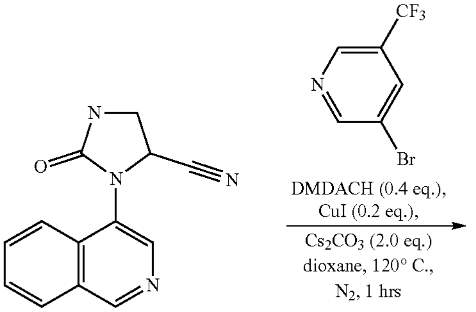

(Int-1)

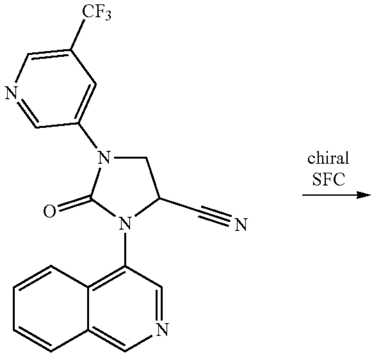

(104)

-continued

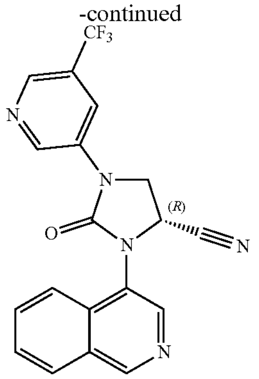

(104a)

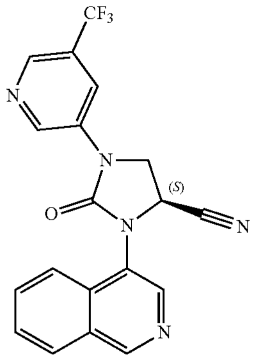

(104b)

Racemic 3-(isoquinolin-4-yl)-2-oxo-1-(5-(trifluoromethyl)pyridin-3-yl)imidazolidine-4-carbonitrile (104) was prepared in a manner similar to Example 4, using 3-bromo-5-(trifluoromethyl)pyridine in place of 4-trifluoromethyl-iodobenzene. The crude product was purified by prep-HPLC (column: Phenomenex C18 75 mm×30 mm, 3 μm; liquid phase: [A-$H_2O$ (0.1% FA); B-ACN]B %: 5%-45%, 20 min]). The racemic product was resolved by prep-SFC (column: DAICEL CHIRALPAK IC [250 mm×30 mm, 10 μm; 0.1% $NH_3H_2O$ IPA; B % 55%-55%, 6 min]) to give two peaks.

Peak 1: (R)-3-(isoquinolin-4-yl)-2-oxo-1-(5-(trifluoromethyl)pyridin-3-yl)imidazolidine-4-carbonitrile (104a). LCMS (Method 3): $t_R$=2.81 min, $[M+1]^+$ 384.1. SFC (Method 38): $t_R$=1.45 min, 100.0%. $^1H$ NMR: (400 MHz, CHLOROFORM-d) δ=9.38 (s, 1H), 8.91 (d, J=2.4 Hz, 1H), 8.71 (br s, 2H), 8.49 (s, 1H), 8.15 (d, J=8.2 Hz, 1H), 7.92-7.83 (m, 2H), 7.78-7.72 (m, 1H), 5.19 (dd, J=9.2, 4.4 Hz, 1H), 4.66-4.58 (m, 1H), 4.49 (dd, J=9.6, 4.5 Hz, 1H).

Peak 2: (S)-3-(isoquinolin-4-yl)-2-oxo-1-(5-(trifluoromethyl)pyridin-3-yl)imidazolidine-4-carbonitrile (104b). LCMS (Method 3): $t_R$=2.81 min. $[M+1]^+$ 384.1. SFC (Method 38): $t_R$=1.59 min, 100.0%. $^1H$ NMR: (400 MHz, CHLOROFORM-d) δ=9.38 (s, 1H), 8.91 (d, J=2.4 Hz, 1H), 8.71 (br s, 2H), 8.49 (s, 1H), 8.15 (d, J=8.2 Hz, 1H), 7.92-7.83 (m, 2H), 7.78-7.72 (m, 1H), 5.19 (dd, J=9.2, 4.4 Hz, 1H), 4.66-4.58 (m, 1H), 4.49 (dd, J=9.6, 4.5 Hz, 1H).

Example 105: Synthesis of 1-(5-fluoro-2-methoxyphenyl)-3-(isoquinolin-4-yl)-2-oxoimidazolidine-4-carbonitrile (105), (R)-1-(5-fluoro-2-methoxyphenyl)-3-(isoquinolin-4-yl)-2-oxoimidazolidine-4-carbonitrile (105a) and (S)-1-(5-fluoro-2-methoxyphenyl)-3-(isoquinolin-4-yl)-2-oxoimidazolidine-4-carbonitrile (105b)

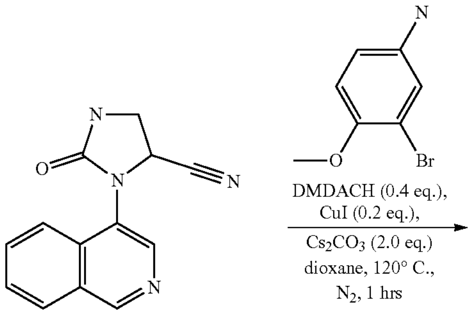

(Int-1)

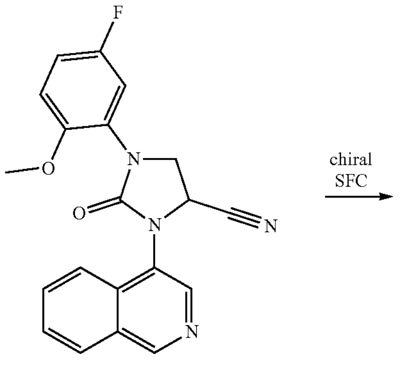

(105)

-continued

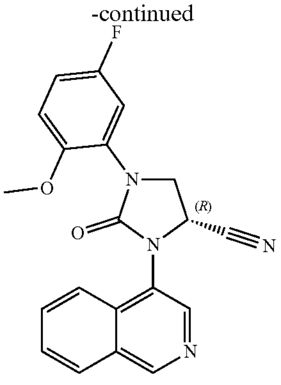

(105a)

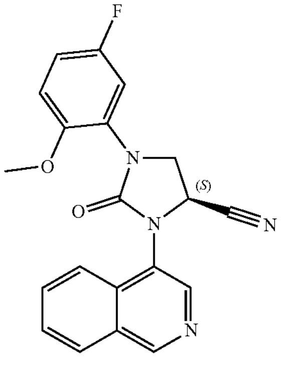

(105b)

Racemic 1-(5-fluoro-2-methoxyphenyl)-3-(isoquinolin-4-yl)-2-oxoimidazolidine-4-carbonitrile (105) was prepared in a manner similar to Example 4, using 2-bromo-4-fluoro-1-methoxybenzene in place of 4-trifluoromethyl-iodobenzene. The crude product was purified by prep-HPLC (column: Phenomenex Luna C18 75 mm×30 mm, 3 μm; liquid phase: [A-FA/$H_2O$=0.1% v/v; B-ACN]B %: 35%-65%, 8 min]) to give racemic product. The racemic product was resolved by prep-SFC (column: REGIS(S,S)WHELK-01 (250 mm×25 mm, 10 μm); mobile phase: 0.1% $NH_3H_2O$ ETOH; B % 35%-35%, 20 min]) to give two peaks.

Peak 1: (S)-1-(5-fluoro-2-methoxyphenyl)-3-(isoquinolin-4-yl)-2-oxoimidazolidine-4-carbonitrile (105b). LCMS (Method 13): $t_R$=2.10 min, $[M+1]^+$ 363.1. SFC (Method 39): $t_R$=2.68 min, 100.0%. $^1H$ NMR: (400 MHz, METHANOL-$d_4$) δ=9.35 (s, 1H), 8.63 (s, 1H), 8.26 (d, J=8.3 Hz, 1H), 8.13 (d, J=8.3 Hz, 1H), 7.96 (ddd, J=8.4, 7.1, 1.1 Hz, 1H), 7.86-7.78 (m, 1H), 7.29 (dd, J=8.8, 2.6 Hz, 1H), 7.19-7.10 (m, 2H), 5.49 (dd, J=9.1, 4.3, Hz, 1H), 4.49 (dd, J=9.6, 9.1 Hz, 1H), 4.30 (dd, J=9.6, 4.3 Hz, 1H), 3.98 (s, 3H).

Peak 2: (R)-1-(5-fluoro-2-methoxyphenyl)-3-(isoquinolin-4-yl)-2-oxoimidazolidine-4-carbonitrile (105a). LCMS (Method 13): $t_R$=2.10 min, $[M+1]^+$ 363.1. SFC (Method 39): $t_R$=2.91 min, 99.8%. $^1H$ NMR: (400 MHz, METHANOL-$d_4$) δ=9.35 (s, 1H), 8.63 (s, 1H), 8.26 (d, J=8.3 Hz, 1H), 8.13 (d, J=8.3 Hz, 1H), 7.96 (ddd, J=8.4, 7.1, 1.1 Hz, 1H), 7.86-7.78 (m, 1H), 7.29 (dd, J=8.8, 2.6 Hz, 1H), 7.19-7.10 (m, 2H), 5.49 (dd, J=9.1, 4.3, Hz, 1H), 4.49 (dd, J=9.6, 9.1 Hz, 1H), 4.30 (dd, J=9.6, 4.3 Hz, 1H), 3.98 (s, 3H).

Example 106: Synthesis of 3-(isoquinolin-4-yl)-2-oxo-1-(3-(trifluoromethyl)phenyl)imidazolidine-4-carbonitrile (106), (R)-3-(isoquinolin-4-yl)-2-oxo-1-(3-(trifluoromethyl)phenyl)imidazolidine-4-carbonitrile (106a) and (S)-3-(isoquinolin-4-yl)-2-oxo-1-(3-(trifluoromethyl)phenyl)imidazolidine-4-carbonitrile (106b)

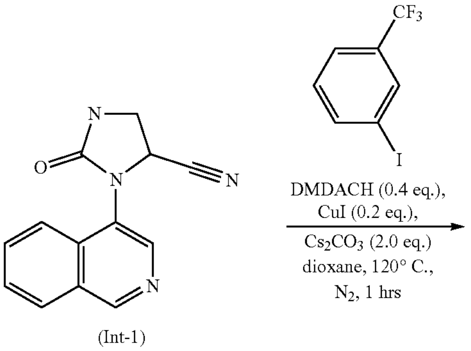

(Int-1)

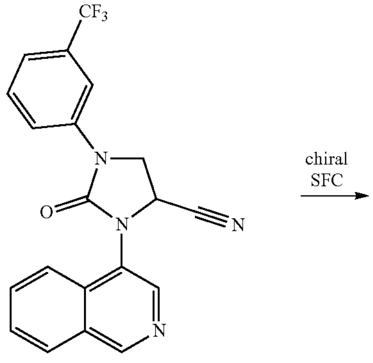

(106)

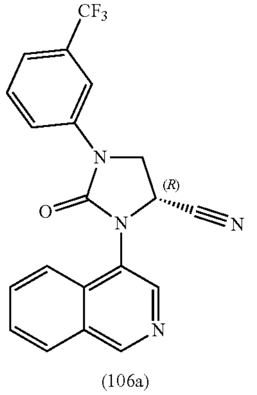

(106a)

-continued

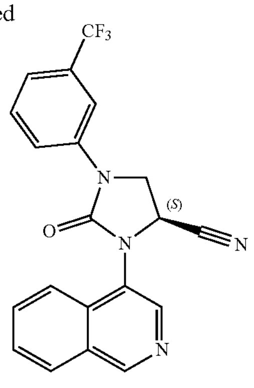

(106b)

Racemic 3-(isoquinolin-4-yl)-2-oxo-1-(3-(trifluoromethyl)phenyl)imidazolidine-4-carbonitrile (106) was prepared in a manner similar to Example 4, using 1-iodo-3-(trifluoromethyl)benzene in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 40%-90%, 20 min]). The racemic product was resolved by prep-SFC (column:DAICEL CHIRALPAK AD[250 mm×30 mm, 10 μm; 0.1% $NH_3H_2O$ EtOH; B % 42%-42%, 7 min]) to give two peaks.

Peak 1: (R)-3-(isoquinolin-4-yl)-2-oxo-1-(3-(trifluoromethyl)phenyl)imidazolidine-4-carbonitrile (106a). LCMS (Method 3): $t_R$=2.67 min, $[M+1]^+$ 383.1. SFC (Method 16): $t_R$=3.57 min, 98.8%. $^1H$ NMR: (400 MHz, CHLOROFORM-d) δ=9.36 (s, 1H), 8.70 (s, 1H), 8.13 (d, J=8.3 Hz, 1H), 7.95-7.88 (m, 1H), 7.88-7.82 (m, 3H), 7.77-7.71 (m, 1H), 7.56 (t, J=8.3 Hz, 1H), 7.45 (d, J=7.8 Hz, 1H), 5.14 (dd, J=9.1, 4.6 Hz, 1H), 4.57 (dd, J=9.6, 9.1 Hz, 1H), 4.44 (dd, J=9.6, 4.6 Hz, 1H).

Peak 2: (S)-3-(isoquinolin-4-yl)-2-oxo-1-(3-(trifluoromethyl)phenyl)imidazolidine-4-carbonitrile (106b). LCMS (Method 3): $t_R$=2.67 min, $[M+1]^+$ 383.1. SFC (Method 16): $t_R$=4.44 min, 99.9%. $^1H$ NMR: (400 MHz, CHLOROFORM-d) δ=9.36 (s, 1H), 8.70 (s, 1H), 8.13 (d, J=8.3 Hz, 1H), 7.95-7.88 (m, 1H), 7.88-7.82 (m, 3H), 7.77-7.71 (m, 1H), 7.56 (t, J=8.3 Hz, 1H), 7.45 (d, J=7.8 Hz, 1H), 5.14 (dd, J=9.1, 4.6 Hz, 1H), 4.57 (dd, J=9.6, 9.1 Hz, 1H), 4.44 (dd, J=9.6, 4.6 Hz, 1H).

Example 107: Synthesis of 3-(isoquinolin-4-yl)-1-(4-methoxy-6-(trifluoromethyl)pyridin-3-yl)-2-oxoimidazolidine-4-carbonitrile (107), (R)-3-(isoquinolin-4-yl)-1-(4-methoxy-6-(trifluoromethyl)pyridin-3-yl)-2-oxoimidazolidine-4-carbonitrile (107a) and (S)-3-(isoquinolin-4-yl)-1-(4-methoxy-6-(trifluoromethyl)pyridin-3-yl)-2-oxoimidazolidine-4-carbonitrile (107b)

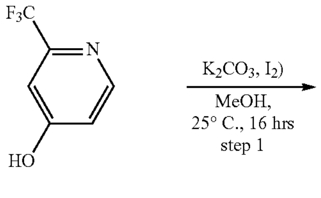

-continued

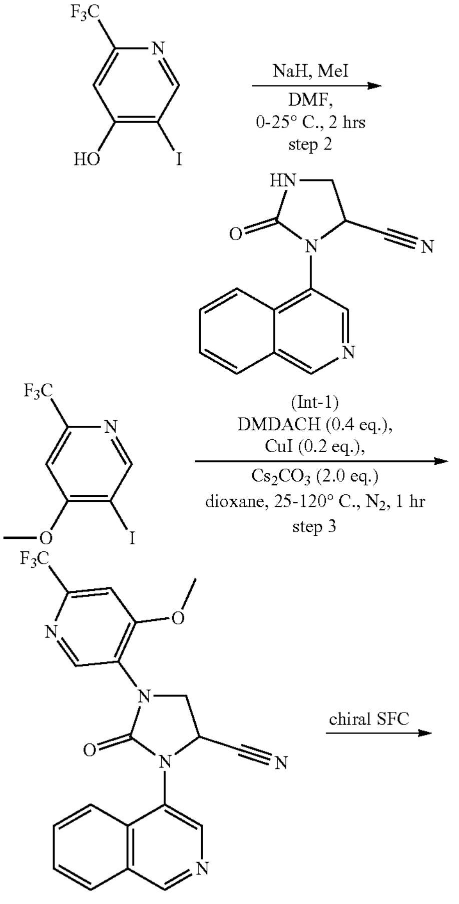

(107)

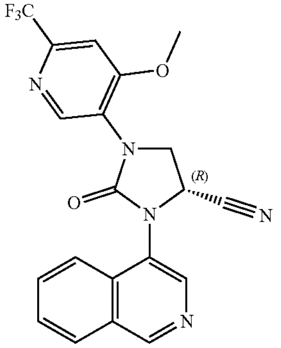

(107a)

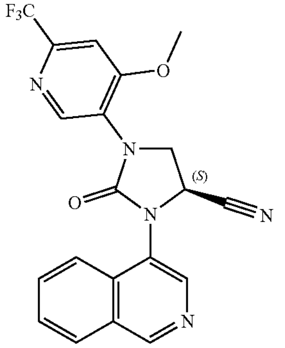

(107b)

Step 1: To a mixture of 2-(trifluoromethyl)pyridin-4-ol (1.0 g, 6.13 mmol, 1.0 eq.) and $K_2CO_3$ (930 mg, 6.74 mmol, 1.1 eq.) in MeOH (5 mL) was added $I_2$ (1.7 g, 6.74 mmol, 1.0 eq.) in three portions at 0° C. The reaction was stirred at 25° C. for 16 hrs under $N_2$. The reaction mixture was quenched with $Na_2SO_3$ (20 mL). The reaction mixture was extracted with ethyl acetate (20 mL×3). The combined organic layers were washed with brine (20 mL×3), dried over $Na_2SO_4$, filtered and concentrated under reduced pressure to give a residue. The residue was purified by MPLC (Petroleum ether/Ethyl acetate=4/1-5/2) to give 5-iodo-2-(trifluoromethyl)pyridin-4-ol.

Step 2: To a mixture of 5-iodo-2-(trifluoromethyl)pyridin-4-ol (280 mg, 0.96 mmol, 1.0 eq.) in DMF (5 mL) was added NaH (46 mg, 1.91 mmol, 2.0 eq.) at 0° C. The mixture was stirred at 0° C. under $N_2$ for 0.5 hrs. MeI (272 mg, 1.91 mmol, 2.0 eq.) was added dropwise at 0° C. Then the mixture was stirred at 25° C. for 16 hrs under $N_2$. The reaction mixture was quenched with saturated aq. $NH_4Cl$ (20 mL), extracted with ethyl acetate (20 mL×2). The combined organic layers were washed with brine (30 mL×5), dried over $Na_2SO_4$, filtered and concentrated to give crude product which was purified by MPLC (Petroleum ether/Ethyl acetate=5/1-3/1) to give 5-iodo-4-methoxy-2-(trifluoromethyl)pyridine.

Step 3: 3-(isoquinolin-4-yl)-1-(4-methoxy-6-(trifluoromethyl)pyridin-3-yl)-2-oxoimidazolidine-4-carbonitrile (107) was prepared in a manner similar to Example 4, using 5-iodo-4-methoxy-2-(trifluoromethyl)pyridine in place of 4-trifluoromethyl-iodobenzene. The crude product was purified by MPLC (Eluent of Petroleum ether/Ethyl acetate=10/1 to 5/1, 40 mL/min). The racemic product was resolved by SFC (column: DAICEL CHIRALCEL OJ (250 mm×30 mm, µm); liquid phase: [0.1% $NH_3H_2O$ EtOH]B %: 45%-45%, 6 min]) to give two peaks.

Peak 1: (S)-3-(isoquinolin-4-yl)-1-(4-methoxy-6-(trifluoromethyl)pyridin-3-yl)-2-oxoimidazolidine-4-carbonitrile (107b). LCMS (Method 37): $t_R$=2.73 min. $[M+1]^+$ 414.1. SFC (Method 44): $t_R$=0.86 min, 100.0%. $^1H$ NMR: (400 MHz, DMSO-$d_6$) δ=9.42 (s, 1H), 8.73 (s, 1H), 8.68 (s, 1H), 8.28 (d, J=8.1 Hz, 1H), 8.13-8.04 (m, 1H), 7.94 (t, J=7.7 Hz, 1H), 7.84-7.76 (m, 1H), 7.70 (s, 1H), 5.71 (dd, J=9.1, 4.4 Hz, 1H), 4.55-4.45 (m, 1H), 4.32 (dd, J=9.7, 4.3 Hz, 1H), 4.11 (s, 3H).

Peak 2: (R)-3-(isoquinolin-4-yl)-1-(4-methoxy-6-(trifluoromethyl)pyridin-3-yl)-2-oxoimidazolidine-4-carbonitrile (107a). LCMS (Method 37): $t_R$=2.73 min, $[M+1]^+$ 414.1. SFC (Method 44): $t_R$=0.93 min, 99.6%. $^1H$ NMR: (400 MHz, DMSO-$d_6$) δ=9.42 (s, 1H), 8.73 (s, 1H), 8.68 (s, 1H), 8.28 (d, J=8.1 Hz, 1H), 8.13-8.04 (m, 1H), 7.94 (t, J=7.7 Hz, 1H), 7.84-7.76 (m, 1H), 7.70 (s, 1H), 5.71 (dd, J=9.1, 4.4 Hz, 1H), 4.55-4.45 (m, 1H), 4.32 (dd, J=9.7, 4.3 Hz, 1H), 4.11 (s, 3H).

Example 108: Synthesis of 1-(4-(difluoromethyl)phenyl)-3-(isoquinolin-4-yl)-2-oxoimidazolidine-4-carbonitrile (108), (R)-1-(4-(difluoromethyl)phenyl)-3-(isoquinolin-4-yl)-2-oxoimidazolidine-4-carbonitrile (108a) and (S)-1-(4-(difluoromethyl)phenyl)-3-(isoquinolin-4-yl)-2-oxoimidazolidine-4-carbonitrile (108b)

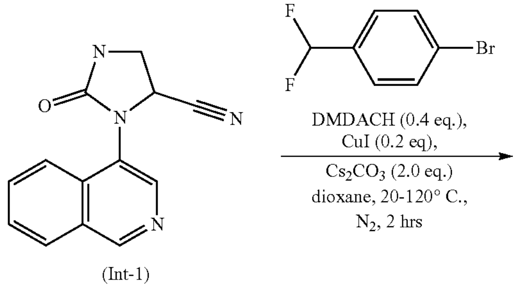

(Int-1)

-continued

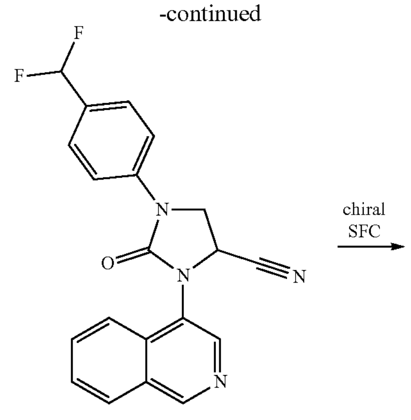

(108)

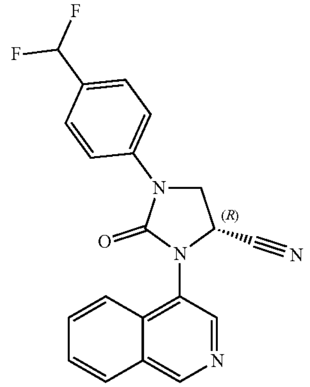

(108a)

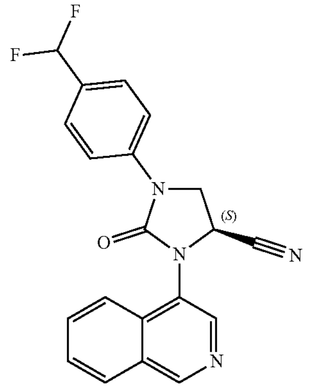

(108b)

Racemic 1-(4-(difluoromethyl)phenyl)-3-(isoquinolin-4-yl)-2-oxoimidazolidine-4-carbonitrile (108) was prepared in a manner similar to Example 4, using 1-bromo-4-(difluoromethyl)benzene in place of 4-trifluoromethyl-iodobenzene. The crude product was purified by column (Petroleum ether/EtOAc=100%-0%). The racemic product was resolved by SFC (Column: DAICEL CHIRALPAK IG (250 mm×30 mm, 10 µm); Mobile phase: A $CO_2$ and B EtOH (0.1% $NH_3H_2O$); Gradient: B %=46%, 10 min.) to give two peaks.

Peak 1: (R)-1-(4-(difluoromethyl)phenyl)-3-(isoquinolin-4-yl)-2-oxoimidazolidine-4-carbonitrile (108a). LCMS (Method 31): $t_R$=2.76 min, $[M+1]^+$ 365.1; SFC (Method 15): $t_R$=1.68 min, 100.0%; $^1H$ NMR: (400 MHz, CHLOROFORM-d) δ=9.36 (s, 1H), 8.70 (s, 1H), 8.13 (d, J=8.3 Hz, 1H), 7.92 (br d, J=8.4 Hz, 1H), 7.86-7.80 (m, 1H), 7.77-7.68

(m, 3H), 7.58 (d, J=8.8 Hz, 2H), 6.67 (t, J=56.6, 1H), 5.13 (dd, J=9.1, 4.6 Hz, 1H), 4.56 (dd, J=9.7, 9.1 Hz, 1H), 4.43 (dd, J=9.7, 4.6 Hz, 1H).

Peak 2: (S)-1-(4-(difluoromethyl)phenyl)-3-(isoquinolin-4-yl)-2-oxoimidazolidine-4-carbonitrile (108b). LCMS (Method 31): $t_R$=2.76 min, $[M+1]^+$ 365.1. SFC (Method 15): $t_R$=2.07 min, 99.9%; $^1$H NMR: (400 MHz, CHLOROFORM-d) δ=9.36 (s, 1H), 8.70 (s, 1H), 8.13 (d, J=8.3 Hz, 1H), 7.92 (br d, J=8.4 Hz, 1H), 7.86-7.80 (m, 1H), 7.77-7.68 (m, 3H), 7.58 (d, J=8.8 Hz, 2H), 6.67 (t, J=56.6, 1H), 5.13 (dd, J=9.1, 4.6 Hz, 1H), 4.56 (dd, J=9.7, 9.1 Hz, 1H), 4.43 (dd, J=9.7, 4.6 Hz, 1H).

Example 109: Synthesis of 1-(2,5-difluorophenyl)-3-(isoquinolin-4-yl)-2-oxoimidazolidine-4-carbonitrile (109), (R)-1-(2,5-difluorophenyl)-3-(isoquinolin-4-yl)-2-oxoimidazolidine-4-carbonitrile (109a) and (S)-1-(2,5-difluorophenyl)-3-(isoquinolin-4-yl)-2-oxoimidazolidine-4-carbonitrile (109b)

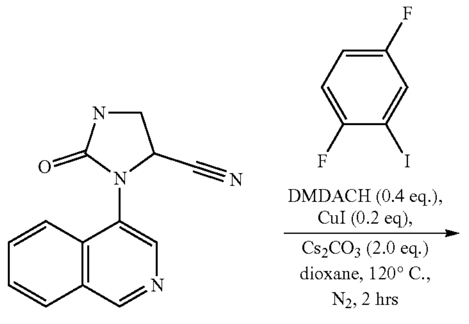

(Int-1)

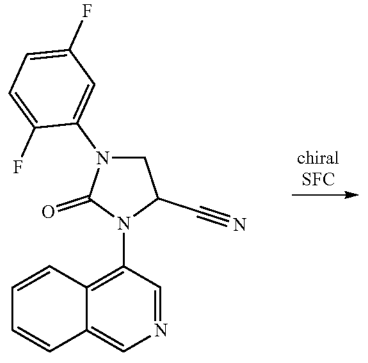

(109)

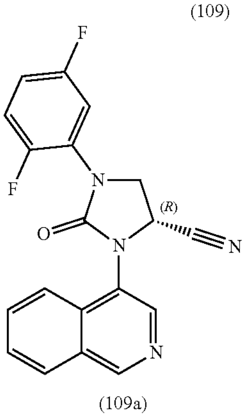

(109a)

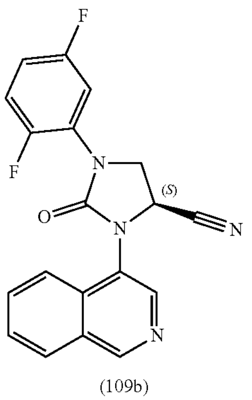

(109b)

Racemic 1-(2,5-difluorophenyl)-3-(isoquinolin-4-yl)-2-oxoimidazolidine-4-carbonitrile (116) was prepared in a manner similar to Example 4, using 1,4-difluoro-2-iodobenzene in place of 4-trifluoromethyl-iodobenzene. The crude product was purified by column ($SiO_2$, Petroleum ether/EtOAc=100%~45%). The racemic product was resolved by SFC (column: DAICEL CHIRALCEL OJ (250 mm×30 mm, 10 μm); liquid phase: 0.1% $NH_3H_2O$ IPA B %: 18%-18%, 15 min]) to give two peaks.

Peak 1: (R)-1-(2,5-difluorophenyl)-3-(isoquinolin-4-yl)-2-oxoimidazolidine-4-carbonitrile (109a). LCMS (Method 4): $t_R$=2.75 min, $[M+1]^+$ 351.1. SFC (Method 2): $t_R$=1.10 min, 100.0%. $^1$H NMR: (400 MHz, CHLOROFORM-d) δ=9.35 (s, 1H), 8.70 (s, 1H), 8.12 (d, J=8.1 Hz, 1H), 7.95-7.89 (m, 1H), 7.88-7.81 (m, 1H), 7.77-7.69 (m, 1H), 7.48 (ddd, J=9.2, 6.2, 3.1 Hz, 1H), 7.18 (ddd, J=10.7, 9.3, 4.9 Hz, 1H), 7.02-6.95 (m, 1H), 5.09 (dd, J=8.9, 4.5 Hz, 1H), 4.59 (dd, J=9.8, 8.9 Hz, 1H), 4.42 (dd, J=9.8, 4.5, Hz, 1H).

Peak 2: (S)-1-(2,5-difluorophenyl)-3-(isoquinolin-4-yl)-2-oxoimidazolidine-4-carbonitrile (109b). LCMS (LCMS Method 4): $t_R$=2.75 min, $[M+1]^+$ 351.1. SFC (Method 2): $t_R$=1.18 min, 99.5%. $^1$H NMR: (400 MHz, CHLOROFORM-d) δ=9.35 (s, 1H), 8.70 (s, 1H), 8.12 (d, J=8.1 Hz, 1H), 7.95-7.89 (m, 1H), 7.88-7.81 (m, 1H), 7.77-7.69 (m, 1H), 7.48 (ddd, J=9.2, 6.2, 3.1 Hz, 1H), 7.18 (ddd, J=10.7, 9.3, 4.9 Hz, 1H), 7.02-6.95 (m, 1H), 5.09 (dd, J=8.9, 4.5 Hz, 1H), 4.59 (dd, J=9.8, 8.9 Hz, 1H), 4.42 (dd, J=9.8, 4.5, Hz, 1H).

Example 110: Synthesis of 1-(3,5-difluorophenyl)-3-(isoquinolin-4-yl)-2-oxoimidazolidine-4-carbonitrile (110), (R)-1-(3,5-difluorophenyl)-3-(isoquinolin-4-yl)-2-oxoimidazolidine-4-carbonitrile (110a) and (S)-1-(3,5-difluorophenyl)-3-(isoquinolin-4-yl)-2-oxoimidazolidine-4-carbonitrile (110b)

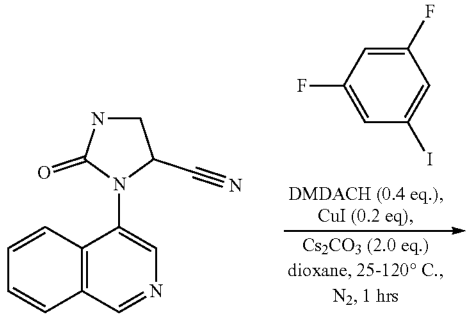

(Int-1)

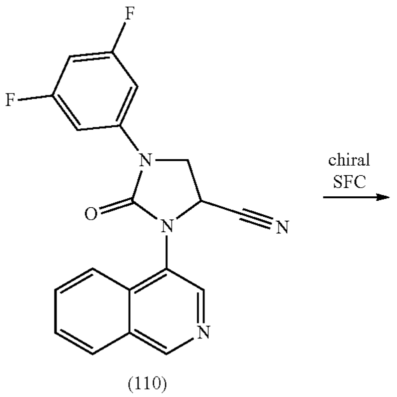

(110)

-continued

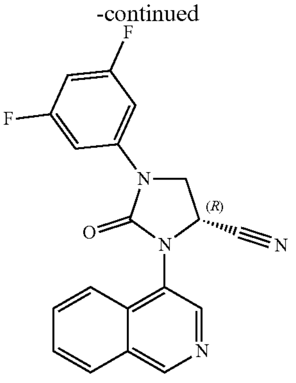

(110a)

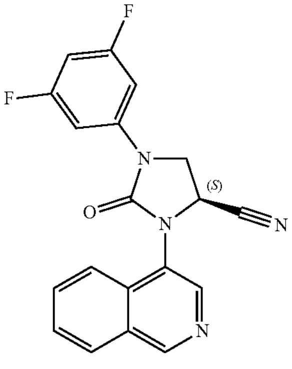

(110b)

Racemic 1-(3,5-difluorophenyl)-3-(isoquinolin-4-yl)-2-oxoimidazolidine-4-carbonitrile (110) was prepared in a manner similar to Example 4, using 1,3-difluoro-5-iodobenzene in place of 4-trifluoromethyl-iodobenzene. The crude product was purified by prep-HPLC (column: Phenomenex Luna C18 75 mm×30 mm, 3 μm; liquid phase: [A-FA/$H_2O$=0.1% v/v; B-ACN]B %: 35%-65%, 8 min]). LCMS (Method 31): $t_R$=2.83 min, $[M+1]^+$ 351.1. $^1$H NMR: (400 MHz, DMSO-$d_6$) δ=9.44 (s, 1H), 8.69 (s, 1H), 8.29 (d, J=8.1 Hz, 1H), 8.13 (d, J=8.4 Hz, 1H), 7.90 (t, J=7.7 Hz, 1H), 7.83-7.78 (m, 1H), 7.42 (dd, J=9.9, 1.9 Hz, 2H), 7.03-6.96 (m, 1H), 5.71 (dd, J=9.3, 4.9 Hz, 1H), 4.59-4.53 (m, 1H), 4.51-4.46 (m, 1H).

The racemic product was resolved by prep-SFC (column: REGIS(S,S)WHELK-01(250 mm×25 mm, 10 μm); mobile phase: 0.1% $NH_3H_2O$ IPA; B % 35%-35%, 20 min]) to give two peaks.

Peak 1: (R)-1-(3,5-difluorophenyl)-3-(isoquinolin-4-yl)-2-oxoimidazolidine-4-carbonitrile (110a). LCMS (Method 31): $t_R$=2.83 min, $[M+1]^+$ 351.1. SFC (Method 1): $t_R$=1.28 min, 100.0%. $^1$H NMR: (400 MHz, DMSO-$d_6$) δ=9.44 (s, 1H), 8.69 (s, 1H), 8.29 (d, J=8.1 Hz, 1H), 8.13 (d, J=8.4 Hz, 1H), 7.90 (t, J=7.7 Hz, 1H), 7.83-7.78 (m, 1H), 7.42 (dd, J=9.9, 1.9 Hz, 2H), 7.03-6.96 (m, 1H), 5.71 (dd, J=9.3, 4.9 Hz, 1H), 4.59-4.53 (m, 1H), 4.51-4.46 (m, 1H).

Peak 2: (S)-1-(3,5-difluorophenyl)-3-(isoquinolin-4-yl)-2-oxoimidazolidine-4-carbonitrile (110b). LCMS (Method 31): $t_R$=2.82 min, $[M+1]^+$ 351.1. SFC (Method 1): $t_R$=1.39 min, 99.6%. $^1$H NMR: (400 MHz, DMSO-$d_6$) δ=9.44 (s, 1H), 8.69 (s, 1H), 8.29 (d, J=8.1 Hz, 1H), 8.13 (d, J=8.4 Hz, 1H), 7.90 (t, J=7.7 Hz, 1H), 7.83-7.78 (m, 1H), 7.42 (dd, J=9.9, 1.9 Hz, 2H), 7.03-6.96 (m, 1H), 5.71 (dd, J=9.3, 4.9 Hz, 1H), 4.59-4.53 (m, 1H), 4.51-4.46 (m, 1H).

Example 111: Synthesis of 1-(6-chloropyridin-2-yl)-3-(isoquinolin-4-yl)-2-oxoimidazolidine-4-carbonitrile (111), (R)-1-(6-chloropyridin-2-yl)-3-(isoquinolin-4-yl)-2-oxoimidazolidine-4-carbonitrile(111a) and (S)-1-(6-chloropyridin-2-yl)-3-(isoquinolin-4-yl)-2-oxoimidazolidine-4-carbonitrile (111 b)

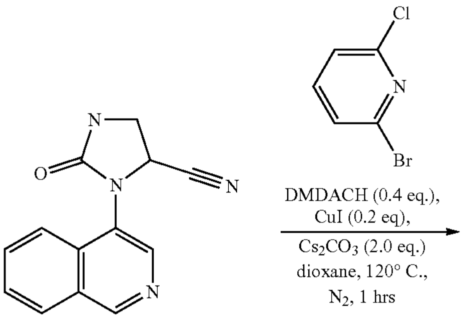

(Int-1)

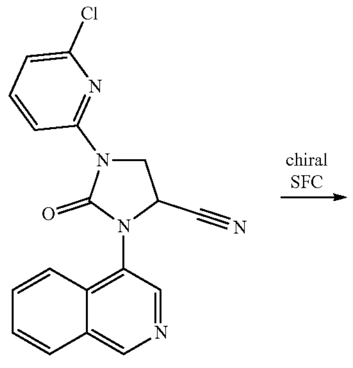

(111)

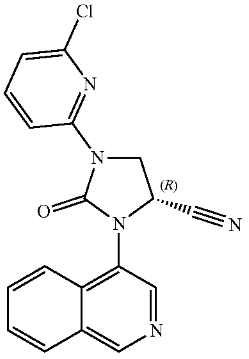

(111a)

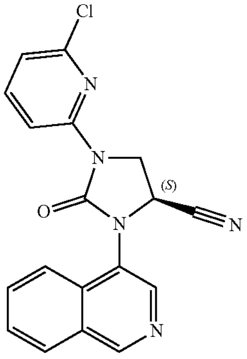

(111b)

Racemic 1-(6-chloropyridin-2-yl)-3-(isoquinolin-4-yl)-2-oxoimidazolidine-4-carbonitrile (111) was prepared in a manner similar to Example 4, using 2-bromo-6-chloropyridine in place of 4-trifluoromethyl-iodobenzene. The crude product was purified by prep-HPLC (column: Phenomenex C18 75 mm×30 mm, 3 μm; liquid phase: [A-$H_2O$ (0.1% FA); B-ACN]B %: 30%-60%, 8 min]). The racemic product was resolved by SFC (column: DAICEL CHIRALPAK AD (250 mm×30 mm, 10 μm); liquid phase: 0.1% $NH_3H_2O$ IPA B %: 30%-30%, 15 min]) to give two peaks.

Peak 1: (R)-1-(6-chloropyridin-2-yl)-3-(isoquinolin-4-yl)-2-oxoimidazolidine-4-carbonitrile (111a). LCMS (Method 4): $t_R$=2.61 min, $[M+1]^+$ 350.1. SFC (Method 1):

$t_R$=1.41 min, 99.9%. $^1$H NMR: (400 MHz, CHLOROFORM-d) δ=9.37 (s, 1H), 8.69 (s, 1H), 8.56 (d, J=2.3 Hz, 1H), 8.41 (d, J=1.9 Hz, 1H), 8.31 (t, J=2.1 Hz, 1H), 8.14 (d, J=8.1 Hz, 1H), 7.95-7.81 (m, 2H), 7.78-7.71 (m, 1H), 5.16 (dd, J=9.2, 4.4 Hz, 1H), 4.56 (dd, J=9.7, 9.2 Hz, 1H), 4.43 (dd, J=9.7, 4.4 Hz, 1H).

Peak 2: (S)-1-(6-chloropyridin-2-yl)-3-(isoquinolin-4-yl)-2-oxoimidazolidine-4-carbonitrile (111b). LCMS (Method 4): $t_R$=2.61 min, $[M+1]^+$ 350.1. SFC (Method 1): $t_R$=1.52 min, 97.7%. $^1$H NMR: (400 MHz, CHLOROFORM-d) δ=9.37 (s, 1H), 8.69 (s, 1H), 8.56 (d, J=2.3 Hz, 1H), 8.41 (d, J=1.9 Hz, 1H), 8.31 (t, J=2.1 Hz, 1H), 8.14 (d, J=8.1 Hz, 1H), 7.95-7.81 (m, 2H), 7.78-7.71 (m, 1H), 5.16 (dd, J=9.2, 4.4 Hz, 1H), 4.56 (dd, J=9.7, 9.2 Hz, 1H), 4.43 (dd, J=9.7, 4.4 Hz, 1H).

Example 112: Synthesis of 3-(isoquinolin-4-yl)-1-(6-methoxypyridin-3-yl)-2-oxoimidazolidine-4-carbonitrile (112), (R)-3-(isoquinolin-4-yl)-1-(6-methoxypyridin-3-yl)-2-oxoimidazolidine-4-carbonitrile (112a) and (S)-3-(isoquinolin-4-yl)-1-(6-methoxypyridin-3-yl)-2-oxoimidazolidine-4-carbonitrile (112b)

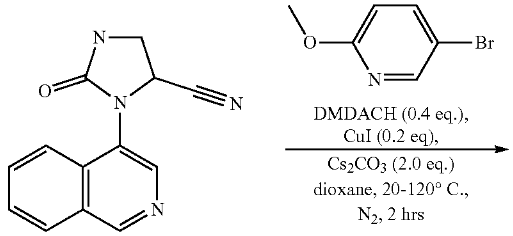

(Int-1)

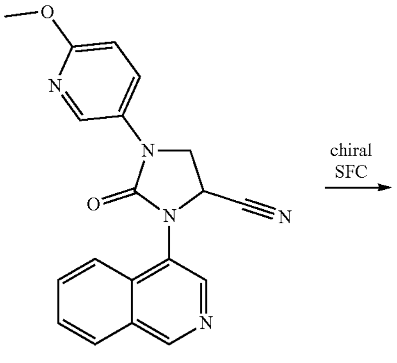

(112)

-continued

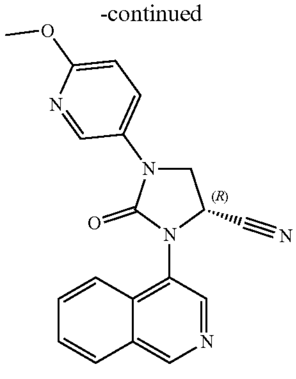

(112a)

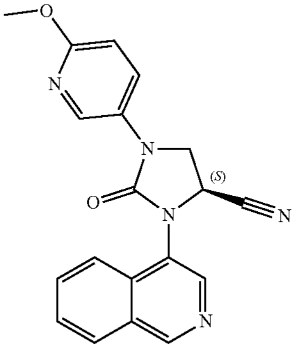

(112b)

Racemic 3-(isoquinolin-4-yl)-1-(6-methoxypyridin-3-yl)-2-oxoimidazolidine-4-carbonitrile (112) was prepared in a manner similar to Example 4, using 5-bromo-2-methoxypyridine in place of 4-trifluoromethyl-iodobenzene. The crude product was purified by prep-HPLC (column: Phenomenex C18 80 mm×40 mm, 3 μm; mobile phase: [water ($NH_4HCO_3$)-ACN]; B %: 15%-35%, 8 min). The racemic product was resolved by SFC (Column: DAICEL CHIRALPAK IG (250 mm×30 mm, 10 μm); Mobile phase: A for $CO_2$ and B for IPA (0.1% $NH_3H_2O$); Gradient: B %=40% isocratic elution mode; Flow rate: 70 g/min; Wavelength: 220 nm; Column temperature: 35° C.; System back pressure: 120 bar.) to give two peaks.

Peak 1: (R)-3-(isoquinolin-4-yl)-1-(6-methoxypyridin-3-yl)-2-oxoimidazolidine-4-carbonitrile (112a). LCMS (Method 31): $t_R$=2.43 min, $[M+1]^+$ 346.1. SFC (Method 2): $t_R$=1.34 min, 100.0%. $^1$H NMR: (400 MHz, CHLOROFORM-d) δ=9.35 (s, 1H), 8.72 (s, 1H), 8.17 (d, J=2.6 Hz, 1H), 8.13 (d, J=8.1 Hz, 1H), 8.10 (dd, J=9.1, 2.8 Hz, 1H), 7.97-7.91 (m, 1H), 7.85 (t, J=7.4 Hz, 1H), 7.77-7.71 (m, 1H), 6.84 (d, J=9.0 Hz, 1H), 5.19-5.10 (m, 1H), 4.52 (br t, J=9.0 Hz, 1H), 4.37 (dd, J=9.3, 3.8 Hz, 1H), 3.96 (s, 3H).

Peak 2: (S)-3-(isoquinolin-4-yl)-1-(6-methoxypyridin-3-yl)-2-oxoimidazolidine-4-carbonitrile (112b). LCMS (Method 31): $t_R$=2.42 min, $[M+1]^+$ 346.2. SFC (Method 2): $t_R$=1.44 min, 99.5%. $^1$H NMR: (400 MHz, CHLOROFORM-d) δ=9.35 (s, 1H), 8.72 (s, 1H), 8.17 (d, J=2.6 Hz, 1H), 8.13 (d, J=8.1 Hz, 1H), 8.10 (dd, J=9.1, 2.8 Hz, 1H), 7.97-7.91 (m, 1H), 7.85 (t, J=7.4 Hz, 1H), 7.77-7.71 (m, 1H), 6.84 (d, J=9.0 Hz, 1H), 5.19-5.10 (m, 1H), 4.52 (br t, J=9.0 Hz, 1H), 4.37 (dd, J=9.3, 3.8 Hz, 1H), 3.96 (s, 3H).

Example 113: Synthesis of 3-(isoquinolin-4-yl)-2-oxo-1-(6-oxo-1,6-dihydropyridin-3-yl)imidazolidine-4-carbonitrile (113)

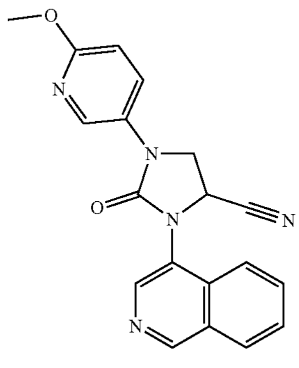

(112)

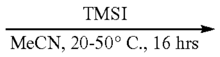

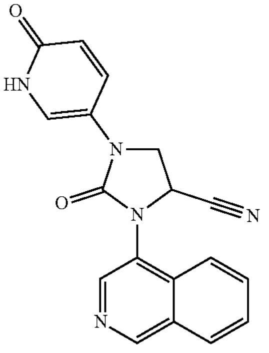

(113)

To a solution of 3-(isoquinolin-4-yl)-1-(6-methoxypyridin-3-yl)-2-oxoimidazolidine-4-carbonitrile (112) (370 mg) in MeCN (5 mL) was added TMSI (642 mg, 3.21 mmol, 3.0 eq.) at 20° C. The mixture was stirred at 50° C. for 16 hrs. The reaction mixture was quenched with 10% saturated aqueous $Na_2SO_3$ and extracted with ethyl acetate (5 mL×3). The combined organic layers were washed with saturated aqueous $NaHCO_3$ (5 mL), dried over $Na_2SO_4$, filtered and concentrated to give crude product which was purified by prep-HPLC (column: Phenomenex C18 75 mm×30 mm, 3 μm; mobile phase: [water ($NH_4HCO_3$)-ACN]; B %: 5%-40%, 8 min) to give racemic 3-(isoquinolin-4-yl)-2-oxo-1-(6-oxo-1,6-dihydropyridin-3-yl)imidazolidine-4-carbonitrile (113). LCMS (Method 31): $t_R$=1.90 min, $[M+1]^+$ 332.1. $^1H$ NMR: (400 MHz, DMSO-$d_6$) δ=11.88-11.30 (m, 1H), 9.40 (s, 1H), 8.63 (s, 1H), 8.27 (d, J=8.3 Hz, 1H), 8.09 (d, J=8.5 Hz, 1H), 7.90 (td, J=7.7, 1.1 Hz, 1H), 7.82-7.76 (m, 2H), 7.62 (d, J=2.8 Hz, 1H), 6.43 (d, J=9.8 Hz, 1H), 5.63 (dd, J=9.1, 4.6 Hz, 1H), 4.42 (dd, J=9.4, 9.1 Hz, 1H), 4.31 (dd, J=9.4, 4.7 Hz, 1H).

Example 114: Synthesis of 1-(5-chloro-2-methylphenyl)-3-(isoquinolin-4-yl)-2-oxoimidazolidine-4-carbonitrile (114), (R)-1-(5-chloro-2-methylphenyl)-3-(isoquinolin-4-yl)-2-oxoimidazolidine-4-carbonitrile (114a) and (S)-1-(5-chloro-2-methylphenyl)-3-(isoquinolin-4-yl)-2-oxoimidazolidine-4-carbonitrile (114b)

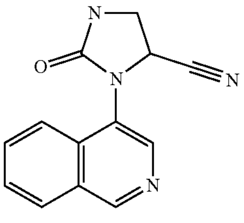

(Int-1)

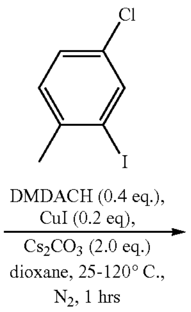

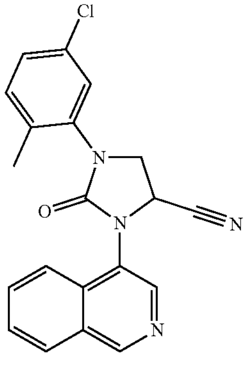

(114)

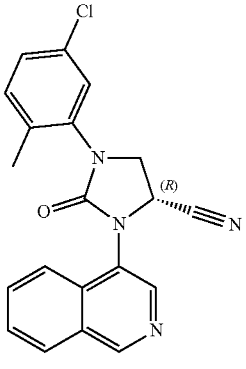

(114a)

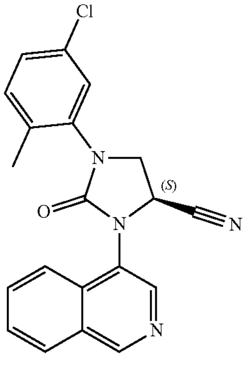

(114b)

Racemic 1-(5-chloro-2-methylphenyl)-3-(isoquinolin-4-yl)-2-oxoimidazolidine-4-carbonitrile (114) was prepared in a manner similar to Example 4, using 4-chloro-2-iodo-1-methylbenzene in place of 4-trifluoromethyl-iodobenzene. The crude product was purified by prep-HPLC (column: Phenomenex Luna C18 200 mm×40 mm, 10 μm; liquid phase: [A-$H_2O$ (0.1% FA); B-ACN]B %: 20%-60%, 20 min]) to give racemic product. The racemic product was resolved by SFC (column: Phenomenex Luna C18 200 mm×40 mm, 10 μm; mobile phase: water (FA)-ACN; B % 20%-60%, 8 min]) to give two peaks.

Peak 1: (S)-1-(5-chloro-2-methylphenyl)-3-(isoquinolin-4-yl)-2-oxoimidazolidine-4-carbonitrile (114b). LCMS (Method 3): $t_R$=2.52 min, $[M+1]^+$ 347.3. SFC (Method 42): $t_R$=1.08 min, 100.0%. $^1H$ NMR: (400 MHz, CHLOROFORM-d) δ=9.34 (s, 1H), 8.71 (s, 1H), 8.12 (d, J=8.3 Hz, 1H), 7.94 (br d, J=8.4 Hz, 1H), 7.85 (t, J=7.6 Hz, 1H), 7.73 (t, J=7.6 Hz, 1H), 7.36 (s, 1H), 7.29 (s, 2H), 5.08 (dd, J=8.6, 3.8 Hz, 1H), 4.42 (dd, J=9.6, 8.6 Hz, 1H), 4.21 (dd, J=9.6, 3.8 Hz, 1H), 2.4 (s, 3H).

Peak 2: (R)-1-(5-chloro-2-methylphenyl)-3-(isoquinolin-4-yl)-2-oxoimidazolidine-4-carbonitrile (114a). LCMS (Method 3): $t_R$=2.52 min, $[M+1]^+$ 347.3. SFC (Method 42): $t_R$=1.16 min, 99.4%. $^1H$ NMR: (400 MHz, CHLOROFORM-d) δ=9.34 (s, 1H), 8.71 (s, 1H), 8.12 (d, J=8.3 Hz, 1H), 7.94 (br d, J=8.4 Hz, 1H), 7.85 (t, J=7.6 Hz, 1H), 7.73 (t, J=7.6 Hz, 1H), 7.36 (s, 1H), 7.29 (s, 2H), 5.08 (dd, J=8.6, 3.8 Hz, 1H), 4.42 (dd, J=9.6, 8.6 Hz, 1H), 4.21 (dd, J=9.6, 3.8 Hz, 1H), 2.4 (s, 3H).

Example 115: Synthesis of 1-(5-chloro-2-methoxyphenyl)-3-(isoquinolin-4-yl)-2-oxoimidazolidine-4-carbonitrile (115), (R)-1-(5-chloro-2-methoxyphenyl)-3-(isoquinolin-4-yl)-2-oxoimidazolidine-4-carbonitrile (115a) and (S)-1-(5-chloro-2-methoxyphenyl)-3-(isoquinolin-4-yl)-2-oxoimidazolidine-4-carbonitrile (115b)

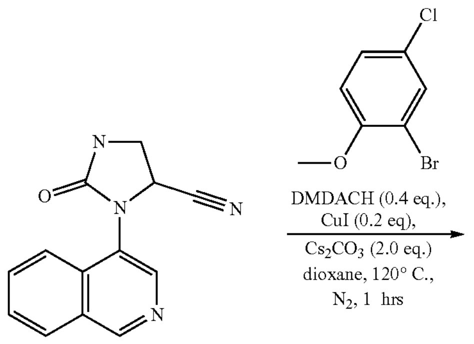

(Int-1)

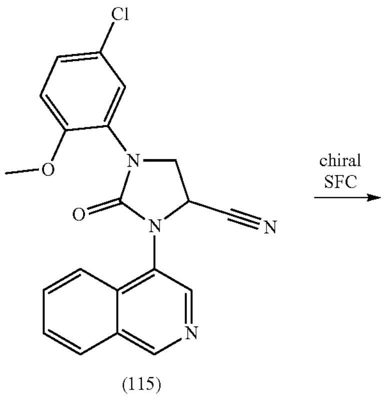

(115)

-continued

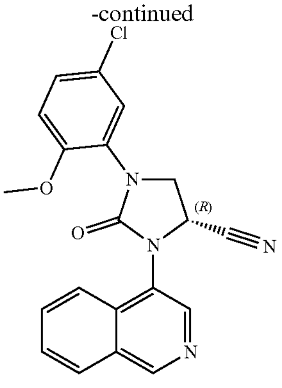

(115a)

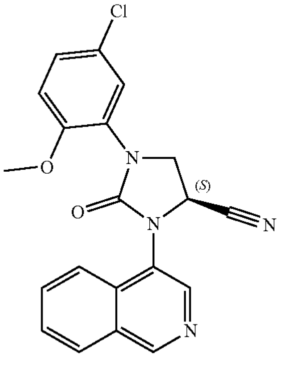

(115b)

Racemic 1-(5-chloro-2-methoxyphenyl)-3-(isoquinolin-4-yl)-2-oxoimidazolidine-4-carbonitrile (115) was prepared in a manner similar to Example 4, using 2-bromo-4-chloro-1-methoxybenzene in place of 4-trifluoromethyl-iodobenzene. The crude product was purified by prep-HPLC (column: Phenomenex Luna C18 75 mm×30 mm, 3 μm; liquid phase: [A-HCOOH/$H_2O$=0.1% v/v; B-ACN]B %: 35%-65%, 8 min]). The racemic product was resolved by prep-SFC (column: REGIS (S, S) WHELK-01 (250 mm×25 mm, 10 μm); mobile phase: 0.1% $NH_3H_2O$ EtOH; B % 45%-45%, 16 min]) to give two peaks.

Peak 1: (S)-1-(5-chloro-2-methoxyphenyl)-3-(isoquinolin-4-yl)-2-oxoimidazolidine-4-carbonitrile (115b). LCMS (Method 13): $t_R$=2.23 min, $[M+1]^+$ 379.1. SFC (Method 39): $t_R$=2.99 min, 100.0%. $^1H$ NMR: (400 MHz, METHANOL-$d_4$) δ=9.35 (s, 1H), 8.63 (s, 1H), 8.26 (d, J=8.1 Hz, 1H), 8.12 (d, J=8.5 Hz, 1H), 7.96 (t, J=7.7 Hz, 1H), 7.84-7.78 (m, 1H), 7.50 (d, J=2.6 Hz, 1H), 7.38 (dd, J=8.8, 2.6 Hz, 1H), 7.17 (d, J=9.0 Hz, 1H), 5.49 (dd, J=9.1, 4.3 Hz, 1H), 4.48 (dd, J=9.6, 9.1 Hz, 1H), 4.28 (dd, J=9.6, 4.3 Hz, 1H), 3.99 (s, 3H).

Peak 2: (R)-1-(5-chloro-2-methoxyphenyl)-3-(isoquinolin-4-yl)-2-oxoimidazolidine-4-carbonitrile (115a). LCMS (Method 13): $t_R$=2.20 min, $[M+1]^+$ 379.1. SFC (Method 39): $t_R$=3.47 min, 99.9%. $^1H$ NMR: (400 MHz, METHANOL-$d_4$) δ=9.35 (s, 1H), 8.63 (s, 1H), 8.26 (d, J=8.1 Hz, 1H), 8.12 (d, J=8.5 Hz, 1H), 7.96 (t, J=7.7 Hz, 1H), 7.84-7.78 (m, 1H), 7.50 (d, J=2.6 Hz, 1H), 7.38 (dd, J=8.8, 2.6 Hz, 1H), 7.17 (d, J=9.0 Hz, 1H), 5.49 (dd, J=9.1, 4.3 Hz, 1H), 4.48 (dd, J=9.6, 9.1 Hz, 1H), 4.28 (dd, J=9.6, 4.3 Hz, 1H), 3.99 (s, 3H).

Example 116: Synthesis of 1-(2-cyano-5-methylphenyl)-3-(isoquinolin-4-yl)-2-oxoimidazolidine-4-carbonitrile (116), (R)-1-(2-cyano-5-methylphenyl)-3-(isoquinolin-4-yl)-2-oxoimidazolidine-4-carbonitrile (116a) and (S)-1-(2-cyano-5-methylphenyl)-3-(isoquinolin-4-yl)-2-oxoimidazolidine-4-carbonitrile (116b)

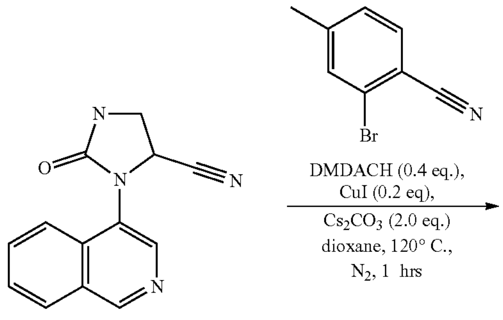

(Int-1)

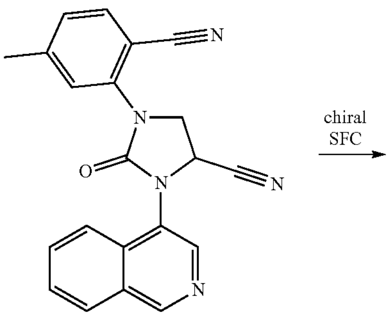

(116)

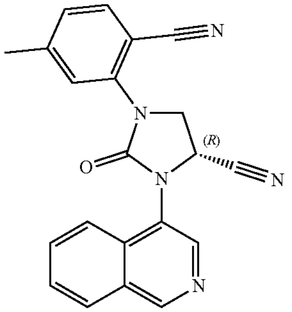

(116a)

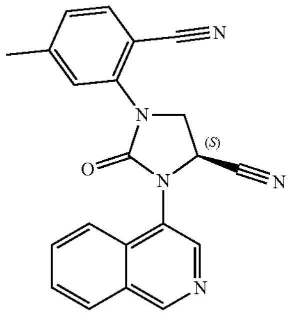

(116b)

Racemic 1-(2-cyano-5-methylphenyl)-3-(isoquinolin-4-yl)-2-oxoimidazolidine-4-carbonitrile (116) was prepared in a manner similar to Example 4, using 2-bromo-4-methylbenzonitrile in place of 4-trifluoromethyl-iodobenzene. The crude product was purified by column chromatography ($SiO_2$, Petroleum ether/Ethyl acetate=100/1 to 0/1). LCMS (Method 1): $t_R$=2.55 min, $[M+1]^+$354.2. $^1H$ NMR: (400 MHz, DMSO-$d_6$) δ=9.43 (s, 1H), 8.66 (s, 1H), 8.29 (d, J=8.1 Hz, 1H), 8.14 (d, J=8.3 Hz, 1H), 7.95-7.85 (m, 1H), 7.83-7.78 (m, 2H), 7.58 (s, 1H), 7.33 (d, J=7.9 Hz, 1H), 5.74 (dd, J=8.7, 3.7 Hz, 1H), 4.70 (dd, J=9.4, 8.7 Hz, 1H), 4.43 (dd, J=9.4, 3.7 Hz, 1H), 2.44 (s, 3H).

The racemic product was resolved by prep-SFC (column: REGIS(S, S) WHELK-01 (250 mm×25 mm, 10 μm); mobile phase: 0.1% $NH_3H_2O$ EtOH; B % 35%-35%, 20 min]) to give two peaks.

Peak 1: (R)-1-(2-cyano-5-methylphenyl)-3-(isoquinolin-4-yl)-2-oxoimidazolidine-4-carbonitrile (116a). LCMS (Method 31): $t_R$=2.55 min, $[M+1]^+$ 354.2. SFC (Method 15): $t_R$=1.54 min, 99.5%. $^1H$ NMR: (400 MHz, DMSO-$d_6$) δ=9.43 (s, 1H), 8.66 (s, 1H), 8.29 (d, J=8.1 Hz, 1H), 8.14 (d, J=8.3 Hz, 1H), 7.95-7.85 (m, 1H), 7.83-7.78 (m, 2H), 7.58 (s, 1H), 7.33 (d, J=7.9 Hz, 1H), 5.74 (dd, J=8.7, 3.7 Hz, 1H), 4.70 (dd, J=9.4, 8.7 Hz, 1H), 4.43 (dd, J=9.4, 3.7 Hz, 1H), 2.44 (s, 3H).

Peak 2: (S)-1-(2-cyano-5-methylphenyl)-3-(isoquinolin-4-yl)-2-oxoimidazolidine-4-carbonitrile (116b). LCMS (Method 31): $t_R$=2.56 min, $[M+1]^+$ 354.2. SFC (Method 15): $t_R$=1.65 min, 99.26%. $^1H$ NMR: (400 MHz, DMSO-$d_6$) δ=9.43 (s, 1H), 8.66 (s, 1H), 8.29 (d, J=8.1 Hz, 1H), 8.14 (d, J=8.3 Hz, 1H), 7.95-7.85 (m, 1H), 7.83-7.78 (m, 2H), 7.58 (s, 1H), 7.33 (d, J=7.9 Hz, 1H), 5.74 (dd, J=8.7, 3.7 Hz, 1H), 4.70 (dd, J=9.4, 8.7 Hz, 1H), 4.43 (dd, J=9.4, 3.7 Hz, 1H), 2.44 (s, 3H).

Example 117: Synthesis of 4-(4-cyano-3-(isoquinolin-4-yl)-2-oxoimidazolidin-1-yl)-6-(trifluoromethyl)nicotinonitrile (117), (R)-4-(4-cyano-3-(isoquinolin-4-yl)-2-oxoimidazolidin-1-yl)-6-(trifluoromethyl)nicotinonitrile (117a) and (S)-4-(4-cyano-3-(isoquinolin-4-yl)-2-oxoimidazolidin-1-yl)-6-(trifluoromethyl)nicotinonitrile (117b)

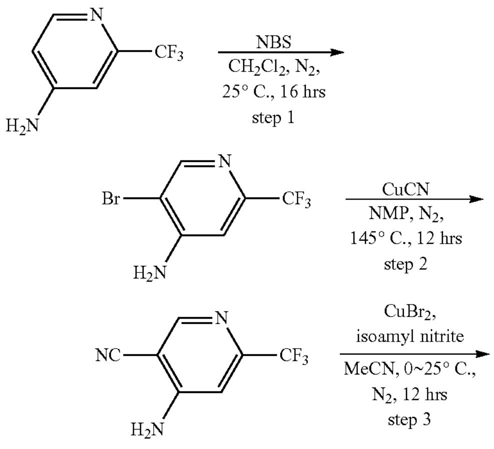

-continued

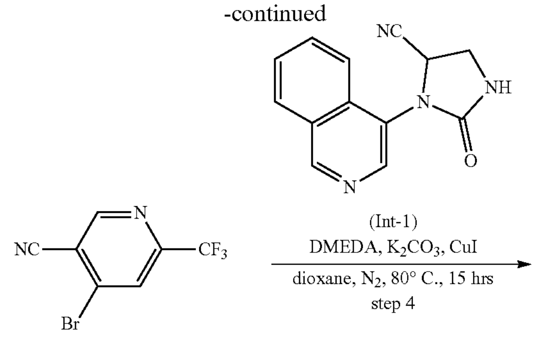

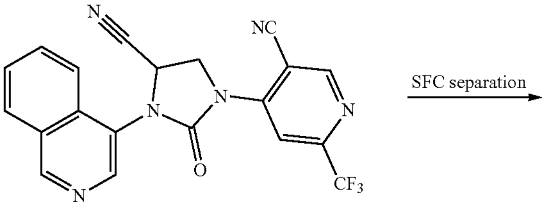

(117)

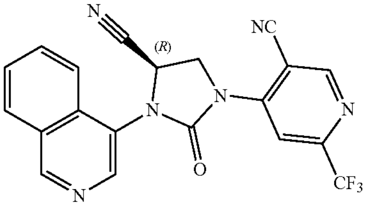

(117a)

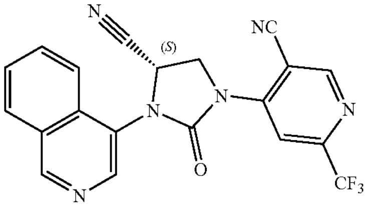

(117b)

Step 1: To a mixture of 2-(trifluoromethyl)pyridin-4-amine (3.0 g, 18.50 mmol, 1.0 eq.) in $CH_2Cl_2$ (25 mL) was added NBS (3.3 g, 18.50 mmol, 1.0 eq.) portion wised at 25° C. under $N_2$. The mixture was stirred at 25° C. for 16 hrs under $N_2$. Then the reaction mixture was quenched into water (50 mL) and extracted with $CH_2Cl_2$ (25 mL×3). The combined organic layers were washed with brine (50 mL), dried over $Na_2SO_4$, filtered and concentrated under reduced pressure to give the crude product. The crude product was purified by flash silica gel chromatography (25 g Sepa-Flash® Silica Flash Column, Eluent of 10-20% Ethyl acetate/Petroleum ether gradient at 100 mL/min) to give 5-bromo-2-(trifluoromethyl)pyridin-4-amine.

Step 2: To a solution of 5-bromo-2-(trifluoromethyl) pyridin-4-amine (3.3 g, 13.69 mmol, 1.0 eq.) in NMP (50 mL) was added CuCN (1.8 g, 20.54 mmol, 1.5 eq.) at 145° C. The reaction was stirred at 145° C. under $N_2$ for 12 hrs. The mixture was stirred with LS_2000 thiourea resin (10.0 g) at 25° C. for 2 hrs to remove Cu catalyst. Then the reaction mixture was quenched with $H_2O$ (150 mL), extracted with ethyl acetate (50 mL×3). The combined organic layers were washed with brine (50 mL), dried over $Na_2SO_4$, filtered and concentrated under reduced pressure to give crude product. The crude product was purified by flash silica gel chromatography (25 g SepaFlash® Silica Flash Column, Eluent of 20-30% Ethyl acetate/Petroleum ether gradient at 100 mL/min) to give 4-amino-6-(trifluoromethyl)nicotinonitrile.

Step 3: To a mixture of 4-amino-6-(trifluoromethyl)nicotinonitrile (187 mg, 1.00 mmol, 1.0 eq.) and $CuBr_2$ (447 mg, 2.00 mmol, 2.0 eq.) in MeCN (5 mL) was added isoamyl nitrite (293 mg, 2.50 mmol, 2.5 eq.) dropwise at 0° C. under $N_2$. The reaction was stirred at 0° C. under $N_2$ for 5 hrs. Then the mixture was stirred at 25° C. for 7 hrs. The mixture was stirred with LS_2000 thiourea resin (3.0 g) at 25° C. for 2 hrs to remove Cu catalyst. Then the reaction mixture was quenched with $H_2O$ (15 mL), extracted with ethyl acetate (5 mL×3). The combined organic layers were washed with brine (15 mL), dried over $Na_2SO_4$, filtered and concentrated under reduced pressure to give crude product. The residue was purified by flash silica gel chromatography (4 g Sepa-Flash® Silica Flash Column, Eluent of 10-20% Ethyl acetate/Petroleum ether gradient at 50 mL/min) to give 4-bromo-6-(trifluoromethyl)nicotinonitrile.

Step 4: A mixture of 4-bromo-6-(trifluoromethyl)nicotinonitrile (190 mg, 0.76 mmol, 1.2 eq.), 3-(isoquinolin-4-yl)-2-oxoimidazolidine-4-carbonitrile (Int-1) (150 mg, 0.63 mmol, 1.0 eq.), DMEDA (5 mg, 0.06 mmol, 0.1 eq.), CuI (11 mg, 0.06 mmol, 0.1 eq.) and $K_2CO_3$ (348 mg, 2.52 mmol, 4.0 eq.) in dioxane (3 mL) was stirred at 80° C. under $N_2$ for 15 hrs. The reaction was quenched with $H_2O$ (20 mL) and extracted with EtOAc (10 mL×3). The combined organic layers were washed with brine (30 mL), dried over $Na_2SO_4$, filtered and concentrated under reduced pressure to give crude product. The crude product was purified by flash silica gel chromatography (10 g SepaFlash® Silica Flash Column, Eluent of 50-100% Ethyl acetate/Petroleum ethergradient at 50 mL/min) to give racemic 4-(4-cyano-3-(isoquinolin-4-yl)-2-oxoimidazolidin-1-yl)-6-(trifluoromethyl)nicotinonitrile (117). LCMS (Method 22): $t_R$=1.827 min, $[M+1]^+$ 409.1.

Racemic 4-(4-cyano-3-(isoquinolin-4-yl)-2-oxoimidazolidin-1-yl)-6-(trifluoromethyl)nicotinonitrile (117) was separated by chiral SFC (column: DAICEL CHIRALPAK AD (250 mm×30 mm, 10 μm); mobile phase: [0.1% $NH_3H_2O$ in ETOH]; B %: 40%-40%, 12 min) to obtain two peaks.

Peak 1: (R)-4-(4-cyano-3-(isoquinolin-4-yl)-2-oxoimidazolidin-1-yl)-6-(trifluoromethyl) nicotinonitrile (117a). LCMS (Method 17): $t_R$=2.735 min, $[M+1]^+$ 409.1. SFC (Method 3): $t_R$=3.461 min, 98.07%. 1H NMR (400 MHz, CHLOROFORM-d) δ=9.41 (s, 1H), 8.98 (s, 1H), 8.73 (s, 1H), 8.47 (s, 1H), 8.17 (d, J=8.1 Hz, 1H), 7.94-7.84 (m, 2H), 7.81-7.76 (m, 1H), 5.21-5.15 (m, 1H), 5.13-5.06 (m, 1H), 4.80 (dd, J=3.5, 9.9 Hz, 1H).

Peak 2: (S)-4-(4-cyano-3-(isoquinolin-4-yl)-2-oxoimidazolidin-1-yl)-6-(trifluoromethyl) nicotinonitrile (117b). LCMS (Method 17): $t_R$=2.734 min, $[M+1]^+$ 409.1. SFC (Method 3): $t_R$=4.177 min, 98.42%. $^1H$ NMR (400 MHz, CHLOROFORM-d) δ=9.41 (s, 1H), 8.98 (s, 1H), 8.73 (s, 1H), 8.46 (s, 1H), 8.17 (d, J=8.2 Hz, 1H), 7.94-7.85 (m, 2H), 7.81-7.75 (m, 1H), 5.21-5.15 (m, 1H), 5.13-5.06 (m, 1H), 4.80 (dd, J=3.7, 9.9 Hz, 1H).

Example 118: Synthesis of 3-(isoquinolin-4-yl)-1-(4-methyl-1H-imidazol-2-yl)-2-oxoimidazolidine-4-carbonitrile (118), (R)-3-(isoquinolin-4-yl)-1-(4-methyl-1H-imidazol-2-yl)-2-oxoimidazolidine-4-carbonitrile (118a) and (S)-3-(isoquinolin-4-yl)-1-(4-methyl-1H-imidazol-2-yl)-2-oxoimidazolidine-4-carbonitrile (118b)

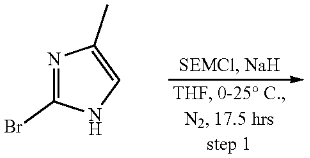

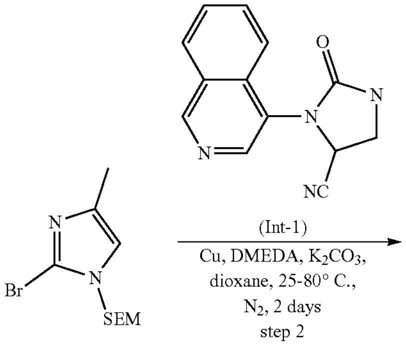

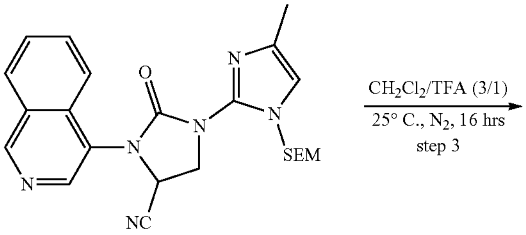

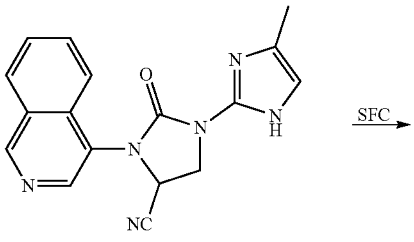

(118)

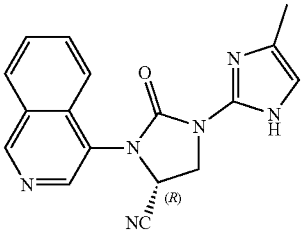

(118a)

-continued

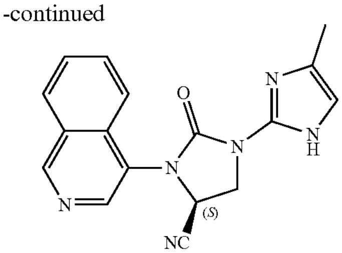

(118b)

Step 1: To a mixture of NaH (1.1 g, 27.33 mmol, 1.1 eq.) in THE (30 mL) was added a solution of 2-bromo-4-methyl-1H-imidazole (4.0 g, 24.84 mmol, 1.0 eq.) in THE (10 mL) at 0° C. under $N_2$. The mixture was stirred at 25° C. for 1.5 hrs under $N_2$. A solution of SEMCI (5.4 g, 32.30 mmol, 1.3 eq.) in THE (10 mL) was added to the reaction mixture at 0° C. Then the mixture was stirred at 25° C. for 16 hrs under $N_2$. The reaction was quenched with $H_2O$ (200 mL) and extracted with EtOAc (80 mL×3). The combined organic layers were washed with brine (200 mL), dried over $Na_2SO_4$, filtered and concentrated under reduced pressure to give a residue. The residue was purified by MPLC (Eluent of Ethyl acetate/Petroleum ether=1/4 to 3/7, 40 mL/min) to give 2-bromo-4-methyl-1-((2-(trimethylsilyl)ethoxy)methyl)-1H-imidazole. 1H NMR: (400 MHz, CHLOROFORM-d) δ=6.84-6.69 (m, 1H), 5.25-5.23 (m, 1H), 5.19 (s, 1H), 3.58-3.49 (m, 2H), 2.30-2.24 (m, 1H), 2.23-2.17 (m, 2H), 0.95-0.89 (m, 2H), 0.03-0.01 (m, 9H).

Step 2: To a mixture of 3-(isoquinolin-4-yl)-2-oxoimidazolidine-4-carbonitrile (Int-1) (500 mg, 2.10 mmol, 1.0 eq.) in dioxane (8 mL) was added 2-bromo-4-methyl-1-((2-(trimethylsilyl)ethoxy)methyl)-1H-imidazole (1.9 g, 6.30 mmol, 3.0 eq.), $K_2CO_3$ (1.2 g, 8.40 mmol, 4.0 eq.), 4A MS (300 mg), DMEDA (50 mg, Cat., 0.3 eq.) and CuI (40 mg, Cat., 0.1 eq.) at 25° C. Then the solution was stirred at 80° C. for 2 days under $N_2$. The reaction was quenched with $H_2O$ (50 mL) and extracted with EtOAc (20 mL×3). The combined organic layers were washed with brine (50 mL), dried over $Na_2SO_4$, filtered and concentrated under reduced pressure to give a residue. The residue was purified by MPLC (Eluent of Ethyl acetate/Petroleum ether=1/1 to 7/3, 50 mL/min) to give 3-(isoquinolin-4-yl)-1-(4-methyl-1-((2-(trimethylsilyl)ethoxy)methyl)-1H-imidazol-2-yl)-2-oxo-imidazolidine-4-carbonitrile. LCMS (Method 12): $t_R$=0.724 min, $[M+1]^+$ 449.2.

Step 3: A mixture of 3-(isoquinolin-4-yl)-1-(4-methyl-1-((2-(trimethylsilyl)ethoxy)methyl)-1H-imidazol-2-yl)-2-oxoimidazolidine-4-carbonitrile (650 mg crude, 1.0 eq.) in $CH_2Cl_2$/TFA=3/1 (10 mL) was stirred at 25° C. for 16 hrs under $N_2$. The reaction was concentrated to give a residue. The residue was purified by prep-HPLC (column: Waters Xbridge BEH C18 250 mm×50 mm, μm; liquid phase: [A-$H_2O$ (10 mM $NH_4HCO_3$); B-ACN]B %: 15%-40%, 20 min]) to give racemic 3-(isoquinolin-4-yl)-1-(4-methyl-1H-imidazol-2-yl)-2-oxoimidazolidine-4-carbonitrile (118). LCMS (Method 37): $t_R$=2.270 min, $[M+1]^+$ 319.1. $^1$H NMR: (400 MHz, DMSO-d6) δ=11.45 (br s, 0.5H), 11.20 (br s, 0.5H), 9.43 (s, 1H), 8.68 (s, 1H), 8.28 (d, J=8.1 Hz, 1H), 8.14 (d, J=8.0 Hz, 1H), 7.93-7.87 (m, 1H), 7.83-7.78 (m, 1H), 6.58 (s, 0.5H), 6.40 (s, 0.5H), 5.66 (dd, J=4.5, 9.4 Hz, 1H), 4.60-4.53 (m, 1H), 4.39-4.30 (m, 1H), 2.13 (s, 1H), 2.08 (s, 2H).

The racemate was separated by SFC (column: DAICEL CHIRALPAK AD (250 mm×30 mm, μm); liquid phase: [0.1% NH3H2O ETOH]B %: 55%-55%, 25 min]) to give two peaks.

Peak 1: (R)-3-(isoquinolin-4-yl)-1-(4-methyl-1H-imidazol-2-yl)-2-oxoimidazolidine-4-carbonitrile (118a). LCMS (Method 2): $t_R$=2.266 min, $[M+1]^+$ 319.1. SFC (Method 4): $t_R$=0.711 min, 100%. $^1$H NMR: (400 MHz, DMSO-$d_6$) δ=11.45 (br s, 0.36H), 11.20 (br s, 0.53H), 9.43 (s, 1H), 8.68 (s, 1H), 8.28 (d, J=8.1 Hz, 1H), 8.14 (d, J=7.9 Hz, 1H), 7.90 (dt, J=1.1, 7.7 Hz, 1H), 7.79 (dt, J=1.1, 7.7 Hz, 1H), 6.58 (s, 0.54H), 6.40 (s, 0.36H), 5.66 (dd, J=4.5, 9.4 Hz, 1H), 4.57 (dt, J=4.2, 9.8 Hz, 1H), 4.39-4.29 (m, 1H), 2.13 (d, J=0.9 Hz, 1H), 2.08 (d, J=0.8 Hz, 2H).

Peak 2: (S)-3-(isoquinolin-4-yl)-1-(4-methyl-1H-imidazol-2-yl)-2-oxoimidazolidine-4-carbonitrile (118b). LCMS (Method 2): $t_R$=2.267 min, $[M+1]^+$ 319.1. SFC (Method 4): $t_R$=1.846 min, 99.93%. $^1$H NMR: (400 MHz, DMSO-$d_6$) δ=11.45 (br s, 0.36H), 11.20 (br s, 0.55H), 9.43 (s, 1H), 8.68 (s, 1H), 8.28 (d, J=8.1 Hz, 1H), 8.14 (d, J=8.4 Hz, 1H), 7.93-7.86 (m, 1H), 7.84-7.77 (m, 1H), 6.58 (s, 0.55H), 6.40 (s, 0.37H), 5.66 (dd, J=4.5, 9.4 Hz, 1H), 4.57 (dt, J=4.2, 9.8 Hz, 1H), 4.40-4.29 (m, 1H), 2.13 (d, J=0.8 Hz, 1H), 2.08 (d, J=0.8 Hz, 2H).

Example 126: Synthesis of 1-(4-chloro-1H-imidazol-2-yl)-3-(isoquinolin-4-yl)-2-oxoimidazolidine-4-carbonitrile (119), (R)-1-(4-chloro-1H-imidazol-2-yl)-3-(isoquinolin-4-yl)-2-oxoimidazolidine-4-carbonitrile (119a) and (R)-1-(4-chloro-1H-imidazol-2-yl)-3-(isoquinolin-4-yl)-2-oxoimidazolidine-4-carbonitrile (119b)

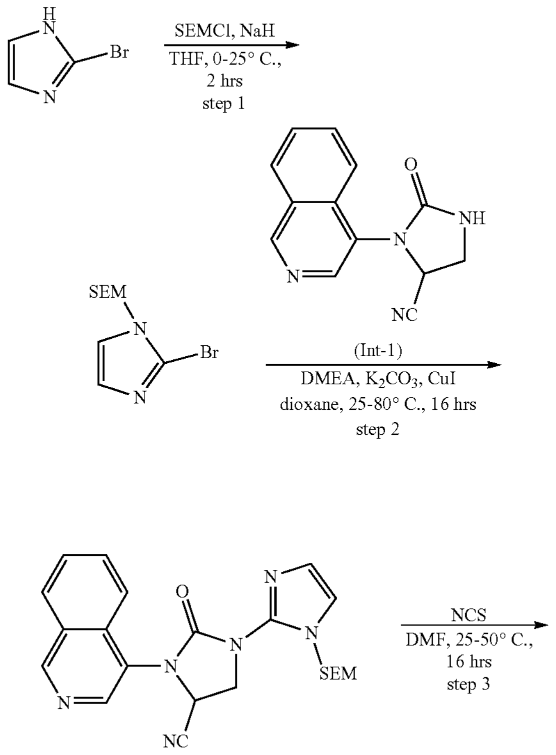

-continued

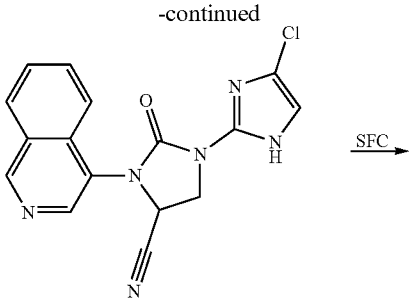

(119)

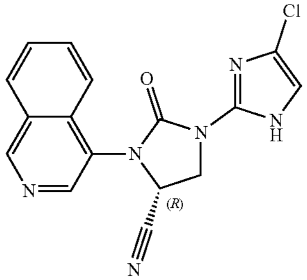

(119a)

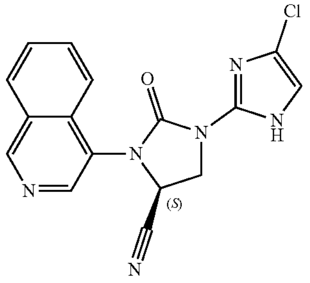

(119b)

Step 1: To a mixture of NaH (150 mg, 3.77 mmol, 1.1 eq.) in THE (3 mL) was added a solution of 2-bromo-1H-imidazole (500 mg, 3.43 mmol, 1.0 eq.) in THE (10 mL) at 0° C. under $N_2$. The solution was stirred at 25° C. for 30 min and SEMCI (743 mg, 4.45 mmol, 1.3 eq.) was added at 25° C. The mixture was stirred at 25° C. for 1.5 hrs. The reaction was quenched with aq. $NH_4Cl$ (15 mL) and extracted with EtOAc (30 mL×3). The combined organic layers were washed with brine (30 mL×3), dried over $Na_2SO_4$, filtered and concentrated under reduced pressure to give crude product which was purified by MPLC (Petroleum ether/EtOAc=100%-0%) to give 2-bromo-1-((2-(trimethylsilyl) ethoxy) methyl)-1H-imidazole.

Step 2: A solution of 3-(isoquinolin-4-yl)-2-oxoimidazolidine-4-carbonitrile (Int-1) (100 mg, 0.42 mmol, 1.0 eq.), 2-bromo-1-((2-(trimethylsilyl)ethoxy) methyl)-1H-imidazole (320 mg, 1.26 mmol, 3.0 eq.), N,N'-dimethylethylenediamine (4 mg, 0.04 mmol, 0.1 eq.), CuI (8 mg, 0.04 mmol, 0.1 eq.) and $K_2CO_3$ (232 mg, 1.68 mmol, 4.0 eq.) in dioxane (1 mL) at 25° C. was stirred at 80° C. under $N_2$ for 16 hrs. The mixture was stirred with LS_2000 thiourea resin (1.0 g) at 25° C. for 2 hrs to remove Cu catalyst. Then the mixture was filtered, and the filtrate was concentrated to give crude product. The crude product was purified by column ($SiO_2$, Petroleum ether/EtOAc=100%~30%) to give 3-(isoquinolin-4-yl)-2-oxo-1-(1-((2-(trimethylsilyl)ethoxy) methyl)-1H-imidazol-2-yl)imidazolidine-4-carbonitrile. LCMS (Method 28): $t_R$=0.629 min, $[M+1]^+$ 435.2.

Step 3: To a mixture of 3-(isoquinolin-4-yl)-2-oxo-1-(1-((2-(trimethylsilyl)ethoxy) methyl)-1H-imidazol-2-yl)imidazolidine-4-carbonitrile (177 mg, 0.41 mmol, 1.0 eq.) in DMF (2 mL) was added NCS (65 mg, 0.49 mmol, 1.2 eq.) and the mixture stirred at 50° C. for 16 hrs. The reaction mixture was concentrated to give crude product which was purified by prep-HPLC (column: Phenomenex Luna C18 75 mm×30 mm, 3 μm; liquid phase: water (HCOOH)-ACN B %: 1%-35%, 8 min]) to give racemic 1-(4-chloro-1H-imidazol-2-yl)-3-(isoquinolin-4-yl)-2-oxoimidazolidine-4-carbonitrile (119). LCMS (Method 13): $t_R$=1.839 min, M+1 (339.1). $^1$H NMR: (400 MHz, CHLOROFORM-d) δ=10.16 (br s, 1H), 9.38 (s, 1H), 8.68 (s, 1H), 8.15 (d, J=8.1 Hz, 1H), 7.90-7.83 (m, 2H), 7.79-7.73 (m, 1H), 6.78 (s, 1H), 5.14 (dd, J=5.6, 8.2 Hz, 1H), 4.67-4.59 (m, 2H).

The racemate was separated by SFC (column: DAICEL CHIRALPAK AD (250 mm×30 mm, μm); liquid phase: 0.1% $NH_3H_2O$ IPA B %: 50%-50%, 8 min]) to give two peaks.

Peak 1: (R)-1-(4-chloro-1H-imidazol-2-yl)-3-(isoquinolin-4-yl)-2-oxoimidazolidine-4-carbonitrile (119a). LCMS (Method 13): $t_R$=1.836 min, $[M+1]^+$ 339.0. SFC (Method 1): $t_R$=1.346 min, 100%. 1H NMR: (400 MHz, CHLOROFORM-d) δ=10.17 (br s, 1H), 9.50-9.30 (m, 1H), 8.69 (br s, 1H), 8.15 (d, J=8.3 Hz, 1H), 7.90-7.82 (m, 2H), 7.76 (ddd, J=2.7, 5.4, 8.1 Hz, 1H), 6.78 (s, 1H), 5.14 (dd, J=5.6, 8.1 Hz, 1H), 4.67-4.60 (m, 2H).

Peak 2: (S)-1-(4-chloro-1H-imidazol-2-yl)-3-(isoquinolin-4-yl)-2-oxoimidazolidine-4-carbonitrile (119b). LCMS (Method 13): $t_R$=1.835 min, $[M+1]^+$ 339.0. SFC (Method 1): $t_R$=1.589 min, 99.73%. 1H NMR: (400 MHz, CHLOROFORM-d) δ=10.17 (br s, 1H), 9.39 (br s, 1H), 8.68 (br s, 1H), 8.15 (d, J=8.3 Hz, 1H), 7.89-7.83 (m, 2H), 7.79-7.72 (m, 1H), 6.77 (d, J=1.4 Hz, 1H), 5.14 (dd, J=5.6, 8.3 Hz, 1H), 4.67-4.62 (m, 2H).

Example 120: Synthesis of 3-(isoquinolin-4-yl)-1-(3-methylcyclobutyl)-2-oxoimidazolidine-4-carbonitrile (120), (R)-3-(isoquinolin-4-yl)-1-((1s,3S)-3-methylcyclobutyl)-2-oxoimidazolidine-4-carbonitrile (120a), (R)-3-(isoquinolin-4-yl)-1-((1 r,3R)-3-methylcyclobutyl)-2-oxoimidazolidine-4-carbonitrile (120b), (S)-3-(isoquinolin-4-yl)-1-((1s,3R)-3-methylcyclobutyl)-2-oxoimidazolidine-4-carbonitrile (120c), and (S)-3-(isoquinolin-4-yl)-1-((1 r,3S)-3-methylcyclobutyl)-2-oxoimidazolidine-4-carbonitrile (120d)

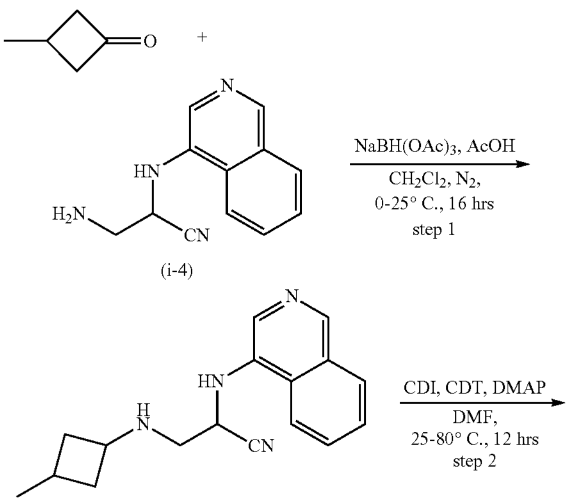

(i-4)

-continued

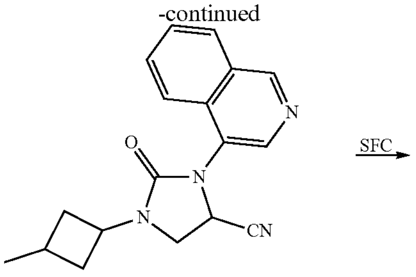

(120)

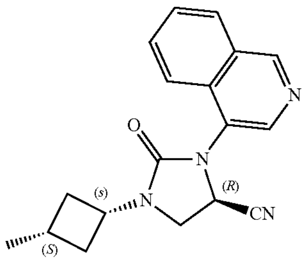

(120a)
Peak 1

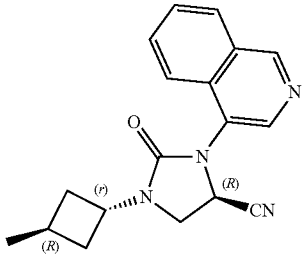

(120b)
Peak 2

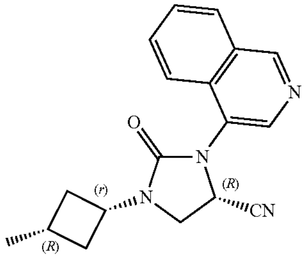

(120c)
Peak 3

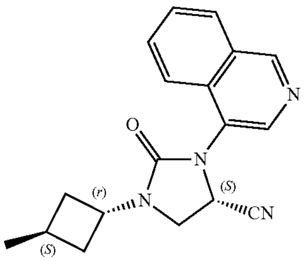

(120d)
Peak 4

Step 1: To a solution of 3-methylcyclobutan-1-one (200 mg, 2.38 mmol, 1.0 eq.) in $CH_2Cl_2$ (3 10 mL) was added 3-amino-2-(isoquinolin-4-ylamino)propanenitrile (i-4) (606 mg, 2.85 mmol, 1.0 eq.), AcOH (10 mg, 0.17 mmol, Cat.) and $NaBH(OAc)_3$ (1008 mg, 4.76 mmol, 2.0 eq.) in turn at 0° C. under $N_2$. The reaction was stirred at 25° C. for 16 hrs under $N_2$. The reaction was quenched with $H_2O$ (5 mL) and extracted with EtOAc (5 mL×2). The combined organic layers were washed with brine (5 mL×2), dried over $Na_2SO_4$, filtered and concentrated under reduced pressure to give crude product. The crude product was purified by flash silica gel chromatography (4 g SepaFlash® Silica Flash Column, Eluent of 0-100% Ethyl acetate/Petroleum ether-gradient 80 mL/min) to give 2-(isoquinolin-4-ylamino)-3-((3-methylcyclobutyl)amino)propanenitrile. LCMS (Method 34): $t_R$=0.735 min, [M+1]$^+$ 281.2.

Step 2: To a solution of 2-(isoquinolin-4-ylamino)-3-((3-methylcyclobutyl)amino)propanenitrile (170 mg, 0.61 mmol, 1.0 eq.) in DMF (5 mL) was added CDI (198 mg, 1.22 mmol, 2.0 eq.), CDT (200 mg, 1.22 mmol, 2.0 eq.) and DMAP (7 mg, 0.06 mmol, 0.1 eq.) in turn at 25° C. under $N_2$. The reaction was stirred at 80° C. for 12 hrs under $N_2$. The reaction was filtered and quenched with $H_2O$ (10 mL) and extracted with EtOAc (10 mL×2). The combined organic layers were washed with brine (5 mL×3), dried over $Na_2SO_4$, filtered and concentrated under reduced pressure to give crude product. The residue was purified by flash silica gel chromatography (4 g SepaFlash® Silica Flash Column, Eluent of 0-100% Ethyl acetate/Petroleum ether 60 mL/min) to give 3-(isoquinolin-4-yl)-1-(3-methylcyclobutyl)-2-oxoimidazolidine-4-carbonitrile (120). LCMS (Method 35): $t_R$=0.688 min. [M+1]$^+$ 307.1. $^1$H NMR (400 MHz, CHLOROFORM-d), δ=1.11 (d, J=6.50 Hz, 1H), 1.21 (d, J=6.88 Hz, 2H), 1.69-2.17 (m, 3H), 2.28-2.50 (m, 3H), 3.88-3.98 (m, 1H), 4.05 (m, 1H), 4.36 (m, 1H), 4.68-4.81 (m, 1H), 4.94 (m, 1H), 7.62-7.70 (m, 1H), 7.76 (t, J=7.44 Hz, 1H), 7.81-7.88 (m, 1H), 8.05 (d, J=8.13 Hz, 1H), 8.57 (s, 1H), 9.26 (s, 1H).

Step 3: 3-(isoquinolin-4-yl)-1-(3-methylcyclobutyl)-2-oxoimidazolidine-4-carbonitrile (120) was separated by chiral SFC (REGIS (s,s) DAICEL CHIRALCEL OJ(250 mm×30 mm, 10 μm); mobile phase: 0.1% $NH_3H_2O$ IPA; B %: 10%-30%, 17 min]) to obtain four peaks. Note: cis and trans configuration was confirmed by 2D NMR; R and S configuration was confirmed by activity.

Peak 1: (R)-3-(isoquinolin-4-yl)-1-((1s,3S)-3-methylcyclobutyl)-2-oxoimidazolidine-4-carbonitrile (120a). LCMS (Method 17): $t_R$=2.618 min, [M+1]$^+$ 307.2. SFC (Method 2): $t_R$=2.485 min, 99.47%. $^1$H NMR: (400 MHz, CHLOROFORM-d), δ=1.14-1.22 (m, 3H), 1.82-1.99 (m, 2H), 2.21-2.32 (m, 1H), 2.32-2.46 (m, 2H), 3.91 (m, 1H), 3.97-4.07 (m, 1H), 4.71 (m, 1H), 4.87 (m, 1H), 7.57-7.65 (m, 1H), 7.68-7.75 (m, 1H), 7.76-7.82 (m, 1H), 8.00 (d, J=8.00 Hz, 1H), 8.52 (s, 1H), 9.22 (s, 1H).

Peak 2: (R)-3-(isoquinolin-4-yl)-1-((1 r,3R)-3-methylcyclobutyl)-2-oxoimidazolidine-4-carbonitrile (120b). LCMS (Method 35): $t_R$=2.620 min, [M+1]$^+$ 307.2. SFC (Method 2): $t_R$=2.608 min, 95.73%. $^1$H NMR: (400 MHz, CHLOROFORM-d), δ=1.07 (d, J=6.50 Hz, 3H), 1.65-1.82 (m, 2H), 1.99-2.11 (m, 1H), 2.27-2.45 (m, 2H), 3.84-3.89 (m, 1H), 3.92-4.02 (m, 1H), 4.32 (m, 1H), 4.85 (m, 1H), 7.61 (m, 1H), 7.71 (m, 1H), 7.75-7.81 (m, 1H), 8.00 (d, J=8.13 Hz, 1H), 8.52 (s, 1H), 9.21 (s, 1H).

Peak 3: (S)-3-(isoquinolin-4-yl)-1-((1s,3R)-3-methylcyclobutyl)-2-oxoimidazolidine-4-carbonitrile (120c). LCMS (Method 35): $t_R$=2.625 min, [M+1]$^+$ 307.2. SFC (Method 2): $t_R$=2.657 min, 97.77%. $^1$H NMR: (400 MHz, CHLOROFORM-d), δ=1.06 (br t, J=6.88 Hz, 3H), 1.64-1.81 (m, 2H), 1.97-2.11 (m, 1H), 2.26-2.46 (m, 2H), 3.82-3.91 (m, 1H), 3.92-4.02 (m, 1H), 4.24-4.37 (m, 1H), 4.80-4.89 (m, 1H), 7.57-7.64 (m, 1H), 7.67-7.74 (m, 1H), 7.75-7.82 (m, 1H), 8.00 (br t, J=7.50 Hz, 1H), 8.48-8.54 (m, 1H), 9.19-9.24 (m, 1H).

Peak 4: (S)-3-(isoquinolin-4-yl)-1-((1r,3S)-3-methylcyclobutyl)-2-oxoimidazolidine-4-carbonitrile (120d). LCMS (Method 35): $t_R$=2.614 min, [M+1]$^+$ 307.2. SFC (Method 2): $t_R$=2.808 min, 95.58%. $^1$H NMR: (400 MHz, CHLOROFORM-d), δ=1.26 (d, J=6.88 Hz, 3H), 1.74-1.89 (m, 1H), 1.93-2.07 (m, 2H), 2.29-2.41 (m, 1H), 2.41-2.54 (m, 2H), 3.96-4.04 (m, 1H), 4.06-4.16 (m, 1H), 4.80 (m, 1H), 4.97 (m, 1H), 7.67-7.76 (m, 1H), 7.78-7.85 (m, 1H), 7.86-7.93 (m, 1H), 8.11 (d, J=8.13 Hz, 1H), 8.62 (s, 1H), 9.32 (s, 1H).

Example 121: Synthesis of 1-(4-fluorocyclohexyl)-3-(isoquinolin-4-yl)-2-oxoimidazolidine-4-carbonitrile (121), (R)-1-((1r,4R)-4-fluorocyclohexyl)-3-(isoquinolin-4-yl)-2-oxoimidazolidine-4-carbonitrile (121a), (R)-1-((1s,4S)-4-fluorocyclohexyl)-3-(isoquinolin-4-yl)-2-oxoimidazolidine-4-carbonitrile (121 b), (S)-1-((1 r,4S)-4-fluorocyclohexyl)-3-(isoquinolin-4-yl)-2-oxoimidazolidine-4-carbonitrile (121c) and (S)-1-((1s,4R)-4-fluorocyclohexyl)-3-(isoquinolin-4-yl)-2-oxoimidazolidine-4-carbonitrile (121d)

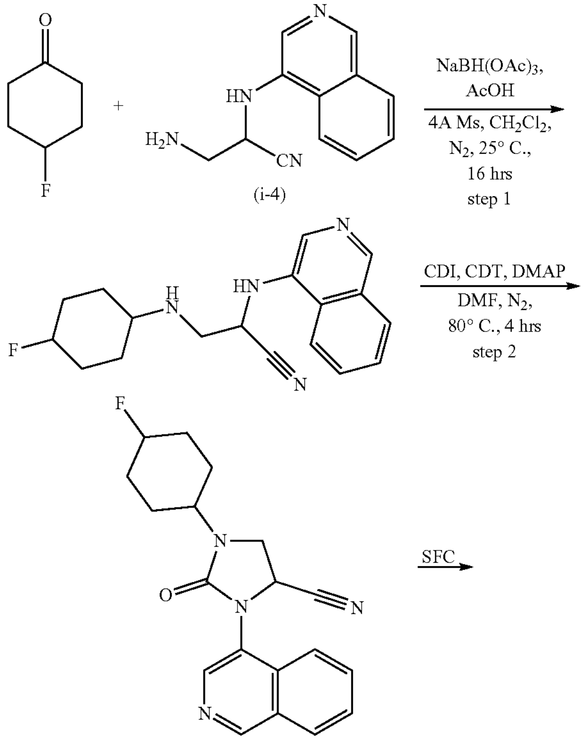

(121)

-continued

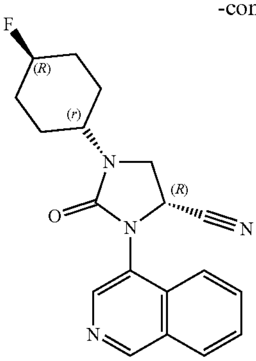

(121a)

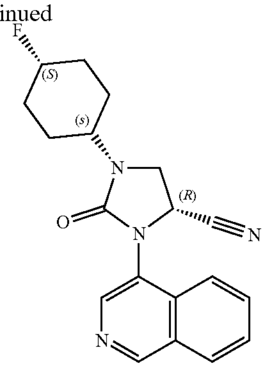

(121b)

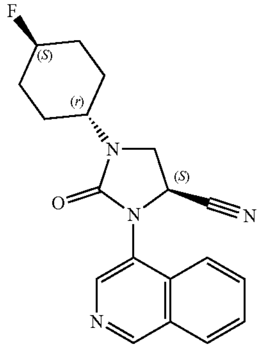

(121c)

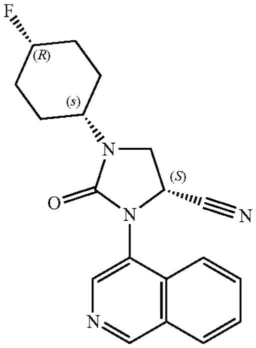

(121d)

Racemic 1-(4-fluorocyclohexyl)-3-(isoquinolin-4-yl)-2-oxoimidazolidine-4-carbonitrile (121) was prepared in a manner similar to Example 120, using 4-fluorocyclohexan-1-one in place of 3-methylcyclobutan-1-one. The racemate was separated by chiral SFC (Column: ChiralPak IH, 250 mm×30 mm, 10 μm; mobile phase: 0.1% $NH_3H_2O$ IPA; B %: 50%-50%, 21 min) to obtain four peaks. Note: cis and trans configuration was confirmed by 2D NMR; R and S configuration was confirmed by activity.

Peak 1: (R)-1-((1r,4R)-4-fluorocyclohexyl)-3-(isoquinolin-4-yl)-2-oxoimidazolidine-4-carbonitrile (121a). LCMS (Method 31): $t_R$=2.497 min, $[M+1]^+$ 339.2. SFC (Method 9): $t_R$=0.741 min, 100%. $^1H$ NMR: (400 MHz, CHLOROFORM-d) δ=9.30 (s, 1H), 8.60 (s, 1H), 8.09 (d, J=8.2 Hz, 1H), 7.86-7.76 (m, 2H), 7.73-7.66 (m, 1H), 4.92 (dd, J=4.6, 8.8 Hz, 1H), 4.64-4.41 (m, 1H), 4.01-3.90 (m, 2H), 3.83 (dd, J=4.7, 9.2 Hz, 1H), 2.33-2.21 (m, 2H), 2.07 (td, J=3.5, 12.0 Hz, 1H), 2.02-1.95 (m, 1H), 1.78-1.54 (m, 4H).

Peak 2: (R)-1-((1s,4S)-4-fluorocyclohexyl)-3-(isoquinolin-4-yl)-2-oxoimidazolidine-4-carbonitrile (121b). LCMS (Method 31): $t_R$=2.496 min, $[M+1]^+$ 339.2. SFC (Method 9): $t_R$=0.865 min, 99.14%. $^1H$ NMR: (400 MHz, DMSO-$d_6$) δ=9.37 (s, 1H), 8.54 (s, 1H), 8.26 (d, J=8.1 Hz, 1H), 7.97-7.93 (m, 1H), 7.91-7.85 (m, 1H), 7.78 (ddd, J=1.1, 6.9, 8.1 Hz, 1H), 5.49 (dd, J=4.2, 8.8 Hz, 1H), 4.93-4.76 (m, 1H), 4.04 (t, J=9.2 Hz, 1H), 3.88 (dd, J=4.2, 9.6 Hz, 1H), 3.82-3.72 (m, 1H), 2.08-2.00 (m, 2H), 1.90-1.74 (m, 3H), 1.72-1.67 (m, 1H), 1.62 (br t, J=11.9 Hz, 2H).

Peak 3: (S)-1-((1 r,4S)-4-fluorocyclohexyl)-3-(isoquinolin-4-yl)-2-oxoimidazolidine-4-carbonitrile (121c). LCMS (Method 31): $t_R$=2.497 min, $[M+1]^+$ 339.2. SFC (Method 9): $t_R$=1.270 min, 99.33%. $^1H$ NMR: (400 MHz, CHLOROFORM-d) δ=9.30 (s, 1H), 8.60 (s, 1H), 8.09 (d, J=8.2 Hz, 1H), 7.86-7.76 (m, 2H), 7.73-7.65 (m, 1H), 4.92 (dd, J=4.6, 8.8 Hz, 1H), 4.64-4.41 (m, 1H), 4.00-3.89 (m, 2H), 3.82 (dd, J=4.6, 9.3 Hz, 1H), 2.31-2.18 (m, 2H), 2.11-2.03 (m, 1H), 2.01-1.94 (m, 1H), 1.77-1.52 (m, 4H).

Peak 4: (S)-1-((1s,4R)-4-fluorocyclohexyl)-3-(isoquinolin-4-yl)-2-oxoimidazolidine-4-carbonitrile (121d). LCMS (Method 31): $t_R$=2.496 min, $[M+1]^+$ 339.2. SFC (Method 9): $t_R$=3.342 min, 100%. $^1H$ NMR: (400 MHz, DMSO-$d_6$) δ=9.37 (s, 1H), 8.54 (s, 1H), 8.25 (d, J=8.1 Hz, 1H), 7.98-7.92 (m, 1H), 7.88 (t, J=7.5 Hz, 1H), 7.81-7.74 (m, 1H), 5.49 (dd, J=4.1, 8.8 Hz, 1H), 4.93-4.74 (m, 1H), 4.04 (t, J=9.2 Hz, 1H), 3.88 (dd, J=4.3, 9.5 Hz, 1H), 3.82-3.72 (m, 1H), 2.11-1.98 (m, 2H), 1.90-1.72 (m, 3H), 1.72-1.67 (m, 1H), 1.66-1.54 (m, 2H).

Example 122: Synthesis of 3-(isoquinolin-4-yl)-2-oxo-1-(spiro[3.3]heptan-2-yl)imidazolidine-4-carbonitrile (122), (R)-3-(isoquinolin-4-yl)-2-oxo-1-(spiro[3.3]heptan-2-yl)imidazolidine-4-carbonitrile (122a) and (S)-3-(isoquinolin-4-yl)-2-oxo-1-(spiro[3.3]heptan-2-yl)imidazolidine-4-carbonitrile (122b)

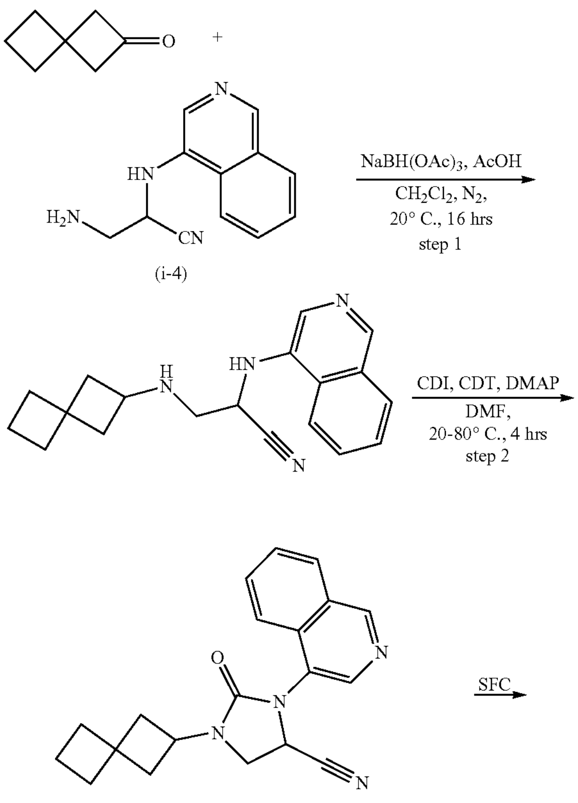

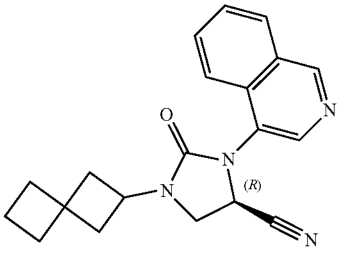

(122a)

-continued

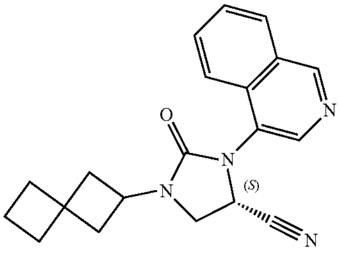

(122b)

Racemic 3-(isoquinolin-4-yl)-2-oxo-1-(spiro[3.3]heptan-2-yl)imidazolidine-4-carbonitrile (122) was prepared in a manner similar to Example 120, using spiro[3.3]heptan-2-one in place of 3-methylcyclobutan-1-one. The racemate was separated by prep-SFC (column: DAICEL CHIRALCEL OJ (250 mm×30 mm, 10 μm); liquid phase: [A-EtOH; B-ACN]B %: 15%, 12 min]) to give two peaks.

Peak 1: (R)-3-(isoquinolin-4-yl)-2-oxo-1-(spiro[3.3]heptan-2-yl)imidazolidine-4-carbonitrile (122a). LCMS (Method 31): $t_R$=2.854 min, $[M+1]^+$ 333.2. SFC (Method 10): $t_R$=1.282 min, 100%. $^1$H NMR: (400 MHz, CHLOROFORM-d) δ=9.29 (s, 1H) 8.59 (br s, 1H) 8.08 (br d, J=8.07 Hz, 1H) 7.83-7.89 (m, 1H) 7.79 (br t, J=7.40 Hz, 1H) 7.65-7.72 (m, 1H) 4.93 (br dd, J=7.52, 4.58 Hz, 1H) 4.41-4.52 (m, 1H) 3.98-4.06 (m, 1H) 3.91 (br dd, J=8.68, 4.52 Hz, 1H) 2.27-2.42 (m, 2H) 2.14-2.25 (m, 2H) 2.11 (br t, J=7.21 Hz, 2H) 1.95-2.03 (m, 2H) 1.89 (q, J=7.46 Hz, 2H).

Peak 2: (S)-3-(isoquinolin-4-yl)-2-oxo-1-(spiro[3.3]heptan-2-yl)imidazolidine-4-carbonitrile (122b). LCMS (Method 31): $t_R$=2.852 min, $[M+1]^+$ 333.2. SFC (Method 10): $t_R$=1.398 min, 99.3%. $^1$H NMR: (400 MHz, CHLOROFORM-d) δ=9.29 (s, 1H) 8.59 (s, 1H) 8.08 (d, J=8.19 Hz, 1H) 7.83-7.89 (m, 1H) 7.79 (t, J=7.52 Hz, 1H) 7.66-7.72 (m, 1H) 4.93 (dd, J=8.86, 4.83 Hz, 1H) 4.40-4.52 (m, 1H) 3.98-4.06 (m, 1H) 3.91 (dd, J=9.29, 4.89 Hz, 1H) 2.35-2.43 (m, 1H) 2.28-2.35 (m, 1H) 2.15-2.24 (m, 2H) 2.12 (br t, J=7.27 Hz, 2H) 1.97-2.04 (m, 2H) 1.84-1.92 (m, 2H).

Example 123: Synthesis of 1-(3-isopropylcyclobutyl)-3-(isoquinolin-4-yl)-2-oxoimidazolidine-4-carbonitrile (123), (R)-1-((1s,3S)-3-isopropylcyclobutyl)-3-(isoquinolin-4-yl)-2-oxoimidazolidine-4-carbonitrile (123a), (R)-1-((1r,3R)-3-isopropylcyclobutyl)-3-(isoquinolin-4-yl)-2-oxoimidazolidine-4-carbonitrile (123b), (S)-1-((1s,3R)-3-isopropylcyclobutyl)-3-(isoquinolin-4-yl)-2-oxoimidazolidine-4-carbonitrile (123c) and (S)-1-((1r,3S)-3-isopropylcyclobutyl)-3-(isoquinolin-4-yl)-2-oxoimidazolidine-4-carbonitrile (123d)

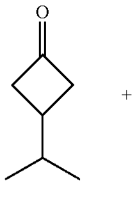

-continued

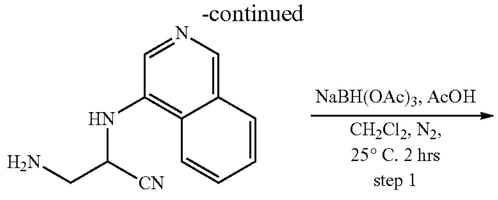

(i-4)

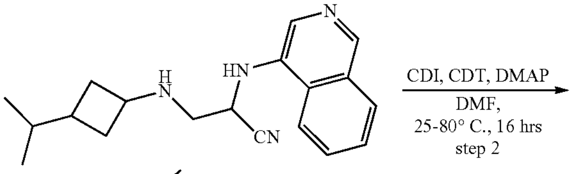

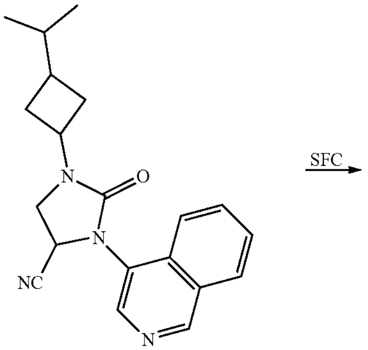

(123)

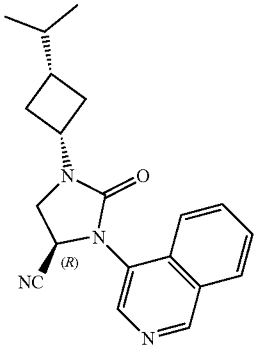

(123a)

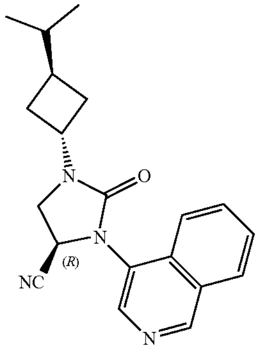

(123b)

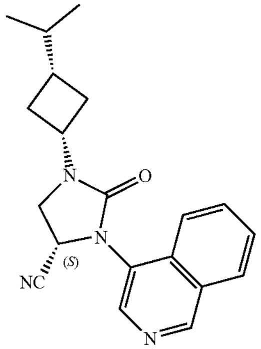

(123c)

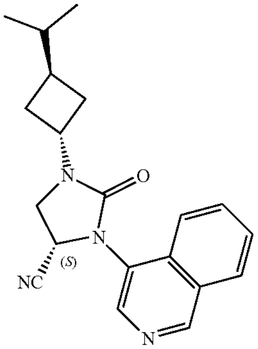

(123d)

Racemic 1-(3-isopropylcyclobutyl)-3-(isoquinolin-4-yl)-2-oxoimidazolidine-4-carbonitrile (123) was prepared in a manner similar to Example 120, using 3-isopropylcyclobutan-1-one in place of 3-methylcyclobutan-1-one. LCMS (Method 26): $t_R$=1.541 min, $[M+1]^+$ 335.3, $^1$H NMR: (400 MHz, CHLOROFORM-d) δ=9.29 (s, 1H), 8.60 (s, 1H), 8.08 (d, J=8.1 Hz, 1H), 7.89-7.84 (m, 1H), 7.79 (t, J=7.6 Hz, 1H), 7.72-7.66 (m, 1H), 4.94 (dt, J=4.9, 8.9 Hz, 1H), 4.62 (t, J=8.1 Hz, 1H), 4.12-3.88 (m, 2H), 2.45-2.29 (m, 2H), 2.24-2.07 (m, 2H), 1.98-1.86 (m, 1H), 1.73-1.64 (m, 1H), 0.92-0.86 (m, 6H).

The racemate was separated by SFC (Column: ChiralPak IH, 250 mm×30 mm, 10 μm); mobile phase: 0.1% $NH_3H_2O$ IPA; B %: 55%-55%, 7 min) to give two parts (Part 1 and Part 2). Part 1 was separated by SFC (Column: DAICEL CHIRALCEL OD (250 mm×30 mm, 10 um)); mobile phase: 0.1% $NH_3H_2O$ IPA; B %: 40%-40%, 8 min) to give two peaks (Peak 1 and Peak 2). Part 2 was separated by SFC (Column: Column DAICEL CHIRALPAK IG (250 mm×30 mm, 10 um); mobile phase: 0.1% $NH_3H_2O$ IPA; B %: 50%-50%, 8 min) to give two peaks (Peak 3 and Peak 4). Note: cis and trans configuration was confirmed by 2D NMR; R and S configuration was confirmed by activity.

Peak 1: (R)-1-((1s,3S)-3-isopropylcyclobutyl)-3-(isoquinolin-4-yl)-2-oxoimidazolidine-4-carbonitrile (123a). LCMS (Method 1): $t_R$=2.358 min, $[M+1]^+$ 335.1. SFC (Method 11): $t_R$=3.033 min, 99.7%. $^1H$ NMR: (400 MHz, CHLOROFORM-d) δ=9.33 (br s, 1H), 8.63 (br s, 1H), 8.11 (d, J=8.2 Hz, 1H), 7.91-7.87 (m, 1H), 7.85-7.80 (m, 1H), 7.74-7.69 (m, 1H), 4.96 (br dd, J=4.8, 8.7 Hz, 1H), 4.46-4.37 (m, 1H), 4.10-4.04 (m, 1H), 3.96 (dd, J=4.8, 9.4 Hz, 1H), 2.48-2.31 (m, 2H), 1.93-1.81 (m, 2H), 1.76-1.67 (m, 1H), 1.57-1.46 (m, 1H), 0.90 (dd, J=3.2, 6.6 Hz, 6H).

Peak 2: (R)-1-((1r,3R)-3-isopropylcyclobutyl)-3-(isoquinolin-4-yl)-2-oxoimidazolidine-4-carbonitrile (123b). LCMS (Method 1): $t_R$=2.347 min, $[M+1]^+$ 335.1. SFC (Method 11): $t_R$=3.402 min, 99.8%. $^1H$ NMR: (400 MHz, CHLOROFORM-d) δ=9.32 (s, 1H), 8.62 (s, 1H), 8.11 (d, J=8.2 Hz, 1H), 7.91-7.86 (m, 1H), 7.84-7.79 (m, 1H), 7.74-7.69 (m, 1H), 4.98 (dd, J=4.8, 8.9 Hz, 1H), 4.64 (quin, J=8.0 Hz, 1H), 4.17-4.11 (m, 1H), 4.03 (dd, J=4.9, 9.3 Hz, 1H), 2.47-2.32 (m, 2H), 2.25-2.10 (m, 2H), 1.98-1.88 (m, 1H), 1.72 (tdd, J=6.6, 10.0, 13.1 Hz, 1H), 0.93 (dd, J=3.5, 6.5 Hz, 6H).

Peak 3: (S)-1-((1s,3R)-3-isopropylcyclobutyl)-3-(isoquinolin-4-yl)-2-oxoimidazolidine-4-carbonitrile (123c). LCMS (Method 1): $t_R$=2.358 min, $[M+1]^+$ 335.1. SFC (Method 11): $t_R$=2.664 min, 100%. $^1H$ NMR: (400 MHz, CHLOROFORM-d) δ=9.30 (s, 1H), 8.60 (s, 1H), 8.08 (d, J=8.2 Hz, 1H), 7.89-7.84 (m, 1H), 7.82-7.77 (m, 1H), 7.71-7.66 (m, 1H), 4.93 (dd, J=4.8, 8.9 Hz, 1H), 4.43-4.33 (m, 1H), 4.08-3.99 (m, 1H), 3.93 (dd, J=4.8, 9.3 Hz, 1H), 2.44-2.28 (m, 2H), 1.91-1.77 (m, 2H), 1.74-1.63 (m, 1H), 1.53-1.43 (m, 1H), 0.87 (dd, J=3.2, 6.5 Hz, 6H).

Peak 4: (S)-1-((1r,3S)-3-isopropylcyclobutyl)-3-(isoquinolin-4-yl)-2-oxoimidazolidine-4-carbonitrile (123d). LCMS (Method 1): $t_R$=2.346 min, $[M+1]^+$ 335.1. SFC (Method 11): $t_R$=2.767 min, 99.84%. $^1H$ NMR: (400 MHz, CHLOROFORM-d) δ=9.29 (s, 1H), 8.59 (s, 1H), 8.08 (d, J=8.2 Hz, 1H), 7.88-7.84 (m, 1H), 7.81-7.76 (m, 1H), 7.71-7.66 (m, 1H), 4.95 (dd, J=4.8, 8.9 Hz, 1H), 4.61 (quin, J=8.1 Hz, 1H), 4.14-4.08 (m, 1H), 4.00 (dd, J=4.8, 9.4 Hz, 1H), 2.43-2.29 (m, 2H), 2.22-2.06 (m, 2H), 1.96-1.84 (m, 1H), 1.71 (br s, 1H), 1.71-1.64 (m, 1H), 0.90 (dd, J=3.5, 6.6 Hz, 6H).

Example 124: Synthesis of 1-(3-cyclopropylcyclobutyl)-3-(isoquinolin-4-yl)-2-oxoimidazolidine-4-carbonitrile (124), (R)-1-((1s,3S)-3-cyclopropylcyclobutyl)-3-(isoquinolin-4-yl)-2-oxoimidazolidine-4-carbonitrile (124a), (R)-1-((1r,3R)-3-cyclopropylcyclobutyl)-3-(isoquinolin-4-yl)-2-oxoimidazolidine-4-carbonitrile (124b), (S)-1-((1r,3S)-3-cyclopropylcyclobutyl)-3-(isoquinolin-4-yl)-2-oxoimidazolidine-4-carbonitrile (124c) and (S)-1-((1s,3R)-3-cyclopropylcyclobutyl)-3-(isoquinolin-4-yl)-2-oxoimidazolidine-4-carbonitrile (124d)

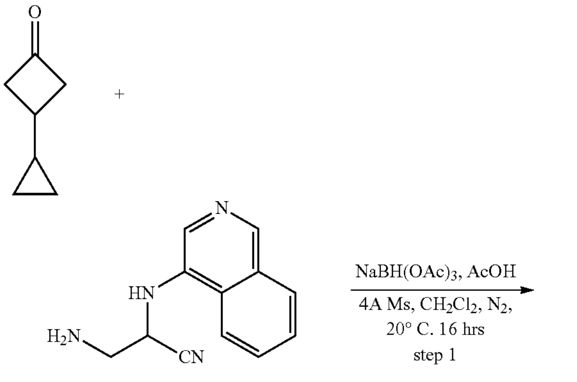

(i-4)

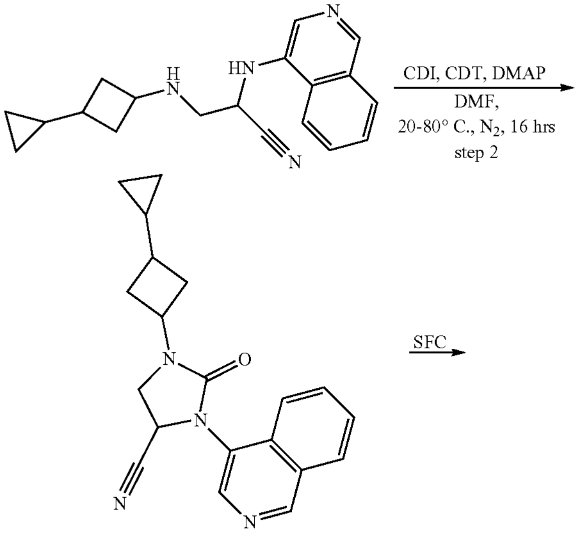

(124)

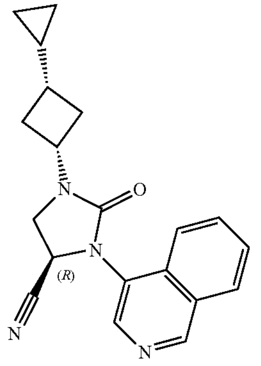

(124a)

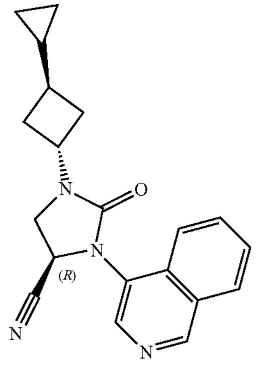

(124b)

-continued

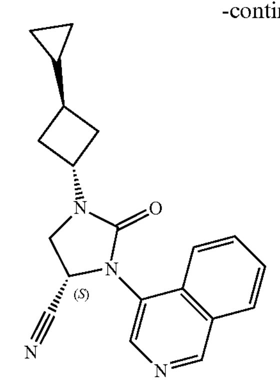

(124c)

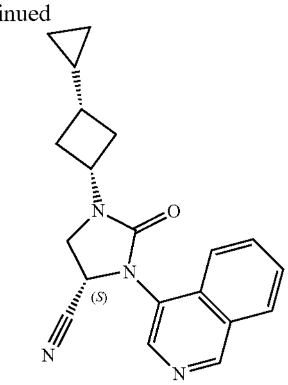

(124d)

Racemic 1-(3-cyclopropylcyclobutyl)-3-(isoquinolin-4-yl)-2-oxoimidazolidine-4-carbonitrile (124) was prepared in a manner similar to Example 120, using 3-cyclopropylcyclobutan-1-one in place of 3-methylcyclobutan-1-one. Separation of the racemate by twice SFC (column: DAICEL CHIRALPAK AD (250 mm×30 mm, 10 μm); liquid phase: 0.1% $NH_3H_2O$ EtOH; B %: 45%-45%, 8 min]) gave Peak 2. Further separation by a third SFC (column: DAICEL CHIRALPAK AD (250 mm×30 mm, 10 μm); liquid phase: 0.1% $NH_3H_2O$ ETOH; B %: 40%-40%, 18 min]) gave Peak 1. Separation of the racemate by SFC (column: ChiralPak IH, 250 mm×30 mm, 10 μm; liquid phase: 0.1% $NH_3H_2O$ IPA B %: 55%-55%, 10 min]) gave Peak 3 and Peak 4. Note: cis and trans configuration was confirmed by 2D NMR; R and S configuration was confirmed by activity.

Peak 1: (R)-1-((1s,3S)-3-cyclopropylcyclobutyl)-3-(isoquinolin-4-yl)-2-oxoimidazolidine-4-carbonitrile (124a). LCMS (Method 17): $t_R$=2.779 min, $[M+1]^+$ 333.2. SFC (Method 9): $t_R$=2.297 min, 100%. $^1H$ NMR: (400 MHz, CHLOROFORM-d) δ=9.29 (s, 1H), 8.60 (s, 1H), 8.08 (d, J=8.1 Hz, 1H), 7.90-7.83 (m, 1H), 7.82-7.76 (m, 1H), 7.72-7.65 (m, 1H), 4.93 (dd, J=4.9, 8.9 Hz, 1H), 4.36 (tt, J=7.6, 9.7 Hz, 1H), 4.11-4.01 (m, 1H), 3.95 (dd, J=4.9, 9.4 Hz, 1H), 2.44-2.22 (m, 2H), 1.90 (qd, J=10.0, 15.2 Hz, 2H), 1.82-1.68 (m, 1H), 0.81 (tq, J=5.0, 7.8 Hz, 1H), 0.50-0.41 (m, 2H), 0.17-0.10 (m, 2H).

Peak 2: (R)-1-((1r,3R)-3-cyclopropylcyclobutyl)-3-(isoquinolin-4-yl)-2-oxoimidazolidine-4-carbonitrile (124b). LCMS (Method 17): $t_R$=2.808 min, $[M+1]^+$ 333.2. SFC (Method 9): $t_R$=2.371 min, 99.9%. $^1H$ NMR: (400 MHz, CHLOROFORM-d) δ=9.30 (br s, 1H), 8.60 (br s, 1H), 8.08 (d, J=8.1 Hz, 1H), 7.89-7.83 (m, 1H), 7.79 (t, J=7.6 Hz, 1H), 7.73-7.65 (m, 1H), 4.94 (dd, J=4.8, 8.8 Hz, 1H), 4.73 (quin, J=8.4 Hz, 1H), 4.12-4.05 (m, 1H), 3.98 (dd, J=4.8, 9.3 Hz, 1H), 2.49-2.34 (m, 2H), 2.21-2.05 (m, 2H), 1.91-1.79 (m, 1H), 1.06-0.94 (m, 1H), 0.50 (br d, J=8.1 Hz, 2H), 0.13 (br d, J=4.8 Hz, 2H).

Peak 3: (S)-1-((1r,3S)-3-cyclopropylcyclobutyl)-3-(isoquinolin-4-yl)-2-oxoimidazolidine-4-carbonitrile (124c). LCMS (Method 17): $t_R$=2.803 min, $[M+1]^+$ 333.2. SFC (Method 9): $t_R$=2.939 min, 99.9%. $^1H$ NMR: (400 MHz, CHLOROFORM-d) δ=9.30 (br s, 1H), 8.60 (br s, 1H), 8.08 (d, J=8.1 Hz, 1H), 7.89-7.83 (m, 1H), 7.83-7.76 (m, 1H), 7.73-7.66 (m, 1H), 4.94 (dd, J=4.9, 8.9 Hz, 1H), 4.73 (quin, J=8.4 Hz, 1H), 4.17-4.03 (m, 1H), 3.98 (dd, J=4.9, 9.3 Hz, 1H), 2.49-2.35 (m, 2H), 2.20-2.06 (m, 2H), 1.90-1.80 (m, 1H), 1.06-0.95 (m, 1H), 0.55-0.46 (m, 2H), 0.13 (br d, J=4.4 Hz, 2H).

Peak 4: (S)-1-((1s,3R)-3-cyclopropylcyclobutyl)-3-(isoquinolin-4-yl)-2-oxoimidazolidine-4-carbonitrile (124d). LCMS (Method 17): $t_R$=2.801 min, $[M+1]^+$ 333.2. SFC (Method 9): $t_R$=3.375 min, 100%. $^1H$ NMR: (400 MHz, CHLOROFORM-d) δ=9.30 (br s, 1H), 8.60 (br s, 1H), 8.08 (d, J=8.1 Hz, 1H), 7.90-7.83 (m, 1H), 7.82-7.76 (m, 1H), 7.73-7.65 (m, 1H), 4.94 (dd, J=4.9, 8.9 Hz, 1H), 4.42-4.30 (m, 1H), 4.09-4.03 (m, 1H), 3.95 (dd, J=4.9, 9.3 Hz, 1H), 2.44-2.25 (m, 2H), 1.90 (qd, J=10.0, 15.2 Hz, 2H), 1.81-1.69 (m, 1H), 0.86-0.75 (m, 1H), 0.51-0.38 (m, 2H), 0.14 (q, J=5.0 Hz, 2H).

Example 125: Synthesis of 3-(isoquinolin-4-yl)-2-oxo-1-(spiro[2.3]hexan-5-yl)imidazolidine-4-carbonitrile (125), (R)-3-(isoquinolin-4-yl)-2-oxo-1-(spiro[2.3]hexan-5-yl)imidazolidine-4-carbonitrile (125a) and (S)-3-(isoquinolin-4-yl)-2-oxo-1-(spiro[2.3]hexan-5-yl)imidazolidine-4-carbonitrile (125b)

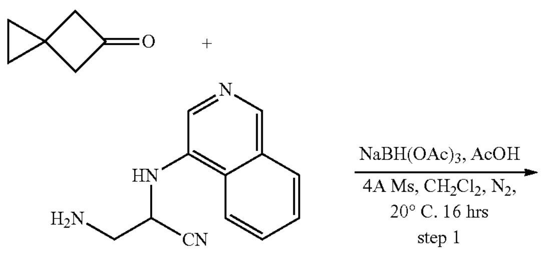

(i-4)

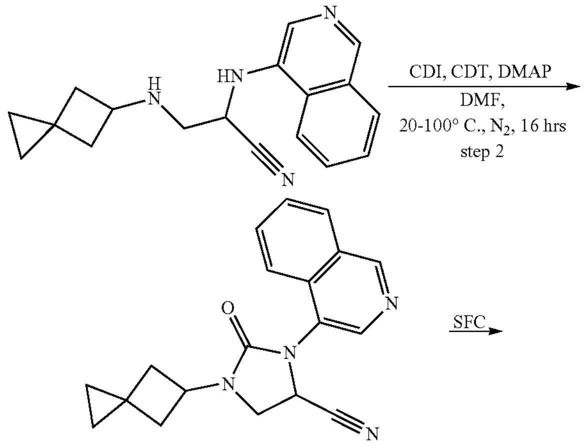

(125)

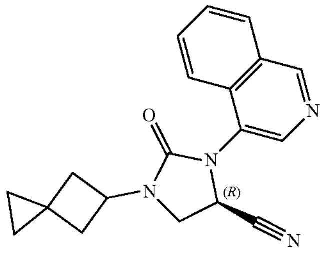

(125a)

-continued

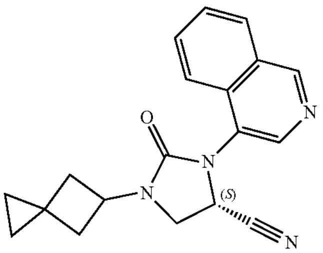

(125b)

Racemic 3-(isoquinolin-4-yl)-2-oxo-1-(spiro[2.3]hexan-5-yl)imidazolidine-4-carbonitrile (125) was prepared in a manner similar to Example 120, using spiro[2.3]hexan-5-one in place of 3-methylcyclobutan-1-one. The racemate was separated by SFC (column: DAICEL CHIRALPAK AD (250 mm×30 mm, 10 μm); liquid phase: [0.1% $NH_3H_2O$ EtOH]B %: 40%-40%, 6 min]) to give two peaks.

Peak 1: (R)-3-(isoquinolin-4-yl)-2-oxo-1-(spiro[2.3]hexan-5-yl)imidazolidine-4-carbonitrile(125a). LCMS (Method 17): $t_R$=2.669 min, $[M+1]^+$ 319.2. SFC (Method 14): $t_R$=1.829 min, 99.9%. $^1$H NMR: (400 MHz, CHLOROFORM-d) δ=9.30 (br s, 1H), 8.61 (br s, 1H), 8.08 (d, J=8.2 Hz, 1H), 7.91-7.84 (m, 1H), 7.80 (t, J=7.6 Hz, 1H), 7.74-7.66 (m, 1H), 4.97 (dd, J=4.8, 8.7 Hz, 1H), 4.87 (quin, J=8.2 Hz, 1H), 4.21-4.10 (m, 1H), 4.09-4.01 (m, 1H), 2.56 (ddd, J=8.4, 11.1, 19.6 Hz, 2H), 2.41-2.18 (m, 2H), 0.63-0.55 (m, 2H), 0.54-0.46 (m, 2H).

Peak 2: (S)-3-(isoquinolin-4-yl)-2-oxo-1-(spiro[2.3]hexan-5-yl)imidazolidine-4-carbonitrile (125b). LCMS (Method 17): $t_R$=2.666 min, $[M+1]^+$ 319.2. SFC (Method 14): $t_R$=1.681 min, 100%. $^1$H NMR: (400 MHz, CHLOROFORM-d) δ=9.30 (br d, J=4.3 Hz, 1H), 8.87-8.39 (m, 1H), 8.08 (br d, J=8.1 Hz, 1H), 7.89-7.83 (m, 1H), 7.83-7.77 (m, 1H), 7.73-7.62 (m, 1H), 4.97 (br s, 1H), 4.86 (quin, J=8.1 Hz, 1H), 4.19-4.11 (m, 1H), 4.08-4.01 (m, 1H), 2.55 (ddd, J=8.1, 11.3, 19.7 Hz, 2H), 2.38-2.22 (m, 2H), 0.62-0.55 (m, 2H), 0.54-0.45 (m, 2H).

Example 126: Synthesis of (3,3-dimethylcyclobutyl)-3-(isoquinolin-4-yl)-2-oxoimidazolidine-4-carbonitrile (126), (R)-1-(3,3-dimethylcyclobutyl)-3-(isoquinolin-4-yl)-2-oxoimidazolidine-4-carbonitrile (126a) and (S)-1-(3,3-dimethylcyclobutyl)-3-(isoquinolin-4-yl)-2-oxoimidazolidine-4-carbonitrile (126b)

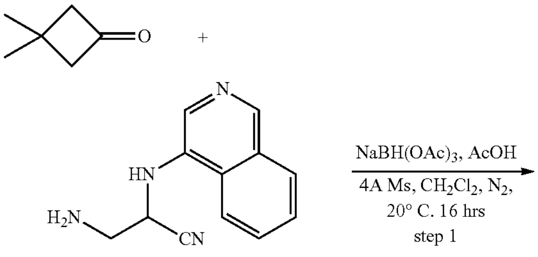

(i-4)

-continued

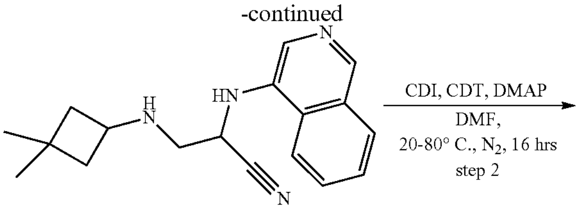

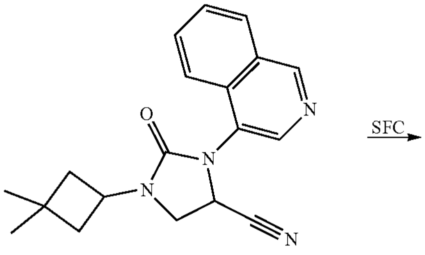

(126)

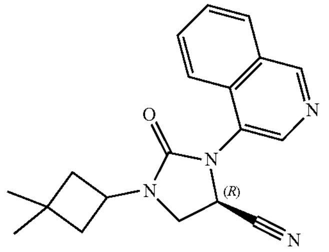

(126a)

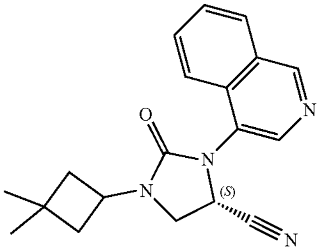

(126b)

Racemic (3,3-dimethylcyclobutyl)-3-(isoquinolin-4-yl)-2-oxoimidazolidine-4-carbonitrile (133) was prepared in a manner similar to Example 120, using 3,3-dimethylcyclobutan-1-one in place of 3-methylcyclobutan-1-one. The racemate was separated by SFC (column: ChiralPak IH, 250 mm×30 mm, 10 μm; liquid phase: Neu-ACN B %: 40%-40%, 7 min) to give two peaks.

Peak 1: (R)-1-(3,3-dimethylcyclobutyl)-3-(isoquinolin-4-yl)-2-oxoimidazolidine-4-carbonitrile (126a). LCMS (Method 2): $t_R$=2.750 min, $[M+1]^+$ 321.2. SFC (Method 13): $t_R$=1.824 min, 100%. $^1$H NMR: (400 MHz, CHLOROFORM-d) δ=9.30 (s, 1H), 8.60 (s, 1H), 8.08 (d, J=8.1 Hz, 1H), 7.90-7.83 (m, 1H), 7.79 (t, J=7.3 Hz, 1H), 7.73-7.66 (m, 1H), 4.94 (dd, J=4.9, 8.9 Hz, 1H), 4.60 (quin, J=8.8 Hz, 1H), 4.11-4.02 (m, 1H), 3.95 (dd, J=4.9, 9.3 Hz, 1H), 2.20-2.13 (m, 1H), 2.12-2.00 (m, 3H), 1.24 (s, 3H), 1.19 (s, 3H).

Peak 2: (S)-1-(3,3-dimethylcyclobutyl)-3-(isoquinolin-4-yl)-2-oxoimidazolidine-4-carbonitrile (1226b). LCMS (Method 2): $t_R$=2.745 min, $[M+1]^+$ 321.2. SFC (Method 13): $t_R$=2.351 min, 100%. $^1$H NMR: (400 MHz, CHLOROFORM-d) δ=9.30 (br s, 1H), 8.60 (s, 1H), 8.09 (d, J=8.1 Hz, 1H), 7.91-7.83 (m, 1H), 7.80 (dt, J=0.8, 7.6 Hz, 1H), 7.74-7.65 (m, 1H), 4.94 (dd, J=4.9, 8.9 Hz, 1H), 4.60 (quin, J=8.8 Hz, 1H), 4.10-4.02 (m, 1H), 3.95 (dd, J=4.9, 9.3 Hz, 1H), 2.21-2.13 (m, 1H), 2.12-1.99 (m, 3H), 1.24 (s, 3H), 1.19 (s, 3H).
Example 127: Synthesis of 1-(6,6-difluorospiro[3.3]heptan-2-yl)-3-(isoquinolin-4-yl)-2-oxoimidazolidine-4-carbonitrile (127), (R)-1-(6,6-difluorospiro[3.3]heptan-2-yl)-3-(isoquinolin-4-yl)-2-oxoimidazolidine-4-carbonitrile (127a) and (S)-1-(6,6-difluorospiro[3.3]heptan-2-yl)-3-(isoquinolin-4-yl)-2-oxoimidazolidine-4-carbonitrile (127b)
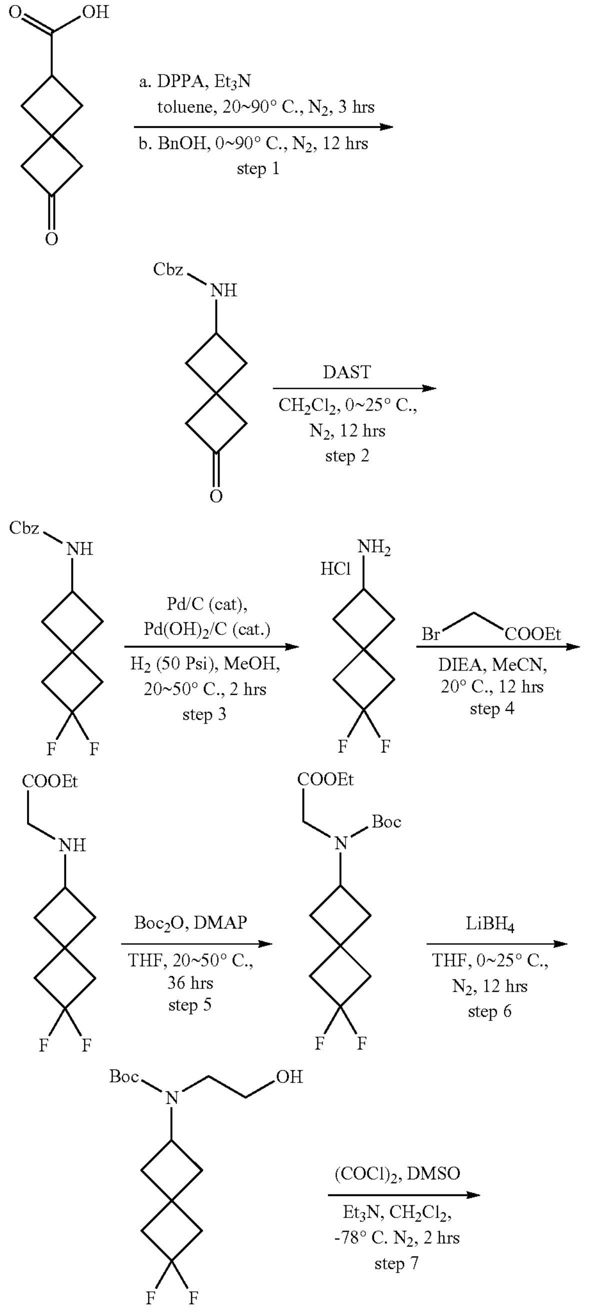
-continued
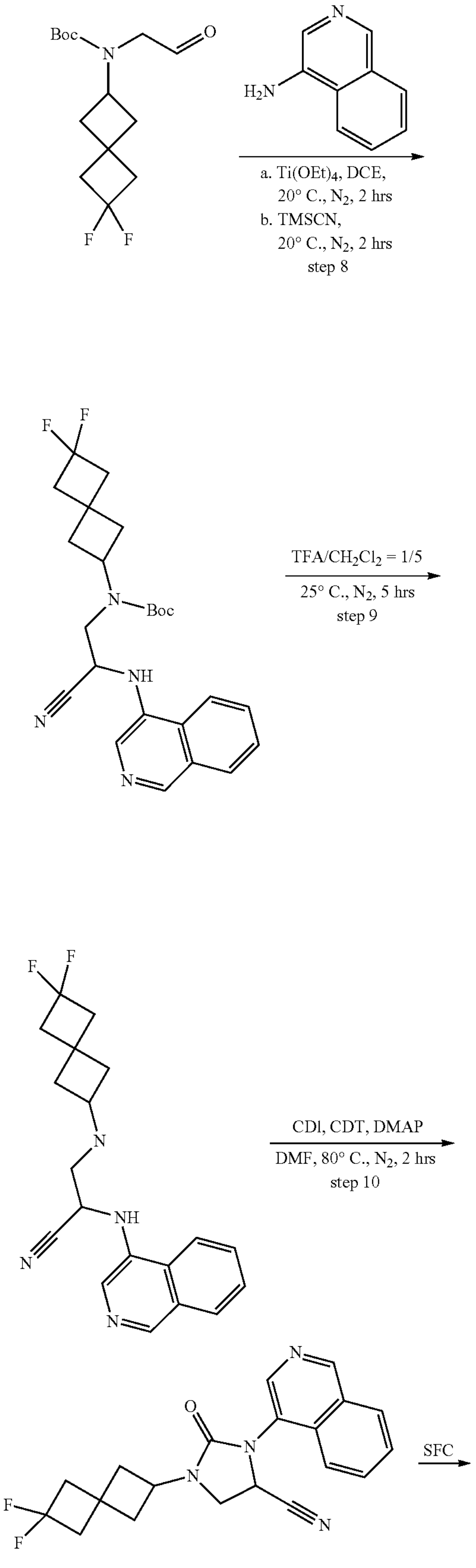
(127)

-continued

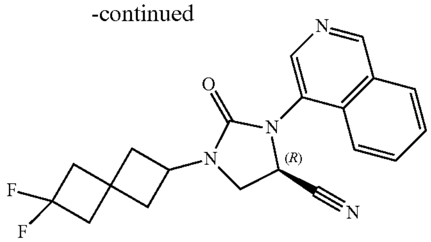

(127a)

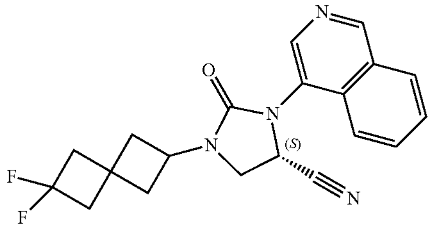

(127b)

Step 1: To a solution of 6-oxospiro[3.3]heptane-2-carboxylic acid (10.0 g, 64.87 mmol, 1.0 eq.), $Et_3N$ (7.9 g, 77.84 mmol, 1.2 eq.) in toluene (250 mL) was added diphenyl phosphoryl azide (21.4 g, 77.84 mmol, 1.2 eq.) dropwise at 20° C. The solution was stirred at 20° C. under $N_2$ for 0.5 hrs and then at 90° C. under $N_2$ for 2.5 hrs. To the solution was added BnOH (8.4 g, 77.84 mmol, 1.2 eq.) dropwise at 0° C. The solution was stirred at 25° C. under $N_2$ for 0.5 hrs and then at 90° C. under $N_2$ for 12 hrs. The reaction was washed with citric acid solution (200 mL), $NaHCO_3$ (200 mL) and brine (200 mL), dried over $Na_2SO_4$, filtered and concentrated under reduced pressure to give crude product. The crude product was purified by flash silica gel chromatography (100 g SepaFlash® Silica Flash Column, Eluent of 20-30% Ethyl acetate/Petroleum ether gradient at 200 mL/min) to give benzyl(6-oxospiro[3.3]heptan-2-yl)carbamate. $^1H$ NMR: (400 MHz, CHLOROFORM-d) δ=7.42-7.29 (m, 5H), 5.09 (s, 2H), 4.36-4.15 (m, 1H), 3.18-3.12 (m, 2H), 3.09-3.04 (m, 2H), 2.65-2.52 (m, 2H), 2.28-2.13 (m, 2H).

Step 2: To a mixture of benzyl(6-oxospiro[3.3]heptan-2-yl)carbamate (10.0 g, 38.57 mmol, 1.0 eq.) in $CH_2Cl_2$ (100 mL) was added DAST (18.6 g, 115.69 mmol, 3.0 eq.) dropwise at 0° C. under $N_2$. The mixture was stirred at 25° C. for 12 hrs under $N_2$. The reaction mixture was quenched with $NaHCO_3$ (200 mL) and extracted with EtOAc (100 mL×2). The combined organic layers were washed with brine (200 mL), dried over $Na_2SO_4$, filtered and concentrated under reduced pressure to give the crude. The crude product was purified by column (Petroleum ether/EtOAc=82/18 to 4/1) to give benzyl(6,6-difluorospiro[3.3]heptan-2-yl)carbamate.

Step 3: To a mixture of $Pd(OH)_2/C$ (2.0 g, cat.) and Pd/C (2.0 g, cat.) in MeOH (100 mL) was added a solution of benzyl(6,6-difluorospiro[3.3]heptan-2-yl)carbamate (16.0 g, 56.87 mmol, 1.0 eq.) in MeOH (100 mL) at 20° C. The mixture was stirred at 50° C. under $H_2$ (50 Psi) for 4 hrs.

The mixture was filtered and HCl/MeOH (4.0 N, 3 mL) was added to the filtrate and the mixture was concentrated to give 6,6-difluorospiro[3.3]heptan-2-amine hydrochloride.

Step 4: To a mixture of 6,6-difluorospiro[3.3]heptan-2-amine hydrochloride (6.0 g, 32.67 mmol, 1.0 eq.) and DIEA (12.7 g, 98.01 mmol, 3.0 eq.) in MeCN (100 mL) was added ethyl 2-bromoacetate (3.8 g, 22.87 mmol, 0.8 eq.) at 20° C. The mixture was stirred at 20° C. for 16 hrs.

The mixture was concentrated to give a residue and the residue was purified by silica column (liquid phase: [A-petroleum ether; B-EtOH/EtOAc=1/3, 0.5% $NH_3H_2O$]B %: 20%-40%) to give ethyl(6,6-difluorospiro[3.3]heptan-2-yl) glycinate. $^1H$ NMR: (400 MHz, CHLOROFORM-d) δ=4.23-4.15 (m, 2H), 3.32 (s, 1H), 2.63-2.44 (m, 4H), 2.35 (ddd, J=2.8, 7.0, 9.6 Hz, 2H), 1.97-1.85 (m, 2H), 1.79-1.56 (m, 2H), 1.31-1.25 (m, 3H).

Step 5: To a mixture of ethyl(6,6-difluorospiro[3.3]heptan-2-yl)glycinate (4.5 g, 19.29 mmol, 1.0 eq.) and $Boc_2O$ (8.5 g, 38.58 mmol, 2.0 eq.) in THE (50 mL) was added DMAP (500 mg, Cat.) at 20° C. The mixture was stirred at 50° C. for 36 hrs. The mixture was concentrated to give a residue and the residue was purified by column (petroleum ether/EtOAc=10/1-5/1) to give ethyl N-(tert-butoxycarbonyl)-N-(6,6-difluorospiro[3.3]heptan-2-yl)glycinate. $^1H$ NMR: (400 MHz, CHLOROFORM-d) δ=4.63-4.43 (m, 1H), 4.19 (q, J=7.1 Hz, 2H), 3.93 (br s, 1H), 3.84 (br s, 1H), 2.62 (br t, J=12.1 Hz, 2H), 2.51 (br t, J=12.3 Hz, 2H), 2.41-2.28 (m, 2H), 2.14 (br s, 2H), 1.48-1.38 (m, 9H), 1.30-1.25 (m, 3H).

Step 6: To a mixture of ethyl N-(tert-butoxycarbonyl)-N-(6,6-difluorospiro[3.3]heptan-2-yl)glycinate (2.0 g, 6.00 mmol, 1.0 eq.) in THE (50 mL) was added $LiBH_4$ (392 mg, 18.0 mmol, 3.0 eq.) in portions under $N_2$ at 0° C. The mixture was stirred at 25° C. under for 12 hrs. The mixture was quenched with acetone (1 mL) at 0° C., diluted with $H_2O$ (40 mL) and citric acid (2.0 g) was added. The mixture was then extracted with EtOAc (20 mL×2) and the combined organic layer was washed with brine (40 mL), dried over $Na_2SO_4$, filtered and concentrated to give a residue. The residue was purified by column (petroleum ether/EtOAc=3/1-2/1) to give tert-butyl(6,6-difluorospiro[3.3]heptan-2-yl)(2-hydroxyethyl)carbamate. $^1H$ NMR: (400 MHz, CHLOROFORM-d) δ=4.31-4.06 (m, 1H), 3.69 (br t, J=5.3 Hz, 2H), 3.44-3.30 (m, 2H), 2.62 (br t, J=12.1 Hz, 2H), 2.53 (br t, J=12.2 Hz, 2H), 2.41-2.30 (m, 2H), 2.27-2.17 (m, 2H), 1.47 (s, 9H).

Step 7: To a mixture of $(COCl)_2$ (914 mg, 7.20 mmol, 1.5 eq.) in $CH_2Cl_2$ (40 mL) was added DMSO (1.1 g, 14.40 mmol, 3.0 eq.) at −78° C. under $N_2$. The mixture was stirred at −78° C. under $N_2$ for 30 mins. To the mixture was added a solution of tert-butyl(6,6-difluorospiro[3.3]heptan-2-yl)(2-hydroxyethyl)carbamate (1.6 g, 4.80 mmol, 1.0 eq.) in $CH_2Cl_2$ (10 mL) at −78° C. under $N_2$. The mixture was stirred at −78° C. under $N_2$ for 30 mins. To the mixture was added $Et_3N$ (2.4 g, 24.00 mmol, 5.0 eq.) at −78° C. under $N_2$. The mixture was stirred at −78° C. under $N_2$ for 1 hr. The mixture was quenched with HCl 0.5 M (50 mL) at 0° C. and extracted with $CH_2Cl_2$ (20 mL×2). The combined organic layer was washed with brine (40 mL), dried over $Na_2SO_4$, filtered and concentrated to give tert-butyl(6,6-difluorospiro[3.3]heptan-2-yl)(2-oxoethyl)carbamate which was used without further purification.

Step 8. To a mixture of tert-butyl(6,6-difluorospiro[3.3]heptan-2-yl)(2-oxoethyl)carbamate (1.5 g, 5.18 mmol, 1.0 eq.) and isoquinolin-4-amine (746 mg, 5.18 mmol, 1.0 eq.) in DCE (20 mL) was added $Ti(OEt)_4$ (2.4 g, 10.36 mmol, 2.0 eq.) at 20° C. under $N_2$. The mixture was stirred at 20° C. for 2 hrs. TMSCN (1.5 g, 15.54 mmol, 3.0 eq.) was added to the reaction dropwise at 20° C. and the mixture stirred at 20° C. for 2 hrs under $N_2$. The reaction was quenched with $H_2O$ (20 mL) and filtered. The filter cake was rinsed with $CH_2Cl_2$ (10 mL×5). Then the filtrate was extracted with $CH_2Cl_2$ (20 mL×2). The combined organic layers were dried over $Na_2SO_4$, filtered and concentrated under reduced pressure to give crude product which was purified by column (Petroleum ether/EtOAc=3/2 to 2/3) to give tert-butyl(2-cyano-2-(isoquinolin-4-ylamino)ethyl)(6,6-difluorospiro[3.3]heptan-2-yl)carbamate. $^1$H NMR: (400 MHz, CHLOROFORM-d) δ=8.82 (s, 1H), 7.99-7.87 (m, 3H), 7.72 (dt, J=1.3, 7.7 Hz, 1H), 7.68-7.62 (m, 1H), 6.67-6.31 (m, 1H), 4.50 (br s, 1H), 4.08 (br s, 1H), 3.81 (dd, J=3.6, 15.0 Hz, 1H), 2.68-2.53 (m, 4H), 2.47-2.41 (m, 2H), 2.37-2.30 (m, 2H), 1.52 (s, 9H).

Step 9. A mixture of tert-butyl(2-cyano-2-(isoquinolin-4-ylamino)ethyl)(6,6-difluorospiro[3.3]heptan-2-yl)carbamate (1.5 g, 3.38 mmol, 1.0 eq.) in $CH_2Cl_2$ (10 mL) and TFA (2 mL) was stirred at 20° C. for 2 hrs. 10% $NaHCO_3$ solution (20 mL) was added and to adjust the pH to 8 and the mixture was stirred for 30 min. The mixture was extracted with $CH_2Cl_2$ (10 mL×2). The combined organic layers were dried over $Na_2SO_4$, filtered and concentrated under reduced pressure to give 3-((6,6-difluorospiro[3.3]heptan-2-yl)amino)-2-(isoquinolin-4-ylamino)propanenitrile which was used without further purification. LCMS (Method 31): $t_R$=0.720 min. [M+1]343.2.

Step 10. A mixture of 3-((6,6-difluorospiro[3.3]heptan-2-yl)amino)-2-(isoquinolin-4-ylamino)propanenitrile (150 mg, 0.44 mmol, 1.0 eq.), CDI (142 mg, 0.88 mmol, 2.0 eq.) CDT (142 mg, 0.88 mmol, 2.0 eq.) and DMAP (20 mg, Cat.) in DMF (5 mL) was stirred at 80° C. under $N_2$ for 2 hrs. The reaction mixture was quenched with water (5 mL) and extracted with EtOAc (5 mL×2). The combined organic layers were washed with brine (5 mL×3), dried over $Na_2SO_4$, filtered and concentrated under reduced pressure to give crude product which was purified by prep-HPLC (column: Phenomenex C18 75 mm×30 mm, 3 μm; liquid phase: [A-10 mM $NH_4HCO_3$ in $H_2O$; B-ACN]B %: 30%-50%, 8 min]) to give racemic 1-(6,6-difluorospiro[3.3]heptan-2-yl)-3-(isoquinolin-4-yl)-2-oxoimidazolidine-4-carbonitrile (127). LCMS (Method 2): $t_R$=2.716 min, $[M+1]^+$ 369.1. $^1$H NMR: (400 MHz, CHLOROFORM-d) δ=9.31 (s, 1H), 8.59 (s, 1H), 8.09 (d, J=8.2 Hz, 1H), 7.86-7.78 (m, 2H), 7.73-7.67 (m, 1H), 4.95 (dd, J=4.8, 8.9 Hz, 1H), 4.52 (quin, J=8.6 Hz, 1H), 4.07-3.99 (m, 1H), 3.92 (dd, J=4.8, 9.3 Hz, 1H), 2.71 (br t, J=12.2 Hz, 2H), 2.66-2.58 (m, 2H), 2.50-2.41 (m, 4H).

Racemic 1-(6,6-difluorospiro[3.3]heptan-2-yl)-3-(isoquinolin-4-yl)-2-oxoimidazolidine-4-carbonitrile was separated by prep-SFC (Column:Chiralpak IH-3,100 mm×4.6 mm, 3 μm; Mobile phase:A: $CO_2$ B:IPA(0.1% IPAm, v/v), 0-2.4 min: 10-50%, 2.4-3.4 min: 50%-50%, 3.4-4 min: 50%-10%) to obtain 2 peaks Peak 1: (R)-1-(6,6-difluorospiro[3.3]heptan-2-yl)-3-(isoquinolin-4-yl)-2-oxoimidazolidine-4-carbonitrile (127a). LCMS (Method 13): $t_R$=2.159 min, $[M+1]^+$ 369.1. SFC (Method 9): $t_R$=1.973 min, 99.93%. $^1$H NMR: (400 MHz, CHLOROFORM-d) δ=9.30 (s, 1H), 8.59 (s, 1H), 8.09 (d, J=8.3 Hz, 1H), 7.87-7.76 (m, 2H), 7.73-7.66 (m, 1H), 4.94 (dd, J=4.8, 8.9 Hz, 1H), 4.52 (quin, J=8.7 Hz, 1H), 4.07-3.99 (m, 1H), 3.92 (dd, J=4.8, 9.3 Hz, 1H), 3.65-3.24 (m, 1H), 2.71 (br t, J=12.1 Hz, 2H), 2.61 (br t, J=12.2 Hz, 2H), 2.51-2.39 (m, 4H).

Peak 2: (S)-1-(6,6-difluorospiro[3.3]heptan-2-yl)-3-(isoquinolin-4-yl)-2-oxoimidazolidine-4-carbonitrile (127b). LCMS (Method 13): $t_R$=2.158 min, $[M+1]^+$ 369.1. SFC (Method 9): $t_R$=2.549 min, 99.90%. $^1$H NMR: (400 MHz, CHLOROFORM-d) δ=9.30 (s, 1H), 8.59 (s, 1H), 8.09 (d, J=8.3 Hz, 1H), 7.87-7.76 (m, 2H), 7.73-7.66 (m, 1H), 4.94 (dd, J=4.8, 8.9 Hz, 1H), 4.52 (quin, J=8.7 Hz, 1H), 4.07-3.99 (m, 1H), 3.92 (dd, J=4.8, 9.3 Hz, 1H), 3.65-3.24 (m, 1H), 2.71 (br t, J=12.1 Hz, 2H), 2.61 (br t, J=12.2 Hz, 2H), 2.51-2.39 (m, 4H).

Example 128: Synthesis of 3-(isoquinolin-4-yl)-2-oxo-1-((1 r,4r)-4-(trifluoromethyl)cyclohexyl)imidazolidine-4-carbonitrile (128), (R)-3-(isoquinolin-4-yl)-2-oxo-1-((1 r,4R)-4-(trifluoromethyl)cyclohexyl)imidazolidine-4-carbonitrile (128a) and (S)-3-(isoquinolin-4-yl)-2-oxo-1-((1 r,4R)-4-(trifluoromethyl)cyclohexyl)imidazolidine-4-carbonitrile (128b)

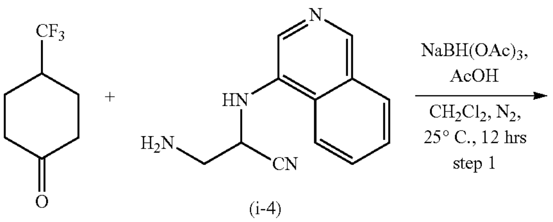

(i-4)

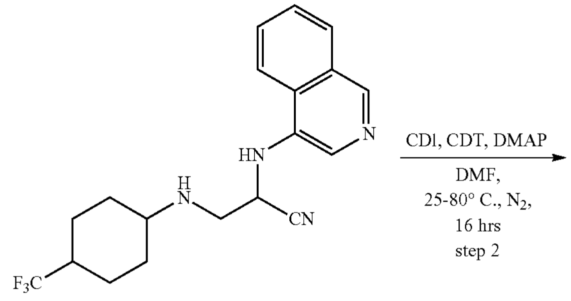

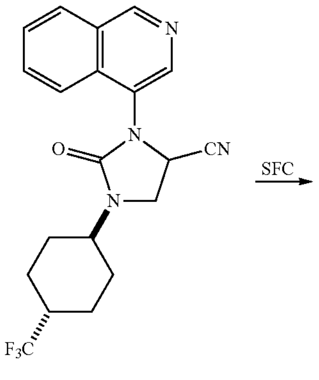

(128)

-continued

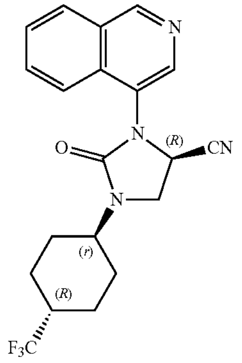

(128a)

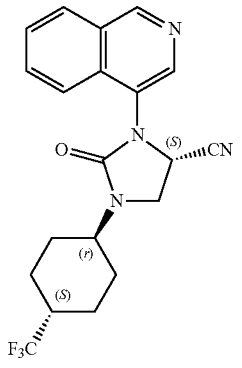

(128b)

Racemic trans-3-(isoquinolin-4-yl)-2-oxo-1-(4-(trifluoromethyl)cyclohexyl)imidazolidine-4-carbonitrile (128) was prepared in a manner similar to Example 120 using 4-(trifluoromethyl)cyclohexan-1-one in place of 3-methylcyclobutan-1-one. The racemate was separated by SFC (column: DAICEL CHIRALPAK AD (250 mm×30 mm, 10 μm); liquid phase: 0.1% $NH_3H_2O$ EtOH B %: 33%-33%, 4 min]) to give two peaks.

Peak 1: (R)-3-(isoquinolin-4-yl)-2-oxo-1-((1 r,4R)-4-(trifluoromethyl)cyclohexyl)imidazolidine-4-carbonitrile (128a). LCMS (Method 13): $t_R$=2.230 min, $[M+1]^+$ 389.1. SFC (Method 16): $t_R$=3.536 min, 100%. $^1H$ NMR: (400 MHz, METHANOL-$d_4$) δ=9.33 (s, 1H), 8.55 (s, 1H), 8.26 (d, J=8.1 Hz, 1H), 8.03 (d, J=8.5 Hz, 1H), 7.96-7.89 (m, 1H), 7.84-7.77 (m, 1H), 5.34 (dd, J=4.1, 8.9 Hz, 1H), 4.16 (t, J=9.3 Hz, 1H), 3.97 (dd, J=4.2, 9.6 Hz, 1H), 3.93-3.85 (m, 1H), 2.44 (td, J=5.1, 10.5 Hz, 1H), 2.16-2.02 (m, 3H), 2.01-1.74 (m, 6H).

Peak 2: (S)-3-(isoquinolin-4-yl)-2-oxo-1-((1 r,4R)-4-(trifluoromethyl)cyclohexyl)imidazolidine-4-carbonitrile (128b). LCMS (Method 13): $t_R$=2.230 min, $[M+1]^+$ 389.1. SFC (Method 16): $t_R$=3.833 min, 99.72%. $^1H$ NMR: (400 MHz, METHANOL-$d_4$) δ=9.31 (s, 1H), 8.53 (s, 1H), 8.24 (d, J=8.3 Hz, 1H), 8.04-7.98 (m, 1H), 7.91 (t, J=7.6 Hz, 1H), 7.79 (t, J=7.6 Hz, 1H), 5.32 (dd, J=4.1, 8.9 Hz, 1H), 4.17-4.10 (m, 1H), 3.95 (dd, J=4.2, 9.6 Hz, 1H), 3.92-3.84 (m, 1H), 2.41 (dt, J=4.8, 10.3 Hz, 1H), 2.14-2.00 (m, 3H), 2.00-1.73 (m, 5H).

Example 129: Synthesis of 3-(isoquinolin-4-yl)-2-oxo-1-(1-((trifluoromethyl)sulfonyl)azetidin-3-yl)imidazolidine-4-carbonitrile (129), (R)-3-(isoquinolin-4-yl)-2-oxo-1-(1-((trifluoromethyl)sulfonyl)azetidin-3-yl)imidazolidine-4-carbonitrile (129a) and (S)-3-(isoquinolin-4-yl)-2-oxo-1-(1-((trifluoromethyl)sulfonyl)azetidin-3-yl)imidazolidine-4-carbonitrile (129b)

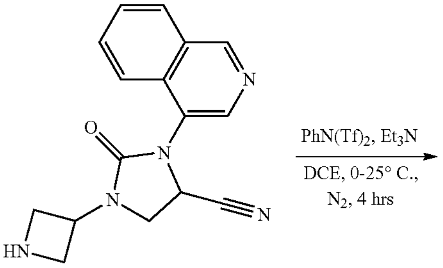

(Int-10)

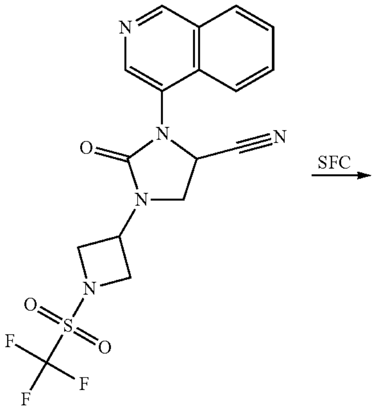

(129)

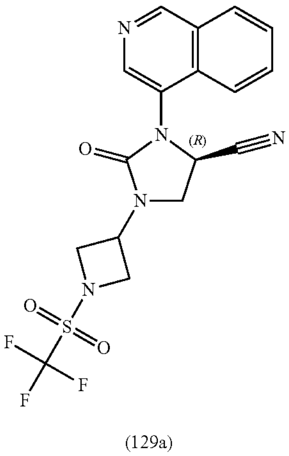

(129a)

-continued

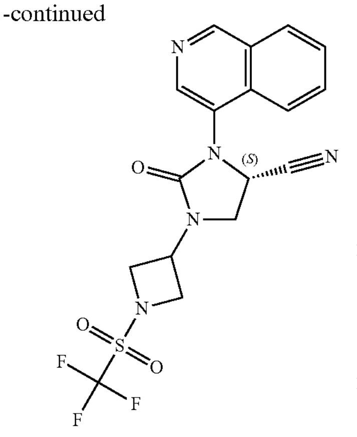

(129b)

To a mixture of 1-(azetidin-3-yl)-3-(isoquinolin-4-yl)-2-oxoimidazolidine-4-carbonitrile (Int-10) (2.0 g, 6.82 mmol, 1.0 eq.) and $Et_3N$ (3.4 g, 34.09 mmol, 5.0 eq.) in DCE (25 mL) was added a solution of N-phenyl-bis(trifluoromethanesulfonimide ($Tf_2NPh$) (2.7 g, 7.50 mmol, 1.1 eq.) in DCE (5 mL) at 0° C. and the reaction stirred at 0-25° C. for 4 hrs under $N_2$. The reaction mixture was poured into water (50 mL) and extracted with $CH_2Cl_2$ (20 mL×3). The combined organic phases were washed with brine (50 mL), dried over $Na_2SO_4$, filtered and concentrated to give crude product. The crude product was first purified by column chromatography on silica gel (petroleum ether/EtOAc=100/0 to 10/90) and then further purified by prep-HPLC (column: Waters Xbridge Prep OBD C18 150 mm×40 mm, 10 μm; liquid phase: [A-10 mM $NH_4HCO_3$ in $H_2O$; B-ACN]B %: 30%-50%, 8 min]) to give racemic 3-(isoquinolin-4-yl)-2-oxo-1-(1-((trifluoromethyl)sulfonyl)azetidin-3-yl)imidazolidine-4-carbonitrile (129). The racemate was separated by chiral SFC (REGIS (s,s) WHELK-01 (250 mm×25 mm, 10 μm); mobile phase: 0.1% $NH_3H_2O$ IPA; B %: 50%-50%, 6 min]) to obtain two peaks.

Peak 1: (R)-3-(isoquinolin-4-yl)-2-oxo-1-(1-((trifluoromethyl)sulfonyl)azetidin-3-yl)imidazolidine-4-carbonitrile (129a). LCMS (Method 31): $t_R$=2.742 min, $[M+1]^+$ 426.1. SFC (Method 17): $t_R$=1.489 min, 100%. $^1$H NMR: (400 MHz, DMSO-$d_6$) δ=9.39 (s, 1H), 8.56 (s, 1H), 8.26 (d, J=8.1 Hz, 1H), 8.01 (d, J=8.3 Hz, 1H), 7.89 (t, J=7.5 Hz, 1H), 7.82-7.74 (m, 1H), 5.56 (dd, J=4.5, 9.0 Hz, 1H), 4.96-4.85 (m, 1H), 4.71-4.61 (m, 2H), 4.54-4.43 (m, 2H), 4.29-4.23 (m, 1H), 4.22-4.15 (m, 1H).

Peak 2: (S)-3-(isoquinolin-4-yl)-2-oxo-1-(1-((trifluoromethyl)sulfonyl)azetidin-3-yl)imidazolidine-4-carbonitrile (129b). LCMS (Method 31): $t_R$=2.736 min, $[M+1]^+$ 426.1. SFC (Method 17): $t_R$=1.645 min, 99.73%. $^1$H NMR: (400 MHz, DMSO-$d_6$) δ=9.40 (s, 1H), 8.56 (s, 1H), 8.27 (d, J=8.1 Hz, 1H), 8.05-7.98 (m, 1H), 7.89 (ddd, J=1.2, 7.0, 8.3 Hz, 1H), 7.79 (dt, J=1.0, 7.5 Hz, 1H), 5.56 (dd, J=4.5, 8.9 Hz, 1H), 4.91 (ddd, J=2.3, 6.1, 8.3 Hz, 1H), 4.72-4.61 (m, 2H), 4.55-4.43 (m, 2H), 4.29-4.23 (m, 1H), 4.22-4.16 (m, 1H).

Example 130: Synthesis of 3-(isoquinolin-4-yl)-1-(1-(methylsulfonyl)azetidin-3-yl)-2-oxoimidazolidine-4-carbonitrile (130), (R)-3-(isoquinolin-4-yl)-1-(1-(methylsulfonyl)azetidin-3-yl)-2-oxoimidazolidine-4-carbonitrile (130a) and (S)-3-(isoquinolin-4-yl)-1-(1-(methylsulfonyl)azetidin-3-yl)-2-oxoimidazolidine-4-carbonitrile (130b)

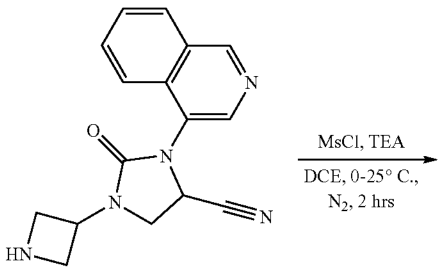

(Int-10)

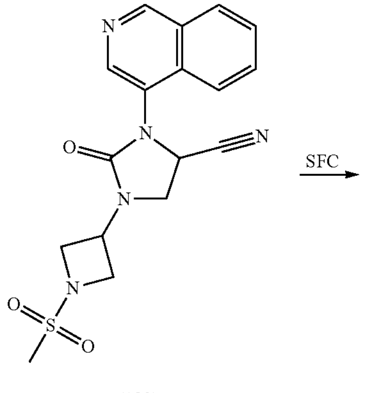

(130)

-continued

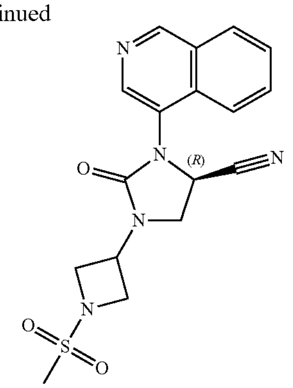

(130a)

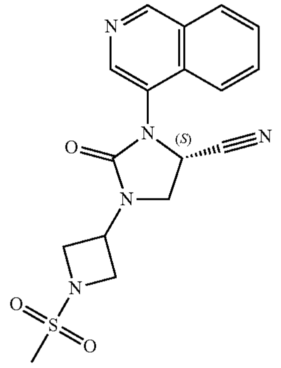

(130b)

Racemic 3-(isoquinolin-4-yl)-1-(1-(methylsulfonyl)azetidin-3-yl)-2-oxoimidazolidine-4-carbonitrile (130) was prepared in a manner similar to Example 129 using methanesulfonyl chloride in place of N-phenyl-bis(trifluoromethanesulfonimide). The racemate was separated by chiral SFC (Column: DAICEL CHIRALPAK IG (250 mm×30 mm, 10 μm); mobile phase: [0.1% $NH_3H_2O$ IPA; B %: 35%-35%, 25 min]) to obtain two peaks. Peak 1 and Peak 2 were further purified by prep-HPLC (column: Waters Xbridge BEH C18 100 mm×30 mm, 10 μm; liquid phase: [A-10 mM $NH_4HCO_3$ in $H_2O$; B-ACN]B %: 20%-50%, 8 min]).

Peak 1: (R)-3-(isoquinolin-4-yl)-1-(1-(methylsulfonyl)azetidin-3-yl)-2-oxoimidazolidine-4-carbonitrile (130a). LCMS (Method 31): $t_R$=2.111 min, $[M+1]^+$ 372.1. SFC (Method 18): $t_R$=3.133 min, 99.92%. $^1H$ NMR: (400 MHz, DMSO-$d_6$) δ=9.39 (s, 1H), 8.56 (s, 1H), 8.26 (d, J=8.1 Hz, 1H), 8.02-7.95 (m, 1H), 7.89 (dt, J=1.1, 7.7 Hz, 1H), 7.81-7.75 (m, 1H), 5.57 (dd, J=4.4, 8.9 Hz, 1H), 4.83-4.72 (m, 1H), 4.30-4.23 (m, 2H), 4.23-4.16 (m, 2H), 4.15-4.09 (m, 1H), 4.09-4.03 (m, 1H), 3.10 (s, 3H).

Peak 2: (S)-3-(isoquinolin-4-yl)-1-(1-(methylsulfonyl)azetidin-3-yl)-2-oxoimidazolidine-4-carbonitrile (130b). LCMS (Method 31): $t_R$=2.109 min, $[M+1]^+$ 372.1. SFC (Method 18): $t_R$=3.569 min, 99.29%. $^1H$ NMR: (400 MHz, DMSO-$d_6$) δ=9.38 (s, 1H), 8.55 (s, 1H), 8.26 (d, J=8.1 Hz, 1H), 8.01-7.95 (m, 1H), 7.89 (t, J=7.2 Hz, 1H), 7.81-7.74 (m, 1H), 5.56 (dd, J=4.5, 9.0 Hz, 1H), 4.82-4.71 (m, 1H), 4.30-4.23 (m, 2H), 4.23-4.15 (m, 2H), 4.12 (t, J=8.6 Hz, 1H), 4.08-4.02 (m, 1H), 3.10 (s, 3H).

Example 131: Synthesis of 1-(1-(cyclopropylsulfonyl)azetidin-3-yl)-3-(isoquinolin-4-yl)-2-oxoimidazolidine-4-carbonitrile (131), (R)-1-(1-(cyclopropylsulfonyl)azetidin-3-yl)-3-(isoquinolin-4-yl)-2-oxoimidazolidine-4-carbonitrile (131a) and (S)-1-(1-(cyclopropylsulfonyl)azetidin-3-yl)-3-(isoquinolin-4-yl)-2-oxoimidazolidine-4-carbonitrile (131b)

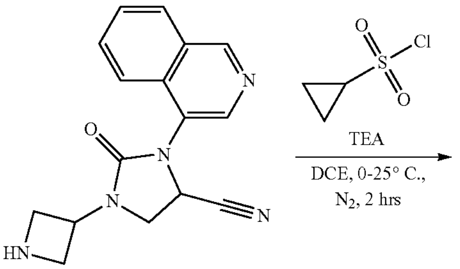

(Int-10)

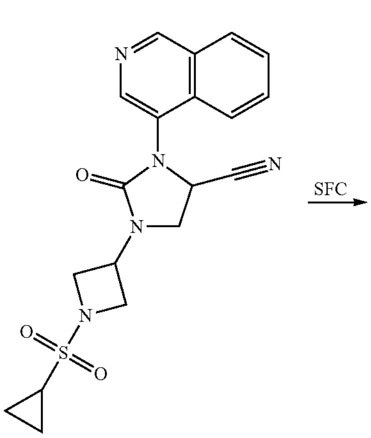

(131)

-continued

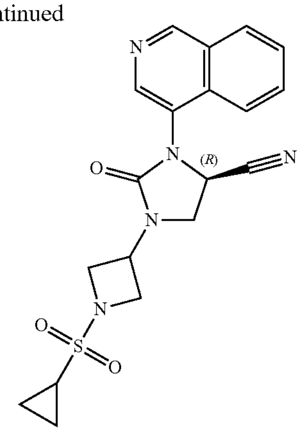

(131a)

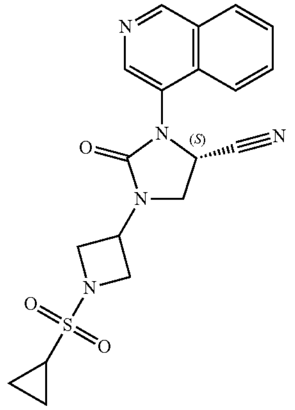

(131b)

Racemic 1-(1-(cyclopropylsulfonyl)azetidin-3-yl)-3-(isoquinolin-4-yl)-2-oxoimidazolidine-4-carbonitrile (131) was prepared in a manner similar to Example 129, using cyclopropanesulfonyl chloride in place of N-phenyl-bis(trifluoromethanesulfonimide). The racemate was first purified by prep-HPLC (column: Waters Xbridge BEH C18 100 mm×30 mm, 10 μm; liquid phase: [A-10 mM $NH_4HCO_3$ in $H_2O$; B-ACN]B %: 20%-50%, 10 min]) and then separated by chiral SFC (Column: DAICEL CHIRALPAK IG (250 mm×30 mm, 10 um); mobile phase: 0.1% $NH_3H_2O$ IPA; B %: 50%-50%, 10 min) to obtain two peaks.

Peak 1: (R)-1-(1-(cyclopropylsulfonyl)azetidin-3-yl)-3-(isoquinolin-4-yl)-2-oxoimidazolidine-4-carbonitrile (131a). LCMS (Method 31): $t_R$=2.282 min, $[M+1]^+$ 398.2. SFC (Method 19): $t_R$=2.200 min, 100%. $^1H$ NMR: (400 MHz, DMSO-$d_6$) δ=9.38 (s, 1H), 8.55 (s, 1H), 8.26 (d, J=8.3 Hz, 1H), 7.99 (d, J=8.3 Hz, 1H), 7.88 (t, J=7.6 Hz, 1H), 7.82-7.75 (m, 1H), 5.55 (br dd, J=4.2, 8.8 Hz, 1H), 4.83-4.74 (m, 1H), 4.35 (br t, J=7.6 Hz, 1H), 4.31-4.23 (m, 2H), 4.20-4.10 (m, 2H), 4.05 (br t, J=8.4 Hz, 1H), 2.87 (br dd, J=3.2, 7.9 Hz, 1H), 1.13-1.04 (m, 2H), 1.03-0.94 (m, 2H)

Peak 2: (S)-1-(1-(cyclopropylsulfonyl)azetidin-3-yl)-3-(isoquinolin-4-yl)-2-oxoimidazolidine-4-carbonitrile (131b). LCMS (Method 31): $t_R$=2.286 min, $[M+1]^+$ 398.2). SFC (Method 19): $t_R$=2.813 min, 99.52%. $^1H$ NMR: (400 MHz, DMSO-$d_6$) δ=9.38 (s, 1H), 8.55 (s, 1H), 8.26 (d, J=8.1 Hz, 1H), 7.99 (d, J=8.3 Hz, 1H), 7.89 (dt, J=1.1, 7.7 Hz, 1H), 7.82-7.75 (m, 1H), 5.55 (dd, J=4.4, 9.1 Hz, 1H), 4.79 (quin, J=7.4 Hz, 1H), 4.35 (dd, J=6.8, 8.6 Hz, 1H), 4.31-4.22 (m, 2H), 4.20-4.10 (m, 2H), 4.05 (t, J=8.4 Hz, 1H), 2.88 (tt, J=4.8, 7.9 Hz, 1H), 1.16-1.05 (m, 2H), 1.04-0.94 (m, 2H).

Example 132: Synthesis of 3-(isoquinolin-4-yl)-1-(1-methylazetidin-3-yl)-2-oxoimidazolidine-4-carbonitrile (132)

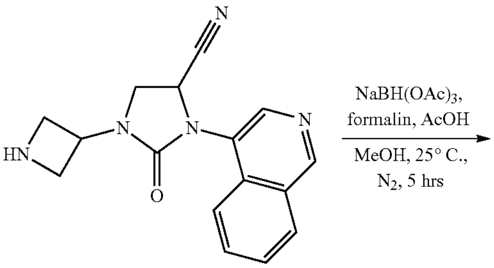

(Int-10)

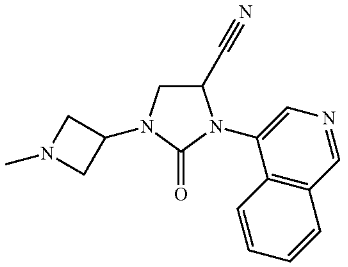

(132)

To a mixture of 1-(azetidin-3-yl)-3-(isoquinolin-4-yl)-2-oxoimidazolidine-4-carbonitrile (Int-10) (100 mg, crude, 0.34 mmol, 1.0 eq.) in MeOH (1 mL) was added formalin (276 mg, 37%, 3.41 mmol, 10.0 eq.), $NaBH(OAc)_3$ (289 mg, 1.36 mmol, 4.0 eq.) and AcOH (0.2 mL) at 25° C. Then the reaction was stirred at 25° C. for 5 hrs under $N_2$. The reaction mixture was directly purified by prep-HPLC (column: Waters Xbridge BEH C18 100 mm×25 mm, 5 μm; liquid phase: [A-10 mM $NH_4HCO_3$ in $H_2O$; B-ACN]B %: 5%-35%, 10 min]) to obtain 3-(isoquinolin-4-yl)-1-(1-methylazetidin-3-yl)-2-oxoimidazolidine-4-carbonitrile (132). LCMS (Method 36): $t_R$=1.370 min, $[M+1]^+$ 308.2. $^1H$ NMR: (400 MHz, DMSO-$d_6$) δ=9.37 (s, 1H), 8.54 (s, 1H), 8.25 (d, J=8.1 Hz, 1H), 7.99-7.95 (m, 1H), 7.87 (t, J=7.5 Hz, 1H), 7.80-7.75 (m, 1H), 5.52 (dd, J=4.3, 8.9 Hz, 1H), 4.43 (t, J=6.7 Hz, 1H), 4.21 (t, J=9.2 Hz, 1H), 4.07 (dd, J=4.3, 9.5 Hz, 1H), 3.48 (t, J=7.2 Hz, 1H), 3.43-3.40 (m, 1H), 3.28-3.23 (m, 1H), 3.20 (t, J=6.8 Hz, 1H), 2.26 (s, 3H).

Example 133: Synthesis of 3-(isoquinolin-4-yl)-2-oxo-1-(1-(2,2,2-trifluoroethyl)azetidin-3-yl)imidazolidine-4-carbonitrile (133),(R)-3-(isoquinolin-4-yl)-2-oxo-1-(1-(2,2,2-trifluoroethyl) azetidin-3-yl) imidazolidine-4-carbonitrile (133a) and (S)-3-(isoquinolin-4-yl)-2-oxo-1-(1-(2,2,2-trifluoroethyl) azetidin-3-yl)imidazolidine-4-carbonitrile (133b)

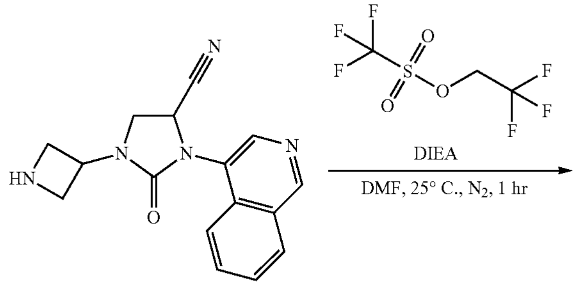

(Int-10)

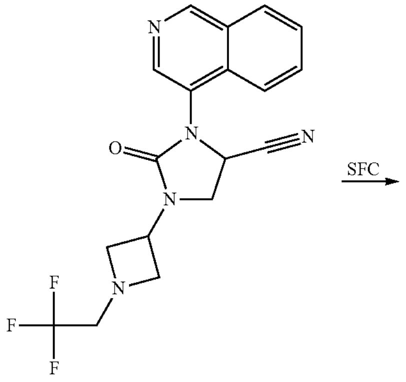

(133)

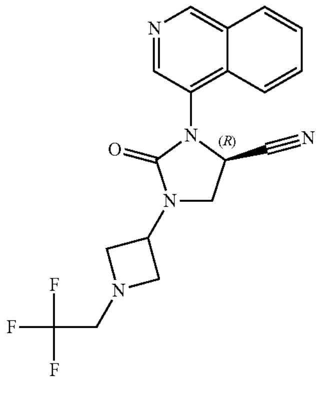

(133a)

-continued

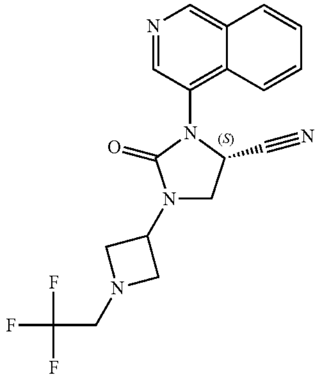

(133b)

To a mixture of 1-(azetidin-3-yl)-3-(isoquinolin-4-yl)-2-oxoimidazolidine-4-carbonitrile (Int-10) (340 mg, 1.16 mmol, 1.0 eq.) in DMF (4 mL) was added 2,2,2-trifluoroethyl trifluoromethanesulfonate (404 mg, 1.74 mmol, 1.5 eq.) and DIEA (449 mg, 3.48 mmol, 3.0 eq.) at 25° C. and the reaction stirred at 25° C. for 1 hr under $N_2$. The reaction mixture was poured into water (10 mL) and extracted with EtOAc (3 mL×3). The combined organic phases were concentrated to give a residue. The residue was purified by column chromatography on silica gel (petroleum ether/EtOAc=100/0 to 10/90) and further purified by prep-TLC (EtOAc) to give racemic to obtain racemic 3-(isoquinolin-4-yl)-2-oxo-1-(1-(2,2,2-trifluoroethyl)azetidin-3-yl)imidazolidine-4-carbonitrile (133). The racemic product was purified by SFC (Column: (s,s) WHELK-01 (250 mm×30 mm, 5 μm); mobile phase: 0.1% $NH_3H_2O$ IPA; B %: 50%-50%, 12 min]) to obtain two peaks.

Peak 1: (R)-3-(isoquinolin-4-yl)-2-oxo-1-(1-(2,2,2-trifluoroethyl)azetidin-3-yl)imidazolidine-4-carbonitrile (133a). LCMS (Method 31): $t_R$=2.474 min, $[M+1]^+$ 376.2. SFC (Method 1): $t_R$=1.484 min, 100%. $^1$H NMR: (400 MHz, METHANOL-$d_4$) δ=9.32 (s, 1H), 8.53 (s, 1H), 8.24 (d, J=8.3 Hz, 1H), 8.03 (d, J=8.5 Hz, 1H), 7.91 (t, J=7.7 Hz, 1H), 7.83-7.74 (m, 1H), 5.38 (dd, J=4.4, 9.0 Hz, 1H), 4.69-4.63 (m, 1H), 4.29 (t, J=9.3 Hz, 1H), 4.15 (dd, J=4.3, 9.6 Hz, 1H), 3.80 (t, J=7.5 Hz, 1H), 3.74 (t, J=7.4 Hz, 1H), 3.64 (td, J=7.2, 11.7 Hz, 2H), 3.22 (q, J=9.6 Hz, 2H).

Peak 2: (S)-3-(isoquinolin-4-yl)-2-oxo-1-(1-(2,2,2-trifluoroethyl)azetidin-3-yl)imidazolidine-4-carbonitrile (133b). LCMS (Method 31): $t_R$=2.458 min, $[M+1]^+$ 376.2. SFC (Method 1): $t_R$=1.649 min, 99.78%. $^1$H NMR: (400 MHz, METHANOL-$d_4$) δ=9.32 (s, 1H), 8.53 (s, 1H), 8.24 (d, J=8.1 Hz, 1H), 8.07-8.00 (m, 1H), 7.93-7.87 (m, 1H), 7.79 (dt, J=1.0, 7.6 Hz, 1H), 5.38 (dd, J=4.3, 9.1 Hz, 1H), 4.65 (quin, J=6.9 Hz, 1H), 4.32-4.25 (m, 1H), 4.15 (dd, J=4.4, 9.6 Hz, 1H), 3.80 (t, J=7.6 Hz, 1H), 3.77-3.70 (m, 1H), 3.64 (td, J=7.2, 11.8 Hz, 2H), 3.22 (q, J=9.7 Hz, 2H).

Example 134: Synthesis of 1-(1-acetylazetidin-3-yl)-3-(isoquinolin-4-yl)-2-oxoimidazolidine-4-carbonitrile (134), (R)-1-(1-acetylazetidin-3-yl)-3-(isoquinolin-4-yl)-2-oxoimidazolidine-4-carbonitrile (134a) and (S)-1-(1-acetylazetidin-3-yl)-3-(isoquinolin-4-yl)-2-oxoimidazolidine-4-carbonitrile (134b)

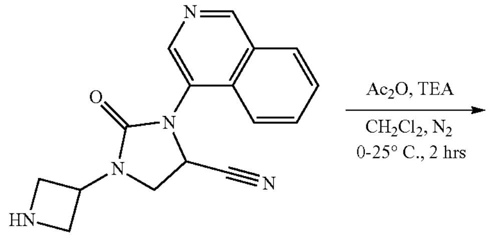

(Int-10)

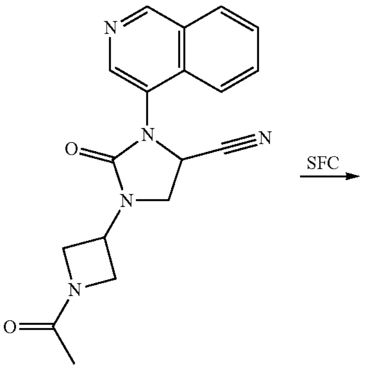

(134)

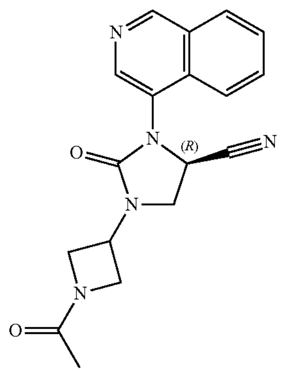

(134a)

-continued

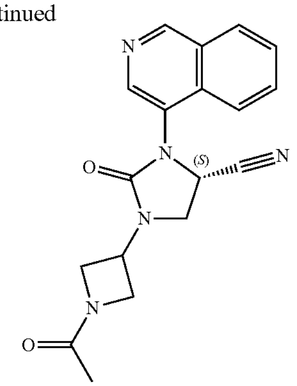

(134b)

To a mixture of 1-(azetidin-3-yl)-3-(isoquinolin-4-yl)-2-oxoimidazolidine-4-carbonitrile (Int-10) (400 mg, 1.36 mmol, 1.0 eq.) and TEA (552 mg, 5.45 mmol, 4.0 eq.) in $CH_2Cl_2$ (3.5 mL) was added a solution of $Ac_2O$ (139 mg, 1.36 mmol, 1.0 eq.) in $CH_2Cl_2$ (0.5 mL) at 0° C. and the reaction stirred at 0-25° C. for 2 hrs under $N_2$. The reaction mixture was poured into water (10 10 mL) and extracted with $CH_2Cl_2$ (5 mL×3). The combined organic phases were washed with brine (10 mL), dried over $Na_2SO_4$, filtered and concentrated to give crude product. The crude product was purified by column chromatography on silica gel (petroleum ether/EtOAc=100/0 to 30/70) to give racemic 1-(1-acetylazetidin-3-yl)-3-(isoquinolin-4-yl)-2-oxoimidazolidine-4-carbonitrile (134). The racemate was purified by chiral SFC (Column: Phenomenex-Cellulose-2 (250 mm×30 mm, 10 μm); mobile phase: [0.1% $NH_3H_2O$ MEOH; B %: 60%-60%, 15 min]) to give two peaks. Peak 1 and Peak 2 were further purified by prep-HPLC (column: Waters Xbridge BEH C18 100 mm×30 mm, 10 μm; liquid phase: [A-10 mM $NH_4HCO_3$ in $H_2O$; B-ACN]B %: 20%-40%, 8 min]).

Peak 1: (R)-1-(1-acetylazetidin-3-yl)-3-(isoquinolin-4-yl)-2-oxoimidazolidine-4-carbonitrile (134a). LCMS (Method 31): $t_R$=1.954 min, $[M+1]^+$ 336.2. SFC (Method 20): $t_R$=2.351 min, 99.96%. $^1H$ NMR: (400 MHz, DMSO-$d_6$) δ=9.38 (s, 1H), 8.55 (d, J=2.4 Hz, 1H), 8.26 (d, J=8.1 Hz, 1H), 7.99 (d, J=8.5 Hz, 1H), 7.91-7.85 (m, 1H), 7.78 (dt, J=1.0, 7.6 Hz, 1H), 5.55 (td, J=4.2, 8.1 Hz, 1H), 4.78-4.69 (m, 1H), 4.47-4.28 (m, 2H), 4.21 (q, J=8.9 Hz, 1H), 4.17-4.00 (m, 3H), 1.80 (d, J=3.1 Hz, 3H).

Peak 2: (S)-1-(1-acetylazetidin-3-yl)-3-(isoquinolin-4-yl)-2-oxoimidazolidine-4-carbonitrile (134b). LCMS (Method 31): $t_R$=1.957 min, $[M+1]^+$ 336.2. SFC (Method 20): $t_R$=3.868 min, 99.95%. $^1H$ NMR: (400 MHz, DMSO-$d_6$) δ=9.38 (s, 1H), 8.55 (d, J=2.4 Hz, 1H), 8.26 (d, J=8.1 Hz, 1H), 7.99 (d, J=8.5 Hz, 1H), 7.88 (dt, J=1.1, 7.6 Hz, 1H), 7.81-7.76 (m, 1H), 5.55 (td, J=4.1, 8.2 Hz, 1H), 4.78-4.69 (m, 1H), 4.46-4.28 (m, 2H), 4.21 (q, J=8.9 Hz, 1H), 4.17-4.00 (m, 3H), 1.80 (d, J=3.1 Hz, 3H).

Example 135: Synthesis of 1-(1-cyclopropylazetidin-3-yl)-3-(isoquinolin-4-yl)-2-oxoimidazolidine-4-carbonitrile (135)

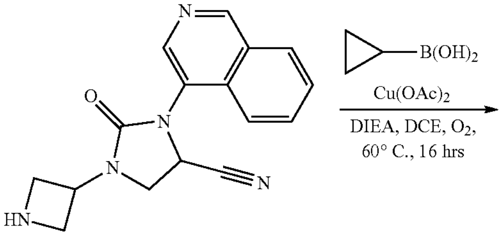

(Int-10)

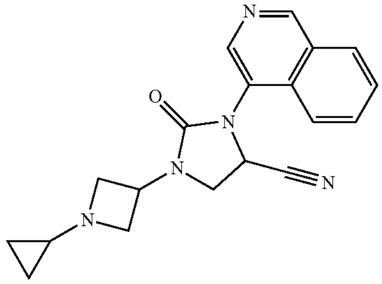

(135)

A mixture of 1-(azetidin-3-yl)-3-(isoquinolin-4-yl)-2-oxoimidazolidine-4-carbonitrile (Int-10) (200 mg, 0.68 mmol, 1.0 eq.), cyclopropylboronic acid (117 mg, 1.36 mmol, 2.0 eq.), $Cu(OAc)_2$ (248 mg, 1.36 mmol, 2.0 eq.) and DIEA (176 mg, 1.36 mmol, 2.0 eq.) in DCE (5 mL) was stirred at 600 C for 16 hrs under $O_2$ (15 Psi). The reaction mixture was filtered, and the filtrate was concentrated to give crude product. The crude was purified by non-aqueous system (column: NP-2; liquid phase: [A-Heptane; B-EtOH]B %: 20%-95%, 15 min]) to obtain racemic 1-(1-cyclopropylazetidin-3-yl)-3-(isoquinolin-4-yl)-2-oxoimidazolidine-4-carbonitrile (135) which was further purified by prep-HPLC (column: Waters Xbridge BEH C18 100 mm×30 mm, 10 μm; liquid phase: [A-10 mM $NH_4HCO_3$ in $H_2O$; B-ACN]B %: 15%-45%, 10 min]). LCMS (Method 17): $t_R$=2.305 min, $[M+1]^+$ 334.2. $^1H$ NMR: (400 MHz, CHLOROFORM-d) δ=9.31 (s, 1H), 8.60 (s, 1H), 8.09 (d, J=8.1 Hz, 1H), 7.88-7.84 (m, 1H), 7.83-7.78 (m, 1H), 7.73-7.67 (m, 1H), 4.97 (dd, J=4.7, 8.8 Hz, 1H), 4.67 (td, J=6.3, 12.7 Hz, 1H), 4.24-4.17 (m, 1H), 4.14-4.08 (m, 1H), 3.76-3.60 (m, 2H), 3.51 (td, 2H), 1.99-1.86 (m, 1H), 0.45 (br d, 4H).

Example 136: Synthesis of 1-(1-cyclopropylazetidin-3-yl)-3-(isoquinolin-4-yl)-2-oxoimidazolidine-4-carbonitrile (135), (R)-1-(1-cyclopropylazetidin-3-yl)-3-(isoquinolin-4-yl)-2-oxoimidazolidine-4-carbonitrile (136a) and (S)-1-(1-cyclopropylazetidin-3-yl)-3-(isoquinolin-4-yl)-2-oxoimidazolidine-4-carbonitrile (136b)

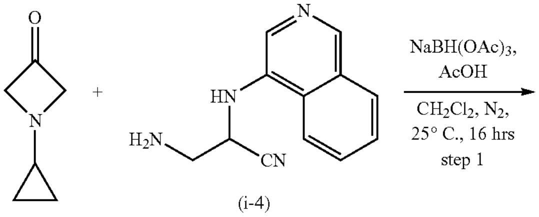

(i-4)

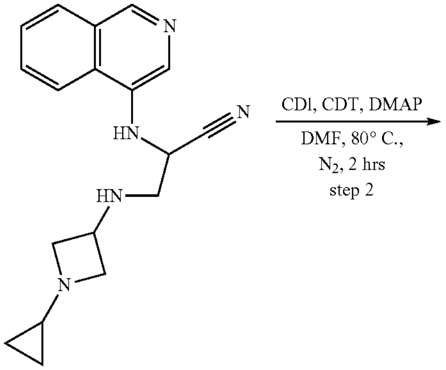

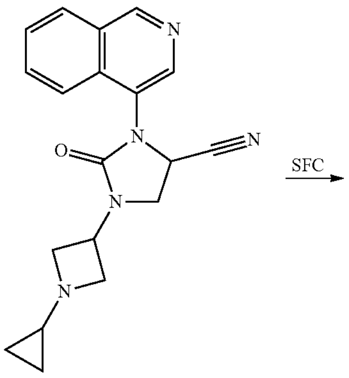

(135)

-continued

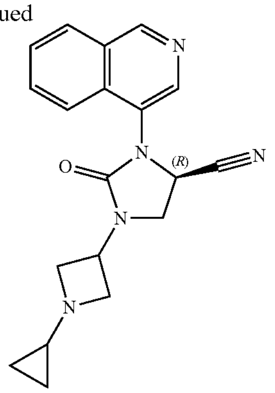

(136a)

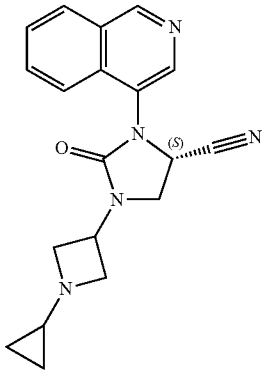

(136b)

Racemic 1-(1-cyclopropylazetidin-3-yl)-3-(isoquinolin-4-yl)-2-oxoimidazolidine-4-carbonitrile (135) was prepared in a manner similar to Example 120, using 1-cyclopropylazetidin-3-one in place of 3-methylcyclobutan-1-one. The racemate was separated by SFC (column: (DAICEL CHIRALPAK IG (250 mm×30 mm, 10 μm); liquid phase: [Neu-EtOH]; B %: 40%-40%, 5 min]) to obtain two peaks.

Peak 1: (R)-1-(1-cyclopropylazetidin-3-yl)-3-(isoquinolin-4-yl)-2-oxoimidazolidine-4-carbonitrile (136a). LCMS (Method 31): $t_R$=2.220 min, $[M+1]^+$ 334.1, SFC (Method 1): $t_R$=1.298 min, 100.0%, H NMR: (400 MHz, METHANOL-d4) δ=9.32 (s, 1H), 8.53 (s, 1H), 8.24 (d, J=8.1 Hz, 1H), 8.03 (d, J=8.4 Hz, 1H), 7.94-7.86 (m, 1H), 7.83-7.75 (m, 1H), 5.37 (dd, J=4.4, 9.0 Hz, 1H), 4.56 (quin, J=7.3 Hz, 1H), 4.30-4.19 (m, 1H), 4.12 (dd, J=4.4, 9.5 Hz, 1H), 3.75-3.51 (m, 4H), 2.05 (tt, J=3.5, 6.8 Hz, 1H), 0.51-0.4s3 (m, 2H), 0.43-0.33 (m, 2H).

Peak 2: (S)-1-(1-cyclopropylazetidin-3-yl)-3-(isoquinolin-4-yl)-2-oxoimidazolidine-4-carbonitrile (136b). LCMS (Method 31): $t_R$=2.217 min, $[M+1]^+$ 334.1, SFC (Method 1): $t_R$=1.429 min, 98.9%, HNMR: (400 MHz, METHANOL-d4) δ=9.33 (br s, 1H), 8.54 (br s, 1H), 8.23 (d, J=8.3 Hz, 1H), 8.02 (d, J=8.4 Hz, 1H), 7.90 (dt, J=0.9, 7.7 Hz, 1H), 7.83-7.73 (m, 1H), 5.37 (dd, J=4.4, 9.0 Hz, 1H), 4.56 (quin, J=7.3 Hz, 1H), 4.24 (t, J=9.3 Hz, 1H), 4.12 (dd, J=4.4, 9.6 Hz, 1H), 3.76-3.47 (m, 4H), 2.04 (tt, J=3.5, 6.7 Hz, 1H), 0.55-0.44 (m, 2H), 0.43 (br s, 1H), 0.43-0.33 (m, 1H).

Example 137: Synthesis of 3-(isoquinolin-4-yl)-2-oxo-1-(3-(trifluoromethyl)bicyclo[1.1.1]pentan-1-yl)imidazolidine-4-carbonitrile (137); (R)-3-(isoquinolin-4-yl)-2-oxo-1-(3-(trifluoromethyl)bicyclo[1.1.1]pentan-1-yl)imidazolidine-4-carbonitrile (137a) and (S)-3-(isoquinolin-4-yl)-2-oxo-1-(3-(trifluoromethyl)bicyclo[1.1.1]pentan-1-yl)imidazolidine-4-carbonitrile (137b)

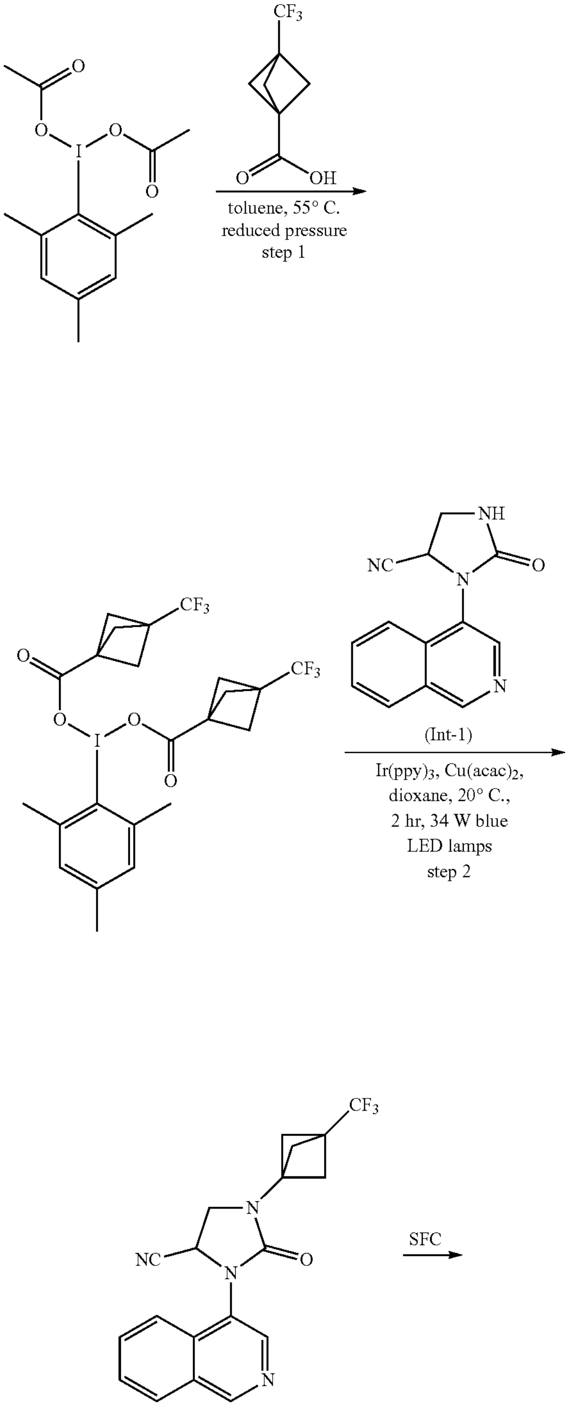

(137)

-continued

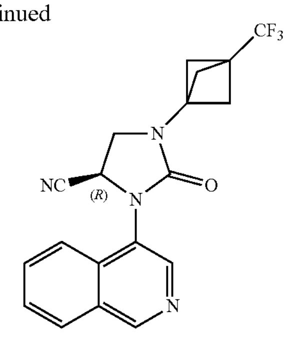

(137a)

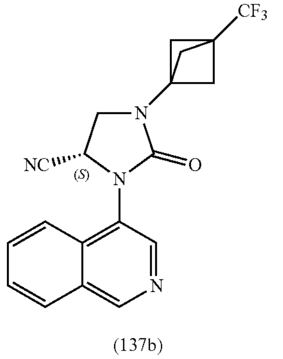

(137b)

Step 1. A flask was charged with 3-(trifluoromethyl) bicyclo[1.1.1]pentane-1-carboxylic acid (913 mg, 5.07 mmol, 2.05 eq.), mesityl-$\lambda^3$-iodanediyl diacetate (900 mg, 2.47 mmol, 1.00 eq.) and toluene (135 mL). The flask was attached to a rotary evaporator with the water bath heated to 55° C. and the volatiles were removed over a time period of ~10 min. A second 90 mL aliquot of toluene was added to the flask and the evaporation step was repeated. The evaporation step was repeated two more times with 75 mL toluene each time. After further removal of residual toluene under high-vacuum, mesityl-$\lambda^3$-iodanediyl bis(3-(trifluoromethyl) bicyclo[1.1.1]pentane-1-carboxylate) was obtained. $^1$H NMR: (400 MHz, CHLOROFORM-d) δ=7.10 (s, 2H), 2.70 (s, 6H), 2.39 (s, 3H), 2.12 (s, 12H).

Step 2. A solution of 3-(isoquinolin-4-yl)-2-oxoimidazolidine-4-carbonitrile (Int-1) (200 mg, 0.84 mmol, 1.0 eq.), mesityl-$\lambda^3$-iodanediyl bis(3-(trifluoromethyl)bicyclo[1.1.1] pentane-1-carboxylate) (507 mg, 0.84 mmol, 1.0 eq.), $Ir(ppy)_3$ (13 mg, 0.02 mmol, 0.02 eq.), $Cu(acac)_2$ (110 mg, 0.42 mmol, 0.5 eq.) and dioxane (12 mL) was degassed by sparging with nitrogen for 5 minutes and irradiated using 34 W blue LED lamps (3 cm away, with cooling fan to keep the reaction at 20° C.) for 6 hrs while stirring. The solution was poured into water, extracted with EtOAc, the combined organic layers were washed with brine and dried over $Na_2SO_4$. The mixture was then stirred with LS_2000 thiourea resin (10.0 g) at 25° C. for 2 hr. Then the mixture was filtered and the filtrate was concentrated to give the crude product. The crude product was purified by MPLC (petroleum ether/EtOAc=100%-0%) to give racemic 3-(isoquinolin-4-yl)-2-oxo-1-(3-(trifluoromethyl)bicyclo[1.1.1]pentan-1-yl)imidazolidine-4-carbonitrile (137). The racemic product was purified by chiral SFC (Column: ChiralPak IH, 250 mm×30 mm, 10 μm); Mobile phase: A for $CO_2$ and B for ACN ((0.1% IPAm)); Gradient: B %=15% isocratic elution mode; Flow rate: 70 g/min; Wavelength: 220 nm; Column temperature: 35 degrees centigrade; System back pressure: 120 bar) to give two peaks.

Peak 1: (R)-3-(isoquinolin-4-yl)-2-oxo-1-(3-(trifluoromethyl)bicyclo[1.1.1]pentan-1-yl)imidazolidine-4-carbonitrile (137a). LCMS (Method 1): $t_R$=2.25 min, $[M+1]^+$ 373.1. SFC (Method 13): $t_R$=1.28 min, 99.9%. $^1$H NMR: (400 MHz, DMSO-d6) δ=9.38 (s, 1H), 8.55 (s, 1H), 8.26 (d, J=8.1 Hz, 1H), 7.99-7.94 (m, 1H), 7.89 (t, J=7.6 Hz, 1H), 7.82-7.75 (m, 1H), 5.51 (dd, J=4.2, 8.9 Hz, 1H), 4.06 (t, J=9.3 Hz, 1H), 3.92 (dd, J=4.1, 9.5 Hz, 1H), 2.43-2.32 (m, 6H).

Peak 2: (S)-3-(isoquinolin-4-yl)-2-oxo-1-(3-(trifluoromethyl)bicyclo[1.1.1]pentan-1-yl)imidazolidine-4-carbonitrile (137b). LCMS (Method 1): $t_R$=2.25 min, $[M+1]^+$ 373.1. SFC (Method 13): $t_R$=1.46 min, 99.6%. $^1$H NMR: (400 MHz, DMSO-d6) δ=9.38 (s, 1H), 8.55 (s, 1H), 8.26 (d, J=8.1 Hz, 1H), 8.01-7.93 (m, 1H), 7.90 (dt, J=1.1, 7.6 Hz, 1H), 7.82-7.76 (m, 1H), 5.50 (dd, J=4.1, 9.0 Hz, 1H), 4.06 (t, J=9.3 Hz, 1H), 3.92 (dd, J=4.1, 9.5 Hz, 1H), 2.43-2.33 (m, 6H).

Example 138. 1-(4,4-difluorocyclohexyl)-3-(isoquinolin-4-yl)-2-oxoimidazolidine-4-carbonitrile (138), (R)-1-(4,4-difluorocyclohexyl)-3-(isoquinolin-4-yl)-2-oxoimidazolidine-4-carbonitrile (138a) and (S)-1-(4,4-difluorocyclohexyl)-3-(isoquinolin-4-yl)-2-oxoimidazolidine-4-carbonitrile (138b)

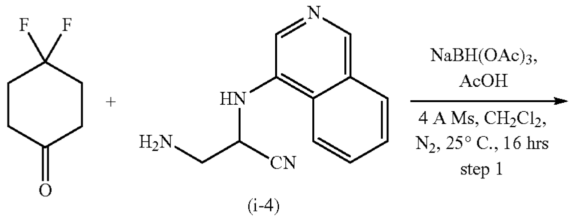

(i-4)

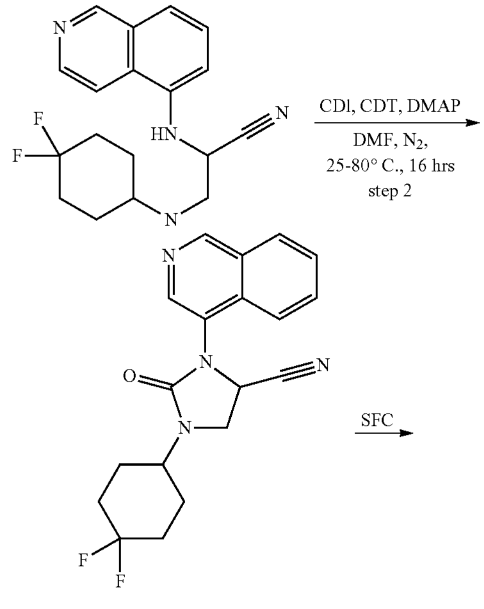

(138)

-continued

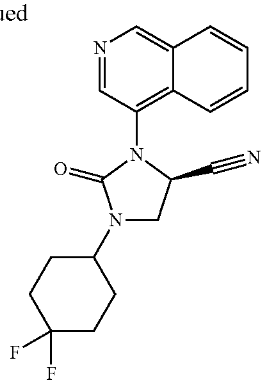

(138a)

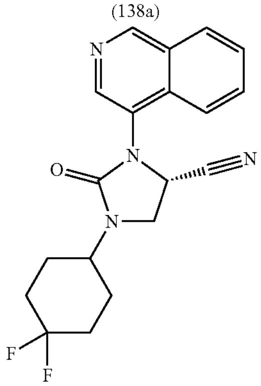

(138b)

Racemic 1-(4,4-difluorocyclohexyl)-3-(isoquinolin-4-yl)-2-oxoimidazolidine-4-carbonitrile (138) was prepared in a manner similar to Example 120, using 4,4-difluorocyclohexan-1-one in place of 3-methylcyclobutan-1-one. The racemate was separated by chiral SFC (column: ChiralPak IH, 250 mm×30 mm, 10 μm; liquid phase: [Neu-ACN]B %: [45%-45%, 5 min]) to give two peaks.

Peak 1 was further purified by prep-HPLC (column: Phenomenex Luna C18 200 mm×40 mm, μm; liquid phase: [water (FA)-ACN]B %: [15%-45%, 8 min]) to give (R)-1-(4,4-difluorocyclohexyl)-3-(isoquinolin-4-yl)-2-oxoimidazolidine-4-carbonitrile (145a) and Peak 2 was was further purified by prep-HPLC (column: Phenomenex Luna C18 200*40 mm*10 um; liquid phase: [water (FA)-ACN]B %: [25%-50%, 8 min]) to give (S)-1-(4,4-difluorocyclohexyl)-3-(isoquinolin-4-yl)-2-oxoimidazolidine-4-carbonitrile (145b).

Peak 1: (R)-1-(4,4-difluorocyclohexyl)-3-(isoquinolin-4-yl)-2-oxoimidazolidine-4-carbonitrile (138a). LCMS (Method 1): $t_R$=2.06 min, $[M+1]^+$ 357.1. SFC (Method 13): $t_R$=0.52 min, 100%. $^1$H NMR: (400 MHz, DMSO-d6) δ=9.37 (s, 1H), 8.54 (s, 1H), 8.25 (d, J=8.1 Hz, 1H), 7.96-7.92 (m, 1H), 7.90-7.85 (m, 1H), 7.78 (dt, J=1.1, 7.5 Hz, 1H), 5.49 (dd, J=4.3, 8.8 Hz, 1H), 4.03 (t, J=9.2 Hz, 1H), 3.88 (dd, J=4.3, 9.5 Hz, 2H), 2.15-1.77 (m, 8H)

Peak 2: (S)-1-(4,4-difluorocyclohexyl)-3-(isoquinolin-4-yl)-2-oxoimidazolidine-4-carbonitrile (138b). LCMS (Method 1): $t_R$=2.06 min, $[M+1]^+$ 357.1. SFC (Method 13): $t_R$=0.80 min, 100%. $^1$H NMR: (400 MHz, DMSO-$d_6$) δ=9.37 (s, 1H), 8.54 (s, 1H), 8.25 (d, J=8.1 Hz, 1H), 7.96-7.92 (m, 1H), 7.90-7.85 (m, 1H), 7.78 (dt, J=1.1, 7.5 Hz, 1H), 5.49 (dd, J=4.3, 8.8 Hz, 1H), 4.03 (t, J=9.2 Hz, 1H), 3.89 (dd, J=4.3, 9.5 Hz, 2H), 2.16-1.77 (m, 8H)

Example 139: 1-(3-fluorobicyclo[1.1.1]pentan-1-yl)-3-(isoquinolin-4-yl)-2-oxoimidazolidine-4-carbonitrile (139a), (R)-1-(3-fluorobicyclo[1.1.1]pentan-1-yl)-3-(isoquinolin-4-yl)-2-oxoimidazolidine-4-carbonitrile (139a) and (S)-1-(3-fluorobicyclo[1.1.1]pentan-1-yl)-3-(isoquinolin-4-yl)-2-oxoimidazolidine-4-carbonitrile (139b)

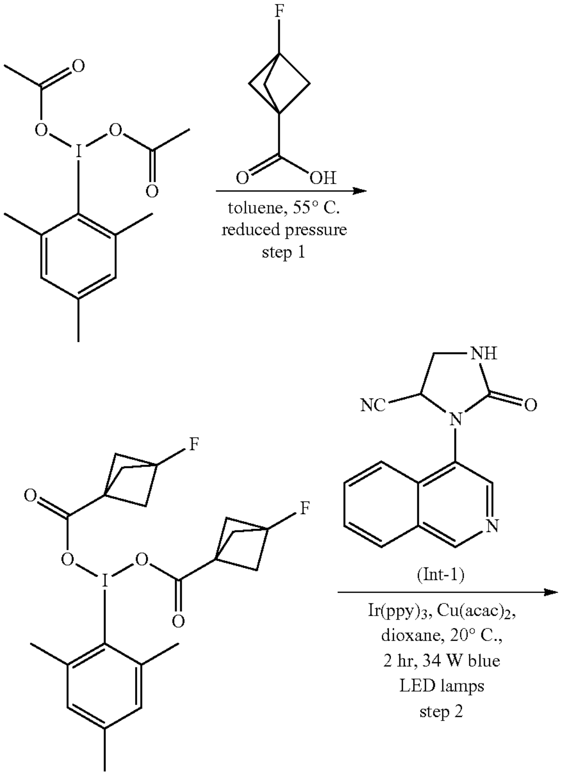

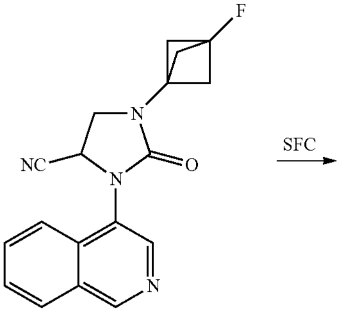

(139)

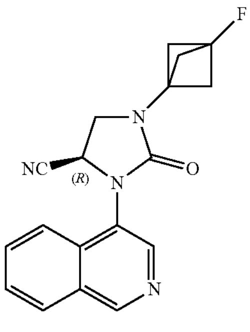

(139a)

-continued

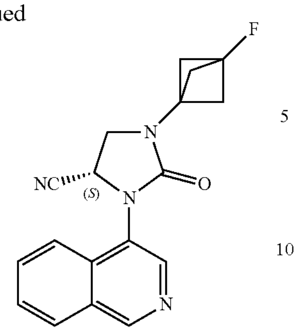

(139b)

Racemic 1-(3-fluorobicyclo[1.1.1]pentan-1-yl)-3-(isoquinolin-4-yl)-2-oxoimidazolidine-4-carbonitrile (139) were prepared in a similar manner to Example 144 using 3-fluorobicyclo[1.1.1]pentane-1-carboxylic acid in place of 3-(trifluoromethyl)bicyclo[1.1.1]pentane-1-carboxylic acid. Achiral purification was achieved by flash column chromatography (petroleum ether/EtOAc=10/1 to 0/1), followed by trituration (petroleum ether/EtOAc=10/1). Chiral separation of the racemate by SFC (column: ChiralPak IH, 250*30 mm, 10 um; liquid phase: [A: $CO_2$ B: ACN: 0.25%-0.25%, 20 min]) to give 2 peaks.

Peak 1: (R)-1-(3-fluorobicyclo[1.1.1]pentan-1-yl)-3-(isoquinolin-4-yl)-2-oxoimidazolidine-4-carbonitrile (139a). LCMS (Method 31): $t_R$=2.51 min, M+1 (323.2); SFC (Method 13): $t_R$=1.55 min, 100.0%; $^1$H NMR: (400 MHz, DMSO-d6) δ=9.38 (s, 1H), 8.55 (s, 1H), 8.26 (d, J=8.1 Hz, 1H), 7.99-7.93 (m, 1H), 7.93-7.85 (m, 1H), 7.78 (td, J=7.5, 1.0 Hz, 1H), 5.50 (dd, J=8.9, 4.1 Hz, 1H), 4.03 (dd, J=9.5, 8.9 Hz, 1H), 3.89 (dd, J=4.1, 9.5 Hz, 1H), 2.49-2.43 (m, 6H).

Peak 2: (S)-1-(3-fluorobicyclo[1.1.1]pentan-1-yl)-3-(isoquinolin-4-yl)-2-oxoimidazolidine-4-carbonitrile (139b). LCMS (Method 31): $t_R$=2.51 min, M+1 (323.2); SFC (Method 13): $t_R$=1.74 min, 100.0%; $^1$H NMR: (400 MHz, DMSO-d6) δ=9.38 (s, 1H), 8.55 (s, 1H), 8.26 (d, J=8.1 Hz, 1H), 7.99-7.93 (m, 1H), 7.93-7.85 (m, 1H), 7.78 (td, J=7.5, 1.0 Hz, 1H), 5.50 (dd, J=8.9, 4.1 Hz, 1H), 4.03 (dd, J=9.5, 8.9 Hz, 1H), 3.89 (dd, J=4.1, 9.5 Hz, 1H), 2.49-2.43 (m, 6H).

Example 140: 3-(isoquinolin-4-yl)-1-neopentyl-2-oxoimidazolidine-4-carbonitrile (140), (R)-3-(isoquinolin-4-yl)-1-neopentyl-2-oxoimidazolidine-4-carbonitrile (140a) and (S)-3-(isoquinolin-4-yl)-1-neopentyl-2-oxoimidazolidine-4-carbonitrile (140b)

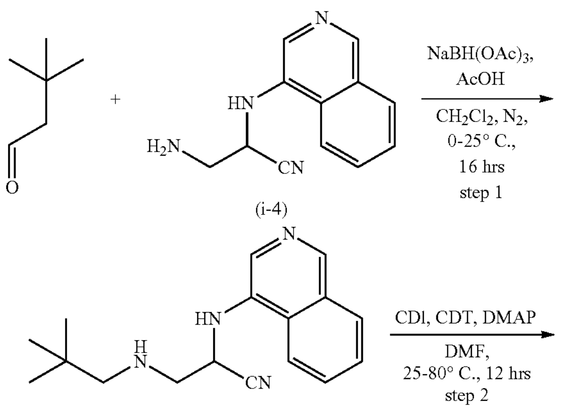

(i-4)

-continued

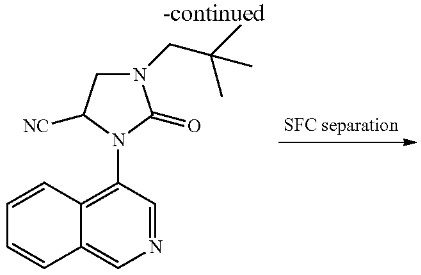

(140)

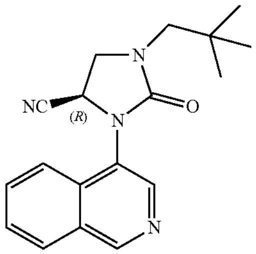

(140a)

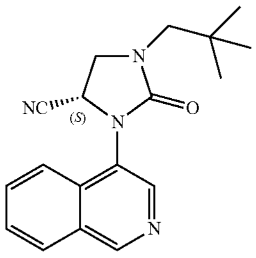

(140b)

Racemic 3-(isoquinolin-4-yl)-1-neopentyl-2-oxoimidazolidine-4-carbonitrile (140) was prepared in a similar manner to Example 127 using 3,3-dimethylbutanal in place of 3-methylcyclobutan-1-one. Achiral purification was achieved using MPLC (Petroleum ether/Ethyl acetate=I/O to 0/1, 40 mL/min). Chiral separation of the racemate by SFC (column: DAICEL CHIRALCEL OD (250 mm×30 mm, 10 μm); liquid phase: [Neu-ACN]B %: 27%-27%, 6 min]) gave 2 peaks.

Peak 1: (S)-3-(isoquinolin-4-yl)-1-neopentyl-2-oxoimidazolidine-4-carbonitrile (140b). LCMS (Method 13): $t_R$=2.12 min, M+1(309.1); SFC (Method 46): $t_R$=3.24 min, 99.8%; $^1$H NMR: (400 MHz, CHLOROFORM-d) δ=9.30 (s, 1H), 8.62 (s, 1H), 8.08 (d, J=8.2 Hz, 1H), 7.88-7.83 (m, 1H), 7.83-7.77 (m, 1H), 7.73-7.66 (m, 1H), 4.92 (dd, J=8.4, 4.3 Hz, 1H), 4.12-4.05 (m, 1H), 4.04-4.00 (m, 1H), 3.33 (d, J=14.1 Hz, 1H), 2.97 (d, J=14.1 Hz, 1H), 1.08 (s, 9H)

Peak 2: (R)-3-(isoquinolin-4-yl)-1-neopentyl-2-oxoimidazolidine-4-carbonitrile (140a). LCMS (Method 13): $t_R$=2.12 min, M+1(309.1); SFC (Method 46): $t_R$=3.50 min, 99.5%; $^1$H NMR: (400 MHz, CHLOROFORM-d) δ=9.30 (s, 1H), 8.62 (s, 1H), 8.08 (d, J=8.2 Hz, 1H), 7.88-7.83 (m, 1H), 7.83-7.77 (m, 1H), 7.73-7.66 (m, 1H), 4.92 (dd, J=8.4, 4.3 Hz, 1H), 4.12-4.05 (m, 1H), 4.04-4.00 (m, 1H), 3.33 (d, J=14.1 Hz, 1H), 2.97 (d, J=14.1 Hz, 1H), 1.08 (s, 9H).

Example 141: 1-(3,3-difluorocyclopentyl)-3-(isoquinolin-4-yl)-2-oxoimidazolidine-4-carbonitrile (141), (R)-1-((R or S)-3,3-difluorocyclopentyl)-3-(isoquinolin-4-yl)-2-oxoimidazolidine-4-carbonitrile (141a); (R)-1-((R or S)-3,3-difluorocyclopentyl)-3-(isoquinolin-4-yl)-2-oxoimidazolidine-4-carbonitrile (141b); (S)-1-((R or S)-3,3-difluorocyclopentyl)-3-(isoquinolin-4-yl)-2-oxoimidazolidine-4-carbonitrile (141c); (S)-1-((R or S)-3,3-difluorocyclopentyl)-3-(isoquinolin-4-yl)-2-oxoimidazolidine-4-carbonitrile (141d)

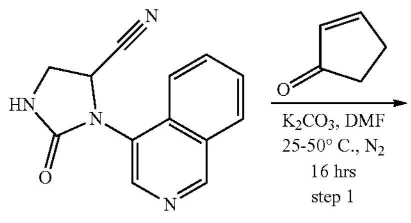

(Int-1)

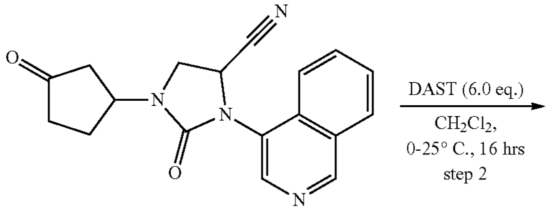

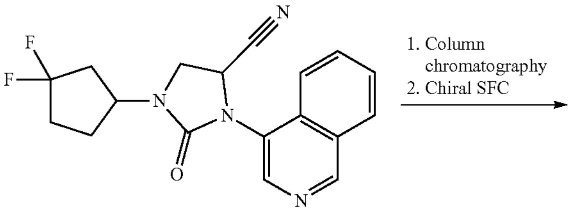

(148)

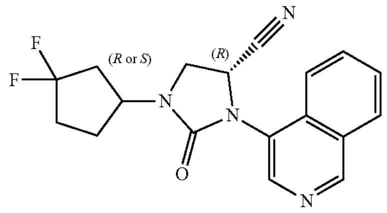

(141a)

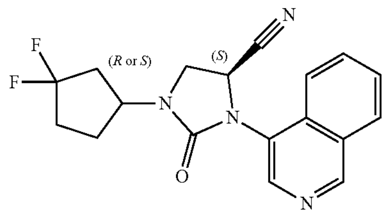

(141b)

-continued

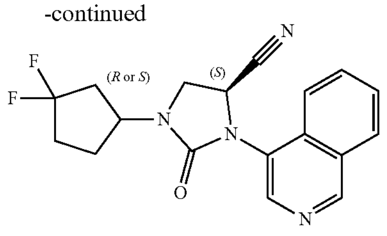

(141c)

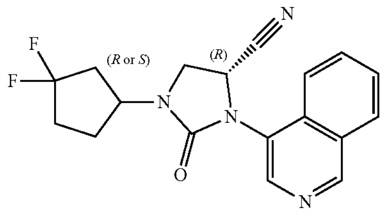

(141d)

Step 1. To a mixture of 3-(isoquinolin-4-yl)-2-oxoimidazolidine-4-carbonitrile (Int-1) (3.5 g, 14.69 mmol, 1.0 eq.) in DMF (40 mL) was added cyclopent-2-en-1-one (2.4 g, 29.38 mmol, 2.0 eq.), $K_2CO_3$ (4.1 g, 29.38 mmol, 2.0 eq.) at 25° C. The mixture was stirred at 50° C. under $N_2$ for 16 hrs. The reaction was quenched with $H_2O$ (100 mL) and extracted with ethyl acetate (100 mL×2). The combined organic layers were washed with brine (200 mL), dried over $Na_2SO_4$, filtered and concentrated to give crude product which was purified by column chromatography (ethyl acetate) to give a residue that was further purified by prep-HPLC (column: Xtimate C18 250 mm×80 mm, 10 μm); liquid phase: [A-$H_2O$ (10 mM $NH_4HCO_3$); B-ACN]B %: 5%-35%, 20 min]) to give 3-(isoquinolin-4-yl)-2-oxo-1-(3-oxocyclopentyl)imidazolidine-4-carbonitrile. $^1$H NMR: (400 MHz, CHLOROFORM-d) δ=9.31 (s, 1H), 8.61 (s, 1H), 8.09 (d, J=8.3 Hz, 1H), 7.87-7.77 (m, 2H), 7.74-7.67 (m, 1H), 4.97 (ddd, J=2.8, 4.5, 8.7 Hz, 1H), 4.73-4.56 (m, 1H), 4.02 (td, J=8.9, 14.1 Hz, 1H), 3.89 (td, J=4.8, 9.3 Hz, 1H), 2.76-2.58 (m, 1H), 2.52-2.26 (m, 4H), 2.22-2.07 (m, 1H).

Step 2. To a mixture of 3-(isoquinolin-4-yl)-2-oxo-1-(3-oxocyclopentyl)imidazolidine-4-carbonitrile (1.0 g, 3.12 mmol, 1.0 eq.) in $CH_2Cl_2$ (30 mL) was added DAST (3.0 g, 18.72 mmol, 6.0 eq.) at 0° C. The mixture was stirred at 25° C. under $N_2$ for 16 hrs. The reaction mixture was quenched with saturated aqueous $NaHCO_3$ (30 mL), extracted with $CH_2Cl_2$ (30 mL×2). The combined organic layers were washed with brine (30 mL), dried over $Na_2SO_4$, filtered and concentrated to give crude product. Purification by silical gel column chromatography (ethyl acetate) gave 1-(3,3-difluorocyclopentyl)-3-(isoquinolin-4-yl)-2-oxoimidazolidine-4-carbonitrile (141) as two racemic diastereomers.

Diastereomer 1: LCMS (Method 38): $t_R$=1.966 min, $[M+1]^+$ 343.1. SFC (Method 13): $t_R$=1.67 min, 49.6% and 1.95 min, 50.4%

Diastereomer 2: LCMS (Method 38): $t_R$=1.947 min, $[M+1]^+$ 343.1. SFC (Method 47): $t_R$=3.30 min, 50.5% and 3.88 min, 49.5%

Diastereomer 1 was resolved by chiral SFC (column: ChiralPak IH, 250 mm×30 mm, 10 μm; mobile phase: Neu-ACN; B % 40%-40%, 12 min]) to give 2 peaks Peak 1 (141a): (R)-1-((S)-3,3-difluorocyclopentyl)-3-(isoquinolin-4-yl)-2-oxoimidazolidine-4-carbonitrile or (R)-1-((R)-3,3-difluorocyclopentyl)-3-(isoquinolin-4-yl)-2-oxoimidazolidine-4-carbonitrile. LCMS (Method 32): $t_R$=2.51 min, $[M+1]^+$ 343.2. SFC (Method 13): $t_R$=1.69 min, 100%. $^1H$ NMR: (400 MHz, CHLOROFORM-d) δ=9.31 (s, 1H), 8.61 (s, 1H), 8.10 (d, J=8.1 Hz, 1H), 7.86-7.78 (m, 2H), 7.74-7.68 (m, 1H), 4.96 (dd, J=4.5, 8.8 Hz, 1H), 4.69-4.75 (m, 1H), 4.07-3.98 (m, 1H), 3.90 (dd, J=4.5, 9.4 Hz, 1H), 2.50-2.56 (m, 1H), 2.08-2.36 (m, 4H), 2.08-1.96 (m, 1H).

Peak 2 (141b): (S)-1-((S)-3,3-difluorocyclopentyl)-3-(isoquinolin-4-yl)-2-oxoimidazolidine-4-carbonitrile or (S)-1-((R)-3,3-difluorocyclopentyl)-3-(isoquinolin-4-yl)-2-oxoimidazolidine-4-carbonitrile. LCMS (Method 32): $t_R$=2.51 min, $[M+1]^+$ 343.2. SFC (Method 13): $t_R$=1.96 min, 99.9%. $^1H$ NMR: (400 MHz, CHLOROFORM-d) δ=9.32 (s, 1H), 8.62 (s, 1H), 8.10 (d, J=8.1 Hz, 1H), 7.86-7.79 (m, 2H), 7.74-7.68 (m, 1H), 4.96 (dd, J=4.5, 8.8 Hz, 1H), 4.76-4.66 (m, 1H), 4.06-3.99 (m, 1H), 3.90 (dd, J=4.5, 9.4 Hz, 1H), 2.50-2.56 (m, 1H), 2.07-2.42 (m, 4H), 2.07-1.96 (m, 1H).

Diastereomer 2 was resolved by chiral SFC (DAICEL CHIRALCEL OD (250 mm*30 mm, 10 μm); mobile phase: Neu-ACN; B % 35%-35%, 9 min]) to give 2 peaks Peak 1 (141c): (S)-1-((S)-3,3-difluorocyclopentyl)-3-(isoquinolin-4-yl)-2-oxoimidazolidine-4-carbonitrile or (S)-1-((R)-3,3-difluorocyclopentyl)-3-(isoquinolin-4-yl)-2-oxoimidazolidine-4-carbonitrile. LCMS (Method 32): $t_R$=2.51 min, $[M+1]^+$ 343.2. SFC (Method 47): $t_R$=3.26 min, 100%. $^1H$ NMR: (400 MHz, CHLOROFORM-d) δ 9.31 (s, 1H), 8.60 (s, 1H), 8.10 (d, J=8.3 Hz, 1H), 7.86-7.78 (m, 2H), 7.74-7.67 (m, 1H), 4.95 (dd, J=4.5, 8.8 Hz, 1H), 4.66-4.70 (m, 1H), 4.03 (t, J=9.1 Hz, 1H), 3.86-3.90 (m 1H), 2.58-2.62 (m, 1H), 2.39-2.24 (m, 2H), 2.23-2.07 (m, 2H), 2.03-1.93 (m, 1H).

Peak 2 (141d): (R)-1-((S)-3,3-difluorocyclopentyl)-3-(isoquinolin-4-yl)-2-oxoimidazolidine-4-carbonitrile or (R)-1-((R)-3,3-difluorocyclopentyl)-3-(isoquinolin-4-yl)-2-oxoimidazolidine-4-carbonitrile. LCMS (Method 32): $t_R$=2.51 min, $[M+1]^+$ 343.2. SFC (Method 47): $t_R$=3.83 min, 100%. $^1H$ NMR: (400 MHz, CHLOROFORM-d) δ=9.32 (s, 1H), 8.61 (s, 1H), 8.10 (d, J=8.3 Hz, 1H), 7.87-7.78 (m, 2H), 7.75-7.68 (m, 1H), 4.96 (dd, J=4.5, 8.9 Hz, 1H), 4.64-4.71 (m, 1H), 4.04 (t, J=9.1 Hz, 1H), 3.87-3.91 (m, 1H), 2.58-2.62 (m, 1H), 2.40-2.25 (m, 2H), 2.24-2.06 (m, 2H), 2.03-1.94 (m, 1H).

Example 142: Preparation methods and Characterization of Modification A (Type IV) crystalline form of (R)-3-(isoquinolin-4-yl)-2-oxo-1-(6-(trifluoromethyl)pyridin-3-yl)imidazolidine-4-carbonitrile (11a)

Preparation methods of (R)-3-(isoquinolin-4-yl)-2-oxo-1-(6-(trifluoromethyl)pyridin-3-yl)imidazolidine-4-carbonitrile (1a) Modification A (Type IV) crystalline form The Modification A (Type IV) crystalline form of (R)-3-(isoquinolin-4-yl)-2-oxo-1-(6-(trifluoromethyl)pyridin-3-yl)imidazolidine-4-carbonitrile (11a) was obtained using any one of the following methods:

Method 142-1: (R)-3-(isoquinolin-4-yl)-2-oxo-1-(6-(trifluoromethyl)pyridin-3-yl)imidazolidine-4-carbonitrile (11a) (50 mg) in acetone (0.5 mL) was heated to 35° C. to obtain a clear solution. Antisolvent (0.5 mL) was slowly added (3 times over 5 min) at 25° C. and the mixture stirred at 5° C. overnight (stirring at 100-200 rpm). The solid was collected by centrifuge filtration and dried at 45° C. for 24 h. (R)-3-(isoquinolin-4-yl)-2-oxo-1-(6-(trifluoromethyl)pyridin-3-yl)imidazolidine-4-carbonitrile (11a) Modification A (Type IV) crystalline form was obtained for each of the antisolvents selected from MTBE, water and heptane.

Method 142-2: (R)-3-(isoquinolin-4-yl)-2-oxo-1-(6-(trifluoromethyl)pyridin-3-yl)imidazolidine-4-carbonitrile (11a) (40 mg) in THE (0.5 mL) was heated to 35° C. to obtain a clear solution. Antisolvent (0.5 mL) was slowly added (3 times over 5 min) at 25° C. and the mixture stirred at 5° C. overnight (stirring at 100-200 rpm). The solid was collected by centrifuge filtration and dried at 45° C. for 24 h. (R)-3-(isoquinolin-4-yl)-2-oxo-1-(6-(trifluoromethyl)pyridin-3-yl)imidazolidine-4-carbonitrile (11a) Modification A (Type IV) crystalline form was obtained for each of the antisolvents selected from MTBE, water and heptane Method 142-3: (R)-3-(isoquinolin-4-yl)-2-oxo-1-(6-(trifluoromethyl)pyridin-3-yl)imidazolidine-4-carbonitrile (11a) (40 mg) in MEK (0.5 mL) was heated to 35° C. to obtain a clear solution. Antisolvent (0.5 mL) was slowly added (3 times over 5 min) at 25° C. and the mixture stirred at 5° C. overnight (stirring at 100-200 rpm). The solid was collected by centrifuge filtration and dried at 45° C. for 24 h. (R)-3-(isoquinolin-4-yl)-2-oxo-1-(6-(trifluoromethyl)pyridin-3-yl)imidazolidine-4-carbonitrile (11a) Modification A (Type IV) crystalline form was obtained for each of the antisolvents selected from MTBE and heptane Method 142-4: (R)-3-(isoquinolin-4-yl)-2-oxo-1-(6-(trifluoromethyl)pyridin-3-yl)imidazolidine-4-carbonitrile (11a) (175 mg) in acetone (1.2 mL) and water (0.12 mL) was heated to 40° C. to obtain a clear solution. Water (0.12 mL) was slowly added over 30 min while maintaining a clear solution. The mixture was then seeded with 0.85 mg of Modification A (Type IV) crystalline form of (R)-3-(isoquinolin-4-yl)-2-oxo-1-(6-(trifluoromethyl)pyridin-3-yl)imidazolidine-4-carbonitrile (11a), followed by ageing for 1 h. Water (1.56 mL) was slowly added over 3-5 hrs while maintaining a slurry for 30 min at 40° C. The slurry was cooled to 5° C. over 5 hrs and then stirred at 5° C. overnight. The solid was collected by centrifuge filtration and dried at 50° C. for 24 h.

Example 142-5: (R)-3-(isoquinolin-4-yl)-2-oxo-1-(6-(trifluoromethyl)pyridin-3-yl)imidazolidine-4-carbonitrile (11a) (2.1g) in acetone/water (95/5 v/v) (15 mL) was heated to 35° C. to obtain a clear solution. Water (0.83 mL) was slowly added and the mixture cooled to 25° C. over 1 h. The mixture was then seeded with 0.01 g of Modification A (Type IV) crystalline form of (R)-3-(isoquinolin-4-yl)-2-oxo-1-(6-(trifluoromethyl)pyridin-3-yl)imidazolidine-4-carbonitrile (11a), followed by ageing for 1 h. Water (19.8 mL) was slowly added over 5 hrs while maintaining a slurry for 3 h at 25° C. The solid was collected by centrifuge filtration and dried at 50° C. for 24 h.

Example 142-6: (R)-3-(isoquinolin-4-yl)-2-oxo-1-(6-(trifluoromethyl)pyridin-3-yl)imidazolidine-4-carbonitrile (11a) (6.0g) in acetone/water (95/5 v/v) (43 mL) was heated to 30° C. to obtain a clear solution. The mixture was then cooled to 25° C. over 1 h. Water (2.4 mL) was slowly added over 1 h and the mixture was then seeded with 30 mg of Modification A (Type IV) crystalline form of (R)-3-(isoquinolin-4-yl)-2-oxo-1-(6-(trifluoromethyl)pyridin-3-yl)imidazolidine-4-carbonitrile (11a), followed by ageing for 1 h. Water (57 mL) was slowly added over 5 hrs while maintaining a slurry overnight at 25° C. The solid was collected by centrifuge filtration and dried at 50° C. for 24 h.

Example 142-7: (R)-3-(isoquinolin-4-yl)-2-oxo-1-(6-(trifluoromethyl)pyridin-3-yl)imidazolidine-4-carbonitrile (11a) (1.0g) in EtOH (6 mL) was stirred at 20~25° C. for 1 hr resulting in a suspension. Water (12 mL) was added and the suspension stirred for 18 hr at 20~25° C. The suspension was filtered and the wet cake was washed with EtOH/$H_2O$ (1/3, v/v) (4 mL). The wet cake was dried at 50° C. for 18 hr.

Example 142-8: (R)-3-(isoquinolin-4-yl)-2-oxo-1-(6-(trifluoromethyl)pyridin-3-yl)imidazolidine-4-carbonitrile (11a) (1.0g) in CH,CN (7 mL) was heated to 50~55° C. and stirred for 1 hr to obtain a clear solution. Water (7 mL) was added resulting in the formation of a precipitate. Additional water (7 mL) was added and the suspension cooled to 20~25° C. and stirred for 1 hr at 20~25° C. The suspension was filtered and the wet cake was washed with CH3CN/$H_2O$ (1/3, v/v) (10 mL). The wet cake was dried at 50° C. for 18 hr.

Example 142-9: (R)-3-(isoquinolin-4-yl)-2-oxo-1-(6-(trifluoromethyl)pyridin-3-yl)imidazolidine-4-carbonitrile (11a) (1.0g) in $CH_3CN$ (7 mL) was heated to 50-55° C. and stirred for 1 hr to obtain a clear solution. Water (7 mL) was added resulting in the formation of a precipitate. Additional water (7 mL) was added and the suspension cooled to 20~25° C. and stirred for 3 days at 20~25° C. The suspension was filtered and the wet cake was washed with $CH_3CN$/$H_2O$ (1/3, v/v) (10 mL). The wet cake was dried at 50° C. for 18 hr.

Example 142-10: (R)-3-(isoquinolin-4-yl)-2-oxo-1-(6-(trifluoromethyl)pyridin-3-yl)imidazolidine-4-carbonitrile (11a) (5.0g) in EtOH (30 mL) was stirred at 20~25° C. for 3 hrs resulting in a suspension. Water (60 mL) was added and the suspension stirred for 18 hr at 20~25° C. The suspension was filtered and the wet cake washed with EtOH/$H_2O$ (1/3, v/v) (40 mL). The wet cake was dried at 50° C. for 18 hr.

Example 142-11: (R)-3-(isoquinolin-4-yl)-2-oxo-1-(6-(trifluoromethyl)pyridin-3-yl)imidazolidine-4-carbonitrile (11a) (177g) in isopropanol (700 mL) was heated to 50-55° C. and stirred for 1 hr resulting in a suspension. Water (1 L) was added and the suspension cooled to 20~25° C. and then stirred for 12 hrs at 20~25° C. The suspension was filtered and the wet cake washed with isopropanol/$H_2O$ (1/2, v/v) (100 mL). The wet cake was dried at 50° C. for 18 hr.

Characterization of (R)-3-(isoquinolin-4-yl)-2-oxo-1-(6-(trifluoromethyl)pyridin-3-yl)imidazolidine-4-carbonitrile (1a) Modification A (Type IV) crystalline form A: XRPD analysis A representative XRPD diffractogram of the (R)-3-(isoquinolin-4-yl)-2-oxo-1-(6-(trifluoromethyl)pyridin-3-yl) imidazolidine-4-carbonitrile (11a) Modification A (Type IV) is shown in FIG. 1 and the corresponding reflection list (peak list) from 6 to 30° 2-Theta and relative peak intensities are provided in Table 2 below.

TABLE 2

Table 2: Reflection (peak) positions of the (R)-3-(isoquinolin-4-yl)-2-oxo-1-(6-(trifluoromethyl)pyridin-3-yl)imidazolidine-4-carbonitrile (11a) Modification A (Type IV) in the range from 6 to 30° 2-Theta; A typical precision of the 2-Theta values is in the range of ±0.2° 2-Theta, preferably of ±0.1° 2-Theta. The most characteristic XRPD peaks are bold and in italics.

| Peak | Angle (° 2-Theta) | d Value | Rel. Intensity |
|---|---|---|---|
| 1 | 6.85 | 12.90 | 22.7% |
| 2 | 8.52 | 10.37 | 31.9% |
| ***3*** | ***10.41*** | ***8.49*** | ***43.3%*** |
| 4 | 13.71 | 6.46 | 26.5% |
| ***5*** | ***16.90*** | ***5.24*** | ***100.0%*** |
| ***6*** | ***17.06*** | ***5.19*** | ***74.4%*** |
| 7 | 18.40 | 4.82 | 54.0% |
| 8 | 19.05 | 4.65 | 26.9% |
| ***9*** | ***21.76*** | ***4.08*** | ***45.2%*** |
| 10 | 22.55 | 3.94 | 24.7% |
| 11 | 23.50 | 3.78 | 21.6% |
| 12 | 24.82 | 3.58 | 26.3% |
| 13 | 26.89 | 3.31 | 32.5% |
| 14 | 28.17 | 3.17 | 26.6% |

Figure 2:
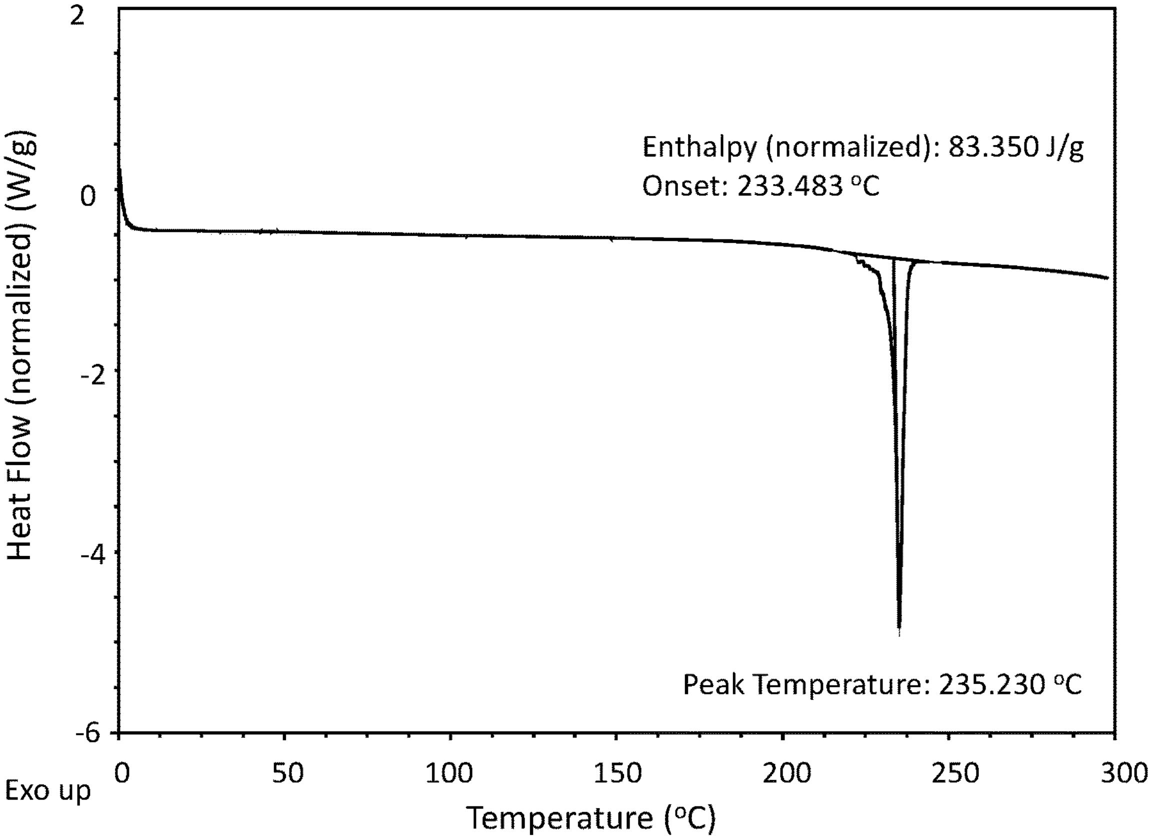
FIG. 2: illustrates a representative differential scanning calorimetry (DSC) curve of (R)-3-(isoquinolin-4-yl)-2-oxo-1-(6-(trifluoromethyl)pyridin-3-yl)imidazolidine-4-carbonitrile Modification A. The x-axis shows the temperature in degree Celsius (° C.), the y-axis shows the heat flow rate in Watt per gram (W/g) with endothermic peaks going up.

B: Differential scanning calorimetry (DSC) analysis (R)-3-(isoquinolin-4-yl)-2-oxo-1-(6-(trifluoromethyl) pyridin-3-yl)imidazolidine-4-carbonitrile (11a) Modification A (Type IV) was investigated by DSC using a TA Discovery instrument. A sample of approximately 2-4 mg was heated in an aluminum pan with pierced lid from 0 to 300° C. at a rate of 10 K/min. Nitrogen (50 mL/min) was used as purge gas. The DSC curve of (R)-3-(isoquinolin-4-yl)-2-oxo-1-(6-(trifluoromethyl)pyridin-3-yl)imidazolidine-4-carbonitrile (11a) Modification A (Type IV) is shown in FIG. 2 where a single endothermic peak with an onset temperature of about 233.5° C. and a peak temperature of about 235.2° C. is obtained.

Figure 3:
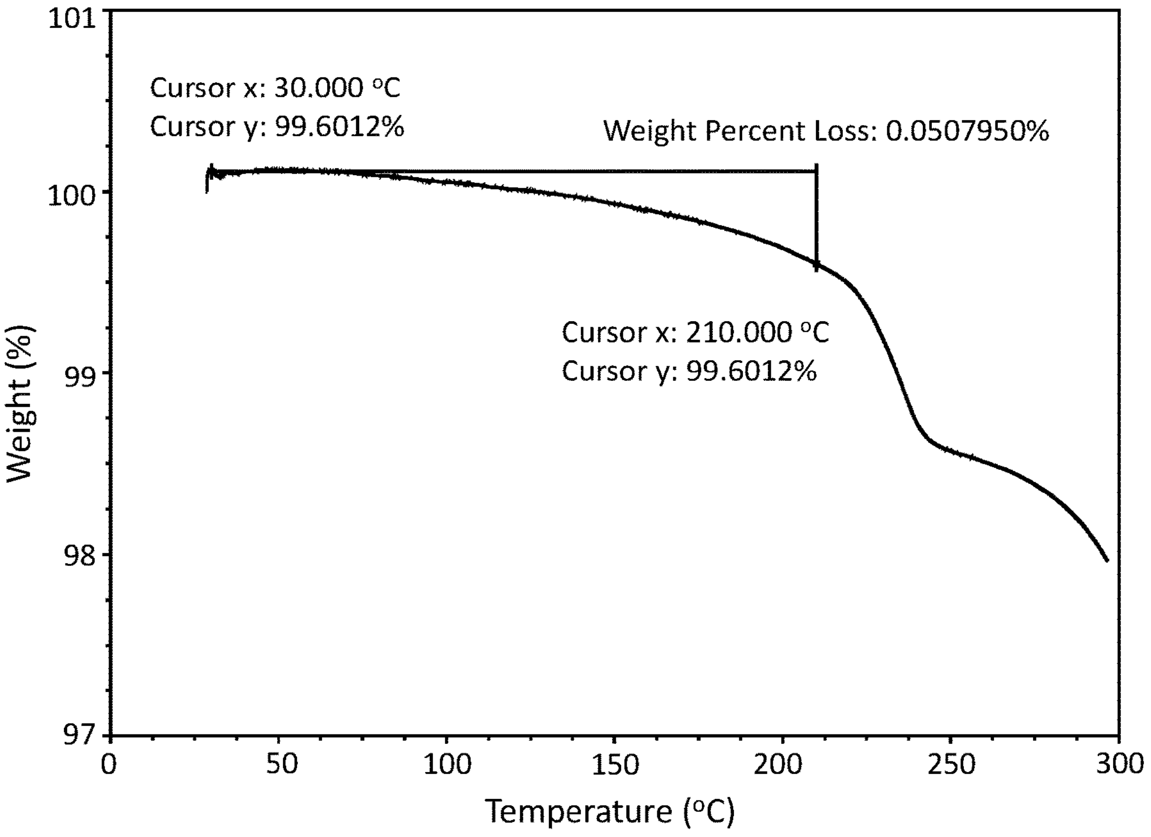
FIG. 3: illustrates a representative thermogravimetric analysis (TGA) curve of (R)-3-(isoquinolin-4-yl)-2-oxo-1-(6-(trifluoromethyl)pyridin-3-yl)imidazolidine-4-carbonitrile Modification A. The x-axis shows the temperature in degree Celsius (° C.), the y-axis shows the mass (loss) of the sample in weight percent (weight %).

C: Thermogravimetric analysis (TGA) analysis (R)-3-(isoquinolin-4-yl)-2-oxo-1-(6-(trifluoromethyl)pyridin-3-yl)imidazolidine-4-carbonitrile (11a) Modification A (Type IV) was investigated by TGA using a TA Discovery instrument. A sample of approximately 2-10 mg was heated in a 100 microliter aluminum pan closed with an aluminum lid. The lid was manually pierced at the beginning of the measurement. The sample was heated from room temperature to 300° C. at a rate of 10K/min. Nitrogen (20 mL/min) was used as purge gas. The TGA curve is shown in FIG. 3, where 0.51% mass loss is observed prior to the sample melting.

Example 143: Preparation methods and Characterization of Modification B (Type III) crystalline form of (R)-3-(isoquinolin-4-yl)-2-oxo-1-(6-(trifluoromethyl)pyridin-3-yl)imidazolidine-4-carbonitrile (11a)

Preparation methods of (R)-3-(isoquinolin-4-yl)-2-oxo-1-(6-(trifluoromethyl)pyridin-3-yl)imidazolidine-4-carbonitrile (1a) Modification B (Type III) crystalline form The Modification B (Type III) crystalline form of (R)-3-(isoquinolin-4-yl)-2-oxo-1-(6-(trifluoromethyl)pyridin-3-yl)imidazolidine-4-carbonitrile (11a) was obtained using any one of the following methods:

Method 143-1: (R)-3-(isoquinolin-4-yl)-2-oxo-1-(6-(trifluoromethyl)pyridin-3-yl)imidazolidine-4-carbonitrile (11a) (2.5g) was dissolved in EtOH (12 mL) at room temperature and water (18 mL) was slowly added resulting in a suspension. The suspension was then seeded with 50 mg of Modification B (Type III) crystalline form of (R)-3-(isoquinolin-4-yl)-2-oxo-1-(6-(trifluoromethyl)pyridin-3-yl)imidazolidine-4-carbonitrile (11a). Additional water (18 mL) was added and the suspension was slurried for 1 day. Ethanol/ water (1/3, v/v) (12 mL) was then added and the suspension slurried for another 2 days. The solid was collected by centrifuge filtration.

Method 143-2: (R)-3-(isoquinolin-4-yl)-2-oxo-1-(6-(trifluoromethyl)pyridin-3-yl)imidazolidine-4-carbonitrile (11a) (2.5g) was dissolved in EtOH (15 mL) at room temperature and water (20 mL) was slowly added resulting in a suspension. The suspension was then seeded with 50 mg of Modification B (Type III) crystalline form of (R)-3-(isoquinolin-4-yl)-2-oxo-1-(6-(trifluoromethyl)pyridin-3-yl)imidazolidine-4-carbonitrile (11a) and the suspension turned gel-like before becoming suspension again after 1 h equilibration. Additional water (25 mL) was added and the suspension was slurried for 1 day. The solid was collected by centrifuge filtration.

Figure 4:
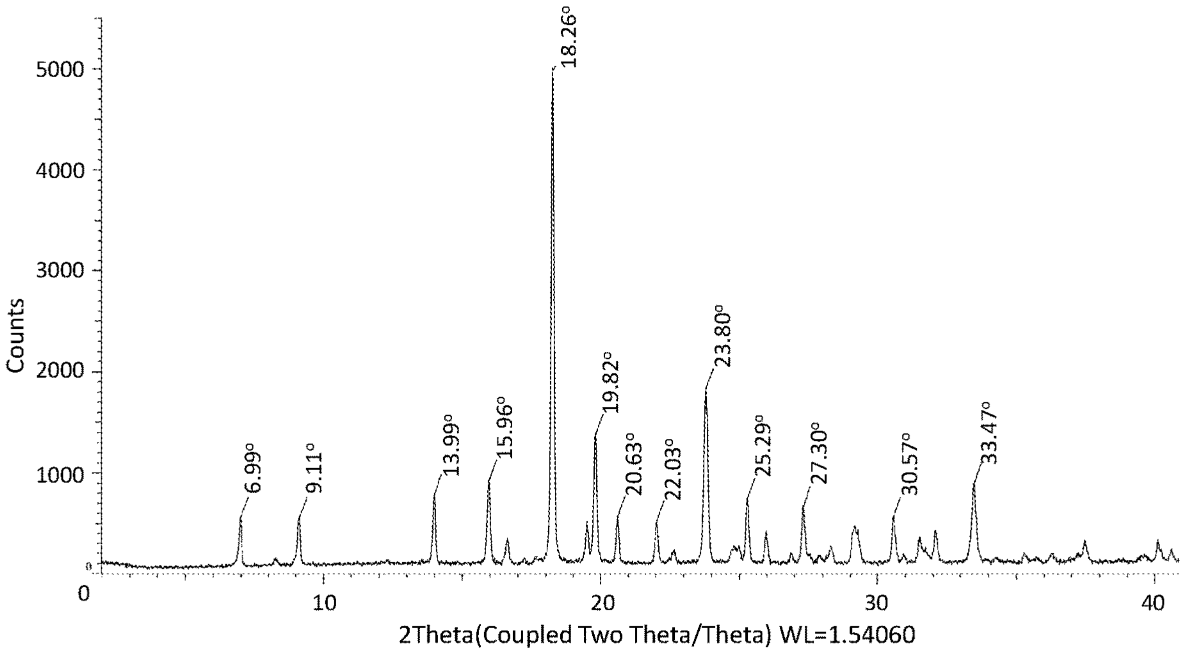
FIG. 4: illustrates a representative powder X-ray diffractogram (PXRD) curve of (R)-3-(isoquinolin-4-yl)-2-oxo-1-(6-(trifluoromethyl)pyridin-3-yl)imidazolidine-4-carbonitrile Modification B. The x-axis shows the scattering angle in ° 2-Theta, the y-axis shows the intensity of the scattered X-ray beam in counts of detected photons.

Characterization of (R)-3-(isoquinolin-4-yl)-2-oxo-1-(6-(trifluoromethyl)pyridin-3-yl)imidazolidine-4-carbonitrile (1a) Modification B (Type III) crystalline form A: XRPD analysis A representative XRPD diffractogram of the (R)-3-(isoquinolin-4-yl)-2-oxo-1-(6-(trifluoromethyl)pyridin-3-yl)imidazolidine-4-carbonitrile (11a) Modification B (Type III) is shown in FIG. 4 and the corresponding reflection list (peak list) from 6 to 340 2-Theta and relative peak intensities are provided in Table 3 below.

TABLE 3

Table 3: Reflection (peak) positions of the (R)-3-(isoquinolin-4-yl)-2-oxo-1-(6-(trifluoromethyl)pyridin-3-yl)imidazolidine-4-carbonitrile (11a) Modification B (Type III) in the range from 6 to 34° 2-Theta; A typical precision of the 2-Theta values is in the range of ±0.2° 2-Theta, preferably of ±0.1° 2-Theta. The most characteristic XRPD peaks are bold and in italics.

| Index | Angle | d Value | Rel. Intensity |
|---|---|---|---|
| 1 | 6.99 | 12.64 | 9.8% |
| 2 | 9.11 | 9.70 | 9.6% |
| 3 | 13.99 | 6.33 | 13.9% |
| ***4*** | ***15.96*** | ***5.55*** | ***16.8%*** |
| ***5*** | ***18.26*** | ***4.85*** | ***100.0%*** |
| ***6*** | ***19.82*** | ***4.48*** | ***25.8%*** |
| 7 | 20.63 | 4.30 | 9.3% |
| 8 | 22.03 | 4.03 | 8.5% |
| ***9*** | ***23.80*** | ***3.74*** | ***35.3%*** |
| 10 | 25.29 | 3.52 | 12.8% |
| 11 | 27.30 | 3.26 | 11.3% |
| 12 | 30.57 | 2.92 | 9.0% |
| 13 | 33.47 | 2.67 | 16.1% |

Figure 5:
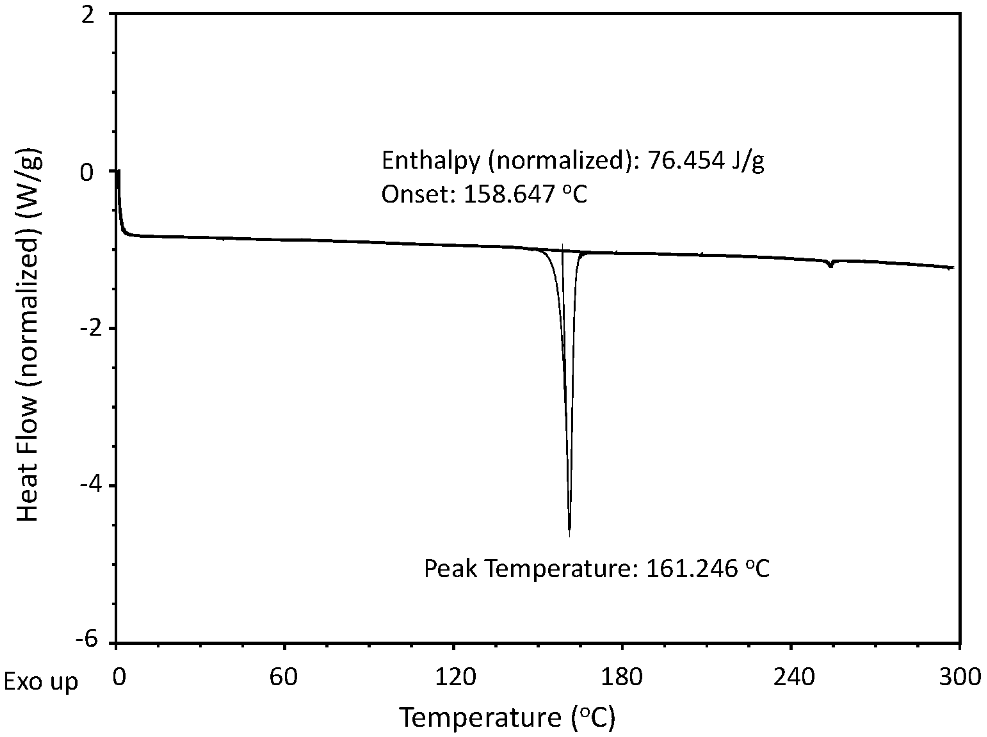
FIG. 5: illustrates a representative differential scanning calorimetry (DSC) curve of (R)-3-(isoquinolin-4-yl)-2-oxo-1-(6-(trifluoromethyl)pyridin-3-yl)imidazolidine-4-carbonitrile Modification B. The x-axis shows the temperature in degree Celsius (° C.), the y-axis shows the heat flow rate in Watt per gram (W/g) with endothermic peaks going up.

B: Differential scanning calorimetry (DSC) analysis (R)-3-(isoquinolin-4-yl)-2-oxo-1-(6-(trifluoromethyl)pyridin-3-yl)imidazolidine-4-carbonitrile (11a) Modification B (Type III) was investigated by DSC using a TA Discovery instrument. A sample of approximately 2-4 mg was heated in an aluminum pan with pierced lid from 0 to 300° C. at a rate of 10 K/min. Nitrogen (50 mL/min) was used as purge gas. The DSC curve of (R)-3-(isoquinolin-4-yl)-2-oxo-1-(6-(trifluoromethyl)pyridin-3-yl)imidazolidine-4-carbonitrile (11a) Modification B (Type III) is shown in FIG. 5 where a single endothermic peak with an onset temperature of about 158.6° C. and a peak temperature of about 161.3° C. is obtained.

Figure 6:
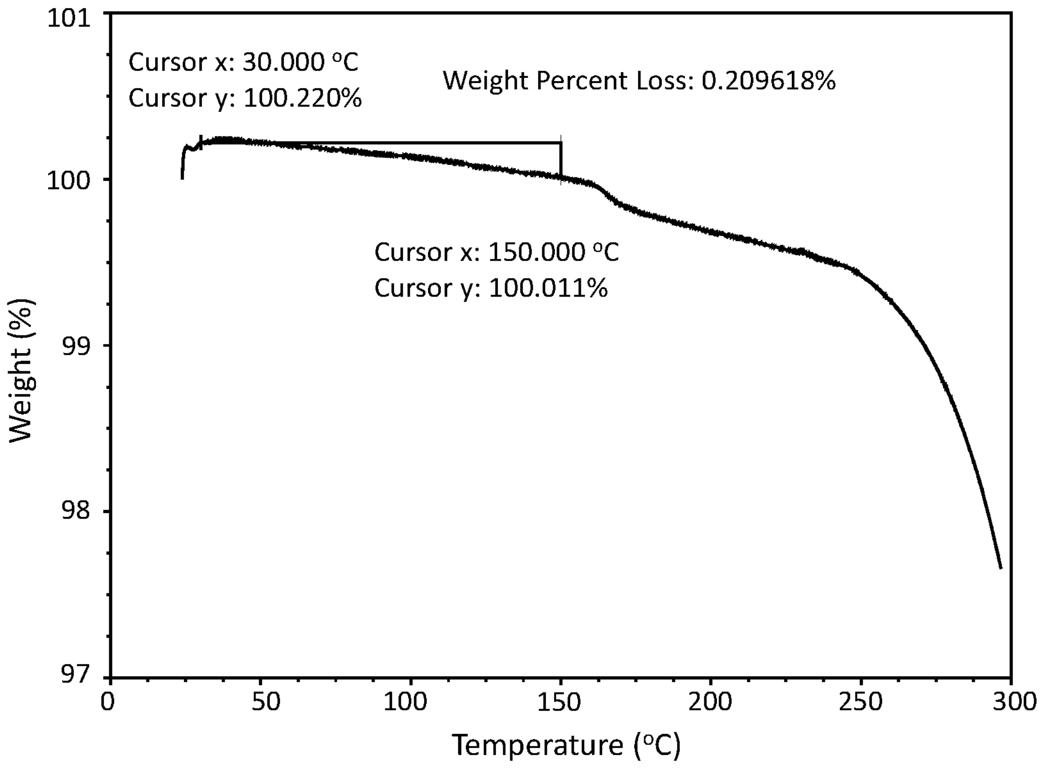
FIG. 6: illustrates a representative thermogravimetric analysis (TGA) curve of (R)-3-(isoquinolin-4-yl)-2-oxo-1-(6-(trifluoromethyl)pyridin-3-yl)imidazolidine-4-carbonitrile Modification B. The x-axis shows the temperature in degree Celsius (° C.), the y-axis shows the mass (loss) of the sample in weight percent (weight %).

C: Thermogravimetric analysis (TGA) analysis (R)-3-(isoquinolin-4-yl)-2-oxo-1-(6-(trifluoromethyl)pyridin-3-yl)imidazolidine-4-carbonitrile (11a) Modification B (Type III) was investigated by TGA using a TA Discovery instrument. A sample of approximately 2-10 mg was heated in a 100 microliter aluminum pan closed with an aluminum lid. The lid was manually pierced at the beginning of the measurement. The sample was heated from room temperature to 300° C. at a rate of 10K/min. Nitrogen (20 mL/min) was used as purge gas. The TGA curve is shown in FIG. 6, where 0.21% mass loss is observed prior to the sample melting.

Biological Assays:

Production of SARS-CoV-2 Main Protease expression plasmid

The coding sequence for SARS-CoV-2 main protease was codon-optimized for *E. coli* and synthesized by Integrated DNA Technologies. The sequence was amplified by PCR and cloned into the pGEX6P-1 vector, downstream of GST and an HRV 3C protease cleavage site, using the Gibson Assembly Master Mix kit (New England BioLabs, Inc). To ensure authentic termini, the amino acids AVLQ were added to the N-terminus of the main protease by addition of their coding sequence to the 5' end of the gene product. This sequence reconstitutes the NSP4/5 cleavage site, resulting in auto-cleavage by the main protease protein product. Similarly, we added a gly-pro-$(his)_6$ tag to the C-terminus (the GP completes a non-consensus 3C cleavage site along with the C-terminus of the main protease which allows for cleavage of the poly-histidine tag after purification by HRV-3C protease, resulting in an authentic C-terminus). The expressed protein sequence (SEQ ID NO:1) is shown below (autocleavage site indicated with underline with a slash where the cleavage takes place; $M^{pro}$ sequence in bold):

MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPKSDLEVLFQGPLGSAVLQ/SGFRKMAFP

SGKVEGCMVQVTCGTTTLNGLWLDDVVYCPRHVICTSEDMLNPNYEDLL

IRKSNHNFLVQAGNVQLRVIGHSMQNCVLKLKVDTANPKTPKYKFVRIQ

PGQTFSVLACYNGSPSGVYQCAMRPNFTIKGSFLNGSCGSVGFNIDYDC

VSFCYMHHMELPTGVHAGTDLEGNFYGPFVDRQTAQAAGTDTTITVNVL

AWLYAAVINGDRWFLNRFTTTLNDFNLVAMKYNYEPLTQDHVDILGPLS

AQTGIAVLDMCASLKELLQNGMNGRTILGSALLEDEFTPFDVVRQCSGV

TFQGPHHHHHH*

Production of SARS-CoV-2 Main Protease protein

Hi Control BL21(DE3) cells (Lucigen Corporation) were transformed with the expression plasmid via heat shock at 42° C. followed by recovery in LB media at 37° C. for one hour. Transformed cells were selected via growth on LB agar plates containing 100 μg/mL carbenicillin. We used Hi Control cells as we observed expression of the main protease was toxic in other standard *E. coli* cell lines. A single colony was used to start an overnight culture in LB+carbenicillin media. This culture was used to inoculate 1 L cultures in Terrific Broth, supplemented with 50 mM sodium phosphate pH 7.0 and 100 μg/mL carbenicillin. These cultures grew in Fernbach flasks at 37° C. while shaking at 225 rpm, until the OD600 reached approximately 2.0, at which point the temperature was reduced to 20° C. and 0.5 mM IPTG (final) was added to each culture. The cells were allowed to grow overnight.

The next day, the cultures were centrifuged at 6,000×g for 20 minutes at 4° C., and the resulting cell pellets were resuspended in IMAC_A buffer (50 mM Tris pH 8.0, 400 mM NaCl, 1 mM Tris(2-carboxyethyl)phosphine (TCEP)). Cells were lysed with two to three passes through a cell homogenizer (Microfluidics model M-110P) at 18,000 psi. The lysate was clarified with centrifugation at 42,000×g for 30 minutes and the cleared lysate was loaded onto 3×5 mL HiTrap Ni-NTA silica gel chromatographys (GE) pre-equilibrated with IMAC_A buffer, using an AKTA Pure FPLC. After loading, the silica gel chromatographys were washed with IMAC_A buffer until the A280 levels reached a sustained baseline. The protein was then eluted with a linear gradient with IMAC_B buffer (50 mM Tris pH 8.0, 400 mM NaCl, 500 mM imidazole, 1 mM TCEP) across 25 silica gel chromatography volumes, while 2 mL fractions were collected automatically. Peak fractions were analyzed by SDS-PAGE and those containing SARS-CoV-2 main protease were pooled. Importantly, auto-cleavage of the N-terminal GST tag was observed and the eluted protein had a mass consistent with SARS-CoV-2 main protease along with the C-terminal GP-6xHis tag, as determined by ESI-LC/MS. Pooled fractions were treated with HRV 3C protease (also known as "PreScission" protease) while dialyzing against IMAC_A buffer at room temperature (2×2 L dialyses for 1 hour each).

Room temperature dialysis was important as we observed a tendency for the main protease protein to precipitate with prolonged exposure to 4° C. temperatures. Cleavage of the C-terminal GP-6xHis tag was confirmed after 2 hours by electrospray ionization-liquid chromatography/mass spectrometry (ESI-LC/MS). The dialyzed and cleaved protein was then re-run through a 5 mL HiTrap Ni-NTA silica gel chromatography pre-equilibrated with IMAC_A buffer. The main protease eluted in the flow-through as expected.

The protein was then concentrated to approximately 5 mL and loaded onto a Superdex 75 16/60 silica gel chromatography pre-equilibrated with SEC Buffer (25 mM HEPES pH 7.5, 150 mM NaCl, 1 mM TCEP). The protein was run through the silica gel chromatography at 1 mL/min and eluted as one peak well in the included volume (at −75 mL). Fractions from this peak were analyzed by SDS-PAGE and pure fractions were pooled and concentrated to 10 mg/mL, aliquotted, and stored at −80° C.

Rapid-Fire MS Biochemical Assay measuring $M^{pro}$ activity

Assay buffer preparation: 50 mM HEPES pH 7.3, 150 mM NaCl, 1 mM EDTA, 0.01% pluronic f-127(Catalog #59005, Biotium) was prepared using UltraPure Distilled Water (Catalog #10977015, Thermo Scientific). The $M^{pro}$ enzyme stock consisted of a 25 nM solution of $M^{pro}$ made in buffer. The substrate solution stock consisted of a 10 μM solution of $M^{pro}$ peptide (AVLSGFRKK (SEQ ID NO:2); Purchased from Vivitide) made in buffer. The quench solution consisted of a 200 nM solution of 2% acetic acid spiked with 200 nM of the internal standard peptide ($^{13}$C AVLQ; Purchased from Vivitide).

The Rapidfire Mass Spectrometry setup consisted of a Rapidfire autosampler platform (Agilent) coupled with a Sciex 6500 QQQ Mass Spectrometer (Sciex). A C18 Rapidfire cartridge type C (Catalog #G9205 Å) was used in the analysis, the load solvent consisted of 0.1% formic acid flowed at 1.5 mL/min and the elute solvent consisted of 75% acetonitrile, 5% isopropal alcohol, 20% ultrapure distilled water with 0.1% formic acid. MS transitions were created for the substrate peptide AVLQSGFRKK (SEQ ID NO:3) (378.6 Da-482.6 Da), product peptide AVLQ (430.3 Da-260.4 Da) and the internal standard peptide $^{13}$C AVLQ (434.3 Da-288.3 Da) Compound plates were prepared in 384 Echo plate (cat #LPLO200, Labcyte) and the starting concentration of compound was 10 mM, then 1 to 3 serial dilution in 100% DMSO, 8 μl/well). To generate assay ready plates, 50 nl compounds were transferred to a 384-well clear assay plate using an Echo®555 Liquid Handler (Labcyte). 5 μL of $M^{pro}$ enzyme solution was dispensed in each well throughout entire plate (Col 1-24) using buffer distributor (Multidrop ComB1 from Thermo Scientific) with 5 μL of assay buffer only dispensed to no enzyme control in Col 24. Enzyme allowed to preincubate with compounds for 15 minutes at room temperature (25° C.) prior to starting reaction by addition of 5 μL of substrate peptide solution to all wells in the plate (Col 1-24). The plates were incubated for 30 minutes at room temperature with a final volume of 10 μl/well buffer, such that the compound concentration was 200-fold of final concentration. Final assay concentrations were 12.5 nM $M^{pro}$ and 5 μM substrate peptide. After incubation, reaction was quenched by adding 40 μL of quench solution and plates were analyzed by the Rapidfire/Sciex MS platform.

Mass spectral data was analyzed as ratiometric measurements between the integrated areas of the peak for the product peptide and the labeled internal standard peptide for each sample (Multiquant, Sciex). Percent activity measurements were calculated comparing each ratio of product/Internal standard from compound treatments to the ratios calculated for the DMSO only wells with and without enzyme (Neutral and active controls respectively). $M^{pro}$ Inhibitor qualified absolute $IC_{50}$ values (concentration of inhibitor that inhibits $M^{pro}$ activity at least 50%), were determined with 8 inhibitor concentrations measured in duplicate for each inhibitor. The qualified absolute $IC_{50}$ was calculated by non-linear regression analysis to sigmoidal-logistic curves by HELIOS (PROD 2) system.

Rapid-Fire MS Biochemical Assay measuring $M^{pro}$ activity (5 nM $M^{pro}$)

Assay buffer preparation: 50 mM HEPES pH 7.3, 150 mM NaCl, 1 mM EDTA, 0.01% pluronic f-127(Catalog #59005, Biotium) was prepared using UltraPure Distilled Water (Catalog #10977015, Thermo Scientific). The $M^{pro}$ enzyme stock consisted of a 10 nM solution of $M^{pro}$ made in buffer. The substrate solution stock consisted of a 10 μM solution of $M^{pro}$ peptide (AVLSGFRKK (SEQ ID NO:2); Purchased from Vivitide) made in buffer. The quench solution consisted of a 2% acetic acid solution spiked with 200 nM of the internal standard peptide (13C AVLQ; Purchased from Vivitide).

The Rapidfire Mass Spectrometry setup consisted of a Rapidfire autosampler platform (Agilent) coupled with a Sciex 6500 QQQ Mass Spectrometer (Sciex). A C18 Rapidfire cartridge type C (Catalog #G9205 Å) was used in the analysis, the load solvent consisted of 0.1% formic acid flowed at 1.5 mL/min and the elute solvent consisted of 75% acetonitrile, 5% isopropal alcohol, 20% ultrapure distilled water with 0.1% formic acid. MS transitions were created for the substrate peptide AVLQSGFRKK (SEQ ID NO:3) (378.6 Da-482.6 Da), product peptide AVLQ (430.3 Da-260.4 Da) and the internal standard peptide 13C AVLQ (434.3 Da-288.3 Da) Compound plates were prepared in 384 Echo plate (cat #LPLO200, Labcyte) and the starting concentration of compound was 10 mM, then 1 to 3 serial dilution in 100% DMSO, 8 μl/well). To generate assay ready plates, 10 nl of compound were transferred to a 384-well clear assay plate using an Echo®555 Liquid Handler (Labcyte). 5 μL of $M^{pro}$ enzyme solution was dispensed in each well throughout entire plate (Col 1-24) using buffer distributor (Multidrop Combi from Thermo Scientific) with 5 μL of assay buffer only dispensed to no enzyme control in Col 24. Enzyme allowed to preincubate with compounds for 15 minutes at room temperature (25° C.) prior to starting reaction by addition of 5 μL of substrate peptide solution to all wells in the plate (Col 1-24). The plates were incubated for 120 minutes at room temperature with a final volume of 10 μl/well buffer, such that the compound concentration was diluted 1000-fold to final concentration. Final assay concentrations were 5 nM $M^{pro}$ and 5 μM substrate peptide. After incubation, reaction was quenched by adding 40 μL of quench solution and plates were analyzed by the Rapidfire/Sciex MS platform.

Mass spectral data was analyzed as ratiometric measurements between the integrated areas of the peak for the product peptide and the labeled internal standard peptide for each sample (Multiquant, Sciex). Percent activity measurements were calculated comparing each ratio of product/Internal standard from compound treatments to the ratios calculated for the DMSO only wells with and without enzyme (Neutral and active controls respectively). $M^{pro}$ Inhibitor qualified absolute $IC_{50}$ values (concentration of inhibitor that inhibits $M^{pro}$ activity at least 50%), were determined with 8 inhibitor concentrations measured in duplicate for each inhibitor. The qualified absolute $IC_{50}$ was calculated by non-linear regression analysis to sigmoidal-logistic curves by HELIOS (PROD 2) system.

Biological Data:

The compounds described herein were evaluated using the assay described above. Table 1A lists the corresponding $IC_{50}$ (μM) values obtained for each example compound described above.

TABLE 1A

| Example Number | $IC_{50}$ (μM) |
|---|---|
| 1 - racemate | 0.037 |
| 1 - enantiomer 1 | 0.009 |
| 1 - enantiomer 2 | 6.4 |
| 2 - racemate | 0.005 |
| 2 - enantiomer 1 | <0.005 |
| 2 - enantiomer 2 | 3.0 |
| 3 | 0.007 |
| 4 | <0.005 |
| 5 | <0.005 |
| 6 | 0.027 |
| 7 | 0.006 |
| 8 | 0.077 |
| 9 | 0.010 |
| 10 | 0.005 |
| 11a | <0.005 |
| 11b | 1.7 |

Table 1B lists the corresponding $IC_{50}$ (μM) values obtained using the Rapid-Fire MS Biochemical Assay measuring $M^{pro}$ activity (5 nM $M^{pro}$) described above.

TABLE 1B

| Compound Number | Rapid-Fire Assay $IC_{50}$ |
|---|---|
| 1 | B |
| 1a | A |
| 1b | D |
| 2 | A |
| 2a | A |
| 2b | D |
| 3 | A |
| 4 | A |

TABLE 1B-continued

| Compound Number | Rapid-Fire Assay $IC_{50}$ |
|---|---|
| 5 | A |
| 6 | B |
| 7 | A |
| 8 | B |
| 9 | A |
| 10 | A |
| 11a | A |
| 11b | D |
| 12 | B |
| 12a | A |
| 12b | D |
| 13 | n.d |
| 13a | A |
| 13b | D |
| 14 | n.d. |
| 14a | A |
| 14b | D |
| 15 | A |
| 15a | A |
| 15b | D |
| 16 | n.d. |
| 16a | A |
| 16b | C |
| 17 | n.d. |
| 17a | A |
| 17b | D |
| 18 | n.d. |
| 18a | A |
| 18b | D |
| 19 | C |
| 19a | A |
| 19b | D |
| 20 | A |
| 20a | A |
| 20b | D |
| 21 | n.d. |
| 21a | A |
| 21b | D |
| 22 | n.d. |
| 22a | A |
| 22b | D |
| 23 | n.d. |
| 23a | A |
| 23b | D |
| 24 | n.d. |
| 24a | A |
| 24b | D |
| 25 | n.d. |
| 25a | C |
| 25b | D |
| 26 | n.d. |
| 26a | C |
| 26b | D |
| 27 | B |
| 28 | B |
| 29 | B |
| 30 | n.d. |
| 30a | A |
| 30b | D |
| 31 | n.d. |
| 31a | B |
| 31b | D |
| 32 | n.d. |
| 32a | A |
| 32b | D |
| 33 | A |
| 33a | A |
| 33b | D |
| 34 | A |
| 35 | A |
| 36 | B |
| 37 | A |
| 37a | A |
| 37b | D |
| 38 | n.d. |
| 38a | A |

TABLE 1B-continued

| Compound Number | Rapid-Fire Assay $IC_{50}$ |
|---|---|
| 38b | D |
| 39 | n.d. |
| 39a | A |
| 39b | D |
| 40 | n.d. |
| 40a | C |
| 40b | D |
| 41a | A |
| 41b | C |
| 42 | n.d. |
| 42a | A |
| 42b | D |
| 43 | n.d. |
| 43a | A |
| 43b | C |
| 44 | n.d. |
| 44a | B |
| 44b | D |
| 45 | D |
| 45a | A |
| 45b | C |
| 46 | n.d. |
| 46a | D |
| 46b | D |
| 47 | n.d. |
| 47a | B |
| 47b | D |
| 48 | n.d. |
| 48a | A |
| 48b | D |
| 49 | n.d. |
| 49a | B |
| 49b | D |
| 50 | n.d. |
| 50a | A |
| 50b | D |
| 51 | n.d. |
| 51a | B |
| 51b | D |
| 52 | n.d. |
| 52a | A |
| 52b | C |
| 53 | n.d. |
| 53a | C |
| 53b | D |
| 54 | n.d. |
| 54a | B |
| 54b | C |
| 55 | n.d. |
| 55a | B |
| 55b | D |
| 56 | n.d. |
| 56a | B |
| 56b | D |
| 57 | A |
| 57a | A |
| 57b | D |
| 58 | C |
| 58a | B |
| 58b | D |
| 59 | n.d. |
| 59a | B |
| 59b | D |
| 60 | B |
| 60a | A |
| 60b | C |
| 61 | n.d. |
| 61a | B |
| 61b | D |
| 62 | n.d. |
| 62a | C |
| 62b | D |
| 63 | n.d. |
| 63a | A |
| 63b | D |
| 64 | B |

TABLE 1B-continued

| Compound Number | Rapid-Fire Assay $IC_{50}$ |
|---|---|
| 64a | A |
| 64b | D |
| 65 | C |
| 65a | B |
| 65b | D |
| 66 | B |
| 66a | A |
| 66b | D |
| 67 | n.d. |
| 67a | B |
| 67b | D |
| 68 | n.d. |
| 68a | B |
| 68b | D |
| 69 | n.d. |
| 69a | B |
| 69b | D |
| 70-1 | B |
| 70-2 | n.d. |
| 70a | A |
| 70b | D |
| 71 | n.d. |
| 71a | A |
| 71b | D |
| 72 | A |
| 72a | A |
| 72b | C |
| 73 | n.d. |
| 73a | A |
| 73b | C |
| 74 | C |
| 74a | C |
| 74b | D |
| 75 | n.d. |
| 75a | A |
| 75b | D |
| 76a | A |
| 76b | D |
| 77 | n.d. |
| 77a | A |
| 77b | B |
| 78 | n.d. |
| 78a | A |
| 78b | D |
| 79 | n.d. |
| 79a | B |
| 79b | D |
| 80 | B |
| 80a | B |
| 80b | D |
| 81 | n.d. |
| 81a | A |
| 81b | D |
| 82 | n.d. |
| 82a | B |
| 82b | D |
| 83 | n.d. |
| 83a | B |
| 83b | D |
| 84 | n.d. |
| 84a | B |
| 84b | D |
| 85 | n.d. |
| 85a | A |
| 85b | D |
| 86 | n.d. |
| 86a | B |
| 86b | D |
| 87 | A |
| 87a | A |
| 87b | D |
| 88 | n.d. |
| 88a | A |
| 88b | D |
| 89 | C |
| 89a | A |

TABLE 1B-continued

| Compound Number | Rapid-Fire Assay $IC_{50}$ |
|---|---|
| 89b | D |
| 90 | A |
| 90a | A |
| 90b | D |
| 91 | n.d. |
| 91a | A |
| 91b | D |
| 92 | A |
| 92a | A |
| 92b | C |
| 93 | n.d. |
| 93a | A |
| 93b | D |
| 94 | n.d. |
| 94a | A |
| 94b | D |
| 95 | n.d. |
| 95a | A |
| 95b | D |
| 96 | n.d. |
| 96a | B |
| 96b | D |
| 97a | A |
| 97b | D |
| 98 | n.d. |
| 98a | A |
| 98b | D |
| 99a | A |
| 99b | C |
| 100 | n.d. |
| 100a | A |
| 100b | C |
| 101 | n.d. |
| 101a | A |
| 101b | D |
| 102 | n.d. |
| 102a | A |
| 102b | C |
| 103 | B |
| 103a | A |
| 103b | D |
| 104 | n.d. |
| 104a | A |
| 104b | D |
| 105 | n.d. |
| 105a | A |
| 105b | D |
| 106 | n.d. |
| 106a | A |
| 106 | D |
| 107 | n.d. |
| 107a | B |
| 107b | D |
| 108 | n.d. |
| 108a | A |
| 108b | D |
| 109 | n.d. |
| 109a | A |
| 109b | D |
| 110 | A |
| 110a | A |
| 110b | C |
| 111 | n.d. |
| 111a | A |
| 111b | C |
| 112 | n.d. |
| 112a | A |
| 112b | D |
| 113 | D |
| 114 | n.d. |
| 114a | A |
| 114b | D |
| 115 | n.d. |
| 115a | A |
| 115b | D |
| 116 | A |

TABLE 1B-continued

| Compound Number | Rapid-Fire Assay $IC_{50}$ |
|---|---|
| 116a | A |
| 116b | C |
| 117 | n.d. |
| 117a | A |
| 117b | C |
| 118 | C |
| 118a | C |
| 118b | D |
| 119 | B |
| 119a | B |
| 119b | D |
| 120 | n.d. |
| 120a | A |
| 120b | B |
| 120c | D |
| 120d | D |
| 121 | n.d. |
| 121a | A |
| 121b | A |
| 121c | D |
| 121d | D |
| 122 | n.d. |
| 122a | A |
| 122b | D |
| 123 | n.d. |
| 123a | A |
| 123b | A |
| 123c | D |
| 123d | D |
| 124 | n.d. |
| 124a | A |
| 124b | A |
| 124c | D |
| 124d | D |
| 125 | n.d. |
| 125a | A |
| 125b | D |
| 126 | n.d. |
| 126a | A |
| 126b | D |
| 127 | A |
| 127a | A |
| 127b | D |
| 128 | A |
| 128a | A |
| 128b | D |
| 129 | n.d. |
| 129a | B |
| 129b | D |
| 130 | n.d. |
| 130a | C |
| 130b | D |
| 131 | n.d. |
| 131a | B |
| 131b | D |
| 132 | D |
| 133 | A |
| 133a | A |
| 133b | B |
| 134 | n.d. |
| 134a | C |
| 134b | D |
| 135 | B |
| 136a | A |
| 136b | D |
| 137 | n.d. |
| 137a | A |
| 137b | D |
| 138 | n.d. |
| 138a | A |
| 138b | D |
| 139 | B |
| 139a | A |
| 139b | D |
| 140 | n.d. |
| 140a | B |

TABLE 1B-continued

| Compound Number | Rapid-Fire Assay $IC_{50}$ |
|---|---|
| 140b | D |
| 141 | n.d. |
| 141a | B |
| 141b | D |
| 141c | D |
| 141d | B |

Note:
A refers to $IC_{50}$ values <20 nM;
B refers to $IC_{50}$ values from 20 nM to 200 nM;
C refers to $IC_{50}$ values from >200 nM to 1000 nM; and
D refers to $IC_{50}$ values >1000 nM
n.d. refers to not determined

The invention claimed is:

1. A compound of Formula (I), a stereoisomer thereof, or a pharmaceutically acceptable salt thereof,

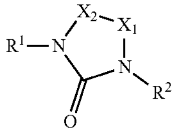

(I)

wherein:

$X_1$ is $CR^{3a}R^{3b}$, C═O or $NR^{3c}$;

$X_2$ is $CR^{4a}R^{4b}$ or C═O;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 4, 5 or 6 membered heterocycloalkyl is unsubstituted or is substituted with 1 to 4 $R^5$ groups and wherein the 5 or 6 membered heterocycloalkyl is optionally substituted with oxo;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O) 2, Y is $NR^6$, O, S, S═O or S(═O) 2 and Z is $NR^6$, O or S, and wherein the 5 or 6 membered heterocyclyl is unsubstituted or substituted with 1, 2, 3 or 4 $R^{12}$ groups and is optionally substituted with oxo;

vii) a 9 or 10 membered bicyclic heterocyclyl wherein 1, 2, 3, 4 or 5 ring members are each independently selected from N, $NR^6$, O and S, wherein the 9 or 10 membered bicyclic heterocyclyl is unsubstituted or is substituted with 1 to 4 $R^5$ groups;

viii) spiro attached $C_3$-$C_8$cycloalkyl which is unsubstituted or is substituted with 1 to 4 $R^5$ groups;

ix) bicyclic $C_3$-$C_8$cycloalkyl which is unsubstituted or is substituted with 1 to 4 $R^5$ groups;

x) $C_5$-$C_6$cycloalkenyl;

and xi) a 9 or 10 membered bicyclic heteroaryl wherein 1, 2, 3, 4 or 5 ring members are each independently selected from N, O and S, wherein the 9 or 10 membered bicyclic heteroaryl is unsubstituted or is substituted with 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

ii) a 10 membered bicyclic heteroaryl with an attachment point at a carbon atom ring member and with a N heteroatom as a ring member which is located at a beta (β) position relative to the attachment point, wherein the 10 membered bicyclic heteroaryl further has 0, 1, 2, 3, or 4 ring members each independently selected from N, O and S, and wherein the 10 membered bicyclic heteroaryl is unsubstituted or is substituted with 1, 2, 3 or 4 $R^{12}$ groups;

iii) a 9 membered bicyclic heteroaryl with an attachment point at a carbon atom ring member and with a N heteroatom as a ring member which is located at a beta (β) position relative to the attachment point, wherein the 9 membered bicyclic heteroaryl has 0, 1, 2, 3 or 4 additional N heteroatoms as ring members, and wherein the 9 membered bicyclic heteroaryl is unsubstituted or is substituted with 1, 2, 3 or 4 $R^{12}$ groups;

iv) a 9 membered bicyclic heteroaryl with an attachment point at a carbon atom ring member and with a N heteroatom as a ring member which is located at a beta (β) position relative to the attachment point, wherein the 9 membered bicyclic heteroaryl further has 0, 1, 2, 3, or 4 ring members each independently selected from N, $NR^6$, O and S, and wherein the 9 membered bicyclic heteroaryl is unsubstituted or is substituted with 1, 2, 3 or 4 $R^{12}$ groups;

v) a 9 or 10 membered bicyclic heterocyclyl with an attachment point at a carbon atom ring member and with a $NR^6$ as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

vi) a 9 or 10 membered bicyclic heterocyclyl with an attachment point at a carbon atom ring member and with a O heteroatom as a ring member which is located at a beta (β) position relative to the attachment point, wherein the 9 or 10 membered heterocyclyl further has 0, 1, 2, 3, or 4 ring members each independently selected from N, $NR^6$, O and S, and wherein the 9 or 10 membered heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

vii) a 9 or 10 membered bicyclic heteroaryl wherein 1, 2, 3, 4 or 5 ring members are each independently selected from N, $NR^6$, O and S, and wherein the 9 or 10 membered bicyclic heteroaryl is unsubstituted or is substituted with 1, 2, 3 or 4 $R^{12}$ groups;

viii) a 9 or 10 membered bicyclic heterocyclyl wherein 1, 2, 3, 4 or 5 ring members are each independently selected from N, $NR^6$, O and S, and wherein the 9 or 10 membered bicyclic heterocyclyl is substituted with 1 or 2 oxo, or the 9 or 10 membered heterocyclyl is unsubstituted or substituted with 1, 2, 3 or 4 $R^{12}$ groups and optionally substituted with 1 or 2 oxo;

and ix) a 10 membered bicyclic heterocyclyl with an attachment point at a carbon atom ring member and with a carbon atom as a ring member which is substituted with oxo and located at a beta (β) position relative to the attachment point, wherein the 10 membered heterocyclyl further has 1, 2, 3, or 4 ring members each independently selected from N, $NR^6$, O and S, and wherein the 10 membered heterocyclyl is unsubstituted or the 10 membered heterocyclyl is substituted with 1, 2, 3 or 4 $R^{12}$ groups and optionally substituted with an additional oxo;

$R^{3a}$ is —CN, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or substituted with —C(═O)OH, —OH, CN or $NH_2$;

$R^{3b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or substituted with —C(═O)OH, —OH, CN or $NH_2$;

$R^{4a}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or substituted with —C(═O)OH, —OH, CN or $NH_2$;

$R^{4b}$ is H, $C_3$-$C_8$cycloalkyl, 4 to 7 membered heterocycloalkyl wherein 1, 2 or 3 ring members are each independently selected from N, $NR^6$, O and S, $C_1$-$C_6$alkyl that is unsubstituted or is substituted with one or more $R^{15}$ groups or $C_2$-$C_6$alkenyl that is unsubstituted or is substituted with one or more $R^{15}$ groups, and wherein the cycloalkyl and heterocycloalkyl are unsubstituted or the cycloalkyl and heterocycloalkyl are substituted with 1 or 2 substituents independently selected from the group consisting of CN, —C(═O)OH, $NH_2$, OH, $C_1$-$C_6$haloalkyl, and $C_1$-$C_6$alkyl that is unsubstituted or substituted with —C(═O)OH, —OH, CN or $NH_2$;

$R^{3c}$ is H, —C(═O)$C_2$-$C_6$alkenyl or $C_1$-$C_6$alkyl substituted with one or more $R^{15}$ groups;

each $R^5$ is independently selected from the group consisting of —CN, —OH, —$NR^7R^8$, $NR^6C$(═O)$C_2$-$C_6$alkenyl, —$SF_5$, S(═O)$_2C_1$-$C_6$alkyl, —C(═O)N$(R^7)_2$, $C_1$-$C_6$haloalkyl, halo, $C_1$-$C_6$haloalkoxy, $C_1$-$C_6$alkoxy, $C_3$-$C_6$cycloalkyl, 4 to 6 membered heterocycloalkyl wherein 1, 2, 3 or 4 ring members are each independently selected from N, $NR^6$, O and S, a 5 or 6 membered heteroaryl wherein 1, 2 or 3 ring members are each independently selected from N, O and S, and a $C_1$-$C_6$alkyl that is unsubstituted or is substituted with CN, $NH_2$ or OH, and wherein the cycloalkyl and heterocycloalkyl are unsubstituted or are substituted with 1, 2, 3 or 4 $R^9$ groups;

each $R^6$ is independently selected from the group consisting of H, $C_1$-$C_6$haloalkyl, $C_1$-$C_6$haloalkoxy, —S(═O)$_2$N$(R^7)_2$, S(═O)$_2C_1$-$C_6$alkyl, S(═O)$_2C_1$-$C_6$haloalkyl, —S(═O)$_2C_3$-$C_6$cycloalkyl, —C(═O)$R^7$, —C(═O)N$(R^7)_2$, $C_3$-$C_6$cycloalkyl, and $C_1$-$C_6$alkyl that is unsubstituted or is substituted with —OH, CN or —C(═O)OH;

each $R^7$ is independently selected from the group consisting of H, and $C_1$-$C_6$alkyl that is unsubstituted or is substituted with OH or $C_1$-$C_6$alkoxy;

$R^8$ is H, $C_1$-$C_6$alkyl that is unsubstituted, $C_3$-$C_8$cycloalkyl or 4 to 6 membered heterocycloalkyl wherein 1, 2, 3 or 4 ring members are each independently selected from N, $NR^6$, O and S, and wherein the cycloalkyl and heterocycloalkyl are unsubstituted or are substituted with 1, 2, 3 or 4 $R^9$ groups;

each $R^9$ is independently selected from the group consisting of $NR^{10}R^{11}$, —C(═O) N $(R^7)_2$ and $C_1$-$C_6$alkyl substituted with —OH or —N$(R^7)_2$;

$R^{10}$ is H or $C_1$-$C_6$alkyl that is unsubstituted;

$R^{11}$ is H, $C_1$-$C_6$alkyl that is unsubstituted or —S(═O)$_2$ $C_1$-$C_6$alkyl;

each $R^{12}$ is independently selected from the group consisting of —C(═O)N$(R^7)_2$, —C(═O)OH, —N$(R^7)_2$, —CN, —OH, —S(═O)$_2R^7$, —S(═O)$_2$N $(R^7)_2$,

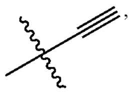, halo, phenyl, $C_3$-$C_8$cycloalkyl, 4 to 6 membered heterocycloalkyl wherein 1, 2, 3 or 4 ring members are each independently selected from N, $NR^6$, O and S, 5 or 6 membered heteroaryl wherein 1, 2 or 3 ring members are each independently selected from N, O and S, and $C_1$-$C_6$alkyl that is substituted or is substituted with $NH_2$, CN or OH, and wherein the phenyl, heterocycloalkyl and heteroaryl are unsubstituted or are substituted with 1 or 2 OH groups;

and each $R^{15}$ is independently selected from the group consisting of CN, $NH_2$, —OH, —C(═O)OH, —C(═O) N$(R^7)_2$, —C(═O) C(═O)OH, $C_1$-$C_6$alkoxy, halo, $C_1$-$C_6$haloalkyl, $C_3$-$C_8$cycloalkyl, a 5 or a 6 membered heteroaryl wherein 1, 2, 3, or 4 ring members are each independently selected from N, $NR^6$, O and S, and a 3 to 6 membered heterocycloalkyl wherein 1, 2 or 3 ring members are each independently selected from N, $NR^6$, O and S, and wherein the cycloalkyl, heteroaryl and heterocycloalkyl are unsubstituted or are substituted with 1, 2 or 3 substituents independently selected from the group consisting of CN, —C(═O)OH, $NH_2$, OH and $C_1$-$C_6$alkyl that is unsubstituted.

2. The compound of claim 1, a stereoisomer thereof, or a pharmaceutically acceptable salt thereof, wherein:

$X_1$ is $CR^{3a}R^{3b}$;

$X_2$ is $CR^{4a}R^{4b}$;

$R^1$ is selected from the group consisting of:

i) a 5 or 6 membered heteroaryl wherein 1, 2, 3 or 4 ring members are each independently selected from N, $NR^6$, O and S, wherein the 5 or 6 membered heteroaryl is unsubstituted or is substituted with 1 to 4 $R^5$ groups;

ii) phenyl which is unsubstituted or is substituted with 1 to 4 $R^5$ groups;

iii) a 4, 5 or 6 membered heterocycloalkyl wherein 1, 2, 3 or 4 ring members are each independently selected from N, $NR^6$, O and S, wherein the 5 or 6 membered heterocycloalkyl is unsubstituted or is substituted with 1 to 4 $R^5$ groups;

iv) $C_3$-$C_8$cycloalkyl which is unsubstituted or is substituted with 1 to 4 $R^5$ groups;

v) $C_1$-$C_6$alkyl that is unsubstituted;

vi) 5 or 6 membered heterocyclyl wherein 1, 2 or 3 ring members are each independently selected from W, Y and Z, wherein W is $NR^6$, O, S, S═O or S(═O) 2, Y is $NR^6$, O, S, S═O or S(═O) 2 and Z is $NR^6$, O or S, and wherein the 5 or 6 membered heterocyclyl is unsubstituted or substituted with 1 or 2 $R^{12}$ groups and is optionally substituted with oxo;

vii) a 9 or 10 membered bicyclic heterocyclyl wherein 1 or 2 ring members is each independently selected from N and $NR^6$, wherein the 9 or 10 membered bicyclic heterocyclyl is unsubstituted or is substituted with 1 to 2 $R^5$ groups; and viii) bicyclic $C_3$-$C_8$cycloalkyl which is unsubstituted or is substituted with 1 to 4 $R^5$ groups;

$R^2$ is selected from the group consisting of:

i) a 10 membered bicyclic heteroaryl with an attachment point at a carbon atom ring member and with a N heteroatom as a ring member which is located at a beta (β) position relative to the attachment point, wherein the 10 membered bicyclic heteroaryl has 0, 1, 2 or 3 additional N heteroatoms as ring members, and wherein the 10 membered bicyclic heteroaryl is unsubstituted or is substituted with 1, 2, 3 or 4 $R^{12}$ groups;

and ii) a 9 or 10 membered bicyclic heteroaryl wherein 1, 2, 3, 4 or 5 ring members are each independently selected from N, $NR^6$, O and S, and wherein the 9 or 10 membered bicyclic heteroaryl is unsubstituted or is substituted with 1, 2, 3 or 4 $R^{12}$ groups;

$R^{3a}$ is —CN;

$R^{3b}$ is H or $C_1$-$C_6$alkyl that is unsubstituted;

$R^{4a}$ is H or $C_1$-$C_6$alkyl that is unsubstituted;

$R^{4b}$ is H or $C_1$-$C_6$alkyl that is unsubstituted;

each $R^5$ is independently selected from the group consisting of CN, —OH, $S(=O)_2C_1$-$C_6$alkyl, $C_1$-$C_6$haloalkyl, halo, $C_1$-$C_6$haloalkoxy, $C_1$-$C_6$alkoxy, $C_3$-$C_8$cycloalkyl, and $C_1$-$C_6$alkyl that is unsubstituted or is substituted with OH;

each $R^6$ is independently selected from the group consisting of H, $C_1$-$C_6$haloalkyl, $C_1$-$C_6$haloalkoxy, $S(=O)_2C_1$-$C_6$alkyl, $S(=O)_2C_1$-$C_6$haloalkyl, —S(=O) $2C_3$-$C_6$cycloalkyl, $—C(=O)R^7$, $C_3$-$C_6$cycloalkyl, and $C_1$-$C_6$alkyl that is unsubstituted or is substituted with —OH;

each $R^7$ is independently selected from the group consisting of H, and $C_1$-$C_6$alkyl that is unsubstituted or is substituted with OH or $C_1$-$C_6$alkoxy; and each $R^{12}$ is independently selected from the group consisting of $—C(=O)N(R^7)_2$, —C(=O)OH, —CN, $—S(=O)_2R^7$ and $C_1$-$C_6$alkyl substituted with OH.

3. The compound of claim 1, a stereoisomer thereof, or a pharmaceutically acceptable salt thereof, wherein $R^2$ is isoquinolin-4-yl which is unsubstituted or substituted with 1 or 2 $R^{12}$ groups.

4. The compound of claim 1, a stereoisomer thereof, or a pharmaceutically acceptable salt thereof, wherein $R^2$ is isoquinolin-4-yl which is unsubstituted.

5. The compound of claim 1, a stereoisomer thereof, or a pharmaceutically acceptable salt thereof, wherein each $R^{12}$ is independently selected from the group consisting of —C(=O) N $(R^7)_2$, —C(=O)OH, —CN, $—S(=O)_2R^7$ and $C_1$-$C_6$alkyl substituted with OH.

6. The compound of claim 1, a stereoisomer thereof, or a pharmaceutically acceptable salt thereof, wherein each $R^{12}$ is independently selected from the group consisting of —C(=O) $NH_2$, $—C(=O)NH(CH_2)_2OCH_3$, —C(=O)OH, —CN, $—S(=O)_2CH_3$ and $—C(CH_3)_2OH$.

7. The compound of claim 1, a stereoisomer thereof, or a pharmaceutically acceptable salt thereof, wherein $R^1$ is phenyl or a 5 or 6 membered heteroaryl wherein 1 or 2 ring members are each independently selected from N, $NR^6$, O and S, wherein the phenyl or heteroaryl is unsubstituted or is substituted with 1 to 2 $R^5$ groups.

8. The compound of claim 1, a stereoisomer thereof, or a pharmaceutically acceptable salt thereof, wherein $R^1$ is phenyl, pyridyl, pyridazinyl, pyrimidinyl or pyrazinyl, each of which is unsubstituted or is substituted with 1 to 2 $R^5$ groups independently selected from Cl, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

9. The compound of claim 1, a stereoisomer thereof, or a pharmaceutically acceptable salt thereof, wherein $R^1$ is phenyl or pyridyl, each of which is unsubstituted or is substituted with 1 to 2 $R^5$ group independently selected from Cl, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

10. The compound of claim 1, a stereoisomer thereof, or a pharmaceutically acceptable salt thereof, wherein $R^1$ is pyridyl, which is unsubstituted or is substituted with 1 to 2 $R^5$ group independently selected from Cl, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

11. The compound of claim 1, a stereoisomer thereof, or a pharmaceutically acceptable salt thereof, wherein $R^1$ is pyridyl, which is unsubstituted or is substituted with $CF_3$.

12. The compound of claim 1, a stereoisomer thereof, or a pharmaceutically acceptable salt thereof, wherein $R^1$ is pyridyl, which is substituted with $CF_3$.

13. The compound of claim 1, a stereoisomer thereof, or a pharmaceutically acceptable salt thereof, wherein $R^1$ is pyrazolyl or imidazolyl, each of which is unsubstituted or is substituted with 1 to 2 $R^5$ group independently selected from Cl, F, $CF_3$, $—CHF_2$, $—CH_3$, $—CH(CH_3)_2$, $—OCH_3$, $—OCHF_2$, $—OCF_3$, CN, $—SO_2CH_3$ and $—C(CH_3)_2OH$.

14. The compound of claim 1, a stereoisomer thereof, or a pharmaceutically acceptable salt thereof, wherein $R^1$ is $C_3$-$C_8$cycloalkyl or bicyclic $C_3$-$C_8$cycloalkyl, each of which is unsubstituted or is substituted with 1 to 2 $R^5$ groups.

15. The compound of claim 1, a stereoisomer thereof, or a pharmaceutically acceptable salt thereof, wherein $R^1$ is $C_3$-$C_8$cycloalkyl or bicyclic $C_3$-$C_8$cycloalkyl, each of which is unsubstituted or is substituted with 1 to 2 $R^5$ groups, where each $R^5$ is independently selected from the group consisting of halo, OH, $C_1$-$C_6$haloalkyl, $C_1$-$C_6$alkyl that is unsubstituted and $C_3$-$C_8$cycloalkyl that is unsubstituted.

16. The compound of claim 1, a stereoisomer thereof, or a pharmaceutically acceptable salt thereof, wherein $R^1$ is cyclobutyl, cyclopentyl, cyclohexyl, bicyclo[1.1.1]pentan-1-yl), (spiro[3.3]heptan-2-yl) or (spiro[2.3]hexan-5-yl), each of which is unsubstituted or is substituted with 1 to 2 $R^5$ groups, where each $R^5$ is independently selected from the group consisting of F, $—CF_3$, $—CH_3$, $—CH(CH_3)_2$ and cyclopropyl.

17. The compound of claim 1, a stereoisomer thereof, or a pharmaceutically acceptable salt thereof, wherein $R^1$ is 5 or 6 membered heterocyclyl wherein 1, 2 or 3 ring members are each independently selected from W, Y and Z, wherein W is $NR^6$, O, S, S=O or S(=O) 2, Y is $NR^6$, O, S, S=O or $S(=O)_2$ and Z is $NR^6$, O or S, and wherein the 5 or 6 membered heterocyclyl is substituted with oxo and substituted with an $R^5$ group.

18. The compound of claim 1, a stereoisomer thereof, or a pharmaceutically acceptable salt thereof, wherein $R^1$ is 5 or 6 membered heterocyclyl wherein 1, 2 or 3 ring members are each independently selected from W, Y and Z, wherein W is $NR^6$, O, S, S=O or $S(=O)_2$, Y is $NR^6$, O, S, S=O or $S(=O)_2$ and Z is $NR^6$, O or S, and wherein the 5 or 6 membered heterocyclyl is substituted with oxo, wherein $R^6$ is H or $—CH_3$, and wherein $R^5$ is $—CF_3$.

19. The compound of claim 1, a stereoisomer thereof, or a pharmaceutically acceptable salt thereof, wherein $R^1$ is a 4, 5 or 6 membered heterocycloalkyl wherein 1 or 2 ring members are each independently selected from N, $NR^6$, O and S, and wherein the 4, 5 or 6 membered heterocycloalkyl is unsubstituted.

20. The compound of claim 1, a stereoisomer thereof, or a pharmaceutically acceptable salt thereof, wherein $R^1$ is a 4 or 5 membered heterocycloalkyl wherein 1 ring member is selected from N, $NR^6$, O and S, and wherein $R^6$ is —C(═O) $CH_2OH$, —$(CH_2)_2OH$, —$(CH_2)_2CF_3$, —$CH_2CF_3$, —C(═O) $CH_3$, —$SO_2CH_3$, —$SO_2CF_3$, —$SO_2$-cyclopropyl or cyclopropyl.

21. The compound of claim 1, a stereoisomer thereof, or a pharmaceutically acceptable salt thereof, wherein $R^1$ is azetidinyl or pyrrolidinyl, each of which is substituted with a group selected from —C(═O) $CH_2OH$, —$(CH_2)_2OH$, —$(CH_2)_2CF_3$, —$CH_2CF_3$, —C(═O) $CH_3$, —$SO_2CH_3$, —$SO_2CF_3$, —$SO_2$-cyclopropyl and cyclopropyl.

22. The compound of claim 1, a stereoisomer thereof, or a pharmaceutically acceptable salt thereof, wherein:

$R^{3a}$ is —CN;

$R^{3b}$ is H or $C_1$-$C_6$alkyl that is unsubstituted;

$R^{4a}$ is H or $C_1$-$C_6$alkyl that is unsubstituted; and $R^{4b}$ is H or $C_1$-$C_6$alkyl that is unsubstituted.

23. The compound of claim 1, or a pharmaceutically acceptable salt or stereoisomer thereof, having the structure of a compound of Formula (I-i), or a pharmaceutically acceptable salt or stereoisomer thereof, (I-i)

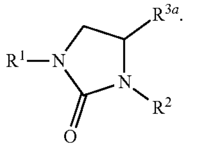

wherein:

$R^1$ is pyridin-3-yl substituted with —$CF_3$;

$R^2$ is isoquinolin-4-yl 3 (isoquinolin 4 yl) which is unsubstituted; and $R^{3a}$ is —CN.

24. The compound of claim 1, or a pharmaceutically acceptable salt or stereoisomer thereof, wherein the compound is selected from:

3-(isoquinolin-4-yl)-2-oxo-1-phenylimidazolidine-4-carbonitrile;

(R)-3-(isoquinolin-4-yl)-2-oxo-1-phenylimidazolidine-4-carbonitrile;

1-(3-chlorophenyl)-3-(isoquinolin-4-yl)-2-oxoimidazolidine-4-carbonitrile;

(R)-1-(3-chlorophenyl)-3-(isoquinolin-4-yl)-2-oxoimidazolidine-4-carbonitrile;

3-(isoquinolin-4-yl)-2-oxo-1-(5-(trifluoromethyl) pyridin-2-yl) imidazolidine-4-carbonitrile;

3-(isoquinolin-4-yl)-2-oxo-1-(4-(trifluoromethyl) phenyl) imidazolidine-4-carbonitrile;

1-(4-chlorophenyl)-3-(isoquinolin-4-yl)-2-oxoimidazolidine-4-carbonitrile;

1-(4-fluorophenyl)-3-(isoquinolin-4-yl)-2-oxoimidazolidine-4-carbonitrile;

1-(3-fluorophenyl)-3-(isoquinolin-4-yl)-2-oxoimidazolidine-4-carbonitrile;

1-(5-fluoropyridin-2-yl)-3-(isoquinolin-4-yl)-2-oxoimidazolidine-4-carbonitrile;

3-(isoquinolin-4-yl)-2-oxo-1-(6-(trifluoromethyl) pyridin-3-yl) imidazolidine-4-carbonitrile;

1-(5-chloropyridin-2-yl)-3-(isoquinolin-4-yl)-2-oxoimidazolidine-4-carbonitrile;

(R)-3-(isoquinolin-4-yl)-2-oxo-1-(6-(trifluoromethyl) pyridin-3-yl) imidazolidine-4-carbonitrile;

3-(isoquinolin-4-yl)-1-(2-methoxy-4-(trifluoromethyl) phenyl)-2-oxoimidazolidine-4-carbonitrile;

(R)-3-(isoquinolin-4-yl)-1-(2-methoxy-4-(trifluoromethyl) phenyl)-2-oxoimidazolidine-4-carbonitrile;

3-(isoquinolin-4-yl)-2-oxo-1-(6-(trifluoromethyl) pyridazin-4-yl) imidazolidine-4-carbonitrile;

(R)-3-(isoquinolin-4-yl)-2-oxo-1-(6-(trifluoromethyl) pyridazin-4-yl) imidazolidine-4-carbonitrile;

3-(isoquinolin-4-yl)-1-(5-methoxy-2-(trifluoromethyl) pyridin-4-yl)-2-oxoimidazolidine-4-carbonitrile;

(R)-3-(isoquinolin-4-yl)-1-(5-methoxy-2-(trifluoromethyl) pyridin-4-yl)-2-oxoimidazolidine-4-carbonitrile;

1-(5-cyano-2-methoxyphenyl)-3-(isoquinolin-4-yl)-2-oxoimidazolidine-4-carbonitrile;

(R)-1-(5-cyano-2-methoxyphenyl)-3-(isoquinolin-4-yl)-2-oxoimidazolidine-4-carbonitrile;

1-(5-chloropyrimidin-2-yl)-3-(isoquinolin-4-yl)-2-oxoimidazolidine-4-carbonitrile;

(R)-1-(5-chloropyrimidin-2-yl)-3-(isoquinolin-4-yl)-2-oxoimidazolidine-4-carbonitrile;

3-(isoquinolin-4-yl)-1-(2-methoxy-5-(trifluoromethyl) phenyl)-2-oxoimidazolidine-4-carbonitrile;

(R)-3-(isoquinolin-4-yl)-1-(2-methoxy-5-(trifluoromethyl) phenyl)-2-oxoimidazolidine-4-carbonitrile;

5-(4-cyano-3-(isoquinolin-4-yl)-2-oxoimidazolidin-1-yl)-2-(trifluoromethyl) isonicotinonitrile;

(R)-5-(4-cyano-3-(isoquinolin-4-yl)-2-oxoimidazolidin-1-yl)-2-(trifluoromethyl) isonicotinonitrile;

1-(4-cyano-2-methoxyphenyl)-3-(isoquinolin-4-yl)-2-oxoimidazolidine-4-carbonitrile;

(R)-1-(4-cyano-2-methoxyphenyl)-3-(isoquinolin-4-yl)-2-oxoimidazolidine-4-carbonitrile;

1-(5-chloro-2-cyanophenyl)-3-(isoquinolin-4-yl)-2-oxoimidazolidine-4-carbonitrile;

(R)-1-(5-chloro-2-cyanophenyl)-3-(isoquinolin-4-yl)-2-oxoimidazolidine-4-carbonitrile;

1-(5-fluoro-2-methylphenyl)-3-(isoquinolin-4-yl)-2-oxoimidazolidine-4-carbonitrile;

(R)-1-(5-fluoro-2-methylphenyl)-3-(isoquinolin-4-yl)-2-oxoimidazolidine-4-carbonitrile;

1-(3-(difluoromethyl) phenyl)-3-(isoquinolin-4-yl)-2-oxoimidazolidine-4-carbonitrile;

(R)-1-(3-(difluoromethyl) phenyl)-3-(isoquinolin-4-yl)-2-oxoimidazolidine-4-carbonitrile;

3-(isoquinolin-4-yl)-1-(2-methoxypyridin-4-yl)-2-oxoimidazolidine-4-carbonitrile;

(R)-3-(isoquinolin-4-yl)-1-(2-methoxypyridin-4-yl)-2-oxoimidazolidine-4-carbonitrile;

3-(isoquinolin-4-yl)-1-(2-methyl-5-(trifluoromethyl) phenyl)-2-oxoimidazolidine-4-carbonitrile;

(R)-3-(isoquinolin-4-yl)-1-(2-methyl-5-(trifluoromethyl) phenyl)-2-oxoimidazolidine-4-carbonitrile;

1-(R)-1-(2-hydroxyacetyl) pyrrolidin-3-yl)-3-(isoquinolin-4-yl)-2-oxoimidazolidine-4-carbonitrile;

(R)-1-(R)-1-(2-hydroxyacetyl) pyrrolidin-3-yl)-3-(isoquinolin-4-yl)-2-oxoimidazolidine-4-carbonitrile;

3-(isoquinolin-4-yl)-2-oxo-1-(R)-1-(3,3,3-trifluoropropyl) pyrrolidin-3-yl) imidazolidine-4-carbonitrile;

(R)-3-(isoquinolin-4-yl)-2-oxo-1-(R)-1-(3,3,3-trifluoropropyl) pyrrolidin-3-yl) imidazolidine-4-carbonitrile;

1-(3,3-difluorocyclobutyl)-3-(isoquinolin-4-yl)-2-oxoimidazolidine-4-carbonitrile;

1-(3-hydroxy-3-(trifluoromethyl) cyclobutyl)-3-(isoquinolin-4-yl)-2-oxoimidazolidine-4-carbonitrile;

1-(3,3-difluorocyclohexyl)-3-(isoquinolin-4-yl)-2-oxoimidazolidine-4-carbonitrile;

3-(isoquinolin-4-yl)-2-oxo-1-(5-(trifluoromethyl) pyridazin-3-yl) imidazolidine-4-carbonitrile;

(R)-3-(isoquinolin-4-yl)-2-oxo-1-(5-(trifluoromethyl) pyridazin-3-yl) imidazolidine-4-carbonitrile;

3-(isoquinolin-4-yl)-1-(5-methoxy-2-(trifluoromethyl) pyrimidin-4-yl)-2-oxoimidazolidine-4-carbonitrile;

(R)-3-(isoquinolin-4-yl)-1-(5-methoxy-2-(trifluoromethyl) pyrimidin-4-yl)-2-oxoimidazolidine-4-carbonitrile;

3-(isoquinolin-4-yl)-2-oxo-1-(5-(trifluoromethyl) pyrazin-2-yl) imidazolidine-4-carbonitrile;

(R)-3-(isoquinolin-4-yl)-2-oxo-1-(5-(trifluoromethyl) pyrazin-2-yl) imidazolidine-4-carbonitrile;

4-(3-(3-chlorophenyl)-5-cyano-2-oxoimidazolidin-1-yl) isoquinoline-6-carboxylic acid;

(R)-4-(3-(3-chlorophenyl)-5-cyano-2-oxoimidazolidin-1-yl) isoquinoline-6-carboxylic acid;

1-(3-chlorophenyl)-3-(6-(2-hydroxypropan-2-yl) isoquinolin-4-yl)-2-oxoimidazolidine-4-carbonitrile;

4-(3-(3-chlorophenyl)-5-cyano-2-oxoimidazolidin-1-yl) isoquinoline-6-carboxamide;

4-(3-(3-chlorophenyl)-5-cyano-2-oxoimidazolidin-1-yl)-N-(2-methoxyethyl) isoquinoline-6-carboxamide;

1-(3-chlorophenyl)-3-(6-(methylsulfonyl) isoquinolin-4-yl)-2-oxoimidazolidine-4-carbonitrile;

(R)-1-(3-chlorophenyl)-3-(6-(methylsulfonyl) isoquinolin-4-yl)-2-oxoimidazolidine-4-carbonitrile;

1-(2-methoxy-5-(trifluoromethyl) phenyl)-3-(6-(methylsulfonyl) isoquinolin-4-yl)-2-oxoimidazolidine-4-carbonitrile;

(R)-1-(2-methoxy-5-(trifluoromethyl) phenyl)-3-(6-(methylsulfonyl) isoquinolin-4-yl)-2-oxoimidazolidine-4-carbonitrile;

4-(3-(3-chlorophenyl)-5-cyano-2-oxoimidazolidin-1-yl) isoquinoline-6-carbonitrile;

(R)-4-(3-(3-chlorophenyl)-5-cyano-2-oxoimidazolidin-1-yl) isoquinoline-6-carbonitrile;

1-(3-chlorophenyl)-3-(isoquinolin-4-yl)-4-methyl-2-oxoimidazolidine-4-carbonitrile;

(R)-1-(3-chlorophenyl)-3-(isoquinolin-4-yl)-4-methyl-2-oxoimidazolidine-4-carbonitrile;

(R)-1-(5-chloropyridin-2-yl)-3-(isoquinolin-4-yl)-2-oxoimidazolidine-4-carbonitrile;

3-(isoquinolin-4-yl)-2-oxo-1-(5-(trifluoromethyl) pyrimidin-2-yl) imidazolidine-4-carbonitrile;

(R)-3-(isoquinolin-4-yl)-2-oxo-1-(5-(trifluoromethyl) pyrimidin-2-yl) imidazolidine-4-carbonitrile;

(5S)-1-(3-chlorophenyl)-3-(isoquinolin-4-yl)-5-methyl-2-oxoimidazolidine-4-carbonitrile;

(4R,5S)-1-(3-chlorophenyl)-3-(isoquinolin-4-yl)-5-methyl-2-oxoimidazolidine-4-carbonitrile;

3-(isoquinolin-4-yl)-1-(2-methylpyridin-4-yl)-2-oxoimidazolidine-4-carbonitrile;

(R)-3-(isoquinolin-4-yl)-1-(2-methylpyridin-4-yl)-2-oxoimidazolidine-4-carbonitrile;

(R)-3-(isoquinolin-4-yl)-2-oxo-1-(1r,3R)-3-(trifluoromethyl) cyclobutyl) imidazolidine-4-carbonitrile;

(R)-3-(isoquinolin-4-yl)-2-oxo-1-(1s,3S)-3-(trifluoromethyl) cyclobutyl) imidazolidine-4-carbonitrile;

1-(R)-1-(2-hydroxyethyl) pyrrolidin-3-yl)-3-(isoquinolin-4-yl)-2-oxoimidazolidine-4-carbonitrile;

(R)-1-(R)-1-(2-hydroxyethyl) pyrrolidin-3-yl)-3-(isoquinolin-4-yl)-2-oxoimidazolidine-4-carbonitrile;

3-(isoquinolin-4-yl)-1-(3-methoxy-6-(trifluoromethyl) pyridin-2-yl)-2-oxoimidazolidine-4-carbonitrile;

(R)-3-(isoquinolin-4-yl)-1-(3-methoxy-6-(trifluoromethyl) pyridin-2-yl)-2-oxoimidazolidine-4-carbonitrile;

3-(isoquinolin-4-yl)-1-(3-(methylsulfonyl) phenyl)-2-oxoimidazolidine-4-carbonitrile;

(R)-3-(isoquinolin-4-yl)-1-(3-(methylsulfonyl) phenyl)-2-oxoimidazolidine-4-carbonitrile;

3-(isoquinolin-4-yl)-2-oxo-1-(4-(trifluoromethyl) pyrimidin-2-yl) imidazolidine-4-carbonitrile;

(R)-3-(isoquinolin-4-yl)-2-oxo-1-(4-(trifluoromethyl) pyrimidin-2-yl) imidazolidine-4-carbonitrile;

1-(4-cyanophenyl)-3-(isoquinolin-4-yl)-2-oxoimidazolidine-4-carbonitrile;

(R)-1-(4-cyanophenyl)-3-(isoquinolin-4-yl)-2-oxoimidazolidine-4-carbonitrile;

3-(isoquinolin-4-yl)-2-oxo-1-(6-(trifluoromethyl) pyridin-2-yl) imidazolidine-4-carbonitrile;

(R)-3-(isoquinolin-4-yl)-2-oxo-1-(6-(trifluoromethyl) pyridin-2-yl) imidazolidine-4-carbonitrile;

1-(3-cyanophenyl)-3-(isoquinolin-4-yl)-2-oxoimidazolidine-4-carbonitrile;

(R)-1-(3-cyanophenyl)-3-(isoquinolin-4-yl)-2-oxoimidazolidine-4-carbonitrile;

3-(isoquinolin-4-yl)-1-(4-methylpyrimidin-2-yl)-2-oxoimidazolidine-4-carbonitrile;

(R)-3-(isoquinolin-4-yl)-1-(4-methylpyrimidin-2-yl)-2-oxoimidazolidine-4-carbonitrile;

1-(5-chloropyridazin-3-yl)-3-(isoquinolin-4-yl)-2-oxoimidazolidine-4-carbonitrile;

(R)-1-(5-chloropyridazin-3-yl)-3-(isoquinolin-4-yl)-2-oxoimidazolidine-4-carbonitrile;

1-(6-fluoropyridin-3-yl)-3-(isoquinolin-4-yl)-2-oxoimidazolidine-4-carbonitrile;

(R)-1-(6-fluoropyridin-3-yl)-3-(isoquinolin-4-yl)-2-oxoimidazolidine-4-carbonitrile;

1-(2-fluorophenyl)-3-(isoquinolin-4-yl)-2-oxoimidazolidine-4-carbonitrile;

(R)-1-(2-fluorophenyl)-3-(isoquinolin-4-yl)-2-oxoimidazolidine-4-carbonitrile;

3-(isoquinolin-4-yl)-2-oxo-1-(2-(trifluoromethyl) pyridin-4-yl) imidazolidine-4-carbonitrile;

(R)-3-(isoquinolin-4-yl)-2-oxo-1-(2-(trifluoromethyl) pyridin-4-yl) imidazolidine-4-carbonitrile;

1-(5-chloro-3-methoxypyridin-2-yl)-3-(isoquinolin-4-yl)-2-oxoimidazolidine-4-carbonitrile;

(R)-1-(5-chloro-3-methoxypyridin-2-yl)-3-(isoquinolin-4-yl)-2-oxoimidazolidine-4-carbonitrile;

1-(5-(difluoromethoxy)-2-fluorophenyl)-3-(isoquinolin-4-yl)-2-oxoimidazolidine-4-carbonitrile;

(R)-1-(5-(difluoromethoxy)-2-fluorophenyl)-3-(isoquinolin-4-yl)-2-oxoimidazolidine-4-carbonitrile;

1-(4-chloro-2-cyanophenyl)-3-(isoquinolin-4-yl)-2-oxoimidazolidine-4-carbonitrile;

(R)-1-(4-chloro-2-cyanophenyl)-3-(isoquinolin-4-yl)-2-oxoimidazolidine-4-carbonitrile;

1-(6-fluoropyridin-2-yl)-3-(isoquinolin-4-yl)-2-oxoimidazolidine-4-carbonitrile;

(R)-1-(6-fluoropyridin-2-yl)-3-(isoquinolin-4-yl)-2-oxoimidazolidine-4-carbonitrile;

3-(isoquinolin-4-yl)-1-(5-methyl-2-(trifluoromethyl) pyrimidin-4-yl)-2-oxoimidazolidine-4-carbonitrile;

(R)-3-(isoquinolin-4-yl)-1-(5-methyl-2-(trifluoromethyl) pyrimidin-4-yl)-2-oxoimidazolidine-4-carbonitrile;

1-(1H-indazol-7-yl)-3-(isoquinolin-4-yl)-2-oxoimidazolidine-4-carbonitrile;

(R)-1-(1H-indazol-7-yl)-3-(isoquinolin-4-yl)-2-oxoimidazolidine-4-carbonitrile;

1-(1-isopropyl-1H-pyrazol-4-yl)-3-(isoquinolin-4-yl)-2-oxoimidazolidine-4-carbonitrile;

(R)-1-(1-isopropyl-1H-pyrazol-4-yl)-3-(isoquinolin-4-yl)-2-oxoimidazolidine-4-carbonitrile;

3-(isoquinolin-4-yl)-1-(1-methyl-1H-pyrazol-4-yl)-2-oxoimidazolidine-4-carbonitrile;
(R)-3-(isoquinolin-4-yl)-1-(1-methyl-1H-pyrazol-4-yl)-2-oxoimidazolidine-4-carbonitrile;
1-(2,4-difluorophenyl)-3-(isoquinolin-4-yl)-2-oxoimidazolidine-4-carbonitrile;
(R)-1-(2,4-difluorophenyl)-3-(isoquinolin-4-yl)-2-oxoimidazolidine-4-carbonitrile;
3-(isoquinolin-4-yl)-1-(1-methyl-2-oxo-1,2-dihydropyridin-4-yl)-2-oxoimidazolidine-4-carbonitrile;
(R)-3-(isoquinolin-4-yl)-1-(1-methyl-2-oxo-1,2-dihydropyridin-4-yl)-2-oxoimidazolidine-4-carbonitrile;
3-(isoquinolin-4-yl)-2-oxo-1-(5-(trifluoromethyl)-1H-imidazol-2-yl) imidazolidine-4-carbonitrile;
(R)-3-(isoquinolin-4-yl)-2-oxo-1-(5-(trifluoromethyl)-1H-imidazol-2-yl) imidazolidine-4-carbonitrile;
1-(3-(2-hydroxypropan-2-yl) phenyl)-3-(isoquinolin-4-yl)-2-oxoimidazolidine-4-carbonitrile;
(R)-1-(3-(2-hydroxypropan-2-yl) phenyl)-3-(isoquinolin-4-yl)-2-oxoimidazolidine-4-carbonitrile;
1-(5-chloro-2-(trifluoromethyl) pyridin-4-yl)-3-(isoquinolin-4-yl)-2-oxoimidazolidine-4-carbonitrile;
3-(isoquinolin-4-yl)-1-(5-methyl-2-(trifluoromethyl) pyridin-4-yl)-2-oxoimidazolidine-4-carbonitrile;
(R)-3-(isoquinolin-4-yl)-1-(5-methyl-2-(trifluoromethyl) pyridin-4-yl)-2-oxoimidazolidine-4-carbonitrile;
1-(4-(difluoromethoxy) phenyl)-3-(isoquinolin-4-yl)-2-oxoimidazolidine-4-carbonitrile;
(R)-1-(4-(difluoromethoxy) phenyl)-3-(isoquinolin-4-yl)-2-oxoimidazolidine-4-carbonitrile;
1-(3,4-difluorophenyl)-3-(isoquinolin-4-yl)-2-oxoimidazolidine-4-carbonitrile;
(R)-1-(3,4-difluorophenyl)-3-(isoquinolin-4-yl)-2-oxoimidazolidine-4-carbonitrile;
1-(4-cyano-3-fluorophenyl)-3-(isoquinolin-4-yl)-2-oxoimidazolidine-4-carbonitrile;
(R)-1-(4-cyano-3-fluorophenyl)-3-(isoquinolin-4-yl)-2-oxoimidazolidine-4-carbonitrile;
3-(isoquinolin-4-yl)-1-(2-methylpyridin-3-yl)-2-oxoimidazolidine-4-carbonitrile;
(R)-3-(isoquinolin-4-yl)-1-(2-methylpyridin-3-yl)-2-oxoimidazolidine-4-carbonitrile;
1-(6-(difluoromethyl) pyridin-3-yl)-3-(isoquinolin-4-yl)-2-oxoimidazolidine-4-carbonitrile;
(R)-1-(6-(difluoromethyl) pyridin-3-yl)-3-(isoquinolin-4-yl)-2-oxoimidazolidine-4-carbonitrile;
(R)-1-(3-fluorophenyl)-3-(isoquinolin-4-yl)-2-oxoimidazolidine-4-carbonitrile;
1-(5-fluoro-6-(trifluoromethyl) pyridin-3-yl)-3-(isoquinolin-4-yl)-2-oxoimidazolidine-4-carbonitrile;
(R)-1-(5-fluoro-6-(trifluoromethyl) pyridin-3-yl)-3-(isoquinolin-4-yl)-2-oxoimidazolidine-4-carbonitrile;
1-(5-(difluoromethyl) pyridin-2-yl)-3-(isoquinolin-4-yl)-2-oxoimidazolidine-4-carbonitrile;
(R)-1-(5-(difluoromethyl) pyridin-2-yl)-3-(isoquinolin-4-yl)-2-oxoimidazolidine-4-carbonitrile;
3-(isoquinolin-4-yl)-1-(2-methylpyrimidin-5-yl)-2-oxoimidazolidine-4-carbonitrile;
(R)-3-(isoquinolin-4-yl)-1-(2-methylpyrimidin-5-yl)-2-oxoimidazolidine-4-carbonitrile;
1-(5-chloro-3-methylpyridin-2-yl)-3-(isoquinolin-4-yl)-2-oxoimidazolidine-4-carbonitrile;
(R)-1-(5-chloro-3-methylpyridin-2-yl)-3-(isoquinolin-4-yl)-2-oxoimidazolidine-4-carbonitrile;
3-(isoquinolin-4-yl)-2-oxo-1-(6-(trifluoromethyl) pyridazin-3-yl) imidazolidine-4-carbonitrile;
(R)-3-(isoquinolin-4-yl)-2-oxo-1-(6-(trifluoromethyl) pyridazin-3-yl) imidazolidine-4-carbonitrile;
3-(isoquinolin-4-yl)-1-(3-methyl-6-(trifluoromethyl) pyridin-2-yl)-2-oxoimidazolidine-4-carbonitrile;
(R)-3-(isoquinolin-4-yl)-1-(3-methyl-6-(trifluoromethyl) pyridin-2-yl)-2-oxoimidazolidine-4-carbonitrile;
1-(4-(difluoromethoxy)-2-fluorophenyl)-3-(isoquinolin-4-yl)-2-oxoimidazolidine-4-carbonitrile;
(R)-1-(4-(difluoromethoxy)-2-fluorophenyl)-3-(isoquinolin-4-yl)-2-oxoimidazolidine-4-carbonitrile;
1-(4-(2-hydroxypropan-2-yl) phenyl)-3-(isoquinolin-4-yl)-2-oxoimidazolidine-4-carbonitrile;
(R)-1-(4-(2-hydroxypropan-2-yl) phenyl)-3-(isoquinolin-4-yl)-2-oxoimidazolidine-4-carbonitrile;
1-(3,4-difluorophenyl)-3-(6-(methylsulfonyl) isoquinolin-4-yl)-2-oxoimidazolidine-4-carbonitrile;
(R)-1-(3,4-difluorophenyl)-3-(6-(methylsulfonyl) isoquinolin-4-yl)-2-oxoimidazolidine-4-carbonitrile;
1-(3,5-difluorophenyl)-3-(6-(methylsulfonyl) isoquinolin-4-yl)-2-oxoimidazolidine-4-carbonitrile;
(R)-1-(3,5-difluorophenyl)-3-(6-(methylsulfonyl) isoquinolin-4-yl)-2-oxoimidazolidine-4-carbonitrile;
1-(3-chloro-4-fluorophenyl)-3-(isoquinolin-4-yl)-2-oxoimidazolidine-4-carbonitrile;
(R)-1-(3-chloro-4-fluorophenyl)-3-(isoquinolin-4-yl)-2-oxoimidazolidine-4-carbonitrile;
3-(isoquinolin-4-yl)-1-(2-methyl-5-(trifluoromethyl) pyridin-3-yl)-2-oxoimidazolidine-4-carbonitrile;
(R)-3-(isoquinolin-4-yl)-1-(2-methyl-5-(trifluoromethyl) pyridin-3-yl)-2-oxoimidazolidine-4-carbonitrile;
1-(3-(difluoromethoxy) phenyl)-3-(isoquinolin-4-yl)-2-oxoimidazolidine-4-carbonitrile;
(R)-1-(3-(difluoromethoxy) phenyl)-3-(isoquinolin-4-yl)-2-oxoimidazolidine-4-carbonitrile;
1-(2-cyano-5-(trifluoromethyl) phenyl)-3-(isoquinolin-4-yl)-2-oxoimidazolidine-4-carbonitrile;
(R)-1-(2-cyano-5-(trifluoromethyl) phenyl)-3-(isoquinolin-4-yl)-2-oxoimidazolidine-4-carbonitrile;
3-(isoquinolin-4-yl)-2-oxo-1-(4-(trifluoromethoxy) phenyl) imidazolidine-4-carbonitrile;
(R)-3-(isoquinolin-4-yl)-2-oxo-1-(4-(trifluoromethoxy) phenyl) imidazolidine-4-carbonitrile;
3-(isoquinolin-4-yl)-2-oxo-1-(3-(trifluoromethoxy) phenyl) imidazolidine-4-carbonitrile;
(R)-3-(isoquinolin-4-yl)-2-oxo-1-(3-(trifluoromethoxy) phenyl) imidazolidine-4-carbonitrile;
3-(isoquinolin-4-yl)-2-oxo-1-(2-(trifluoromethyl) pyrimidin-5-yl) imidazolidine-4-carbonitrile;
(R)-3-(isoquinolin-4-yl)-2-oxo-1-(2-(trifluoromethyl) pyrimidin-5-yl) imidazolidine-4-carbonitrile;
1-(6-isopropylpyridin-3-yl)-3-(isoquinolin-4-yl)-2-oxoimidazolidine-4-carbonitrile;
(R)-1-(6-isopropylpyridin-3-yl)-3-(isoquinolin-4-yl)-2-oxoimidazolidine-4-carbonitrile;
3-(isoquinolin-4-yl)-1-(2-methoxy-6-(trifluoromethyl) pyridin-3-yl)-2-oxoimidazolidine-4-carbonitrile;
(R)-3-(isoquinolin-4-yl)-1-(2-methoxy-6-(trifluoromethyl) pyridin-3-yl)-2-oxoimidazolidine-4-carbonitrile;
3-(isoquinolin-4-yl)-1-(1-methyl-2-oxo-6-(trifluoromethyl)-1,2-dihydropyridin-3-yl)-2-oxoimidazolidine-4-carbonitrile;
(R)-3-(isoquinolin-4-yl)-1-(1-methyl-2-oxo-6-(trifluoromethyl)-1,2-dihydropyridin-3-yl)-2-oxoimidazolidine-4-carbonitrile;
(R)-3-(isoquinolin-4-yl)-2-oxo-1-(5-(trifluoromethyl) pyridin-2-yl) imidazolidine-4-carbonitrile;

1-(5,6-dimethylpyridin-3-yl)-3-(isoquinolin-4-yl)-2-oxo-imidazolidine-4-carbonitrile;

(R)-1-(5,6-dimethylpyridin-3-yl)-3-(isoquinolin-4-yl)-2-oxoimidazolidine-4-carbonitrile;

(R)-3-(isoquinolin-4-yl)-2-oxo-1-(4-(trifluoromethyl) phenyl) imidazolidine-4-carbonitrile;

3-(isoquinolin-4-yl)-1-(2-methoxy-5-(trifluoromethyl) pyridin-3-yl)-2-oxoimidazolidine-4-carbonitrile;

(R)-3-(isoquinolin-4-yl)-1-(2-methoxy-5-(trifluoromethyl) pyridin-3-yl)-2-oxoimidazolidine-4-carbonitrile;

1-(5-(difluoromethoxy)-2-methylphenyl)-3-(isoquinolin-4-yl)-2-oxoimidazolidine-4-carbonitrile;

(R)-1-(5-(difluoromethoxy)-2-methylphenyl)-3-(isoquinolin-4-yl)-2-oxoimidazolidine-4-carbonitrile;

1-(2,6-dimethylpyridin-4-yl)-3-(isoquinolin-4-yl)-2-oxo-imidazolidine-4-carbonitrile;

(R)-1-(2,6-dimethylpyridin-4-yl)-3-(isoquinolin-4-yl)-2-oxoimidazolidine-4-carbonitrile;

1-(4-chloro-2-methoxyphenyl)-3-(isoquinolin-4-yl)-2-oxoimidazolidine-4-carbonitrile;

(R)-1-(4-chloro-2-methoxyphenyl)-3-(isoquinolin-4-yl)-2-oxoimidazolidine-4-carbonitrile;

3-(isoquinolin-4-yl)-2-oxo-1-(5-(trifluoromethyl) pyridin-3-yl) imidazolidine-4-carbonitrile;

(R)-3-(isoquinolin-4-yl)-2-oxo-1-(5-(trifluoromethyl) pyridin-3-yl) imidazolidine-4-carbonitrile;

1-(5-fluoro-2-methoxyphenyl)-3-(isoquinolin-4-yl)-2-oxoimidazolidine-4-carbonitrile;

(R)-1-(5-fluoro-2-methoxyphenyl)-3-(isoquinolin-4-yl)-2-oxoimidazolidine-4-carbonitrile;

3-(isoquinolin-4-yl)-2-oxo-1-(3-(trifluoromethyl) phenyl) imidazolidine-4-carbonitrile;

(R)-3-(isoquinolin-4-yl)-2-oxo-1-(3-(trifluoromethyl) phenyl) imidazolidine-4-carbonitrile;

3-(isoquinolin-4-yl)-1-(4-methoxy-6-(trifluoromethyl) pyridin-3-yl)-2-oxoimidazolidine-4-carbonitrile;

(R)-3-(isoquinolin-4-yl)-1-(4-methoxy-6-(trifluoromethyl) pyridin-3-yl)-2-oxoimidazolidine-4-carbonitrile;

1-(4-(difluoromethyl) phenyl)-3-(isoquinolin-4-yl)-2-oxoimidazolidine-4-carbonitrile;

(R)-1-(4-(difluoromethyl) phenyl)-3-(isoquinolin-4-yl)-2-oxoimidazolidine-4-carbonitrile;

1-(2,5-difluorophenyl)-3-(isoquinolin-4-yl)-2-oxoimidazolidine-4-carbonitrile;

(R)-1-(2,5-difluorophenyl)-3-(isoquinolin-4-yl)-2-oxo-imidazolidine-4-carbonitrile;

1-(3,5-difluorophenyl)-3-(isoquinolin-4-yl)-2-oxoimidazolidine-4-carbonitrile;

(R)-1-(3,5-difluorophenyl)-3-(isoquinolin-4-yl)-2-oxo-imidazolidine-4-carbonitrile;

1-(6-chloropyridin-2-yl)-3-(isoquinolin-4-yl)-2-oxoimidazolidine-4-carbonitrile;

(R)-1-(6-chloropyridin-2-yl)-3-(isoquinolin-4-yl)-2-oxo-imidazolidine-4-carbonitrile;

3-(isoquinolin-4-yl)-1-(6-methoxypyridin-3-yl)-2-oxo-imidazolidine-4-carbonitrile;

(R)-3-(isoquinolin-4-yl)-1-(6-methoxypyridin-3-yl)-2-oxoimidazolidine-4-carbonitrile;

3-(isoquinolin-4-yl)-2-oxo-1-(6-oxo-1,6-dihydropyridin-3-yl) imidazolidine-4-carbonitrile;

1-(5-chloro-2-methylphenyl)-3-(isoquinolin-4-yl)-2-oxo-imidazolidine-4-carbonitrile;

(R)-1-(5-chloro-2-methylphenyl)-3-(isoquinolin-4-yl)-2-oxoimidazolidine-4-carbonitrile;

1-(5-chloro-2-methoxyphenyl)-3-(isoquinolin-4-yl)-2-oxoimidazolidine-4-carbonitrile;

(R)-1-(5-chloro-2-methoxyphenyl)-3-(isoquinolin-4-yl)-2-oxoimidazolidine-4-carbonitrile;

1-(2-cyano-5-methylphenyl)-3-(isoquinolin-4-yl)-2-oxo-imidazolidine-4-carbonitrile;

(R)-1-(2-cyano-5-methylphenyl)-3-(isoquinolin-4-yl)-2-oxoimidazolidine-4-carbonitrile;

4-(4-cyano-3-(isoquinolin-4-yl)-2-oxoimidazolidin-1-yl)-6-(trifluoromethyl) nicotinonitrile;

(R)-4-(4-cyano-3-(isoquinolin-4-yl)-2-oxoimidazolidin-1-yl)-6-(trifluoromethyl) nicotinonitrile;

3-(isoquinolin-4-yl)-1-(4-methyl-1H-imidazol-2-yl)-2-oxoimidazolidine-4-carbonitrile;

(R)-3-(isoquinolin-4-yl)-1-(4-methyl-1H-imidazol-2-yl)-2-oxoimidazolidine-4-carbonitrile;

1-(4-chloro-1H-imidazol-2-yl)-3-(isoquinolin-4-yl)-2-oxoimidazolidine-4-carbonitrile;

(R)-1-(4-chloro-1H-imidazol-2-yl)-3-(isoquinolin-4-yl)-2-oxoimidazolidine-4-carbonitrile;

3-(isoquinolin-4-yl)-1-(3-methylcyclobutyl)-2-oxoimidazolidine-4-carbonitrile;

(R)-3-(isoquinolin-4-yl)-1-(1s,3S)-3-methylcyclobutyl)-2-oxoimidazolidine-4-carbonitrile;

(R)-3-(isoquinolin-4-yl)-1-(1r,3R)-3-methylcyclobutyl)-2-oxoimidazolidine-4-carbonitrile;

1-(4-fluorocyclohexyl)-3-(isoquinolin-4-yl)-2-oxoimidazolidine-4-carbonitrile;

(R)-1-(1r,4R)-4-fluorocyclohexyl)-3-(isoquinolin-4-yl)-2-oxoimidazolidine-4-carbonitrile;

(R)-1-(1s,4S)-4-fluorocyclohexyl)-3-(isoquinolin-4-yl)-2-oxoimidazolidine-4-carbonitrile;

3-(isoquinolin-4-yl)-2-oxo-1-(spiro[3.3]heptan-2-yl) imidazolidine-4-carbonitrile;

(R)-3-(isoquinolin-4-yl)-2-oxo-1-(spiro[3.3]heptan-2-yl) imidazolidine-4-carbonitrile;

1-(3-isopropylcyclobutyl)-3-(isoquinolin-4-yl)-2-oxoimidazolidine-4-carbonitrile;

(R)-1-(1s,3S)-3-isopropylcyclobutyl)-3-(isoquinolin-4-yl)-2-oxoimidazolidine-4-carbonitrile;

(R)-1-(1r,3R)-3-isopropylcyclobutyl)-3-(isoquinolin-4-yl)-2-oxoimidazolidine-4-carbonitrile;

1-(3-cyclopropylcyclobutyl)-3-(isoquinolin-4-yl)-2-oxo-imidazolidine-4-carbonitrile;

(R)-1-(1s,3S)-3-cyclopropylcyclobutyl)-3-(isoquinolin-4-yl)-2-oxoimidazolidine-4-carbonitrile;

(R)-1-(1r,3R)-3-cyclopropylcyclobutyl)-3-(isoquinolin-4-yl)-2-oxoimidazolidine-4-carbonitrile;

3-(isoquinolin-4-yl)-2-oxo-1-(spiro[2.3]hexan-5-yl) imidazolidine-4-carbonitrile;

(R)-3-(isoquinolin-4-yl)-2-oxo-1-(spiro[2.3]hexan-5-yl) imidazolidine-4-carbonitrile;

1-(3,3-dimethylcyclobutyl)-3-(isoquinolin-4-yl)-2-oxo-imidazolidine-4-carbonitrile;

(R)-1-(3,3-dimethylcyclobutyl)-3-(isoquinolin-4-yl)-2-oxoimidazolidine-4-carbonitrile;

1-(6,6-difluorospiro[3.3]heptan-2-yl)-3-(isoquinolin-4-yl)-2-oxoimidazolidine-4-carbonitrile;

(R)-1-(6,6-difluorospiro[3.3]heptan-2-yl)-3-(isoquinolin-4-yl)-2-oxoimidazolidine-4-carbonitrile;

3-(isoquinolin-4-yl)-2-oxo-1-(1r,4r)-4-(trifluoromethyl) cyclohexyl) imidazolidine-4-carbonitrile;

(R)-3-(isoquinolin-4-yl)-2-oxo-1-(1r,4R)-4-(trifluoromethyl) cyclohexyl) imidazolidine-4-carbonitrile;

3-(isoquinolin-4-yl)-2-oxo-1-(1-(trifluoromethyl) sulfonyl) azetidin-3-yl) imidazolidine-4-carbonitrile;

(R)-3-(isoquinolin-4-yl)-2-oxo-1-(1-(trifluoromethyl) sulfonyl) azetidin-3-yl) imidazolidine-4-carbonitrile;

3-(isoquinolin-4-yl)-1-(1-(methylsulfonyl) azetidin-3-yl)-2-oxoimidazolidine-4-carbonitrile;
(R)-3-(isoquinolin-4-yl)-1-(1-(methylsulfonyl) azetidin-3-yl)-2-oxoimidazolidine-4-carbonitrile;
1-(1-(cyclopropylsulfonyl) azetidin-3-yl)-3-(isoquinolin-4-yl)-2-oxoimidazolidine-4-carbonitrile;
(R)-1-(1-(cyclopropylsulfonyl) azetidin-3-yl)-3-(isoquinolin-4-yl)-2-oxoimidazolidine-4-carbonitrile;
3-(isoquinolin-4-yl)-1-(1-methylazetidin-3-yl)-2-oxoimidazolidine-4-carbonitrile;
3-(isoquinolin-4-yl)-2-oxo-1-(1-(2,2,2-trifluoroethyl) azetidin-3-yl) imidazolidine-4-carbonitrile;
(R)-3-(isoquinolin-4-yl)-2-oxo-1-(1-(2,2,2-trifluoroethyl) azetidin-3-yl) imidazolidine-4-carbonitrile;
1-(1-acetylazetidin-3-yl)-3-(isoquinolin-4-yl)-2-oxoimidazolidine-4-carbonitrile;
(R)-1-(1-acetylazetidin-3-yl)-3-(isoquinolin-4-yl)-2-oxoimidazolidine-4-carbonitrile;
1-(1-cyclopropylazetidin-3-yl)-3-(isoquinolin-4-yl)-2-oxoimidazolidine-4-carbonitrile;
(R)-1-(1-cyclopropylazetidin-3-yl)-3-(isoquinolin-4-yl)-2-oxoimidazolidine-4-carbonitrile;
3-(isoquinolin-4-yl)-2-oxo-1-(3-(trifluoromethyl) bicyclo[1.1.1]pentan-1-yl) imidazolidine-4-carbonitrile;
(R)-3-(isoquinolin-4-yl)-2-oxo-1-(3-(trifluoromethyl) bicyclo[1.1.1]pentan-1-yl) imidazolidine-4-carbonitrile;
1-(4,4-difluorocyclohexyl)-3-(isoquinolin-4-yl)-2-oxoimidazolidine-4-carbonitrile;
(R)-1-(4,4-difluorocyclohexyl)-3-(isoquinolin-4-yl)-2-oxoimidazolidine-4-carbonitrile;
1-(3-fluorobicyclo[1.1.1]pentan-1-yl)-3-(isoquinolin-4-yl)-2-oxoimidazolidine-4-carbonitrile;
(R)-1-(3-fluorobicyclo[1.1.1]pentan-1-yl)-3-(isoquinolin-4-yl)-2-oxoimidazolidine-4-carbonitrile;
3-(isoquinolin-4-yl)-1-neopentyl-2-oxoimidazolidine-4-carbonitrile;
(R)-3-(isoquinolin-4-yl)-1-neopentyl-2-oxoimidazolidine-4-carbonitrile;
1-(3,3-difluorocyclopentyl)-3-(isoquinolin-4-yl)-2-oxoimidazolidine-4-carbonitrile;
(R)-1-(R or S)-3,3-difluorocyclopentyl)-3-(isoquinolin-4-yl)-2-oxoimidazolidine-4-carbonitrile, and (R)-1-(R or S)-3,3-difluorocyclopentyl)-3-(isoquinolin-4-yl)-2-oxoimidazolidine-4-carbonitrile.

25. A pharmaceutical composition comprising a compound of any one of claims 1 to 24, a stereoisomer thereof, or a pharmaceutically acceptable salt thereof, and one or more pharmaceutically acceptable carriers.

26. The pharmaceutical composition of claim 25 comprising one or more additional therapeutic agents.

27. A method for treating, managing and/or preventing a coronaviral-related disease in a subject in need thereof, wherein the method comprises administering to the subject a therapeutically effective amount of a compound of any one of claims 1 to 24, a stereoisomer thereof, or a pharmaceutically acceptable salt thereof.

28. The method of claim 27, wherein the coronaviral-related disease is COVID-19.

29. The compound of Formula (I) of claim 1, wherein the compound is (R)-3-(isoquinolin-4-yl)-2-oxo-1-(6-(trifluoromethyl) pyridin-3-yl) imidazolidine-4-carbonitrile and has the structure

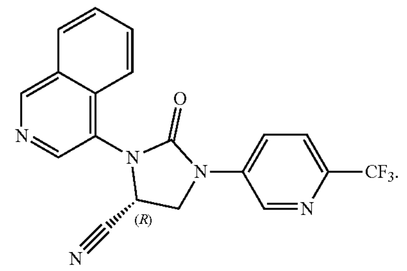

30. The compound of claim 29, which is crystalline (R)-3-(isoquinolin-4-yl)-2-oxo-1-(6-(trifluoromethyl) pyridin-3-yl) imidazolidine-4-carbonitrile.

31. The compound of claim 30, which is characterized by having a powder X-ray diffractogram comprising at least four reflections at 2-Theta angles selected from the group consisting of (6.85±0.2)°, (8.52±0.2)°, (10.41±0.2)°, (13.71±0.2)°, (16.90±0.2)°, (17.06±0.2)°, (18.40±0.2)°, (19.05±0.2)°, (21.76±0.2)°, (22.55±0.2)°, (23.50±0.2)°, (24.82±0.2)°, (26.89±0.2)°, and (28.17±0.2)°, when measured at a temperature in the range of from 20 to 40° C. with Cu-Kalpha radiation having a wavelength of 0.15418 nm.

32. The compound of claim 31, which is characterized by having a powder X-ray diffractogram comprising reflections at 2-Theta angles of (10.41±0.2)°, (16.90±0.2)°, (17.06±0.2°) and (21.76±0.2)°, when measured at a temperature in the range of from 20 to 40° C. with Cu-Kalpha radiation having a wavelength of 0.15418 nm.

33. The compound of claim 31, which is characterized by having a differential scanning calorimetry curve comprising an endothermic peak having a peak temperature of (235.2° C.±0.5° C.), when measured at a heating rate of 10 K/min.

34. The compound of claim 31, which is characterized by having a thermogravimetric analysis curve showing a mass loss of not more than 0.51 weight %, based on the weight of the crystalline form, when heated from 30° C. to 210° C. at a rate of 10 K/min.

35. The compound of claim 30, which is (R)-3-(isoquinolin-4-yl)-2-oxo-1-(6-(trifluoromethyl) pyridin-3-yl) imidazolidine-4-carbonitrile Modification A.

36. The compound of claim 30 which is characterized by having a powder X-ray diffractogram comprising at least four reflections at 2-Theta angles selected from the group consisting of (6.99±0.2)°, (9.11±0.2)°, (13.99±0.2)°, (15.96±0.2)°, (18.26±0.2)°, (19.82±0.2)°, (20.63±0.2)°, (22.03±0.2)°, (23.80±0.2)°, (25.29±0.2)°, (27.30±0.2)°, (30.57±0.2)°, and (33.47±0.2)°, when measured at a temperature in the range of from 20 to 40° C. with Cu-Kalpha radiation having a wavelength of 0.15418 nm.

37. The compound of claim 36 which is characterized by having a powder X-ray diffractogram comprising reflections at 2-Theta angles of (15.96±0.2)°, (18.26±0.2)°, (19.82±0.2)°, and (23.80±0.2)°, when measured at a temperature in the range of from 20 to 40° C. with Cu-Kalpha radiation having a wavelength of 0.15418 nm.

38. The compound of claim 36, which is characterized by having a differential scanning calorimetry curve comprising an endothermic peak having a peak temperature of (161.3° C.±0.5° C.), when measured at a heating rate of 10 K/min.

39. The compound of claim 36, which is characterized by having a thermogravimetric analysis curve showing a mass loss of not more than 0.21 weight %, based on the weight of the crystalline form, when heated from 30° C. to 150° C. at a rate of 10 K/min.

40. The compound of claim 30, which is (R)-3-(isoquinolin-4-yl)-2-oxo-1-(6-(trifluoromethyl) pyridin-3-yl) imidazolidine-4-carbonitrile Modification B.

41. The compound of claim 29, which is amorphous (R)-3-(isoquinolin-4-yl)-2-oxo-1-(6-(trifluoromethyl) pyridin-3-yl) imidazolidine-4-carbonitrile.

* * * * *